US008680159B2

(12) United States Patent
Reich et al.

(10) Patent No.: US 8,680,159 B2
(45) Date of Patent: Mar. 25, 2014

(54) BRADYKININ 1 RECEPTOR MODULATING COMPOUNDS

(75) Inventors: Melanie Reich, Aachen (DE); Stefan Schunk, Aachen (DE); Ruth Jostock, Stolberg (DE); Jean De Vry, Herentals (BE); Christa Kneip, Aachen (DE); Tieno Germann, Aachen (DE); Michael Engels, Turnhout (BE)

(73) Assignee: Gruenenthal GmbH, Aachen (DE)

( * ) Notice: Subject to any disclaimer, the term of this patent is extended or adjusted under 35 U.S.C. 154(b) by 57 days.

(21) Appl. No.: 13/240,598

(22) Filed: Sep. 22, 2011

(65) Prior Publication Data
US 2012/0071461 A1 Mar. 22, 2012

Related U.S. Application Data

(60) Provisional application No. 61/385,313, filed on Sep. 22, 2010.

(30) Foreign Application Priority Data

Sep. 22, 2010 (EP) ..................... 10010200

(51) Int. Cl.
*A61K 31/015* (2006.01)

(52) U.S. Cl.
USPC ........... 514/766; 540/484; 544/238; 544/242; 544/262; 544/264; 544/279; 544/283; 544/336; 544/403; 546/122; 546/149; 546/205; 546/348; 548/126; 548/128; 548/247; 548/335.1; 548/400; 548/469; 548/950; 549/356

(58) Field of Classification Search
USPC ........... 514/766; 540/484; 544/238, 242, 262, 544/264, 279, 283, 336, 403; 546/122, 149, 546/205, 348; 548/126, 128, 247, 335.1, 548/400, 469, 950; 549/356
See application file for complete search history.

(56) References Cited

U.S. PATENT DOCUMENTS

| 2008/0153843 A1 | 6/2008 | Oberboersch et al. |
| 2008/0249128 A1 | 10/2008 | Oberboersch et al. |

FOREIGN PATENT DOCUMENTS

| WO | WO 00/12077 A1 | 3/2000 |
| WO | WO 2005/087236 A1 | 9/2005 |
| WO | WO 2005/095387 A1 | 10/2005 |
| WO | WO 2006/113140 A2 | 10/2006 |
| WO | WO 2007/101007 A2 | 9/2007 |
| WO | WO 2007/140383 A2 | 12/2007 |
| WO | WO 2008/040492 A1 | 4/2008 |
| WO | WO 2008/046573 A1 | 4/2008 |
| WO | WO 2012/038081 | * 3/2012 |

OTHER PUBLICATIONS

Jordan, V. C. Nature Reviews: Drug Discovery, 2, 2003, 205.*
Hackam, et al. JAMA, 296(14), 2006, 1731-1732.*
Corresponding International Search Report with English Translation dated Jan. 12, 2012 (six (6) pages).
Muriel Amatore et al., "CoBrz(Bpy): An Efficient Catalyst for the Direct Conjugate Addition of Aryl Halides or Triflates onto Activated Olefins", The Journal of Organic Chemistry, 2006, (three (3) pages).
Sara H. Bengtson et al., "Kinin Receptor Expression during Staphylococcus Aureus Infection", Blood, Sep. 2006, vol. 108, No. 6, American Society of Hematology, www.bloodjournal.org, (ten (10) pages).
Kaustav Biswas et al., "Potent Nonpeptide Antagonists of the Bradykinin B1 Receptor: Structure-Activity Relationship Studies with Novel Diaminochroman Carboxamides", J. Med. Chem., vol. 50, 2007, pp. 2200-2212.
João B. Calixto et al., "Kinin $B_1$ Receptors: Key G-Protein-Coupled Receptors and their Role in Inflammatory and Painful Processes", British Journal of Pharmacology, vol. 143, 2004, pp. 803-818.
Christopher Fotsch et al., "A new Class of Bradykinin 1 Receptor Antagonists Containing the Piperidine Acetic Acid Tetralin Core", Bioorganic & Medicinal Chemistry Letters, vol. 16, 2006, Elsevier, pp. 2071-2075.
Bichoy H. Gabra et al., "The Kinin System Mediates Hyperalgesia Through the Inducible Bradykinin B1 Receptor Subtype: Evidence in Various Experimental Animal Models of Type 1 and Type 2 Diabetic Neuropathy", Bio. Chem., vol. 387, Feb. 2006, pp. 127-143.
European Search Report with English Translation dated May 3, 2011, (eleven (11) pages).
Dieter Hamprecht et al., "5-$HT_{2c}$ Antagonists based on Fused Heterotricyclic Templates:Design, Synthesis and Biological Evaluation", Bioorganic & Medicinal Chemistry Letters, vol. 17, 2007, Elsevier, pp. 424-427.
R. Hayashi et al., "Bradykinin Stimulates IL-6 and IL-8 Production by Human Lung Fibroblasts Through ERK- and P38 MAPK-Dependent Mechanisms", European Respiratory Journal, vol. 16, 2000, pp. 452-458.
J. Fred Hess et al., "Generation and Characterization of a Humanized Bradykinin B1 Receptor Mouse", Biol. Chem., vol. 387, Feb. 2006, pp. 195-201.
Hakaru Horiguchi et al., "Palladium/Phosphite-Catalyzed 1, 4-Addition of Arylboronic Acids to Acrylic Acid Derivatives", J. Org. Chem., vol. 73, No. 4, 2008, (two (2) pages).

(Continued)

*Primary Examiner* — Douglas M Willis
(74) *Attorney, Agent, or Firm* — Crowell & Moring LLP

(57) ABSTRACT

Substituted benzamide compounds corresponding to formula (I)

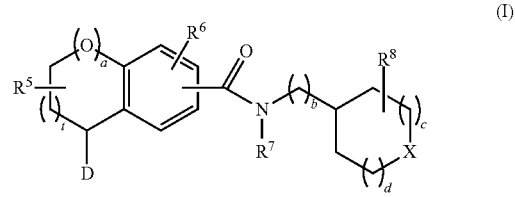

in which R5, R6, R7, R8, a, b, c, d, t, D and X have defined meanings, a process for their preparation, pharmaceutical compositions comprising such compounds, and a method of using such compounds to treat pain and other conditions mediated at least in part via the bradykinin 1 receptor.

25 Claims, No Drawings

(56) References Cited

OTHER PUBLICATIONS

David C. Howell et al., "The Design of Dipeptide Helical Mimetics, Part I: The Synthesis of 1,6-Disubstituted Indanes", Pergamon, Tetrahedron, vol. 51, No. 1, 1995, pp. 203-216.

Yoshihiko Kotake et al., "Synthesis and Antitumor Activities of Novel 6.5 Fused Ring Heterocycle Antifolates: N-[.omega.-(2-Amino-4-Substituted-6,7-dihydroclopenta[d]pyrimidin-5-yl)alky]benzoyl)-L-Glutamic Acids", J. Med. Chem., vol. 37, No. 11, 1994, pp. 1616-1624.

E. D. Matveeva et al., Syntheses of Compounds Active Toward Glutamate Receptors: I. New Preparative Synthesis of Aminoindandicarboxylic Acid (AIDA), Russian Journal of Organic Chemistry, vol. 38, No. 12, 2002, (five (5) pages).

Nathan Moses, Ueber p-Oyanbansylohlorid, Chemische Berichte, pp. 2623-2630, (1900).

Giselle F. Passos et al., "Kinin $B_1$ Receptor Up-Regulation After Lipopolysaccharide Administration: Role of Proinflammatory Cytokines and Neutrophil Influx", The Journal of Immunology, vol. 172, 2004, pp. 1839-1847.

Roberto Pellicclari et al., "1-Aminoindan-1,5-Dicarboxylic Acid: A Novel Antagonist at Phospholipase C-Linked Metabotropic Glutamate Receptors", J. Med. Chem., vol. 38, 1995, pp. 3717-3719.

João B. Pesquero et al., "Hypoalgesia and Altered Inflammatory Responses in Mice Lacking Kinin B1 Receptors", PNAS, Johns Hopkins University School of Medicine, vol. 97, No. 14, 2000, pp. 8140-8145.

João B. Pesquero et al., "Genetically Altered Animal Models in the Kallikrein-kinin System", Biol. Chem., vol. 387, 2006, pp. 119-126.

A. Prat et al., "Bradykinin $B_1$ Receptor Expression and Function on T Lymphocytes in Active Multiple Sclerosis", American Academy of Neurology, vol. 53, No. 9, 1999, (six (6) pages).

Von Siegfried Skraup et al., "Zum Oxydativen Abbau Von Carbonsauren", 1928, pp. 135-158.

Antoni Stadnicki et al., "Immunolocalization and Expression of Kinin $B_1R$ and $B_2R$ Receptors in Human Inflammatory Bowel Disease", Am J. Physiol Gastrointest Liver Physiol, vol. 289, 2005, (seven (7) pages).

Hideki Takahashi et al., "Novel Rh Catalysis in Cross-Coupling Between Alkyl Halides and Arylzinc Compounds Possessing Ortho-COX (X= OR, NMe, or Ph) Groups", Organic Letters, vol. 8, No. 14, 2006, pp. 3037-3040.

Ryo Takeuchi et al., "Rhodium Complex-Catalyzed Desilylative Cyclocarbonylation of 1-aryl-2-(trimethylsilyl)acetylenes: a New Route to 2,3-dihydro-1H-inden-1-ones", The Journal of Organic Chemistry, vol. 58, 1993.

Form PCT/ISA/237 dated Jan. 12, 2012 (six (6) pages) with English translation (nine (9) pages).

Gomes et al., "Addition of Electrochemically Prepared Arylzinc Species onto Activated Olefins via a Cobalt Catalysis," Synleit 2002, No. 10, 1673-1676 (two (2) pages).

Hamprecht et al., "Isoindolone derivatives, a new class of 5-HT2C antagonists: Synthesis and biological evaluation," Bioorganic & Medicinal Chemistry Letters 17 (2007) 428-433, available online Oct. 17, 2006 (three (3) pages).

Leeb-Lundberg et al., "International Union of Pharmacology. XLV. Classification of the Kinin Receptor Family: from Molecular Mechanisms to Pathophysiological Consequences," Pharmacol Rev 57:27-77, 2005 (fifty-one (51) pages).

\* cited by examiner

BRADYKININ 1 RECEPTOR MODULATING COMPOUNDS

CROSS REFERENCE TO RELATED APPLICATIONS

This application claims priority from U.S. provisional patent application No. 61/385,313, filed Sep. 22, 2010, the entire disclosure of which is incorporated herein by reference. Priority is also claimed based on European patent application no. EP 10010200.3, filed Sep. 22, 2010, which likewise is incorporated by reference herein in its entirety.

BACKGROUND OF THE INVENTION

The present invention relates to substituted benzamide compounds, to a process for their preparation, to medicaments comprising these compounds, and to the use of substituted benzamide compounds in the preparation of medicaments.

Unlike the constitutive expression of the bradykinin 2 receptor (B2R), the bradykinin 1 receptor (B1R) is not expressed or is expressed only weakly in most tissues. However, the expression of B1R in various cells is inducible. For example, following inflammation reactions there is a rapid and pronounced induction of B1R in neuronal cells but also in various peripheral cells such as fibroblasts, endothelial cells, granulocytes, macrophages and lymphocytes. Accordingly, in the course of inflammation reactions there is a switch from B2R to B1R dominance in the cells that are involved. The cytokines interleukin-1 (IL-1) and tumour necrosis factor alpha (TNFα) play a substantial part in this B1R up-regulation (Passos et al., J. Immunol. 2004, 172, 1839-1847). Following activation with specific ligands, B1R-expressing cells are then themselves able to secrete inflammation-promoting cytokines such as IL-6 and IL-8 (Hayashi et al., Eur. Respir. J. 2000, 16, 452-458). This results in the immigration of further inflammatory cells, for example neutrophilic granulocytes (Pesquero et al., PNAS 2000, 97, 8140-8145). By way of these mechanisms, the bradykinin B1R system can contribute to the chronification of diseases. This is proved by a large number of animal experiments (overviews in Leeb-Lundberg et al., Pharmacol. Rev. 2005, 57, 27-77 and Pesquero et al., Biol. Chem. 2006, 387, 119-126). In humans too, enhanced expression of B1R is found, for example, in enterocytes and macrophages in the affected tissue of patients with inflammatory intestinal diseases (Stadnicki et al., Am. J. Physiol. Gastrointest. Liver Physiol. 2005, 289, G361-366) or in T-lymphocytes of patients with multiple sclerosis (Prat et al., Neurology, 1999; 53, 2087-2092), or activation of the bradykinin B2R-B1R system is found in the course of infections with *Staphylococcus aureus* (Bengtson et al., Blood 2006, 108, 2055-2063). Infections with *Staphylococcus aureus* are responsible for symptoms such as superficial skin infections to septic shock.

Due to the described pathophysiological relationships there is a great therapeutic potential for the use of B1R antagonists in acute and, in particular, chronic inflammatory diseases. These include respiratory diseases (Asthma bronchiale, allergies, COPD/chronic-obstructive pulmonary disease, cystic fibrosis, etc.), inflammatory intestinal diseases (ulcerative colitis, CD/Crohn's disease, etc.), neurological diseases (multiple sclerosis, neurodegeneration, etc.), inflammations of the skin (atopic dermatitis, psoriasis, bacterial infections, etc.) and mucosa (Behcet's disease, pelvitis, prostatitis, etc.), rheumatic diseases (rheumatoid arthritis, osteoarthritis, etc.), septic shock and reperfusion syndrome (following heart attack, stroke).

In addition, the bradykinin (receptor) system is also involved in regulating angiogenesis (potential as an angiogenesis inhibitor in cancer and macular degeneration of the eye), and B1R knockout mice are protected against the induction of excess weight as a result of a particularly high-fat diet (Pesquero et al., Biol. Chem. 2006, 387, 119-126). B1R antagonists are therefore suitable also for the treatment of obesity.

B1R antagonists are suitable in particular for the treatment of pain, in particular inflammatory pain and neuropathic pain (Calixto et al., Br. J. Pharmacol. 2004, 1-16), in particular diabetic neuropathy (Gabra et al., Biol. Chem. 2006, 387, 127-143). They are also suitable for the treatment of migraine.

In the development of B1R modulators there is the problem, however, that the human and the rat B1R receptor differ so widely that many compounds which are good B1R modulators on the human receptor have only a poor or no affinity for the rat receptor. This makes animal pharmacology studies considerably more difficult, since many studies are usually conducted on the rat. However, if there is no activity on the rat receptor, neither action nor side-effect can be investigated on the rat. This has already meant that transgenic animals with human B1 receptors have been produced for animal pharmacology studies (Hess et al., Biol. Chem. 2006; 387(2):195-201). Working with transgenic animals is more expensive, however, than working with the unmodified animals.

International patent application nos. WO 2008/040492 and WO 2008/046573 describe compounds that exhibit antagonistic activity both on the human B1 receptor and on the B1 receptor of the rat in in vitro assays.

International patent application nos. WO 2007/140383 and WO 2007/101007 describe compounds that exhibit an antagonistic activity on the macaque B1 receptor in in vitro assays. Experimental data relating to activity on the human B1 receptor or on the B1 receptor of the rat are not disclosed.

There is a continued need for novel B1R modulators, B1R modulators that bind both to the rat receptor and to the human receptor offering particular advantages.

SUMMARY OF THE INVENTION

An object of the present invention was, therefore, to provide novel compounds which are suitable in particular as pharmacological active ingredients in medicaments, especially in medicaments for the treatment of disorders or diseases that are mediated at least in part by B1R receptors.

That object is achieved by the substituted benzamide compounds according to the invention.

The present invention accordingly provides substituted benzamide compounds of the general formula (I)

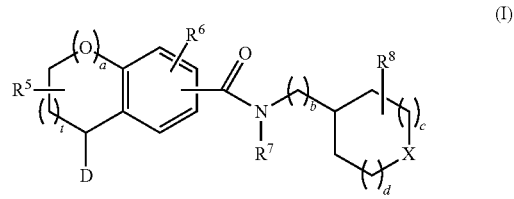

wherein
a represents 0 or 1;
t represents 1, 2 or 3;
b represents 0, 1 or 2;

c and d each independently of the other represents 0, 1 or 2, with the proviso that the ring has not more than 7 ring members;

X represents $N(R^{9a})$ or $C(R^{9b})(H)$;

D represents one of the following radicals D1 or D2

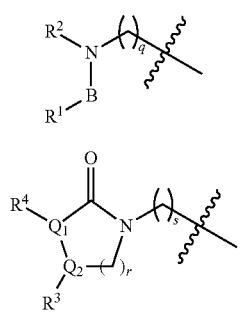

q represents 0 or 1;
represents 0 or 1;
r represents 1, 2 or 3;

B represents $C(=O)$, $S(=O)_2$ or the group $C(=O)-N(R^{10})$, wherein the nitrogen atom thereof is bonded to the radical $R^1$;

$Q_1$ and $Q_2$ each independently of the other represents C, CH or N;

$R^1$ represents $C_{1-9}$-alkyl, aryl, heteroaryl, $CH(aryl)_2$, $C_{3-8}$-cycloalkyl, heterocyclyl, or aryl, heteroaryl, $CH(aryl)_2$, $C_{3-8}$-cycloalkyl or heterocyclyl bonded via a $C_{1-6}$-alkylene group, $C_{2-6}$-alkenylene group or $C_{2-6}$-alkynylene group;

$R^2$ represents H, $C_{1-6}$-alkyl, $C_{3-8}$-cycloalkyl, heterocyclyl, aryl, heteroaryl, or $C_{3-8}$-cycloalkyl, heterocyclyl, aryl or heteroaryl bonded via a $C_{1-6}$-alkylene group;

$R^3$ and $R^4$, together with the group $-Q_1-Q_2-$ linking them, form a ring which is unsubstituted or substituted on one or more, for example 1, 2 or 3, of its carbon ring members by one or more, for example 1, 2, 3 or 4, substituents selected independently of one another from the group consisting of F, Cl, Br, I, $CF_3$, $C_{1-6}$-alkyl, $O-C_{1-6}$-alkyl, OH, $OCF_3$, SH, $SCF_3$, aryl and heteroaryl and/or can be fused with at least one, for example 1 or 2, aryl or heteroaryl, wherein the ring is saturated, mono- or poly-unsaturated, for example mono- or di-unsaturated, or aromatic, is 4-, 5-, 6- or 7-membered and can optionally contain one or more, for example 1, 2 or 3, heteroatoms or heteroatom groups selected independently of one another from the group consisting of N, $NR^{11}$, O, S, $S(=O)$ and $S(=O)_2$; wherein the radical $R^{11}$ denotes H, $C_{1-6}$-alkyl, $C(=O)-R^{12}$, $C_{3-8}$-cycloalkyl, aryl, heteroaryl, or $C_{3-8}$-cycloalkyl, aryl or heteroaryl bonded via a $C_{1-3}$-alkylene group, and $R^{12}$ denotes $C_{1-6}$-alkyl, $C_{3-8}$-cycloalkyl, aryl, heteroaryl, or $C_{3-8}$-cyclo-alkyl, aryl or heteroaryl bonded via a $C_{1-3}$-alkylene group;

$R^5$ represents 0, 1, 2, 3 or 4 substituents selected independently of one another from the group consisting of F, Cl, $CF_3$, $OCF_3$, $C_{1-6}$-alkyl and $O-C_{1-6}$-alkyl, and/or two adjacent substituents $R^5$ form a fused aryl, heteroaryl or $C_{4-8}$-cycloalkyl, and/or two substituents $R^5$ bonded to a carbon atom form a 3-, 4- or 5-membered, saturated carbocyclic ring which is unsubstituted or substituted on one or more of its carbon ring members by one or more substituents selected independently of one another from the group consisting of F, $CF_3$ and $C_{1-6}$-alkyl;

$R^6$ represents 0, 1, 2 or 3 substituents selected independently of one another from the group consisting of F, Cl, Br, $CF_3$, $OCF_3$, OH, $C_{1-6}$-alkyl, $C_{3-8}$-cycloalkyl, $O-C_{1-6}$-alkyl, $NO_2$, $NH_2$, $N(H)(C_{1-6}$-alkyl) and $N(C_{1-6}$-alkyl)$_2$, and/or two adjacent substituents $R^6$ form a fused aryl, heteroaryl or $C_{4-8}$-cycloalkyl;

$R^7$ represents H, $C_{1-6}$-alkyl, $C_{3-8}$-cycloalkyl, heterocyclyl, aryl or heteroaryl, or denotes $C_{3-8}$-cycloalkyl, heterocyclyl, aryl or heteroaryl bonded via a $C_{1-6}$-alkylene group, $R^8$ represents 0, 1, 2, 3 or 4 substituents selected independently of one another from the group consisting of $CF_3$, $C_{1-6}$-alkyl and $C_{3-8}$-cycloalkyl, and/or two substituents $R^8$ bonded to a carbon atom form a $C(=O)$ group or a 3-, 4-, 5-, 6-, 7- or 8-membered, saturated carbocyclic ring which is unsubstituted or substituted on one or more of its carbon ring members by one or more substituents selected independently of one another from the group consisting of F, $CF_3$ and $C_{1-6}$-alkyl;

$R^{9a}$ represents $C(=O)-R^{13}$, $S(=O)_2-R^{13}$, $C(=O)-N(R^{14})-R^{13}$, $CHR^{15}R^{16}$, $C_{3-8}$-cycloalkyl, heterocyclyl, aryl or heteroaryl, or denotes $CHR^{15}R^{16}$, $C_{3-8}$-cycloalkyl, heterocyclyl, aryl or heteroaryl bonded via a $C_{1-6}$-alkylene group, $R^{9b}$ represents $NR^{17}R^{18}$, $C_{1-6}$-alkylene-$NR^{17}R^{18}$, $O-C_{1-6}$-alkylene-$NR^{17}R^{18}$, $C(=O)-NR^{17}R^{18}$, $OR^{19}$, $C_{1-6}$-alkylene-$OR^{19}$, $C_{1-6}$-alkylene-$O-C_{1-6}$-alkylene-$OR^{19}$, $C_{1-6}$-alkyl, $C_{3-6}$-cycloalkyl, heterocyclyl, aryl, heteroaryl, or $C_{3-8}$-cycloalkyl, heterocyclyl, aryl or heteroaryl bonded via a $C_{1-6}$-alkylene group;

$R^{10}$ represents H, $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

$R^{13}$ represents $C_{1-6}$-alkyl, aryl, heteroaryl, $CH(aryl)_2$, $C_{3-8}$-cycloalkyl, heterocyclyl, or aryl, heteroaryl, $C_{3-8}$-cycloalkyl or heterocyclyl bonded via a $C_{1-6}$-alkylene group, $C_{2-6}$-alkenylene group or $C_{2-6}$-alkynylene group;

$R^{14}$ represents H, $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

$R^{15}$ and $R^{16}$ each independently of the other represents H, $C_{1-4}$-alkyl, $C_{3-8}$-cycloalkyl, aryl or heteroaryl, or $R^{15}$ and $R^{16}$, together with the CH grouping linking them, form a ring which is unsubstituted or substituted on one or more, for example 1, 2 or 3, of its carbon ring members by one or more, for example 1, 2, 3 or 4, substituents selected independently of one another from the group consisting of F, Cl, Br, I, $CF_3$, $C_{1-6}$-alkyl, $O-C_{1-6}$-alkyl, OH, $OCF_3$, SH, $SCF_3$, $NR^{20}R^{21}$, aryl and heteroaryl, wherein the ring is saturated or mono- or poly-unsaturated, for example mono- or di-unsaturated, but is not aromatic, is 4-, 5-, 6- or 7-membered and can optionally contain one or more, for example 1, 2 or 3, heteroatoms or heteroatom groups selected independently of one another from the group consisting of N, $NR^{24}$, O, S, $S(=O)$ and $S(=O)_2$; wherein $R^{24}$ denotes H, $C_{1-6}$-alkyl, $C(=O)-R^{25}$, $C_{3-8}$-cycloalkyl, aryl, heteroaryl, or $C_{3-8}$-cycloalkyl, aryl or heteroaryl bonded via a $C_{1-3}$-alkylene group, and $R^{25}$ denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

$R^{17}$ and $R^{18}$ each independently of the other represents H, $C_{1-6}$-alkyl or $C_{3-8}$-cycloalkyl, or $R^{17}$ and $R^{18}$, together with the nitrogen atom linking them, form a heterocyclic ring which is unsubstituted or substituted on one or more, for example 1, 2 or 3, of its carbon ring members by one or more, for example 1, 2, 3 or 4, substituents selected independently of one another from the group consisting of F, Cl, Br, I, $CF_3$, $C_{1-6}$-alkyl, $O-C_{1-6}$-alkyl, OH, $OCF_3$, SH, $SCF_3$, $NR^{20}R^{21}$, aryl and heteroaryl and/or can be fused with at least one, for example 1 or 2, aryl or heteroaryl, wherein the heterocyclic ring is saturated or mono- or poly-unsaturated, for example mono- or di-unsaturated, is 4-, 5-, 6- or 7-membered and can optionally contain one or more, for example 1, 2 or 3, heteroatoms or heteroatom groups selected independently of one another from the group consisting of N, $NR^{22}$, O, S, $S(=O)$ and $S(=O)_2$; wherein $R^{22}$ denotes H, $C_{1-6}$-alkyl, $—C(=O)—R^{23}$, $C_{3-8}$-cycloalkyl, aryl, heteroaryl, or $C_{3-8}$-cycloalkyl, aryl or heteroaryl bonded via a $C_{1-3}$-alkylene group, and $R^{23}$ denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

$R^{19}$ represents H, $C_{1-6}$-alkyl, $C_{3-8}$-cycloalkyl, heterocyclyl, aryl, heteroaryl or $C_{2-6}$-alkylene-$NR^{17}R^{18}$, or heterocyclyl, $C_{3-8}$-cycloalkyl, aryl or heteroaryl bonded via a $C_{1-6}$-alkylene group;

$R^{20}$ and $R^{21}$ each independently of the other represents H, $C_{1-6}$-alkyl or $C_{3-8}$-cycloalkyl, or $R^{20}$ and $R^{21}$, together with the nitrogen atom linking them, form a heterocyclic ring which is unsubstituted or substituted on one or more, for example 1, 2 or 3, of its carbon ring members by one or more, for example 1, 2, 3 or 4, substituents selected independently of one another from the group consisting of F, Cl, Br, I, $CF_3$, $C_{1-6}$-alkyl, $O—C_{1-6}$-alkyl, OH, $OCF_3$, SH, $SCF_3$, aryl and heteroaryl, wherein the heterocyclic ring is saturated or mono- or poly-unsaturated, for example mono- or di-unsaturated, but is not aromatic, is 4-, 5-, 6- or 7-membered and can optionally contain one or more, for example 1, 2, 3 or 4, heteroatoms or heteroatom groups selected independently of one another from the group consisting of N, $NR^{26}$, O, S, $S(=O)$ and $S(=O)_2$; wherein $R^{26}$ denotes H, $C_{1-6}$-alkyl, $C(=O)—R^{27}$, $C_{3-8}$-cycloalkyl, aryl, heteroaryl, or $C_{3-8}$-cycloalkyl, aryl or heteroaryl bonded via a $C_{1-3}$-alkylene group, and $R^{27}$ denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

wherein the above-mentioned radicals $C_{1-4}$-alkyl, $C_{1-6}$-alkyl, $C_{1-3}$-alkylene, $C_{1-6}$-alkylene, $C_{2-6}$-alkylene, $C_{2-6}$-alkenylene, $C_{2-6}$-alkynylene, $C_{3-8}$-cycloalkyl, $C_{4-8}$-cycloalkyl, heterocyclyl, aryl and heteroaryl can in each case be unsubstituted or substituted one or more times by identical or different radicals, and the above-mentioned radicals $C_{1-4}$-alkyl, $C_{1-6}$-alkyl, $C_{1-3}$-alkylene, $C_{1-6}$-alkylene, $C_{2-6}$-alkylene, $C_{2-6}$-alkenylene and $C_{2-6}$-alkynylene can in each case be branched or unbranched;

in the form of the free compound; of the tautomers; of the N-oxides; of the racemate; of the enantiomers, diastereoisomers, mixtures of the enantiomers or diastereoisomers or of a single enantiomer or diastereoisomer; or in the form of the salts of physiologically acceptable acids or bases.

Within the scope of the present invention, the term "halogen" preferably denotes the radicals F, Cl, Br and I, in particular the radicals F and Cl.

Within the scope of this invention, the term "$C_{1-9}$-alkyl", "$C_{1-6}$-alkyl", "$C_{1-4}$-alkyl" or "$C_{1-3}$-alkyl" includes acyclic saturated hydrocarbon radicals having 1, 2, 3, 4, 5, 6, 7, 8 or 9 carbon atoms or 1, 2, 3, 4, 5 or 6 carbon atoms or 1, 2, 3 or 4 carbon atoms or 1, 2 or 3 carbon atoms, which can be branched- or straight-chained (unbranched) as well as unsubstituted or substituted one or more times, for example 2, 3, 4 or 5 times, by identical or different radicals. The alkyl radicals can preferably be selected from the group consisting of methyl, ethyl, n-propyl, isopropyl, n-butyl, isobutyl, sec-butyl, tert-butyl, n-pentyl, isopentyl, neopentyl and hexyl. Particularly preferred alkyl radicals can be selected from the group consisting of methyl, ethyl, n-propyl, isopropyl, n-butyl, sec-butyl, isobutyl and tert-butyl.

Within the scope of this invention, the term "$C_{3-8}$-cycloalkyl", "$C_{4-8}$-cycloalkyl" or "$C_{3-6}$-cycloalkyl" denotes cyclic saturated hydrocarbons having 3, 4, 5, 6, 7 or 8, having 4, 5, 6, 7 or 8 or having 3, 4, 5 or 6 carbon atoms, which can be unsubstituted or substituted on one or more ring members by one or more, for example by 2, 3, 4 or 5, identical or different radicals. If the cycloalkyl radicals have at least 4 carbon atoms, they can also be fused with further saturated, (partially) unsaturated or aromatic or heteroaromatic ring systems, which in turn can be unsubstituted or substituted one or more times, for example 2, 3, 4 or 5 times, by identical or different radicals. $C_{3-8}$-Cycloalkyl can preferably be selected from the group consisting of cyclopropyl, cyclobutyl, cyclopentyl, cyclohexyl, cycloheptyl and cyclooctyl. Tetrahydronaphthalene (tetrahydronaphthyl) may be mentioned as an example of a cycloalkyl radical fused with a phenyl radical.

The term "heterocyclyl" includes saturated or unsaturated (but not aromatic) cycloalkyls having from four to seven ring members, in which one, two or three carbon atoms have been replaced by a heteroatom selected in each case independently from the group S, N and O, wherein the ring members can be unsubstituted or substituted one or more times. Bonding of the heterocyclyl to the main general structure can take place via any desired and possible ring member of the heterocyclyl radical. The heterocyclyl radicals can also be fused with further saturated, (partially) unsaturated or aromatic or heteroaromatic ring systems, which in turn can be unsubstituted or substituted one or more times, for example 2, 3, 4 or 5 times. Preference is given to heterocyclyl radicals from the group azetidinyl, oxetanyl, azepanyl, dioxanyl, dioxolanyl, morpholinyl, pyranyl, pyrrolidinyl, piperazinyl, piperidinyl, pyrazolidinyl, pyrazolinonyl, dihydroindenyl, tetrahydropyranyl, chromanyl or thiomorpholinyl. Particular preference is given to heterocyclyl radicals from the group azetidinyl, oxetanyl, azepanyl, dioxanyl, dioxolanyl, morpholinyl, pyranyl, pyrrolidinyl, piperazinyl, piperidinyl, pyrazolidinyl, pyrazolinonyl or thiomorpholinyl.

Within the scope of this invention, the term "aryl" denotes aromatic hydrocarbons, in particular phenyls and naphthyls. The aryl radicals can also be fused with further saturated, (partially) unsaturated or aromatic ring systems. Each aryl radical can be unsubstituted or substituted one or more times, for example 2, 3, 4 or 5 times, it being possible for the aryl substituents to be identical or different and to be located at any desired and possible position of the aryl. Aryl can advantageously be selected from the group consisting of phenyl, 1-naphthyl and 2-naphthyl, which can in each case be unsubstituted or substituted one or more times, for example by 2, 3, 4 or 5 radicals.

Within the scope of the present invention, the term "heteroaryl" denotes a 5-, 6- or 7-membered cyclic aromatic radical containing at least one, optionally also 2, 3, 4 or 5, heteroatom(s), it being possible for the heteroatoms to be identical or different and for the heteroaryl to be unsubstituted or substituted one or more times, for example 2, 3, 4 or 5 times, by identical or different radicals. The substituents can be bonded at any desired and possible position of the heteroaryl. The heterocyclic ring can also be part of a bi- or poly-cyclic system, in particular of a mono-, bi- or tri-cyclic system, which can then be more than 7-membered in total, preferably up to 14-membered. Preferred heteroatoms are selected independently of one another from the group consisting of N, O and S. The heteroaryl radical can preferably be selected from the group consisting of pyrrolyl, indolyl, furyl (furanyl), benzofuranyl, thienyl (thiophenyl), benzimidazolyl, benzothienyl, benzothiadiazolyl, benzothiazolyl, benzotriazolyl, benzodioxolanyl, benzodioxanyl, benzooxazolyl, benzooxadiazolyl, imidazothiazolyl, dibenzofuranyl, dibenzothienyl, pyrazolo[1,5-a]pyrimidinyl, phthalazinyl, pyrazolyl, imidazolyl, thiazolyl, oxazolyl, isooxazolyl, oxadiazolyl, oxathiazolyl, triazinyl, tetrazolyl, isooxazolyl, pyridinyl(pyridyl), pyridazinyl, pyrimidinyl, pyrazinyl, pyranyl, indazolyl, purinyl, indolizinyl, quinolinyl, isoquinolinyl, quinazolinyl, quinoxalinyl, carbazolyl, phenazinyl, phenothiazinyl and oxadiazolyl, in particular from the group consisting of thienyl(thiophenyl), pyridinyl (pyridyl), pyrimidinyl, thiazolyl, thiadiazolyl, triazolyl, imidazolyl, oxazolyl, pyridazinyl, pyrazinyl, isooxazolyl, oxadiazolyl, quinazolinyl, quinolinyl and isoquinolinyl, it being possible for bonding to the general structure (I) to take place via any desired and possible ring member of the heteroaryl radical. The heteroaryl radical can particularly preferably be selected from the group consisting of isooxazolyl, oxazolyl, pyridazinyl, pyrazinyl, thienyl, imidazolyl, thiazolyl, triazolyl, pyridinyl and pyrimidinyl.

Within the scope of the present invention, the expression "$C_{1-3}$-alkylene group", "$C_{1-6}$-alkylene group" or "$C_{2-6}$-alkylene group" includes acyclic saturated hydrocarbon radicals having 1, 2 or 3 carbon atoms, 1, 2, 3, 4, 5 or 6 carbon atoms or 2, 3, 4, 5 or 6 carbon atoms, which can be branched- or straight-chained (unbranched) as well as unsubstituted or substituted one or more times, for example 2, 3, 4 or 5 times, by identical or different radicals and which link a corresponding radical to the main general structure. The alkylene groups can preferably be selected from the group consisting of —CH$_2$—, —CH$_2$—CH$_2$—, —CH(CH$_3$)—, —CH$_2$—CH$_2$—CH$_2$—, —CH(CH$_3$)—CH$_2$—, —CH(CH$_2$CH$_3$)—, —CH$_2$—(CH$_2$)$_2$—CH$_2$—, —CH(CH$_3$)—CH$_2$—CH$_2$—, —CH$_2$—CH(CH$_3$)—CH$_2$—, —CH(CH$_3$)—CH(CH$_3$)—, —CH(CH$_2$CH$_3$)—CH$_2$—, —C(CH$_3$)$_2$—CH$_2$—, —CH(CH$_2$CH$_2$CH$_3$)—, —C(CH$_3$)(CH$_2$CH$_3$)—, —CH$_2$—(CH$_2$)$_3$—CH$_2$—, —CH(CH$_3$)—CH$_2$—CH$_2$—CH$_2$—, —CH$_2$—CH(CH$_3$)—CH$_2$—CH$_2$—, —CH(CH$_3$)—CH$_2$—CH(CH$_3$)—, —CH(CH$_3$)—CH(CH$_3$)—CH$_2$—, —C(CH$_3$)$_2$—CH$_2$—CH$_2$—, —CH$_2$—C(CH$_3$)$_2$—CH$_2$—, —CH(CH$_2$CH$_3$)—CH$_2$—CH$_2$—, —CH$_2$—CH(CH$_2$CH$_3$)—CH$_2$—, —C(CH$_3$)$_2$ —CH(CH$_3$)—, —CH(CH$_2$CH$_3$)—CH(CH$_3$)—, —C(CH$_3$)(CH$_2$CH$_3$)—CH$_2$—, —CH(CH$_2$CH$_2$CH$_3$)—CH$_2$—, —C(CH$_2$CH$_2$CH$_3$)—CH$_2$—, —CH(CH$_2$CH$_2$CH$_2$CH$_3$)—, —C(CH$_3$)(CH$_2$CH$_2$CH$_3$)—, —C(CH$_2$CH$_3$)$_2$— and —CH$_2$—(CH$_2$)$_4$—CH$_2$—. Particularly preferably, the alkylene groups can be selected from the group consisting of —CH$_2$—, —CH$_2$—CH$_2$— and —CH$_2$—CH$_2$—CH$_2$—.

Within the scope of the present invention, the expression "$C_{2-6}$-alkenylene group" includes acyclic, mono- or poly-unsaturated, for example di-, tri- or tetra-unsaturated, hydrocarbon radicals having 2, 3, 4, 5 or 6 carbon atoms, which can be branched- or straight-chained (unbranched) as well as unsubstituted or substituted one or more times, for example 2, 3, 4 or 5 times, by identical or different radicals and which link a corresponding radical to the main general structure. The alkenylene groups contain at least one C═C double bond. The alkenylene groups can preferably be selected from the group consisting of —CH═CH—, —CH═CH—CH$_2$—, —C(CH$_3$)═CH$_2$—, —CH═CH—CH$_2$—CH$_2$—, —CH$_2$—CH═CH—CH$_2$—, —CH═CH—CH═CH—, —C(CH$_3$)═CH—CH$_2$—, —CH═C(CH$_3$)—CH$_2$—, —C(CH$_3$)═C(CH$_3$)—, —C(CH$_2$CH$_3$)═CH—, —CH═CH—CH$_2$—CH$_2$—CH$_2$—, —CH$_2$—CH═CH—CH$_2$—CH$_2$—, —CH═CH═CH—CH$_2$—CH$_2$— and —CH$_2$—CH$_2$—CH═CH—CH$_2$—.

Within the scope of the invention, the expression "$C_{2-6}$-alkynylene group" includes acyclic, mono- or poly-unsaturated, for example di-, tri- or tetra-unsaturated, hydrocarbon radicals having 2, 3, 4, 5 or 6 carbon atoms, which can be branched- or straight-chained (unbranched) as well as unsubstituted or substituted one or more times, for example 2, 3, 4 or 5 times, by identical or different radicals and which link a corresponding radical to the main general structure. The alkynylene groups contain at least one C≡C triple bond. The alkynylene groups can preferably be selected from the group consisting of —C≡C—, —C≡C—CH$_2$—, —C≡C—CH$_2$—CH$_2$—, —C≡C—CH(CH$_3$)—, —CH$_2$—C≡C—CH$_2$—, —C≡C—C≡C—, —C≡C—C(CH$_3$)$_2$—, —C≡C—CH$_2$—CH$_2$—CH$_2$—, —CH$_2$—C≡C—CH$_2$—CH$_2$—, —C≡C—C≡C—CH$_2$— and —C≡C—CH$_2$—C≡C—.

Within the scope of the present invention, the expression "aryl or heteroaryl bonded via a $C_{1-3}$-alkylene group, $C_{1-6}$-alkylene group, $C_{2-6}$-alkylene group, $C_{2-6}$-alkenylene group or $C_{2-6}$-alkynylene group" means that the $C_{1-3}$-alkylene groups, $C_{1-6}$-alkylene groups, $C_{2-6}$-alkylene groups, $C_{2-6}$-alkenylene groups, $C_{2-6}$-alkynylene groups as well as aryl or heteroaryl have the meanings defined above and the aryl or heteroaryl is bonded to the main general structure via a $C_{1-3}$-alkylene group, $C_{1-6}$-alkylene group, $C_{2-6}$-alkylene group, $C_{2-6}$-alkenylene group or $C_{2-6}$-alkynylene group. Benzyl, phenethyl and phenylpropyl may be mentioned as examples.

Within the scope of the present invention, the expression "$C_{3-8}$-cycloalkyl and heterocyclyl bonded via a $C_{1-3}$-alkylene group, $C_{1-6}$-alkylene group, $C_{2-6}$-alkylene group, $C_{2-6}$-alkenylene group or $C_{2-6}$-alkynylene group" means that the $C_{1-3}$-alkylene group, $C_{1-6}$-alkylene group, $C_{2-6}$-alkylene group, $C_{2-6}$-alkenylene group, $C_{2-6}$-alkynylene group, $C_{3-8}$-cycloalkyl and heterocyclyl have the meanings defined above and $C_{3-8}$-cycloalkyl and heterocyclyl are bonded to the main general structure via a $C_{1-3}$-alkylene group, $C_{1-6}$-alkylene group, $C_{2-6}$-alkylene group, $C_{2-6}$-alkenylene group or $C_{2-6}$-alkynylene group.

In connection with "alkyl", "alkylene", "alkenylene", "alkynylene", "cycloalkyl" and "heterocyclyl", the term "substituted" is understood within the scope of this invention as meaning the substitution of a hydrogen radical by F, Cl, Br, I, CF$_3$, OCF$_3$, CN, NH$_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, NO$_2$, SH, S—$C_{1-6}$-alkyl, $C_{1-6}$-alkyl, S-benzyl, O—$C_{1-6}$-alkyl, OH, O—$C_{1-6}$-alkylene-OH, ═O, O-benzyl, C(═O) $C_{1-6}$-alkyl, CO$_2$H, CO$_2$—$C_{1-6}$-alkyl, phenyl, phenoxy, benzyl, naphthyl, furyl, thienyl and pyridinyl, wherein polysubstituted radicals are to be understood as being radicals which are polysubstituted, for example di- or tri-substituted, either on different atoms or on the same atom, for example trisubstituted on the same carbon atom, as in the case of CF$_3$ or CH$_2$CF$_3$, or at different positions, as in the case of CH(Cl)—CH═CH—CHCl$_2$. Polysubstitution can be carried out with the same or with different substituents, such as, for example, in the case of CH(OH)—CH═CH—CHCl$_2$. In particular, it is here to be understood as meaning the substitution of one or more hydrogen radicals by F, CN, CF$_3$, NH$_2$, N(CH$_3$)$_2$, OH, phenyl, O—CF$_3$ or O—$C_{1-6}$-alkyl.

In relation to "aryl" and "heteroaryl", "substituted" is understood within the scope of this invention as meaning the substitution of one or more hydrogen atoms of the corresponding ring system one or more times, for example 2, 3, 4 or 5 times, by F, Cl, Br, I, CN, NH$_2$, N(CH$_3$)$_2$, NR$^{20}$R$^{21}$, C(═O)NR$^{20}$R$^{21}$, C(═O)—NH$_2$, C(═O)—N(CH$_3$)$_2$,

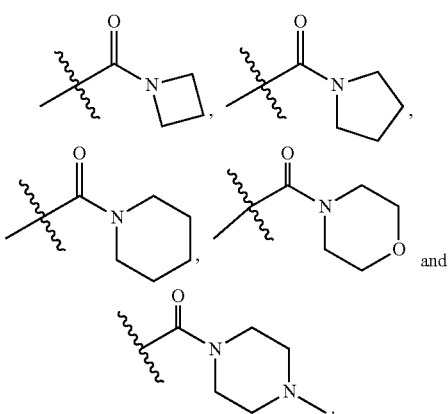

NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, pyrrolidinyl, piperazinyl, N-methyl-piperazinyl, morpholinyl, azetidinyl, piperidinyl, thiazolinyl, azepanyl, diazepanyl, ($C_{1-3}$-alkylene)-azetidinyl, ($C_{1-3}$-alkylene)-pyrrolinyl, ($C_{1-3}$-alkylene)-piperidinyl, ($C_{1-3}$-alkylene)-morpholinyl, ($C_{1-3}$-alkylene)-piperazinyl, ($C_{1-3}$-alkylene)-thiazolinyl, ($C_{1-3}$-alkylene)-azepanyl, ($C_{1-3}$-alkylene)-diazepanyl, NO$_2$, SH, S—$C_{1-6}$-alkyl, S(=O)$_2$—$C_{1-6}$-alkyl, OH, O—$C_{1-6}$-alkyl, O—$C_{1-6}$-alkyl-OH, C(=O)$C_{1-6}$-alkyl, NHSO$_2$$C_{1-6}$-alkyl, NHCOC$_{1-6}$-alkyl, CO$_2$H, CH$_2$SO$_2$-phenyl, CO$_2$—$C_{1-6}$-alkyl, OCF$_3$, CF$_3$, —O—CH$_2$—O—, —O—CH$_2$—CH$_2$—O—, —O—C(CH$_3$)$_2$—CH$_2$—, $C_{1-6}$-alkyl, $C_{3-6}$-cycloalkyl, O—$C_{3-6}$-cycloalkyl, pyrrolidinyl, imidazolyl, benzyloxy, phenoxy, phenyl, naphthyl, pyridinyl, pyrimidinyl, —$C_{1-3}$-alkylene-aryl$^1$, benzyl, thienyl, furyl, or OCF$_3$, OH, O—$C_{1-6}$-alkyl, SH, S—$C_{1-6}$-alkyl, $C_{3-6}$-cycloalkyl, O—$C_{3-6}$-cycloalkyl, NR$^{20}$R$^{21}$, C(=O)—NR$^{20}$R$^{21}$, phenyl, pyridyl or pyrimidyl bonded via a $C_{1-6}$-alkylene group, wherein aryl$^1$ represents phenyl, thiazolyl, thienyl or pyridinyl, on one atom or on different atoms, wherein the above-mentioned substituents—unless indicated otherwise—can themselves optionally be substituted by the mentioned substituents. The polysubstitution of aryl and heteroaryl can be carried out with the same or with different substituents.

Preferred substituents for "aryl" and "heteroaryl" are selected independently of one another from the group consisting of F, Cl, Br, I, CN, NH$_2$, N(CH$_3$)$_2$, NR$^{20}$R$^{21}$, C(=O)—NR$^{20}$R$^{21}$, C(=O)—NH$_2$, C(=O)—N(CH$_3$)$_2$,

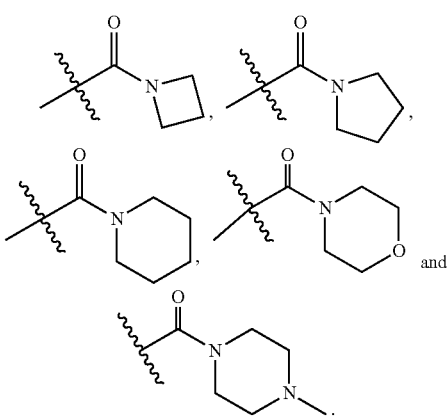

NH—$C_{1-6}$-alkyl, NH—$C_{1-6}$-alkylene-OH, N($C_{1-6}$-alkyl)$_2$, N($C_{1-6}$-alkylene-OH)$_2$, NH-aryl$^1$, N(aryl$^1$)$_2$, N($C_{1-6}$-alkyl)aryl$^1$, pyrrolinyl, pyrrolidinyl, piperazinyl, N-methyl-piperazinyl, morpholinyl, azetidinyl, piperidinyl, thiazolinyl, azepanyl, diazepanyl, ($C_{1-3}$-alkylene)-azetidinyl, ($C_{1-3}$-alkylene)-pyrrolinyl, ($C_{1-3}$-alkylene)-piperidinyl, ($C_{1-3}$-alkylene)-morpholinyl, ($C_{1-3}$-alkylene)-piperazinyl, ($C_{1-3}$-alkylene)-thiazolinyl, ($C_{1-3}$-alkylene)-azepanyl, ($C_{1-3}$-alkylene)-diazepanyl, NO$_2$, SH, S—$C_{1-6}$-alkyl, OH, O—$C_{1-6}$-alkyl, O—$C_{1-6}$-alkyl-OH, C(=O)$C_{1-6}$-alkyl, NHSO$_2$$C_{1-6}$-alkyl, NHCOC$_{1-6}$-alkyl, CO$_2$H, CH$_2$SO$_2$-phenyl, CO$_2$—$C_{1-6}$-alkyl, OCF$_3$, CF$_3$, —O—CH$_2$—O—, —O—CH$_2$—CH$_2$—O—, —O—C(CH$_3$)$_2$—CH$_2$—, $C_{1-6}$-alkyl, $C_{3-6}$-cycloalkyl, O—$C_{3-6}$-cycloalkyl, pyrrolidinyl, imidazolyl, benzyloxy, phenoxy, phenyl, naphthyl, pyridinyl, pyrimidinyl, —$C_{1-3}$-alkylene-aryl$^1$, benzyl, thienyl, furyl, or OCF$_3$, OH, O—$C_{1-6}$-alkyl, SH, S—$C_{1-6}$-alkyl, $C_{3-6}$-cycloalkyl, O—$C_{3-6}$-cycloalkyl, NR$^{20}$R$^{21}$, C(=O)—NR$^{20}$R$^{21}$, phenyl, pyridyl or pyrimidyl bonded via a $C_{1-6}$-alkylene group, wherein aryl$^1$ represents phenyl, thiazolyl, thienyl or pyridinyl. Particularly preferred substituents for aryl and heteroaryl can be selected from the group consisting of -O—$C_{1-3}$-alkyl, unsubstituted $C_{1-6}$-alkyl, F, Cl, CN, CF$_3$, OCF$_3$, OH, NH$_2$, NR$^{20}$R$^{21}$, phenyl, naphthyl, thiazolyl, thienyl and pyridinyl, in particular from the group consisting of tert-butyl, F, Cl, CN, CF$_3$, CH$_3$; OCH$_3$, OCF$_3$, NH$_2$ and NR$^{20}$R$^{21}$.

In the chemical structural formulae which are used here to describe the compounds according to the invention, the symbol

is also used to describe one or more substitution patterns, that group, in contrast to the representation of a bond to a specific atom, not being bonded to a specific atom within the chemical structural formula (R$^a$ here represents, for example, a substituent R having a numbering represented by the variable "a"). For example, it is possible—in so far as the symbol is used in connection with a ring, for the substituent in question to be bonded to any possible ring atom.

Within the scope of the present invention, the symbol

used in formulas denotes the linking of a corresponding radical to the respective main general structure.

Persons skilled in the art will understand that the same radicals used to define different substituents are in each case independent of one another, such as, for example, the radicals R$^{17}$ and R$^{18}$ in the groupings NR$^{17}$R$^{18}$, $C_{1-6}$-alkylene-NR$^{17}$R$^{18}$, O—$C_{1-6}$-alkylene-NR$^{17}$R$^{18}$ and C(=O)—NR$^{17}$R$^{18}$. Accordingly, whenever they occur, such radicals can have a meaning that is independent of their meaning in other groupings containing those radicals. The same is also true of groupings such as N($C_{1-6}$-alkyl)$_2$ or ($C_{1-4}$-alkyl)$_2$, in which the two $C_{1-4}$-alkyl groups can be the same or different, such as, for example, in N(CH$_3$)$_2$ or N(CH$_3$)(C$_2$H$_5$).

Within the scope of this invention, the expression "physiologically acceptable salt" is understood as meaning preferably salts of the compounds according to the invention with inorganic or organic acids which are physiologically acceptable—in particular when used in humans and/or mammals, such as, for example, salts of hydrochloric acid (hydrochlorides). Further, this expression is also understood as meaning compounds that are obtained by quaternization of a nitrogen atom present in the structure (e.g. pyridyl, N-methylpiperidinyl). Such compounds can be obtained, for example, by alkylation with formation of the corresponding cation using counter-ions such as, for example, Cl⁻ and F⁻.

As used herein, the term "isolated" with respect to a stereoisomer (i.e., enantiomer or diastereomer) means substantially free of the opposite stereoisomer, but not necessarily from other substances.

In preferred embodiments of the compounds according to the invention, q represents 0, so that the radical D1 assumes the following form D1':

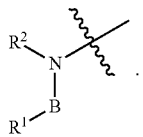

In embodiments of the compounds according to the invention that are likewise preferred, s represents 0, so that the radical D2 assumes the following form D2':

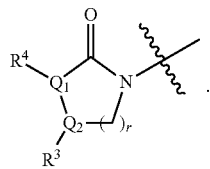

Preferably, the partial structure

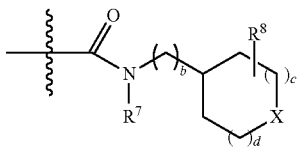

is bonded at position x or y to the basic structure

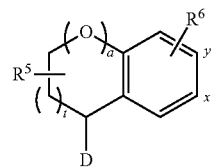

so that the following general formulae (I-x)

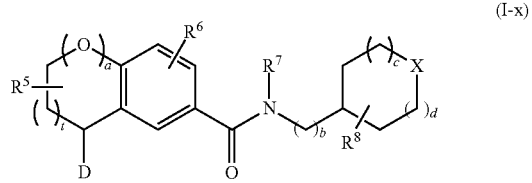

or (I-y)

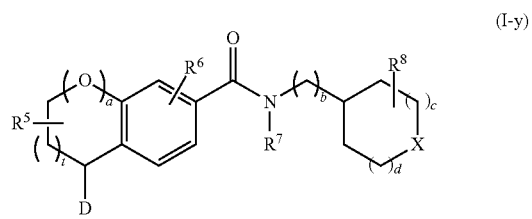

are obtained, wherein the radicals, variables and indices have the meanings described herein in connection with the compounds according to the invention and preferred embodiments thereof. Compounds of the general formula (I-x) are particularly preferred.

In a preferred embodiment of the compounds according to the invention, a represents 0 or 1 and t represents 1 or 2.

In further preferred embodiments of the compounds according to the invention, the partial structure (Ac)

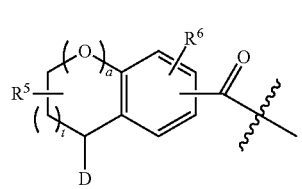

can represent a partial structure selected from the group consisting of

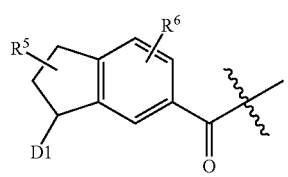

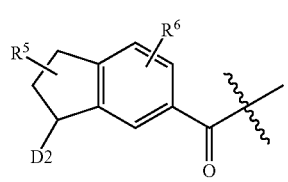

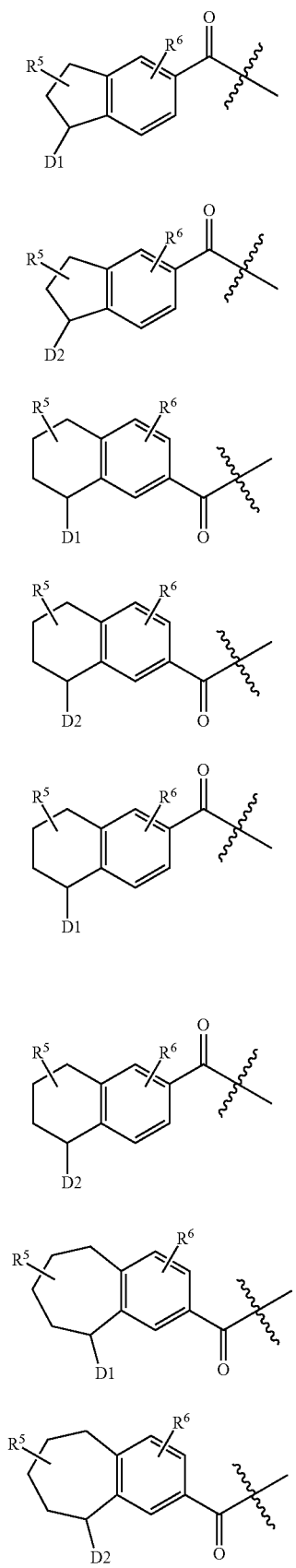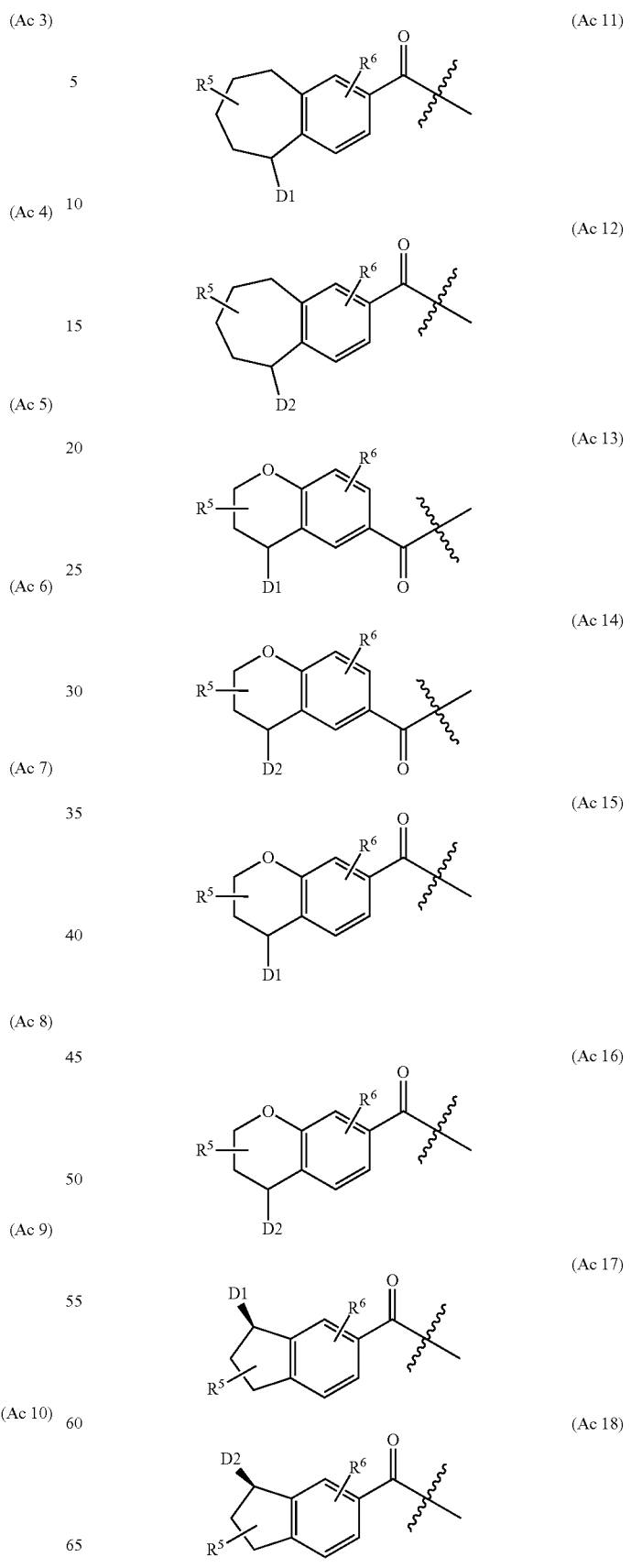

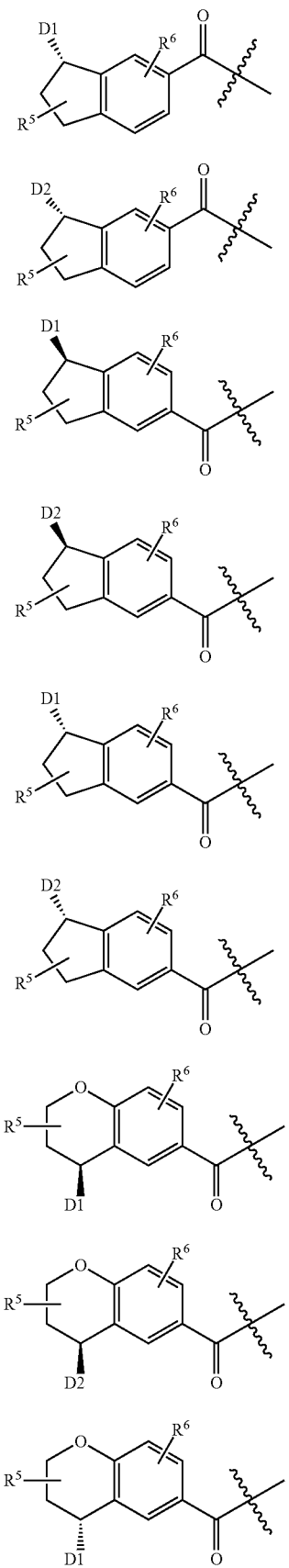

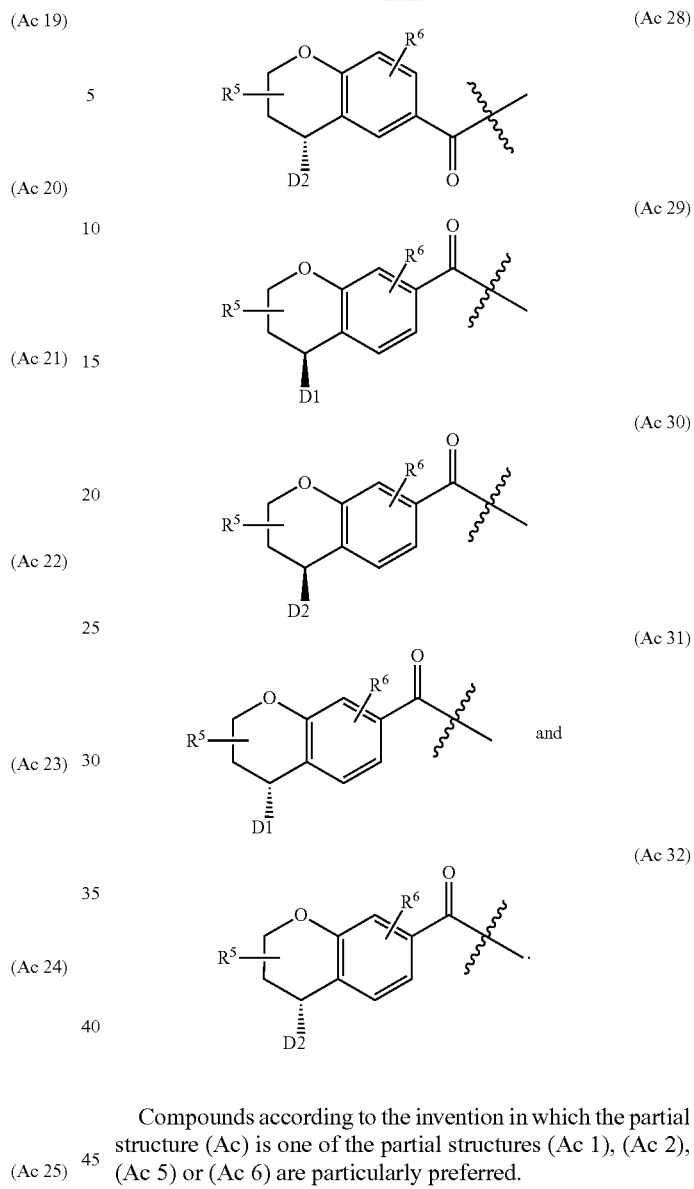

Compounds according to the invention in which the partial structure (Ac) is one of the partial structures (Ac 1), (Ac 2), (Ac 5) or (Ac 6) are particularly preferred.

Compounds according to the invention which have the partial structure D1 are particularly preferred.

In further preferred embodiments of the compounds according to the invention, the partial structure D1 is selected from the group consisting of

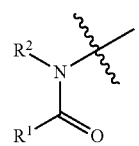

D1-1

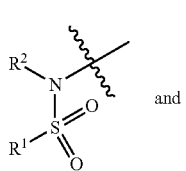

and

D1-2

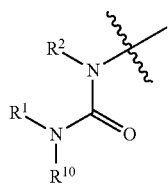

D1-3

Compounds which have the partial structure D1-1 or D1-2 are most particularly preferred.

In the compounds according to the invention, the radical $R^1$ preferably represents $C_{1-9}$-alkyl, $CH(phenyl)_2$, $C_{3-8}$-cycloalkyl, heterocyclyl, phenyl, naphthyl, tetrahydronaphthyl, chromanyl, indolyl, benzofuranyl, benzothiophenyl(benzothienyl), benzooxazolyl, benzooxadiazolyl, pyrrolyl, furanyl, thienyl, oxazolyl, isoxazolyl, pyridinyl, pyridazinyl, pyrimidinyl, pyrazolo[1,5-a]pyrimidinyl, pyrazinyl, imidazothiazolyl, carbazolyl, dibenzofuranyl, dibenzothiophenyl (dibenzothienyl), dihydroindenyl, isoquinolinyl, or phenyl, naphthyl, $C_{3-8}$-cycloalkyl or heterocyclyl bonded via a $C_{1-3}$-alkylene group, particularly preferably $C_{1-6}$-alkyl, $CH(phenyl)_2$, $C_{3-6}$-cycloalkyl, $C_{4-6}$-heterocyclyl, phenyl, naphthyl, tetrahydronaphthyl, chromanyl, benzothiophenyl(benzothienyl), benzooxadiazolyl, thienyl, oxazolyl, isoxazolyl, pyridinyl, pyrimidinyl, pyrazolo[1,5-a]pyrimidinyl, imidazothiazolyl, dibenzofuranyl, dihydroindenyl, isoquinolinyl, or phenyl, $C_{3-6}$-cycloalkyl or $C_{4-6}$-heterocyclyl bonded via a $C_{1-3}$-alkylene group; most particularly preferably $C_{1-6}$-alkyl, $CH(phenyl)_2$, cyclopropyl, cyclobutyl, cyclopentyl, cyclohexyl, tetrahydropyranyl, oxetanyl, tetrahydrofuranyl, piperidinyl, phenyl, naphthyl, tetrahydronaphthyl, pyridinyl, pyrimidinyl, pyrazolo[1,5-a]pyrimidinyl, dihydroindenyl, chromanyl, isoquinolinyl, oxazolyl, isoxazolyl, or phenyl, cyclopropyl, cyclobutyl, cyclopentyl, cyclohexyl, tetrahydropyranyl, oxetanyl, tetrahydrofuranyl or piperidinyl bonded via a $C_{1, 2\ or\ 3}$-alkylene group, wherein the above-mentioned aryl or heteroaryl radicals are in each case unsubstituted or substituted one or more times, for example 2, 3, 4 or 5 times, by identical or different substituents, the substituents being selected independently of one another in particular from the group consisting of $O$—$C_{1-3}$-alkyl, $C_{1-6}$-alkyl, F, Cl, CN, $CF_3$, $OCF_3$, and OH, and wherein the above-mentioned alkyl, alkylene, cycloalkyl and heterocyclyl groups are in each case unsubstituted or substituted one or more times, for example 2, 3, 4 or 5 times, by identical or different substituents, the substituents being selected independently of one another in particular from the group consisting of $O$—$C_{1-3}$-alkyl, $C_{1-4}$-alkyl, F, Cl, $CF_3$, $OCF_3$, OH, cyclopropyl, cyclobutyl, cyclopentyl, cyclohexyl, phenyl, phenoxy, naphthyl, furyl, thienyl and pyridinyl, and wherein cyclopropyl, cyclobutyl, cyclopentyl, cyclohexyl, phenyl, phenoxy, naphthyl, furyl, thienyl and pyridinyl occurring as substituents are themselves in each case unsubstituted or substituted one or more times, for example 2, 3, 4 or 5 times, by identical or different substituents, the substituents being selected independently of one another in particular from the group consisting of $C_{1-4}$-alkyl, $O$—$C_{1-3}$-alkyl, F, Cl, $CF_3$, $OCF_3$ and OH.

In a further preferred embodiment, the radical $R^1$ in the compounds according to the invention represents $C_{1-9}$-alkyl, $CH(phenyl)_2$, $C_{3-8}$-cycloalkyl, heterocyclyl, phenyl, naphthyl, tetrahydronaphthyl, chromanyl, indolyl, benzofuranyl, benzothiophenyl(benzothienyl), benzooxazolyl, benzooxadiazolyl, pyrrolyl, furanyl, thienyl, oxazolyl, isoxazolyl, pyridinyl, pyridazinyl, pyrimidinyl, pyrazolo[1,5-a]pyrimidinyl, pyrazinyl, imidazothiazolyl, carbazolyl, dibenzofuranyl, dibenzothiophenyl(dibenzothienyl), or phenyl, naphthyl, $C_{3-8}$-cycloalkyl or heterocyclyl bonded via a $C_{1-3}$-alkylene group; preferably $C_{1-6}$-alkyl, $CH(phenyl)_2$, $C_{3-6}$-cycloalkyl, $C_{4-6}$-heterocyclyl, phenyl, naphthyl, tetrahydronaphthyl, chromanyl, benzothiophenyl (benzothienyl), benzooxadiazolyl, thienyl, oxazolyl, isoxazolyl, pyridinyl, pyrimidinyl, pyrazolo[1,5-a]pyrimidinyl, imidazothiazolyl, dibenzofuranyl, or phenyl, $C_{3-6}$-cycloalkyl or $C_{4-6}$-heterocyclyl bonded via a $C_{1-3}$-alkylene group; particularly preferably $C_{1-6}$-alkyl, $CH(phenyl)_2$, cyclopropyl, cyclobutyl, cyclopentyl, cyclohexyl, tetrahydropyranyl, oxetanyl, tetrahydrofuranyl, piperidinyl, phenyl, naphthyl, tetrahydronaphthyl, pyridinyl, pyrimidinyl, pyrazolo[1,5-a]pyrimidinyl, oxazolyl, isoxazolyl, or phenyl, cyclopropyl, cyclobutyl, cyclopentyl, cyclohexyl, tetrahydropyranyl, oxetanyl, tetrahydrofuranyl or piperidinyl bonded via a $C_{1, 2\ or\ 3}$-alkylene group, wherein the above-mentioned aryl or heteroaryl radicals are in each case unsubstituted or substituted one or more times, for example 2, 3, 4 or 5 times, by identical or different substituents, the substituents being selected independently of one another in particular from the group consisting of $O$—$C_{1-3}$-alkyl, $C_{1-6}$-alkyl, F, Cl, CN, $CF_3$, $OCF_3$ and OH and wherein the above-mentioned alkyl, alkylene, cycloalkyl and heterocyclyl groups are in each case unsubstituted or substituted one or more times, for example 2, 3, 4 or 5 times, by identical or different substituents, the substituents being selected independently of one another in particular from the group consisting of $O$—$C_{1-3}$-alkyl, F, Cl, $CF_3$, $OCF_3$, OH, cyclopropyl, cyclobutyl, cyclopentyl, cyclohexyl, phenyl, phenoxy, naphthyl, thienyl and pyridinyl, and wherein cyclopropyl, cyclobutyl, cyclopentyl, cyclohexyl, phenyl, phenoxy, naphthyl, furyl, thienyl and pyridinyl occurring as substituents are themselves in each case unsubstituted or substituted one or more times, for example 2, 3, 4 or 5 times, by identical or different substituents, the substituents being selected independently of one another in particular from the group consisting of $C_{1-4}$-alkyl, $O$—$C_{1-3}$-alkyl, F, Cl, $CF_3$, $OCF_3$ and OH.

The radical $R^1$ can in particular represent $C_{1-6}$-alkyl, cyclopropyl, cyclobutyl, cyclopentyl, cyclohexyl, tetrahydropyranyl, dihydroindenyl, chromanyl, isoquinolinyl, oxetanyl, tetrahydrofuranyl, piperidinyl, phenyl, naphthyl, tetrahydronaphthyl, pyridinyl, pyrimidinyl, pyrazolo[1,5-a]pyrimidinyl, thienyl, oxazolyl, isoxazolyl, or phenyl, cyclopropyl, cyclobutyl, cyclopentyl or cyclohexyl bonded via a $C_{1, 2\ or\ 3}$-alkylene group, wherein the above-mentioned aryl or heteroaryl radicals are in each case unsubstituted or substituted one or more times, for example 2, 3, 4 or 5 times, by identical or different substituents, the substituents being selected independently of one another in particular from the group consisting of $O$—$C_{1-3}$-alkyl, $C_{1-4}$-alkyl, F, Cl, $CF_3$, $OCF_3$ and OH, and wherein the above-mentioned alkyl, alkylene and cycloalkyl groups are in each case unsubstituted or substituted one or more times, for example 2, 3, 4 or 5 times, by identical or different substituents, the substituents being selected independently of one another in particular from the group consisting of $O$—$C_{1-3}$-alkyl, F, Cl, $CF_3$, $OCF_3$, OH, cyclopropyl, cyclobutyl, cyclopentyl, cyclohexyl, phenyl, thienyl and pyridinyl, and wherein cyclobutyl, cyclopentyl, cyclohexyl, phenyl, thienyl and pyridinyl occurring as substituents are themselves in each case unsubstituted or substituted one or more times, for example 2, 3, 4 or 5 times, by identical or different substituents, the substituents being selected independently of one another in particular from the group consisting of $C_{1-4}$-alkyl, O—$C_{1-3}$-alkyl, F, Cl, $CF_3$, $OCF_3$ and OH.

In a further preferred embodiment, the radical $R^1$ can in particular represent $C_{1-6}$-alkyl, cyclopropyl, cyclobutyl, cyclopentyl, cyclohexyl, tetrahydropyranyl, oxetanyl, tetrahydrofuranyl, piperidinyl, phenyl, naphthyl, tetrahydronaphthyl, pyridinyl, pyrimidinyl, pyrazolo[1,5-a]pyrimidinyl, thienyl, oxazolyl, isoxazolyl, or phenyl, cyclopropyl, cyclobutyl, cyclopentyl or cyclohexyl bonded via a $C_{1,\,2\,or\,3}$-alkylene group, wherein the above-mentioned aryl or heteroaryl radicals are in each case unsubstituted or substituted one or more times, for example 2, 3, 4 or 5 times, by identical or different substituents, the substituents being selected independently of one another in particular from the group consisting of O—$C_{1-3}$-alkyl, $C_{1-4}$-alkyl, F, Cl, $CF_3$, $OCF_3$ and OH, and wherein the above-mentioned alkyl, alkylene and cycloalkyl groups are in each case unsubstituted or substituted one or more times, for example 2, 3, 4 or 5 times, by identical or different substituents, the substituents being selected independently of one another in particular from the group consisting of O—$C_{1-3}$-alkyl, F, Cl, $CF_3$, $OCF_3$, OH, cyclopropyl, cyclobutyl, cyclopentyl, cyclohexyl, phenyl, thienyl and pyridinyl, and wherein cyclopropyl, cyclobutyl, cyclopentyl, cyclohexyl, phenyl, thienyl and pyridinyl occurring as substituents are themselves in each case unsubstituted or substituted one or more times, for example 2, 3, 4 or 5 times, by identical or different substituents, the substituents being selected independently of one another in particular from the group consisting of $C_{1-4}$-alkyl, O—$C_{1-3}$-alkyl, F, Cl, $CF_3$, $OCF_3$ and OH.

In further preferred embodiments of the compounds according to the invention, the radical $R^1$ can be selected from the group consisting of

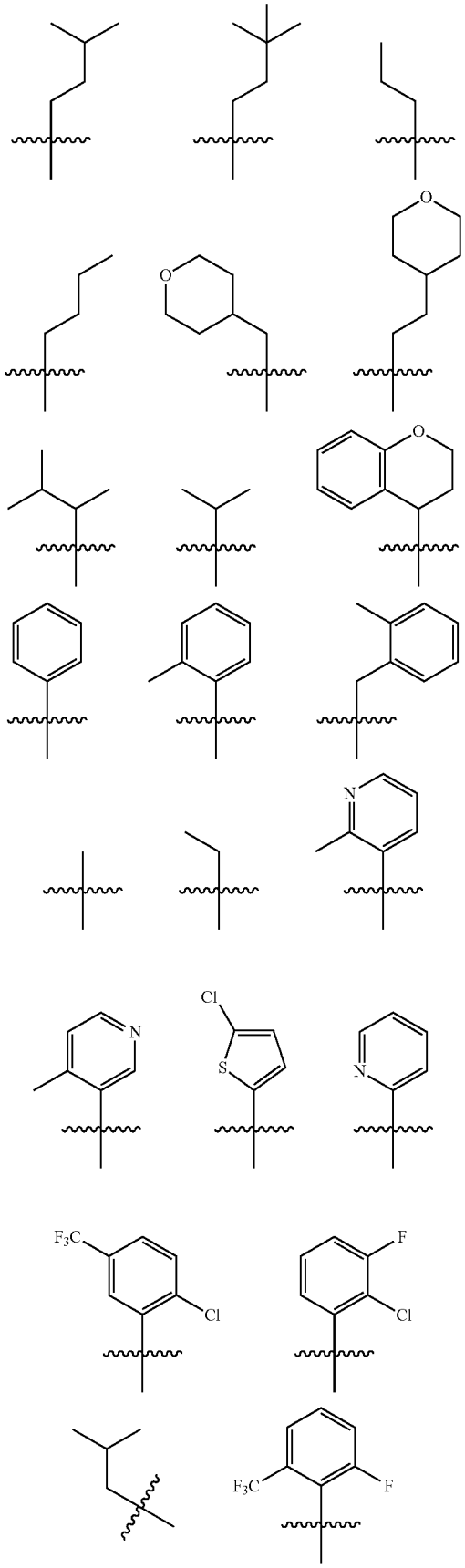

-continued
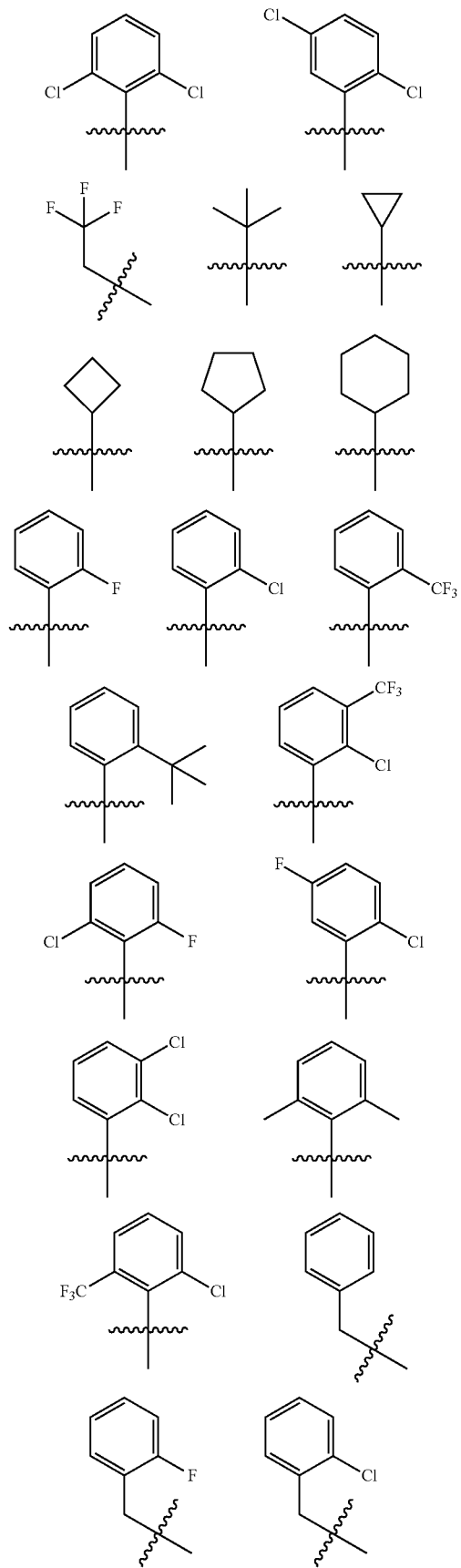
-continued
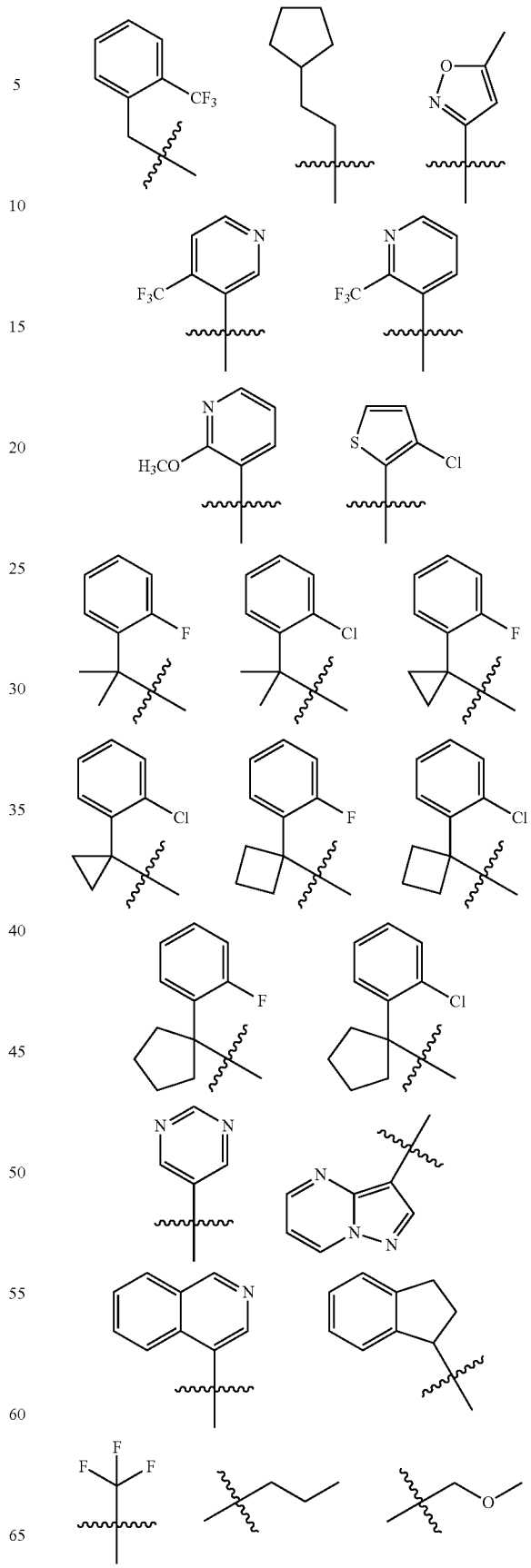

-continued
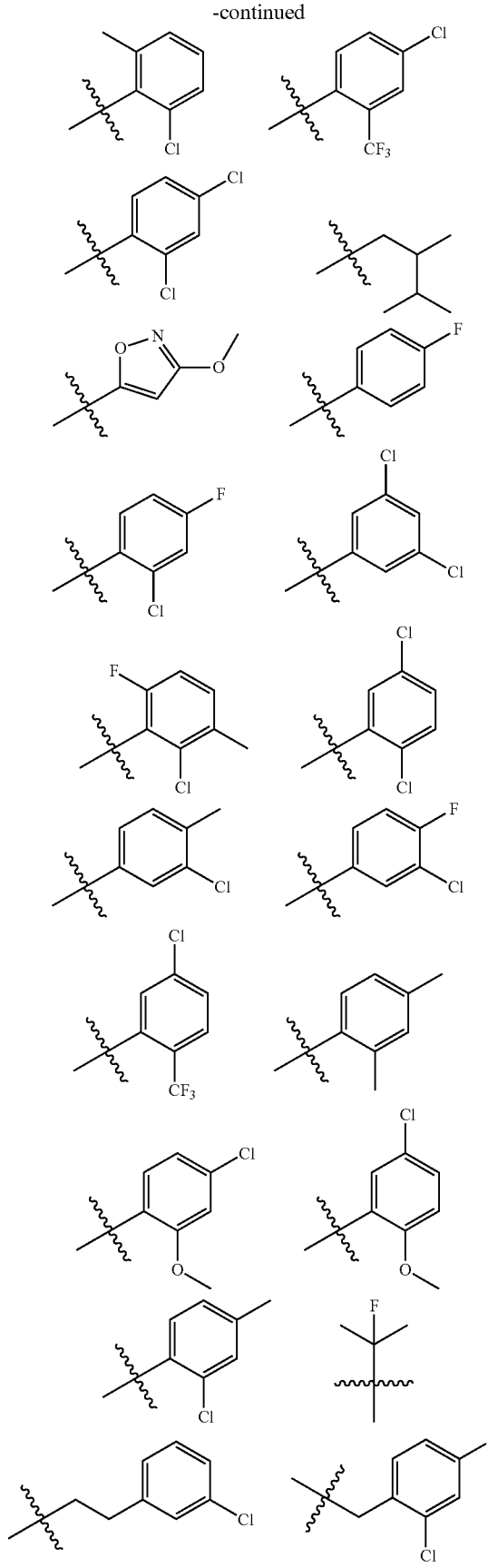
In further particularly preferred embodiments of the compounds according to the invention, the radical $R^1$ can be selected from the group consisting of
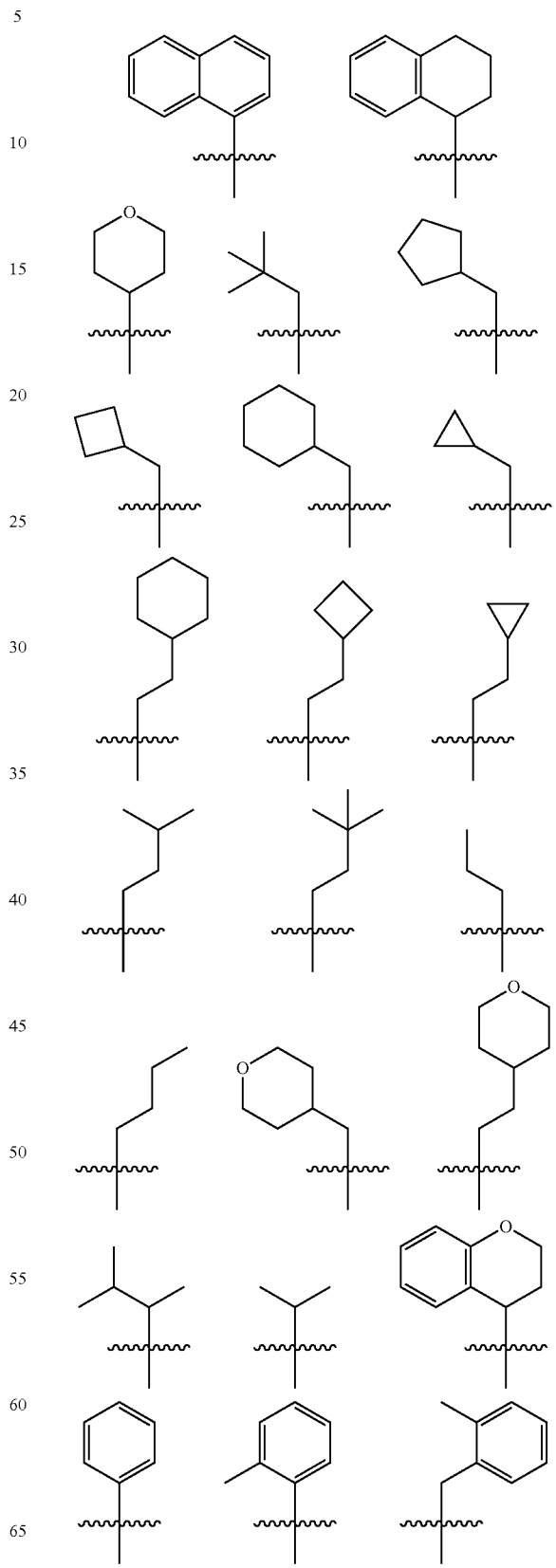

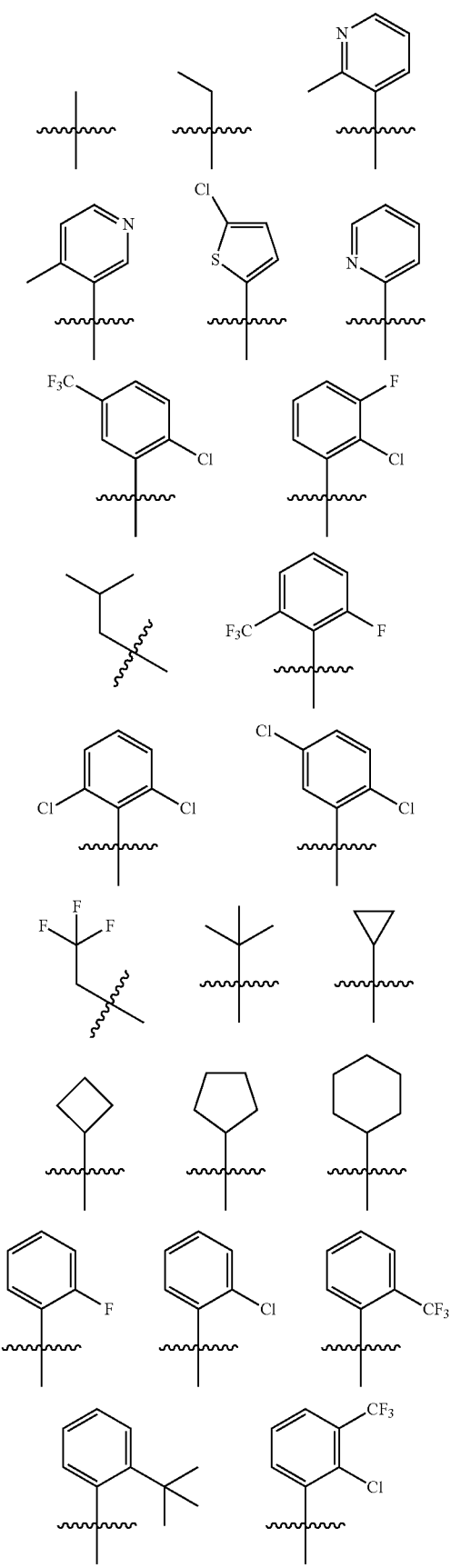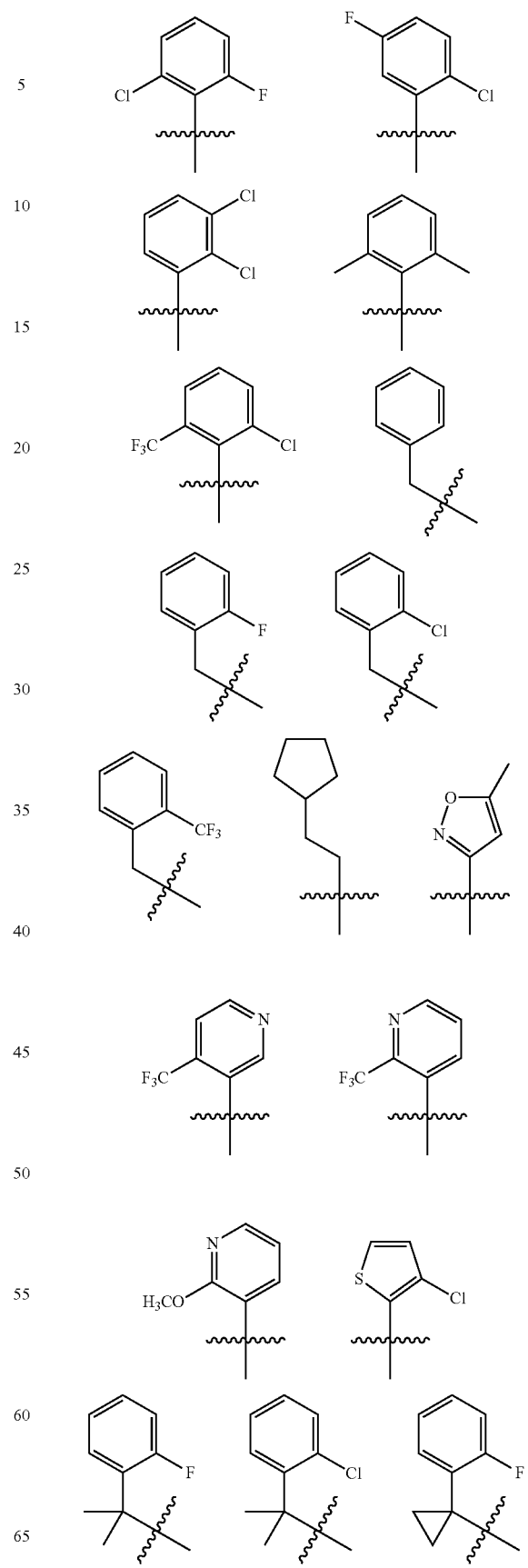

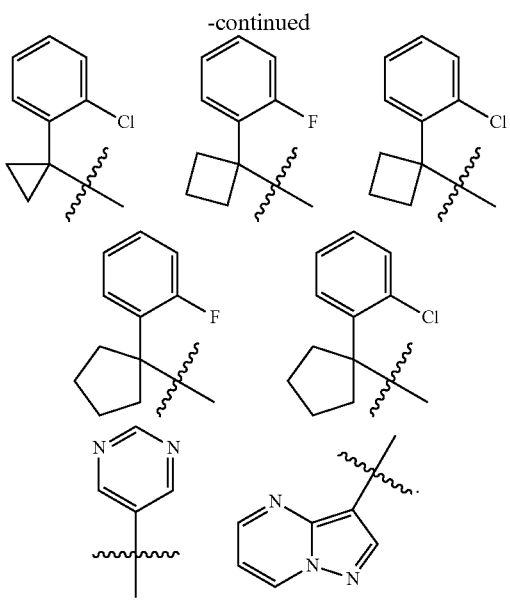

Where the radical D1 represents the group D1-2, $R^1$ can in particular also represent $C_{1-9}$-alkyl, $C_{3-9}$-cycloalkyl or heterocyclyl, or $C_{3-6}$-cycloalkyl or heterocyclyl bonded via a $C_{1-6}$-alkylene group, wherein $C_{1-6}$-alkyl can be unsubstituted or substituted one or more times, for example 2, 3, 4 or 5 times, in particular by radicals selected from the group consisting of F, $CF_3$, $OCF_3$, OH and methoxy, and wherein $C_{3-6}$-cycloalkyl and heterocyclyl can optionally be fused with phenyl and can be unsubstituted or substituted one or more times, for example 2, 3, 4 or 5 times, in particular by radicals selected from the group consisting of F, $CF_3$, $OCF_3$, OH and methoxy.

In a most particularly preferred embodiment, the compounds according to the invention have the partial structure D1-1, in which $R^1$ represents phenyl, pyridyl, preferably 3-pyridyl, oxazolyl or isoxazolyl, wherein each of these radicals is in each case unsubstituted or substituted one or more times, for example 2, 3, 4 or 5 times, by identical or different substituents, the substituents being selected independently of one another in particular from the group consisting of O—$C_{1-3}$-alkyl, $C_{1-6}$-alkyl, F, Cl, CN, $CF_3$, $OCF_3$ and OH, preferably from the group consisting of O—$CH_3$, $CH_3$, F, $C_1$ and $CF_3$; or $R^1$ represents $C_{1-6}$-alkyl, $C_{3-6}$-cycloalkyl, $C_{4-6}$-heterocyclyl, or $C_{3-6}$-cycloalkyl or $C_{4-6}$-heterocyclyl bonded via a $C_{1-3}$-alkylene group, wherein the above-mentioned alkyl, alkylene, cycloalkyl and heterocyclyl groups are in each case unsubstituted or substituted one or more times, for example 2, 3, 4 or 5 times, by identical or different substituents, the substituents being selected independently of one another in particular from the group consisting of O—$C_{1-3}$-alkyl, $C_{1-4}$-alkyl, F, Cl, $CF_3$, $OCF_3$ and OH;

or the compounds according to the invention have the partial structure D1-2, in which $R^1$ represents $C_{1-6}$-alkyl, $C_{3-6}$-cycloalkyl, $C_{4-6}$-heterocyclyl, or $C_{3-6}$-cycloalkyl or $C_{4-6}$-heterocyclyl bonded via a $C_{1-3}$-alkylene group, wherein the above-mentioned alkyl, alkylene, cycloalkyl and heterocyclyl groups are in each case unsubstituted or substituted one or more times, for example 2, 3, 4 or 5 times, by identical or different substituents, the substituents being selected independently of one another in particular from the group consisting of O—$C_{1-3}$-alkyl, $C_{1-4}$-alkyl, F, Cl, $CF_3$, $OCF_3$ and OH, or the compounds according to the invention have the partial structure D2-1, in which $R^{300}$ represents 1 or 2 substituents selected independently of one another from the group consisting of F, Cl, $CF_3$ and $CH_3$.

In the compounds according to the invention, the radical $R^2$ preferably represents H, methyl, ethyl, n-propyl, isopropyl, n-butyl, isobutyl, sec-butyl, tert-butyl, $CH_2$—$CF_3$, cyclopropyl, cyclobutyl, cyclopentyl or cyclohexyl, particularly preferably H, methyl, ethyl, isopropyl, isobutyl, tert-butyl or cyclopropyl.

In preferred embodiments of the compounds according to the invention, $R^5$ can represent 0, 1, 2, 3 or 4 substituents selected independently of one another from the group consisting of F, $CF_3$, $OCF_3$ and $C_{1-6}$-alkyl. In particular, $R^5$ can be absent or represent 1, 2, 3 or 4 methyl groups.

In further preferred embodiments of the compounds according to the invention, $R^5$ can represent 0, 1, 2, 3 or 4 substituents selected independently of one another from the group consisting of F, $CF_3$ and $OCF_3$, in particular can represent fluorine.

In most particularly preferred embodiments of the compounds according to the invention, $R^5$ can represent 0 substituents, that is to say can be absent.

In embodiments that are likewise preferred, $R^6$ can represent 0, 1, 2 or 3 substituents selected independently of one another from the group consisting of F, Cl, $CF_3$, $OCF_3$, OH, $C_{1-6}$-alkyl and O—$C_{1-6}$-alkyl. In particular, $R^6$ can be absent or represent 1, 2 or 3 fluorine substituents.

In further preferred embodiments of the compounds according to the invention, $R^6$ can represent 0 substituents, that is to say can be absent.

In the compounds according to the invention, the radical $R^{10}$ preferably represents H, methyl, ethyl, n-propyl, isopropyl, n-butyl, isobutyl, sec-butyl, tert-butyl, $CH_2$—$CF_3$, cyclopropyl, cyclobutyl, cyclopentyl or cyclohexyl, particularly preferably H, methyl, ethyl, isopropyl, isobutyl, tert-butyl or cyclopropyl, most particularly preferably H.

Further preferred embodiments of the compounds according to the invention are those in which the partial structure D2 is selected from the group consisting of

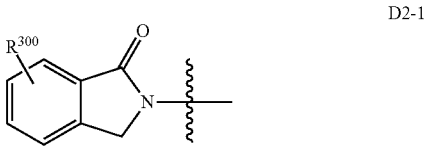

D2-1

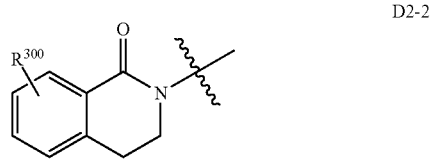

D2-2

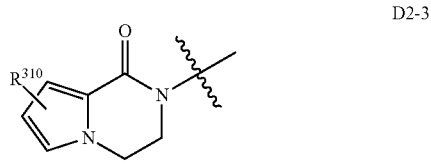

D2-3

-continued

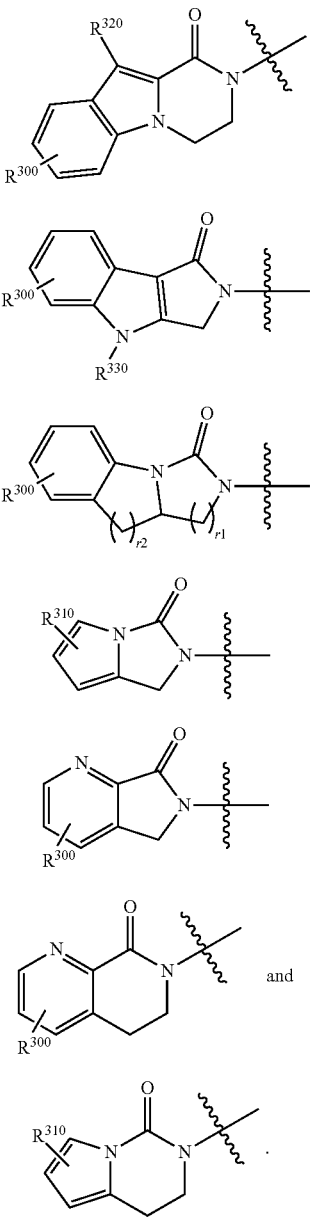

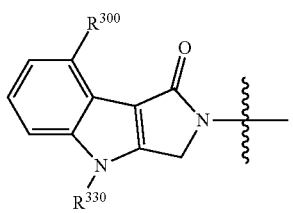

wherein

R$^{300}$ represents 0, 1, 2, 3 or 4 substituents selected independently of one another from the group consisting of F, Cl, Br, I, CF$_3$, O—CF$_3$, C$_{1-4}$-alkyl and O—C$_{1-4}$-alkyl;

R$^{310}$ represents 0, 1, 2 or 3 substituents selected independently of one another from the group consisting of F, Cl, Br, I, CF$_3$, O—CF$_3$, C$_{1-4}$-alkyl and O—C$_{1-4}$-alkyl;

R$^{320}$ represents a substituent selected from the group consisting of H, F, Cl, Br, I, CF$_3$, O—CF$_3$ and C$_{1-4}$-alkyl;

R$^{330}$ represents a substituent selected from the group consisting of H, C$_{1-4}$-alkyl, aryl, CH$_2$-aryl and heteroaryl;

r1 represents 1 or 2 and r2 represents 1 or 2.

In embodiments of the compounds according to the invention that are likewise preferred, D2 represents a radical selected from the group consisting of wherein R$^{300}$ represents a substituent selected from the group consisting of H, F, Cl, Br, I, CF$_3$, —O—CF$_3$, C$_{1-4}$-alkyl and O—C$_{1-4}$-alkyl;

R$^{310}$ represents a substituent selected from the group consisting of H, F, Cl, Br, I, CF$_3$, —O—CF$_3$, C$_{1-4}$-alkyl and O—C$_{1-4}$-alkyl;

R$^{320}$ represents a substituent selected from the group consisting of H, F, Cl, Br, I, CF$_3$, —O—CF$_3$ and C$_{1-4}$-alkyl and R$^{330}$ represents a substituent selected from the group consisting of H, C$_{1-4}$-alkyl, aryl, CH$_2$-aryl and heteroaryl.

In further preferred embodiments of the compounds according to the invention, D2 represents a radical selected from the group consisting of

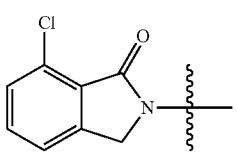 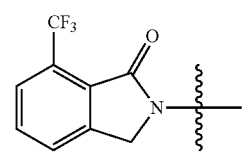

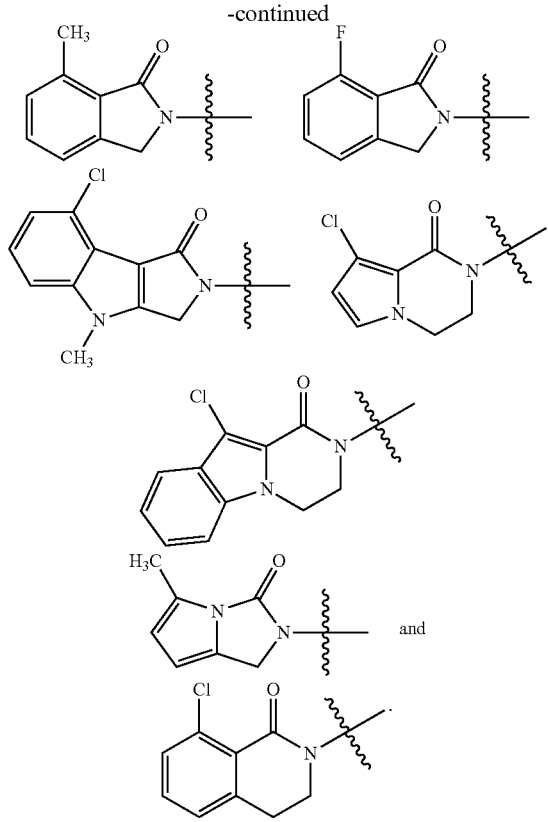

Particularly preferably, the radical D2 in the compounds according to the invention can represent the following radical:

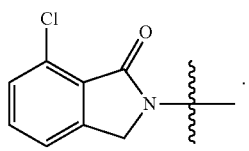 [SMILES: *N1Cc2cccc(Cl)c2C1=O]

In the compounds according to the invention, the radical $R^7$ preferably represents H, methyl, ethyl, n-propyl, isopropyl, n-butyl, isobutyl, sec-butyl, tert-butyl, $CH_2$—$CF_3$, cyclopropyl, cyclobutyl, cyclopentyl or cyclohexyl, particularly preferably H, methyl, ethyl, isopropyl, isobutyl, tert-butyl or cyclopropyl. Most particularly preferably, the radical $R^7$ represents H or methyl.

In a preferred embodiment of the compounds according to the invention, b represents 0. In an embodiment of the compounds according to the invention that is likewise preferred, b represents 1. In a further preferred embodiment of the compounds according to the invention, b represents 2. In a further preferred embodiment of the compounds according to the invention, b represents 0 or 2, preferably 0.

In a further preferred embodiment of the compounds according to the invention, X represents $N(R^{9a})$. In another preferred embodiment of the compounds according to the invention, X represents $C(R^{9b})H$.

Embodiments of the substituted compounds according to the invention that are likewise preferred are those in which the following partial structure (Cy)

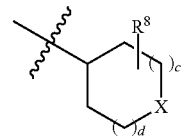 (Cy)

is selected from the group consisting of

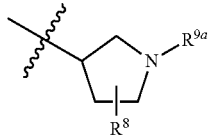 (Cy 1)

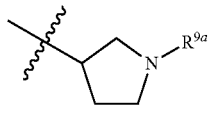 (Cy 2)

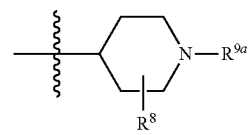 (Cy 3)

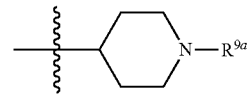 (Cy 4)

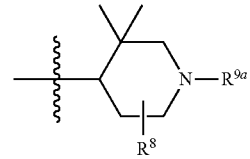 (Cy 5)

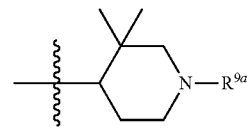 (Cy 6)

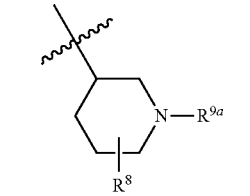 (Cy 7)

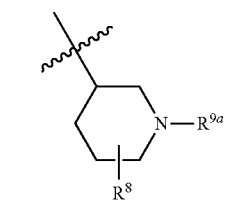 (Cy 8)

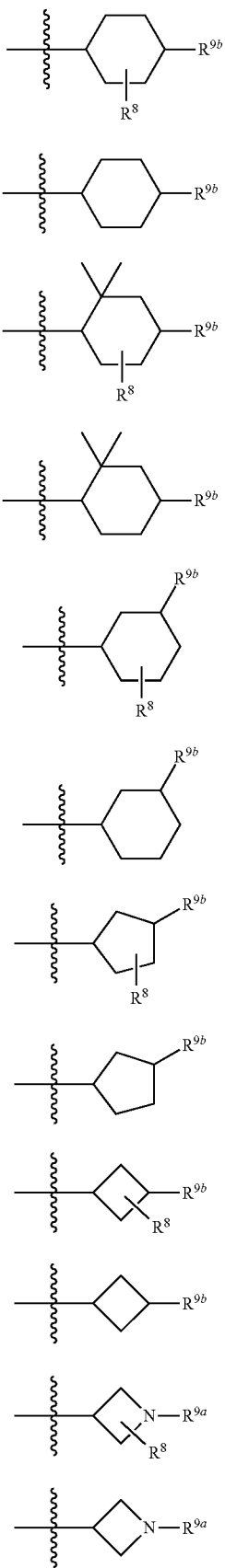

(Cy 9)
(Cy 10)
(Cy 11)
(Cy 12)
(Cy 13)
(Cy 14)
(Cy 15)
(Cy 16)
(Cy 17)
(Cy 18)
(Cy 19)
(Cy 20)

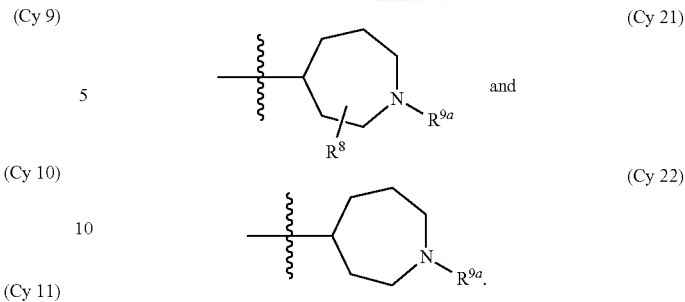

(Cy 21)
(Cy 22)

Embodiments of the substituted compounds according to the invention that are likewise preferred are those in which the partial structure (Cy) is selected from the list of the above-mentioned radicals (Cy 1) to (Cy 22) and b represents 0.

Further preferred embodiments of the compounds according to the invention are those in which the partial structure (Cy) is selected from the list of the above-mentioned radicals (Cy 1) to (Cy 22) and $R^{9a}$ or $R^{9b}$ represents pyridinyl or pyrimidyl and wherein the pyridyl and pyrimidyl are in each case unsubstituted or substituted one or more times, for example 2, 3 or 4 times, by identical or different substituents, the substituents being selected independently of one another from the group consisting of azetidinyl, pyrrolidinyl, piperidinyl, morpholinyl, N-methylpiperazinyl, pyridinyl, cyclopropyl, $S(=O)_2$—$C_{1-4}$-alkyl, F, Cl, $CF_3$, $OCF_3$, OH, CN, $NH_2$, $N(C_{1-4}$-alkyl$)_2$, $NH(C_{1-4}$-alkyl), $C(=O)$—$NH_2$, $C(=O)$—$N(C_{1-4}$-alkyl$)_2$, $C(=O)$—$NH(C_{1-4}$-alkyl),

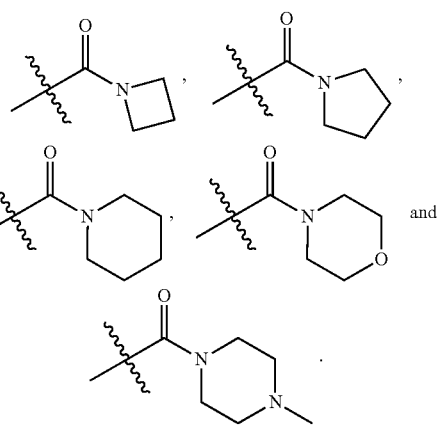

Preference is given to radicals containing a N—$R^{9a}$ grouping, that is to say (Cy 1) to (Cy 8) and (Cy 19) to (Cy 22).

Further preferred embodiments of the compounds according to the invention are those in which the partial structure (Cy) is selected from the list of the above-mentioned radicals (Cy 1) to (Cy 22) and $R^{9a}$ or $R^{9b}$ represents pyridinyl or pyrimidyl and wherein the pyridyl and pyrimidyl are in each case unsubstituted or substituted one or more times, for example 2, 3 or 4 times, by identical or different substituents, wherein the substituents are selected independently of one another from the group consisting of azetidinyl, pyrrolidinyl, piperidinyl, morpholinyl, N-methylpiperazinyl, pyridinyl, O—$C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), $C(=O)$—$NH_2$, $C(=O)$—$N(C_{1-4}$-alkyl$)_2$, $C(=O)$—$NH(C_{1-4}$-alkyl),

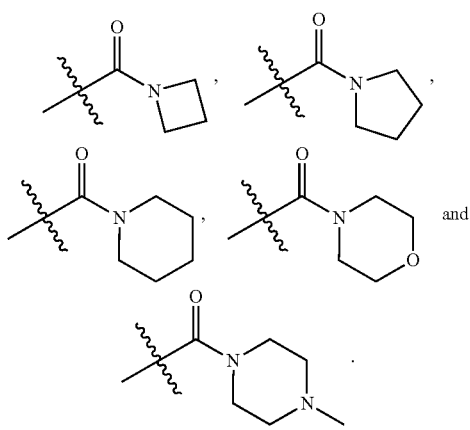

Preference is given to radicals containing a N—$R^{9a}$ grouping, that is to say (Cy 1) to (Cy 8) and (Cy 19) to (Cy 22).

Preferably, the radical $R^8$ can represent 0, 1 or 2 substituents selected independently of one another from the group consisting of methyl, ethyl, n-propyl, isopropyl, n-butyl, isobutyl, tert-butyl and phenyl, and/or two substituents $R^8$ bonded to a carbon atom form a C(=O) group or a 3-, 4-, 5- or 6-membered, saturated carbocyclic ring which is unsubstituted or substituted on one or more of its carbon ring members by one or more substituents selected independently of one another from the group consisting of F, $CF_3$ and $C_{1-6}$-alkyl.

Particularly preferably, the radical $R^8$ is absent or represents 1 or 2 methyl groups, and/or two substituents $R^8$ bonded to a carbon atom form a (C=O) group or a cyclopropyl or cyclobutyl radical which is unsubstituted or substituted on one or more of its carbon ring members by one or more substituents selected independently of one another from the group consisting of F, $CF_3$ and $C_{1-6}$-alkyl.

Preference is given to substituted compounds according to the invention wherein $R^{9a}$ represents $CHR^{15}R^{16}$, aryl, heteroaryl, or $CHR^{15}R^{16}$, aryl or heteroaryl bonded via a $C_{1-3}$-alkylene group, $R^{15}$ and $R^{16}$, together with the CH grouping linking them, form a ring which is unsubstituted or substituted by 1, 2, 3 or 4 substituents selected independently of one another from the group consisting of F, Cl, Br, I, $CF_3$, $C_{1-4}$-alkyl, O—$C_{1-4}$-alkyl, OH, =O, $OCF_3$, SH, $SCF_3$, $NR^{20}R^{21}$, aryl and heteroaryl, wherein the ring is saturated or mono- or poly-unsaturated but is not aromatic, is 4-, 5-, 6- or 7-membered and can optionally contain one or more heteroatoms or heteroatom groups selected independently of one another from the group consisting of N, $NR^{24}$, O, S, S(=O) and S(=O)$_2$; wherein $R^{24}$ denotes H, $C_{1-4}$-alkyl, C(=O)—$R^{25}$, $C_{3-6}$-cycloalkyl, aryl, heteroaryl, or $C_{3-6}$-cycloalkyl, aryl or heteroaryl bonded via a $C_{1-3}$-alkylene group, and $R^{25}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group; particularly preferably, together with the CH grouping linking them, form a ring which is unsubstituted or substituted by 1, 2, 3 or 4 substituents selected independently of one another from the group consisting of F, Cl, Br, I, $CF_3$, $C_{1-4}$-alkyl, O—$C_{1-4}$-alkyl, OH, $OCF_3$, SH, $SCF_3$, $NR^{20}R^{21}$, aryl and heteroaryl, wherein the ring is saturated or mono- or poly-unsaturated but is not aromatic, is 4-, 5-, 6- or 7-membered and can optionally contain one or more heteroatoms or heteroatom groups selected independently of one another from the group consisting of N, $NR^{24}$, O, S, S(=O) and S(=O)$_2$; wherein $R^{24}$ denotes H, $C_{1-4}$-alkyl, C(=O)—$R^{25}$, $C_{3-6}$-cycloalkyl, aryl, heteroaryl, or $C_{3-6}$-cycloalkyl, aryl or heteroaryl bonded via a $C_{1-3}$-alkylene group, and $R^{25}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$alkylene group;

$R^{20}$ and $R^{21}$, together with the nitrogen atom linking them, form a heterocyclic ring which is unsubstituted or substituted by 1, 2, 3 or 4 substituents selected independently of one another from the group consisting of F, Cl, Br, I, $CF_3$, $C_{1-4}$-alkyl, O—$C_{1-4}$-alkyl, OH, $OCF_3$, SH, $SCF_3$, aryl and heteroaryl, wherein the heterocyclic ring is saturated or mono- or poly-unsaturated but is not aromatic, is 4-, 5-, 6- or 7-membered and can optionally contain one or more heteroatoms or heteroatom groups selected independently of one another from the group consisting of N, $NR^{26}$, O, S, S(=O) and S(=O)$_2$; wherein $R^{26}$ denotes H, $C_{1-4}$-alkyl, C(=O)—$R^{27}$, $C_{3-6}$-cycloalkyl, aryl, heteroaryl, or $C_{3-6}$-cycloalkyl, aryl or heteroaryl bonded via a $C_{1-3}$-alkylene group, and $R^{27}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group; wherein aryl in each case represents phenyl or naphthyl;

heteroaryl in each case represents pyridinyl, triazinyl, pyrimidinyl, pyrazinyl, pyridazinyl, quinolinyl, isoquinolinyl, quinazolinyl, purinyl, thiazolyl, thiadiazolyl, imidazolyl, triazolyl, oxazolyl, isoxazolyl, thienyl, pyrrolyl, tetrazolyl, oxadiazolyl or oxathiazolyl, particularly preferably in each case pyridinyl, triazinyl, pyrimidinyl, pyrazinyl, pyridazinyl, quinolinyl, isoquinolinyl, quinazolinyl, thiazolyl, thiadiazolyl, imidazolyl, triazolyl, oxazolyl, isoxazolyl, thienyl, pyrrolyl, tetrazolyl, oxadiazolyl or oxathiazolyl, most particularly preferably pyridinyl, pyrimidinyl, pyrazinyl, pyridazinyl, isoquinolinyl, thiazolyl or imidazolyl, in particular pyridinyl or pyrimidinyl;

the above-mentioned aryl or heteroaryl radicals are in each case unsubstituted or substituted one or more times, for example 1, 2, 3, 4 or 5 times, by identical or different substituents, the substituents being selected independently of one another from the group consisting of azetidinyl, pyrrolidinyl, piperidinyl, morpholinyl, N-methylpiperazinyl, pyridinyl, cyclopropyl, O—$C_{1-3}$-alkyl, $C_{1-4}$-alkyl, F, Cl, $CF_3$, $OCF_3$, OH, CN, $NH_2$, $N(C_{1-4}$-alkyl)$_2$, $NH(C_{1-4}$-alkyl), C(=O)—$NH_2$, C(=O)—$N(C_{1-4}$-alkyl)$_2$, C(=O)—$NH(C_{1-4}$-alkyl), S(=O)$_2$—$C_{1-4}$-alkyl,

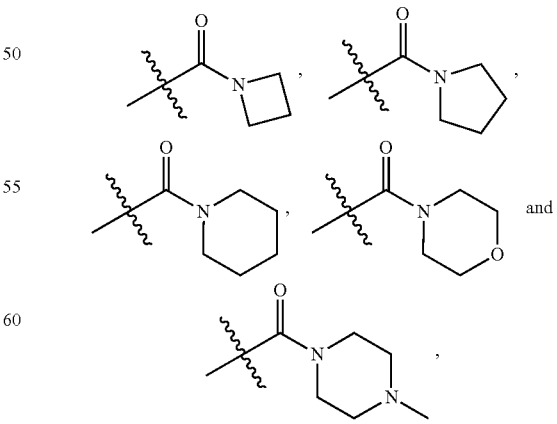

preferably from the group consisting of methyl, isopropyl, tert-butyl, F, Cl, $CF_3$, $OCF_3$, methoxy, OH, S(=O)$_2$—$CH_3$, $NH_2$, $NH(CH_3)$, $N(CH_3)_2$, pyrrolidinyl, piperidinyl, cyclopropyl, CN, $C(=O)-NH_2$, $C(=O)-N(CH_3)_2$ and

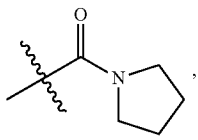 [SMILES: *C(=O)N1CCCC1]

or wherein the above-mentioned aryl or heteroaryl radicals are in each case unsubstituted or substituted one or more times, for example 1, 2, 3, 4 or 5 times, by identical or different substituents, the substituents being selected independently of one another from the group consisting of azetidinyl, pyrrolidinyl, piperidinyl, morpholinyl, N-methylpiperazinyl, pyridinyl, $O-C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), $C(=O)-NH_2$, $C(=O)-N(C_{1-4}$-alkyl$)_2$, $C(=O)-NH(C_{1-4}$-alkyl),

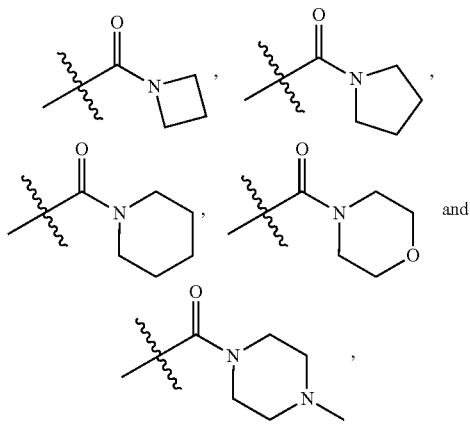

preferably from the group consisting of methyl, F, Cl, $CF_3$, $OCF_3$, methoxy, OH, $NH_2$, $N(CH_3)_2$, pyrrolidinyl, CN, $C(=O)-NH_2$, $C(=O)-N(CH_3)_2$ and

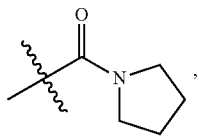 [SMILES: *C(=O)N1CCCC1]

and wherein the above-mentioned alkyl, alkylene and cycloalkyl groups are in each case unsubstituted or substituted one or more times, for example 1, 2, 3, 4 or 5 times, by identical or different substituents, the substituents being selected independently of one another from the group consisting of $O-C_{1-3}$-alkyl, F, Cl, Br, I, $CF_3$, $OCF_3$, OH, $=O$, SH, cyclopropyl, cyclobutyl, cyclopentyl, cyclohexyl, phenyl, phenoxy, naphthyl, furyl, thienyl and pyridinyl, preferably being selected independently of one another from the group consisting of $O-C_{1-3}$-alkyl, F, Cl, Br, I, $CF_3$, $OCF_3$, OH, SH, cyclopropyl, cyclobutyl, cyclopentyl, cyclohexyl, phenyl, phenoxy, naphthyl, furyl, thienyl and pyridinyl.

Preference is further given to substituted compounds according to the invention wherein $R^{9b}$ represents $NR^{17}R^{18}$, $C_{1-3}$-alkylene-$NR^{17}R^{18}$, $O-C_{1-3}$-alkylene-$NR^{17}R^{18}$, $C(=O)-NR^{17}R^{18}$, $OR^{19}$, $C_{1-3}$-alkylene-$OR^{19}$, $C_{1-3}$-alkylene-$O-C_{1-3}$-alkylene-$OR^{19}$, $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group, wherein $R^{17}$ and $R^{18}$ each independently of the other represents H, $C_{1-4}$-alkyl or $C_{3-6}$-cycloalkyl, or $R^{17}$ and $R^{18}$, together with the nitrogen atom linking them, form a heterocyclic ring which is unsubstituted or substituted by 1, 2, 3 or 4 substituents selected independently of one another from the group consisting of F, Cl, $CF_3$, $C_{1-4}$-alkyl, $O-C_{1-4}$-alkyl, OH, $=O$, $OCF_3$, $NR^{20}R^{21}$, aryl and heteroaryl, preferably from the group consisting of F, Cl, $CF_3$, $C_{1-4}$-alkyl, $O-C_{1-4}$-alkyl, OH, $=O$, $OCF_3$, $NR^{20}R^{21}$, aryl and heteroaryl, and/or can be fused with at least one aryl or heteroaryl, wherein the heterocyclic ring is saturated or mono- or poly-unsaturated, is 4-, 5-, 6- or 7-membered and can optionally contain one or more heteroatoms or heteroatom groups selected independently of one another from the group consisting of N, $NR^{22}$, O, S, $S(=O)$ and $S(=O)_2$; wherein $R^{22}$ denotes H, $C_{1-4}$-alkyl, $C(=O)-R^{23}$, $C_{3-6}$-cycloalkyl, aryl, heteroaryl, or $C_{3-6}$-cycloalkyl, aryl or heteroaryl bonded via a $C_{1-3}$-alkylene group, and $R^{23}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group;

$R^{19}$ represents H, $C_{1-4}$-alkyl, $C_{3-6}$-cycloalkyl, aryl, heteroaryl or $C_{2-3}$-alkylene-$NR^{17}R^{18}$, or $C_{3-6}$-cycloalkyl, aryl or heteroaryl bonded via a $C_{1-4}$-alkylene group;

$R^{20}$ and $R^{21}$, together with the nitrogen atom linking them, form a heterocyclic ring which is unsubstituted or substituted by 1, 2, 3 or 4 substituents selected independently of one another from the group consisting of F, Cl, $CF_3$, $C_{1-4}$-alkyl, $O-C_{1-4}$-alkyl, OH, $OCF_3$, $SCF_3$, aryl and heteroaryl, wherein the heterocyclic ring is saturated or mono- or poly-unsaturated but is not aromatic, is 4-, 5-, 6- or 7-membered and can optionally contain one or more heteroatoms or heteroatom groups selected independently of one another from the group consisting of N, $NR^{26}$, O, S, $S(=O)$ and $S(=O)_2$; wherein $R^{26}$ denotes H, $C_{1-4}$-alkyl, $C(=O)-R^{27}$, $C_{3-6}$-cycloalkyl, aryl, heteroaryl, or $C_{3-6}$-cycloalkyl, aryl or heteroaryl bonded via a $C_{1-3}$-alkylene group, and $R^{27}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group;

wherein aryl in each case represents phenyl or naphthyl;

heteroaryl in each case represents pyridinyl, triazinyl, pyrimidinyl, pyrazinyl, pyridazinyl, quinolinyl, isoquinolinyl, quinazolinyl, thiazolyl, thiadiazolyl, imidazolyl, triazolyl, oxazolyl, isoxazolyl, thienyl, pyrrolyl, tetrazolyl, oxadiazolyl, oxathiazolyl, preferably pyridinyl, pyrimidinyl, pyrazinyl, pyridazinyl, pyrrolyl, isoquinolinyl, thiazolyl or imidazolyl, particularly preferably pyridinyl, pyrimidinyl, pyrazinyl, pyridazinyl, isoquinolinyl, thiazolyl or imidazolyl;

the above-mentioned aryl or heteroaryl radicals are in each case unsubstituted or substituted one or more times, for example 1, 2, 3, 4 or 5 times, by identical or different substituents, the substituents being selected independently of one another from the group consisting of azetidinyl, pyrrolidinyl, piperidinyl, morpholinyl, N-methylpiperazinyl, pyridinyl, $O-C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), $C(=O)-NH_2$, $C(=O)-NH(C_{1-4}$-alkyl), $C(=O)-N(C_{1-4}$-alkyl$)_2$,

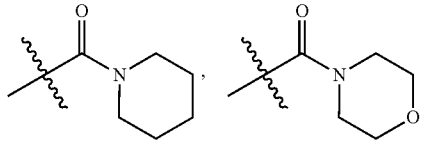

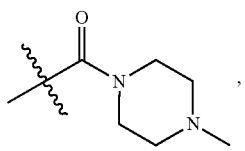

preferably from the group consisting of methyl, F, Cl, CF$_3$, OCF$_3$, methoxy, OH, NH$_2$, N(CH$_3$)$_2$, pyrrolidinyl, CN, C(=O)—NH$_2$, C(=O)—N(CH$_3$)$_2$ and

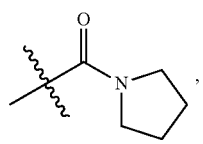

wherein the above-mentioned alkyl, alkylene, alkenylene and cycloalkyl groups are in each case unsubstituted or substituted one or more times, for example 1, 2, 3, 4 or 5 times, by identical or different substituents, the substituents being selected independently of one another from the group consisting of O—C$_{1-3}$-alkyl, F, Cl, Br, I, CF$_3$, OCF$_3$, OH, SH, cyclopropyl, cyclobutyl, cyclopentyl, cyclohexyl, phenyl, phenoxy, naphthyl, furyl, thienyl and pyridinyl.

Embodiments of the substituted compounds according to the invention that are likewise preferred are those in which the following partial structure (Cyc)

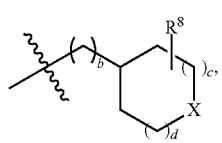

(Cyc)

is selected from the group consisting of

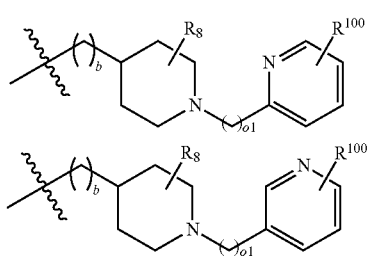

-continued

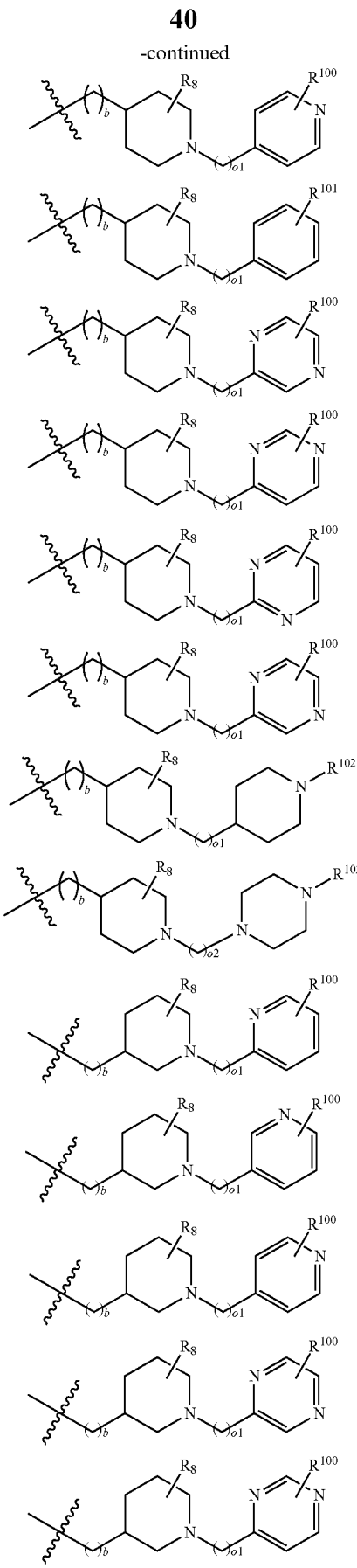

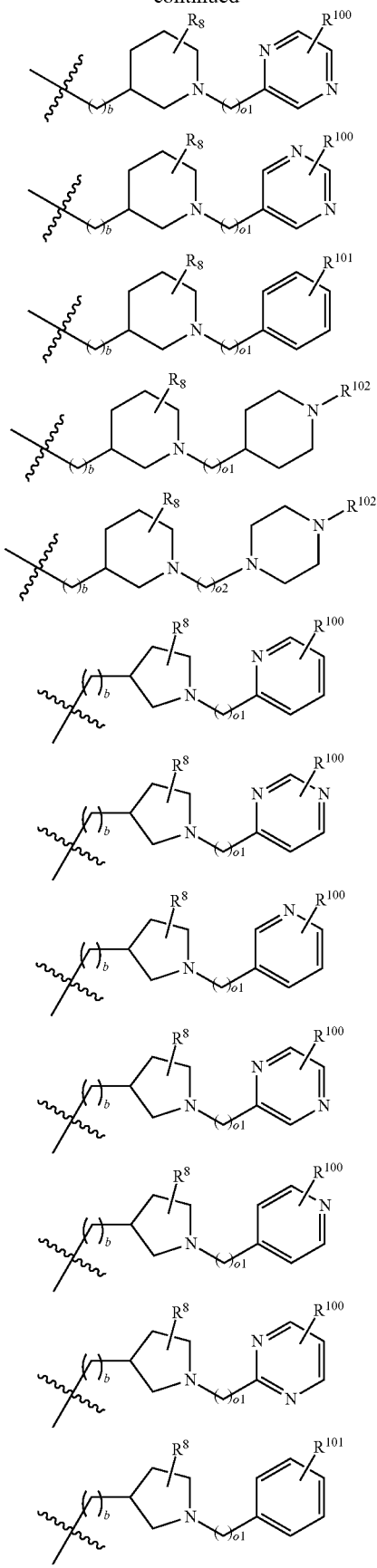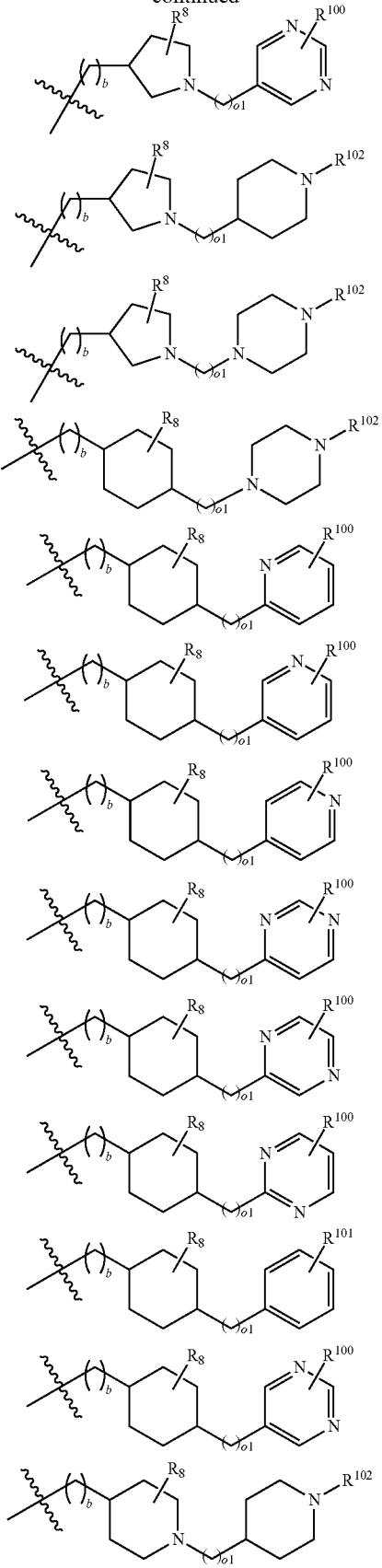

wherein in each case b represents 0, 1 or 2;

o1 represents 0, 1, 2 or 3;

o2 represents 2 or 3;

$R^8$ represents 0, 1 or 2 methyl groups;

$R^{100}$ represents 0, 1 or 2 or 3, preferably 0, 1 or 2, substituents selected independently of one another from the group consisting of methyl, ethyl, isopropyl, tert-butyl, F, Cl, CN, $CF_3$, $OCF_3$, cyclopropyl, cyclobutyl, C(=O)—N(CH$_3$)$_2$, $NH_2$, NH($C_{1-6}$-alkyl), in particular NH(CH$_3$), N($C_{1-6}$-alkyl)$_2$, in particular N(CH$_3$)$_2$, methoxy, OH, S(=O)$_2$—$CH_3$, pyrrolidinyl, piperidinyl and morpholinyl, preferably from the group consisting of methyl, ethyl, isopropyl, tert-butyl, F, Cl, CN, $CF_3$, $OCF_3$, cyclopropyl, cyclobutyl, $NH_2$, N($C_{1-6}$-alkyl)$_2$, in particular N(CH$_3$)$_2$, methoxy, OH and morpholinyl;

$R^{101}$ represents 0, 1, 2 or 3 substituents selected independently of one another from the group consisting of methyl, ethyl, isopropyl, tert-butyl, F, Cl, $CF_3$, $OCF_3$, cyclopropyl, cyclobutyl, $NH_2$, N($C_{1-6}$-alkyl)$_2$, in particular N(CH$_3$)$_2$, methoxy, OH and morpholinyl and $R^{102}$ represents a substituent selected from the group consisting of H, methyl, ethyl, n-propyl, isopropyl, n-butyl, isobutyl, sec-butyl, tert-butyl, $CH_2$—$CF_3$, cyclopropyl and cyclobutyl.

Embodiments of the substituted compounds according to the invention that are likewise preferred are those in which (Cy) represents a radical from the group (Cy 1) to (Cy 8) and (Cy 19) to (Cy 22), in particular (Cy 2), (Cy 4), (Cy 6) or (Cy 8), and $R^{9a}$ is in each case selected from the group consisting of

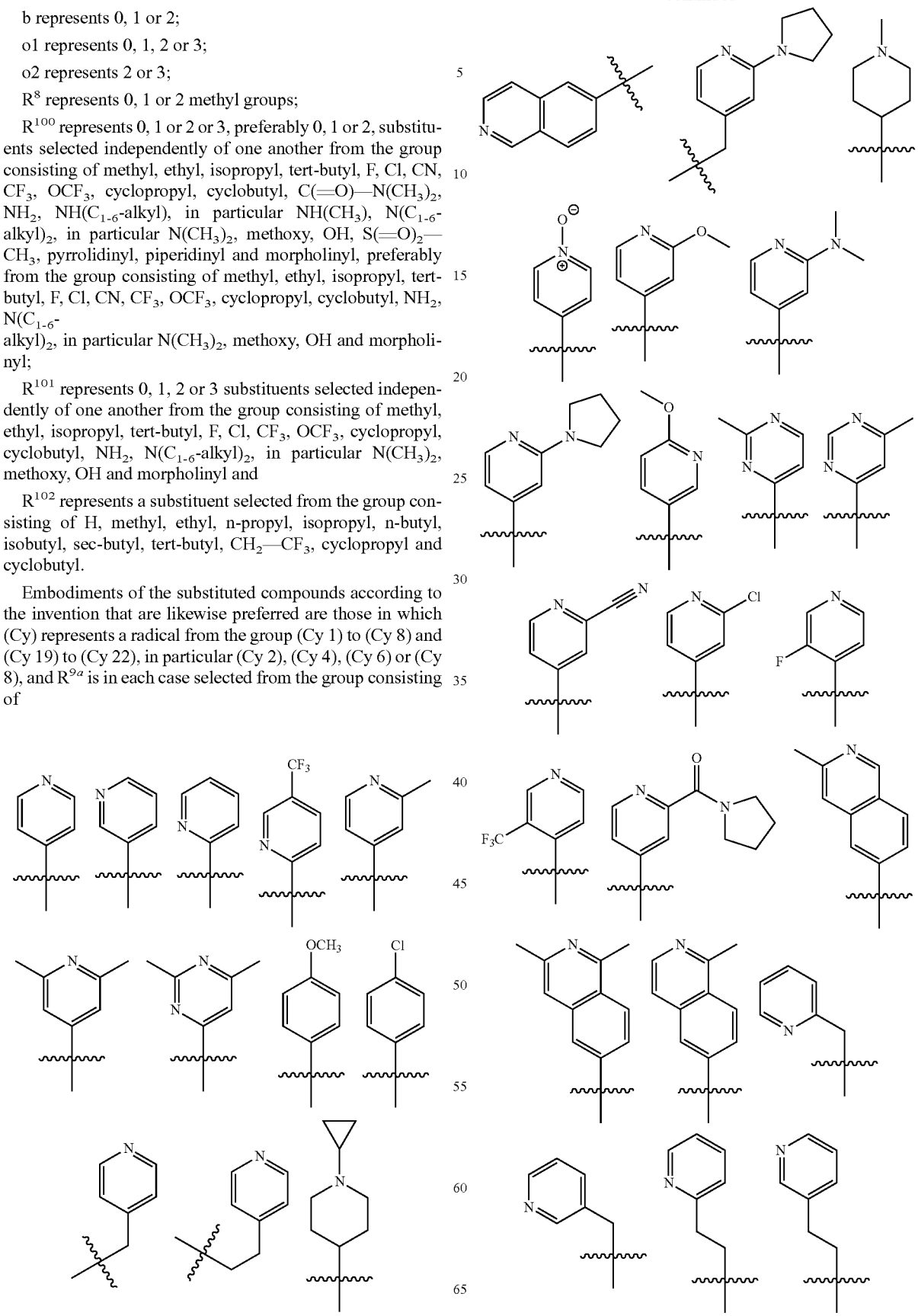

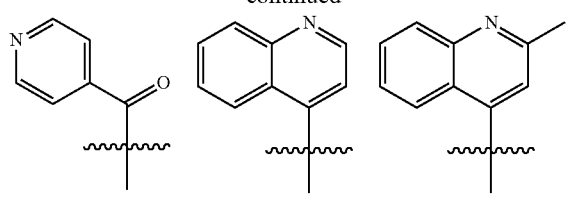
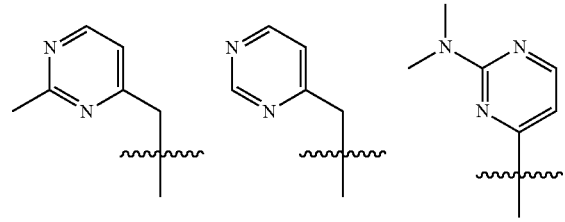
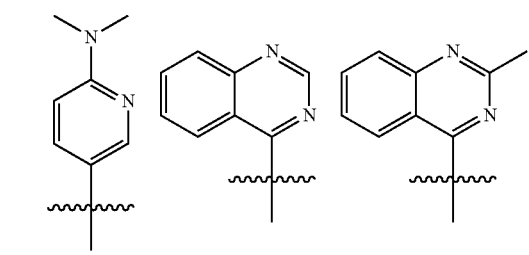
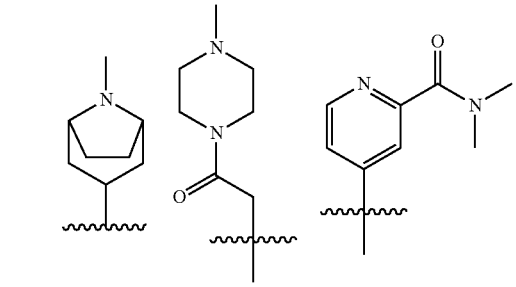
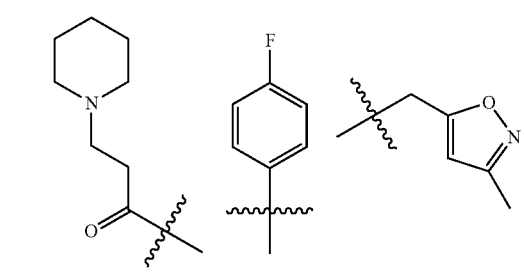
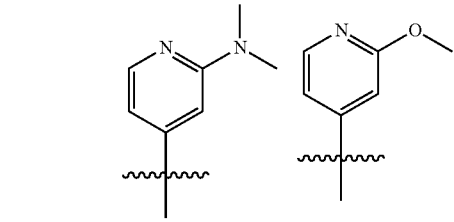
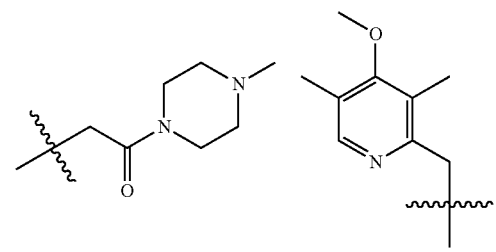
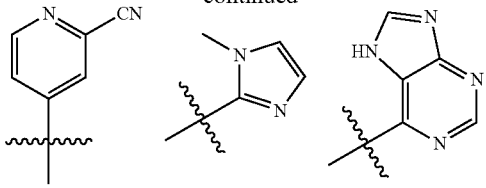
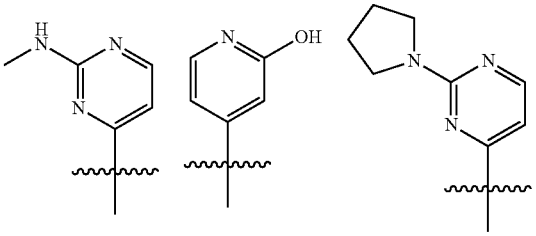
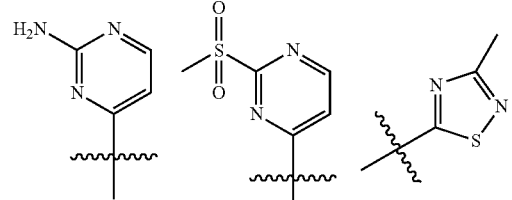
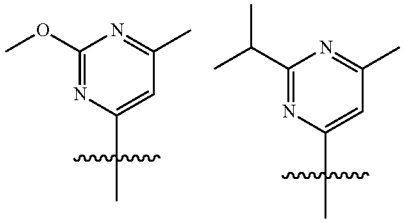
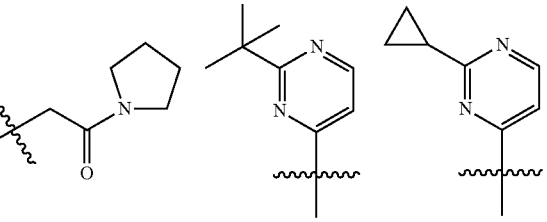
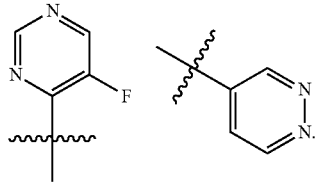
Other preferred embodiments of the substituted compounds according to the invention are those in which (Cy) represents a radical from the group (Cy 1) to (Cy 8) and (Cy 19) to (Cy 22), in particular (Cy 2), (Cy 4), (Cy 6) or (Cy 8), and $R^{9a}$ is in each case selected from the group consisting of
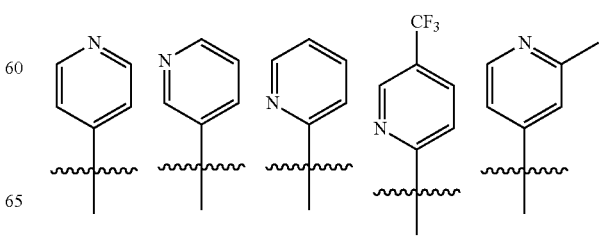

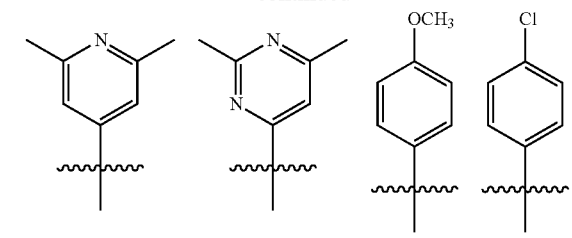
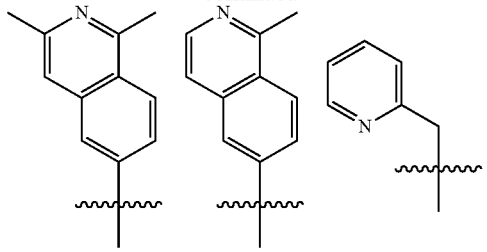
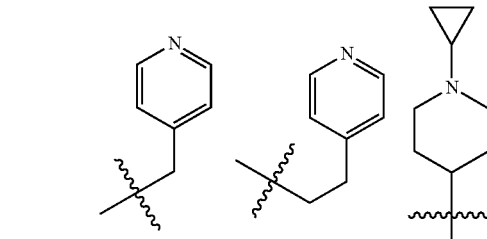
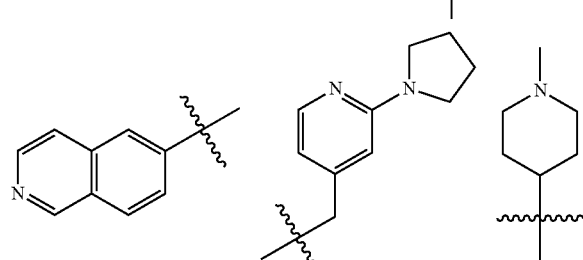
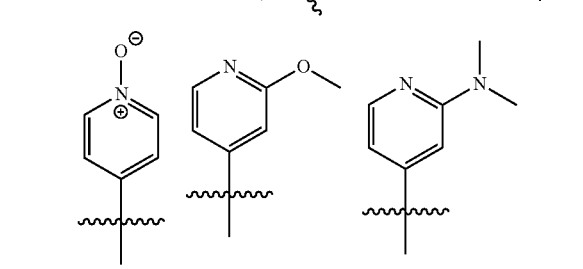
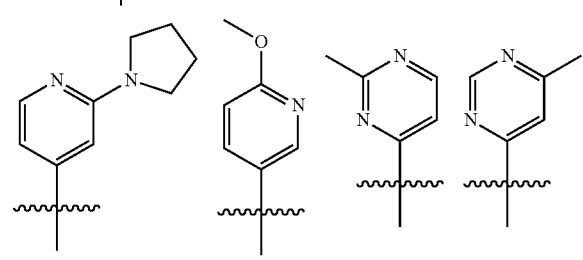
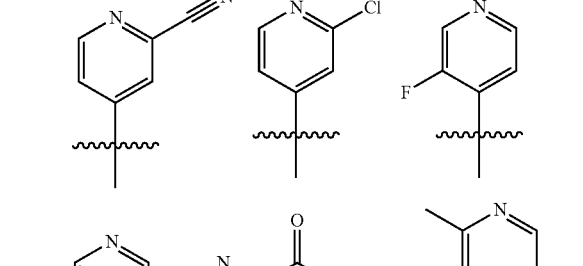
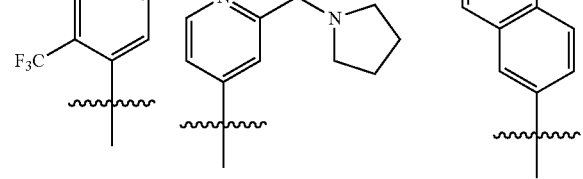
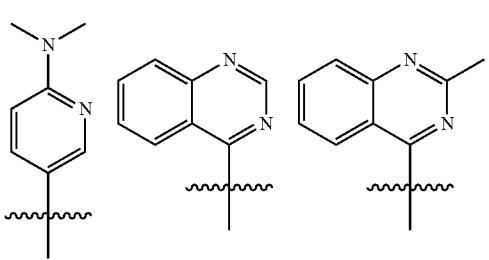
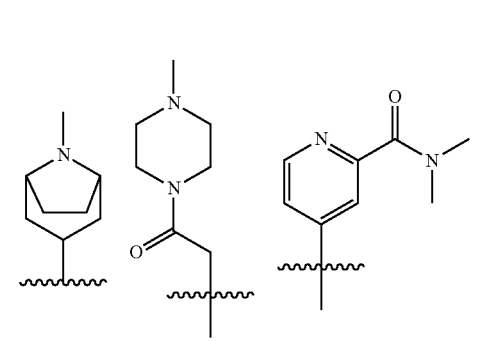
Particularly preferred embodiments of the substituted compounds according to the invention are those in which (Cy) represents (Cy 2), (Cy 4), (Cy 6) or (Cy 8) and $R^{9a}$ is in each case selected from the group consisting of

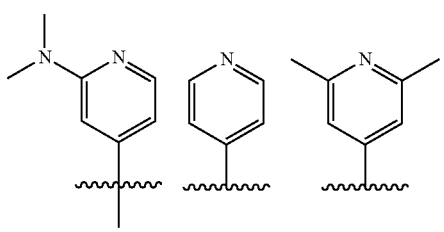

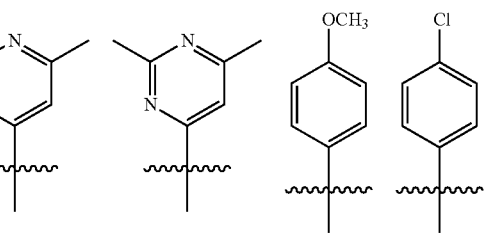

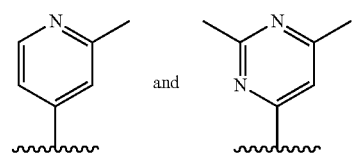

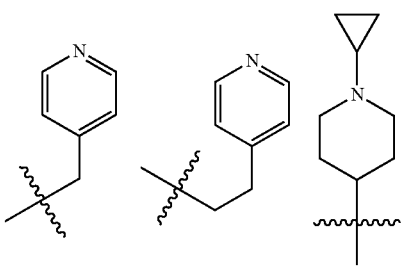

In a further particularly preferred embodiment of the substituted compounds according to the invention, in which (Cy) represents (Cy 1) to (Cy 8) or (Cy 19) to (Cy 22), particularly preferably in which (Cy) represents (Cy 2), (Cy 4), (Cy 6) or (Cy 8), and for which parameter b preferably represents 0 or 2, particularly preferably 0, the radical $R^{9a}$ is selected from

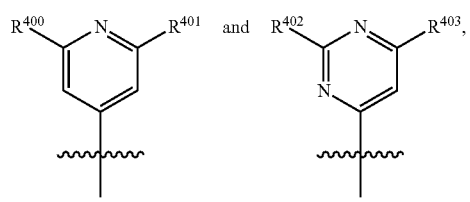

wherein $R^{400}$, $R^{401}$, $R^{402}$ and $R^{403}$ are selected independently of one another from the group consisting of azetidinyl, pyrrolidinyl, piperidinyl, morpholinyl, N-methylpiperazinyl, pyridinyl, cyclopropyl, O—$C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), C(=O)—$NH_2$, C(=O)—$N(C_{1-4}$-alkyl$)_2$, C(=O)—NH($C_{1-4}$-alkyl), S(=O)$_2$—$C_{1-4}$-alkyl, preferably from the group consisting of methyl, isopropyl, tert-butyl, F, Cl, $CF_3$, $OCF_3$, methoxy, OH, S(=O)$_2$—$CH_3$, $NH_2$, $NH(CH_3)$, $N(CH_3)_2$, pyrrolidinyl, piperidinyl, cyclopropyl, CN, C(=O)—$NH_2$ and C(=O)—$N(CH_3)_2$.

Embodiments of the substituted compounds according to the invention that are likewise preferred are those in which (Cy) represents a radical from the group (Cy 9) to (Cy 18), in particular (Cy 10) or (Cy 12), and $R^{9b}$ is in each case selected from the group consisting of

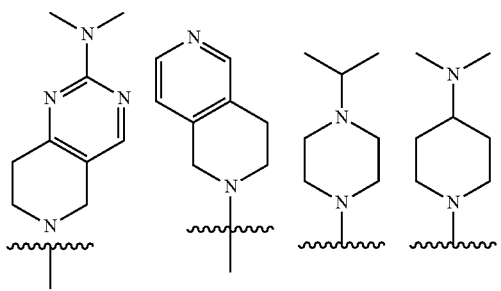

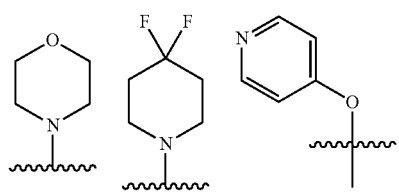

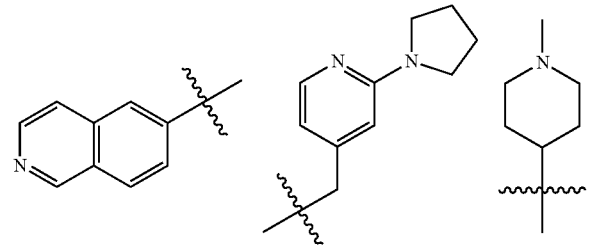

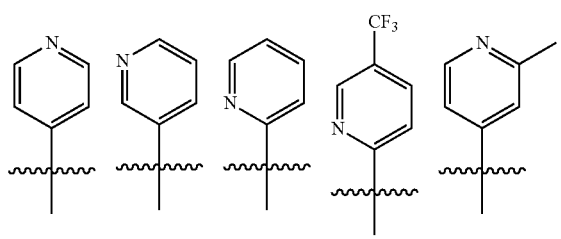

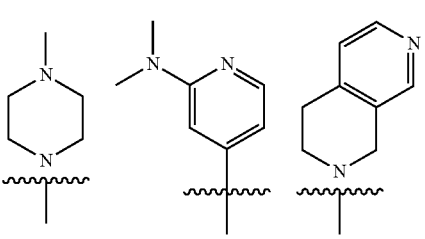

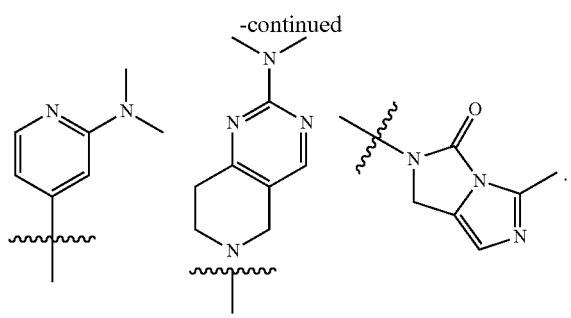

Further embodiments of the compounds according to the invention are those represented by the general formulae (C1)-(C17) shown hereinbelow:

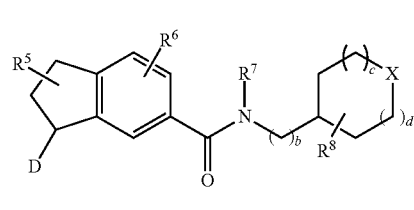
(C1)

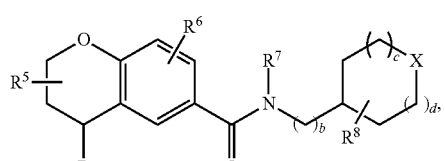
(C5)

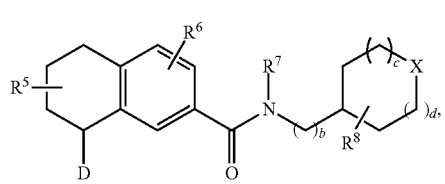
(C6)

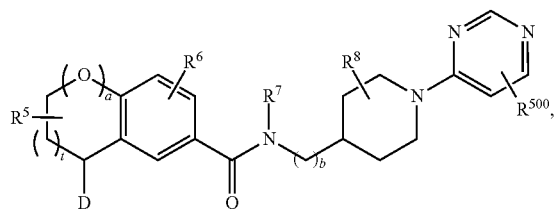
(C2)

wherein $R^{600}$ is not present or represents one or two substituents selected independently of one another from the group consisting of H, methyl, isopropyl, tert-butyl, F, Cl, $CF_3$, CN, $OCF_3$, methoxy, OH, $NH_2$, $NH(CH_3)$, $N(CH_3)_2$, pyrrolidinyl, CN, C(=O)—$N(CH_3)_2$, S(=O)$_2$—$CH_3$, C(=O)—$NH_2$ or C(=O)-pyrrolidine, preferably is not present or represents one or two substituents selected independently of one another from the group consisting of H, methyl, F, Cl, $CF_3$, $OCF_3$, methoxy, OH, $NH_2$, $N(CH_3)_2$, pyrrolidinyl, CN, C(=O)—$N(CH_3)_2$, C(=O)—$NH_2$ or C(=O)-pyrrolidine, (C3)

(C4)

wherein $R^6$ represents H or F and
$R^{9a}$ represents unsubstituted or mono- or poly-substituted heteroaryl, (C7)

wherein $R^{500}$ is not present or represents one or two substituents selected independently of one another from the group consisting of H, methyl, isopropyl, tert-butyl, F, Cl, $CF_3$, CN, $OCF_3$, methoxy, OH, $NH_2$, $NH(CH_3)$, $N(CH_3)_2$, pyrrolidinyl, CN, C(=O)—$N(CH_3)_2$, S(=O)$_2$—$CH_3$, C(=O)—$NH_2$ or C(=O)-pyrrolidine, preferably is not present or represents one or two substituents selected independently of one another from the group consisting of H, methyl, F, Cl, $CF_3$, $OCF_3$, methoxy, OH, $NH_2$, $N(CH_3)_2$, pyrrolidinyl, CN, C(=O)—N$(CH_3)_2$, C(=O)—$NH_2$ or C(=O)-pyrrolidine, (C8)

wherein $R^{501}$ represents F, Cl, $CF_3$ or methyl;

(C9)

(C10)

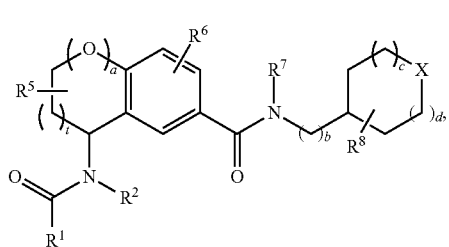

wherein R¹ represents $C_{1-6}$-alkyl, $C_4$-$C_6$-cycloalkyl or $C_4$-$C_6$-heterocyclyl, or $C_4$-$C_6$-cycloalkyl or $C_4$-$C_6$-heterocyclyl bonded via a $C_{1,\,2\,or\,3}$-alkylene group, and wherein R² represents H, methyl, ethyl, n-propyl, isopropyl, isobutyl, tert-butyl or cyclopropyl, (C11)

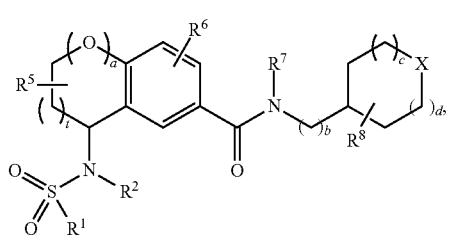

wherein R¹ represents $C_{1-6}$-alkyl, $C_4$-$C_6$-cycloalkyl or $C_4$-$C_6$-heterocyclyl, or $C_4$-$C_6$-cycloalkyl or $C_4$-$C_6$-heterocyclyl bonded via a $C_{1,\,2\,or\,3}$-alkylene group, and wherein R² represents H, methyl, ethyl, n-propyl, isopropyl, isobutyl, tert-butyl or cyclopropyl, (C12)

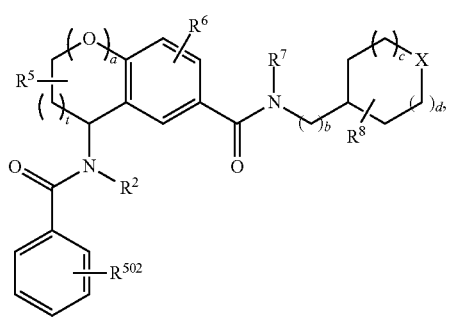

wherein R² represents H, methyl, ethyl, n-propyl, isopropyl, isobutyl, tert-butyl or cyclopropyl, and $R^{502}$ represents 0, 1 or 2 substituents in each case selected independently of one another from the group consisting of F, Cl, methyl, methoxy and $CF_3$;

(C13)

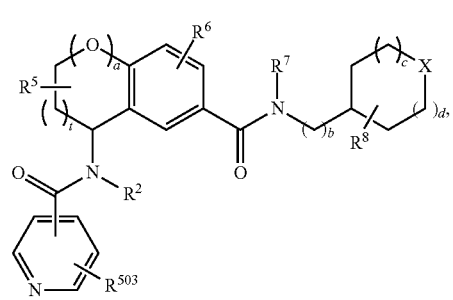

wherein R² represents H, methyl, ethyl, n-propyl, isopropyl, isobutyl, tert-butyl or cyclopropyl, and $R^{503}$ represents 0, 1 or 2 substituents in each case selected independently of one another from the group consisting of F, Cl, methyl, methoxy and $CF_3$;

(C14)

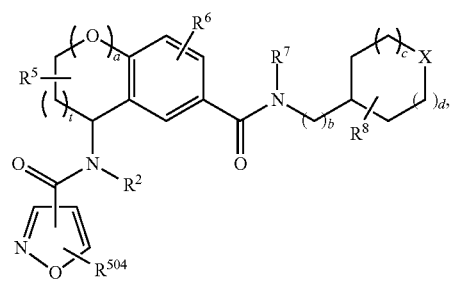

wherein R² represents H, methyl, ethyl, n-propyl, isopropyl, isobutyl, tert-butyl or cyclopropyl, and $R^{504}$ represents 0, 1 or 2 substituents in each case selected independently of one another from the group consisting of F, Cl, methyl, methoxy and $CF_3$;

(C15)

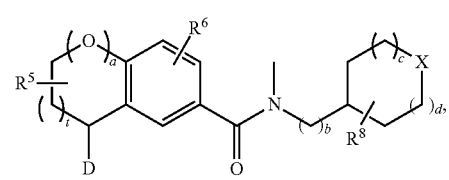

(C16)

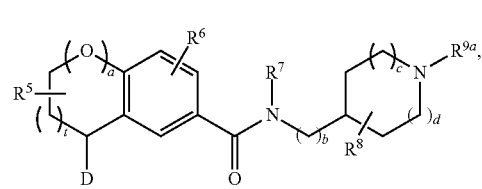

wherein $R^{9a}$ represents unsubstituted or monosubstituted or polysubstituted heteroaryl; and

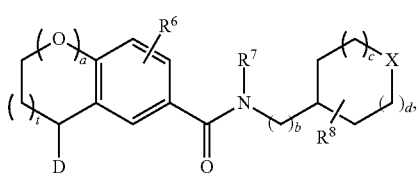
(C17)

wherein $R^6$ represents H or F; and wherein in each of the general formulae (C1)-(C17) the radicals, variables and indices—unless indicated otherwise—have the meanings described herein in connection with the compounds according to the invention and preferred embodiments thereof.

Further preferred embodiments of the present invention are compounds of the general formulas (I-x) and (I-y)

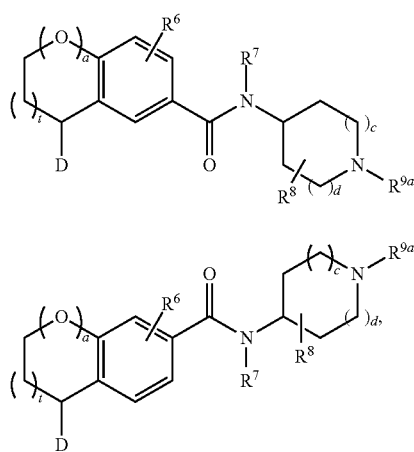
(I-x)

(I-y)

wherein a represents 0 or 1;

t represents 1, 2 or 3;

c and d each independently of the other represents 0, 1 or 2, with the proviso that the ring has not more than 7 ring members;

D is selected from the group consisting of

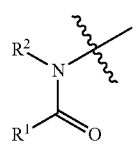
D1-1

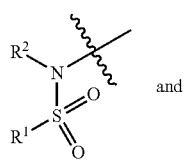
D1-2 and

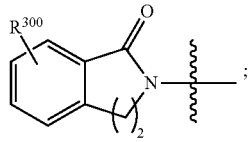
D2-1

$R^1$ represents $C_{1-6}$-alkyl, $C_{3-8}$-cycloalkyl, heterocyclyl, phenyl, or $C_{3-8}$-cycloalkyl or heterocyclyl bonded via a $C_{1-3}$-alkylene group;

$R^2$ represents H, methyl, ethyl, n-propyl, isopropyl, isobutyl, tert-butyl or cyclopropyl;

$R^6$ represents H or F;

$R^7$ represents H, methyl, ethyl, n-propyl, isopropyl, isobutyl, tert-butyl or cyclopropyl, preferably methyl;

$R^8$ represents 1, 2, 3 or 4 substituents selected independently of one another from the group consisting of H and methyl;

$R^{9a}$ represents pyridyl or pyrimidyl;

$R^{10}$ represents H, methyl, ethyl, n-propyl, isopropyl, isobutyl, tert-butyl or cyclopropyl, preferably methyl;

$R^{300}$ represents 0, 1 or 2 substituents selected independently of one another from the group consisting of F, Cl, $CF_3$ and methyl;

wherein the above-mentioned alkyl, alkylene, cycloalkyl and heterocyclyl groups are in each case unsubstituted or substituted one or more times, for example 2, 3, 4 or 5 times, by identical or different substituents, the substituents being selected independently of one another from the group consisting of O—$C_{1-3}$-alkyl, F, Cl, $CF_3$, $OCF_3$, OH, =O, cyclopropyl, cyclobutyl, cyclopentyl, cyclohexyl, phenyl, phenoxy, naphthyl, thienyl and pyridinyl, preferably from the group consisting of O—$C_{1-3}$-alkyl, F, Cl, $CF_3$, $OCF_3$, OH, cyclopropyl, cyclobutyl, cyclopentyl, cyclohexyl, phenyl, phenoxy, naphthyl, thienyl and pyridinyl, wherein the above-mentioned phenyl radical is in each case unsubstituted or substituted one or more times, for example 2, 3, 4 or 5 times, by identical or different substituents, the substituents being selected independently of one another from the group consisting of O—$C_{1-3}$-alkyl, $C_{1-4}$-alkyl, F, Cl, CN, $CF_3$, $OCF_3$ and OH, wherein the above-mentioned pyridyl and pyrimidyl are in each case unsubstituted or substituted one or more times, for example 2, 3, 4 or 5 times, by identical or different substituents, the substituents being selected independently of one another from the group consisting of azetidinyl, pyrrolidinyl, piperidinyl, morpholinyl, N-methylpiperazinyl, pyridinyl, O—$C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), C(=O)—$NH_2$, C(=O)—N$(C_{1-4}$-alkyl$)_2$, C(=O)—NH$(C_{1-4}$-alkyl), S(=O)$_2$—$(C_{1-4}$-alkyl), cyclopropyl,

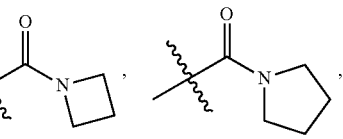

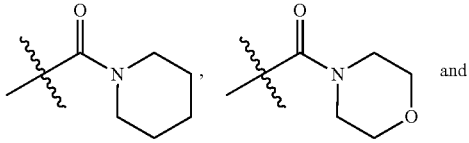

and

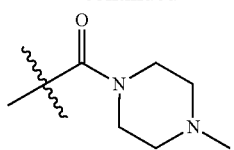 5

In a further preferred embodiment of the present invention, the compounds according to the invention can be selected from the group consisting of

| | |
|---|---|
| H-01 | 3-[(2-Chloro-benzoyl)amino]-N-[2-(1-pyridin-4-yl-piperidin-4-yl)-ethyl]-2,3-dihydro-1H-indene-5-carboxylic acid amide |
| H-03 | (3R)-3-[(2-Chloro-benzoyl)amino]-N-[(1-pyridin-4-yl-piperidin-4-yl)-methyl]-2,3-dihydro-1H-indene-5-carboxylic acid amide |
| H-04 | (3R)-3-[(2-Chloro-benzoyl)amino]-N-[1-[5-(trifluoromethyl)-pyridin-2-yl]-pyrrolidin-3-yl]-2,3-dihydro-1H-indene-5-carboxylic acid amide |
| H-06 | (3R)-3-[(2-Chloro-benzoyl)amino]-N-methyl-N-(1-pyridin-4-yl-piperidin-4-yl)-2,3-dihydro-1H-indene-5-carboxylic acid amide |
| H-07 | (3R)-3-[(2-Chloro-benzoyl)amino]-N-(1-pyridin-4-yl-piperidin-4-yl)-2,3-dihydro-1H-indene-5-carboxylic acid amide |
| H-09 | (3R)-3-[(2-Chloro-benzoyl)amino]-N-[(3S)-1-(1-cyclopropyl-piperidin-4-yl)-pyrrolidin-3-yl]-2,3-dihydro-1H-indene-5-carboxylic acid amide |
| H-10 | (3R)-3-[(2-Chloro-benzoyl)amino]-N-[(1-pyridin-4-yl-piperidin-3-yl)-methyl]-2,3-dihydro-1H-indene-5-carboxylic acid amide |
| H-11 | (1R)-1-(4-Chloro-3-oxo-1,2-dihydro-isoindol-2-yl)-N-methyl-N-(1-pyridin-4-yl-piperidin-4-yl)-2,3-dihydro-1H-indene-5-carboxylic acid amide |
| H-12 | (3R)-3-(4-Chloro-3-oxo-1,2-dihydro-isoindol-2-yl)-N-methyl-N-(1-pyridin-4-yl-piperidin-4-yl)-2,3-dihydro-1H-indene-5-carboxylic acid amide |
| H-14 | (3R)-3-[(2-Chloro-benzoyl)amino]-N-[2,2-dimethyl-4-(4-methyl-piperazin-1-yl)-cyclohexyl]-2,3-dihydro-1H-indene-5-carboxylic acid amide |
| H-15 | (3R)-3-[(2-Chloro-benzoyl)amino]-N-[2-(1-pyridin-4-yl-piperidin-4-yl)-ethyl]-2,3-dihydro-1H-indene-5-carboxylic acid amide |
| H-16 | (1R)-1-[[(2-Chlorophenyl)sulfonyl]amino]-N-methyl-N-(1-pyridin-4-yl-piperidin-4-yl)-2,3-dihydro-1H-indene-5-carboxylic acid amide |
| H-17 | (1R)-1-[(2-Chloro-benzoyl)amino]-N-methyl-N-(1-pyridin-4-yl-piperidin-4-yl)-2,3-dihydro-1H-indene-5-carboxylic acid amide |
| H-18 | (3R)-3-(Cyclobutanecarbonylamino)-N-methyl-N-(1-pyridin-4-yl-piperidin-4-yl)-2,3-dihydro-1H-indene-5-carboxylic acid amide |
| H-19 | (3R)-3-(2,2-Dimethyl-propanoylamino)-N-methyl-N-(1-pyridin-4-yl-piperidin-4-yl)-2,3-dihydro-1H-indene-5-carboxylic acid amide |
| H-20 | (4R)-4-[(2-Chloro-benzoyl)amino]-N-methyl-N-(1-pyridin-4-yl-piperidin-4-yl)-3,4-dihydro-2H-chromene-6-carboxylic acid amide |
| H-21 | (3S)-3-[(2-Chloro-benzoyl)amino]-N-methyl-N-(1-pyridin-4-yl-piperidin-4-yl)-2,3-dihydro-1H-indene-5-carboxylic acid amide |
| H-22 | N-[(1R)-6-[Methyl-(1-pyridin-4-yl-piperidin-4-yl)-carbamoyl]-2,3-dihydro-1H-inden-1-yl]-pyrazolo[1,5-a]pyrimidine-3-carboxylic acid amide |
| H-23 | (3R)-3-[(2-Chloro-benzoyl)amino]-N-methyl-N-(1-pyridin-2-yl-piperidin-4-yl)-2,3-dihydro-1H-indene-5-carboxylic acid amide |
| H-24 | (3R)-3-[[2-Chloro-3-(trifluoromethyl)-benzoyl]amino]-N-methyl-N-(1-pyridin-4-yl-piperidin-4-yl)-2,3-dihydro-1H-indene-5-carboxylic acid amide |
| H-25 | (3R)-N-Methyl-3-[(2-phenyl-acetyl)amino]-N-(1-pyridin-4-yl-piperidin-4-yl)-2,3-dihydro-1H-indene-5-carboxylic acid amide |
| H-26 | (1R)-1-(4-Chloro-3-oxo-1,2-dihydro-isoindol-2-yl)-N-methyl-N-(1-pyridin-2-yl-piperidin-4-yl)-2,3-dihydro-1H-indene-5-carboxylic acid amide |
| H-27 | (1R)-1-(4-Chloro-3-oxo-1,2-dihydro-isoindol-2-yl)-N-methyl-N-[1-(pyridin-4-yl-methyl)-piperidin-4-yl]-2,3-dihydro-1H-indene-5-carboxylic acid amide |
| H-28 | (3R)-N-Methyl-3-(3-methyl-butanoylamino)-N-(1-pyridin-4-yl-piperidin-4-yl)-2,3-dihydro-1H-indene-5-carboxylic acid amide |
| H-29 | (3R)-3-[(2-Fluoro-benzoyl)amino]-N-methyl-N-(1-pyridin-4-yl-piperidin-4-yl)-2,3-dihydro-1H-indene-5-carboxylic acid amide |
| H-30 | (3R)-N-Methyl-N-(1-pyridin-4-yl-piperidin-4-yl)-3-[[2-(trifluoromethyl)-benzoyl]amino]-2,3-dihydro-1H-indene-5-carboxylic acid amide |
| H-31 | N-[(1R)-6-[Methyl-(1-pyridin-4-yl-piperidin-4-yl)-carbamoyl]-2,3-dihydro-1H-inden-1-yl]-pyrimidine-5-carboxylic acid amide |
| H-32 | (3R)-3-[(2-Chloro-6-fluoro-benzoyl)amino]-N-methyl-N-(1-pyridin-4-yl-piperidin-4-yl)-2,3-dihydro-1H-indene-5-carboxylic acid amide |
| H-33 | (3R)-3-[[(2-Chlorophenyl)sulfonyl]amino]-N-methyl-N-(1-pyridin-4-yl-piperidin-4-yl)-2,3-dihydro-1H-indene-5-carboxylic acid amide |
| H-34 | (1R)-N-Methyl-1-(3-methyl-butanoylamino)-N-(1-pyridin-4-yl-piperidin-4-yl)-2,3-dihydro-1H-indene-5-carboxylic acid amide |
| H-35 | (3R)-3-[[2-(2-Chlorophenyl)-acetyl]amino]-N-methyl-N-(1-pyridin-4-yl-piperidin-4-yl)-2,3-dihydro-1H-indene-5-carboxylic acid amide |

| | |
|---|---|
| H-36 | N-[(1R)-6-[Methyl-(1-pyridin-4-yl-piperidin-4-yl)-carbamoyl]-2,3-dihydro-1H-inden-1-yl]-4-(trifluoromethyl)-pyridine-3-carboxylic acid amide |
| H-37 | N-[(1R)-6-[Methyl-(1-pyridin-4-yl-piperidin-4-yl)-carbamoyl]-2,3-dihydro-1H-inden-1-yl]-2-(trifluoromethyl)-pyridine-3-carboxylic acid amide |
| H-38 | (3R)-3-[(2-Chloro-benzoyl)amino]-N-cyclopropyl-N-(1-pyridin-4-yl-piperidin-4-yl)-2,3-dihydro-1H-indene-5-carboxylic acid amide |
| H-39 | (3R)-3-[(2-Chloro-benzoyl)amino]-N-methyl-N-(1-pyridin-4-yl-pyrrolidin-3-yl)-2,3-dihydro-1H-indene-5-carboxylic acid amide |
| H-40 | (3R)-3-[(2-Chloro-benzoyl)amino]-N-methyl-N-[1-(1-methyl-piperidin-4-yl)-piperidin-4-yl]-2,3-dihydro-1H-indene-5-carboxylic acid amide |
| H-41 | 2-Methoxy-N-[(1R)-6-[methyl-(1-pyridin-4-yl-piperidin-4-yl)-carbamoyl]-2,3-dihydro-1H-inden-1-yl]-pyridine-3-carboxylic acid amide |
| H-42 | (1R)-1-(4-Chloro-3-oxo-1,2-dihydro-isoindol-2-yl)-N-[1-(1-methyl-piperidin-4-yl)-piperidin-4-yl]-2,3-dihydro-1H-indene-5-carboxylic acid amide |
| H-43 | (1R)-1-(4-Chloro-3-oxo-1,2-dihydro-isoindol-2-yl)-N-methyl-N-[1-(2-pyridin-4-yl-ethyl)-piperidin-4-yl]-2,3-dihydro-1H-indene-5-carboxylic acid amide |
| H-44 | (4R)-4-[(2-Chloro-benzoyl)amino]-N-methyl-N-(1-pyridin-4-yl-piperidin-4-yl)-3,4-dihydro-2H-chromene-7-carboxylic acid amide |
| H-45 | (4R)-4-(4-Chloro-3-oxo-1,2-dihydro-isoindol-2-yl)-N-methyl-N-(1-pyridin-4-yl-piperidin-4-yl)-3,4-dihydro-2H-chromene-7-carboxylic acid amide |
| H-46 | (3R)-3-[[[1-(2-Fluorophenyl)-cyclopropanecarbonyl]amino]-N-methyl-N-(1-pyridin-4-yl-piperidin-4-yl)-2,3-dihydro-1H-indene-5-carboxylic acid amide |
| H-47 | (3R)-3-[[1-(2-Fluorophenyl)-cyclopentanecarbonyl]amino]-N-methyl-N-(1-pyridin-4-yl-piperidin-4-yl)-2,3-dihydro-1H-indene-5-carboxylic acid amide |
| H-48 | (3R)-3-[(2-Chloro-benzoyl)amino]-N-methyl-N-[1-[(2-pyrrolidin-1-yl-pyridin-4-yl)-methyl]-piperidin-4-yl]-2,3-dihydro-1H-indene-5-carboxylic acid amide |
| H-49 | (3R)-3-[(2-Chloro-benzoyl)amino]-N-methyl-N-[[1-(2-methyl-pyridin-4-yl)-piperidin-4-yl]-methyl]-2,3-dihydro-1H-indene-5-carboxylic acid amide |
| H-50 | (3R)-3-[(2-Chloro-benzoyl)amino]-N-[1-(4-methoxyphenyl)-piperidin-4-yl]-N-methyl-2,3-dihydro-1H-indene-5-carboxylic acid amide |
| H-51 | (3R)-3-[[1-(2-Chlorophenyl)-cyclopropanecarbonyl]amino]-N-methyl-N-(1-pyridin-4-yl-piperidin-4-yl)-2,3-dihydro-1H-indene-5-carboxylic acid amide |
| H-52 | (1R)-1-(4-Chloro-3-oxo-1,2-dihydro-isoindol-2-yl)-N-methyl-N-[[1-(2-methyl-pyridin-4-yl)-piperidin-4-yl]-methyl]-2,3-dihydro-1H-indene-5-carboxylic acid amide |
| H-53 | (1R)-1-(4-Chloro-3-oxo-1,2-dihydro-isoindol-2-yl)-N-methyl-N-[1-[(2-pyrrolidin-1-yl-pyridin-4-yl)-methyl]-piperidin-4-yl]-2,3-dihydro-1H-indene-5-carboxylic acid amide |
| H-54 | (3R)-3-[(2-Chloro-benzoyl)amino]-N-[1-(4-chlorophenyl)-piperidin-4-yl]-N-methyl-2,3-dihydro-1H-indene-5-carboxylic acid amide |
| H-55 | (3R)-3-[(2-Chloro-benzoyl)amino]-N-methyl-N-[1-(2-methyl-pyridin-4-yl)-piperidin-4-yl]-2,3-dihydro-1H-indene-5-carboxylic acid amide |
| H-56 | (3R)-3-[(2-Chloro-benzoyl)amino]-N-[2-[1-(2-methyl-pyridin-4-yl)-piperidin-4-yl]-ethyl]-2,3-dihydro-1H-indene-5-carboxylic acid amide |
| H-57 | (1R)-1-[(2-Chloro-benzoyl)amino]-6-fluoro-N-methyl-N-(1-pyridin-4-yl-piperidin-4-yl)-2,3-dihydro-1H-indene-5-carboxylic acid amide |
| H-58 | (3R)-3-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide |
| H-59 | (3R)-3-[(2-Chloro-benzoyl)amino]-N-[1-(2,6-dimethyl-pyrimidin-4-yl)-piperidin-4-yl]-N-methyl-2,3-dihydro-1H-indene-5-carboxylic acid amide |
| H-60 | (3R)-3-[(2-Chloro-benzoyl)amino]-N-(3,3-dimethyl-1-pyridin-4-yl-piperidin-4-yl)-N-methyl-2,3-dihydro-1H-indene-5-carboxylic acid amide |
| H-61 | (3R)-3-[(2-Chloro-benzoyl)amino]-N-methyl-N-(4-pyridin-4-yl-cyclohexyl)-2,3-dihydro-1H-indene-5-carboxylic acid amide |
| H-62 | 5-Methyl-N-[(1R)-6-[methyl-(1-pyridin-4-yl-piperidin-4-yl)-carbamoyl]-2,3-dihydro-1H-inden-1-yl]-isoxazole-3-carboxylic acid amide |
| H-63 | (3R)-N-Methyl-N-(1-pyridin-4-yl-piperidin-4-yl)-3-(3,3,3-trifluoro-propanoylamino)-2,3-dihydro-1H-indene-5-carboxylic acid amide |
| H-64 | (3R)-3-[(2-Chloro-benzoyl)amino]-N-methyl-N-[(1-pyridin-4-yl-piperidin-4-yl)-methyl]-2,3-dihydro-1H-indene-5-carboxylic acid amide |
| H-65 | (3R)-3-[(2-Chloro-benzoyl)-(2-methyl-propyl)-amino]-N-methyl-N-(1-pyridin-4-yl-piperidin-4-yl)-2,3-dihydro-1H-indene-5-carboxylic acid amide |
| H-66 | (3R)-3-[(2-Chloro-benzoyl)amino]-N-methyl-N-[2-(1-pyridin-4-yl-piperidin-4-yl)-ethyl]-2,3-dihydro-1H-indene-5-carboxylic acid amide |
| H-67 | (3R)-3-[(2-tert-Butyl-benzoyl)amino]-N-methyl-N-(1-pyridin-4-yl-piperidin-4-yl)-2,3-dihydro-1H-indene-5-carboxylic acid amide |
| H-68 | (3R)-N-Methyl-3-[(2-methyl-propylsulfonyl)amino]-N-(1-pyridin-4-yl-piperidin-4-yl)-2,3-dihydro-1H-indene-5-carboxylic acid amide |
| H-69 | (1S)-N-[(1R)-6-[Methyl-(1-pyridin-4-yl-piperidin-4-yl)-carbamoyl]-2,3-dihydro-1H-inden-1-yl]-1,2,3,4-tetrahydro-naphthalene-1-carboxylic acid amide |
| H-70 | N-[(1R)-6-[Methyl-(1-pyridin-4-yl-piperidin-4-yl)-carbamoyl]-2,3-dihydro-1H-inden-1-yl]-1,2,3,4-tetrahydro-naphthalene-1-carboxylic acid amide |
| H-71 | (3R)-3-Benzoylamino-N-methyl-N-(1-pyridin-4-yl-piperidin-4-yl)-2,3-dihydro-1H-indene-5-carboxylic acid amide |
| H-72 | (3R)-3-[[(4-Fluorophenyl)sulfonyl]amino]-N-methyl-N-(1-pyridin-4-yl-piperidin-4-yl)-2,3-dihydro-1H-indene-5-carboxylic acid amide |
| H-73 | N-[(1R)-6-[Methyl-(1-pyridin-4-yl-piperidin-4-yl)-carbamoyl]-2,3-dihydro-1H-inden-1-yl]-naphthalene-1-carboxylic acid amide |
| H-74 | (3R)-3-(Benzenesulfonamido)-N-methyl-N-(1-pyridin-4-yl-piperidin-4-yl)-2,3-dihydro-1H-indene-5-carboxylic acid amide |

| | |
|---|---|
| H-75 | (3R)-3-[(4-Fluoro-benzoyl)amino]-N-methyl-N-(1-pyridin-4-yl-piperidin-4-yl)-2,3-dihydro-1H-indene-5-carboxylic acid amide |
| H-76 | N-[(1R)-6-[Methyl-(1-pyridin-4-yl-piperidin-4-yl)-carbamoyl]-2,3-dihydro-1H-inden-1-yl]-tetrahydro-pyran-4-carboxylic acid amide |
| H-77 | (3R)-3-[(2-Chloro-benzoyl)amino]-N-ethyl-N-(1-pyridin-4-yl-piperidin-4-yl)-2,3-dihydro-1H-indene-5-carboxylic acid amide |
| H-78 | (3R)-3-[(2-Chloro-benzoyl)amino]-N-[1-(4-fluorophenyl)-piperidin-4-yl]-N-methyl-2,3-dihydro-1H-indene-5-carboxylic acid amide |
| H-79 | (3R)-3-[(2-Chloro-benzoyl)amino]-N-ethyl-N-[1-(2-methyl-pyridin-4-yl)-piperidin-4-yl]-2,3-dihydro-1H-indene-5-carboxylic acid amide |
| H-80 | (4R)-4-[(2-Chloro-benzoyl)amino]-8-fluoro-N-methyl-N-(1-pyridin-4-yl-piperidin-4-yl)-3,4-dihydro-2H-chromene-6-carboxylic acid amide |
| H-81 | (4R)-4-[(2-Chloro-benzoyl)amino]-N-[1-(2,6-dimethyl-pyrimidin-4-yl)-piperidin-4-yl]-8-fluoro-N-methyl-3,4-dihydro-2H-chromene-6-carboxylic acid amide |
| H-82 | (3R)-3-(2,3-Dihydro-1H-indene-1-carbonylamino)-N-methyl-N-(1-pyridin-4-yl-piperidin-4-yl)-2,3-dihydro-1H-indene-5-carboxylic acid amide |
| H-83 | N-[(1R)-6-[Methyl-(1-pyridin-4-yl-piperidin-4-yl)-carbamoyl]-2,3-dihydro-1H-inden-1-yl]-isoquinoline-4-carboxylic acid amide |
| H-84 | N-[(1R)-6-[Methyl-(1-pyridin-4-yl-piperidin-4-yl)-carbamoyl]-2,3-dihydro-1H-inden-1-yl]-3,4-dihydro-2H-chromene-4-carboxylic acid amide |
| H-85 | (3R)-N-Methyl-3-(3-methyl-butanoylamino)-N-[1-(2-methyl-pyridin-4-yl)-piperidin-4-yl]-2,3-dihydro-1H-indene-5-carboxylic acid amide |
| H-86 | (3R)-N-[1-(2,6-Dimethyl-pyrimidin-4-yl)-piperidin-4-yl]-N-methyl-3-(3-methyl-butanoylamino)-2,3-dihydro-1H-indene-5-carboxylic acid amide |
| H-87 | (4R)-4-(4-Chloro-3-oxo-1,2-dihydro-isoindol-2-yl)-8-fluoro-N-methyl-N-(1-pyridin-4-yl-piperidin-4-yl)-3,4-dihydro-2H-chromene-6-carboxylic acid amide |
| H-88 | N-[(1R)-6-[Methyl-[1-(2-methyl-pyridin-4-yl)-piperidin-4-yl]-carbamoyl]-2,3-dihydro-1H-inden-1-yl]-tetrahydro-pyran-4-carboxylic acid amide |
| H-89 | N-[(1R)-6-[[1-(2,6-Dimethyl-pyrimidin-4-yl)-piperidin-4-yl]-methyl-carbamoyl]-2,3-dihydro-1H-inden-1-yl]-tetrahydro-pyran-4-carboxylic acid amide |
| H-90 | (3R)-3-[(2-Chloro-benzoyl)amino]-N-methyl-N-[1-(3-piperidin-1-yl-propanoyl)-piperidin-4-yl]-2,3-dihydro-1H-indene-5-carboxylic acid amide |
| H-91 | N-[(1R)-6-[[1-(2,6-Dimethyl-pyrimidin-4-yl)-piperidin-4-yl]-methyl-carbamoyl]-2,3-dihydro-1H-inden-1-yl]-2-(trifluoromethyl)-pyridine-3-carboxylic acid amide |
| H-92 | N-[(1R)-6-[Methyl-[1-(2-methyl-pyridin-4-yl)-piperidin-4-yl]-carbamoyl]-2,3-dihydro-1H-inden-1-yl]-2-(trifluoromethyl)-pyridine-3-carboxylic acid amide |
| H-93 | (3R)-3-(3-Cyclopentyl-propanoylamino)-N-methyl-N-[1-(2-methyl-pyridin-4-yl)-piperidin-4-yl]-2,3-dihydro-1H-indene-5-carboxylic acid amide |
| H-94 | (3R)-3-(3-Cyclopentyl-propanoylamino)-N-[1-(2,6-dimethyl-pyrimidin-4-yl)-piperidin-4-yl]-N-methyl-2,3-dihydro-1H-indene-5-carboxylic acid amide |
| H-95 | 5-Methyl-N-[(1R)-6-[methyl-[1-(2-methyl-pyridin-4-yl)-piperidin-4-yl]-carbamoyl]-2,3-dihydro-1H-inden-1-yl]-isoxazole-3-carboxylic acid amide |
| H-96 | N-[(1R)-6-[[1-(2,6-Dimethyl-pyrimidin-4-yl)-piperidin-4-yl]-methyl-carbamoyl]-2,3-dihydro-1H-inden-1-yl]-5-methyl-isoxazole-3-carboxylic acid amide |
| H-98 | (3R)-3-[(2-Chloro-benzoyl)amino]-N-methyl-N-[1-(1-oxido-pyridin-1-ium-4-yl)-piperidin-4-yl]-2,3-dihydro-1H-indene-5-carboxylic acid amide |
| H-99 | (3R)-3-[(2-Chloro-benzoyl)amino]-N-methyl-N-[4-(1,2,3,4-tetrahydro-[2,6]-naphthyridin-2-yl)-cyclohexyl]-2,3-dihydro-1H-indene-5-carboxylic acid amide |
| H-100 | (3R)-3-[(2-Chloro-benzoyl)amino]-N-[1-(2-dimethylamino-pyridin-4-yl)-piperidin-4-yl]-N-methyl-2,3-dihydro-1H-indene-5-carboxylic acid amide |
| H-101 | (3R)-3-[(2-Chloro-benzoyl)amino]-N-[1-(6-methoxy-pyridin-3-yl)-piperidin-4-yl]-N-methyl-2,3-dihydro-1H-indene-5-carboxylic acid amide |
| H-102 | (3R)-3-[(2-Chloro-benzoyl)amino]-N-[4-(2-dimethylamino-5,6,7,8-tetrahydro-pyrido[4,3-d]pyrimidin-6-yl)-cyclohexyl]-N-methyl-2,3-dihydro-1H-indene-5-carboxylic acid amide |
| H-103 | (3R)-3-[(2-Chloro-benzoyl)amino]-N-methyl-N-[(1S,3R)-3-(4-methyl-piperazin-1-yl)-cyclohexyl]-2,3-dihydro-1H-indene-5-carboxylic acid amide |
| H-104 | (3R)-3-[[(2-Chlorophenyl)sulfonyl]amino]-N-methyl-N-[(1S,3R)-3-(4-methyl-piperazin-1-yl)-cyclohexyl]-2,3-dihydro-1H-indene-5-carboxylic acid amide |
| H-110 | 3-[tert-Butyl-(2-chloro-benzoyl)-amino]-N-methyl-N-(1-pyridin-4-yl-piperidin-4-yl)-2,3-dihydro-1H-indene-5-carboxylic acid amide |
| H-111 | (1R)-1-(4-Chloro-3-oxo-1,2-dihydro-isoindol-2-yl)-N-methyl-N-[(1S,3R)-3-(4-methyl-piperazin-1-yl)-cyclohexyl]-2,3-dihydro-1H-indene-5-carboxylic acid amide |
| H-112 | (3R)-3-[(2-Chloro-benzoyl)amino]-N-[1-(2-methoxy-pyridin-4-yl)-piperidin-4-yl]-N-methyl-2,3-dihydro-1H-indene-5-carboxylic acid amide |
| H-113 | (3R)-3-[(2-Chloro-benzoyl)amino]-N-[1-(6-dimethylamino-pyridin-3-yl)-piperidin-4-yl]-N-methyl-2,3-dihydro-1H-indene-5-carboxylic acid amide |
| H-114 | (3R)-3-[(2-Chloro-benzoyl)amino]-N-methyl-N-(4-pyridin-4-yloxy-cyclohexyl)-2,3-dihydro-1H-indene-5-carboxylic acid amide |
| H-115 | (3R)-3-[(2-Chloro-benzoyl)amino]-N-methyl-N-(1-pyridin-4-yl-piperidin-3-yl)-2,3-dihydro-1H-indene-5-carboxylic acid amide |
| H-116 | (3R)-3-[(2-Chloro-benzoyl)amino]-N-methyl-N-(1-pyridin-4-yl-azepan-4-yl)-2,3-dihydro-1H-indene-5-carboxylic acid amide |
| H-117 | (3R)-3-[(2-Chloro-benzoyl)amino]-N-[1-(3-fluoro-pyridin-4-yl)-piperidin-4-yl]-N-methyl-2,3-dihydro-1H-indene-5-carboxylic acid amide |
| H-118 | (3R)-3-[(2-Chloro-benzoyl)amino]-N-[1-(2-dimethylamino-pyrimidin-4-yl)-piperidin-4-yl]-N-methyl-2,3-dihydro-1H-indene-5-carboxylic acid amide |
| H-119 | (3R)-N-[1-(2-Dimethylamino-pyridin-4-yl)-piperidin-4-yl]-3-[isopropyl-(3-methyl-butanoyl)-amino]-N-methyl-2,3-dihydro-1H-indene-5-carboxylic acid amide |

-continued

| | |
|---|---|
| H-120 | (3R)-N-[1-(2-Dimethylamino-pyrimidin-4-yl)-piperidin-4-yl]-3-[isopropyl-(3-methyl-butanoyl)-amino]-N-methyl-2,3-dihydro-1H-indene-5-carboxylic acid amide |
| H-122 | (3R)-3-[(2-Chloro-benzoyl)amino]-N-methyl-N-[1-(2-methyl-pyrimidin-4-yl)-piperidin-4-yl]-2,3-dihydro-1H-indene-5-carboxylic acid amide |
| H-123 | (3R)-3-[(2-Chloro-benzoyl)amino]-N-[1-(2-cyano-pyridin-4-yl)-piperidin-4-yl]-N-methyl-2,3-dihydro-1H-indene-5-carboxylic acid amide |
| H-124 | (3R)-3-[(2-Chloro-benzoyl)amino]-N-methyl-N-[1-(2-pyrrolidin-1-yl-pyridin-4-yl)-piperidin-4-yl]-2,3-dihydro-1H-indene-5-carboxylic acid amide |
| H-125 | (3R)-3-[(2-Chloro-benzoyl)amino]-N-methyl-N-[1-(3-methyl-[1,2,4]thiadiazol-5-yl)-piperidin-4-yl]-2,3-dihydro-1H-indene-5-carboxylic acid amide |
| H-126 | (3R)-3-[(2-Chloro-benzoyl)amino]-N-[1-(2-methoxy-6-methyl-pyrimidin-4-yl)-piperidin-4-yl]-N-methyl-2,3-dihydro-1H-indene-5-carboxylic acid amide |
| H-127 | (3R)-3-[(2-Chloro-benzoyl)amino]-N-methyl-N-(1-quinazolin-4-yl-piperidin-4-yl)-2,3-dihydro-1H-indene-5-carboxylic acid amide |
| H-128 | (3R)-N-[1-(2,6-Dimethyl-pyrimidin-4-yl)-piperidin-4-yl]-3-[(2-fluoro-benzoyl)amino]-N-methyl-2,3-dihydro-1H-indene-5-carboxylic acid amide |
| H-129 | (3R)-3-[(2-Chloro-3-fluoro-benzoyl)amino]-N-[1-(2,6-dimethyl-pyrimidin-4-yl)-piperidin-4-yl]-N-methyl-2,3-dihydro-1H-indene-5-carboxylic acid amide |
| H-130 | (3R)-3-(4-Chloro-3-oxo-1,2-dihydro-isoindol-2-yl)-N-[1-(2,6-dimethyl-pyrimidin-4-yl)-piperidin-4-yl]-N-methyl-2,3-dihydro-1H-indene-5-carboxylic acid amide |
| H-131 | (3R)-3-[(2-Chloro-benzoyl)amino]-N-[1-[(4-methoxy-3,5-dimethyl-pyridin-2-yl)-methyl]-piperidin-4-yl]-N-methyl-2,3-dihydro-1H-indene-5-carboxylic acid amide |
| H-132 | (3R)-N-[1-(2,6-Dimethyl-pyrimidin-4-yl)-piperidin-4-yl]-N-methyl-3-[[2-(trifluoromethyl)-benzoyl]amino]-2,3-dihydro-1H-indene-5-carboxylic acid amide |
| H-133 | (3R)-3-[(2-Chloro-5-fluoro-benzoyl)amino]-N-[1-(2,6-dimethyl-pyrimidin-4-yl)-piperidin-4-yl]-N-methyl-2,3-dihydro-1H-indene-5-carboxylic acid amide |
| H-134 | (3R)-3-[(2-Chloro-benzoyl)amino]-N-methyl-N-[1-[(3-methyl-isoxazol-5-yl)-methyl]-piperidin-4-yl]-2,3-dihydro-1H-indene-5-carboxylic acid amide |
| H-135 | (3R)-3-[[2-Chloro-3-(trifluoromethyl)-benzoyl]amino]-N-[1-(2,6-dimethyl-pyrimidin-4-yl)-piperidin-4-yl]-N-methyl-2,3-dihydro-1H-indene-5-carboxylic acid amide |
| H-136 | (3R)-3-[(2-Chloro-benzoyl)amino]-N-methyl-N-[(1-pyrimidin-4-yl-piperidin-4-yl)-methyl]-2,3-dihydro-1H-indene-5-carboxylic acid amide |
| H-137 | (3R)-3-[[2-Chloro-5-(trifluoromethyl)-benzoyl]amino]-N-[1-(2,6-dimethyl-pyrimidin-4-yl)-piperidin-4-yl]-N-methyl-2,3-dihydro-1H-indene-5-carboxylic acid amide |
| H-138 | (3R)-3-[(2-Chloro-benzoyl)amino]-N-methyl-N-[1-[2-(4-methyl-piperazin-1-yl)-2-oxo-ethyl]-piperidin-4-yl]-2,3-dihydro-1H-indene-5-carboxylic acid amide |
| H-139 | (3R)-3-[(2-Chloro-benzoyl)amino]-N-[1-(2-isopropyl-6-methyl-pyrimidin-4-yl)-piperidin-4-yl]-N-methyl-2,3-dihydro-1H-indene-5-carboxylic acid amide |
| H-140 | (3R)-3-[(2-Chloro-benzoyl)amino]-N-methyl-N-[1-(2-oxo-2-pyrrolidin-1-yl-ethyl)-piperidin-4-yl]-2,3-dihydro-1H-indene-5-carboxylic acid amide |
| H-141 | (3R)-3-[(2-Chloro-benzoyl)amino]-N-methyl-N-[1-(6-methyl-pyrimidin-4-yl)-piperidin-4-yl]-2,3-dihydro-1H-indene-5-carboxylic acid amide |
| H-142 | (1R)-1-(4-Chloro-3-oxo-1,2-dihydro-isoindol-2-yl)-N-[1-(2,6-dimethyl-pyrimidin-4-yl)-piperidin-4-yl]-6-fluoro-N-methyl-2,3-dihydro-1H-indene-5-carboxylic acid amide |
| H-143 | N-[(1R)-5-[[1-(2,6-Dimethyl-pyrimidin-4-yl)-piperidin-4-yl]-methyl-carbamoyl]-6-fluoro-2,3-dihydro-1H-inden-1-yl]-5-methyl-isoxazole-3-carboxylic acid amide |
| H-144 | (3R)-3-[(2-Chloro-benzoyl)-isopropyl-amino]-N-[1-(2,6-dimethyl-pyrinnidin-4-yl)-piperidin-4-yl]-N-methyl-2,3-dihydro-1H-indene-5-carboxylic acid amide |
| H-145 | (3R)-3-[(2-Chloro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide |
| H-146 | (3R)-3-[(2-Chloro-benzoyl)amino]-N-methyl-N-(1-pyridin-4-yl-azetidin-3-yl)-2,3-dihydro-1H-indene-5-carboxylic acid amide |
| H-147 | (3R)-3-[(2-Chloro-benzoyl)amino]-N-methyl-N-(1-pyrimidin-4-yl-piperidin-4-yl)-2,3-dihydro-1H-indene-5-carboxylic acid amide |
| H-148 | (3R)-3-[(2-Chloro-benzoyl)-methyl-amino]-N-methyl-N-(1-pyrimidin-4-yl-piperidin-4-yl)-2,3-dihydro-1H-indene-5-carboxylic acid amide |
| H-149 | (3R)-3-[(2-Chloro-benzoyl)-methyl-amino]-N-[1-(2,6-dimethyl-pyrimidin-4-yl)-piperidin-4-yl]-N-methyl-2,3-dihydro-1H-indene-5-carboxylic acid amide |
| H-150 | (3R)-3-[(2-Chloro-benzoyl)-isopropyl-amino]-N-methyl-N-(1-pyridin-4-yl-piperidin-4-yl)-2,3-dihydro-1H-indene-5-carboxylic acid amide |
| H-151 | (1R)-1-[(2-Chloro-benzoyl)amino]-N-[1-(2,6-dimethyl-pyrimidin-4-yl)-piperidin-4-yl]-6-fluoro-N-methyl-2,3-dihydro-1H-indene-5-carboxylic acid amide |
| H-152 | (1R)-1-[(2-Chloro-benzoyl)amino]-6-fluoro-N-methyl-N-[1-(6-methyl-pyrimidin-4-yl)-piperidin-4-yl]-2,3-dihydro-1H-indene-5-carboxylic acid amide |
| H-153 | (3R)-3-[(2-Chloro-benzoyl)-methyl-amino]-N-methyl-N-(1-pyridin-4-yl-piperidin-4-yl)-2,3-dihydro-1H-indene-5-carboxylic acid amide |
| H-155 | (3R)-3-[(2-Chloro-benzoyl)-isopropyl-amino]-6-fluoro-N-methyl-N-(1-pyridin-4-yl-piperidin-4-yl)-2,3-dihydro-1H-indene-5-carboxylic acid amide |
| H-156 | (3R)-3-[(2-Chloro-benzoyl)amino]-N-ethyl-N-[1-(7H-purin-6-yl)-piperidin-4-yl]-2,3-dihydro-1H-indene-5-carboxylic acid amide |
| H-158 | (1R)-1-[(2-Chloro-benzoyl)-isopropyl-amino]-6-fluoro-N-methyl-N-(1-pyridin-4-yl-piperidin-4-yl)-2,3-dihydro-1H-indene-5-carboxylic acid amide |
| H-160 | (3R)-3-[(2-Chloro-benzoyl)amino]-N-methyl-N-[1-(2-methyl-pyridin-4-yl)-azetidin-3-yl]-2,3-dihydro-1H-indene-5-carboxylic acid amide |
| H-161 | (3R)-3-(4-Chloro-3-oxo-1,2-dihydro-isoindol-2-yl)-N-methyl-N-[1-(2-methyl-pyridin-4-yl)-azetidin-3-yl]-2,3-dihydro-1H-indene-5-carboxylic acid amide |

-continued

| | |
|---|---|
| H-162 | (3R)-N-[1-(2,6-Dimethyl-pyrimidin-4-yl)-piperidin-4-yl]-N-methyl-3-[(2-methyl-benzoyl)amino]-2,3-dihydro-1H-indene-5-carboxylic acid amide |
| H-163 | (3R)-3-[(2-Chloro-6-fluoro-benzoyl)amino]-N-[1-(2,6-dimethyl-pyrimidin-4-yl)-piperidin-4-yl]-N-methyl-2,3-dihydro-1H-indene-5-carboxylic acid amide |
| H-164 | (3R)-3-[(2-Chloro-3-fluoro-benzoyl)amino]-N-methyl-N-(1-pyrimidin-4-yl-piperidin-4-yl)-2,3-dihydro-1H-indene-5-carboxylic acid amide |
| H-165 | (3R)-3-[(2-Chloro-4-fluoro-benzoyl)amino]-N-[1-(2,6-dimethyl-pyrimidin-4-yl)-piperidin-4-yl]-N-methyl-2,3-dihydro-1H-indene-5-carboxylic acid amide |
| H-166 | (3R)-3-[(2-Chloro-benzoyl)-isopropyl-amino]-N-[1-(2-isopropyl-6-methyl-pyrimidin-4-yl)-piperidin-4-yl]-N-methyl-2,3-dihydro-1H-indene-5-carboxylic acid amide |
| H-167 | (3R)-3-[(2-Chloro-4-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide |
| H-168 | (3R)-3-[(2-Chloro-4-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide |
| H-169 | (3R)-N-[1-(2,6-Dimethyl-pyrimidin-4-yl)-piperidin-4-yl]-N-methyl-3-[methyl-(2-methyl-benzoyl)-amino]-2,3-dihydro-1H-indene-5-carboxylic acid amide |
| H-170 | (3R)-N-[1-(2,6-Dimethyl-pyrimidin-4-yl)-piperidin-4-yl]-3-[ethyl-(2-methyl-benzoyl)-amino]-N-methyl-2,3-dihydro-1H-indene-5-carboxylic acid amide |
| H-171 | N-[(1R)-6-[[1-(2,6-Dimethyl-pyrimidin-4-yl)-piperidin-4-yl]-methyl-carbamoyl]-2,3-dihydro-1H-inden-1-yl]-N-methyl-2-(trifluoromethyl)-pyridine-3-carboxylic acid amide |
| H-172 | (3R)-N-[1-(2,6-Dimethyl-pyrimidin-4-yl)-piperidin-4-yl]-3-[isopropyl-(2-methyl-benzoyl)-amino]-N-methyl-2,3-dihydro-1H-indene-5-carboxylic acid amide |
| H-174 | N-[(1R)-6-[[1-(2,6-Dimethyl-pyrimidin-4-yl)-piperidin-4-yl]-methyl-carbamoyl]-2,3-dihydro-1H-inden-1-yl]-N-ethyl-2-(trifluoromethyl)-pyridine-3-carboxylic acid amide |
| H-175 | (3R)-3-[(2-Chloro-6-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide |
| H-176 | (3R)-3-[(2-Chloro-6-fluoro-benzoyl)-ethyl-amino]-N-[4-(2,6-dimethyl-pyrimidin-4-yl)-cyclohexyl]-N-methyl-2,3-dihydro-1H-indene-5-carboxylic acid amide |
| H-178 | (3R)-3-[(2-Chloro-benzoyl)amino]-N-isopropyl-N-(1-pyridin-4-yl-piperidin-4-yl)-2,3-dihydro-1H-indene-5-carboxylic acid amide |
| H-179 | (3R)-3-[(2-Fluoro-2-methyl-propanoyl)amino]-N-methyl-N-[1-(2-methyl-pyridin-4-yl)-piperidin-4-yl]-2,3-dihydro-1H-indene-5-carboxylic acid amide |
| H-180 | (3R)-3-[(2-Chloro-benzoyl)amino]-N-methyl-N-[1-(1-methyl-1H-imidazol-2-yl)-piperidin-4-yl]-2,3-dihydro-1H-indene-5-carboxylic acid amide |
| H-181 | (3R)-3-[(2-Chloro-benzoyl)amino]-N-methyl-N-[1-(6-methyl-pyrazin-2-yl)-piperidin-4-yl]-2,3-dihydro-1H-indene-5-carboxylic acid amide |
| H-182 | (3R)-3-[(2-Chloro-benzoyl)amino]-N-methyl-N-(2-oxo-1-pyridin-4-yl-piperidin-4-yl)-2,3-dihydro-1H-indene-5-carboxylic acid amide |
| H-183 | (3R)-3-[(2-Chloro-benzoyl)amino]-N-methyl-N-[1-[3-(trifluoromethyl)-pyridin-4-yl]-piperidin-4-yl]-2,3-dihydro-1H-indene-5-carboxylic acid amide |
| H-184 | (3R)-3-[(2-Chloro-benzoyl)amino]-N-[4-(2-dimethylamino-pyridin-4-yl)-cyclohexyl]-N-methyl-2,3-dihydro-1H-indene-5-carboxylic acid amide |
| H-185 | (3R)-3-(3-Cyclopentyl-propanoyl-methyl-amino)-N-[1-(2-dimethylamino-pyridin-4-yl)-piperidin-4-yl]-N-methyl-2,3-dihydro-1H-indene-5-carboxylic acid amide |
| H-186 | (3R)-3-(3-Cyclopentyl-propanoyl-methyl-amino)-N-[1-(2-dimethylamino-pyrimidin-4-yl)-piperidin-4-yl]-N-methyl-2,3-dihydro-1H-indene-5-carboxylic acid amide |
| H-188 | (3R)-3-(3-Cyclopentyl-propanoyl-methyl-amino)-N-[1-(3-fluoro-pyridin-4-yl)-piperidin-4-yl]-N-methyl-2,3-dihydro-1H-indene-5-carboxylic acid amide |
| H-191 | (3R)-N-[1-(2,6-Dimethyl-pyrimidin-4-yl)-piperidin-4-yl]-N-methyl-3-[(2-methyl-propylsulfonyl)amino]-2,3-dihydro-1H-indene-5-carboxylic acid amide |
| H-195 | (3R)-3-[(2-Chloro-3-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide |
| H-196 | (3R)-3-[(2-Chloro-3-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide |
| H-197 | (3R)-3-[(2-Chloro-3-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide |
| H-198 | (3R)-3-[(2-Chloro-4-fluoro-benzoyl)-isopropyl-amino]-N-[1-(2,6-dimethyl-pyrimidin-4-yl)-piperidin-4-yl]-6-fluoro-N-methyl-2,3-dihydro-1H-indene-5-carboxylic acid amide |
| H-199 | (3R)-3-[(2-Chloro-4-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide |
| H-202 | (3R)-3-[(2-Chloro-3-fluoro-benzoyl)-isopropyl-amino]-N-methyl-N-(1-pyridin-4-yl-piperidin-4-yl)-2,3-dihydro-1H-indene-5-carboxylic acid amide |
| H-203 | (3R)-3-[(2-Chloro-3-fluoro-benzoyl)-ethyl-amino]-N-methyl-N-(1-pyridin-4-yl-piperidin-4-yl)-2,3-dihydro-1H-indene-5-carboxylic acid amide |
| H-204 | (3R)-3-[(2-Chloro-4-fluoro-benzoyl)-isopropyl-amino]-N-methyl-N-(1-pyridin-4-yl-piperidin-4-yl)-2,3-dihydro-1H-indene-5-carboxylic acid amide |
| H-205 | (3R)-3-[(2-Chloro-3-fluoro-benzoyl)-methyl-amino]-N-methyl-N-(1-pyridin-4-yl-piperidin-4-yl)-2,3-dihydro-1H-indene-5-carboxylic acid amide |
| H-206 | (3R)-3-[(2-Chloro-4-fluoro-benzoyl)-isopropyl-amino]-6-fluoro-N-methyl-N-(1-pyridin-4-yl-piperidin-4-yl)-2,3-dihydro-1H-indene-5-carboxylic acid amide |

| | |
|---|---|
| H-207 | N-[(1R)-6-[[1-(2,6-Dimethyl-pyrimidin-4-yl)-piperidin-4-yl]-methyl-carbamoyl]-2,3-dihydro-1H-inden-1-yl]-N-isopropyl-2-(trifluoromethyl)-pyridine-3-carboxylic acid amide |
| H-208 | N-Isopropyl-N-[(1R)-6-[methyl-(1-pyridin-4-yl-piperidin-4-yl)-carbamoyl]-2,3-dihydro-1H-inden-1-yl]-2-(trifluoromethyl)-pyridine-3-carboxylic acid amide |
| H-209 | N-[(1R)-6-[[1-(2,6-Dimethyl-pyrimidin-4-yl)-piperidin-4-yl]-methyl-carbamoyl]-5-fluoro-2,3-dihydro-1H-inden-1-yl]-N-isopropyl-2-(trifluoromethyl)-pyridine-3-carboxylic acid amide |
| H-210 | (3R)-3-[(2-Chloro-5-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide |
| H-211 | (3R)-3-[(2-Chloro-5-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide |
| H-212 | (3R)-3-[(2-Chloro-5-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide |
| H-213 | (3R)-3-[(2-Chloro-benzoyl)amino]-N-[1-(2,6-dimethyl-pyrimidin-4-yl)-piperidin-4-yl]-6-fluoro-N-methyl-2,3-dihydro-1H-indene-5-carboxylic acid amide |
| H-214 | (3R)-3-[(2-Chloro-benzoyl)amino]-N-methyl-N-[1-(2-methylamino-pyrimidin-4-yl)-piperidin-4-yl]-2,3-dihydro-1H-indene-5-carboxylic acid amide |
| H-215 | (3R)-3-[(2-Chloro-benzoyl)amino]-N-[2-[1-(2,6-dimethyl-pyrimidin-4-yl)-piperidin-4-ylFethyl]-2,3-dihydro-1H-indene-5-carboxylic acid amide |
| H-216 | (3R)-3-[(2-Chloro-benzoyl)amino]-N-[1-(2,6-dimethyl-pyrimidin-4-yl)-piperidin-4-yl]-N-ethyl-2,3-dihydro-1H-indene-5-carboxylic acid amide |
| H-217 | (3R)-3-[(2-Chloro-benzoyl)amino]-N-[1-(2,6-dimethyl-pyrimidin-4-yl)-piperidin-4-yl]-7-fluoro-N-methyl-2,3-dihydro-1H-indene-5-carboxylic acid amide |
| H-219 | (3R)-3-[(2-Chloro-benzoyl)amino]-N-methyl-N-[1-(2-oxo-1H-pyridin-4-yl)-piperidin-4-yl[-2,3-dihydro-1H-indene-5-carboxylic acid amide |
| H-220 | (3R)-3-[(2-Chloro-6-fluoro-benzoyl)-ethyl-amino]-N-methyl-N-(1-pyridin-4-yl-piperidin-4-yl)-2,3-dihydro-1H-indene-5-carboxylic acid amide |
| H-221 | (3R)-3-[(2-Chloro-5-fluoro-benzoyl)-ethyl-amino]-N-methyl-N-(1-pyridin-4-yl-piperidin-4-yl)-2,3-dihydro-1H-indene-5-carboxylic acid amide |
| H-222 | (3R)-3-(3,4-Dimethyl-pentanoylamino)-N-methyl-N-[1-(2-methyl-pyridin-4-yl)-piperidin-4-yl]-2,3-dihydro-1H-indene-5-carboxylic acid amide |
| H-223 | (3R)-3-(3,4-Dimethyl-pentanoylamino)-N-[1-(2,6-dimethyl-pyrimidin-4-yl)-piperidin-4-yl]-N-methyl-2,3-dihydro-1H-indene-5-carboxylic acid amide |
| H-224 | N-[(1R)-6-[[1-(2,6-Dimethyl-pyrimidin-4-yl)-piperidin-4-yl]-methyl-carbamoyl]-2,3-dihydro-1H-inden-1-yl]-3-methoxy-isoxazole-5-carboxylic acid amide |
| H-225 | 3-Methoxy-N-[(1R)-6-[methyl-[-(2-methyl-pyridin-4-yl)-piperidin-4-yl]-carbamoyl]-2,3-dihydro-1H-inden-1-yl]-isoxazole-5-carboxylic acid amide |
| H-226 | (3R)-3-(Cyclopentanecarbonylamino)-N-[1-(2,6-dimethyl-pyrimidin-4-yl)-piperidin-4-yl]-N-methyl-2,3-dihydro-1H-indene-5-carboxylic acid amide |
| H-227 | (3R)-3-(Cyclopentanecarbonylamino)-N-methyl-N-[1-(2-methyl-pyridin-4-yl)-piperidin-4-yl]-2,3-dihydro-1H-indene-5-carboxylic acid amide |
| H-228 | (3R)-3-(Cyclopentanecarbonylamino)-N-[1-(2-dimethylamino-pyrimidin-4-yl)-piperidin-4-yl]-N-methyl-2,3-dihydro-1H-indene-5-carboxylic acid amide |
| H-229 | (3R)-3-(Cyclopentanecarbonyl-ethyl-amino)-N-[1-(2,6-dimethyl-pyrimidin-4-yl)-piperidin-4-yl]-N-methyl-2,3-dihydro-1H-indene-5-carboxylic acid amide |
| H-230 | (3R)-3-(Cyclopentanecarbonyl-methyl-amino)-N-[1-(2,6-dimethyl-pyrimidin-4-yl)-piperidin-4-yl]-N-methyl-2,3-dihydro-1H-indene-5-carboxylic acid amide |
| H-231 | (3R)-3-[(2-Cyclopentyl-acetyl)-methyl-amino]-N-[1-(2,6-dimethyl-pyrimidin-4-yl)-piperidin-4-yl]-N-methyl-2,3-dihydro-1H-indene-5-carboxylic acid amide |
| H-232 | (3R)-3-(3,4-Dimethyl-pentanoyl-methyl-amino)-N-[1-(2,6-dimethyl-pyrimidin-4-yl)-piperidin-4-yl]-N-methyl-2,3-dihydro-1H-indene-5-carboxylic acid amide |
| H-233 | (3R)-3-(3,4-Dimethyl-pentanoyl-ethyl-amino)-N-[1-(2,6-dimethyl-pyrimidin-4-yl)-piperidin-4-yl]-N-methyl-2,3-dihydro-1H-indene-5-carboxylic acid amide |
| H-234 | (8R)-8-[(2-Chloro-benzoyl)amino]-N-[1-(2,6-dimethyl-pyrimidin-4-yl)-piperidin-4-yl]-N-methyl-5,6,7,8-tetrahydro-naphthalene-2-carboxylic acid amide |
| H-235 | (8R)-8-(4-Chloro-3-oxo-1,2-dihydro-isoindol-2-yl)-N-[1-(2,6-dimethyl-pyrimidin-4-yl)-piperidin-4-yl]-N-methyl-5,6,7,8-tetrahydro-naphthalene-2-carboxylic acid amide |
| H-236 | (8R)-8-[(2-Chloro-benzoyl)amino]-N-[1-(2-dimethylamino-pyrimidin-4-yl)-piperidin-4-yl]-N-methyl-5,6,7,8-tetrahydro-naphthalene-2-carboxylic acid amide |
| H-237 | (8R)-8-[(2-Chloro-benzoyl)amino]-N-[1-(2-dimethylamino-6-methyl-pyrimidin-4-yl)-piperidin-4-yl]-N-methyl-5,6,7,8-tetrahydro-naphthalene-2-carboxylic acid amide |
| H-238 | (3R)-3-[(2-Cyclopentyl-acetyl)amino]-N-[1-(2,6-dimethyl-pyrimidin-4-yl)-piperidin-4-yl]-N-methyl-2,3-dihydro-1H-indene-5-carboxylic acid amide |
| H-239 | N-[(1R)-6-[[1-(2-Dimethylamino-pyrimidin-4-yl)-piperidin-4-yl]-methyl-carbamoyl]-2,3-dihydro-1H-inden-1-yl]-3-methoxy-isoxazole-5-carboxylic acid amide |
| H-240 | (8R)-N-[1-(2,6-Dimethyl-pyrimidin-4-yl)-piperidin-4-yl]-N-methyl-8-(3-methyl-butanoylamino)-5,6,7,8-tetrahydro-naphthalene-2-carboxylic acid amide |
| H-241 | (3R)-3-[(2-Chloro-benzoyl)amino]-N-methyl-N-[1-(2-pyrrolidin-1-yl-pyrimidin-4-yl)-piperidin-4-yl]-2,3-dihydro-1H-indene-5-carboxylic acid amide |
| H-242 | (8R)-8-[(2-Chloro-benzoyl)amino]-N-methyl-N-(1-pyridin-4-yl-piperidin-4-yl)-5,6,7,8-tetrahydro-naphthalene-2-carboxylic acid amide |
| H-243 | (3R)-3-[(2-Chloro-benzoyl)amino]-N-[1-(2-dimethylamino-6-methyl-pyrimidin-4-yl)-piperidin-4-yl]-N-methyl-2,3-dihydro-1H-indene-5-carboxylic acid amide |
| H-244 | (3R)-N-[1-(2-Amino-pyrimidin-4-yl)-piperidin-4-yl]-3-[(2-chloro-benzoyl)amino]-N-methyl-2,3-dihydro-1H-indene-5-carboxylic acid amide |

-continued

| | |
|---|---|
| CC_H-01 | 3-Chloro-N-[6-[2-(1-pyridin-4-yl-piperidin-4-yl)-ethyl-carbamoyl]-2,3-dihydro-1H-inden-1-yl]-thiophene-2-carboxylic acid amide |
| CC_H-02 | 3-[[(2-Chlorophenyl)-methyl-carbamoyl]amino]-N-[2-(1-pyridin-4-yl-piperidin-4-yl)-ethyl]-2,3-dihydro-1H-indene-5-carboxylic acid amide |
| CC_H-03 | 8-[(2,3-Dichloro-benzoyl)amino]-N-methyl-N-(1-pyridin-4-yl-piperidin-4-yl)-5,6,7,8-tetrahydro-naphthalene-2-carboxylic acid amide |
| CC_H-04 | 8-[(2-Chloro-5-fluoro-benzoyl)amino]-N-methyl-N-(1-pyridin-4-yl-piperidin-4-yl)-5,6,7,8-tetrahydro-naphthalene-2-carboxylic acid amide |
| CC_H-05 | 8-(Cyclohexanecarbonylamino)-N-methyl-N-(1-pyridin-4-yl-piperidin-4-yl)-5,6,7,8-tetrahydro-naphthalene-2-carboxylic acid amide |
| CC_H-06 | 8-(3-Cyclopentyl-propanoylamino)-N-methyl-N-(1-pyridin-4-yl-piperidin-4-yl)-5,6,7,8-tetrahydro-naphthalene-2-carboxylic acid amide |
| CC_H-07 | 3-Chloro-N-[7-[methyl-(1-pyridin-4-yl-piperidin-4-yl)-carbamoyl]-1,2,3,4-tetrahydro-naphthalen-1-yl]-thiophene-2-carboxylic acid amide |
| CC_H-08 | N-[7-[Methyl-(1-pyridin-4-yl-piperidin-4-yl)-carbamoyl]-1,2,3,4-tetrahydro-naphthalen-1-yl]-pyrimidine-5-carboxylic acid amide |
| CC_H-09 | 8-[(2,6-Dimethyl-benzoyl)amino]-N-methyl-N-(1-pyridin-4-yl-piperidin-4-yl)-5,6,7,8-tetrahydro-naphthalene-2-carboxylic acid amide |
| CC_H-10 | N-[7-[Methyl-(1-pyridin-4-yl-piperidin-4-yl)-carbamoyl]-1,2,3,4-tetrahydro-naphthalen-1-yl]-4-(trifluoromethyl)-pyridine-3-carboxylic acid amide |
| CC_H-11 | 8-[[2-Chloro-6-(trifluoromethyl)-benzoyl]amino]-N-methyl-N-(1-pyridin-4-yl-piperidin-4-yl)-5,6,7,8-tetrahydro-naphthalene-2-carboxylic acid amide |
| CC_H-12 | N-[3,3-Dimethyl-6-[methyl-(1-pyridin-4-yl-piperidin-4-yl)-carbamoyl]-1,2-dihydro-inden-1-yl]-4-(trifluoromethyl)-pyridine-3-carboxylic acid amide |
| CC_H-13 | 3-Chloro-N-[5-[methyl-(1-pyridin-4-yl-piperidin-4-yl)-carbamoyl]-2,3-dihydro-1H-inden-1-yl]-thiophene-2-carboxylic acid amide |
| CC_H-14 | 3-(Cyclohexanecarbonylamino)-N,1,1-trimethyl-N-(1-pyridin-4-yl-piperidin-4-yl)-2,3-dihydro-indene-5-carboxylic acid amide |
| CC_H-15 | 3-[[(2-Chlorophenyl)-methyl-carbamoyl]amino]-N,1,1-trimethyl-N-(1-pyridin-4-yl-piperidin-4-yl)-2,3-dihydro-indene-5-carboxylic acid amide |
| CC_H-16 | 8-[[[2-Chloro-6-(trifluoromethyl)-phenyl]sulfonyl]amino]-N-methyl-N-(1-pyridin-4-yl-piperidin-4-yl)-5,6,7,8-tetrahydro-naphthalene-2-carboxylic acid amide |
| CC_H-17 | 3-[[2-Chloro-6-(trifluoromethyl)-benzoyl]amino]-N,1,1-trimethyl-N-(1-pyridin-4-yl-piperidin-4-yl)-2,3-dihydro-indene-5-carboxylic acid amide |
| CC_H-18 | 3-(3-Cyclopentyl-propanoylamino)-N,1,1-trimethyl-N-(1-pyridin-4-yl-piperidin-4-yl)-2,3-dihydro-indene-5-carboxylic acid amide |
| CC_H-19 | 3-[(2,3-Dichloro-benzoyl)amino]-N,1,1-trimethyl-N-(1-pyridin-4-yl-piperidin-4-yl)-2,3-dihydro-indene-5-carboxylic acid amide |
| CC_H-20 | 3-Chloro-N-[3,3-dimethyl-6-[methyl-(1-pyridin-4-yl-piperidin-4-yl)-carbamoyl]-1,2-dihydro-inden-1-yl]-thiophene-2-carboxylic acid amide |
| CC_H-21 | 3-[(2-Chloro-5-fluoro-benzoyl)amino]-N,1,1-trimethyl-N-(1-pyridin-4-yl-piperidin-4-yl)-2,3-dihydro-indene-5-carboxylic acid amide |
| CC_H-22 | N-[3,3-Dimethyl-6-[methyl-(1-pyridin-4-yl-piperidin-4-yl)-carbamoyl]-1,2-dihydro-inden-1-yl]-pyrimidine-5-carboxylic acid amide |
| CC_H-23 | 3-[(2-Chloro-benzoyl)amino]-N,1,1-trimethyl-N-(1-pyridin-4-yl-piperidin-4-yl)-2,3-dihydro-indene-5-carboxylic acid amide |
| CC_H-24 | 3-[(2-Chloro-benzoyl)amino]-N-methyl-N-(1-pyridin-4-yl-piperidin-4-yl)-2,3-dihydro-1H-indene-5-carboxylic acid amide |
| CC_H-25 | 3-[(2,3-Dichloro-benzoyl)-methyl-amino]-N-methyl-N-(1-pyridin-4-yl-piperidin-4-yl)-2,3-dihydro-1H-indene-5-carboxylic acid amide |
| CC_H-26 | 3-[(2-Chloro-5-fluoro-benzoyl)amino]-N-methyl-N-(1-pyridin-4-yl-piperidin-4-yl)-2,3-dihydro-1H-indene-5-carboxylic acid amide |
| CC_H-27 | 3-[(2-Chloro-5-fluoro-benzoyl)-methyl-amino]-N-methyl-N-(1-pyridin-4-yl-piperidin-4-yl)-2,3-dihydro-1H-indene-5-carboxylic acid amide |
| CC_H-28 | N-Methyl-3-[methyl-(3-methyl-butanoyl)-amino]-N-(1-pyridin-4-yl-piperidin-4-yl)-2,3-dihydro-1H-indene-5-carboxylic acid amide |
| CC_H-29 | 3-Chloro-N-[6-[methyl-(1-pyridin-4-yl-piperidin-4-yl)-carbamoyl]-2,3-dihydro-1H-inden-1-yl]-thiophene-2-carboxylic acid amide |
| CC_H-30 | 3-Chloro-N-methyl-N-[6-[methyl-(1-pyridin-4-yl-piperidin-4-yl)-carbamoyl]-2,3-dihydro-1H-inden-1-yl]-thiophene-2-carboxylic acid amide |
| CC_H-31 | N-[6-[Methyl-(1-pyridin-4-yl-piperidin-4-yl)-carbamoyl]-2,3-dihydro-1H-inden-1-yl]-4-(trifluoromethyl)-pyridine-3-carboxylic acid amide |
| CC_H-32 | N-Methyl-N-[6-[methyl-(1-pyridin-4-yl-piperidin-4-yl)-carbamoyl]-2,3-dihydro-1H-inden-1-yl]-4-(trifluoromethyl)-pyridine-3-carboxylic acid amide |
| CC_H-33 | 4-[(2-Chloro-benzoyl)amino]-N-methyl-N-(1-pyridin-4-yl-piperidin-4-yl)-3,4-dihydro-2H-chromene-6-carboxylic acid amide |
| CC_H-34 | 3-[(2-Chloro-benzoyl)amino]-N-[2-(1-pyridin-4-yl-piperidin-4-yl)-ethyl]-2,3-dihydro-1H-indene-5-carboxylic acid amide |
| CC_H-35 | 4-[(2,3-Dichloro-benzoyl)amino]-N-methyl-N-(1-pyridin-4-yl-piperidin-4-yl)-3,4-dihydro-2H-chromene-6-carboxylic acid amide |
| CC_H-36 | 3-[(2-Chloro-5-fluoro-benzoyl)amino]-N-[2-(1-pyridin-4-yl-piperidin-4-yl)-ethyl]-2,3-dihydro-1H-indene-5-carboxylic acid amide |
| CC_H-37 | N-[6-[2-(1-Pyridin-4-yl-piperidin-4-yl)-ethyl-carbamoyl]-2,3-dihydro-1H-inden-1-yl]-4-(trifluoromethyl)-pyridine-3-carboxylic acid amide |
| CC_H-38 | 4-(Cyclohexanecarbonylamino)-N-methyl-N-(1-pyridin-4-yl-piperidin-4-yl)-3,4-dihydro-2H-chromene-6-carboxylic acid amide |
| CC_H-39 | N-Methyl-4-(3-methyl-butanoylamino)-N-(1-pyridin-4-yl-piperidin-4-yl)-3,4-dihydro-2H-chromene-6-carboxylic acid amide |
| CC_H-40 | 4-[(3-Chloro-thiophene-2-carbonyl)amino]-N-methyl-N-(1-pyridin-4-yl-piperidin-4-yl)-3,4-dihydro-2H-chromene-6-carboxylic acid amide |

-continued

| | |
|---|---|
| CC_H-41 | N-Methyl-3-(3-methyl-butanoylamino)-N-(1-pyridin-4-yl-piperidin-4-yl)-2,3-dihydro-1H-indene-5-carboxylic acid amide |
| CC_H-42 | N-[6-[Methyl-(1-pyridin-4-yl-piperidin-4-yl)-carbamoyl]-3,4-dihydro-2H-chromen-4-yl]-4-(trifluoromethyl)-pyridine-3-carboxylic acid amide |
| CC_H-43 | N,1,1-Trimethyl-3-(3-methyl-butanoylamino)-N-(1-pyridin-4-yl-piperidin-4-yl)-2,3-dihydro-indene-5-carboxylic acid amide |
| CC_H-44 | 3-[[(2-Chlorophenyl)-methyl-carbamoyl]amino]-N-methyl-N-(1-pyridin-4-yl-piperidin-4-yl)-2,3-dihydro-1H-indene-5-carboxylic acid amide |
| CC_H-45 | N-Methyl-N-[6-[methyl-(1-pyridin-4-yl-piperidin-4-yl)-carbamoyl]-2,3-dihydro-1H-inden-1-yl]-pyrimidine-5-carboxylic acid amide |
| CC_H-46 | N-Methyl-3-[methyl-R2-(trifluoromethyl)-phenyl]-methylsulfonyl]-amino]-N-(1-pyridin-4-yl-piperidin-4-yl)-2,3-dihydro-1H-indene-5-carboxylic acid amide |
| CC_H-47 | 4-[[[2-Chloro-6-(trifluoromethyl)-phenyl]sulfonyl]amino]-N-methyl-N-(1-pyridin-4-yl-piperidin-4-yl)-3,4-dihydro-2H-chromene-6-carboxylic acid amide |
| CC_H-48 | N-[6-[Methyl-(1-pyridin-4-yl-piperidin-4-yl)-carbamoyl]-2,3-dihydro-1H-inden-1-yl]-pyrimidine-5-carboxylic acid amide |
| CC_H-49 | 4-(3-Cyclopentyl-propanoylamino)-N-methyl-N-(1-pyridin-4-yl-piperidin-4-yl)-3,4-dihydro-2H-chromene-6-carboxylic acid amide |
| CC_H-50 | 3-[[[2-Chloro-6-(trifluoromethyl)-phenyl]sulfonyl]amino]-N-[2-(1-pyridin-4-yl-piperidin-4-yl)-ethyl]-2,3-dihydro-1H-indene-5-carboxylic acid amide |
| CC_H-51 | 3-[[(2-Chlorophenyl)-methyl-carbamoyl]-methyl-amino]-N-methyl-N-(1-pyridin-4-yl-piperidin-4-yl)-2,3-dihydro-1H-indene-5-carboxylic acid amide |
| CC_H-52 | 3-[(2,3-Dichloro-benzoyl)amino]-N-(1-isoquinolin-6-yl-piperidin-4-yl)-N-methyl-2,3-dihydro-1H-indene-5-carboxylic acid amide |
| CC_H-53 | N-[5-[Methyl-(1-pyridin-4-yl-piperidin-4-yl)-carbamoyl]-2,3-dihydro-1H-inden-1-yl]-pyrimidin-5-carboxylic acid amide |
| CC_H-54 | 3-[[[2-Chloro-6-(trifluoromethyl)-phenyl]sulfonyl]amino]-N-methyl-N-(1-pyridin-4-yl-piperidin-4-yl)-2,3-dihydro-1H-indene-5-carboxylic acid amide |
| CC_H-55 | N-(1-Isoquinolin-6-yl-piperidin-4-yl)-N-methyl-3-[[[2-(trifluoromethyl)-phenyl]-methylsulfonyl]amino]-2,3-dihydro-1H-indene-5-carboxylic acid amide |
| CC_H-56 | N-Methyl-N-(1-pyridin-4-yl-piperidin-4-yl)-4-[[[2-(trifluoromethyl)-phenyl]-methylsulfonyl]amino]-3,4-dihydro-2H-chromene-6-carboxylic acid amide |
| CC_H-57 | 4-[[(2-Chlorophenyl)-methyl-carbamoyl]amino]-N-methyl-N-(1-pyridin-4-yl-piperidin-4-yl)-3,4-dihydro-2H-chromene-6-carboxylic acid amide |
| CC_H-58 | 1-(Cyclohexanecarbonylamino)-N-methyl-N-(1-pyridin-4-yl-piperidin-4-yl)-2,3-dihydro-1H-indene-5-carboxylic acid amide |
| CC_H-59 | 3-(3-Cyclopentyl-propanoylamino)-N-methyl-N-(1-pyridin-4-yl-piperidin-4-yl)-2,3-dihydro-1H-indene-5-carboxylic acid amide |
| CC_H-60 | N-[6-[(1-Isoquinolin-6-yl-piperidin-4-yl)-methyl-carbamoyl]-2,3-dihydro-1H-inden-1-yl]-4-(trifluoromethyl)-pyridine-3-carboxylic acid amide |
| CC_H-61 | N-Methyl-N-(1-pyridin-4-yl-piperidin-4-yl)-1-[[[2-(trifluoromethyl)-phenyl]-methylsulfonyl]amino]-2,3-dihydro-1H-indene-5-carboxylic acid amide |
| CC_H-62 | 3-[[2-Chloro-6-(trifluoromethyl)-benzoyl]amino]-N-(1-isoquinolin-6-yl-piperidin-4-yl)-N-methyl-2,3-dihydro-1H-indene-5-carboxylic acid amide |
| CC_H-63 | 4-[(2-Chloro-5-fluoro-benzoyl)amino]-N-methyl-N-(1-pyridin-4-yl-piperidin-4-yl)-3,4-dihydro-2H-chromene-6-carboxylic acid amide |
| CC_H-64 | 1-[(2-Chloro-5-fluoro-benzoyl)amino]-N-methyl-N-(1-pyridin-4-yl-piperidin-4-yl)-2,3-dihydro-1H-indene-5-carboxylic acid amide |
| CC_H-65 | 1-(3-Cyclopentyl-propanoylamino)-N-methyl-N-(1-pyridin-4-yl-piperidin-4-yl)-2,3-dihydro-1H-indene-5-carboxylic acid amide |
| CC_H-66 | 1-[(2,6-Dimethyl-benzoyl)amino]-N-methyl-N-(1-pyridin-4-yl-piperidin-4-yl)-2,3-dihydro-1H-indene-5-carboxylic acid amide |
| CC_H-67 | 1-[(2,3-Dichloro-benzoyl)amino]-N-methyl-N-(1-pyridin-4-yl-piperidin-4-yl)-2,3-dihydro-1H-indene-5-carboxylic acid amide |
| CC_H-68 | 1-[(2-Chloro-benzoyl)amino]-N-methyl-N-(1-pyridin-4-yl-piperidin-4-yl)-2,3-dihydro-1H-indene-5-carboxylic acid amide |
| CC_H-69 | 3-(Cyclohexanecarbonyl-methyl-amino)-N-methyl-N-(1-pyridin-4-yl-piperidin-4-yl)-2,3-dihydro-1H-indene-5-carboxylic acid amide |
| CC_H-70 | 3-(3-Cyclopentyl-propanoyl-methyl-amino)-N-methyl-N-(1-pyridin-4-yl-piperidin-4-yl)-2,3-dihydro-1H-indene-5-carboxylic acid amide |
| CC_H-71 | 4-[(2,6-Dimethyl-benzoyl)amino]-N-methyl-N-(1-pyridin-4-yl-piperidin-4-yl)-3,4-dihydro-2H-chromene-6-carboxylic acid amide |
| CC_H-72 | 4-[[2-Chloro-6-(trifluoromethyl)-benzoyl]amino]-N-methyl-N-(1-pyridin-4-yl-piperidin-4-yl)-3,4-dihydro-2H-chromene-6-carboxylic acid amide |
| CC_H-73 | 8-[(2-Chloro-benzoyl)amino]-N-methyl-N-(1-pyridin-4-yl-piperidin-4-yl)-5,6,7,8-tetrahydro-naphthalene-2-carboxylic acid amide |
| CC_H-74 | 3-[(2,3-Dichloro-benzoyl)amino]-N-[2-(1-pyridin-4-yl-piperidin-4-yl)-ethyl]-2,3-dihydro-1H-indene-5-carboxylic acid amide |
| CC_H-75 | 3-[(2-Chloro-benzoyl)amino]-N-(1-isoquinolin-6-yl-piperidin-4-yl)-N-methyl-2,3-dihydro-1H-indene-5-carboxylic acid amide |
| CC_H-76 | 3-[(2-Chloro-5-fluoro-benzoyl)amino]-N-(1-isoquinolin-6-yl-piperidin-4-yl)-N-methyl-2,3-dihydro-1H-indene-5-carboxylic acid amide |
| CC_H-77 | 3-(Cyclohexanecarbonylamino)-N-(1-isoquinolin-6-yl-piperidin-4-yl)-N-methyl-2,3-dihydro-1H-indene-5-carboxylic acid amide |
| CC_H-78 | 3-(3-Cyclopentyl-propanoylamino)-N-(1-isoquinolin-6-yl-piperidin-4-yl)-N-methyl-2,3-dihydro-1H-indene-5-carboxylic acid amide |
| CC_H-79 | N-(1-Isoquinolin-6-yl-piperidin-4-yl)-N-methyl-3-(3-methyl-butanoylamino)-2,3-dihydro-1H-indene-5-carboxylic acid amide |
| CC_H-80 | 3-Chloro-N-[6-[(1-isoquinolin-6-yl-piperidin-4-yl)-methyl-carbamoyl]-2,3-dihydro-1H-inden-1-yl]-thiophene-2-carboxylic acid amide |

-continued

| | |
|---|---|
| CC_H-81 | 3-(Cyclohexanecarbonyl-methyl-amino)-N-[1-(2,6-dimethyl-pyridin-4-yl)-piperidin-4-yl]-N-methyl-2,3-dihydro-1H-indene-5-carboxylic acid amide |
| CC_H-82 | 3-[(2-Chloro-5-fluoro-benzoyl)-methyl-amino]-N-[1-(2,6-dimethyl-pyridin-4-yl)-piperidin-4-yl]-N-methyl-2,3-dihydro-1H-indene-5-carboxylic acid amide |
| CC_H-83 | 3-[(2,3-Dichloro-benzoyl)-methyl-amino]-N-[1-(2,6-dimethyl-pyridin-4-yl)-piperidin-4-yl]-N-methyl-2,3-dihydro-1H-indene-5-carboxylic acid amide |
| CC_H-84 | 3-(3-Cyclopentyl-propanoyl-methyl-amino)-N-[1-(2,6-dimethyl-pyridin-4-yl)-piperidin-4-yl]-N-methyl-2,3-dihydro-1H-indene-5-carboxylic acid amide |
| CC_H-85 | 3-[(2,6-Dimethyl-benzoyl)amino]-N,1,1-trimethyl-N-(1-pyridin-4-yl-piperidin-4-yl)-2,3-dihydro-indene-5-carboxylic acid amide |
| CC_H-86 | N-[6-[[1-(2,6-Dimethyl-pyridin-4-yl)-piperidin-4-yl]-methyl-carbamoyl]-2,3-dihydro-1H-inden-1-yl]-N-methyl-4-(trifluoromethyl)-pyridine-3-carboxylic acid amide |
| CC_H-87 | 3-[(2-Chloro-benzoyl)-methyl-amino]-N-[1-(2,6-dimethyl-pyridin-4-yl)-piperidin-4-yl]-N-methyl-2,3-dihydro-1H-indene-5-carboxylic acid amide |
| CC_H-88 | 3-Chloro-N-[6-[[1-(2,6-dimethyl-pyridin-4-yl)-piperidin-4-yl]-methyl-carbamoyl]-2,3-dihydro-1H-inden-1-yl]-N-methyl-thiophene-2-carboxylic acid amide |
| CC_H-89 | N,1,1-Trimethyl-N-(1-pyridin-4-yl-piperidin-4-yl)-3-[[[2-(trifluoromethyl)-phenyl]-methylsulfonyl]amino]-2,3-dihydro-indene-5-carboxylic acid amide |
| CC_H-90 | N-[1-(2,6-Dimethyl-pyridin-4-yl)-piperidin-4-yl]-N-methyl-34methyl-(3-methyl-butanoyl)-amino]-2,3-dihydro-1H-indene-5-carboxylic acid amide |
| CC_H-91 | 3-[(2,6-Dimethyl-benzoyl)-methyl-amino]-N-[1-(2,6-dimethyl-pyridin-4-yl)-piperidin-4-yl]-N-methyl-2,3-dihydro-1H-indene-5-carboxylic acid amide |
| CC_H-92 | N-[6-[[1-(2,6-Dimethyl-pyridin-4-yl)-piperidin-4-yl]-methyl-carbamoyl]-2,3-dihydro-1H-inden-1-yl]-N-methyl-pyrimidine-5-carboxylic acid amide |
| CC_H-93 | 3-[[[2-Chloro-6-(trifluoromethyl)-phenyl]sulfonyl]amino]-N,1,1-trimethyl-N-(1-pyridin-4-yl-piperidin-4-yl)-2,3-dihydro-indene-5-carboxylic acid amide |
| CC_H-94 | 8-[[(2-Chlorophenyl)-methyl-carbamoyl]amino]-N-methyl-N-(1-pyridin-4-yl-piperidin-4-yl)-5,6,7,8-tetrahydro-naphthalene-2-carboxylic acid amide |
| CC_H-95 | 3-[[2-(2-Chlorophenyl)-2-methyl-propanoyl]amino]-N,1,1-trimethyl-N-(1-pyridin-4-yl-piperidin-4-yl)-2,3-dihydro-indene-5-carboxylic acid amide |
| CC_H-96 | 3-[(2,3-Dichloro-benzoyl)amino]-N-[1-(2,6-dimethyl-pyridin-4-yl)-piperidin-4-yl]-N-methyl-2,3-dihydro-1H-indene-5-carboxylic acid amide |
| CC_H-97 | 4-[[2-(2-Chlorophenyl)-2-methyl-propanoyl]amino]-N-methyl-N-(1-pyridin-4-yl-piperidin-4-yl)-3,4-dihydro-2H-chromene-6-carboxylic acid amide |
| CC_H-98 | 3-[[2-(2-Chlorophenyl)-2-methyl-propanoyl]amino]-N-(1-isoquinolin-6-yl-piperidin-4-yl)-N-methyl-2,3-dihydro-1H-indene-5-carboxylic acid amide |
| CC_H-99 | 3-[(2-Chloro-benzoyl)amino]-N-[1-(2,6-dimethyl-pyridin-4-yl)-piperidin-4-yl]-N-methyl-2,3-dihydro-1H-indene-5-carboxylic acid amide |
| CC_H-100 | 1-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide |
| CC_H-101 | 3-(3-Cyclopentyl-propanoylamino)-N-[2-(1-pyridin-4-yl-piperidin-4-yl)-ethyl]-2,3-dihydro-1H-indene-5-carboxylic acid amide |
| CC_H-102 | 8-[[2-(2-Chlorophenyl)-2-methyl-propanoyl]amino]-N-methyl-N-(1-pyridin-4-yl-piperidin-4-yl)-5,6,7,8-tetrahydro-naphthalene-2-carboxylic acid amide |
| CC_H-103 | 3-[[2-(2-Chlorophenyl)-2-methyl-propanoyl]amino]-N-[2-(1-pyridin-4-yl-piperidin-4-yl)-ethyl]-2,3-dihydro-1H-indene-5-carboxylic acid amide |
| CC_H-104 | 3-[[(2-Chlorophenyl)-methyl-carbamoyl]amino]-N-(1-isoquinolin-6-yl-piperidin-4-yl)-N-methyl-2,3-dihydro-1H-indene-5-carboxylic acid amide |
| CC_H-105 | 3-[(2,6-Dimethyl-benzoyl)amino]-N-[2-(1-pyridin-4-yl-piperidin-4-yl)-ethyl]-2,3-dihydro-1H-indene-5-carboxylic acid amide |
| CC_H-106 | 3-[(2-Chloro-benzoyl)-methyl-amino]-N-methyl-N-(1-pyridin-4-yl-piperidin-4-yl)-2,3-dihydro-1H-indene-5-carboxylic acid amide |
| CC_H-107 | 3-[[2-Chloro-6-(trifluoromethyl)-benzoyl]amino]-N-[1-(2,6-dimethyl-pyridin-4-yl)-piperidin-4-yl]-N-methyl-2,3-dihydro-1H-indene-5-carboxylic acid amide |
| CC_H-108 | 3-[[2-Chloro-6-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide |
| CC_H-109 | 3-Chloro-N-[6-[[1-(2,6-dimethyl-pyridin-4-yl)-piperidin-4-yl]-methyl-carbamoyl]-2,3-dihydro-1H-inden-1-yl]-thiophene-2-carboxylic acid amide |
| CC_H-110 | N-[5-[Methyl-(1-pyridin-4-yl-piperidin-4-yl)-carbamoyl]-2,3-dihydro-1H-inden-1-yl]-4-(trifluoromethyl)-pyridine-3-carboxylic acid amide |
| CC_H-111 | 3-[[[2-Chloro-6-(trifluoromethyl)-phenyl]sulfonyl]amino]-N-[1-(2,6-dimethyl-pyridin-4-yl)-piperidin-4-yl]-N-methyl-2,3-dihydro-1H-indene-5-carboxylic acid amide |
| CC_H-112 | N-[6-[[1-(2,6-Dimethyl-pyridin-4-yl)-piperidin-4-yl]-methyl-carbamoyl]-2,3-dihydro-1H-inden-1-yl]-4-(trifluoromethyl)-pyridine-3-carboxylic acid amide |
| CC_H-113 | N-Methyl-1-(3-methyl-butanoylamino)-N-(1-pyridin-4-yl-piperidin-4-yl)-2,3-dihydro-1H-indene-5-carboxylic acid amide |
| CC_H-114 | N-[6-[2-(1-Pyridin-4-yl-piperidin-4-yl)-ethyl-carbamoyl]-2,3-dihydro-1H-inden-1-yl]-pyrimidine-5-carboxylic acid amide |
| CC_H-115 | 3-[(2,6-Dimethyl-benzoyl)amino]-N-[1-(2,6-dimethyl-pyridin-4-yl)-piperidin-4-yl]-N-methyl-2,3-dihydro-1H-indene-5-carboxylic acid amide |
| CC_H-116 | 3-(Cyclohexanecarbonylamino)-N-[2-(1-pyridin-4-yl-piperidin-4-yl)-ethyl]-2,3-dihydro-1H-indene-5-carboxylic acid amide |
| CC_H-117 | 3-[(2,3-Dichloro-benzoyl)amino]-N-methyl-N-(1-pyridin-4-yl-piperidin-4-yl)-2,3-dihydro-1H-indene-5-carboxylic acid amide |
| CC_H-118 | N-[6-[[1-(2,6-Dimethyl-pyridin-4-yl)-piperidin-4-yl]-methyl-carbamoyl]-2,3-dihydro-1H-inden-1-yl]-pyrimidine-5-carboxylic acid amide |

-continued

| | |
|---|---|
| CC_H-119 | 3-[(2-Chloro-5-fluoro-benzoyl)amino]-N-[1-(2,6-dimethyl-pyridin-4-yl)-piperidin-4-yl]-N-methyl-2,3-dihydro-1H-indene-5-carboxylic acid amide |
| CC_H-120 | 3-(3-Cyclopentyl-propanoylamino)-N-[1-(2,6-dimethyl-pyridin-4-yl)-piperidin-4-yl]-N-methyl-2,3-dihydro-1H-indene-5-carboxylic acid amide |
| CC_H-121 | N-[1-(2,6-Dimethyl-pyridin-4-yl)-piperidin-4-yl]-N-methyl-3-[[[2-(trifluoromethyl)-phenyl]-methylsulfonyl]amino]-2,3-dihydro-1H-indene-5-carboxylic acid amide |
| CC_H-122 | N-[1-(2,6-Dimethyl-pyridin-4-yl)-piperidin-4-yl]-N-methyl-3-(3-methyl-butanoylamino)-2,3-dihydro-1H-indene-5-carboxylic acid amide |
| CC_H-123 | 3-(Cyclohexanecarbonylamino)-N-[1-(2,6-dimethyl-pyridin-4-yl)-piperidin-4-yl]-N-methyl-2,3-dihydro-1H-indene-5-carboxylic acid amide |
| CC_H-124 | N-[6-[Methyl-(1-pyridin-4-yl-piperidin-4-yl)-carbamoyl]-3,4-dihydro-2H-chromen-4-yl]-pyrimidine-5-carboxylic acid amide |
| CC_H-125 | N-Methyl-N-(1-pyridin-4-yl-piperidin-4-yl)-8-[[[2-(trifluoromethyl)-phenyl]-methylsulfonyl]amino]-5,6,7,8-tetrahydro-naphthalene-2-carboxylic acid amide |
| CC_H-126 | 1-[[[(2-Chlorophenyl)-methyl-carbamoyl]amino]-N-methyl-N-(1-pyridin-4-yl-piperidin-4-yl)-2,3-dihydro-1H-indene-5-carboxylic acid amide |
| CC_H-127 | 1-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide |
| CC_H-128 | N-[2-(1-Pyridin-4-yl-piperidin-4-yl)-ethyl]-3-[[[2-(trifluoromethyl)-phenyl]-methylsulfonyl]amino]-2,3-dihydro-1H-indene-5-carboxylic acid amide |
| CC_H-129 | N-[1-(2,6-Dimethyl-pyridin-4-yl)-piperidin-4-yl]-N-methyl-3-[methyl-[[2-(trifluoromethyl)-phenyl]-methylsulfonyl]-amino]-2,3-dihydro-1H-indene-5-carboxylic acid amide |
| CC_H-130 | N-[6-[(1-Isoquinolin-6-yl-piperidin-4-yl)-methyl-carbamoyl]-2,3-dihydro-1H-inden-1-yl]-pyrimidine-5-carboxylic acid amide |
| CC_H-131 | 3-[[2-(2-Chlorophenyl)-2-methyl-propanoyl]amino]-N-[1-(2,6-dimethyl-pyridin-4-yl)-piperidin-4-yl]-N-methyl-2,3-dihydro-1H-indene-5-carboxylic acid amide |
| CC_H-132 | 3-(3-Methyl-butanoylamino)-N-[2-(1-pyridin-4-yl-piperidin-4-yl)-ethyl]-2,3-dihydro-1H-indene-5-carboxylic acid amide |
| CC_H-133 | 3-[(2,6-Dimethyl-benzoyl)amino]-N-(1-isoquinolin-6-yl-piperidin-4-yl)-N-methyl-2,3-dihydro-1H-indene-5-carboxylic acid amide |
| CC_H-134 | 3-[[[2-Chloro-6-(trifluoromethyl)-phenyl]sulfonyl]-methyl-amino]-N-[1-(2,6-dimethyl-pyridin-4-yl)-piperidin-4-yl]-N-methyl-2,3-dihydro-1H-indene-5-carboxylic acid amide |
| CC_H-135 | N-Methyl-8-(3-methyl-butanoylamino)-N-(1-pyridin-4-yl-piperidin-4-yl)-5,6,7,8-tetrahydro-naphthalene-2-carboxylic acid amide |
| CC_H-136 | 3-[[2-Chloro-6-(trifluoromethyl)-benzoyl]amino]-N-[2-(1-pyridin-4-yl-piperidin-4-yl)-ethyl]-2,3-dihydro-1H-indene-5-carboxylic acid amide |
| CC_H-137 | 3-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide |
| CC_H-138 | 3-[(2,6-Dimethyl-benzoyl)amino]-N-methyl-N-(1-pyridin-4-yl-piperidin-4-yl)-2,3-dihydro-1H-indene-5-carboxylic acid amide |
| CC_H-139 | 3-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide |
| CC_H-140 | 3-(Cyclohexanecarbonylamino)-N-methyl-N-(1-pyridin-4-yl-piperidin-4-yl)-2,3-dihydro-1H-indene-5-carboxylic acid amide |
| CC_H-141 | N-Methyl-N-(1-pyridin-4-yl-piperidin-4-yl)-3-[[[2-(trifluoromethyl)-phenyl]-methylsulfonyl]amino]-2,3-dihydro-1H-indene-5-carboxylic acid amide |
| CC_H-142 | 3-[[(2-Chlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide |
| CC_H-143 | 1-[[[2-Chloro-6-(trifluoromethyl)-phenyl]sulfonyl]amino]-N-methyl-N-(1-pyridin-4-yl-piperidin-4-yl)-2,3-dihydro-1H-indene-5-carboxylic acid amide |
| CC_H-200 | 3-[(2-Chloro-5-fluoro-benzoyl)amino]-N-methyl-N-(1-pyridin-4-yl-piperidin-4-yl)-2,3-dihydro-1H-indene-5-carboxylic acid amide, |
| CC_H-201 | 3-[[2-Chloro-5-(trifluoromethyl)-benzoyl]amino]-N-methyl-N-(1-pyridin-4-yl-piperidin-4-yl)-2,3-dihydro-1H-indene-5-carboxylic acid amide, |
| CC_H-202 | 3-[(2-Chloro-6-fluoro-3-methyl-benzoyl)amino]-N-methyl-N-(1-pyridin-4-yl-piperidin-4-yl)-2,3-dihydro-1H-indene-5-carboxylic acid amide, |
| CC_H-203 | 3-[(2,5-Dichloro-benzoyl)amino]-N-methyl-N-(1-pyridin-4-yl-piperidin-4-yl)-2,3-dihydro-1H-indene-5-carboxylic acid amide, |
| CC_H-204 | 3-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide, |
| CC_H-205 | 3-(Cyclopropanecarbonylamino)-N-methyl-N-(1-pyridin-4-yl-piperidin-4-yl)-2,3-dihydro-1H-indene-5-carboxylic acid amide, |
| CC_H-206 | 3-(3,3-Dimethyl-butanoylamino)-N-methyl-N-(1-pyridin-4-yl-piperidin-4-yl)-2,3-dihydro-1H-indene-5-carboxylic acid amide, |
| CC_H-207 | 3-[(2-Methoxy-acetyl)amino]-N-methyl-N-(1-pyridin-4-yl-piperidin-4-yl)-2,3-dihydro-1H-indene-5-carboxylic acid amide, |
| CC_H-208 | 3-[(2-Chloro-5-fluoro-benzoyl)-methyl-amino]-N-methyl-N-(1-pyridin-4-yl-piperidin-4-yl)-2,3-dihydro-1H-indene-5-carboxylic acid amide, |
| CC_H-209 | 3-[(2-Chloro-6-fluoro-3-methyl-benzoyl)-methyl-amino]-N-methyl-N-(1-pyridin-4-yl-piperidin-4-yl)-2,3-dihydro-1H-indene-5-carboxylic acid amide, |
| CC_H-210 | 3-[(2,5-Dichloro-benzoyl)-methyl-amino]-N-methyl-N-(1-pyridin-4-yl-piperidin-4-yl)-2,3-dihydro-1H-indene-5-carboxylic acid amide, |
| CC_H-211 | 3-(Cyclohexanecarbonyl-methyl-amino)-N-methyl-N-(1-pyridin-4-yl-piperidin-4-yl)-2,3-dihydro-1H-indene-5-carboxylic acid amide, |
| CC_H-212 | 3-(Cyclopropanecarbonyl-methyl-amino)-N-methyl-N-(1-pyridin-4-yl-piperidin-4-yl)-2,3-dihydro-1H-indene-5-carboxylic acid amide, |
| CC_H-213 | 3-(3,3-Dimethyl-butanoyl-methyl-amino)-N-methyl-N-(1-pyridin-4-yl-piperidin-4-yl)-2,3-dihydro-1H-indene-5-carboxylic acid amide, |

-continued

CC_H-214 3-[(2-Methoxy-acetyl)-methyl-amino]-N-methyl-N-(1-pyridin-4-yl-piperidin-4-yl)-2,3-dihydro-1H-indene-5-carboxylic acid amide,
CC_H-215 3-(Acetyl-methyl-amino)-N-methyl-N-(1-pyridin-4-yl-piperidin-4-yl)-2,3-dihydro-1H-indene-5-carboxylic acid amide,
CC_H-216 3-[[2-Chloro-3-(trifluoromethyl)-benzoyl]-methyl-amino]-N-methyl-N-(1-pyridin-4-yl-piperidin-4-yl)-2,3-dihydro-1H-indene-5-carboxylic acid amide,
CC_H-217 3-[[(2-Chlorophenyl)-carbamoyl]-methyl-amino]-N-methyl-N-(1-pyridin-4-yl-piperidin-4-yl)-2,3-dihydro-1H-indene-5-carboxylic acid amide,
CC_H-218 3-[[(3-Chlorophenyl)-carbamoyl]-methyl-amino]-N-methyl-N-(1-pyridin-4-yl-piperidin-4-yl)-2,3-dihydro-1H-indene-5-carboxylic acid amide,
CC_H-219 3-[[(2,6-Dichloro-phenyl)-carbamoyl]-methyl-amino]-N-methyl-N-(1-pyridin-4-yl-piperidin-4-yl)-2,3-dihydro-1H-indene-5-carboxylic acid amide,
CC_H-220 3-[[(2,3-Dichloro-phenyl)-carbamoyl]-methyl-amino]-N-methyl-N-(1-pyridin-4-yl-piperidin-4-yl)-2,3-dihydro-1H-indene-5-carboxylic acid amide,
CC_H-221 3-[[(2,5-Dichloro-phenyl)-carbamoyl]-methyl-amino]-N-methyl-N-(1-pyridin-4-yl-piperidin-4-yl)-2,3-dihydro-1H-indene-5-carboxylic acid amide,
CC_H-222 3-[(2-Chloro-5-fluoro-benzoyl)amino]-N,1,1-trimethyl-N-(1-pyridin-4-yl-piperidin-4-yl)-2,3-dihydro-indene-5-carboxylic acid amide,
CC_H-223 3-[[2-Chloro-5-(trifluoromethyl)-benzoyl]amino]-N,1,1-trimethyl-N-(1-pyridin-4-yl-piperidin-4-yl)-2,3-dihydro-indene-5-carboxylic acid amide,
CC_H-224 3-[(2-Chloro-6-fluoro-3-methyl-benzoyl)amino]-N,1,1-trimethyl-N-(1-pyridin-4-yl-piperidin-4-yl)-2,3-dihydro-indene-5-carboxylic acid amide,
CC_H-225 3-[[2-Chloro-6-(trifluoromethyl)-benzoyl]amino]-N,1,1-trimethyl-N-(1-pyridin-4-yl-piperidin-4-yl)-2,3-dihydro-indene-5-carboxylic acid amide,
CC_H-226 3-(Cyclopropanecarbonylamino)-N,1,1-trimethyl-N-(1-pyridin-4-yl-piperidin-4-yl)-2,3-dihydro-indene-5-carboxylic acid amide,
CC_H-227 3-(3,3-Dimethyl-butanoylamino)-N,1,1-trimethyl-N-(1-pyridin-4-yl-piperidin-4-yl)-2,3-dihydro-indene-5-carboxylic acid amide,
CC_H-228 3-[(2-Methoxy-acetyl)amino]-N,1,1-trimethyl-N-(1-pyridin-4-yl-piperidin-4-yl)-2,3-dihydro-indene-5-carboxylic acid amide,
CC_H-229 3-Acetylamino-N,1,1-trimethyl-N-(1-pyridin-4-yl-piperidin-4-yl)-2,3-dihydro-indene-5-carboxylic acid amide,
CC_H-230 3-[[(2-Chloro-6-methyl-phenyl)sulfonyl]amino]-N,1,1-trimethyl-N-(1-pyridin-4-yl-piperidin-4-yl)-2,3-dihydro-indene-5-carboxylic acid amide,
CC_H-231 3-[[2-Chloro-3-(trifluoromethyl)-benzoyl]amino]-N,1,1-trimethyl-N-(1-pyridin-4-yl-piperidin-4-yl)-2,3-dihydro-indene-5-carboxylic acid amide,
CC_H-232 3-[[(2-Chlorophenyl)-carbamoyl]amino]-N,1,1-trimethyl-N-(1-pyridin-4-yl-piperidin-4-yl)-2,3-dihydro-indene-5-carboxylic acid amide,
CC_H-233 3-[[(3-Chlorophenyl)-carbamoyl]amino]-N,1,1-trimethyl-N-(1-pyridin-4-yl-piperidin-4-yl)-2,3-dihydro-indene-5-carboxylic acid amide,
CC_H-234 3-[[(2,6-Dichloro-phenyl)-carbamoyl]amino]-N,1,1-trimethyl-N-(1-pyridin-4-yl-piperidin-4-yl)-2,3-dihydro-indene-5-carboxylic acid amide,
CC_H-235 3-[[(2,3-Dichloro-phenyl)-carbamoyl]amino]-N,1,1-trimethyl-N-(1-pyridin-4-yl-piperidin-4-yl)-2,3-dihydro-indene-5-carboxylic acid amide,
CC_H-236 3-[[(2,5-Dichloro-phenyl)-carbamoyl]amino]-N,1,1-trimethyl-N-(1-pyridin-4-yl-piperidin-4-yl)-2,3-dihydro-indene-5-carboxylic acid amide,
CC_H-237 3-[[(3,5-Dichloro-phenyl)-carbamoyl]amino]-N,1,1-trimethyl-N-(1-pyridin-4-yl-piperidin-4-yl)-2,3-dihydro-indene-5-carboxylic acid amide,
CC_H-238 3-[[(2,4-Dichlorophenyl)-carbamoyl]amino]-N,1,1-trimethyl-N-(1-pyridin-4-yl-piperidin-4-yl)-2,3-dihydro-indene-5-carboxylic acid amide,
CC_H-239 3-[[[2-Chloro-5-(trifluoromethyl)-phenyl]-carbamoyl]amino]-N,1,1-trimethyl-N-(1-pyridin-4-yl-piperidin-4-yl)-2,3-dihydro-indene-5-carboxylic acid amide,
CC_H-240 3-[[[4-Chloro-2-(trifluoromethyl)-phenyl]-carbamoyl]amino]-N,1,1-trimethyl-N-(1-pyridin-4-yl-piperidin-4-yl)-2,3-dihydro-indene-5-carboxylic acid amide,
CC_H-241 3-[[(3-Chloro-4-methyl-phenyl)-carbamoyl]amino]-N,1,1-trimethyl-N-(1-pyridin-4-yl-piperidin-4-yl)-2,3-dihydro-indene-5-carboxylic acid amide,
CC_H-242 3-[[(3-Chloro-4-fluoro-phenyl)-carbamoyl]amino]-N,1,1-trimethyl-N-(1-pyridin-4-yl-piperidin-4-yl)-2,3-dihydro-indene-5-carboxylic acid amide,
CC_H-243 3-[[(2,4-Dimethyl-phenyl)-carbamoyl]amino]-N,1,1-trimethyl-N-(1-pyridin-4-yl-piperidin-4-yl)-2,3-dihydro-indene-5-carboxylic acid amide,
CC_H-244 3-[[(5-Chloro-2-methoxy-phenyl)-carbamoyl]amino]-N,1,1-trimethyl-N-(1-pyridin-4-yl-piperidin-4-yl)-2,3-dihydro-indene-5-carboxylic acid amide,
CC_H-245 3-[[(2-Chlorophenyl)-methyl-carbamoyl]amino]-N,1,1-trimethyl-N-(1-pyridin-4-yl-piperidin-4-yl)-2,3-dihydro-indene-5-carboxylic acid amide,
CC_H-246 8-[(2-Chloro-5-fluoro-benzoyl)amino]-N-methyl-N-(1-pyridin-4-yl-piperidin-4-yl)-5,6,7,8-tetrahydro-naphthalene-2-carboxylic acid amide,
CC_H-247 8-[[2-Chloro-5-(trifluoromethyl)-benzoyl]amino]-N-methyl-N-(1-pyridin-4-yl-piperidin-4-yl)-5,6,7,8-tetrahydro-naphthalene-2-carboxylic acid amide,
CC_H-248 8-[(2-Chloro-6-fluoro-3-methyl-benzoyl)amino]-N-methyl-N-(1-pyridin-4-yl-piperidin-4-yl)-5,6,7,8-tetrahydro-naphthalene-2-carboxylic acid amide,
CC_H-249 8-[[2-Chloro-6-(trifluoromethyl)-benzoyl]amino]-N-methyl-N-(1-pyridin-4-yl-piperidin-4-yl)-5,6,7,8-tetrahydro-naphthalene-2-carboxylic acid amide,
CC_H-250 8-(Cyclopropanecarbonylamino)-N-methyl-N-(1-pyridin-4-yl-piperidin-4-yl)-5,6,7,8-tetrahydro-naphthalene-2-carboxylic acid amide,
CC_H-251 8-(3,3-Dimethyl-butanoylamino)-N-methyl-N-(1-pyridin-4-yl-piperidin-4-yl)-5,6,7,8-tetrahydro-naphthalene-2-carboxylic acid amide,
CC_H-252 8-[(2-Methoxy-acetyl)amino]-N-methyl-N-(1-pyridin-4-yl-piperidin-4-yl)-5,6,7,8-tetrahydro-naphthalene-2-carboxylic acid amide,
CC_H-253 8-Acetylamino-N-methyl-N-(1-pyridin-4-yl-piperidin-4-yl)-5,6,7,8-tetrahydro-naphthalene-2-carboxylic acid amide,

| | |
|---|---|
| CC_H-254 | 8-[[2-Chloro-3-(trifluoromethyl)-benzoyl]amino]-N-methyl-N-(1-pyridin-4-yl-piperidin-4-yl)-5,6,7,8-tetrahydro-naphthalene-2-carboxylic acid amide, |
| CC_H-255 | 8-[[(2-Chlorophenyl)-carbamoyl]amino]-N-methyl-N-(1-pyridin-4-yl-piperidin-4-yl)-5,6,7,8-tetrahydro-naphthalene-2-carboxylic acid amide, |
| CC_H-256 | 8-[[(3-Chlorophenyl)-carbamoyl]amino]-N-methyl-N-(1-pyridin-4-yl-piperidin-4-yl)-5,6,7,8-tetrahydro-naphthalene-2-carboxylic acid amide, |
| CC_H-257 | 8-[[(2,6-Dichloro-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-258 | 8-[[(2,3-Dichloro-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-259 | 8-[[(2,5-Dichloro-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-260 | 8-[[(3,5-Dichloro-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-261 | 8-[[[2-Chloro-5-(trifluoromethyl)-phenyl]-carbamoyl]amino]-N-methyl-N-(1-pyridin-4-yl-piperidin-4-yl)-5,6,7,8-tetrahydro-naphthalene-2-carboxylic acid amide, |
| CC_H-262 | 8-[[(2,4-Dichlorophenyl)-carbamoyl]amino]-N-methyl-N-(1-pyridin-4-yl-piperidin-4-yl)-5,6,7,8-tetrahydro-naphthalene-2-carboxylic acid amide, |
| CC_H-263 | 8-[[[4-Chloro-2-(trifluoromethyl)-phenyl]-carbamoyl]amino]-N-methyl-N-(1-pyridin-4-yl-piperidin-4-yl)-5,6,7,8-tetrahydro-naphthalene-2-carboxylic acid amide, |
| CC_H-264 | 8-[[(3-Chloro-4-methyl-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-265 | 8-[[(3-Chloro-4-fluoro-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-266 | 8-[[(2,4-Dimethyl-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-267 | 8-[[(5-Chloro-2-methoxy-phenyl)-carbamoyl]amino]-N-methyl-N-(1-pyridin-4-yl-piperidin-4-yl)-5,6,7,8-tetrahydro-naphthalene-2-carboxylic acid amide, |
| CC_H-268 | 8-[[(2-Chlorophenyl)-methyl-carbamoyl]amino]-N-methyl-N-(1-pyridin-4-yl-piperidin-4-yl)-5,6,7,8-tetrahydro-naphthalene-2-carboxylic acid amide, |
| CC_H-269 | 8-[[(2,4-Dichlorophenyl)-methyl-carbamoyl]amino]-N-methyl-N-(1-pyridin-4-yl-piperidin-4-yl)-5,6,7,8-tetrahydro-naphthalene-2-carboxylic acid amide, |
| CC_H-270 | 8-[(Cyclohexylsulfonyl)amino]-N-methyl-N-(1-pyridin-4-yl-piperidin-4-yl)-5,6,7,8-tetrahydro-naphthalene-2-carboxylic acid amide, |
| CC_H-271 | N-Methyl-8-(3-methyl-butanoylamino)-N-(1-pyridin-4-yl-piperidin-4-yl)-5,6,7,8-tetrahydro-naphthalene-2-carboxylic acid amide, |
| CC_H-272 | 4-[[2-Chloro-5-(trifluoromethyl)-benzoyl]amino]-N-methyl-N-(1-pyridin-4-yl-piperidin-4-yl)-3,4-dihydro-2H-chromene-6-carboxylic acid amide, |
| CC_H-273 | 4-[(2-Chloro-6-fluoro-3-methyl-benzoyl)amino]-N-methyl-N-(1-pyridin-4-yl-piperidin-4-yl)-3,4-dihydro-2H-chromene-6-carboxylic acid amide, |
| CC_H-274 | 4-(Cyclopropanecarbonylamino)-N-methyl-N-(1-pyridin-4-yl-piperidin-4-yl)-3,4-dihydro-2H-chromene-6-carboxylic acid amide, |
| CC_H-275 | 4-(3,3-Dimethyl-butanoylamino)-N-methyl-N-(1-pyridin-4-yl-piperidin-4-yl)-3,4-dihydro-2H-chromene-6-carboxylic acid amide, |
| CC_H-276 | 4-[(2-Methoxy-acetyl]amino]-N-methyl-N-(1-pyridin-4-yl-piperidin-4-yl)-3,4-dihydro-2H-chromene-6-carboxylic acid amide, |
| CC_H-277 | 4-Acetylamino-N-methyl-N-(1-pyridin-4-yl-piperidin-4-yl)-3,4-dihydro-2H-chromene-6-carboxylic acid amide, |
| CC_H-278 | 4-[[(2-Chloro-6-methyl-phenyl)sulfonyl]amino]-N-methyl-N-(1-pyridin-4-yl-piperidin-4-yl)-3,4-dihydro-2H-chromene-6-carboxylic acid amide, |
| CC_H-279 | 4-[[2-Chloro-3-(trifluoromethyl)-benzoyl]amino]-N-methyl-N-(1-pyridin-4-yl-piperidin-4-yl)-3,4-dihydro-2H-chromene-6-carboxylic acid amide, |
| CC_H-280 | 4-[[(2-Chlorophenyl)-carbamoyl]amino]-N-methyl-N-(1-pyridin-4-yl-piperidin-4-yl)-3,4-dihydro-2H-chromene-6-carboxylic acid amide, |
| CC_H-281 | 4-[[(3-Chlorophenyl)-carbamoyl]amino]-N-methyl-N-(1-pyridin-4-yl-piperidin-4-yl)-3,4-dihydro-2H-chromene-6-carboxylic acid amide, |
| CC_H-282 | 4-[[(2,3-Dichloro-phenyl)-carbamoyl]amino]-N-methyl-N-(1-pyridin-4-yl-piperidin-4-yl)-3,4-dihydro-2H-chromene-6-carboxylic acid amide, |
| CC_H-283 | 4-[[(2,5-Dichloro-phenyl)-carbamoyl]amino]-N-methyl-N-(1-pyridin-4-yl-piperidin-4-yl)-3,4-dihydro-2H-chromene-6-carboxylic acid amide, |
| CC_H-284 | 4-[[(3,5-Dichloro-phenyl)-carbamoyl]amino]-N-methyl-N-(1-pyridin-4-yl-piperidin-4-yl)-3,4-dihydro-2H-chromene-6-carboxylic acid amide, |
| CC_H-285 | 4-[[[2-Chloro-5-(trifluoromethyl)-phenyl]-carbamoyl]amino]-N-methyl-N-(1-pyridin-4-yl-piperidin-4-yl)-3,4-dihydro-2H-chromene-6-carboxylic acid amide, |
| CC_H-286 | 4-[[(2,4-Dichlorophenyl)-carbamoyl]amino]-N-methyl-N-(1-pyridin-4-yl-piperidin-4-yl)-3,4-dihydro-2H-chromene-6-carboxylic acid amide, |
| CC_H-287 | 4-[[[4-Chloro-2-(trifluoromethyl)-phenyl]-carbamoyl]amino]-N-methyl-N-(1-pyridin-4-yl-piperidin-4-yl)-3,4-dihydro-2H-chromene-6-carboxylic acid amide, |
| CC_H-288 | 4-[[(3-Chloro-4-methyl-phenyl)-carbamoyl]amino]-N-methyl-N-(1-pyridin-4-yl-piperidin-4-yl)-3,4-dihydro-2H-chromene-6-carboxylic acid amide, |
| CC_H-289 | 4-[[(3-Chloro-4-fluoro-phenyl)-carbamoyl]amino]-N-methyl-N-(1-pyridin-4-yl-piperidin-4-yl)-3,4-dihydro-2H-chromene-6-carboxylic acid amide, |
| CC_H-290 | 4-[[(2,4-Dimethyl-phenyl)-carbamoyl]amino]-N-methyl-N-(1-pyridin-4-yl-piperidin-4-yl)-3,4-dihydro-2H-chromene-6-carboxylic acid amide, |
| CC_H-291 | 4-[[(5-Chloro-2-methoxy-phenyl)-carbamoyl]amino]-N-methyl-N-(1-pyridin-4-yl-piperidin-4-yl)-3,4-dihydro-2H-chromene-6-carboxylic acid amide, |
| CC_H-292 | 4-[[(2-Chlorophenyl)-methyl-carbamoyl]amino]-N-methyl-N-(1-pyridin-4-yl-piperidin-4-yl)-3,4-dihydro-2H-chromene-6-carboxylic acid amide, |

-continued

| | |
|---|---|
| CC_H-293 | N-Methyl-4-(3-methyl-butanoylamino)-N-(1-pyridin-4-yl-piperidin-4-yl)-3,4-dihydro-2H-chromene-6-carboxylic acid amide, |
| CC_H-294 | 3-[(2-Chloro-5-fluoro-benzoyl)amino]-N-[1-(2,6-dimethyl-pyridin-4-yl)-piperidin-4-yl]-N-methyl-2,3-dihydro-1H-indene-5-carboxylic acid amide, |
| CC_H-295 | 3-[(2-Chloro-6-fluoro-3-methyl-benzoyl)amino]-N-[1-(2,6-dimethyl-pyridin-4-yl)-piperidin-4-yl]-N-methyl-2,3-dihydro-1H-indene-5-carboxylic acid amide, |
| CC_H-296 | 3-[(2,5-Dichloro-benzoyl)amino]-N-[1-(2,6-dimethyl-pyridin-4-yl)-piperidin-4-yl]-N-methyl-2,3-dihydro-1H-indene-5-carboxylic acid amide, |
| CC_H-297 | 3-(Cyclohexanecarbonylamino)-N-[1-(2,6-dimethyl-pyridin-4-yl)-piperidin-4-yl]-N-methyl-2,3-dihydro-1H-indene-5-carboxylic acid amide, |
| CC_H-298 | 3-(Cyclopropanecarbonylamino)-N-[1-(2,6-dimethyl-pyridin-4-yl)-piperidin-4-yl]-N-methyl-2,3-dihydro-1H-indene-5-carboxylic acid amide, |
| CC_H-299 | 3-(3,3-Dimethyl-butanoylamino)-N-[1-(2,6-dimethyl-pyridin-4-yl)-piperidin-4-yl]-N-methyl-2,3-dihydro-1H-indene-5-carboxylic acid amide, |
| CC_H-300 | N-[1-(2,6-Dimethyl-pyridin-4-yl)-piperidin-4-yl]-3-[(2-methoxy-acetyl)amino]-N-methyl-2,3-dihydro-1H-indene-5-carboxylic acid amide, |
| CC_H-301 | 3-Acetylamino-N-[1-(2,6-dimethyl-pyridin-4-yl)-piperidin-4-yl]-N-methyl-2,3-dihydro-1H-indene-5-carboxylic acid amide, |
| CC_H-302 | N-[1-(2,6-Dimethyl-pyridin-4-yl)-piperidin-4-yl]-N-methyl-3-[[[2-(trifluoromethyl)-phenyl]-methylsulfonyl]amino]-2,3-dihydro-1H-indene-5-carboxylic acid amide, |
| CC_H-303 | 3-[[2-Chloro-3-(trifluoromethyl)-benzoyl]amino]-N-[1-(2,6-dimethyl-pyridin-4-yl)-piperidin-4-yl]-N-methyl-2,3-dihydro-1H-indene-5-carboxylic acid amide, |
| CC_H-304 | 3-[[(2-Chlorophenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-305 | 3-[[(3-Chlorophenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-306 | 3-[[(2,6-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-307 | 3-[[(2,3-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-308 | 3-[[(2,5-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-309 | 3-[[(3,5-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-310 | 3-[[(2,4-Dichlorophenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-311 | 3-[[[2-Chloro-5-(trifluoromethyl)-phenyl]-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-312 | 3-[[[4-Chloro-2-(trifluoromethyl)-phenyl]-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-313 | 3-[[(3-Chloro-4-methyl-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-314 | 3-[[(3-Chloro-4-fluoro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-315 | 3-[[(5-Chloro-2-methoxy-phenyl)-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-316 | 3-[[(2-Chlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-317 | 3-[[(2,4-Dichlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide, |
| CC_H-318 | N-[1-(2,6-Dimethyl-pyridin-4-yl)-piperidin-4-yl]-N-methyl-3-(3-methyl-butanoylamino)-2,3-dihydro-1H-indene-5-carboxylic acid amide, |
| CC_H-319 | 3-(Butanoylamino)-N-[1-(2,6-dimethyl-pyridin-4-yl)-piperidin-4-yl]-N-methyl-2,3-dihydro-1H-indene-5-carboxylic acid amide, |
| CC_H-320 | 3-(3-Cyclopentyl-propanoylamino)-N-[1-(2,6-dimethyl-pyridin-4-yl)-piperidin-4-yl]-N-methyl-2,3-dihydro-1H-indene-5-carboxylic acid amide, |
| CC_H-321 | N-[1-(2,6-Dimethyl-pyridin-4-yl)-piperidin-4-yl]-3-[(ethylsulfonyl)amino]-N-methyl-2,3-dihydro-1H-indene-5-carboxylic acid amide, |
| CC_H-322 | N-[1-(2,6-Dimethyl-pyridin-4-yl)-piperidin-4-yl]-N-methyl-3-[[[3-(trifluoromethyl)phenyl]-methylsulfonyl]amino]-2,3-dihydro-1H-indene-5-carboxylic acid amide, |
| CC_H-323 | N-[1-(2,6-Dimethyl-pyridin-4-yl)-piperidin-4-yl]-3-[[(2-fluorophenyl)-methylsulfonyl]amino]-N-methyl-2,3-dihydro-1H-indene-5-carboxylic acid amide, |
| CC_H-324 | 3-[[2-(2-Chlorophenyl)-ethylsulfonyl]amino]-N-[1-(2,6-dimethyl-pyridin-4-yl)-piperidin-4-yl]-N-methyl-2,3-dihydro-1H-indene-5-carboxylic acid amide, |
| CC_H-325 | 3-[(2-Chloro-5-fluoro-benzoyl)-methyl-amino]-N-[1-(2,6-dimethyl-pyridin-4-yl)-piperidin-4-yl]-N-methyl-2,3-dihydro-1H-indene-5-carboxylic acid amide, |
| CC_H-326 | 3-[[2-Chloro-5-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-327 | 3-[(2-Chloro-6-fluoro-3-methyl-benzoyl)-methyl-amino]-N-[1-(2,6-dimethyl-pyridin-4-yl)-piperidin-4-yl]-N-methyl-2,3-dihydro-1H-indene-5-carboxylic acid amide, |
| CC_H-328 | 3-[(2,5-Dichloro-benzoyl)-methyl-amino]-N-[1-(2,6-dimethyl-pyridin-4-yl)-piperidin-4-yl]-N-methyl-2,3-dihydro-1H-indene-5-carboxylic acid amide, |

| | |
|---|---|
| CC_H-329 | 3-[[2-Chloro-6-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-330 | 3-(Cyclohexanecarbonyl-methyl-amino)-N-[1-(2,6-dimethyl-pyridin-4-yl)-piperidin-4-yl]-N-methyl-2,3-dihydro-1H-indene-5-carboxylic acid amide, |
| CC_H-331 | 3-(Cyclopropanecarbonyl-methyl-amino)-N-[1-(2,6-dimethyl-pyridin-4-yl)-piperidin-4-yl]-N-methyl-2,3-dihydro-1H-indene-5-carboxylic acid amide, |
| CC_H-332 | 3-(3,3-Dimethyl-butanoyl-methyl-amino)-N-[1-(2,6-dimethyl-pyridin-4-yl)-piperidin-4-yl]-N-methyl-2,3-dihydro-1H-indene-5-carboxylic acid amide, |
| CC_H-333 | N-[1-(2,6-Dimethyl-pyridin-4-yl)-piperidin-4-yl]-3-[(2-methoxy-acetyl)-methyl-amino]-N-methyl-2,3-dihydro-1H-indene-5-carboxylic acid amide, |
| CC_H-334 | 3-(Acetyl-methyl-amino)-N-[1-(2,6-dimethyl-pyridin-4-yl)-piperidin-4-yl]-N-methyl-2,3-dihydro-1H-indene-5-carboxylic acid amide, |
| CC_H-335 | 3-[[(2-Chloro-6-methyl-phenyl)sulfonyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-336 | 3-[[(2-Chlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-337 | 3-[[(3-Chlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-338 | 3-[[(2,6-Dichloro-phenyl)-carbamoyn-methyl-amino]-N-[1-(2,6-dimethyl-pyridin-4-yl)-piperidin-4-yl]-N-methyl-2,3-dihydro-1H-indene-5-carboxylic acid amide, |
| CC_H-339 | 3-[[(2,3-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-340 | 3-[[(2,5-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-341 | 3-[[(3,5-Dichloro-phenyl)-carbamoyn-methyl-amino]-N-[1-(2,6-dimethyl-pyridin-4-yl)-piperidin-4-yl]-N-methyl-2,3-dihydro-1H-indene-5-carboxylic acid amide, |
| CC_H-342 | 3-[[(2,4-Dichlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-343 | 3-[[[2-Chloro-5-(trifluoromethyl)-phenyl]-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-344 | 3-[[[4-Chloro-2-(trifluoromethyl)-phenyl]-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-345 | 3-[[(3-Chloro-4-methyl-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-346 | 3-[[(3-Chloro-4-fluoro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-347 | 3-[[(2,4-Dimethyl-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-348 | 3-[[(5-Chloro-2-methoxy-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-349 | 3-[[(2-Chlorophenyl)-methyl-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-350 | 3-[[(2,4-Dichlorophenyl)-methyl-carbamoyl]-methyl-amino]-N-[1-(2,6-dimethyl-pyridin-4-yl)-piperidin-4-yl]-N-methyl-2,3-dihydro-1H-indene-5-carboxylic acid amide, |
| CC_H-351 | N-[1-(2,6-Dimethyl-pyridin-4-yl)-piperidin-4-yl]-N-methyl-3-(methyl-methylsulfonyl-amino)-2,3-dihydro-1H-indene-5-carboxylic acid amide, |
| CC_H-352 | N-[1-(2,6-Dimethyl-pyridin-4-yl)-piperidin-4-yl]-N-methyl-3-[methyl-(3-methyl-butanoyl)-amino]-2,3-dihydro-1H-indene-5-carboxylic acid amide, |
| CC_H-353 | 3-(Butanoyl-methyl-amino)-N-[1-(2,6-dimethyl-pyridin-4-yl)-piperidin-4-yl]-N-methyl-2,3-dihydro-1H-indene-5-carboxylic acid amide, |
| CC_H-354 | 3-(3-Cyclopentyl-propanoyl-methyl-amino)-N-[1-(2,6-dimethyl-pyridin-4-yl)-piperidin-4-yl]-N-methyl-2,3-dihydro-1H-indene-5-carboxylic acid amide, |
| CC_H-355 | N-[1-(2,6-Dimethyl-pyridin-4-yl)-piperidin-4-yl]-N-methyl-3-[methyl-[[3-(trifluoromethyl)phenyq-methylsulfonyl]-amino]-2,3-dihydro-1H-indene-5-carboxylic acid amide, |
| CC_H-356 | 3-[(2-Chloro-5-fluoro-benzoyl)amino]-N-(1-isoquinolin-6-yl-piperidin-4-yl)-N-methyl-2,3-dihydro-1H-indene-5-carboxylic acid amide, |
| CC_H-357 | 3-[[2-Chloro-5-(trifluoromethyl)-benzoyl]amino]-N-(1-isoquinolin-6-yl-piperidin-4-yl)-N-methyl-2,3-dihydro-1H-indene-5-carboxylic acid amide, |
| CC_H-358 | 3-[(2-Chloro-6-fluoro-3-methyl-benzoyl)amino]-N-(1-isoquinolin-6-yl-piperidin-4-yl)-N-methyl-2,3-dihydro-1H-indene-5-carboxylic acid amide, |
| CC_H-359 | 3-[(2,5-Dichloro-benzoyl)amino]-N-(1-isoquinolin-6-yl-piperidin-4-yl)-N-methyl-2,3-dihydro-1H-indene-5-carboxylic acid amide, |
| CC_H-360 | 3-(Cyclohexanecarbonylamino)-N-(1-isoquinolin-6-yl-piperidin-4-yl)-N-methyl-2,3-dihydro-1H-indene-5-carboxylic acid amide, |
| CC_H-361 | 3-(Cyclopropanecarbonylamino)-N-(1-isoquinolin-6-yl-piperidin-4-yl)-N-methyl-2,3-dihydro-1H-indene-5-carboxylic acid amide, |
| CC_H-362 | 3-(3,3-Dimethyl-butanoylamino)-N-(1-isoquinolin-6-yl-piperidin-4-yl)-N-methyl-2,3-dihydro-1H-indene-5-carboxylic acid amide, |
| CC_H-363 | N-(1-Isoquinolin-6-yl-piperidin-4-yl)-3-[(2-methoxy-acetypamino]-N-methyl-2,3-dihydro-1H-indene-5-carboxylic acid amide, |

| | |
|---|---|
| CC_H-364 | 3-[[2-Chloro-3-(trifluoromethyl)-benzoyl]amino]-N-(1-isoquinolin-6-yl-piperidin-4-yl)-N-methyl-2,3-dihydro-1H-indene-5-carboxylic acid amide, |
| CC_H-365 | 3-[[(2-Chlorophenyl)-carbamoyl]amino]-N-(1-isoquinolin-6-yl-piperidin-4-yl)-N-methyl-2,3-dihydro-1H-indene-5-carboxylic acid amide, |
| CC_H-366 | 3-[[(2,6-Dichloro-phenyl)-carbamoyl]amino]-N-(1-isoquinolin-6-yl-piperidin-4-yl)-N-methyl-2,3-dihydro-1H-indene-5-carboxylic acid amide, |
| CC_H-367 | 3-[[(2,3-Dichloro-phenyl)-carbamoyl]amino]-N-(1-isoquinolin-6-yl-piperidin-4-yl)-N-methyl-2,3-dihydro-1H-indene-5-carboxylic acid amide, |
| CC_H-368 | 3-[[(2,5-Dichloro-phenyl)-carbamoyl]amino]-N-(1-isoquinolin-6-yl-piperidin-4-yl)-N-methyl-2,3-dihydro-1H-indene-5-carboxylic acid amide, |
| CC_H-369 | 3-[[(2,4-Dichlorophenyl)-carbamoyl]amino]-N-(1-isoquinolin-6-yl-piperidin-4-yl)-N-methyl-2,3-dihydro-1H-indene-5-carboxylic acid amide, |
| CC_H-370 | 3-[[[2-Chloro-5-(trifluoromethyl)-phenyl]-carbamoyl]amino]-N-(1-isoquinolin-6-yl-piperidin-4-yl)-N-methyl-2,3-dihydro-1H-indene-5-carboxylic acid amide, |
| CC_H-371 | 3-[[[4-Chloro-2-(trifluoromethyl)-phenyl]-carbamoyl]amino]-N-(1-isoquinolin-6-yl-piperidin-4-yl)-N-methyl-2,3-dihydro-1H-indene-5-carboxylic acid amide, |
| CC_H-372 | 3-[[(3-Chloro-4-fluoro-phenyl)-carbamoyl]amino]-N-(1-isoquinolin-6-yl-piperidin-4-yl)-N-methyl-2,3-dihydro-1H-indene-5-carboxylic acid amide, |
| CC_H-373 | 3-[[(2,4-Dimethyl-phenyl)-carbamoyl]amino]-N-(1-isoquinolin-6-yl-piperidin-4-yl)-N-methyl-2,3-dihydro-1H-indene-5-carboxylic acid amide, |
| CC_H-374 | 3-[[(5-Chloro-2-methoxy-phenyl)-carbamoyl]amino]-N-(1-isoquinolin-6-yl-piperidin-4-yl)-N-methyl-2,3-dihydro-1H-indene-5-carboxylic acid amide, |
| CC_H-375 | 3-[[(2-Chlorophenyl)-methyl-carbamoyl]amino]-N-(1-isoquinolin-6-yl-piperidin-4-yl)-N-methyl-2,3-dihydro-1H-indene-5-carboxylic acid amide, |
| CC_H-376 | 3-[[(2,4-Dichlorophenyl)-methyl-carbamoyl]amino]-N-(1-isoquinolin-6-yl-piperidin-4-yl)-N-methyl-2,3-dihydro-1H-indene-5-carboxylic acid amide, |
| CC_H-377 | N-(1-Isoquinolin-6-yl-piperidin-4-yl)-3-(methanesulfonamido)-N-methyl-2,3-dihydro-1H-indene-5-carboxylic acid amide, |
| CC_H-378 | N-(1-Isoquinolin-6-yl-piperidin-4-yl)-N-methyl-3-[(propylsulfonyl)amino]-2,3-dihydro-1H-indene-5-carboxylic acid amide, |
| CC_H-379 | N-(1-Isoquinolin-6-yl-piperidin-4-yl)-N-methyl-3-(3-methyl-butanoylamino)-2,3-dihydro-1H-indene-5-carboxylic acid amide, |
| CC_H-380 | 3-(Butanoylamino)-N-(1-isoquinolin-6-yl-piperidin-4-yl)-N-methyl-2,3-dihydro-1H-indene-5-carboxylic acid amide, |
| CC_H-381 | 3-(3-Cyclopentyl-propanoylamino)-N-(1-isoquinolin-6-yl-piperidin-4-yl)-N-methyl-2,3-dihydro-1H-indene-5-carboxylic acid amide, |
| CC_H-382 | 3-[(Ethylsulfonyl)amino]-N-(1-isoquinolin-6-yl-piperidin-4-yl)-N-methyl-2,3-dihydro-1H-indene-5-carboxylic acid amide, |
| CC_H-383 | N-(1-Isoquinolin-6-yl-piperidin-4-yl)-N-methyl-3-[[[3-(trifluoromethyl)phenyl]-methylsulfonyl]amino]-2,3-dihydro-1H-indene-5-carboxylic acid amide, |
| CC_H-384 | 3-[[(2-Fluorophenyl)-methylsulfonyl]amino]-N-(1-isoquinolin-6-yl-piperidin-4-yl)-N-methyl-2,3-dihydro-1H-indene-5-carboxylic acid amide, |
| CC_H-600 | N-[6-[Methyl-[1-(2-methylsulfonyl-pyrimidin-4-yl)-piperidin-4-yl]-carbamoyl]-2,3-dihydro-1H-inden-1-yl]-2-(trifluoromethyl)-pyridine-3-carboxylic acid amide, |
| CC_H-601 | N-[6-[[1-[2-(Dimethyl-carbamoyl)-pyridin-4-yl]-piperidin-4-yl]-methyl-carbamoyl]-2,3-dihydro-1H-inden-1-yl]-2-(trifluoromethyl)-pyridine-3-carboxylic acid amide, |
| CC_H-603 | N-[6-[Methyl-[1-(2-pyrrolidin-1-yl-pyrimidin-4-yl)-piperidin-4-yl]-carbamoyl]-2,3-dihydro-1H-inden-1-yl]-2-(trifluoromethyl)-pyridine-3-carboxylic acid amide, |
| CC_H-604 | N-[6-[[1-(2-Dimethylamino-6-methyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, |
| CC_H-606 | N-[6-[[1-(2-tert-Butyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, |
| CC_H-607 | N-[6-[Methyl-[4-(5-methyl-3-oxo-1,2-dihydro-imidazo[5,1-e]imidazol-2-yl)-cyclohexyl]-carbamoyl]-2,3-dihydro-1H-inden-1-yl]-2-(trifluoromethyl)-pyridine-3-carboxylic acid amide, |
| CC_H-608 | N-[6-[[1-(2-Dimethylamino-pyrimidin-4-yl)-piperidin-4-yl]-methyl-carbamoyl]-2,3-dihydro-1H-inden-1-yl]-2-(trifluoromethyl)-pyridine-3-carboxylic acid amide, |
| CC_H-609 | 3-[(2-Chloro-benzoyl)amino]-N-methyl-N-[1-(2-methylsulfonyl-pyrimidin-4-yl)-piperidin-4-yl]-2,3-dihydro-1H-indene-5-carboxylic acid amide, |
| CC_H-610 | N-[6-[[1-(2-Cyclopropyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, |
| CC_H-612 | 3-[(2-Chloro-benzoyl)amino]-N-methyl-N-[1-(2-pyrrolidin-1-yl-pyrimidin-4-yl)-piperidin-4-yl]-2,3-dihydro-1H-indene-5-carboxylic acid amide, |
| CC_H-613 | 3-(3-Cyclopentyl-propanoylamino)-N-methyl-N-[1-(2-methylsulfonyl-pyrimidin-4-yl)-piperidin-4-yl]-2,3-dihydro-1H-indene-5-carboxylic acid amide, |
| CC_H-614 | 3-[(2-Chloro-benzoyl)amino]-N-[1-(2-dimethylamino-6-methyl-pyrimidin-4-yl)-piperidin-4-yl]-N-methyl-2,3-dihydro-1H-indene-5-carboxylic acid amide, |
| CC_H-615 | 4-[4-[[3-(3-Cyclopentyl-propanoylamino)-2,3-dihydro-1H-indene-5-carbonyl]-methyl-amino]-piperidin-1-yl]-N,N-dimethyl-pyridine-2-carboxylic acid amide, |
| CC_H-616 | N-[1-(2-tert-Butyl-pyrimidin-4-yl)-piperidin-4-yl]-3-[(2-chloro-benzoyl)amino]-N-methyl-2,3-dihydro-1H-indene-5-carboxylic acid amide, |
| CC_H-618 | 3-[(2-Chloro-benzoyl)amino]-N-methyl-N-[4-(5-methyl-3-oxo-1,2-dihydro-imidazo[5,1-e]imidazol-2-yl)-cyclohexyl]-2,3-dihydro-1H-indene-5-carboxylic acid amide, |
| CC_H-620 | 3-(3-Cyclopentyl-propanoylamino)-N-methyl-N-[1-(2-pyrrolidin-1-yl-pyrimidin-4-yl)-piperidin-4-yl]-2,3-dihydro-1H-indene-5-carboxylic acid amide, |
| CC_H-621 | N-[6-[[1-(5-Fluoro-pyrimidin-4-yl)-piperidin-4-yl]-methyl-carbamoyl]-2,3-dihydro-1H-inden-1-yl]-2-(trifluoromethyl)-pyridine-3-carboxylic acid amide, |

-continued

CC_H-622 3-(3-Cyclopentyl-propanoylamino)-N-[1-(2-dimethylamino-6-methyl-pyrimidin-4-yl)-piperidin-4-yl]-N-methyl-2,3-dihydro-1H-indene-5-carboxylic acid amide,
CC_H-623 3-[(2-Chloro-benzoyl)amino]-N-[1-(2-dimethylamino-pyrimidin-4-yl)-piperidin-4-yl]-N-methyl-2,3-dihydro-1H-indene-5-carboxylic acid amide,
CC_H-624 N-[1-(2-tert-Butyl-pyrimidin-4-yl)-piperidin-4-yl]-3-(3-cyclopentyl-propanoylamino)-N-methyl-2,3-dihydro-1H-indene-5-carboxylic acid amide,
CC_H-626 3-(3-Cyclopentyl-propanoylamino)-N-methyl-N-[4-(5-methyl-3-oxo-1,2-dihydro-imidazo[5,1-e]imidazol-2-yl)-cyclohexyl]-2,3-dihydro-1H-indene-5-carboxylic acid amide,
CC_H-627 3-[(2-Chloro-benzoyl)amino]-N-[1-(2-cyclopropyl-pyrimidin-4-yl)-piperidin-4-yl]-N-methyl-2,3-dihydro-1H-indene-5-carboxylic acid amide,
CC_H-628 N-[6-[Methyl-(1-pyridazin-4-yl-piperidin-4-yl)-carbamoyl]-2,3-dihydro-1H-inden-1-yl]-2-(trifluoromethyl)-pyridine-3-carboxylic acid amide,
CC_H-629 3-(3-Cyclopentyl-propanoylamino)-N-[1-(2-dimethylamino-pyrimidin-4-yl)-piperidin-4-yl]-N-methyl-2,3-dihydro-1H-indene-5-carboxylic acid amide,
CC_H-630 3-(3-Cyclopentyl-propanoylamino)-N-[1-(2-cyclopropyl-pyrimidin-4-yl)-piperidin-4-yl]-N-methyl-2,3-dihydro-1H-indene-5-carboxylic acid amide,
CC_H-631 3-[(2-Chloro-benzoyl)amino]-N-[1-(5-fluoro-pyrimidin-4-yl)-piperidin-4-yl]-N-methyl-2,3-dihydro-1H-indene-5-carboxylic acid amide,
CC_H-632 3-(3-Cyclopentyl-propanoylamino)-N-[1-(5-fluoro-pyrimidin-4-yl)-piperidin-4-yl]-N-methyl-2,3-dihydro-1H-indene-5-carboxylic acid amide,
CC_H-633 3-[(2-Chloro-benzoyl)amino]-N-methyl-N-(1-pyridazin-4-yl-piperidin-4-yl)-2,3-dihydro-1H-indene-5-carboxylic acid amide, and
CC_H-634 3-(3-Cyclopentyl-propanoylamino)-N-methyl-N-(1-pyridazin-4-yl-piperidin-4-yl)-2,3-dihydro-1H-indene-5-carboxylic acid amide in the form of the free compounds; of the tautomers; of the N-oxides; of the racemate; of the enantiomers, diastereoisomers, mixtures of the enantiomers or diastereoisomers or of a single enantiomer or diastereoisomer; or in the form of the salts of physiologically acceptable acids or bases.

The numbering of the individual embodiments of the compounds according to the invention that has been used above is retained in the explanations of the present invention given hereinbelow, in particular in the description of the examples.

According to one aspect of the present invention, the compounds according to the invention preferably exhibit an antagonistic action on the human B1R receptor or the B1R receptor of the rat. In a preferred embodiment of the invention, the compounds according to the invention exhibit an antagonistic action both on the human B1R receptor (hB1R) and on the B1R receptor of the rat (rB1R). In a preferred embodiment of the present invention, the compounds according to the invention exhibit an inhibition of at least 15%, 25%, 50%, 70%, 80% or 90% on the human B1R receptor and/or on the B1R receptor of the rat in the FLIPR assay at a concentration of 10 µM. Most particular preference is given to compounds that exhibit an inhibition of at least 70%, in particular of at least 80% and particularly preferably of at least 90%, on the human B1R receptor and on the B1R receptor of the rat at a concentration of 10 µM.

The agonistic or antagonistic action of substances can be quantified on the bradykinin receptor 1 (B1R) of the species human and rat using ectopically expressing cell lines (CHO K1 cells) and with the aid of a $Ca^{2+}$-sensitive dye (Fluo-4) using a fluorescent imaging plate reader (FLIPR). The indication in % activation is based on the $Ca^{2+}$ signal after addition of Lys-Des-Arg$^9$-bradykinin (0.5 nM) or Des-Arg$^9$-bradykinin (100 nM). Antagonists lead to suppression of the $Ca^{2+}$ influx after the addition of the agonist. % Inhibition compared with the maximum achievable inhibition is indicated.

The substances according to the invention act especially, for example, on B1R, which is relevant in connection with various diseases, so that they are suitable as a pharmaceutical active ingredient in medicaments.

The invention accordingly further provides medicaments comprising at least one compound according to the invention as well as, optionally, suitable additives and/or auxiliary substances and/or optionally further active ingredients.

The medicaments according to the invention optionally comprise, in addition to at least one compound according to the invention, suitable additives and/or auxiliary substances, that is to say also carriers, fillers, solvents, diluents, colourings and/or binders, and can be administered as liquid medicament forms in the form of injection solutions, drops or juices, or as semi-solid medicament forms in the form of granules, tablets, pellets, patches, capsules, plasters/spray-on plasters or aerosols. The choice of the auxiliary substances etc. and the amounts thereof to be employed depend on whether the medicament is to be administered orally, per-orally, parenterally, intravenously, intraperitoneally, intradermally, intramuscularly, nasally, buccally, rectally or topically, for example to the skin, the mucous membranes or into the eyes. Preparations in the form of tablets, dragées, capsules, granules, drops, juices and syrups are suitable for oral administration, and solutions, suspensions, readily reconstitutable dry formulations and sprays are suitable for parenteral, topical and inhalatory administration. Substituted compounds according to the invention in a depot, in dissolved form or in a plaster, optionally with the addition of agents which promote penetration through the skin, are suitable formulations for percutaneous administration. Forms of preparation which can be used orally or percutaneously can release the substituted compounds according to the invention in a delayed manner. The substituted compounds according to the invention can also be used in parenteral long-term depot forms, such as, for example, implants or implanted pumps. In principle, other further active ingredients known to the person skilled in the art can be added to the medicaments according to the invention.

The amount of active ingredient to be administered to the patient varies in dependence on the weight of the patient, the type of administration, the indication and the severity of the disease. From 0.00005 to 50 mg/kg, in particular from 0.01 to 5 mg/kg, of at least one compound according to the invention are usually administered.

In a form of the medicament, a substituted compound according to the invention that is present is optionally in the form of an isolated diastereoisomer and/or enantiomer, in the form of the racemate or in the form of a non-equimolar or equimolar mixture of the diastereoisomers and/or enantiomers. Suitable methods for separating stereoisomers are known to the person skilled in the art.

B1R is involved in particular in the occurrence of pain. Accordingly, the substituted compounds according to the invention can be used in particular in the preparation of a medicament for the treatment of pain, in particular of acute, visceral, neuropathic or chronic pain or inflammatory pain.

Accordingly, the invention further provides the use of at least one substituted compound according to the invention in the preparation of a medicament for the treatment of pain, in particular of acute, visceral, neuropathic or chronic pain. A specific embodiment of the present invention is the use of at least one of the substituted compounds according to the invention in the preparation of a medicament for the treatment of inflammatory pain.

The invention also provides the use of at least one substituted compound according to the invention in the treatment of pain, in particular of acute, visceral, neuropathic or chronic pain or inflammatory pain.

The invention further provides the use of at least one substituted compound according to the invention in the preparation of a medicament for the treatment of diabetes, respiratory diseases, for example Asthma bronchiale, allergies, COPD/chronic-obstructive pulmonary disease or cystic fibrosis; inflammatory intestinal diseases, for example ulcerative colitis or CD/Crohn's disease; neurological diseases, for example multiple sclerosis, neurodegenerative diseases, fibrotic diseases; inflammations of the skin, for example atopic dermatitis, psoriasis or bacterial infections; rheumatic diseases, for example rheumatoid arthritis or osteoarthritis; septic shock; reperfusion syndrome, for example following heart attack or stroke, obesity; and as an angiogenesis inhibitor.

The invention also provides the use of at least one substituted compound according to the invention in the treatment of one of the above-mentioned indications and/or as an angiogenesis inhibitor.

It can be preferred in one of the above uses for a substituted compound that is used to be in the form of an isolated diastereoisomer and/or enantiomer, in the form of the racemate or in the form of a non-equimolar or equimolar mixture of the diastereoisomers and/or enantiomers.

The invention further provides a method of treating, in particular in one of the above-mentioned indications, a non-human mammal or a human being requiring treatment of the corresponding indication, by administering a therapeutically effective dose of a substituted compound according to the invention or of a medicament according to the invention.

The invention further provides a method of treating pain, in particular one of the above-mentioned forms of pain, in a non-human mammal or a human being requiring treatment in particular of pain, in particular of acute, visceral, neuropathic or chronic pain or inflammatory pain, by administering a therapeutically effective dose of a substituted compound according to the invention or of a medicament according to the invention.

The invention further provides a process for the preparation of the substituted compounds according to the invention as indicated in the description and in the examples.

In the following schemes for describing the preparation process according to the invention, the radicals, variables and indices correspond analogously to the respective radicals, variables and indices according to the invention.

General Process for the Preparation of the Derivatives (IX)

Scheme 1: General process for the preparation of the derivatives (IX)

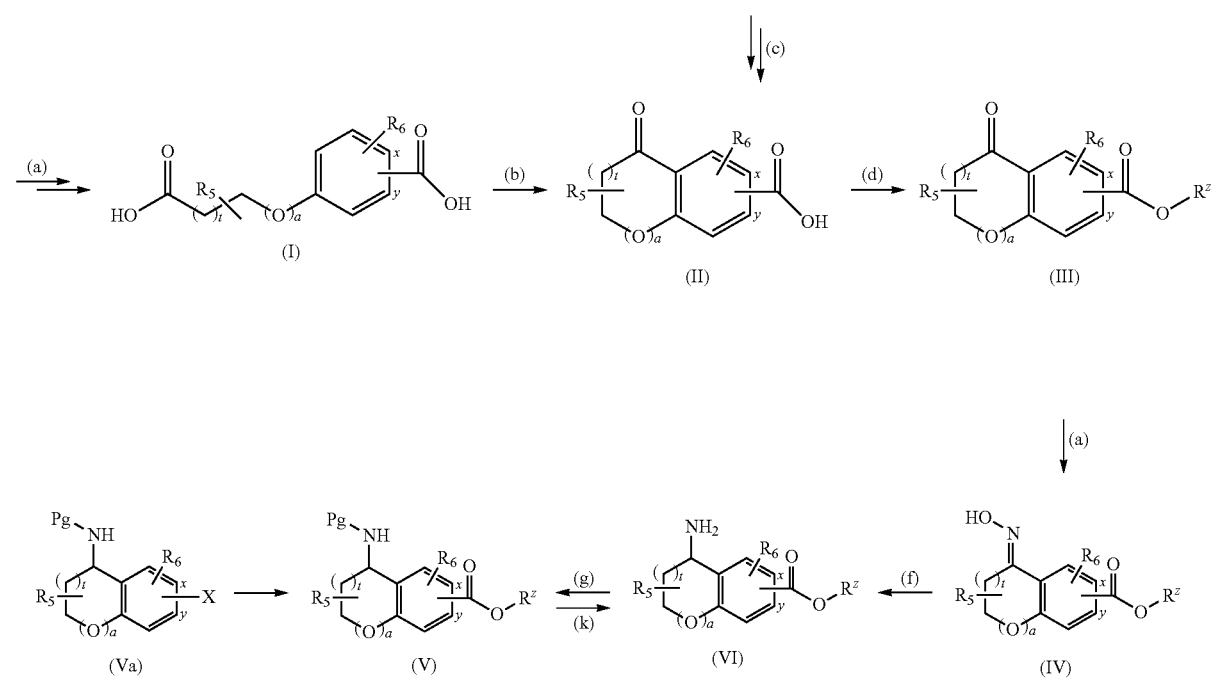

-continued

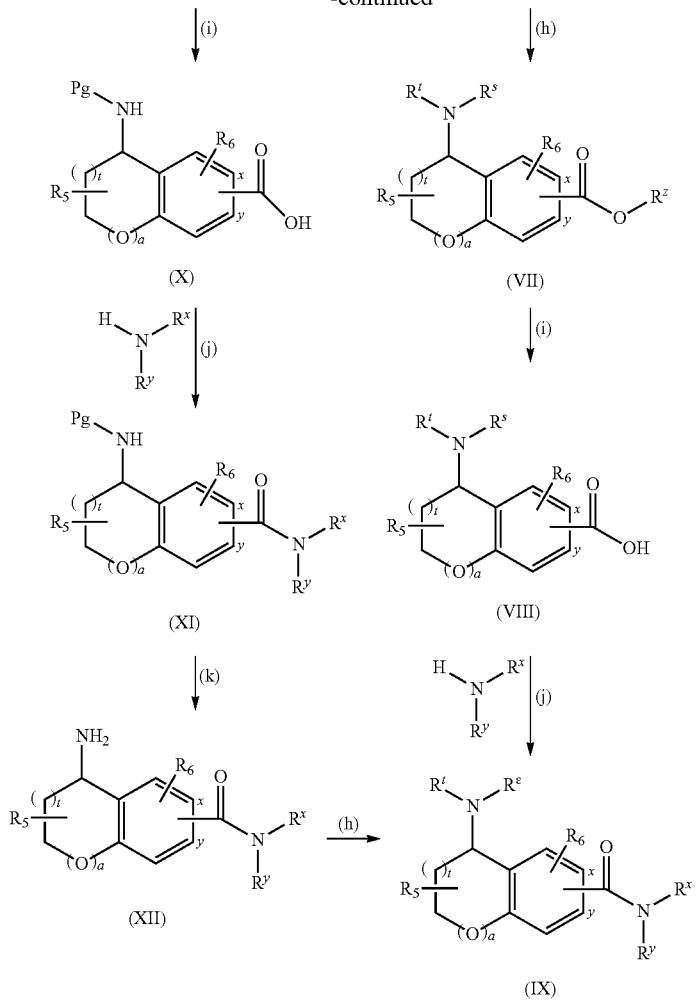

Stage (a): Acids of the general formula (I) can be prepared by methods known in the literature, for example from methyl derivatives by oxidation, for example according to: (Lit. No. 1) Skraup; Schwamberger; Justus Liebigs Annalen der Chemie; Vol. 462; (1928); p. 147, from nitriles by hydrolysis, for example according to (Lit. No. 2) Moses; Chemische Berichte; Vol. 33; (1900); p. 2626, from aryl halides, for example according to (Lit. No. 3) Gomes, Paulo; Gosmini, Corinne; Perichon, Jacques; Synlett; Vol. 10; (2002); p. 1673-1676; and (Lit. No. 4) Amatore, Muriel; Gosmini, Corinne; Perichon, Jacques; Journal of Organic Chemistry; Vol. 71; (2006); p. 6130-6134, from arylzinc compounds, for example according to (Lit. No. 5) Takahashi, Hideki; Inagaki, Shinya; Nishihara, Yasushi; Shibata, Takanori; Takagi, Kentaro; Organic Letters; Vol. 8; (2006); p. 3037-3040, from aldehydes, for example according to (Lit. No. 6) Kotake, Yoshihiko; Iijima, Atsumi; Yoshimatsu, Kentaro; Tamai, Naoko; Ozawa, Yoichi; et al.; Journal of Medicinal Chemistry; Vol. 37; (1994); p. 1616-1624, from arylboronic acids, for example according to (Lit. No. 7) Horiguchi, Hakaru; Tsurugi, Hayato; Satoh, Tetsuya; Miura, Masahiro; Journal of Organic Chemistry; Vol. 73; (2008); p. 1590-1592. Ester derivatives of (I) are optionally obtained by these methods, which ester derivatives are then converted into the acids (I) according to step (j).

Stage (b): Acids of the general formula (II) can be prepared from (I) by methods known in the literature, for example (Lit. No. 8) Norwell, David C.; Howson, William; Nolan, William P. Ratcliffe, Giles S.; Rees, David C.; Willems, Henriette M. G.; Tetrahedron; Vol. 51; (1995); p. 203-216. (Lit. No. 9) or according to WO2005/87236 (A1).

Stage (c): Acids of the general formula (II) can be prepared by methods known in the literature, for example by oxidation (Lit. No. 10) Matveeva, E. D.; Podrugina, T. A.; Zefirova, O. N.; Alekseev, A. S.; Bachurin, S. O.; Pellicciari, R.; Zefirov, N. S.; Russian Journal of Organic Chemistry; Vol. 38; (2002); p. 1764-1768, by carbonyl insertion (Lit. No. 11) WO2005/95387 (A1) and (Lit. No. 12) Takeuchi, Ryo; Yasue, Hiroyuki; Journal of Organic Chemistry; Vol. 58; (1993); p. 5386-5392, by oxidation: (Lit. No. 13) Pelliciari, Roberto; Luneia, Roberto; Costantino, Gabriele; Marinozzi, Maura; Natalini, Benedetto; et al.; Journal of Medicinal Chemistry; Vol. 38; (1995); p. 3717-3719.

In stage (d), acids of the general formula (II) are converted by a method known in the literature (see (a) Protecting Groups, Philip J. Kocienski, Thieme, Stuttgart; 3rd Revised Edition (14 Feb. 2005) (b) Protective Groups in Organic Synthesis, Theodora W. Greene and Peter G. M. Wuts, Wiley & Sons; 4th Edition (30 Oct. 2006)) into an ester preferably selected from the group consisting of methyl, ethyl, isopropyl and tert-butyl esters of the general formula (III).

In stage (e), ketones of the general formula (III) are reacted in at least one solvent, preferably selected from the group consisting of water, dichloromethane, dimethylformamide, diethyl ether, dioxane, tetrahydrofuran, methanol, ethanol and isopropanol, with a reagent preferably selected from the group consisting of hydroxylamine, hydroxylamine hydrochloride and N,O-bis(trimethylsilyl)hydroxylamine, optionally in the presence of at least one inorganic base, preferably selected from the group consisting of potassium hydride, potassium carbonate, sodium carbonate, caesium carbonate, sodium hydroxide and sodium acetate, or an organic base, preferably selected from the group consisting of triethylamine, diisopropylethylamine and pyridine, at temperatures of preferably from −15° C. to 100° C., to give compounds having the general formula (IV).

In stage (f), hydroxylamines of the general formula (IV) are reacted in at least one solvent, preferably selected from the group consisting of dichloromethane, chloroform, dimethylformamide, diethyl ether, dioxane, tetrahydrofuran, water, methanol, ethanol and isopropanol, with at least one reducing agent preferably selected from the group consisting of lithium aluminium hydride, sodium borohydride, lithium borohydride, sodium, sodium amalgam and zinc, optionally in the presence of at least one acid or Lewis acid, preferably selected from the group consisting of hydrochloric acid, sulfuric acid, acetic acid and titanium tetrachloride, at temperatures of preferably from −15° C. to 100° C., to give compounds having the general formula (VI).

Hydroxylamines of the general formula (IV) can optionally also be reacted in stage (f) in at least one solvent, preferably selected from the group consisting of chloroform, ethyl acetate, dimethylformamide, diethyl ether, dioxane, tetrahydrofuran, methanol, ethanol and isopropanol, with hydrogen at pressures of preferably from 1 to 10 bar, in the presence of at least one catalyst, preferably selected from the group consisting of rhodium on carbon, palladium on carbon, palladium black, Raney nickel and platinum oxide, optionally in the presence of at least one acid, preferably selected from the group consisting of hydrochloric acid, sulfuric acid and acetic acid, at temperatures of preferably from 0° C. to 50° C., to give compounds having the general formula (VI).

Compounds having the general formula (VI) can optionally also be obtained by removal of the amine protecting groups (Pg) from molecules of the general formula (V) analogously to stage (k), Pg preferably corresponding to Boc. The compounds having the general formula (V) that are used can be obtained from the corresponding bromides of the general formula (Va) (X=Br) in at least one solvent, preferably selected from the group consisting of benzene, acetonitrile, dimethylformamide, tetrahydrofuran, dimethyl sulfoxide, methanol and ethanol or mixtures of those solvents, in the presence of tetrakis(triphenylphosphine) palladium (0), (1,1'-bis(diphenylphosphino)ferrocene)palladium(II) dichloride, bis-triphenylphosphine-palladium(II) chloride, palladium diacetate or palladium, optionally in the presence of 1,3-bis(diphenylphosphine)propane, triphenylphosphine or 1,1'-bis(diphenylphosphino)ferrocene, and optionally in the presence of triethylamine, butylamine or sodium acetate, under a CO atmosphere at temperatures of preferably from 0° C. to 200° C., optionally under pressure in an autoclave.

In stage (a) amines of the general formula (VI) are provided with suitable protecting groups (Pg), preferably selected from the group consisting of tert-butyloxycarbonyl (Boc) and benzyl carbamate (Cbz), by a method known in the literature (see (a) Protecting Groups, Philip J. Kocienski, Thieme, Stuttgart; 3rd Revised Edition (14 Feb. 2005) (b) Protective Groups in Organic Synthesis, Theodora W. Greene and Peter G. M. Wuts, Wiley & Sons; 4th Edition (30 Oct. 2006)).

1.) In stage (h) amines of the general formula (VI) or (XII) are reacted in at least one solvent, preferably selected from the group consisting of dichloromethane, acetonitrile, dimethylformamide, diethyl ether, dioxane, tetrahydrofuran, methanol, ethanol and isopropanol, with acid chlorides or sulfonyl chlorides, in the presence of at least one inorganic base, preferably selected from the group consisting of potassium carbonate and caesium carbonate, or an organic base, preferably selected from the group consisting of triethylamine, diisopropylethylamine and pyridine, and optionally with the addition of 4-(dimethylamino)pyridine or 1-hydroxybenzotriazole, at temperatures of preferably from −15° C. to 50° C., to give compounds having the general formula (VII) or (IX).

2.) In stage (h) it is possible to use instead of the carboxylic acid chlorides also the corresponding carboxylic acids. Those acids of the general formula R'OH, wherein R' has the meaning given above, are reacted in at least one solvent, preferably selected from the group consisting of dichloromethane, acetonitrile, dimethylformamide, diethyl ether, dioxane and tetrahydrofuran, with amines (VI) or (XII), with the addition of at least one coupling reagent, preferably selected from the group consisting of carbonyldiimidazole (CDI), 2-chloro-1-methylpyridinium iodide (Mukaiyama's reagent), N-(3-dimethylaminopropyl)-N'-ethylcarbo-diimide (EDCI), O-(benzotriazol-1-yl)-N,N,N',N'''-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds having the general formula (VII) or (IX).

3.) Cyclic amide systems are synthesized in stage (h) analogously to procedures known in the literature, for example (Lit. No. 14) Bioorganic & Medicinal Chemistry Letters 17 (2007) 428-433 and (Lit. No. 15) Bioorganic & Medicinal Chemistry Letters 17 (2007) 424-427.

4.) Stage (h) can optionally be carried out in two steps. To that end, the amines of the general formula (VI) or (XII) are first converted into the corresponding alkylated amines before the second step is carried out analogously to the above-described method 1.) or 2.) for stage (h). The alkylated amines are obtained either by reaction of the amines of the general formula (VI) or (XII) with aldhehydes or ketones in at least one organic solvent, preferably from the group consisting of diethyl ether, tetrahydrofuran, methanol, ethanol, dichloroethane, dichloromethane and toluene, with the addition of at least one reducing agent, preferably from the group consisting of borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of preferably from −70° C. to 100° C., or by reaction of the amines of the general formula (VI) or (XII) with halides, preferably bromides or iodides, or sulfonates, preferably mesylates, in the presence of at least one suitable base, preferably sodium hydride or potassium carbonate, in at least one organic solvent, preferably from the group consisting of THF, DMSO and DMF, at temperatures of preferably from −70° C. to 100° C.

In stage (i), compounds of the general formula (V) or (VII) are reacted in at least one solvent, preferably selected from the group consisting of water, methanol, ethanol, isopropanol, diethyl ether, tetrahydrofuran, toluene, acetonitrile, dimethylformamide, dioxane and dimethyl sulfoxide, with an inorganic base, preferably selected from the group consisting of lithium hydroxide, sodium hydroxide, potassium hydroxide, potassium tert-butanolate, lithium propanethiolate and sodium phenylselenolate, optionally with the addition of HMPA or lithium chloride, or with a Lewis acid, preferably selected from the group consisting of trimethylsilyl chloride, boron tribromide and aluminium trichloride, optionally with the addition of thiols, sodium iodide or lithium chloride, at temperatures of preferably from 0° C. to 100° C., to give compounds of the general formula (VIII) or (X).

In stage (j), compounds of the general formula (X) or (VIII) are reacted in at least one solvent, preferably selected from the group consisting of dichloromethane, acetonitrile, dimethylformamide, diethyl ether, dioxane and tetrahydrofuran, with amines $NHR_4R_4'$, wherein $R_4$ and $R_4'$ have the meaning given above, with the addition of at least one coupling reagent, preferably selected from the group consisting of carbonyldiimidazole (CDI), 2-chloro-1-methylpyridinium iodide (Mukaiyama's reagent), N-(3-dimethylaminopropyl)-N'-ethylcarbodiimide (EDCI), O-(benzotriazol-1-yl)-N,N,N,N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds having the general formula (IX) or (XI).

In stage (k), the amine protecting groups (Pg) are removed from molecules of the general formula (XI) by a method known in the literature (see (a) Protecting Groups, Philip J. Kocienski, Thieme, Stuttgart; 3rd Revised Edition (14 Feb. 2005) (b) Protective Groups in Organic Synthesis, Theodora W. Greene and Peter G. M. Wuts, Wiley & Sons; 4th Edition (30 Oct. 2006)).

In particular Pg=Boc: In stage (k) the compounds of the general formula (XI) are reacted in at least one solvent, preferably selected from the group consisting of water, methanol, ethanol, isopropanol, diethyl ether, tetrahydrofuran, acetonitrile, dioxane, dimethylformamide and dimethyl sulfoxide, with an acid, preferably selected from the group consisting of trifluoroacetic acid, sulfuric acid and hydrochloric acid or acetyl chloride/methanol, at temperatures of preferably from 0° C. to 80° C., to give compounds having the general formula (XII).

General Process for the Preparation of Amines

Starting materials of the general formulae (XIII), (XX) and (XXXIII) are either obtainable commercially or can be synthesized by conventional methods known to the person skilled in the art.

In stage (o), the amine protecting groups (Pg) (preferably Boc, Cbz, Bn, PMB) are removed from the corresponding compounds by a method known in the literature (see (a) Protecting Groups, Philip J. Kocienski, Thieme, Stuttgart; 3rd Revised Edition (14 Feb. 2005) (b) Protective Groups in Organic Synthesis, Theodora W. Greene and Peter G. M. Wuts, Wiley & Sons; 4th Edition (30 Oct. 2006)).

In particular Pg=Boc: In stage (o), the corresponding compounds are reacted in at least one solvent, preferably selected from the group consisting of water, methanol, ethanol, isopropanol, diethyl ether, tetrahydrofuran, acetonitrile, dioxane, dimethylformamide and dimethyl sulfoxide, with an acid, preferably selected from the group consisting of trifluoroacetic acid, sulfuric acid and hydrochloric acid or acetyl chloride/methanol, at temperatures of preferably from 0° C. to 80° C., to give the corresponding deprotected compounds.

Part 1—General Process for the Preparation of Amines (XV), (XVII) and (XIX)

Scheme 2: Preparation of amines (XV), (XVII) and (XIX)

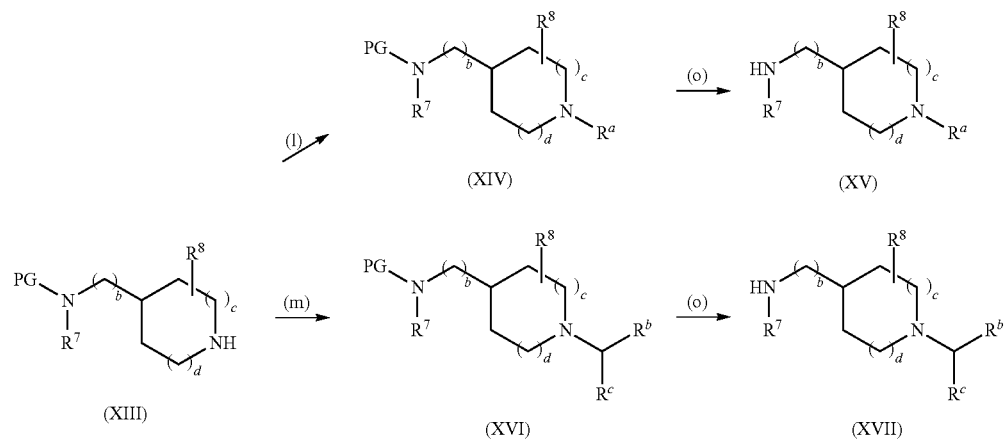

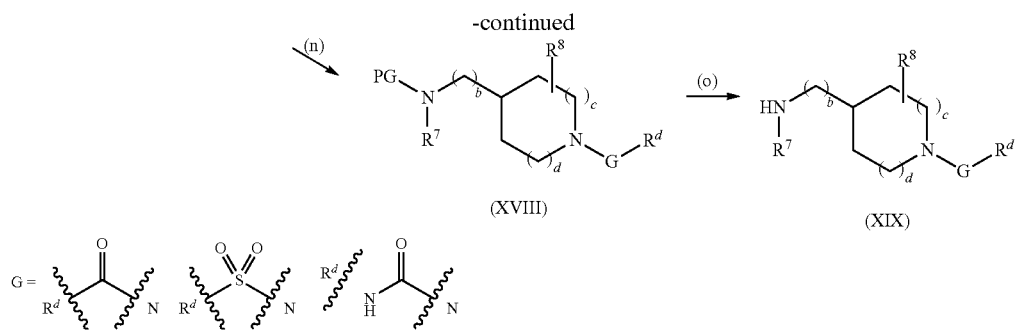

In stage (I), compounds of the general formula (XIII) are reacted in at least one solvent, preferably selected from the group consisting of ethanol, methanol, n-butanol, isopropanol, 2-butanone, DMSO, diethyl ether, water, benzene, toluene, THF, DCM, acetonitrile, acetone, DMF and pentane, with boronic acids, iodide, bromide, chloride or mesylate compounds, optionally with the addition of at least one base, preferably selected from the group consisting of potassium hydroxide, sodium hydroxide, optionally in aqueous or alcoholic solution, potassium carbonate, potassium hexamethyldisilazane, sodium hydride, potassium hydride, sodium methanolate, sodium ethanolate, sodium tert-butylate and diisopropylethylamine, optionally with the addition of an auxiliary substance, preferably selected from the group consisting of 18-crown-6, 15-crown-5, tetrabutylammonium bromide or sulfate, benzyl-triethylammonium chloride, 1-n-butyl-3-methylimidazolium tetrafluoroborate and DMAP, optionally using a catalyst, preferably selected from the group consisting of Pd(Pcyclohexyl$_3$)$_2$Cl$_2$, Pd$_2$(dba)$_3$, Ni(OAc)$_2$, Cu(OAc)$_2$, optionally using a ligand, preferably selected from the group consisting of P(o-tolyl)$_3$, P(1,1'-bis(diphenylphosphino)ferrocene, 2,2'-bipyridine, P(tri-o-tolylphosphine)$_3$, to give compounds of the general formula (XIV). Compounds of the general formula (XIV) are further obtained by reacting compounds of the general formula (XIII) with iodide, bromide, chloride or mesylate compounds, under Buchwald-Hartwig conditions.

In stage (m), compounds of the general formula (XIII) are reacted with aldehydes of the general formula R$^b$CHO or ketones of the general formula R$^b$COR$^c$, wherein R$^b$ and R$^c$ have the meanings given above, in at least one organic solvent, preferably from the group consisting of diethyl ether, tetrahydrofuran, methanol, ethanol, dichloroethane, dichloromethane and toluene, with the addition of at least one reducing agent, preferably from the group consisting of borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of preferably from −70° C. to 100° C., to give compounds of the general formula (XVI).

In stage (n), amines of the general formula (XIII) are reacted in at least one solvent, preferably selected from the group consisting of dichloromethane, acetonitrile, dimethylformamide, diethyl ether, dioxane, tetrahydrofuran, methanol, ethanol and isopropanol, with acid chlorides R$^d$COCl or sulfonyl chlorides R$^d$SO$_2$Cl or isocyanates R$^d$NCO, wherein R$^d$ has the meaning given above, in the presence of at least one inorganic base, preferably selected from the group consisting of potassium carbonate and caesium carbonate, or an organic base, preferably selected from the group consisting of triethylamine, diisopropylethylamine and pyridine, and optionally with the addition of 4-(dimethylamino)pyridine or 1-hydroxy-benzotriazole, at temperatures of preferably from −15° C. to 50° C., to give compounds having the general formula (XVIII).

In stage (n) it is possible to use instead of the carboxylic acid chlorides also the corresponding carboxylic acids. Those acids of the general formula R$^d$CO$_2$H, wherein R$^d$ has the meaning given above, are reacted in at least one solvent, preferably selected from the group consisting of dichloromethane, acetonitrile, dimethylformamide, diethyl ether, dioxane and tetrahydrofuran, with amines (XIII), with the addition of at least one coupling reagent, preferably selected from the group consisting of carbonyldiimidazole (CDI), 2-chloro-1-methylpyridinium iodide (Mukaiyama's reagent), N-(3-dimethylaminopropyl)-N'-ethyl-carbodiimide (EDCI), O-(benzotriazol-1-yl)-N,N,N',N'-tetramethyluronium tetrafluoroborate (TBTU), N,N'-dicyclohexylcarbodiimide (DCC) and 1-benzotriazolyloxy-tris-(dimethylamino)-phosphonium hexafluorophosphate (BOP), optionally in the presence of at least one inorganic base, preferably selected from the group consisting of potassium carbonate and caesium carbonate, or an organic base, preferably selected from the group consisting of triethylamine, diisopropylethylamine and pyridine, and optionally with the addition of 4-(dimethylamino)pyridine or 1-hydroxybenzotriazole, to give compounds having the general formula (XVIII).

Stage (o)—See Above.

Part 2—General Process for the Preparation of Amines (XXII), (XXV), (XXVIII), (XXXI) and (XXXII)

Scheme 3: Preparation of amines (XXII), (XXV), (XXVIII), (XXXI) and (XXXII)

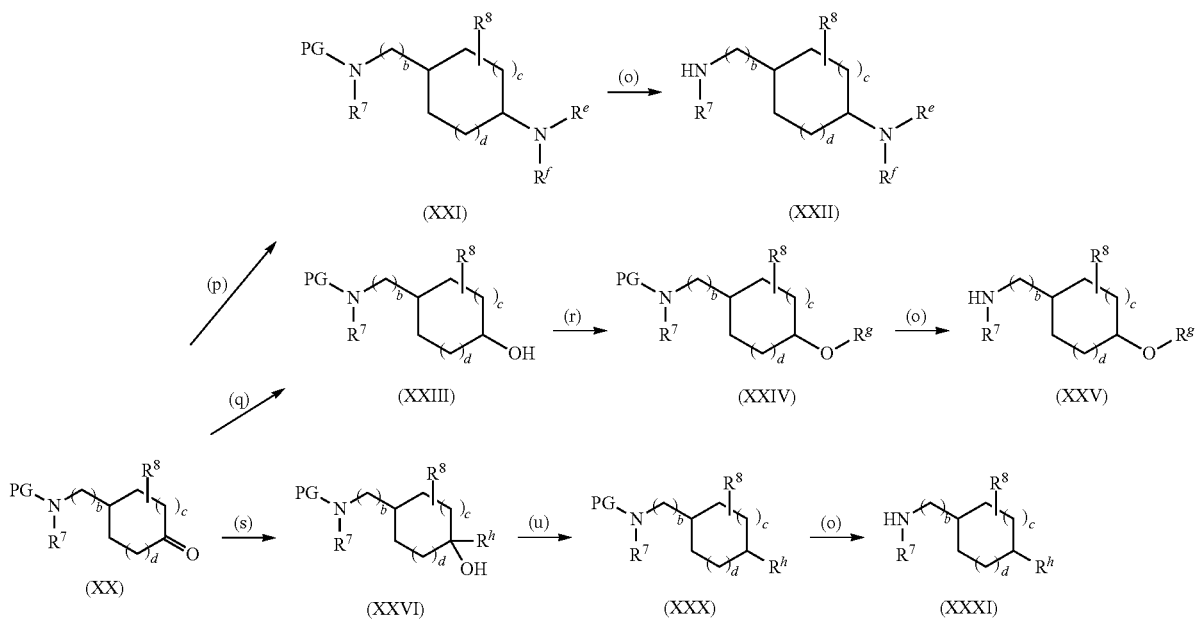

In stage (p), compounds of the general formula (XX) are reacted with amines of the general formula $R^eNHR^f$, wherein $R^e$ and $R^f$ have the meanings given above, in at least one organic solvent, preferably from the group consisting of diethyl ether, tetrahydrofuran, methanol, ethanol, dichloroethane, dichloromethane and toluene, with the addition of at least one reducing agent, preferably from the group consisting of borane-pyridine complex, sodium borohydride, sodium triacetoxyborohydride, sodium cyanoborohydride and triethylsilane, optionally in the presence of at least one acid, preferably selected from the group consisting of formic acid, acetic acid, hydrochloric acid and trifluoroacetic acid, at temperatures of preferably from −70° C. to 100° C., to give compounds of the general formula (XXI).

In stage (q), compounds of the general formula (XX) are reacted in at least one organic solvent, preferably from the group consisting of diethyl ether, tetrahydrofuran, methanol, ethanol, dichloroethane, dichloromethane and toluene, with the addition of at least one reducing agent, preferably from the group consisting of lithium aluminium hydride, RedAl® (sodium bis(2-methoxyethoxy)aluminium hydride), lithium tri-tert-butoxyaluminium hydride, sodium borohydride, sodium triacetoxyborohydride, sodium cyanoborohydride, diborane, Selectride® and triethylsilane, optionally in the presence of at least one acid, preferably selected from the group consisting of formic acid, acetic acid, hydrochloric acid and trifluoro-acetic acid, at temperatures of preferably from −25° C. to 100° C., to give compounds of the general formula (XXIII).

In stage (r), compounds of the general formula (XXIII) are converted into compounds of the general formula (XXIV) by introduction of a suitable leaving group, such as, for example, halogen or mesylate, and subsequent reaction with alcohols. Compounds of the general formula (XII) are converted into the corresponding mesylates in at least one solvent, preferably selected from the group consisting of dichloromethane, dioxane, diethyl ether, tetrahydrofuran, acetonitrile and dimethylformamide, with a sulfonyl chloride, preferably selected from the group consisting of methyl sulfonyl chloride, trifluoromethyl sulfonyl chloride, tolyl sulfonyl chloride, and at least one base, preferably selected from the group consisting of caesium carbonate, calcium carbonate, potassium carbonate, triethylamine, diisopropylethylamine and pyridine, at temperatures of preferably from 0° C. to 80° C. The mesylates are reacted in at least one solvent, preferably selected from the group consisting of dichloromethane, dioxane, diethyl ether, tetrahydrofuran, acetonitrile, toluene and dimethylformamide, with a suitable alcohol in the presence of an excess of base, preferably selected from the group consisting of caesium carbonate, calcium carbonate, potassium carbonate, potassium hydrogen carbonate, sodium hydrogen carbonate, triethylamine, diisopropylethylamine and pyridine, at temperatures of preferably from 0° C. to 80° C., to give compounds of the general formula (XXIV). Alternatively, in stage (r) compounds of the general formula (XXIV) can be prepared in a Mitsunobu reaction from compounds of the general formula (XXIV). Further, stage (r) can be carried out analogously to stage (t).

In stage (s), the carbonyl compounds (XX) are reacted with metal organyls, typically Li or Mg organyls (Grignard), in solvents such as, for example, toluene, benzene, hexane, pentane, THF or diethyl ether, optionally with the addition of, for example, $CeCl_3$, to give the tertiary alcohols (XXVI).

In stage (u), compounds of the general formula (XXVI) are reacted in at least one solvent, preferably selected from the group consisting of methanol, ethanol, isopropanol, dichloromethane, dioxane, diethyl ether, dimethyl sulfoxide, tetrahydrofuran, acetonitrile and dimethyl-formamide, in the presence of at least one acid, preferably selected from the group consisting of formic acid, acetic acid, hydrochloric acid, sulfuric acid and trifluoroacetic acid, at temperatures of preferably from 0° C. to 100° C. The unsaturated systems formed thereby are reduced by a method known to the person skilled in the art to give the compounds of the general formula (XXX).

Stage (o)—See Above.

Pharmacological Methods

Functional Study on the Bradykinin Receptor 1 (B1R)

The agonistic or antagonistic action of substances can be determined on the bradykinin receptor 1 (B1R) of the species human and rat using the following assay. According to this assay, the increase in intracellular $Ca^{2+}$ following administration of a B1R agonist is quantified with the aid of a $Ca^{2+}$-sensitive dye (Fluo-4 type, Molecular Probes Europe BV, Leiden, Netherlands) using a Fluorescent Imaging Plate Reader (FLIPR, Molecular Devices, Sunnyvale, USA) and/or using a Novostar (BMG Labtech GmbH, Offenburg, Germany).

Method:

Chinese hamster ovary cells (CHO K1 cells) which have been stably transfected with the human B1R gene (hB1R cells) or with the B1R gene of the rat (rB1R cells) are used. For functional studies, the cells are plated out on black 96-well plates having a clear base (BD Biosciences, Heidelberg, Germany or Greiner, Frickenhausen, Germany) in a density of 20,000-35,000 cells/well. The cells are left overnight at 37° C. and with 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany), with 10 vol. % FBS (fetal bovine serum, Gibco Invitrogen GmbH, Karlsruhe, Germany or PAN Biotech GmbH, Aidenbach, Germany). On the following day, the cells are loaded for 60 minutes at 37° C. with 2.13 µM Fluo-4 (Molecular Probes Europe BV, Leiden, Netherlands) in HBSS buffer (Hank's buffered saline solution, Gibco Invitrogen GmbH, Karlsruhe, Germany) with 2.5 M probenecid (Sigma-Aldrich, Taufkirchen, Germany) and 10 mM HEPES (Sigma-Aldrich, Taufkirchen, Germany). The plates are then washed twice with HBSS buffer, and HBSS buffer additionally containing 0.1% BSA (bovine serum albumin; Sigma-Aldrich, Taufkirchen, Germany), 5.6 mM glucose and 0.05% gelatin (Merck KGaA, Darmstadt, Germany) is added to the plates. After incubation for a further 20 minutes at room temperature, the plates are inserted into the FLIPR or Novostar for $Ca^{2+}$ measurement. Alternatively, washing is carried out with buffer A (15 mM HEPES, 80 mM NaCl, 5 mM KCl, 1.2 mM $CaCl_2$, 0.7 mM $MgSO_4$, 2 g/l glucose, 2.5 mM probenecid) followed by loading with buffer A with added 2.5 µM Fluo-4 and 0.025% Pluronic F127 (Sigma-Aldrich, Taufkirchen, Germany). The cells are then washed twice with buffer A and incubated for 30 minutes at room temperature with buffer A additionally containing 0.05% BSA and 0.05% gelatin and are then inserted into the FLIPR or Novostar for $Ca^{2+}$ measurement. The $Ca^{2+}$-dependent fluorescence is measured before and after the addition of substances ($\lambda_{ex}$=488 nm, $\lambda_{em}$=540 nm). Quantification is carried out by measuring the highest fluorescence intensity (FC, fluorescence counts) over time.

Fluorescence Assay:

The FLIPR protocol consists of 2 substance additions, which are pipetted in the FLIPR. In the case of measurements using the Novostar, only the second substance addition is pipetted in the device. Both devices measure the fluorescence intensity over time. Test substances (10 µM) are first pipetted onto the cells and the intracellular $Ca^{2+}$ increase is compared with the control (hB1R: Lys-Des-$Arg^9$-bradykinin>=50 nM; rB1R: Des-$Arg^9$-bradykinin>=1 µM). This gives the % activation, based on the $Ca^{2+}$ signal after addition of Lys-Des-$Arg^9$-bradykinin (>=50 nM) or Des-$Arg^9$-bradykinin (>=1 µM). After 6-20 minutes' incubation, Lys-Des-$Arg^9$-bradykinin (hB1R) or Des-$Arg^9$-bradykinin (rB1R) is applied in the concentration of the $EC_{80}$, and the increase in $Ca^{2+}$ is likewise determined. Antagonists lead to suppression of the $Ca^{2+}$ increase in the cells. % Inhibition compared with the maximum achievable inhibition is calculated. In order to determine the $IC_{50}$ value, the substances are added in various concentrations. Duplicate or triplicate determinations (n=2 or n=3) are carried out, and these are repeated in at least one further independent experiment (N>=2). The compounds exhibit especially a B1R antagonistic action on the human receptor and/or on the rat receptor. The data in % inhibition are indicated by way of example in the table below.

The invention will be explained in further detail hereinafter with reference to illustrative examples without limiting the general inventive idea.

EXAMPLES

List of Abbreviations eq, equiv.=equivalent(s)
Boc=tert-butyloxycarbonyl
Cbz=benzyloxycarbonyl
d=day(s)
TLC=thin-layer chromatography
DCM=dichloromethane
DIPEA=diisopropylethylamine
DMF=dimethylformamide
DMSO=dimethyl sulfoxide
EDCI=N-(3-dimethylaminopropyl)-N'-ethylcarbodiimide hydrochloride
sat.=saturated
h=hour(s)
HATU=2-(1H-7-azabenzotriazol-1-yl)-1,1,3,3-tetramethyluronium hexafluorophosphate
HOBt=1-hydroxybenzotriazole
conc.=concentrated
LAH=lithium aluminium hydride
MeOH=methanol
min=minute(s)
M=molar
org.=organic
R.t.=retention time
RT=room temperature
TEA=triethylamine
TFA=trifluoroacetic acid
THF=tetrahydrofuran
wt. %=percent by weight The chemicals and solvents used were obtained commercially from the conventional suppliers (Acros, Aldrich, Fluka, Lancaster, Maybridge, TCI, Fluorochem, Tyger, ABCR, Fulcrum, FrontierScientific, Milestone, etc.). The reactions were in some cases carried out under inert gas (nitrogen). The yields of the prepared compounds are not optimized. The mixing ratios of solvents are always given in the ratio volume/volume. Amount equivalents of the reagents that are used, as well as amounts of solvent, reaction temperatures and times, can vary slightly in different reactions that are carried out by the same method. Working up and purification methods were adapted correspondingly to the characteristic properties of the compounds.

A. Acid Structural Units

1) Amino Acid Esters (A)

Amino Acid Ester Overview:

| No. | Structure | Amino acid ester (A) | Comments |
|---|---|---|---|
| A-01 | 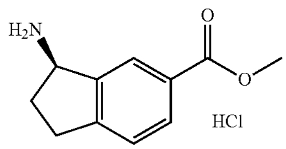 | (3R)-3-Amino-2,3-dihydro-1H-indene-5-carboxylic acid methyl ester hydrochloride (A-01) | commercially available from NetChem (Order No. 517173) |
| A-02 | 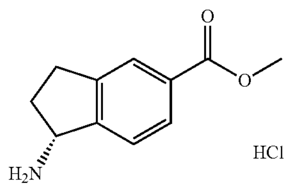 | (R)-Methyl 1-amino-2,3-dihydro-1H-indene-5-carboxylate hydrochloride (A-02) | commercially available from NetChem (Order No. 517171) |
| A-03 | 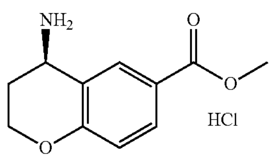 | (R)-Methyl 4-aminochromane-6-carboxylate hydrochloride (A-03) | commercially available from NetChem (Order No. 517145) |
| A-04 | 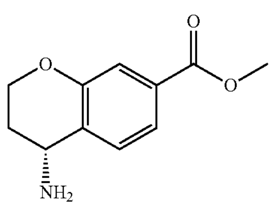 | (R)-Methyl 4-aminochromane-7-carboxylate (A-04) | commercially available from NetChem (Order No. 517155) |
| A-05 | 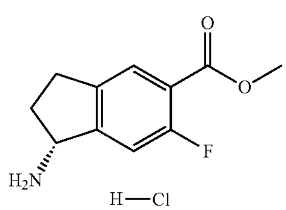 | (R)-Methyl 1-amino-6-fluoro-2,3-dihydro-1H-indene-5-carboxylate hydrochloride (A-05) | see below |
| A-06 | 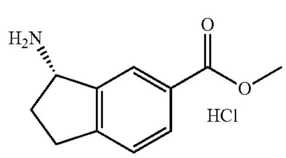 | (3R)-3-Amino-2,3-dihydro-1H-indene-5-carboxylic acid methyl ester hydrochloride (A-06) | commerically available from NetChem (Order 517174) |
| A-07 | 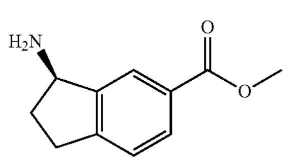 | (R)-Methyl 3-amino-2,3-dihydro-1H-indene-5-carboxylate (A-07) | see below |
| A-08 | 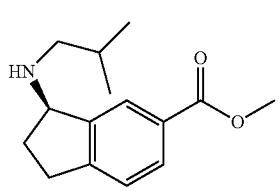 [SMILES: COC(=O)c1ccc2c(c1)[C@H](NCC(C)C)CC2] | (R)-Methyl 3-(isobutylamino)-2,3-dihydro-1H-inden-5-carboxylate (A-08) | see below |

-continued

| No. | Structure | Amino acid ester (A) | Comments |
|---|---|---|---|
| A-09 | 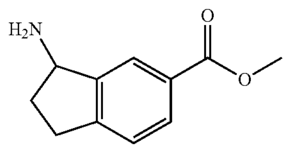 | 3-Amino-2,3-dihydro-1H-indene-5-carboxylic acid methyl ester (A-09) | commercially available from NetChem (Order No. 596829) |
| A-10 | 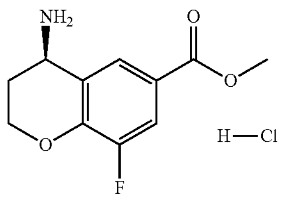 | (R)-Methyl 4-amino-8-fluorochromane-6-carboxylate hydrochloride (A-10) | commercially available from NetChem (Order No. 724633) or from the corresponding carboxylic acid analogously to A-05 |
| A-11 | 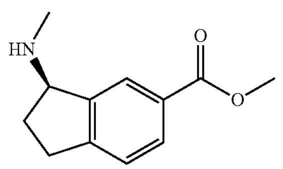 | (R)-Methyl 3-(methylamino)-2,3-dihydro-1H-indene-5-carboxylate (A-11) | see below |
| A-12 | 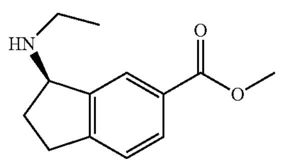 [SMILES: CCN[C@@H]1CCc2ccc(C(=O)OC)cc21] | (R)-Methyl 3-(ethylamino)-2,3-dihydro-1H-indene-5-carboxylate (A-12) | see below |
| A-13 | 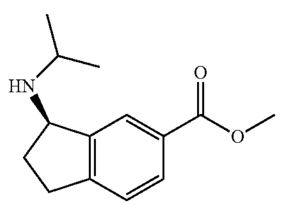 [SMILES: COC(=O)c1ccc2c(c1)[C@H](NC(C)C)CC2] | (R)-Methyl 3-(isopropylamino)-2,3-dihydro-1H-indene-5-carboxylate (A-13) | Yield: 91% The synthesis was carried out starting from A-07 analogously to A-15. |
| A-14 | 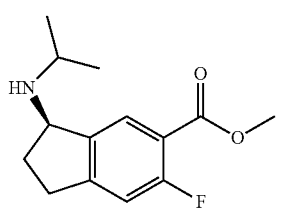 [SMILES: COC(=O)c1cc2c(cc1F)CC[C@H]2NC(C)C] | (R)-Methyl 6-fluoro-3-(isopropylamino)-2,3-dihydro-1H-indene-5-carboxylate (A-14) | Yield: 54% The synthesis was carried out starting from A-17 analogously to A-15. |
| A-15 | 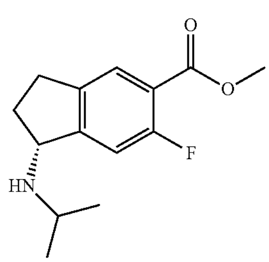 [SMILES: COC(=O)c1cc2c(cc1F)[C@H](NC(C)C)CC2] | (R)-Methyl 6-fluoro-1-(isopropylamino)-2,3-dihydro-1H-indene-5-carboxylate (A-15) | see below |
| A-16 | 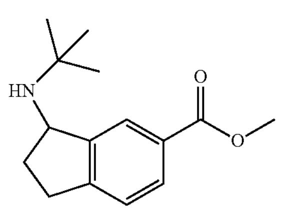 [SMILES: COC(=O)c1ccc2c(c1)C(NC(C)(C)C)CC2] | Methyl 3-(tert-butylamino)-2,3-dihydro-1H-indene-5-carboxylate (A-16) | see below |

| No. | Structure | Amino acid ester (A) | Comments |
|---|---|---|---|
| A-17 | 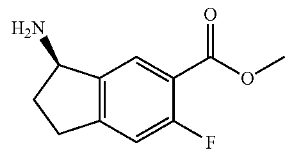 | (R)-Methyl 3-amino-6-fluoro-2,3-dihydro-1H-indene-5-carboxylate (A-17) | see below |
| A-18 | 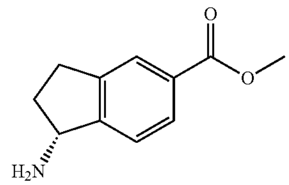 | (R)-Methyl 1-amino-2,3-dihydro-1H-indene-5-carboxylate (A-18) | A-18 was synthesised starting from (R)-5-bromo-2,3-dihydro-1H-inden-1-amine analogously to A-07. |
| A-19 | 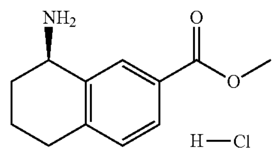 | (R)-Methyl 8-amino-5,6,7,8-tetrahydronaphthalene-2-carboxylate hydrochloride | commercially available from NetChem (Order No. 517119 HCl) |
| A-20 | 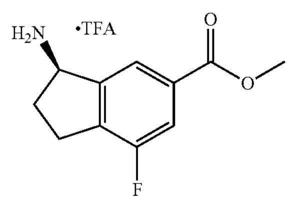 | (R)-Methyl 3-amino-7-fluoro-2,3-dihydro-1H-indene-5-carboxylate trifluoroacetate (A-20) | see below |

Synthesis of Amino Acid Ester A-05

(R)-Methyl 1-amino-6-fluoro-2,3-dihydro-1H-indene-5-carboxylate hydrochloride (A-05)

(R)-1-Amino-6-fluoro-2,3-dihydro-1H-indene-5-carboxylic acid hydrochloride (commercially available from NetChem, Order No. 573039) (0.3 g, 1.298 mmol, 1 eq) was dissolved in methanolic HCl solution (15 eq, 1.25 M) and the mixture was refluxed for 16 h. Concentration was then carried out, the residue was taken up in a little acetone (1 ml), and a white solid was precipitated with diethyl ether (30 ml). The solid was filtered off, washed with diethyl ether and dried to give the desired product. Yield: 94%

As an alternative, this reaction was also carried out with SOCl$_2$ (2.4 eq) in methanol (see A-17).

Synthesis of Amino Acid Ester A-07

(R)-Methyl 3-amino-2,3-dihydro-1H-indene-5-carboxylate (A-07)

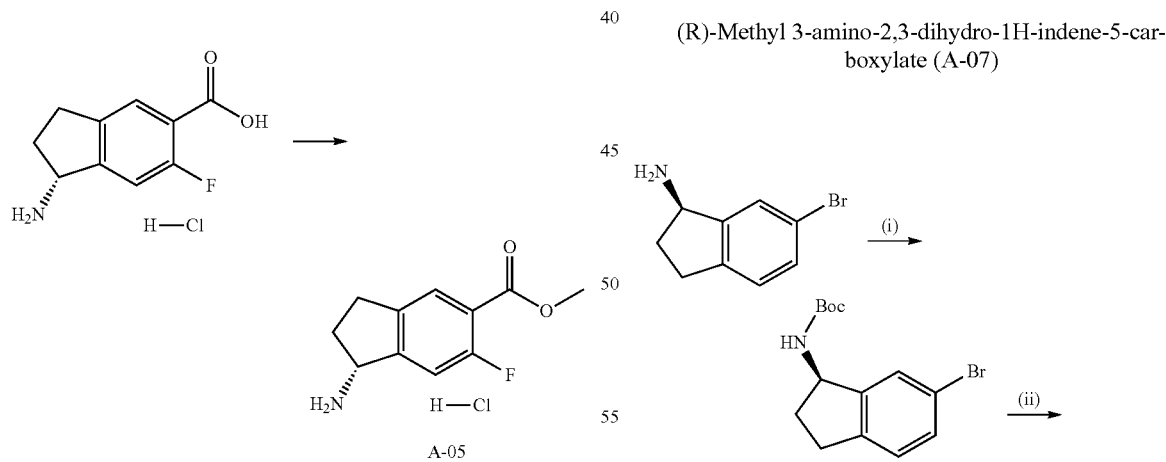

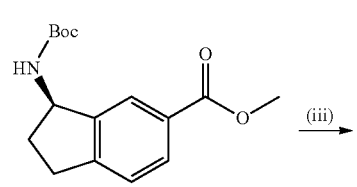

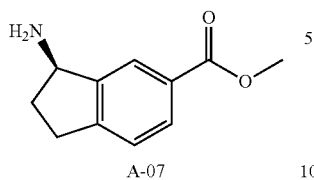

A-07

Stage (i): (R)-tert-Butyl 6-bromo-2,3-dihydro-1H-inden-1-ylcarbamate (R)-6-Bromo-2,3-dihydro-1H-inden-1-amine (5.0 g, 20.16 mmol, 1 eq) was dissolved in dichloromethane (100 ml) and triethylamine (11.2 ml, 80.64 mmol, 4 eq). Boc anhydride (6.47 ml, 30.24 mmol, 1.5 eq) was then added at 0° C., with stirring, and stirring was carried out for 16 h. After monitoring by thin-layer chromatography, the reaction mixture was diluted with dichloromethane (100 ml), washed with water (100 ml) and sat. NaCl solution (100 ml), dried over sodium sulfate and concentrated. The product was used in the next stage without being purified further.

Stage (ii): (R)-Methyl 3-(tert-butoxycarbonylamino)-2,3-dihydro-1H-indene-5-carboxylate (R)-tert-Butyl 6-bromo-2,3-dihydro-1H-inden-1-ylcarbamate (15.0 g, 48.07 mmol, 1 eq) was dissolved in a mixture of methanol (200 ml) and DMSO (30 ml) and degassed for 30 min with argon, and palladium acetate (0.53 g, 2.40 mmol, 0.05 eq), 1,3-bis(diphenylphosphine)-propane (0.99 g, 2.40 mmol, 0.05 eq) and triethylamine (20 ml, 144.21 mmol, 3.0 eq) were added. In an autoclave, the reaction was sealed for 16 h at 75° C. at CO pressure (80 psi). Then the reaction mixture was dried under reduced pressure, and the residue was taken up in water (150 ml) and extracted with ethyl acetate (2×300 ml). The combined organic phases were washed with sat. NaCl solution (100 ml), dried over sodium sulfate and concentrated under reduced pressure. The crude product was purified by column chromatography (silica gel, 5% ethyl acetate in hexane) to give the desired product in the form of a white solid. Yield: 76% (10.6 g, 36.43 mmol).

Stage (iii): (R)-Methyl 3-amino-2,3-dihydro-1H-indene-5-carboxylate (A-07)

TFA (10 ml) was added dropwise at 0° C. to a solution of (R)-methyl 3-(tert-butoxycarbonyl-amino)-2,3-dihydro-1H-indene-5-carboxylate (2.3 g, 7.9 mmol, 1 eq) in dichloromethane (50 ml), and stirring was carried out for 1 h at RT. Then the solvent was reduced under reduced pressure. The crude product was used in the following stage without being purified and analyzed further.

Synthesis of Amino Acid Ester A-08

(R)-Methyl 3-(isobutylamino)-2,3-dihydro-1H-indene-5-carboxylate (A-08)

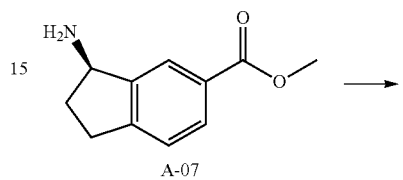

A-07

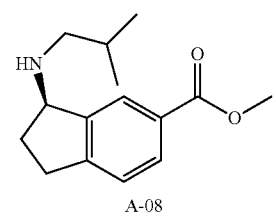

A-08

To a solution of (R)-methyl 3-amino-2,3-dihydro-1H-indene-5-carboxylate (A-07) (5.23 mmol, 1 eq) in MeOH (50 ml) there were added first acetic acid (2 drops) and then, at 0° C., isobutyraldehyde (0.47 ml, 5.23 mmol, 1 eq), and stirring was carried out for 1 h at RT. The reaction mixture was cooled to 0° C. again, NaCNBH$_3$ (821 mg, 13.07 mmol, 2.5 eq) was added, and stirring was carried out for a further 30 min at RT. After monitoring by thin-layer chromatography, the reaction mixture was concentrated, and the residue was taken up in water (50 ml) and extracted with dichloromethane (2×75 ml). The combined organic phases were washed with sat. NaCl solution (2×60 ml), dried over sodium sulfate and concentrated under reduced pressure. After purification by column chromatography (Alox neutral, 3% MeOH in dichloromethane), the desired product was obtained. Yield: 65% (0.850 g, 33.44 mmol).

Synthesis of Amino Acid Ester A-11

(R)-Methyl 3-(methylamino)-2,3-dihydro-1H-indene-5-carboxylate (A-11)

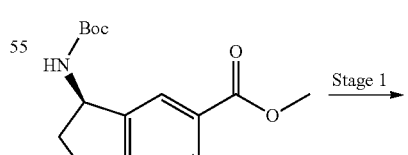

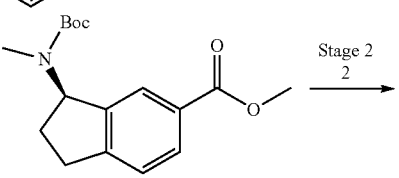

111

-continued

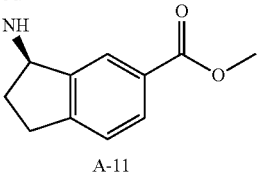

A-11

Stage 1: (R)-Methyl 3-(tert-butoxycarbonyl(methyl)amino)-2,3-dihydro-1H-indene-5-carboxylate A solution of (R)-methyl 3-(tert-butoxycarbonylamino)-2,3-dihydro-1H-indene-5-carboxylate (stage (ii) A-07) (60 g, 20.62 mmol, 1.0 eq.) in DMF (20 ml) was added dropwise at 0° C. to a suspension of NaH (1.24 g, 30.93 mmol, 1.5 eq., 60% in mineral oil) in DCM (20 ml) and stirring was carried out for 30 minutes. Methyl iodide (2.6 ml, 41.24 mmol, 2.0 eq.) was then added at 0° C. and stirring was carried out for 3 hours at RT. After monitoring by TLC, sat. ammonium chloride solution (200 ml) was added and extraction with ethyl acetate (3×250 ml) was carried out. The combined org. phases were washed with water and sat. NaCl solution (in each case 400 ml), dried over sodium sulfate, concentrated under reduced pressure. The crude product was purified by column chromatography (silica gel, 10% ethyl acetate in hexane). Yield: 95% (6.0 g, 19.67 mmol).

Stage 2: (R)-Methyl 3-(methyl amino)-2,3-dihydro-1H-indene-5-carboxylate (A-11)

TFA (25 ml) was added dropwise at 0° C. to a solution of (R)-methyl 3-(tert-butoxycarbonyl-(methyl)amino)-2,3-dihydro-1H-indene-5-carboxylate (11.0 g, 36.60 mmol, 1.0 eq.) in DCM (100 ml) and stirring was carried out for 1 hour at RT. After monitoring by TLC, the reaction solution was concentrated under reduced pressure and the residue was taken up in sat. sodium hydrogen carbonate solution and extracted with ethyl acetate (3×1000 ml). The combined org. phases were dried over sodium sulfate, concentrated and used in the next stage without being purified further. Yield: 92% (6.8 g, 33.17 mmol).

Synthesis of Amino Acid Ester A-12

(R)-Methyl 3-(ethylamino)-2,3-dihydro-1H-indene-5-carboxylate (A-12)

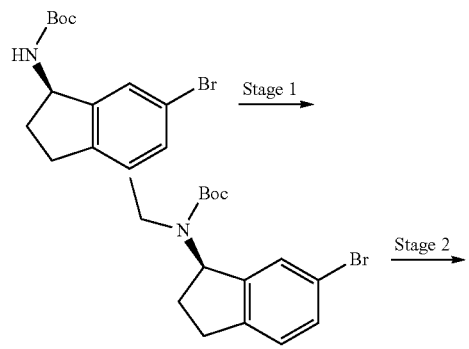

112

-continued

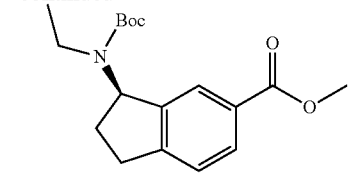

Stage 3

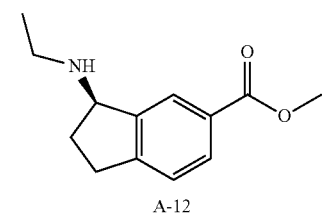

A-12

Stage 1: (R)-tert-Butyl 6-bromo-2,3-dihydro-1H-inden-1-yl(ethyl)carbamate

A solution of (R)-methyl 3-(tert-butoxycarbonylamino)-2,3-dihydro-1H-indene-5-carboxylate (stage (i) A-07) (15 g, 48.07 mmol, 1 eq) in DMF (30 ml) was added dropwise at 0° C. to a suspension of NaH (3.85 g, 96.15 mmol, 2 eq, 60% in mineral oil) in DMF (30 ml), and the mixture was stirred for 30 minutes. Ethyl iodide (11.67 ml, 144.21 mmol, 3 eq) was then added at 0° C. and the reaction mixture was then stirred for 3 hours at RT. After monitoring by TLC, sat. ammonium chloride solution (400 ml) was added and extraction with ethyl acetate (3×500 ml) was carried out. The combined org. phases were washed with water and sat. NaCl solution (in each case 600 ml), dried over sodium sulfate, concentrated under reduced pressure and purified by column chromatography (silica gel, 2% ethyl acetate in hexane). Yield: 91% (15 g, 44.12 mmol)

Stage 2: (R)-methyl 3-(tert-butoxycarbonyl(ethyl)amino)-2,3-dihydro-1H-indene-5-carboxylate (R)-tert-Butyl 6-bromo-2,3-dihydro-1H-inden-1-yl(ethyl)carbamate (15 g, 44.12 mmol, 1 eq) was dissolved in MeOH (180 ml) and DMSO (30 ml). The mixture was degassed for 30 minutes with argon, and then Pd(OAc)$_2$ (0.513 g, 2.21 mmol, 0.05 eq), 1,3-bis(diphenyl-phosphino)propane (0.911 g, 2.21 mmol, 0.05 eq) and TEA (18.4 ml, 132.35 mmol, 3 eq) were added. The reaction mixture was stirred for 16 hours at 80° C. in an autoclave under CO pressure (80 psi) and then concentrated under reduced pressure. The residue was taken up in water (200 ml) and extracted with ethyl acetate (2×400 ml). The combined org. phases were washed with sat. NaCl solution (500 ml), dried over sodium sulfate, concentrated under reduced pressure and purified by column chromatography (silica gel, 8% ethyl acetate in hexane). Yield: 77% (10.84 g, 33.97 mmol)

Stage 3: (R)-Methyl 3-(ethylamino)-2,3-dihydro-1H-indene-5-carboxylate (A-12)

TFA (25 ml) was added dropwise at 0° C. to a solution of (R)-methyl 3-(tert-butoxycarbonyl-(ethyl)amino)-2,3-dihydro-1H-indene-5-carboxylate (10.84 g, 33.97 mmol, 1 eq) in DCM (100 ml), and the mixture was stirred for 1 hour at RT. After monitoring by TLC, the reaction solution was concentrated under reduced pressure, the residue was taken up in sat. sodium hydrogen carbonate solution (500 ml) and extraction with ethyl acetate (3×1000 ml) was carried out. The combined org. phases were washed with sat. sodium chloride solution (800 ml), dried over sodium sulfate, concentrated and used in the following stage without being purified further. The desired product was in the form of a light-brown liquid. Yield: 91% (6.8 g, 31.05 mmol)

Synthesis of Amino Acid Ester A-15

(R)-Methyl 6-fluoro-1-(isopropylamino)-2,3-dihydro-1H-indene-5-carboxylate (A-15)

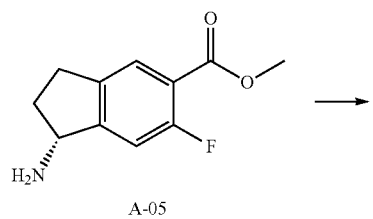

A-05

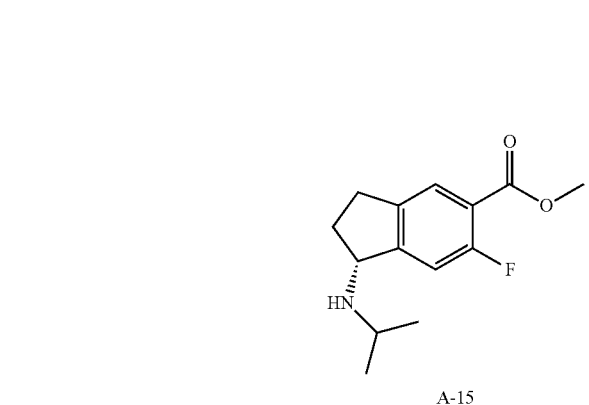

A-15

Glacial acetic acid (0.33 ml) was added to a mixture of (R)-methyl 1-amino-6-fluoro-2,3-dihydro-1H-indene-5-carboxylate hydrochloride (A-05) [see above] (4.1 g, 19.6 mmol, 1 eq) and acetone (28.8 ml, 392.3 mmol, 20 eq) in methanol (100 ml), and the reaction mixture was stirred for 3 h at room temperature. It was then cooled to 0° C. and NaBH$_4$ (2.23 g, 58.8 mmol, 3 eq) was added in portions. Stirring was carried out for a further 2 h at room temperature. After monitoring by TLC, concentration was carried out under reduced pressure and the residue was diluted with water (100 ml). Extraction with dichloromethane (150 ml) was carried out and the organic phase was washed with sat. sodium hydrogen carbonate solution (100 ml) and dried over sodium sulfate. The solvent was distilled off under reduced pressure and then the crude product was purified by column chromatography (Alox, 10% ethyl acetate/hexane) to yield the desired product in the form of a light-brown liquid. Yield: 76% (3.75 g, 19.61 mmol)

Synthesis of Amino Acid Ester A-16

Methyl 3-(tert-butylamino)-2,3-dihydro-1H-indene-5-carboxylate (A-16)

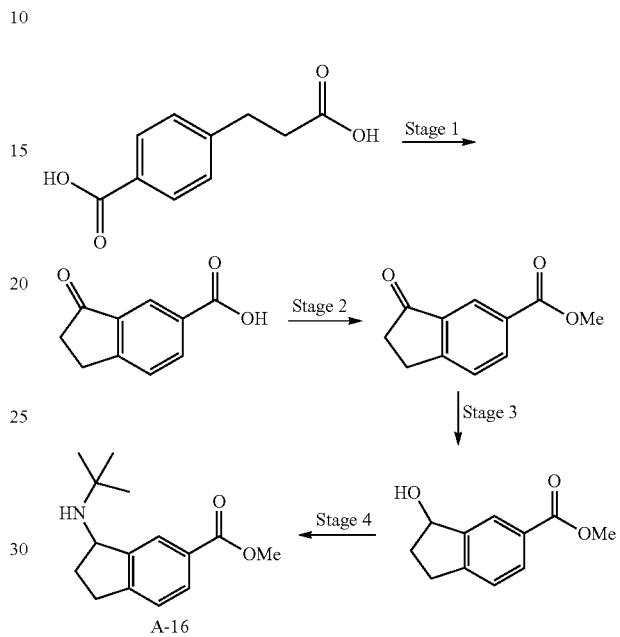

A-16

Stage 1: 3-Oxo-2,3-dihydro-1H-indene-5-carboxylic acid

A mixture of 4-(2-carboxyethyl)benzoic acid (20.0 g, 103.09 mmol, 1.0 eq.), AlCl$_3$ (164.0 g, 1237.11 mmol, 12.0 eq.) and NaCl (16.4 g, 10% mass weight of AlCl$_3$) was heated for 12 hours at 190° C. The mixture was poured onto ice (500 g), and 6 M HCl (500 ml) and ethyl acetate (800 ml) were added. The phases were separated and the aqueous phase was extracted with ethyl acetate (3×400 ml). The combined org. phases were washed with 2 M HCl solution (2×400 ml), water (2×400 ml) and sat. NaCl solution (500 ml), dried over sodium sulfate and concentrated under reduced pressure. The crude product was used in the next stage without being purified further. Yield: 77% (14.0 g, 79.545 mmol)

Stage 2: Methyl 3-oxo-2,3-dihydro-1H-indene-5-carboxylate

3-Oxo-2,3-dihydro-1H-indene-5-carboxylic acid (16.0 g, 90.909 mmol, 1.0 eq.) was dissolved in MeOH (140 ml) and cooled to 0° C.; sulfuric acid (4.5 ml) was added and the mixture was refluxed for 4 hours. The solvent was concentrated under reduced pressure, and the residue was taken up in water, rendered basic with sat. sodium hydrogen carbonate solution (200 ml) and extracted with ethyl acetate (2×400 ml). The combined org. phases were washed with water and sat. NaCl solution (in each case 2×200 ml), dried over sodium sulfate, concentrated under reduced pressure and purified by column chromatography (silica gel, 15% ethyl acetate in hexane). Yield: 58% (10.0 g, 52.63 mmol)

Stage 3: Methyl 3-hydroxy-2,3-dihydro-1H-indene-5-carboxylate

Methyl 3-oxo-2,3-dihydro-1H-indene-5-carboxylate (3.5 g, 18.421 mmol, 1.0 eq.) was dissolved in MeOH (40 ml) and cooled to 0° C.; NaBH$_4$ (749 mg, 20.263 mmol, 1.1 eq.) was added in portions and the mixture was stirred for 3 hours at RT. After monitoring by TLC, the reaction mixture was concentrated to dryness under reduced pressure, and the residue was taken up in water (100 ml) and extracted with dichloromethane (2×100 ml). The combined org. phases were dried over sodium sulfate, concentrated under reduced pressure and used in the next stage without being purified further. Yield: 92% (3.2 g, 16.66 mmol)

Stage 4: Methyl 3-(tert-butylamino)-2,3-dihydro-1H-indene-5-carboxylate (A-16)

A solution of methanesulfonic acid anhydride (6.79 g, 39.062 mmol, 2.5 eq.) in DCM (20 ml) was added dropwise at −78° C. to a solution of methyl 3-hydroxy-2,3-dihydro-1H-indene-5-carboxylate (3.0 g, 15.625 mmol, 1.0 eq.) and TEA (11.0 ml, 78.125 mmol, 5.0 eq.) in DCM (60 ml) and stirred for 2 hours at the same temperature. tert-Butylamine (16 ml, 156.5 mmol, 10.0 eq.) was slowly added dropwise at −78° C., and the mixture was heated to RT and stirred for 14 hours. The reaction solution was diluted with DCM (100 ml), washed with water (2×50 ml) and sat. NaCl solution (50 ml), dried over sodium sulfate, concentrated under reduced pressure and purified by column chromatography (silica gel, 13% ethyl acetate in hexane). Yield: 32% (1.2 g, 4.858 mmol)

Synthesis of Amino Acid Ester A-17

(R)-Methyl 3-amino-6-fluoro-2,3-dihydro-1H-indene-5-carboxylate (A-17)

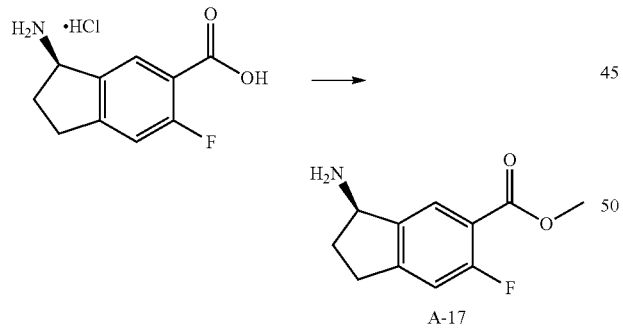

SOCl$_2$ (0.75 ml, 10.365 mmol, 2.4 eq) was added dropwise at 0° C., with stirring, to a suspension of (R)-3-amino-6-fluoro-2,3-dihydro-1H-indene-5-carboxylic acid hydrochloride (commercially available from NetChem (Order No. 573243)) (1 g, 4.319 mmol, 1 eq) in methanol (20 ml). The reaction mixture was stirred for 14 h at room temperature. When the reaction was complete according to TLC monitoring, concentration under reduced pressure was carried out and the residue was diluted with saturated sodium hydrogen carbonate solution (50 ml) and extracted with 10% methanol/dichloromethane (100 ml). The organic phase was dried over sodium sulfate and concentrated under reduced pressure. The desired product was in the form of a light-green solid. Yield: 89% (800 mg, 3.827 mmol)

Synthesis of Amino Acid Ester A-20

(R)-Methyl 3-amino-7-fluoro-2,3-dihydro-1H-indene-5-carboxylate trifluoroacetate (A-20)

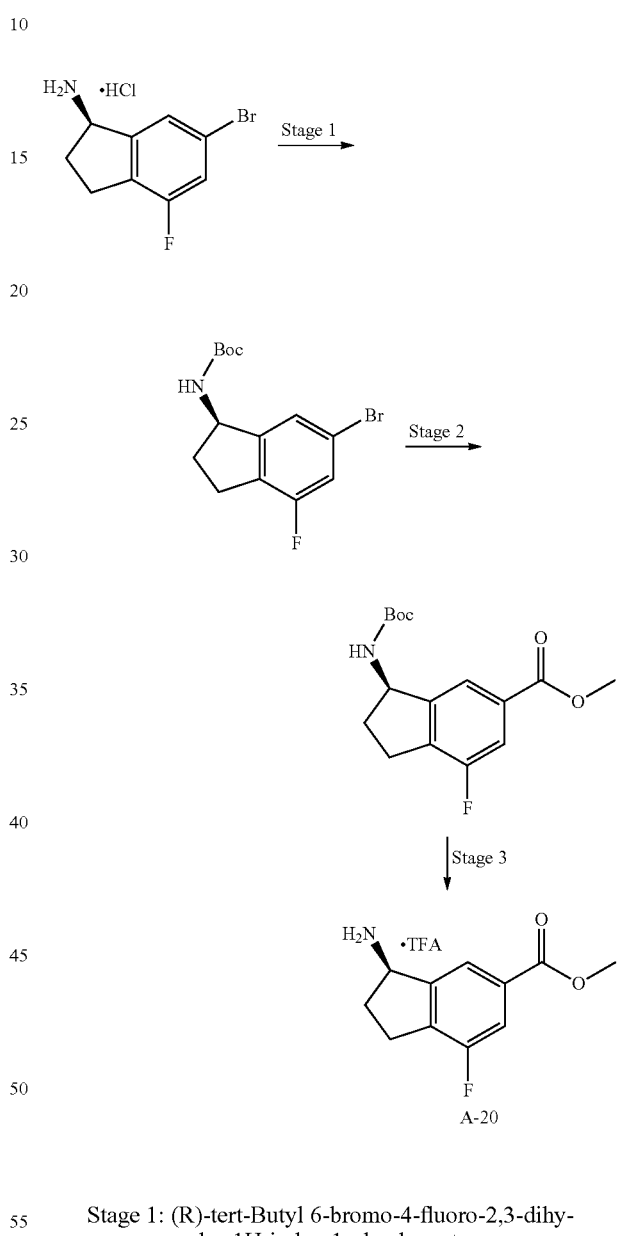

Stage 1: (R)-tert-Butyl 6-bromo-4-fluoro-2,3-dihydro-1H-inden-1-ylcarbamate (R)-6-Bromo-4-fluoro-2,3-dihydro-1H-inden-1-amine hydrochloride (1.0 g, 3.75 mmol, 1.0 eq.) was dissolved in DCM (20 ml); Boc anhydride (1.22 ml, 5.62 mmol, 1.5 eq) was added dropwise at 0° C., and the mixture was stirred for 16 hours at RT. After monitoring by TLC, the reaction solution was diluted with DCM (50 ml), washed with water (30 ml) and sat. NaCl solution (30 ml), dried over sodium sulfate, concentrated under reduced pressure and used in the next stage without being purified further. Yield: 89% (1.10 g, 3.33 mmol)

Stage 2: (R)-Methyl 3-(tert-butoxycarbonylamino)-7-fluoro-2,3-dihydro-1H-indene-5-carboxylate (R)-tert-Butyl 6-bromo-4-fluoro-2,3-dihydro-1H-inden-1-ylcarbamate (1.1 g, 3.33 mol, 1.0 eq.) was dissolved in MeOH (35 ml) and DMSO (30 ml), and the mixture was degassed for 30 minutes with argon. Pd(OAc)$_2$ (0.038 g, 0.166 mmol, 0.05 eq.), 1,3-bis(diphenylphosphino)-propane (0.068 g, 0.166 mmol, 0.05 eq.) and TEA (1.39 ml, 9.99 mmol, 3.0 eq.) were then added, and stirring was carried out for 16 hours in a pressure vessel at 75° C. under CO pressure (80 psi). The reaction mixture was concentrated, diluted with water (50 ml) and extracted with ethyl acetate (2×75 ml). The combined org. phases were washed with sat. NaCl solution (60 ml), dried over sodium sulfate, concentrated under reduced pressure and purified by column chromatography (silica gel, 10% ethyl acetate in hexane). Yield: 83% (0.86 g, 2.783 mmol)

Stage 3: (R)-Methyl 3-amino-7-fluoro-2,3-dihydro-1H-indene-5-carboxylate trifluoro-acetate (A-20)

TFA (4 ml) was added at 0° C. to a solution of (R)-methyl 3-(tert-butoxycarbonylamino)-7-fluoro-2,3-dihydro-1H-indene-5-carboxylate (0.85 g, 2.75 mmol, 1.0 eq.) in DCM (10 ml), and the mixture was stirred for 1 hour at RT. After monitoring by TLC, the reaction mixture was concentrated under reduced pressure, dried and used in the next stage without being purified further.

2) Synthesis of the Acylated & Sulfonylated Amino Acid Esters (B, C & D)
General Method for the Synthesis of Amino Acid Esters (B, C & D)
Synthesis of the Acylated & Sulfonylated Amino Acid Esters (B, C & D)

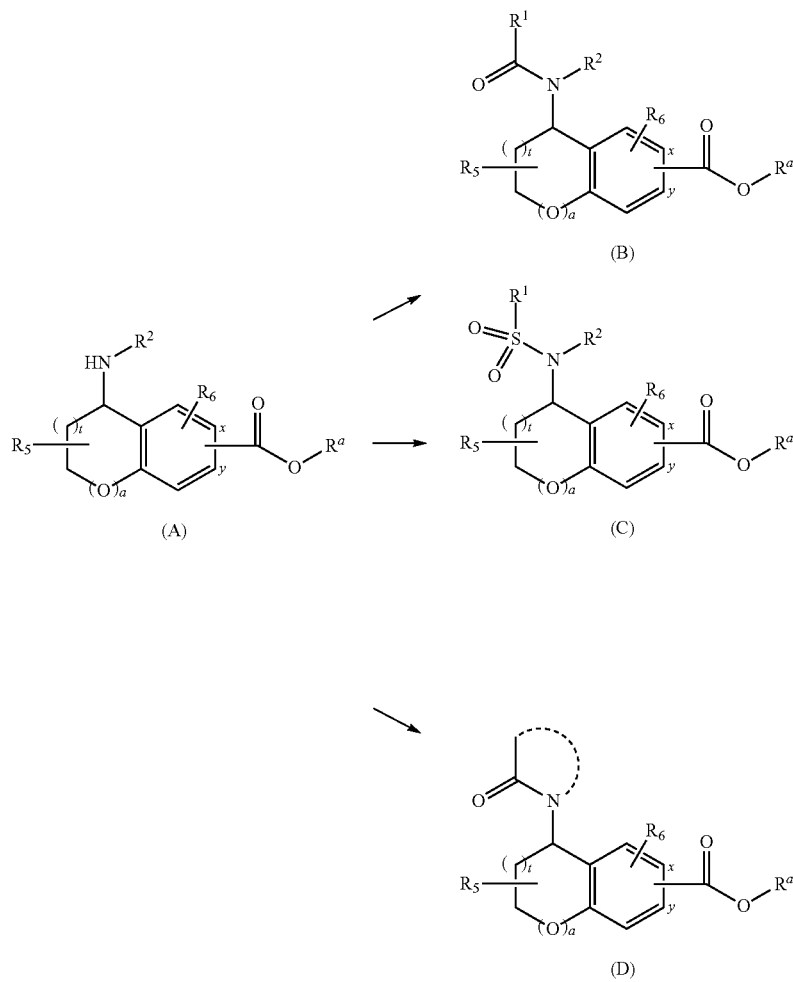

wherein

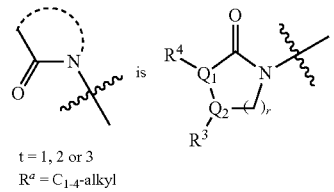

t = 1, 2 or 3
$R^a = C_{1-4}$-alkyl

Amino Acid Ester Overview:

| No. | Structure | Amino acid ester (B, C & D) | Comments |
| --- | --- | --- | --- |
| B-01 | 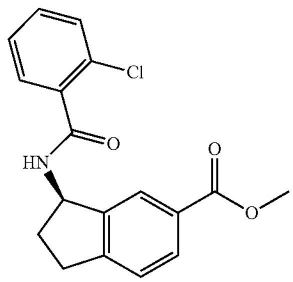 [SMILES: COC(=O)c1ccc2c(c1)[C@H](NC(=O)c1ccccc1Cl)CC2] | (3R)-3-[(2-Chloro-benzoyl)amino]-2,3-dihydro-1H-indene-5-carboxylic acid methyl ester (B-01) | see below |
| B-02 | 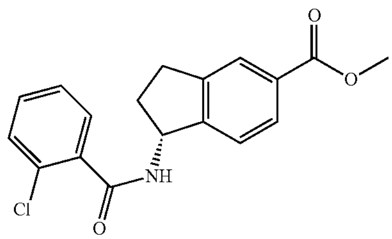 [SMILES: COC(=O)c1ccc2c(c1)CC[C@H]2NC(=O)c1ccccc1Cl] | (R)-Methyl 1-(2-chlorobenzamido)-2,3-dihydro-1H-indene-5-carboxylate (B-02) | see below |
| B-03 | 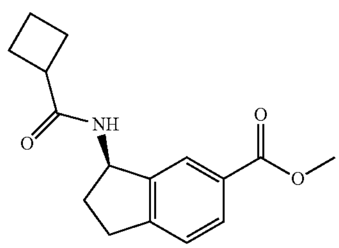 [SMILES: COC(=O)c1ccc2c(c1)[C@H](NC(=O)C1CCC1)CC2] | (R)-Methyl 3-(cyclobutanecarboxamido)-2,3-dihydro-1H-indene-5-carboxylate (B-03) | Yield: 86% The synthesis was carried out starting from A-01 analogously to B-02. |
| B-04 | 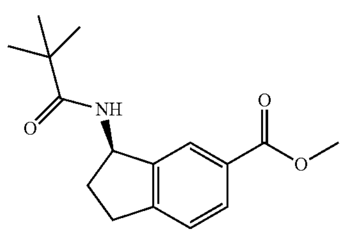 [SMILES: COC(=O)c1ccc2c(c1)[C@H](NC(=O)C(C)(C)C)CC2] | (R)-Methyl 3-pivalamido-2,3-dihydro-1H-indene-5-carboxylate (B-04) | Yield: 96% The synthesis was carried out starting from A-01 analogously to B-02. |
| B-05 | 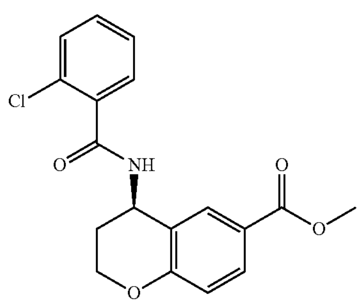 [SMILES: COC(=O)c1ccc2c(c1)[C@H](NC(=O)c1ccccc1Cl)CCO2] | (R)-Methyl 4-(2-chlorobenzamido)chromane-6-carboxylate (B-05) | see below |

-continued

| No. | Structure | Amino acid ester (B, C & D) | Comments |
|---|---|---|---|
| B-06 | 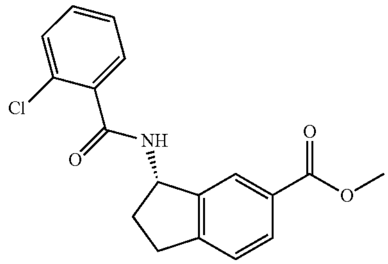 [SMILES: COC(=O)c1ccc2c(c1)[C@@H](NC(=O)c1ccccc1Cl)CC2] | (S)-Methyl 3-(2-chlorobenzamido)-2,3-dihydro-1H-indene-5-carboxylate (B-06) | Yield: 95%<br>The synthesiss was carried out sarting from A-06 analogously to B-01. |
| B-07 | 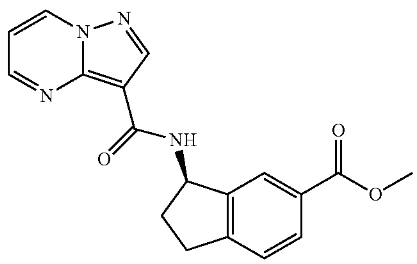 [SMILES: COC(=O)c1ccc2c(c1)[C@H](NC(=O)c1cnn3cccnc13)CC2] | (R)-Methyl 3-(pyrazolo[1,5-a]pyrimidine-3-carboxamido)-2,3-dihydro-1H-indene-5-carboxylate (B-07) | see below |
| B-08 | 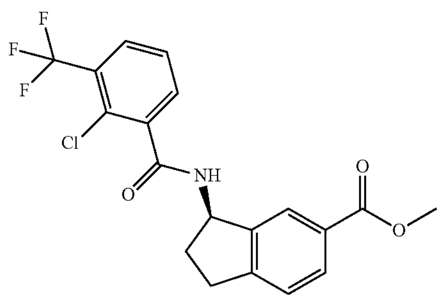 [SMILES: COC(=O)c1ccc2c(c1)[C@H](NC(=O)c1cccc(C(F)(F)F)c1Cl)CC2] | (R)-Methyl 3-(2-chloro-3-(trifluoromethyl)benzamido)-2,3-dihydro-1H-indene-5-carboxylate (B-08) | Yield: 88%<br>The synthesis was carried out starting from A-01 analogously to B-02. |
| B-09 | 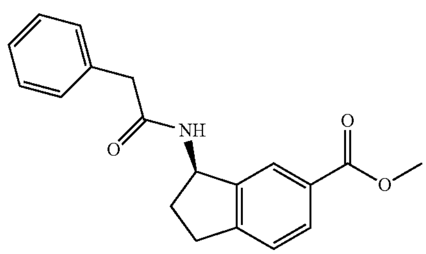 [SMILES: COC(=O)c1ccc2c(c1)[C@H](NC(=O)Cc1ccccc1)CC2] | (R)-Methyl 3-(2-phenylacetamido)-2,3-dihydro-1H-indene-5-carboxylate (B-09) | Yield: 88%<br>The synthesis was carried out starting from A-01 analogously to B-02. |
| B-10 | 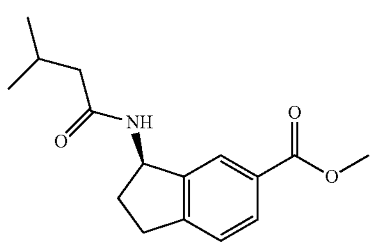 [SMILES: COC(=O)c1ccc2c(c1)[C@H](NC(=O)CC(C)C)CC2] | (R)-Methyl 3-(3-methylbutanamido)-2,3-dihydro-1H-indene-5-carboxylate (B-10) | Yield: 76%<br>The synthesis was carried out starting from A-01 analogously to B-02. |
| B-11 | 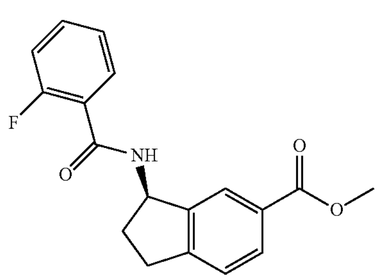 [SMILES: COC(=O)c1ccc2c(c1)[C@H](NC(=O)c1ccccc1F)CC2] | (R)-Methyl 3-(2-fluorobenzamido)-2,3-dihydro-1H-indene-5-carboxylate (B-11) | Yield: 80%<br>The synthesis was carried out starting from A-01 analogously to B-05. |

-continued

| No. | Structure | Amino acid ester (B, C & D) | Comments |
|---|---|---|---|
| B-12 | 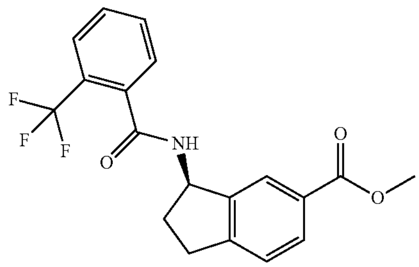 [SMILES: COC(=O)c1ccc2c(c1)[C@H](NC(=O)c1ccccc1C(F)(F)F)CC2] | (R)-Methyl 3-(2-(trifluoromethyl)benzamido)-2,3-dihydro-1H-indene-5-carboxylate (B-12) | Yield: 100%<br>The synthesis was carried out starting from A-01 analogously to B-05. |
| B-13 | 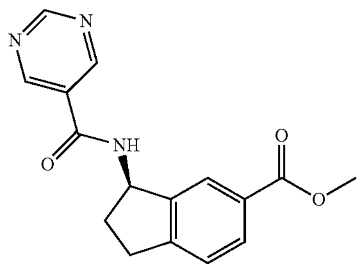 [SMILES: COC(=O)c1ccc2c(c1)[C@H](NC(=O)c1cncnc1)CC2] | (R)-Methyl 3-(pyrimidine-5-carboxamido)-2,3-dihydro-1H-indene-5-carboxylate (B-13) | Yield: 70%<br>The synthesis was carried out starting from A-01 analogously to B-07. |
| B-14 | 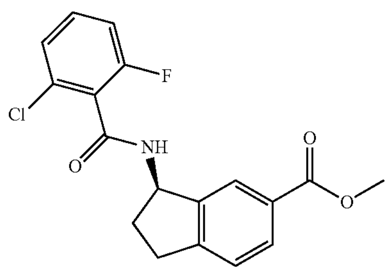 [SMILES: COC(=O)c1ccc2c(c1)[C@H](NC(=O)c1c(F)cccc1Cl)CC2] | (R)-Methyl 3-(2-chloro-6-fluroobenzamido)-2,3-dihydro-1H-indene-5-carboxylate (B-14) | Yield: 100%<br>The synthesis was carried out starting from A-01 analogously to B-05. |
| B-15 | 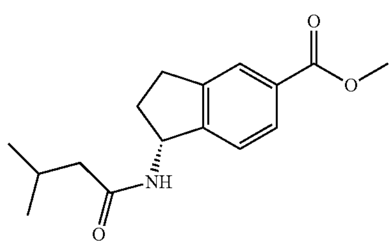 [SMILES: COC(=O)c1ccc2c(c1)CC[C@H]2NC(=O)CC(C)C] | (R)-Methyl 1-(3-methylbutanamido)-2,3-dihydro-1H-indene-5-carboxylate (B-15) | Yield: 78%<br>The synthesis was carried out starting from A-01 analogously to B-02. |
| B-16 | 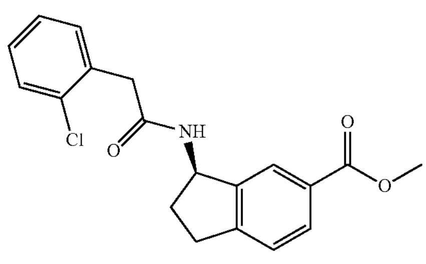 [SMILES: COC(=O)c1ccc2c(c1)[C@H](NC(=O)Cc1ccccc1Cl)CC2] | (R)-Methyl 3-(2-(2-chlorophenyl)acetamido)-2,3-dihydro-1H-indene-5-carboxylate (B-16) | Yield: 79%<br>The synthesis was carried out starting from A-01 analogously to B-07. |
| B-17 | 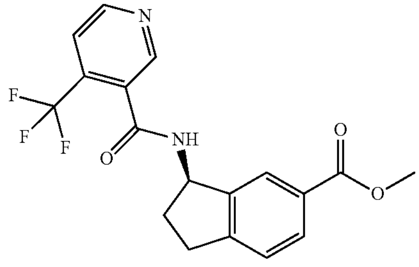 [SMILES: COC(=O)c1ccc2c(c1)[C@H](NC(=O)c1cnccc1C(F)(F)F)CC2] | (R)-Methyl 3-(4-(trifluoromethyl)nicotinamido)-2,3-dihydro-1H-indene-5-carboxylate (B-17) | Yield: 79%<br>The synthesis was carried out starting from A-01 analogously to B-05. |

-continued

| No. | Structure | Amino acid ester (B, C & D) | Comments |
|---|---|---|---|
| B-18 | 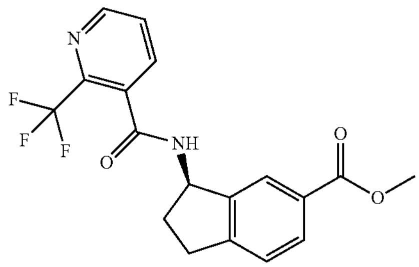 [SMILES: COC(=O)c1ccc2c(c1)[C@H](NC(=O)c1cccnc1C(F)(F)F)CC2] | (R)-Methyl 3-(2-(trifluoromethyl)nicotinamido)-2,3-dihydro-1H-indene-5-carboxylate (B-18) | Yield: 87%<br>The synthesis was carried out starting from A-01 analogously to B-07. |
| B-19 | 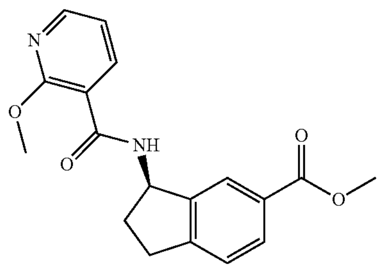 [SMILES: COC(=O)c1ccc2c(c1)[C@H](NC(=O)c1cccnc1OC)CC2] | (R)-Methyl 3-(2-methoxynicotinamido)-2,3-dihydro-1H-indene-5-carboxylate (B-19) | Yield: 90%<br>The synthesis was carried out starting from A-01 analogously to B-07. |
| B-20 | 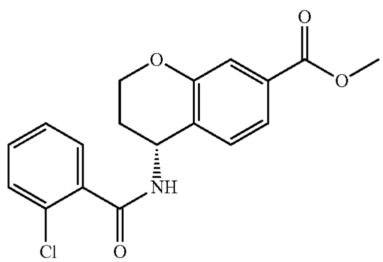 [SMILES: COC(=O)c1ccc2c(c1)OCC[C@H]2NC(=O)c1ccccc1Cl] | (R)-Methyl 4-(2-chlorobenzamido)chromane-7-carboxylate (B-20) | Yield: 76%<br>The synthesis was carried out starting from A-04 analogously to B-05. |
| B-21 | 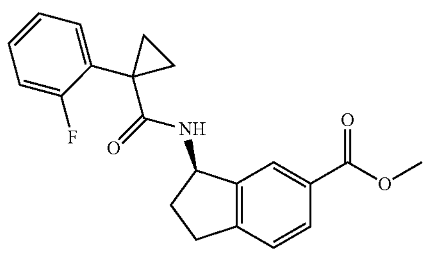 [SMILES: COC(=O)c1ccc2c(c1)[C@H](NC(=O)C1(c3ccccc3F)CC1)CC2] | (R)-Methyl-3-(1-(2-fluorophenyl)cyclopropanecarboxamido)-2,3-dihydro-1H-indene-5-carboxylate (B-21) | Yield: 85%<br>The synthesis was carried out starting from A-01 analogously to B-07. |
| B-22 | 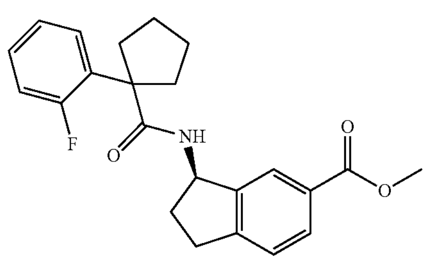 [SMILES: COC(=O)c1ccc2c(c1)[C@H](NC(=O)C1(c3ccccc3F)CCCC1)CC2] | (R)-Methyl 3-(1-(2-fluorophenyl)cyclopentanecarboxamido)-2,3-dihydro-1H-indene-5-carboxylate (B-22) | Yield: 70%<br>The synthesis was carried out starting from A-01 analogously to B-07. |
| B-23 | 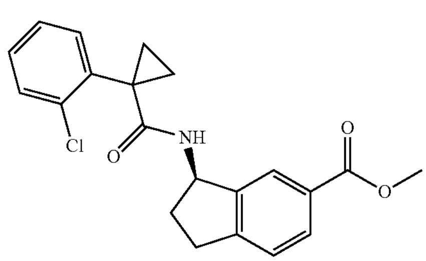 | (R)-Methyl 3-(1-(2-chlorophenyl)cyclopropanecarboxamido)-2,3-dihydro-1H-indene-5-carboxylate (B-23) | Yield: 76%<br>The synthesis was carried out starting from A-01 analogously to B-07. |

-continued

| No. | Structure | Amino acid ester (B, C & D) | Comments |
|---|---|---|---|
| B-24 | 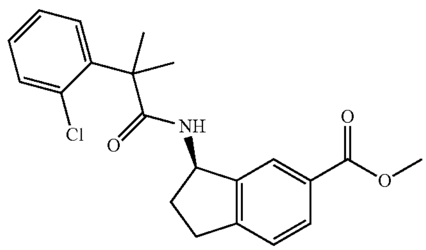 [SMILES: COC(=O)c1ccc2c(c1)[C@H](NC(=O)C(C)(C)c1ccccc1Cl)CC2] | (R)-Methyl 3-(2-(2-chlorophenyl)-2-methylpropanamido)-2,3-dihydro-1H-indene-5-carboxylate (B-24) | Yield: 37% The synthesis was carried out starting from A-01 analogously to B-07. |
| B-25 | 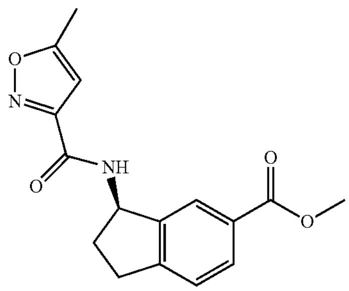 [SMILES: COC(=O)c1ccc2c(c1)[C@H](NC(=O)c1cc(C)on1)CC2] | (R)-Methyl 3-(5-methylisoxazole-3-carboxamido)-2,3-dihydro-1H-indene-5-carboxylate (B-24) | see below |
| B-27 | 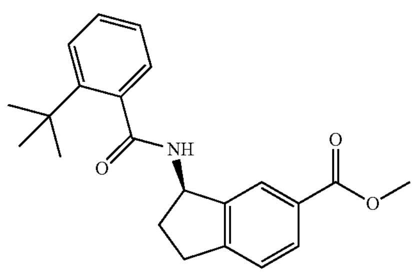 [SMILES: COC(=O)c1ccc2c(c1)[C@H](NC(=O)c1ccccc1C(C)(C)C)CC2] | (R)-Methyl 3-(2-tert-butylbenzamido)-2,3-dihydro-1H-indene-5-carboxylate (B-27) | see below |
| B-28 | 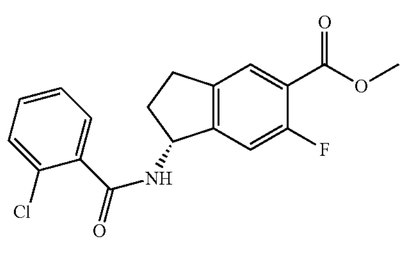 [SMILES: COC(=O)c1cc2c(cc1F)[C@H](NC(=O)c1ccccc1Cl)CC2] | (R)-Methyl 1-(2-chlorobenzamido)-6-fluoro-2,3-dihydro-1H-indene-5-carboxylate (B-28) | see below |
| B-29 | 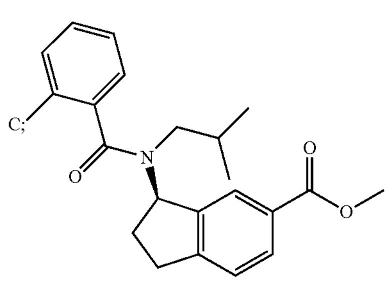 | (R)-Methyl 3-(2-chloro-N-isobutylbenzamido)-2,3-dihydro-1H-indene-5-carboxylate (B-29) | see below |

-continued

| No. | Structure | Amino acid ester (B, C & D) | Comments |
|---|---|---|---|
| B-30 | 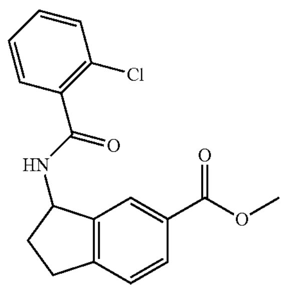 [SMILES: COC(=O)c1ccc2c(c1)C(NC(=O)c1ccccc1Cl)CC2] | 3-[(2-Chloro-benzoyl)amino]-2,3-dihydro-1H-indene-5-carboxylic acid methy lester (B-30) | see below |
| B-32 | 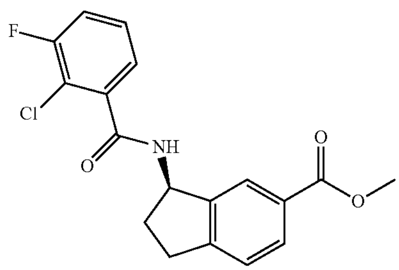 [SMILES: COC(=O)c1ccc2c(c1)[C@H](NC(=O)c1cccc(F)c1Cl)CC2] | (R)-Methyl 3-(2-chloro-3-fluorobenzamido)-2,3-dihydro-1H-indene-5-carboxylate (B-32) | see below |
| B-33 | 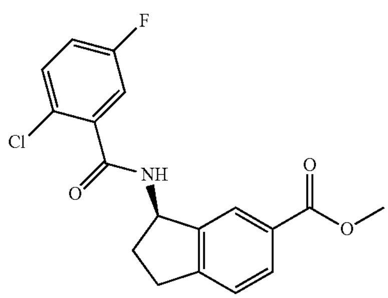 [SMILES: COC(=O)c1ccc2c(c1)[C@H](NC(=O)c1cc(F)ccc1Cl)CC2] | (R)-Methyl 3-(2-chloro-5-florobenzamido)-2,3-dihydro-1H-indene-5-carboxylate (B-33) | Yield: 88%<br>The synthesis was carried out starting from A-01 analogously to B-32 |
| B-34 | 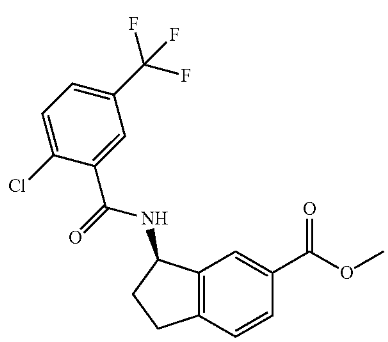 [SMILES: COC(=O)c1ccc2c(c1)[C@H](NC(=O)c1cc(C(F)(F)F)ccc1Cl)CC2] | (R)-Methyl 3-(2-chloro-5-(trifluoromethyl)benzamido)-2,3-dihydro-1H-indene-5-carboxylate (B-34) | Yield: 77%<br>The synthesis was carried out starting from A-01 analgously to B-32 |
| B-35 | 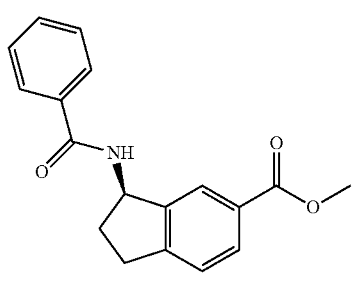 [SMILES: COC(=O)c1ccc2c(c1)[C@H](NC(=O)c1ccccc1)CC2] | (R)-Methyl 3-benzamido-2,3-dihydro-1H-indene-5-carboxylate (B-35) | Yield: 89%<br>The synthesis was carried out starting from A-01 analogously to B-32 |

-continued

| No. | Structure | Amino acid ester (B, C & D) | Comments |
|---|---|---|---|
| B-36 | 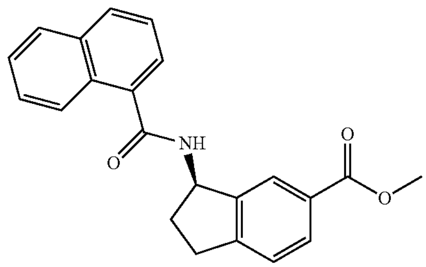 [SMILES: COC(=O)c1ccc2c(c1)[C@H](NC(=O)c1cccc3ccccc13)CC2] | (R)-Methyl 3-(1-naphthamido)-2,3-dihydro-1H-indene-5-carboxylate (B-36) | see below |
| B-37 | 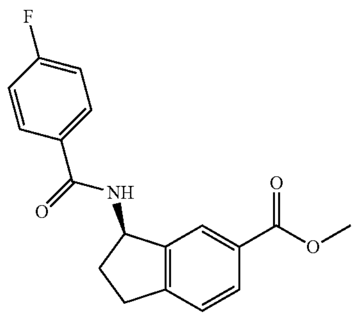 [SMILES: COC(=O)c1ccc2c(c1)[C@H](NC(=O)c1ccc(F)cc1)CC2] | (R)-Methyl 3-(4-fluorobenzamido)-2,3-dihydro-1H-indene-5-carboxylate (B-37) | Yield: 81% The synthesis was carried out starting from A-01 analogously to B-07. |
| B-38 | 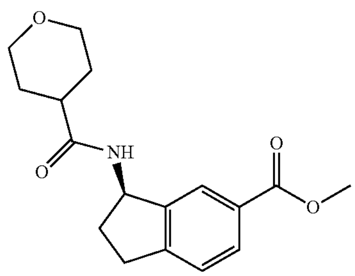 [SMILES: COC(=O)c1ccc2c(c1)[C@H](NC(=O)C1CCOCC1)CC2] | (R)-Methyl 3-(tetrahydro-2H-pyran-4-carboxamido)-2,3-dihydro-1H-indene-5-carboxylate (B-38) | Yield: 87% The synthesis was carried out starting from A-01 analogously to B-07. |
| B-39 | 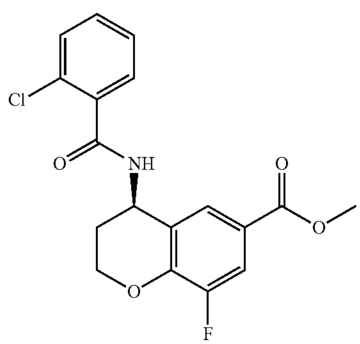 [SMILES: COC(=O)c1cc(F)c2c(c1)[C@H](NC(=O)c1ccccc1Cl)CCO2] | (R)-Methyl 4-(2-chlorobenzamido)-8-fluorochromane-6-carboxylate (B-39) | Yield: 93% The synthesis was carried out starting from A-10 analogously to B-05. |
| B-40 | 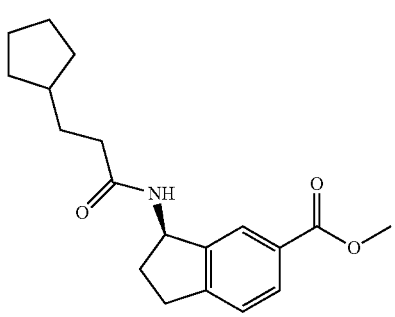 [SMILES: COC(=O)c1ccc2c(c1)[C@H](NC(=O)CCC1CCCC1)CC2] | (R)-Methyl 3-(3-cyclopentylpropanamido)-2,3-dihydro-1H-indene-5-carboxylate (B-40) | Yield: 96% The synthesis was carried out starting from A-01 analogously to B-07. |

| No. | Structure | Amino acid ester (B, C & D) | Comments |
|---|---|---|---|
| B-41 | 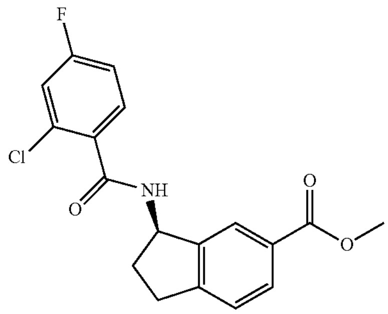 [SMILES: COC(=O)c1ccc2c(c1)[C@H](NC(=O)c1ccc(F)cc1Cl)CC2] | (R)-Methyl 3-(2-chloro-4-fluorobenzamido)-2,3-dihydro-1H-indene-5-carboxylate (B-41) | Yield: 86%<br>The synthesis was carried out starting from A-01 analogously to B-32. |
| B-42 | 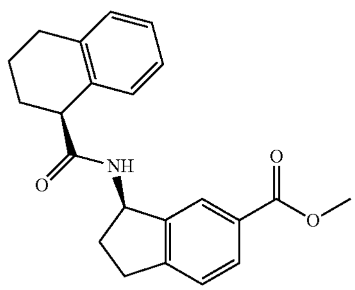 [SMILES: COC(=O)c1ccc2c(c1)[C@H](NC(=O)[C@H]1CCCc3ccccc31)CC2] | (R)-Methyl 3-((S)-1,2,3,4-tetrahydronaphthalene-1-carobxamido)-2,3-dihydro-1H-indene-5-carobxylate (B-42) | Yield: 86%<br>The synthesis was carried out starting from A-01 analogously to B-07. |
| B-43 | 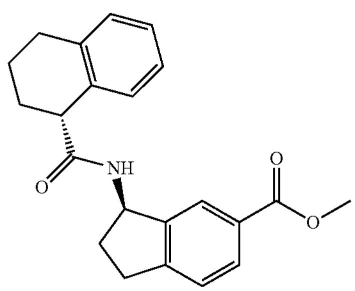 [SMILES: COC(=O)c1ccc2c(c1)[C@H](NC(=O)[C@@H]1CCCc3ccccc31)CC2] | (R)-Methyl 3-((R)-1,2,3,4-tetarahydronaphthalene-1-carboxamido)-2,3-dihydro-1H-indene-5-carboxylate (B-43) | Yield: 89%<br>The synthesis was carried out starting from A-01 analogously to B-07. |
| B-44 | 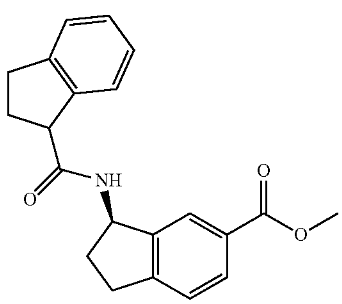 [SMILES: COC(=O)c1ccc2c(c1)[C@H](NC(=O)C1CCc3ccccc31)CC2] | (3R)-Methyl 3-(2,3-dihydro-1H-indene-1-carboxamido)-2,3-dihydro-1H-indene-5-carboxylate (B-44) | Yield: 92%<br>The synthesis was carried out starting from A-01 analogously to B-07. |
| B-45 | 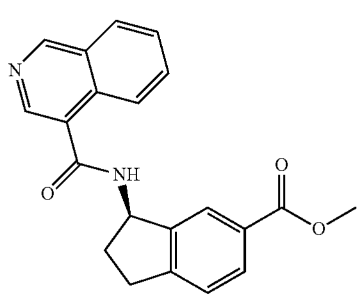 [SMILES: COC(=O)c1ccc2c(c1)[C@H](NC(=O)c1cncc3ccccc13)CC2] | (R)-Methyl 3-(isoquinoline-4-carobxamido)-2,3-dihydro-1H-indene-5-carboxylate (B-45) | Yield: 78%<br>The synthesis was carried out starting from A-01 analogously to B-07. |

-continued

| No. | Structure | Amino acid ester (B, C & D) | Comments |
|---|---|---|---|
| B-46 | 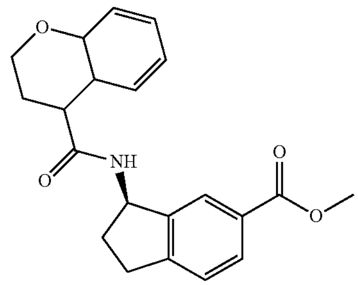 [SMILES: COC(=O)c1ccc2c(c1)[C@H](NC(=O)C1CCOC3C=CC=CC31)CC2] | (3R)-Methyl 3-(3,4,4a,8a-tetrahydro-2H-chromene-4-carboxamido)-2,3-dihydro-1H-indene-5-carboxylate (B-46) | Yield: 82%<br>The synthesis was carried out starting from A-01 analogously to B-07. |
| B-47 | 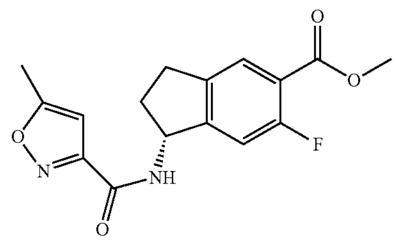 [SMILES: COC(=O)c1cc2c(cc1F)[C@H](NC(=O)c1cc(C)on1)CC2] | (R)-Methyl 6-fluoro-1-(5-methylisoxazole-3-carboxamido)-2,3-dihydro-1H-indene-5-carboxylate (B-47) | Yield: 54%<br>The synthesis was carried out starting from A-05 analogously to B-07. |
| B-48 | 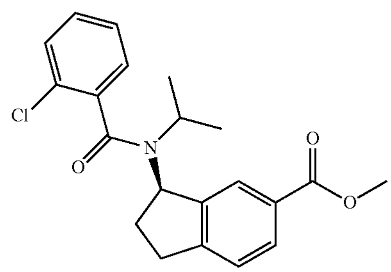 [SMILES: COC(=O)c1ccc2c(c1)[C@H](N(C(=O)c1ccccc1Cl)C(C)C)CC2] | (R)-Methyl 3-(2-chloro-N-isopropylbenzamido)-2,3-dihydro-1H-indene-5-carobxylate (B-48) | Yield: 97%<br>The synthesis was carried out starting from A-13 analogously to B-32. |
| B-49 | 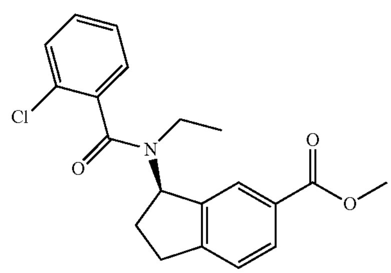 [SMILES: CCN(C(=O)c1ccccc1Cl)[C@@H]1CCc2ccc(C(=O)OC)cc21] | (R)-Methyl 3-(2-chloro-N-ethylbenzamido)-2,3-dihydro-1H-indene-5-carboxylate (B-49) | Yield: 99%<br>The synthesis was carried out starting from A-12 analogously to B-32. |
| B-50 | 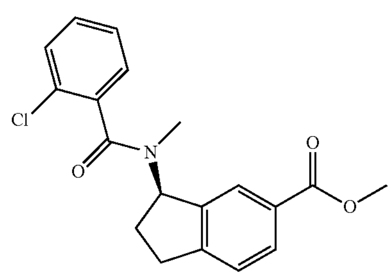 [SMILES: COC(=O)c1ccc2c(c1)[C@H](N(C)C(=O)c1ccccc1Cl)CC2] | (R)-Methyl 3-(2-chloro-N-methylbenzamido)-2,3-dihydro-1H-indene-5-carboxylate (B-50) | Yield: 85%<br>The synthesis was carried out starting from A-11 analogously to B-32. |
| B-51 | 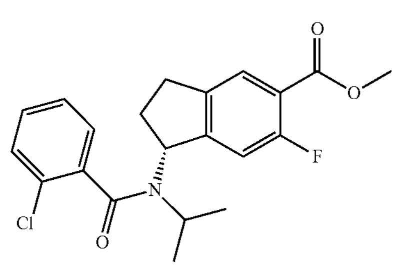 [SMILES: COC(=O)c1cc2c(cc1F)[C@H](N(C(=O)c1ccccc1Cl)C(C)C)CC2] | (R)-Methyl 1-(2-chloro-N-isopropylbenzamido)-6-fluoro-2,3-dihydro-1H-indene-5-carboxylate (B-51) | Yield: 88%<br>The synthesiss was carried out starting from A-15 analogously to B-32. |

-continued

| No. | Structure | Amino acid ester (B, C & D) | Comments |
|---|---|---|---|
| B-52 | 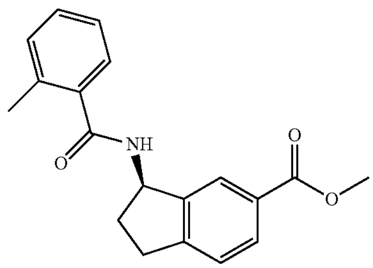 | (R)-Methyl 3-(2-methylbenzamido)-2,3-dihydro-1H-indene-5-carboxylate (B-52) | Yield: 70%<br>The synthesis was carried out starting from A-01 analogously to B-32. |
| B-53 | 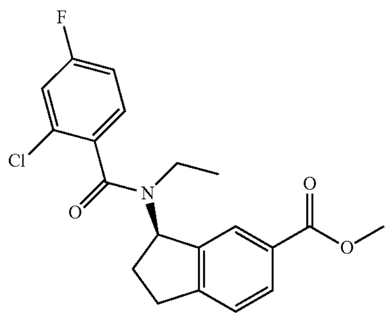 [SMILES: CCN(C(=O)c1ccc(F)cc1Cl)[C@@H]1CCc2ccc(C(=O)OC)cc21] | (R)-Methyl 3-(2-chloro-N-ethyl-4-fluorobenzamido)-2,3-dihydro-1H-indene-5-carboxylate (B-53) | Yield: 96%<br>The synthesis was carried out starting from A-12 analogously to B-32. |
| B-54 | 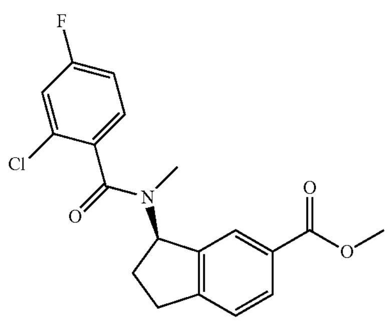 [SMILES: COC(=O)c1ccc2c(c1)[C@H](N(C)C(=O)c1ccc(F)cc1Cl)CC2] | (R)-Methyl 3-(2-chloro-4-fluoro-N-methylbenzamido)-2,3-dihydro-1H-indene-5-carboxylate (B-54) | Yield: 86%<br>The synthesis was carried out starting from A-11 analogously to B-32. |
| B-55 | 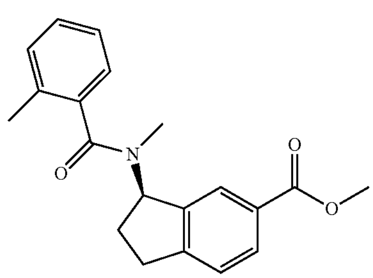 | (R)-Methyl 3-(N,2-dimethylbenzamido)-2,3-dihydro-1H-indene-5-carboxylate (B-55) | Yield: 96%<br>The synthesis was carried out starting from A-11 analogously to B-32. |
| B-56 | 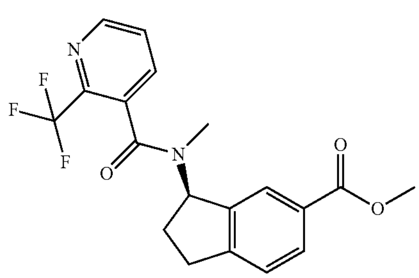 [SMILES: COC(=O)c1ccc2c(c1)[C@H](N(C)C(=O)c1cccnc1C(F)(F)F)CC2] | (R)-Methyl 3-(N-methyl-2-(trifluoromethyl)nicotinamido)-2,3-dihydro-1H-indene-5-carboxylate (B-56) | Yield: 61%<br>The synthesis was carried out starting from A-11 analogously to B-07. |

-continued

| No. | Structure | Amino acid ester (B, C & D) | Comments |
|---|---|---|---|
| B-57 | 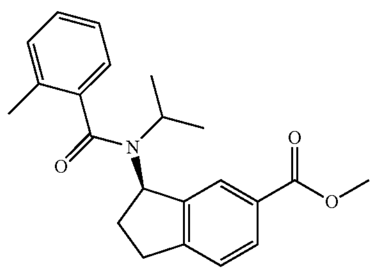 | (R)-Methyl 3-(N-isopropyl-2-methylbenzamido)-2,3-dihydro-1H-indene-5-carboxylate (B-57) | Yield: 86%<br>The synthesis was carried out starting from A-13 analogously to B-32. |
| B-59 | 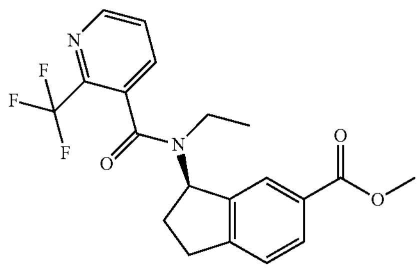 [SMILES: CCN(C(=O)c1cccnc1C(F)(F)F)[C@@H]1CCc2ccc(C(=O)OC)cc21] | (R)-Methyl 3-(N-ethyl-2-(trifluoromethyl)nicotinamido)-2,3-dihydro-1H-indene-5-carboxylate (B-59) | Yield: 36%<br>The synthesis was carried out starting from A-12 analogously to B-07. |
| B-60 | 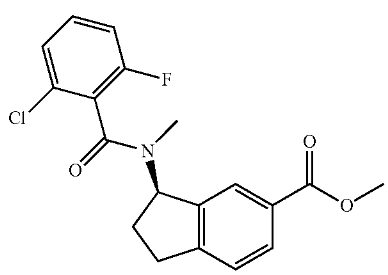 [SMILES: COC(=O)c1ccc2c(c1)[C@H](N(C)C(=O)c1c(F)cccc1Cl)CC2] | (R)-Methyl 3-(2-chloro-6-fluoro-N-methylbenzamido)-2,3-dihydro-1H-indene-5-carboxylate (B-60) | Yield: 93%<br>The synthesis was carried out starting from A-11 analogously to B-32. |
| B-61 | 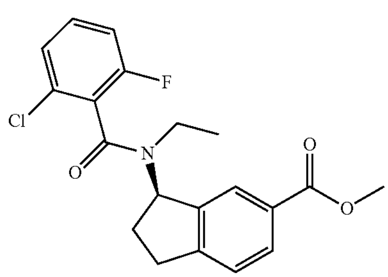 [SMILES: CCN(C(=O)c1c(F)cccc1Cl)[C@@H]1CCc2ccc(C(=O)OC)cc21] | (R)-Methyl 3-(2-chloro-N-ethyl-6-fluorobenzamido)-2,3-dihydro-1H-indene-5-carboxylate (B-61) | Yield: 99%<br>The synthesis was carried out starting from A-12 analogously to B-32. |
| B-63 | 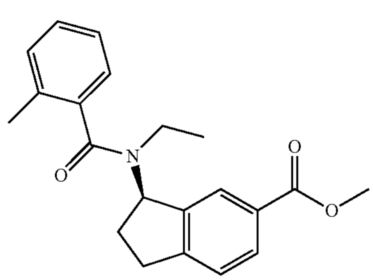 | (R)-Methyl 3-(N-ethyl-2-methylbenzamido)-2,3-dihydro-1H-indene-5-carboxylate (B-63) | Yield: 91%<br>The synthesis was carried out starting from A-12 analogously to B-32. |

-continued

| No. | Structure | Amino acid ester (B, C & D) | Comments |
|---|---|---|---|
| B-66 | 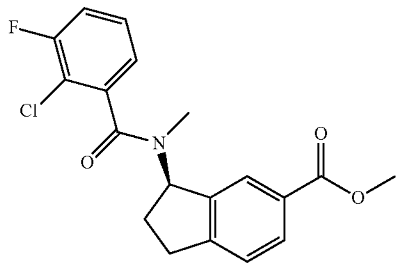 [SMILES: COC(=O)c1ccc2c(c1)[C@H](N(C)C(=O)c1cccc(F)c1Cl)CC2] | (R)-Methyl 3-(2-chloro-3-fluoro-N-methylbenzamido)-2,3-dihydro-1H-indene-5-carboxylate (B-66) | Yield: 91%<br>The synthesis was carried out starting from A-11 analogously to B-32. |
| B-67 | 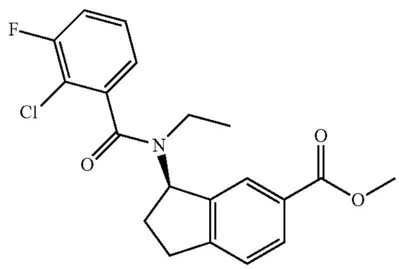 [SMILES: CCN(C(=O)c1cccc(F)c1Cl)[C@@H]1CCc2ccc(C(=O)OC)cc21] | (R)-Methyl 3-(2-chloro-N-ethyl-3-fluorobenzamido)-2,3-dihydro-1H-indene-5-carboxylate (B-67) | Yield: 79%<br>The synthesis was carried out starting from A-12 analogously to B-32. |
| B-68 | 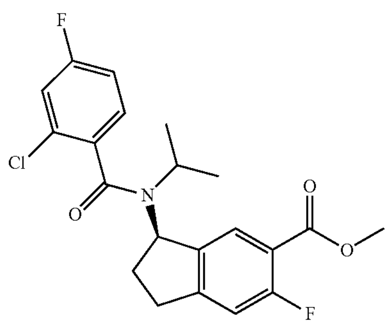 [SMILES: COC(=O)c1cc2c(cc1F)CC[C@H]2N(C(=O)c1ccc(F)cc1Cl)C(C)C] | (R)-Methyl 3-(2-chloro-4-fluoro-N-isopropylbenzamido)-6-fluoro-2,3-dihydro-1H-indene-5-carboxylate (B-68) | Yield: 94%<br>The synthesis was carried out starting from A-14 analogously to B-32. |
| B-69 | 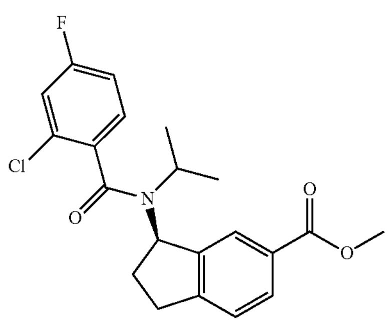 [SMILES: COC(=O)c1ccc2c(c1)[C@H](N(C(=O)c1ccc(F)cc1Cl)C(C)C)CC2] | (R)-Methyl 3-(2-chloro-4-fluoro-N-isopropylbenzamido)-2,3-dihydro-1H-indene-5-carboxylate (B-69) | Yield: 98%<br>The synthesis was carried out starting form A-13 analogously to B-32. |
| B-72 | 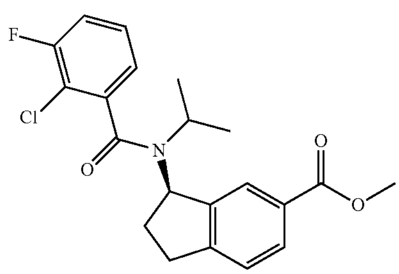 [SMILES: COC(=O)c1ccc2c(c1)[C@H](N(C(=O)c1cccc(F)c1Cl)C(C)C)CC2] | (R)-Methyl 3-(2-chloro-3-fluoro-N-isopropylbenzamido)-2,3-dihydro-1H-indene-5-carboxylate (B072) | Yield: >99%<br>The synthesis was carried out starting from A-13 analogously to B-32. |

-continued

| No. | Structure | Amino acid ester (B, C & D) | Comments |
|---|---|---|---|
| B-73 | 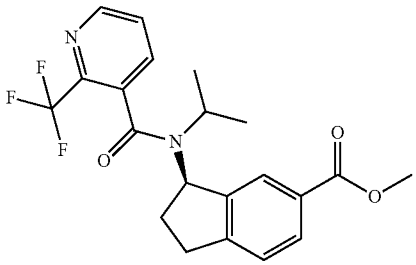 [SMILES: COC(=O)c1ccc2c(c1)[C@H](N(C(=O)c1cccnc1C(F)(F)F)C(C)C)CC2] | (R)-Methyl 3-(N-isopropyl-2-(trifluoromethyl)nicotinamido)-2,3-dihydro-1H-indene-5-carboxylate (B-73) | Yield: 83% The synthesis was carried out starting from A-13 analogously to B-32. |
| B-74 | 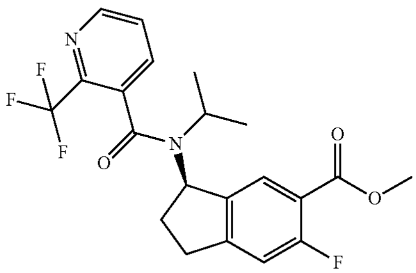 [SMILES: COC(=O)c1cc2c(cc1F)CC[C@H]2N(C(=O)c1cccnc1C(F)(F)F)C(C)C] | (R)-Methyl 6-fluoro-3-(N-isopropyl-2-(trifluoromethyl)nicotinamido)-2,3-dihydro-1H-indene-5-carboxylate (B-74) | Yield: 81% The synthesis was carried out starting from A-14 analogously to B-32. |
| B-75 | 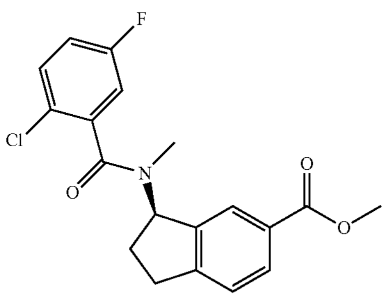 [SMILES: COC(=O)c1ccc2c(c1)[C@H](N(C)C(=O)c1cc(F)ccc1Cl)CC2] | (R)-Methyl 3-(2-chloro-5-fluoro-N-methylbenzamido)-2,3-dihydro-1H-indene-5-carboxylate (B-75) | Yield: >99% The synthesis was carried out starting from A-11 analogously to B-32. |
| B-76 | 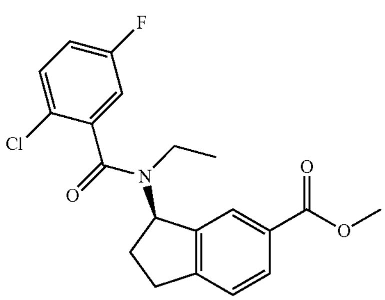 [SMILES: CCN(C(=O)c1cc(F)ccc1Cl)[C@@H]1CCc2ccc(C(=O)OC)cc21] | (R)-Methyl 3-(2-chloro-N-ethyl-5-fluorobenzamido)-2,3-dihydro-1H-indene-5-carboxylate (B-76) | Yield: >99% The synthesis was carried out starting from A-12 analogously to B-32. |
| B-77 | 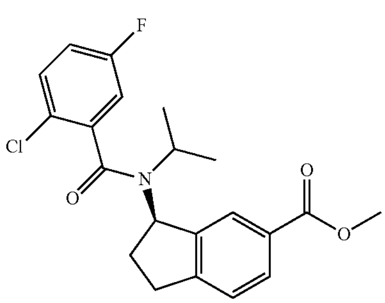 [SMILES: COC(=O)c1ccc2c(c1)[C@H](N(C(=O)c1cc(F)ccc1Cl)C(C)C)CC2] | (R)-Methyl 3-(2-chloro-5-fluoro-N-isopropylbenzamido)-2,3-dihydro-1H-indene-5-carboxylate (B-77) | Yield: 96% The synthesis was carried out starting from A-13 analogously to B-32. |

-continued

| No. | Structure | Amino acid ester (B, C & D) | Comments |
|---|---|---|---|
| B-78 | 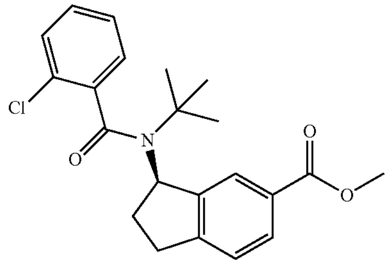 [SMILES: COC(=O)c1ccc2c(c1)[C@H](N(C(=O)c1ccccc1Cl)C(C)(C)C)CC2] | (R)-methyl 3-(1-naphthamido)-2,3-dihydro-1H-indene-5-carboxylate (B-78) | see below |
| B-79 | 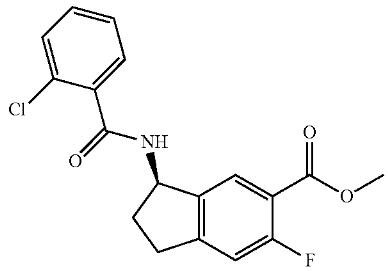 [SMILES: COC(=O)c1cc2c(cc1F)CC[C@H]2NC(=O)c1ccccc1Cl] | (R)-Methyl 3-(2-chlorobenzamido)-6-fluoro-2,3-dihydro-1H-indene-5-carboxylate (B-79) | Yield: 54%<br>The synthesis was carried out starting from A-17 analogously to B-01 Method 2. |
| B-80 | 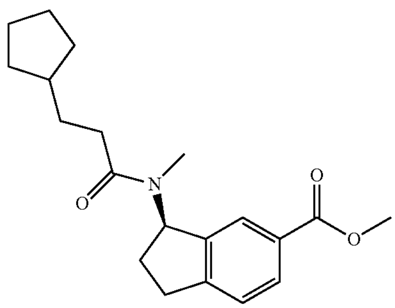 [SMILES: COC(=O)c1ccc2c(c1)[C@H](N(C)C(=O)CCC1CCCC1)CC2] | (R)-Methyl 3-(3-cylcopentyl-N-methylpropanamido)-2,3-dihydro-1H-indene-5-carboxylate (B-80) | see below |
| B-81 | 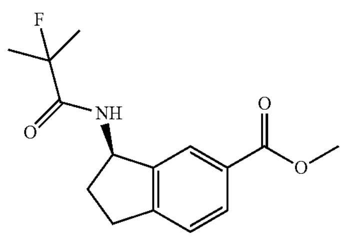 [SMILES: COC(=O)c1ccc2c(c1)[C@H](NC(=O)C(C)(C)F)CC2] | (R)-Methyl 3-(2-fluoro-2-methylpropanamido)-2,3-dihydro-1H-indene-5-carboxylate (B-81) | see below |
| B-82 | 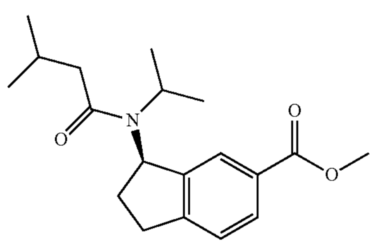 [SMILES: COC(=O)c1ccc2c(c1)[C@H](N(C(=O)CC(C)C)C(C)C)CC2] | (R)-Methyl 3-(N-isopropyl-3-methylbutanamido)-2,3-dihydro-1H-indene-5-carboxylate (B-82) | Yield: 80%<br>The synthesis was carried out starting from A-13 analogously to C-01 Method 2. |
| B-83 | 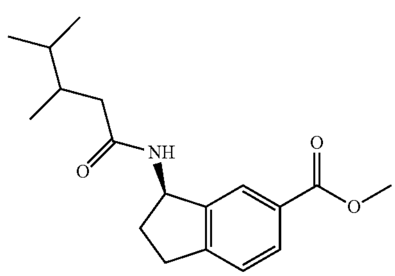 [SMILES: COC(=O)c1ccc2c(c1)[C@H](NC(=O)CC(C)C(C)C)CC2] | (3R)-Methyl 3-(3,4-dimethylpentanamido)-2,3-dihydro-1H-indene-5-carboxylate (B-83) | see below |

-continued

| No. | Structure | Amino acid ester (B, C & D) | Comments |
|---|---|---|---|
| B-84 | 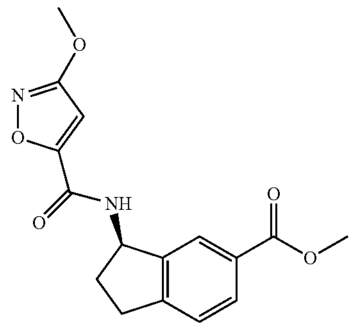 [SMILES: COC(=O)c1ccc2c(c1)[C@H](NC(=O)c1cc(OC)no1)CC2] | (R)-Methyl 3-(3-methoxyisoxazole-5-carboxamido)-2,3-dihydro-1H-indene-5-carobxylate (B-84) | Yield: 69%<br>The synthesis was carried out starting from A-01 analogously to B-83. |
| B-85 | 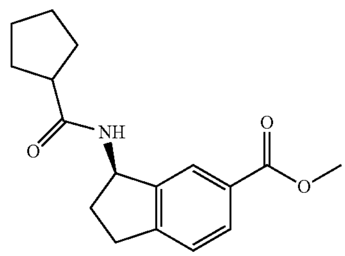 [SMILES: COC(=O)c1ccc2c(c1)[C@H](NC(=O)C1CCCC1)CC2] | (R)-Methyl 3-(cyclopentanecarboxamido)-2,3-dihydro-1H-indene-5-carboxylate (B-85) | Yield: 79%<br>The synthesis was carried out starting from A-01 analogously to B-07. |
| B-86 | 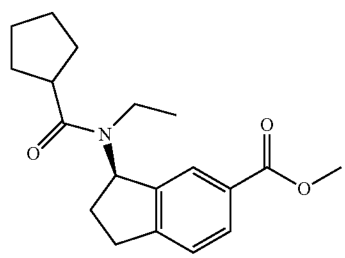 [SMILES: CCN(C(=O)C1CCCC1)[C@@H]1CCc2ccc(C(=O)OC)cc21] | (R)-Methyl 3-N-ethylcyclopentanecarboxamido)-2,3-dihydro-1H-indene-5-carboxylate (B-86) | Yield: 72%<br>The synthesis was carried out starting from A-12 analogously to B-07. |
| B-87 | 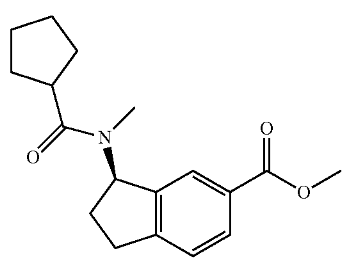 [SMILES: COC(=O)c1ccc2c(c1)[C@H](N(C)C(=O)C1CCCC1)CC2] | (R)-Methyl 3-(N-methylcyclopentanecarboxamido)-2,3-dihydro-1H-indene-5-carboxylate (B-87) | Yield: 87%<br>The synthesis was carried out starting from A-11 analogously to B-07. |
| B-88 | 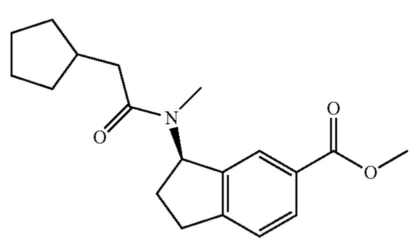 [SMILES: COC(=O)c1ccc2c(c1)[C@H](N(C)C(=O)CC1CCCC1)CC2] | (R)-Methyl 3-(2-cyclopentyl-N-methylacetamido)-2,3-dihydro-1H-indene-5-carboxylate (B-88) | Yield: 50%<br>The synthesis was carried out starting from A-11 analogously to B-83. |

-continued

| No. | Structure | Amino acid ester (B, C & D) | Comments |
|---|---|---|---|
| B-89 | 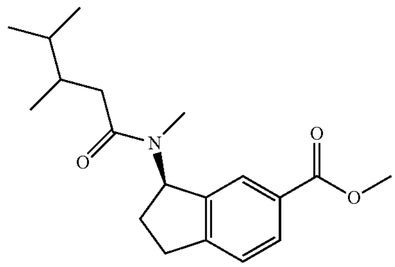 [SMILES: COC(=O)c1ccc2c(c1)[C@H](N(C)C(=O)CC(C)C(C)C)CC2] | (3R)-Methyl 3-(N,3,4-trimethylpentanamido)-2,3-dihydro-1H-indene-5-carboxylate (B-89) | Yield: 94%<br>The synthesis was carried out starting from A-11 analogously to B-83. |
| B-90 | 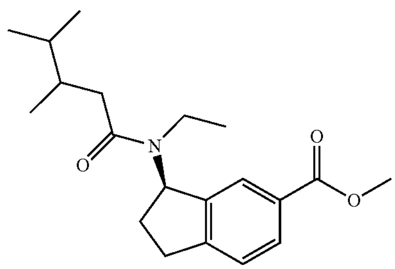 [SMILES: CCN(C(=O)CC(C)C(C)C)[C@@H]1CCc2ccc(C(=O)OC)cc21] | (3R)-Methyl 3-(N-ethyl-3,4-dimethylpentanamido)-2,3-dihydro-1H-indene-5-carboxylate (B-90) | Yield: >99%<br>The synthesis was carried out starting from A-12 analogously to B83-. |
| B-91 | 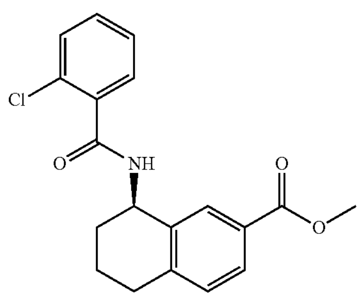 [SMILES: COC(=O)c1ccc2c(c1)[C@H](NC(=O)c1ccccc1Cl)CCC2] | (R)-Methyl 8-(2-chlorobenzamido)-5,6,7,8-tetrahydronaphthalene-2-carboxylate (B-91) | Yield: >99%<br>The synthesis was carried out starting from A-19 analogously to B-28. |
| B-92 | 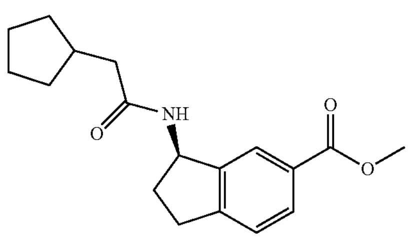 [SMILES: COC(=O)c1ccc2c(c1)[C@H](NC(=O)CC1CCCC1)CC2] | (R)-Methyl 3-(2-cyclopentylacetamido)-2,3-dihydro-1H-indene-5-carboxylate (B-92) | Yield: 64%<br>The synthesis was carried out starting from A-01 analogously to B-83. |
| B-93 | 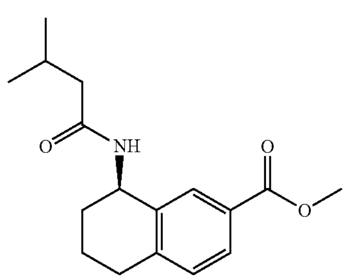 [SMILES: COC(=O)c1ccc2c(c1)[C@H](NC(=O)CC(C)C)CCC2] | (R)-Methyl 8-(3-methylbutanamido)-5,6,7,8-tetrahydronaphthalene-2-carboxylate (B-93) | Yield: 87%<br>The synthesis was carried out starting from A-19 analogously to B-83. |

-continued

| No. | Structure | Amino acid ester (B, C & D) | Comments |
|---|---|---|---|
| B-94 | 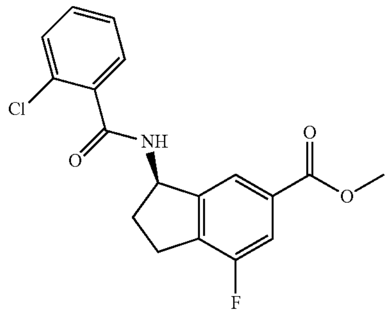 [SMILES: COC(=O)c1cc(F)c2c(c1)[C@H](NC(=O)c1ccccc1Cl)CC2] | (R)-Methyl 3-(2-chlorobenzamido)-7-fluoro-2,3-dihydro-1H-indene-5-carboxylate (B-94) | Yield: 47%<br>The synthesis was carried out starting from A-20 analogously to B-01 Method 2. |
| C-01 | 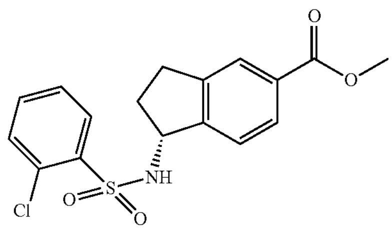 [SMILES: COC(=O)c1ccc2c(c1)CC[C@H]2NS(=O)(=O)c1ccccc1Cl] | (R)-Methyl 1-(2-chlorophenylsulfonamido)-2,3-dihydro-1H-indene-5-carboxylate (C-01) | see below |
| C-02 | 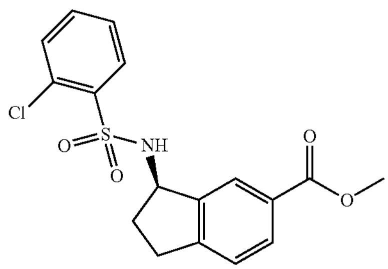 [SMILES: COC(=O)c1ccc2c(c1)[C@H](NS(=O)(=O)c1ccccc1Cl)CC2] | (R)-Methyl 3-(2-chlorophenylsulfonamido)-2,3-dihydro-1H-indene-5-carboxylate (C-02) | Yield: 100%<br>The synthesis was carried out starting from A-01 analogously to C-01 (additionally washed with $NaHCO_3$ solution) |
| C-03 | 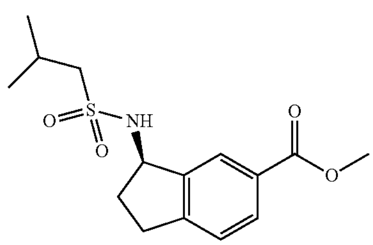 [SMILES: COC(=O)c1ccc2c(c1)[C@H](NS(=O)(=O)CC(C)C)CC2] | (R)-Methyl 3-(2-methylpropylsulfonamido)-2,3-dihydro-1H-indene-5-carboxylate (C-03) | see below |
| C-04 | 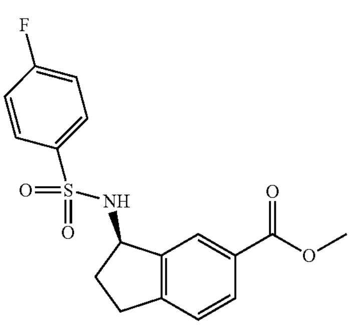 [SMILES: COC(=O)c1ccc2c(c1)[C@H](NS(=O)(=O)c1ccc(F)cc1)CC2] | (R)-Methyl 3-(4-fluorophenylsulfonamido)-2,3-dihydro-1H-indene-5-carboxylate (C-04) | see below |

-continued

| No. | Structure | Amino acid ester (B, C & D) | Comments |
|---|---|---|---|
| C-05 | 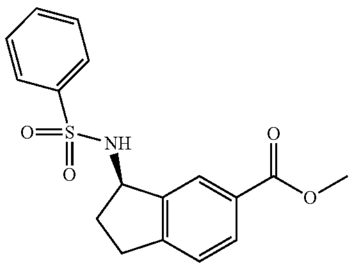 [SMILES: COC(=O)c1ccc2c(c1)[C@H](NS(=O)(=O)c1ccccc1)CC2] | (R)-Methyl 3-(phenylsulfonamido)-2,3-dihydro-1H-indene-5-carboxylate (C-05) | Yield: 86%<br>The synthesis was carried out starting from A-01 analogously to C-04. |
| D-01 | 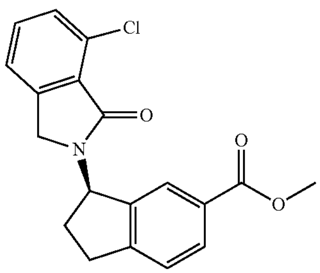 [SMILES: COC(=O)c1ccc2c(c1)[C@H](N1Cc3cccc(Cl)c3C1=O)CC2] | (R)-Methyl 3-(7-chloro-1-oxoisoindolin-2-yl)-2,3-dihydro-1H-indene-5-carboxylate (D-01) | see below |
| D-02 | 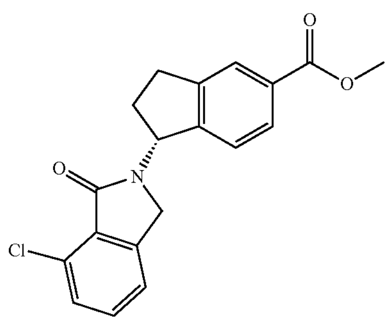 [SMILES: COC(=O)c1ccc2c(c1)CC[C@H]2N1Cc2cccc(Cl)c2C1=O] | (R)-Methyl 1-(7-chloro-1-oxoisoindolin-2-yl)-2,3-dihydro-1H-indene-5-carboxylate (D-02) | Yield: 89%<br>The synthesis was carried out starting from A-02 analogously to D-01. Alternatively, A-18 was used as starting material. |
| D-03 | 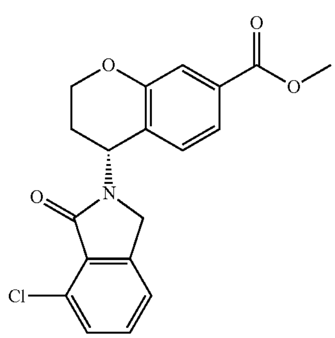 [SMILES: COC(=O)c1ccc2c(c1)OCC[C@H]2N1Cc2cccc(Cl)c2C1=O] | (R)-Methyl 4-(7-chloro-1-oxoisoindolin-2-yl)chromane-7-carboxylate (D-03) | see below |
| D-04 | 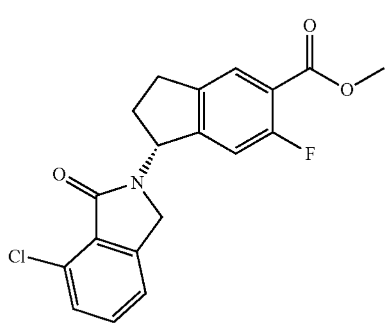 [SMILES: COC(=O)c1cc2c(cc1F)[C@H](N1Cc3cccc(Cl)c3C1=O)CC2] | (R)-Methyl 1-(7-chloro-1-oxoisoindolin-2-yl)-6-fluoro-2,3-dihydro-1H-indene-5-carboxylate (D-04) | see below |

-continued

| No. | Structure | Amino acid ester (B, C & D) | Comments |
|---|---|---|---|
| D-05 | 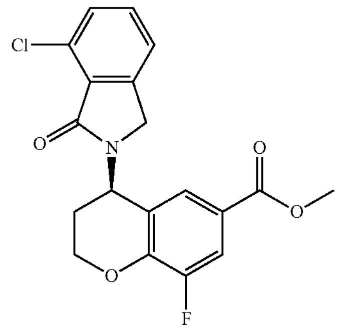 [SMILES: COC(=O)c1cc(F)c2c(c1)[C@H](N1Cc3cccc(Cl)c3C1=O)CCO2] | (R)-Methyl 4-(7-chloro-1-oxoisoindolin-2-yl)-8-fluorochromane-6-carboxylate (D-05) | see below |
| D-06 | 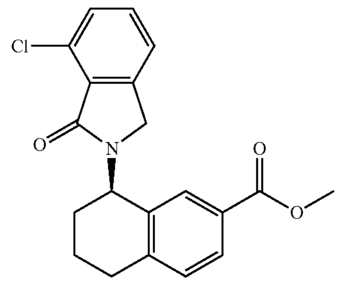 [SMILES: COC(=O)c1ccc2c(c1)[C@H](N1Cc3cccc(Cl)c3C1=O)CCC2] | (R)-Methyl 8-(7-chloro-1-oxoisoindolin-2-yl)-5,6,7,8-tetrahydronaphthalene-2-carboxylate (D-06) | Yield: 66%<br>The synthesis was carried out starting from A-19 analogously to D-04. |

Note: In the case of reactions carried out analogously to a described method, the reaction conditions were optionally adapted, in particular in respect of the reagent equiv., the replacement of Et₃N by DIPEA or of magnesium sulfate by sodium sulfate, and the reaction times (these were adapted according to TLC monitoring). If necessary, the product was purified by column chromatography.

Synthesis of Amino Acid Ester B-01

(3R)-3-[(2-Chloro-benzoyl)amino]-2,3-dihydro-1H-indene-5-carboxylic acid methyl ester (B-01)

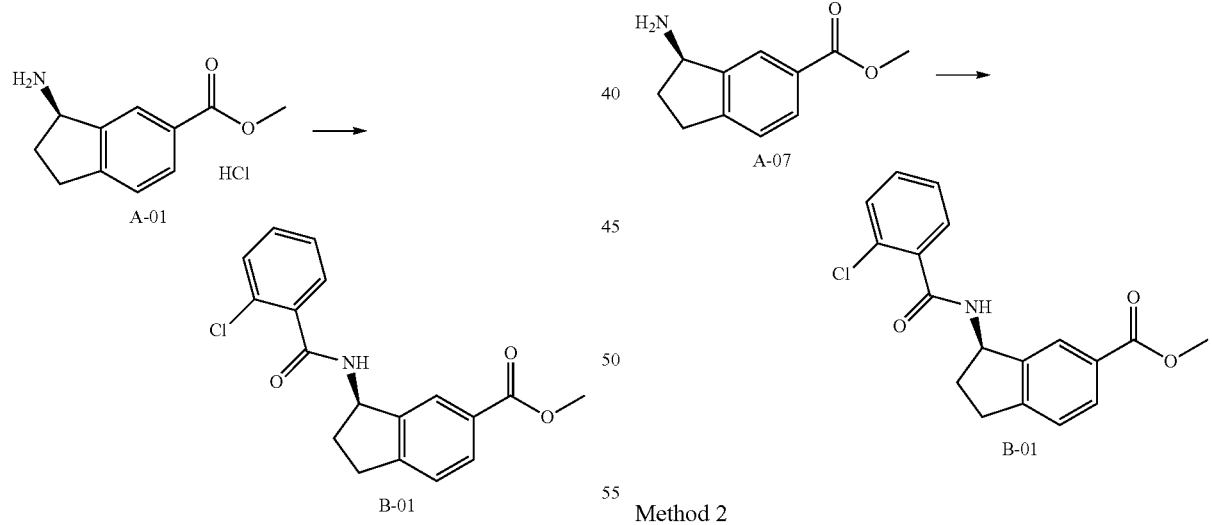

Method 1
(3R)-3-Amino-2,3-dihydro-1H-indene-5-carboxylic acid methyl ester hydrochloride (A-01) (8.784 mmol, 1 eq) was dissolved in dichloromethane, and triethylamine (3 eq) and 2-chlorobenzoic acid chloride (1.2 eq) were added at 0° C. under a protecting gas atmosphere. The reaction mixture was stirred for 1 h at RT. Then the reaction mixture was diluted with sat. NaHCO₃ solution and the aqueous phase was extracted with dichloromethane (3×50 ml). The organic phase was dried over sodium sulfate and concentrated to yield (3R)-3-[(2-chloro-benzoyl)amino]-2,3-dihydro-1H-indene-5-carboxylic acid methyl ester (B-01). Yield: 98%
or Method 2
(R)-Methyl 3-amino-2,3-dihydro-1H-indene-5-carboxylate (A-07) (11 g, 36.06 mmol, 1 eq) was dissolved in dichloromethane (200 ml); triethylamine (12.66 ml, 90.15 mmol, 2.5 eq) was added at 0° C. and stirring was carried out for 15 min. Then 2-chlorobenzoic acid chloride (5 ml, 39.67 mmol, 1.1 eq) was added and stirring was carried out for 1 h at RT. After monitoring by thin-layer chromatography, the reaction solution was diluted with dichloromethane (150 ml), washed with water (200 ml) and sat. NaCl solution (150 ml), dried over sodium sulfate and concentrated under reduced pressure. After purification by column chromatography (silica gel, 25% ethyl acetate in hexane), a white solid was obtained. Yield: 74% (8.6 g, 26.13 mmol).

Synthesis of Amino Acid Ester (B-02)

(R)-Methyl 1-(2-chlorobenzamido)-2,3-dihydro-1H-indene-5-carboxylate (B-02)

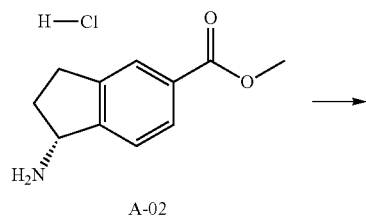

A-02

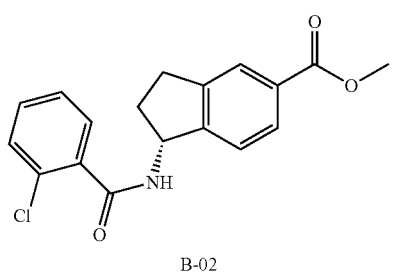

B-02

(R)-Methyl 1-amino-2,3-dihydro-1H-indene-5-carboxylate hydrochloride (A-02) (0.661 mmol, 1 eq) was dissolved in dichloromethane and DIPEA (2.5 eq) under a protecting gas atmosphere, and 2-chlorobenzoic acid chloride (1 eq) was added at 0° C. The reaction mixture was stirred for 2 h at RT. Then the reaction mixture was diluted with 10% ammonium chloride solution and ethyl acetate, and the phases were separated. The organic phase was washed with sat. NaCl solution, dried over magnesium sulfate and concentrated. The crude product was purified by column chromatography (silica gel, cyclohexane:ethyl acetate 2:1) to yield (R)-methyl 1-(2-chlorobenzamido)-2,3-dihydro-1H-indene-5-carboxylate (B-02). Yield: 74%

Synthesis of Amino Acid Ester (B-05)

(R)-Methyl 4-(2-chlorobenzamido)chromane-6-carboxylate (B-05)

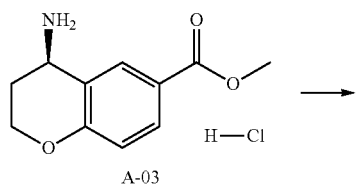

A-03

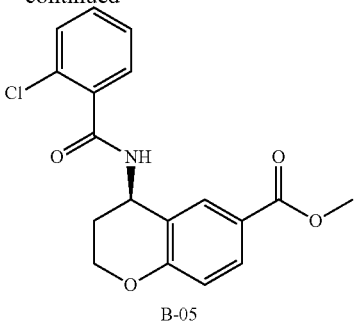

B-05

(R)-Methyl 4-aminochromane-6-carboxylate hydrochloride (A-03) (0.6 g, 2.462 mmol, 1.0 eq) was dissolved in dichloromethane and DIPEA (2.5 eq) under nitrogen, and 2-chlorobenzoic acid chloride (0.37 ml, 2.954 mmol, 1.2 eq) was added at 0° C. The reaction mixture was stirred for 3 h at RT. Then the reaction mixture was concentrated, and the residue was taken up in ethyl acetate, washed with 10% ammonium chloride solution, sat. NaHCO$_3$ solution and with sat. NaCl solution, dried over magnesium sulfate and concentrated. The crude product was purified by column chromatography (silica gel, cyclohexane:ethyl acetate 2:1) to yield (R)-methyl 4-(2-chlorobenzamido)chromane-6-carboxylate (B-05). Yield: 92%

Synthesis of Amino Acid Ester (B-07)

(R)-Methyl 3-(pyrazolo[1,5-a]pyrimidine-3-carboxamido)-2,3-dihydro-1H-indene-5-carboxylate (B-07)

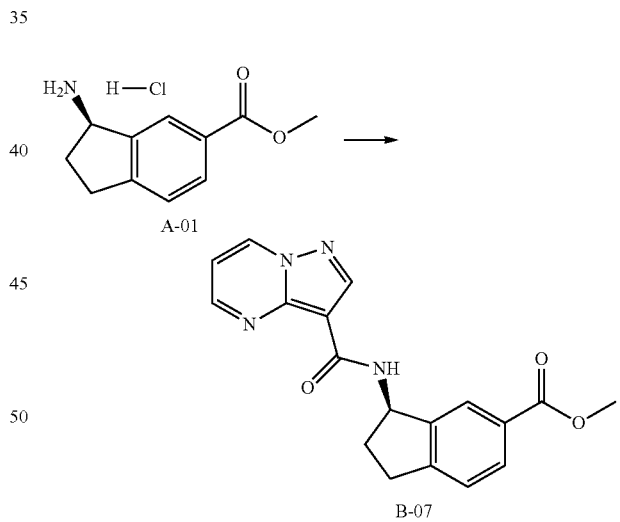

Pyrazolo[1,5-a]pyrimidine-3-carboxylic acid (0.25 g, 1.533 mmol, 1 eq) was dissolved in dichloromethane (20 ml), and the mixture was cooled to 0° C. Then DIPEA (0.65 ml, 2.833 mmol, 2.5 eq), EDCI (0.34 g, 1.84 mmol, 1.2 eq) and HOBT (29 mg, 0.307 mmol, 0.2 eq) were added in succession and stirring was carried out for 15 min at RT. The reaction solution was cooled to 0° C. again, (3R)-3-amino-2,3-dihydro-1H-indene-5-carboxylic acid methyl ester hydrochloride (A-01) (0.34 g, 1.533 mmol, 1 eq), dissolved in dichloromethane (10 ml), was added, and the mixture was stirred for 16 h at RT. After monitoring by thin-layer chromatography, the reaction solution was diluted with ethyl acetate, washed in succession with 10% NH$_4$Cl solution, sat. NaHCO$_3$ solution and sat. NaCl solution (in each case 20 ml), dried over sodium sulfate and concentrated under reduced pressure. The crude product was purified by column chromatography (silica gel, ethyl acetate:cyclohexane 2:1) and the desired product (R)-methyl 3-(pyrazolo[1,5-a]pyrimidine-3-carboxamido)-2,3-dihydro-1H-indene-5-carboxylate (B-07) was thus obtained. Yield: 85%

Synthesis of Amino Acid Ester (B-25)

(R)-Methyl 3-(5-methyl isoxazole-3-carboxamido)-2,3-dihydro-1H-indene-5-carboxylate (B-25)

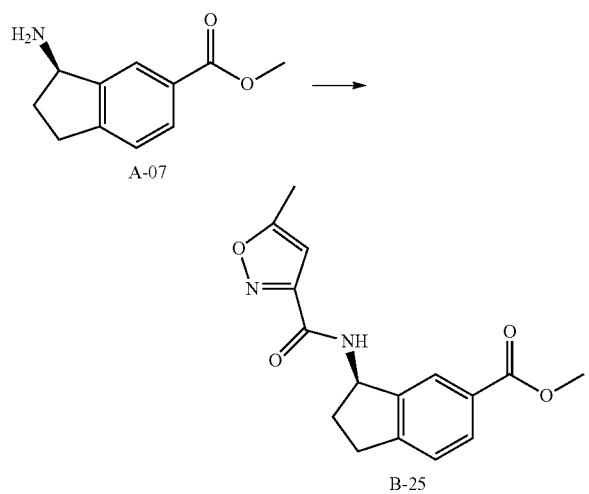

HATU (4.4 g, 11.7 mmol, 1.5 eq) and DIPEA (3.0 ml, 15.6 mmol, 2 eq) were added to an ice-cooled solution of 5-methylisoxazole-3-carboxylic acid (990 mg, 7.8 mmol, 1 eq) in dichloromethane (80 ml), and stirring was carried out for 30 min. (R)-Methyl 3-amino-2,3-dihydro-1H-indene-5-carboxylate (A-07) (7.8 mmol, 1 eq) was dissolved in dichloromethane (20 ml) and added dropwise to the reaction solution, and stirring was carried out for 16 h at RT. The reaction solution was diluted with dichloromethane (250 ml), washed with sat. sodium hydrogen carbonate solution (50 ml), sat. ammonium chloride solution (50 ml), water (50 ml) and sat. NaCl solution (50 ml), dried over sodium sulfate and concentrated under reduced pressure. After purification by column chromatography (silica gel, 2% MeOH in dichloro-methane), the desired product was obtained in the form of a yellowish solid. Yield: 68% (1.6 g, 5.3 mmol).

Synthesis of Amino Acid Ester (B-27)

(R)-Methyl 3-(2-tert-butylbenzamido)-2,3-dihydro-1H-indene-5-carboxylate (B-27)

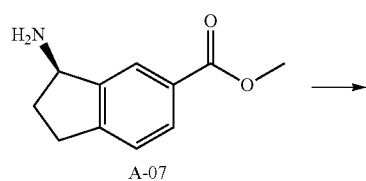

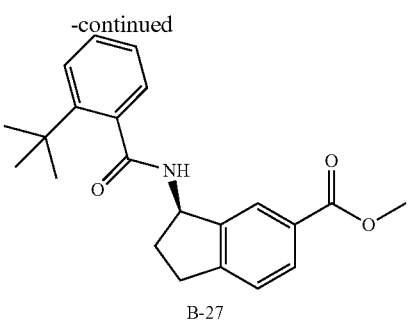

2-tert-Butylbenzoic acid (0.75 g, 4.2 mmol, 1 eq) was dissolved in dichloromethane (40 ml), and at 0° C. HATU (1.5 g, 4.2 mmol, 1 eq) and DIPEA (1.7 ml, 10.52 mmol, 2.5 eq) were added and stirring was carried out for 30 min. Then (R)-methyl 3-amino-2,3-dihydro-1H-indene-5-carboxylate (A-07) (804 mg, 4.2 mmol, 1 eq) dissolved in dichloromethane (20 ml) was added and stirring was carried out for 16 h at RT. After monitoring by thin-layer chromatography, the reaction solution was diluted with dichloromethane (250 ml), washed with sat. sodium hydrogen carbonate solution (50 ml), sat. ammonium chloride solution (50 ml), water (50 ml) and sat. NaCl solution (50 ml), dried over sodium sulfate and concentrated under reduced pressure. The crude product was purified by column chromatography (silica gel, 8-10% ethyl acetate in hexane). Yield: 57% (1.6 g, 4.56 mmol).

Synthesis of Amino Acid Ester (B-28)

(R)-Methyl 1-(2-chlorobenzamido)-6-fluoro-2,3-dihydro-1H-indene-5-carboxylate (B-28)

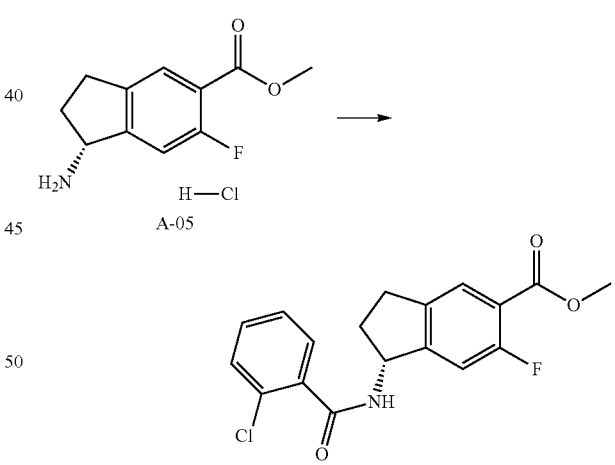

(R)-Methyl 1-amino-6-fluoro-2,3-dihydro-1H-indene-5-carboxylate hydrochloride (A-05) (0.23 g, 1.18 mmol, 1 eq) was dissolved in dichloromethane and DIPEA (2.5 eq), under nitrogen, and 2-chlorobenzoic acid chloride (0.15 ml, 1.18 mmol, 1 eq) was added at 0° C. The reaction mixture was stirred for 2 h at RT. Then the reaction mixture was concentrated and the residue was taken up in ethyl acetate, washed with 10% ammonium chloride solution and with sat. NaCl solution, dried over magnesium sulfate and concentrated. The crude product was purified by column chromatography (silica gel, cyclohexane:ethyl acetate 3:1) and the desired product (R)-methyl 1-(2-chlorobenzamido)-6-fluoro-2,3-dihydro-1H-indene-5-carboxylate (B-28) was thus obtained. Yield: 83%.

Synthesis of Amino Acid Ester (B-29)

(R)-Methyl 3-(2-chloro-N-isobutylbenzamido)-2,3-dihydro-1H-indene-5-carboxylate (B-29)

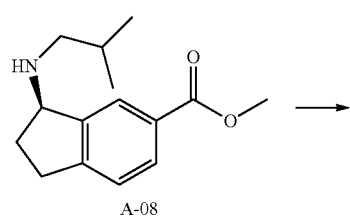

A-08

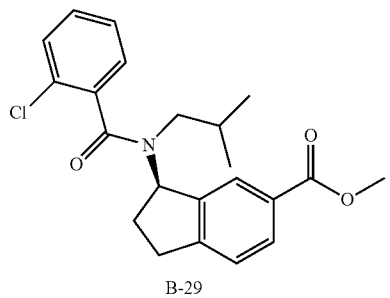

B-29

TEA (1.4 ml, 10.1 mmol, 2.5 eq) was added dropwise at 0° C. to a solution of (R)-methyl 3-(isobutylamino)-2,3-dihydro-1H-indene-5-carboxylate (A-08) (1.0 g, 4.04 mmol, 1 eq) in dichloromethane (25 ml), and stirring was carried out for 15 min. Then 2-chlorobenzoic acid chloride (0.61 ml, 4.858 mmol, 1.2 eq) was added at that temperature, and stirring was carried out for 1 h at RT. After monitoring by thin-layer chromatography, the reaction mixture was diluted with dichloromethane (75 ml), washed with water and sat. NaCl solution (in each case 50 ml), dried over sodium sulfate and purified by column chromatography (silica gel, 2% MeOH in dichloromethane). Yield: 51% (800 mg, 2.078 mmol).

Synthesis of Amino Acid Ester B-30

3-[(2-Chloro-benzoyl)amino]-2,3-dihydro-1H-indene-5-carboxylic acid methyl ester (B-30)

The synthesis of 3-[(2-chloro-benzoyl)amino]-2,3-dihydro-1H-indene-5-carboxylic acid methyl ester (B-30) was carried out starting from A-09 analogously to B-01.

Synthesis of Amino Acid Ester B-32

(R)-Methyl 3-(2-chloro-3-fluorobenzamido)-2,3-dihydro-1H-indene-5-carboxylate (B-32)

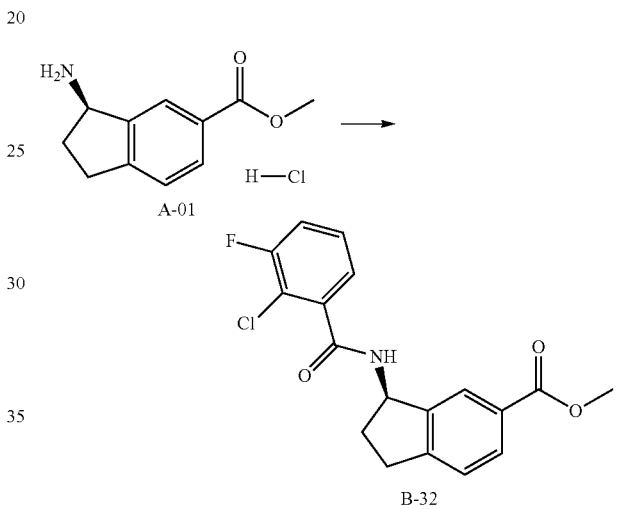

(3R)-3-Amino-2,3-dihydro-1H-indene-5-carboxylic acid methyl ester hydrochloride (A-01) (0.2 mmol, 1 eq) was dissolved in dichloromethane, and DIPEA (2.5 eq) and 2-chloro-3-fluorobenzoic acid chloride (1.2 eq) were added under a protecting gas atmosphere at 0° C. The reaction mixture was stirred for 2 h at RT. Then the reaction mixture was diluted with ethyl acetate, washed 1× with sat. NaHCO₃ solution, 1× with 10% ammonium chloride solution and 1× with sat. NaCl solution, dried over magnesium sulfate and purified by column chromatography (silica gel, cyclohexane:ethyl acetate 4:1). Yield: 92%

Synthesis of Amino Acid Ester B-36

(R)-Methyl 3-(1-naphthamido)-2,3-dihydro-1H-indene-5-carboxylate (B-36)

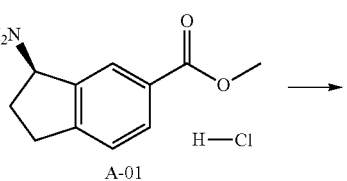

A-01

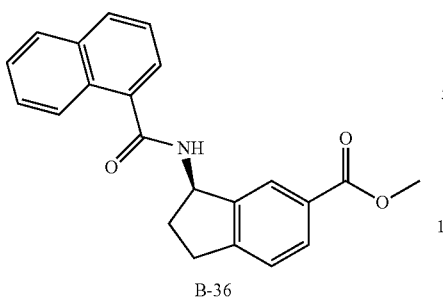

B-36

(3R)-3-Amino-2,3-dihydro-1H-indene-5-carboxylic acid methyl ester hydrochloride (A-01) (1.098 mmol, 1 eq) was dissolved in dichloromethane, and DIPEA (2.5 eq) and naphthalene-1-carboxylic acid chloride (1.0 eq) were added under a protecting gas atmosphere at 0° C. The reaction mixture was stirred for 1.5 h at RT. Then the reaction mixture was diluted with ethyl acetate, washed 1× with 10% ammonium chloride solution and 1× with sat. NaCl solution, dried over magnesium sulfate and purified by column chromatography (silica gel, cyclohexane:ethyl acetate 3:1). Yield: 58%

Synthesis of Amino Acid Ester B-78

(R)-Methyl 3-(1-naphthamido)-2,3-dihydro-1H-indene-5-carboxylate (B-78)

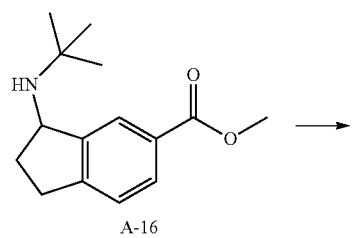

A-16

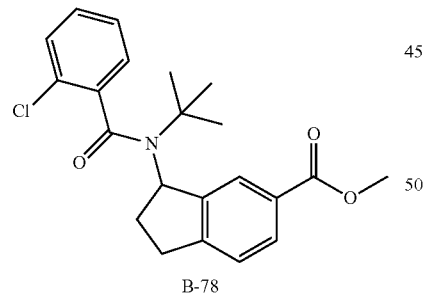

B-78

2-Chlorobenzoic acid chloride (7.0 g, 40.485 mmol, 10.0 eq.) was added at 0° C. to a solution of methyl 3-(tert-butylamino)-2,3-dihydro-1H-indene-5-carboxylate (A-16) (1.0 g, 4.0485 mmol, 1.0 eq.), DMAP (980 mg, 8.097 mmol, 2.0 eq.) and DIPEA (14 ml, 8.9716 mmol, 20.0 eq.) in acetonitrile (40 ml), and the mixture was then refluxed for 20 hours. After monitoring by TLC, the reaction solution was concentrated and the residue was taken up in ethyl acetate (300 ml), washed with sat. sodium hydrogen carbonate solution (100 ml), water (100 ml) and sat. NaCl solution (100 ml), dried over sodium sulfate, concentrated under reduced pressure and purified by column chromatography (silica gel, 10% ethyl acetate in hexane). Yield: 2.0 g Synthesis of Amino Acid Ester B-80

(R)-Methyl 3-(3-cyclopentyl-N-methylpropanamido)-2,3-dihydro-1H-indene-5-carboxylate (B-80)

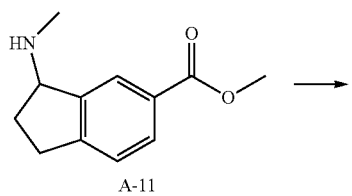

A-11

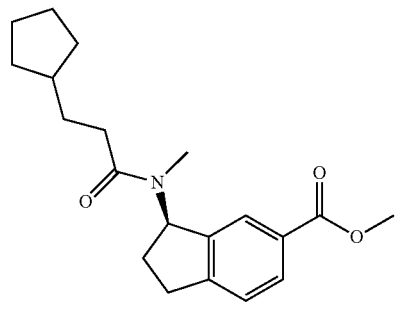

B-80

(R)-Methyl 3-(methylamino)-2,3-dihydro-1H-indene-5-carboxylate (A-11) (1.61 g, 7.85 mmol, 1.0 eq.) was dissolved in DCM (50 ml); TEA (2.72 ml, 19.62 mmol, 2.5 eq.) was added at 0° C., and stirring was carried out for 15 minutes. 3-Cyclopentylpropanoic acid chloride (1.38 ml, 8.635 mmol, 1.1 eq.) was then added, and the mixture was stirred for 4 hours at RT. After monitoring by TLC, the reaction mixture was diluted with DCM (100 ml), washed with water (75 ml) and sat. NaCl solution (75 ml), dried over sodium sulfate, concentrated under reduced pressure and purified by column chromatography (silica gel, 20% ethyl acetate in hexane). Yield: 58% (1.5 g, 4.56 mmol)

Synthesis of Amino Acid Ester B-81

(R)-Methyl 3-(2-fluoro-2-methylpropanamido)-2,3-dihydro-1H-indene-5-carboxylate (B-81)

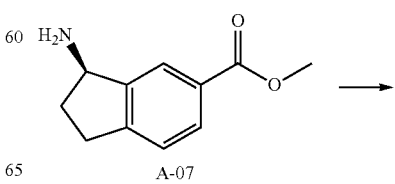

A-07

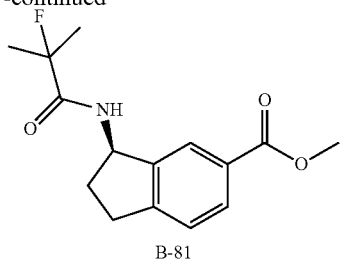

B-81

DIPEA (1.68 ml, 10.2 mmol, 3 eq) and HATU (1.29 g, 3.4 mmol, 1 eq) were added to a solution, cooled to 0° C., of 2-fluoro-2-methylpropanoic acid (360 mg, 3.4 mmol, 1 eq) in THF (15 ml). The reaction mixture was stirred for 15 min, then a solution of (R)-methyl 3-amino-2,3-dihydro-1H-indene-5-carboxylate (A-07) (650 mg, 3.4 mmol, 1 eq) in THF (5 ml) was added and stirring was carried out for 16 h at room temperature. The reaction mixture was concentrated under reduced pressure, taken up in dichloromethane (50 ml) and washed with saturated sodium hydrogen carbonate solution (20 ml), saturated ammonium chloride solution (20 ml), water (20 ml) and saturated sodium chloride solution (20 ml). It was then dried over sodium sulfate and concentrated under reduced pressure, and the crude product was purified by column chromatography (silica gel, 2% methanol/dichloromethane). Yield: 52% (500 mg, 1.79 mmol)

Synthesis of Amino Acid Ester B-83

(3R)-Methyl 3-(3,4-dimethylpentanamido)-2,3-dihydro-1H-indene-5-carboxylate (B-83)

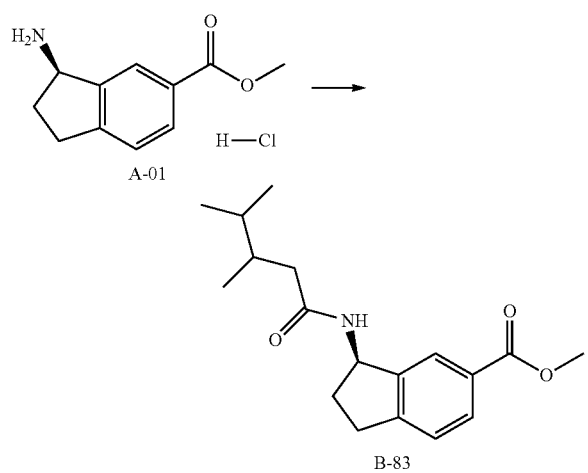

B-83

HATU (0.872 g, 2.3 mmol, 1 eq) and TEA (0.647 ml, 4.6 mmol, 2 eq) were added to an ice-cooled solution of 3,4-dimethylpentanoic acid (300 mg, 2.3 mmol, 1 eq) in THF (26 ml), and stirring was carried out for 15 min. (3R)-3-Amino-2,3-dihydro-1H-indene-5-carboxylic acid methyl ester hydrochloride (A-01) (0.786 g, 3.5 mmol, 1.5 eq) was added to the reaction solution, and the mixture was then stirred overnight at RT. The reaction solution was diluted with ethyl acetate, washed with sat. sodium hydrogen carbonate solution and sat. NaCl solution, dried over magnesium sulfate and concentrated under reduced pressure. After purification by column chromatography (silica gel, cyclohexane:ethyl acetate 2:1), the desired product was obtained. Yield: 87% (0.61 g)

Synthesis of Amino Acid Ester (C-01)

(R)-Methyl 1-(2-chlorophenylsulfonamido)-2,3-dihydro-1H-indene-5-carboxylate (C-01)

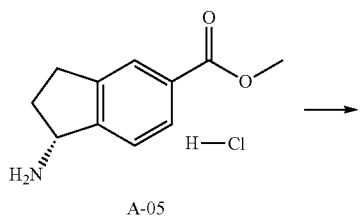

C-01

(R)-Methyl 1-amino-2,3-dihydro-1H-indene-5-carboxylate hydrochloride (A-02) (0.2 g, 0.881 mmol, 1 eq) was dissolved in dichloromethane and triethylamine (2.5 eq) under nitrogen, and 2-chlorobenzenesulfonic acid chloride (0.185 g, 0.881 mmol, 1 eq) was added at 0° C. The reaction mixture was stirred for 2 h at RT. Then concentration was carried out under reduced pressure, and the residue was diluted with ethyl acetate, washed with 10% ammonium chloride solution and sat. NaCl solution, dried over sodium sulfate and concentrated. The crude product was purified by column chromatography (silica gel, cyclohexane:EA 4:1) and the desired product (R)-methyl 1-(2-chlorophenylsulfonamido)-2,3-dihydro-1H-indene-5-carboxylate (C-01) was thus obtained. Yield: 87%

Synthesis of Amino Acid Ester (C-03)

(R)-Methyl 3-(2-methylpropylsulfonamido)-2,3-dihydro-1H-indene-5-carboxylate (C-03)

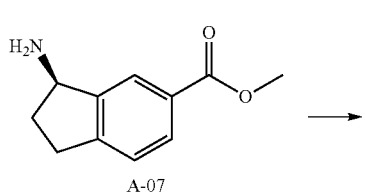

A-07

-continued

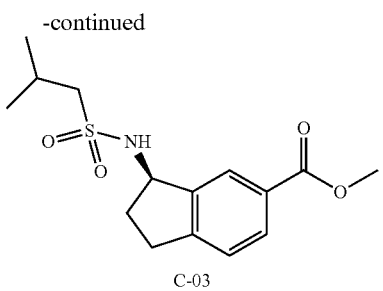

C-03

Triethylamine (750 µl, 5.15 mmol, 3 eq) was added at 0° C. to a solution of (R)-methyl 3-amino-2,3-dihydro-1H-indene-5-carboxylate (A-07) (1.72 mmol, 1 eq) in dichloromethane (10 ml), and stirring was carried out for 10 min. A solution of 2-methylpropane-1-sulfonyl chloride (404 mg, 2.58 mmol, 1.5 eq), dissolved in dichloromethane (5 ml), was added dropwise, and stirring was carried out for 16 h at RT. After monitoring by thin-layer chromatography, the reaction solution was concentrated under reduced pressure and the residue was purified by column chromatography (silica gel, 30% ethyl acetate in hexane). The desired product was obtained in the form of a white solid. Yield: 93% (500 mg, 1.6 mmol).

Synthesis of Amino Acid Ester C-04

(R)-Methyl 3-(4-fluorophenylsulfonamido)-2,3-dihydro-1H-indene-5-carboxylate (C-04)

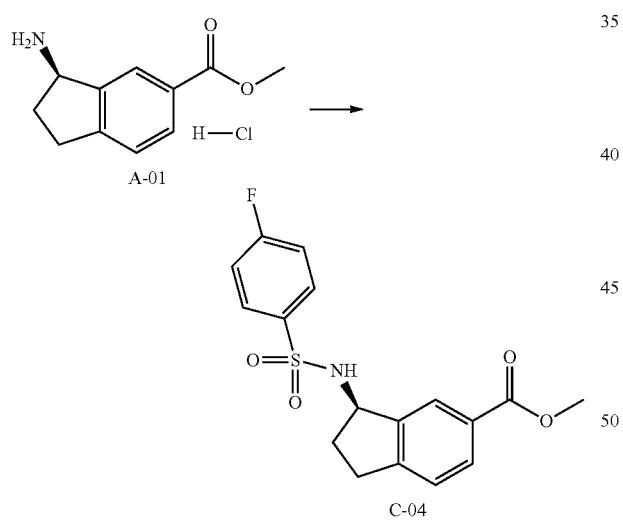

C-04

DIPEA (447 µl, 2.634 mmol, 3 eq) was added at 0° C. to a solution of (3R)-3-amino-2,3-dihydro-1H-indene-5-carboxylic acid methyl ester hydrochloride (A-01) (0.878 mmol, 1 eq) in dichloromethane (10 ml). A solution of 4-fluorobenzene-1-sulfonyl chloride (170 mg, 0.878 mmol, 1 eq) dissolved in dichloromethane (6 ml) was added dropwise and the mixture was stirred for 16 h at RT. After monitoring by thin-layer chromatography, the reaction solution was concentrated under reduced pressure and the residue was taken up in ethyl acetate, washed with 10% ammonium chloride solution, sodium hydrogen carbonate solution and sat. NaCl solution (in each case 1x), dried over sodium sulfate and concentrated. The crude product was purified by column chromatography (silica gel, ethyl acetate:cyclohexane 1:5). Yield: 88%

Synthesis of Amino Acid Ester (D-01)

(R)-Methyl 3-(7-chloro-1-oxoisoindolin-2-yl)-2,3-dihydro-1H-indene-5-carboxylate (D-01)

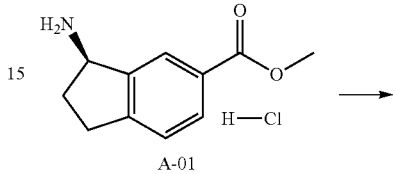

A-01

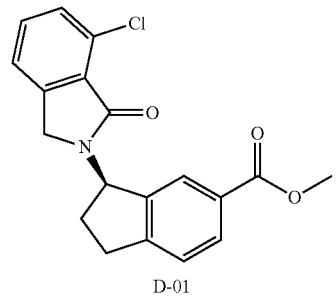

D-01

(3R)-3-Amino-2,3-dihydro-1H-indene-5-carboxylic acid methyl ester hydrochloride (A-01) (1.757 mmol, 1 eq) was added to a solution of 2-bromomethyl-6-chlorobenzoic acid methyl ester (1 eq) in toluene (5.4 ml) and triethylamine (2.1 eq). The reaction mixture was refluxed for 16 h. Then sat. NaHCO$_3$ solution (20 ml) and ethyl acetate (50 ml) were added to the mixture and the phases were separated. The organic phase was extracted with 0.05 N HCl solution and sat. NaCl solution and dried over MgSO$_4$. Concentration of the organic phase yielded the crude product, which was purified by column chromatography (ethyl acetate:cyclohexane, 3:1). The desired product (R)-methyl 3-(7-chloro-1-oxoisoindolin-2-yl)-2,3-dihydro-1H-indene-5-carboxylate (D-01) was thus obtained. Yield: 72%

Synthesis of Amino Acid Ester (D-03)

(R)-Methyl 4-(7-chloro-1-oxoisoindolin-2-yl)chromane-7-carboxylate (D-03)

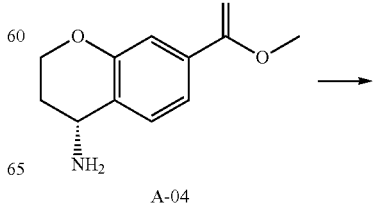

A-04

-continued

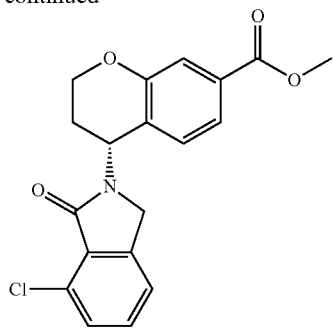

D-03

2-Bromomethyl-6-chlorobenzoic acid methyl ester (1.689 mmol, 1.0 eq) was dissolved in toluene (5.2 ml) and triethylamine (2.534 mmol, 1.5 eq), and (R)-methyl 4-aminochromane-7-carboxylate (A-04) (1.689 mmol, 1 eq) was added. The reaction mixture was refluxed for 16 h and then diluted with water and dichloromethane. The phases were separated and the aqueous phase was extracted with dichloromethane (2×). The organic phases were washed with sat. NaCl solution, dried over magnesium sulfate and concentrated. The crude product was purified by column chromatography (silica gel, cyclohexane:EA 3:1), and the desired product (R)-methyl 4-(7-chloro-1-oxoisoindolin-2-yl)chromane-7-carboxylate (D-03) was thus obtained. Yield: 60%

Synthesis of Amino Acid Ester D-04

(R)-Methyl 1-(7-chloro-1-oxoisoindolin-2-yl)-6-fluoro-2,3-dihydro-1H-indene-5-carboxylate (D-04)

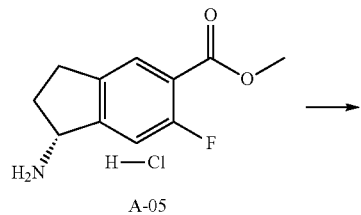

A-05

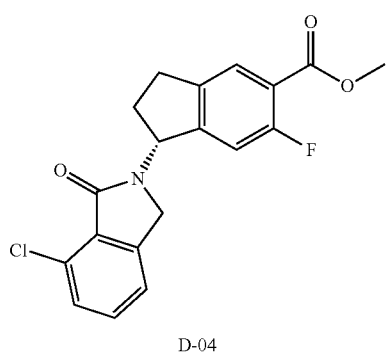

D-04

2-Bromomethyl-6-chlorobenzoic acid methyl ester (1.75 mmol, 1.0 eq) was dissolved in toluene (5.3 ml) and triethylamine (3.675 mmol, 2.1 eq), and (R)-methyl 1-amino-6-fluoro-2,3-dihydro-1H-indene-5-carboxylate hydrochloride (A-05) (1.75 mmol, 1 eq) was added. The reaction mixture was refluxed for 16 h and then diluted with ethyl acetate and sat. NaHCO₃ solution. The phases were separated, and the organic phase was washed with sat. NaCl solution, dried over magnesium sulfate and concentrated. The crude product was purified by column chromatography (silica gel, cyclohexane:EA 2:1). Yield: 65%

Synthesis of Amino Acid Ester D-05

(R)-Methyl 4-(7-chloro-1-oxoisoindolin-2-yl)-8-fluorochromane-6-carboxylate (D-05)

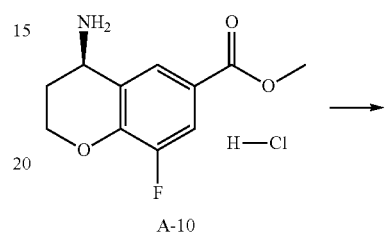

A-10

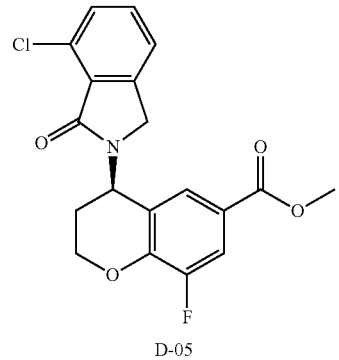

D-05

2-Bromomethyl-6-chlorobenzoic acid methyl ester (1.341 mmol, 1.0 eq) was dissolved in toluene (4 ml) and triethylamine (2.816 mmol, 2.1 eq), and (R)-methyl 4-amino-8-fluoro-chromane-6-carboxylate hydrochloride (A-10) (1.75 mmol, 1 eq) was added. The reaction mixture was refluxed for 16 h and then diluted with DCM and water. The phases were separated, the aqueous phase was extracted 2× with DCM, and the combined organic phases were washed with sat. NaCl solution, dried over magnesium sulfate and concentrated. The crude product was purified by column chromatography (silica gel, cyclohexane:EA 2:1). Yield: 60%

3) Synthesis of the Acylated & Sulfonylated Amino Acids (E, F & G)

General Method for the Synthesis of Amino Acids (E, F & G)

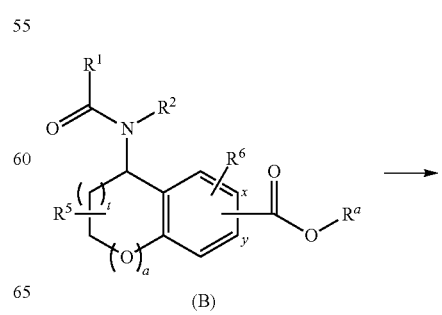

(B)

171
-continued

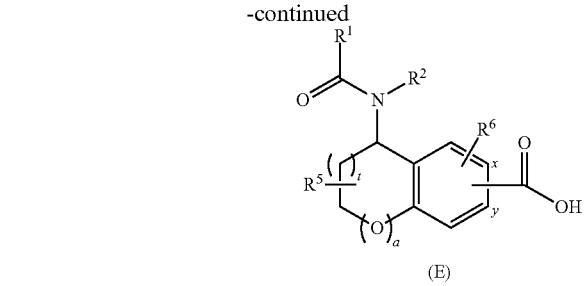

(E)

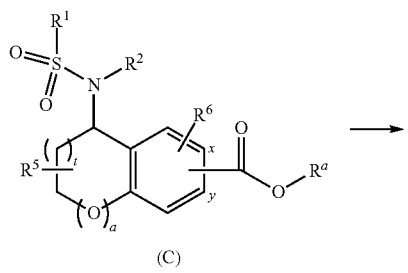

(C)

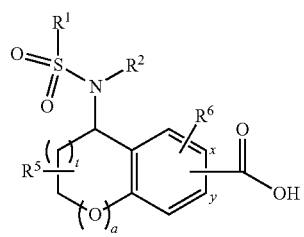

(F)

172
-continued

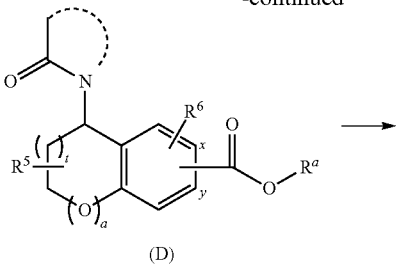

(D)

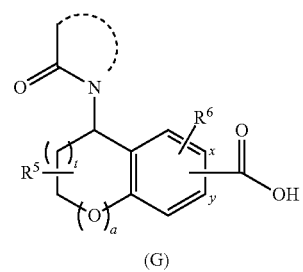

(G)

Synthesis of the acylated & sulfonylated amino acids (E, F & G)

Amino Acid Overview:

| No. | Structure | Amino acid (E, F & G) | Comments |
|---|---|---|---|
| E-01 | 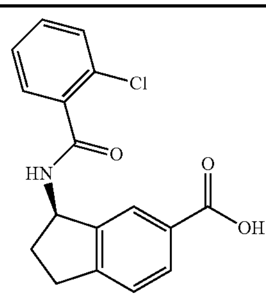 | (3R)-3-[(2-Chloro-benzoyl)amino]-2,3-dihydro-1H-indene-5-carboxylic acid (E-01) | see below |
| E-02 | 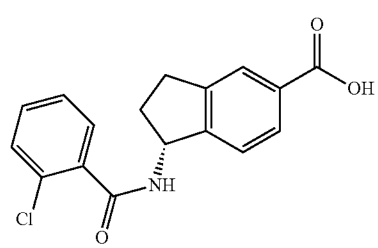 [SMILES: O=C(O)c1ccc2c(c1)CC[C@H]2NC(=O)c1ccccc1Cl] | (R)-1-(2-Chlorobenzamido)-2,3-dihydro-1H-indene-5-carboxylic acid (E-02) | Yield: 78% The synthesis was carried out starting from B-02 analogously to G-01. |
| E-05 | 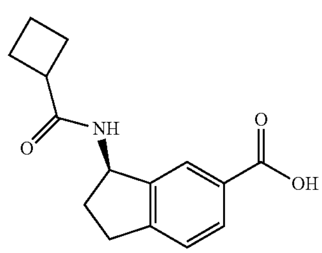 [SMILES: O=C(O)c1ccc2c(c1)[C@H](NC(=O)C1CCC1)CC2] | (R)-3-(Cyclobutanecarboxamido)-2,3-dihydro-1H-indene-5-carboxylic acid (E-05) | Yield: 81% The synthesis was carried out starting from B-03 analogously to G-01. |

-continued

| No. | Structure | Amino acid (E, F & G) | Comments |
|---|---|---|---|
| E-06 | 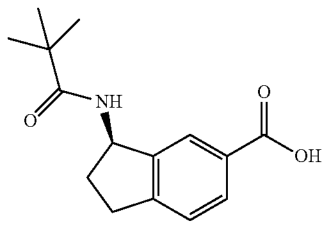 [SMILES: CC(C)(C)C(=O)N[C@@H]1CCc2ccc(C(=O)O)cc21] | (R)-3-Pivalamido-2,3-dihydro-1H-indene-5-carboxylic acid (E-06) | Yield: 81%<br>The synthesis was carried out starting from B-04 analogously to G-01. |
| E-07 | 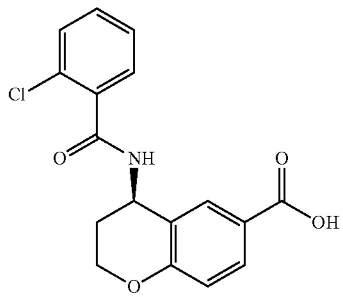 [SMILES: O=C(O)c1ccc2c(c1)[C@H](NC(=O)c1ccccc1Cl)CCO2] | (R)-4-(2-Chlorobenzamido)chromane-6-carboxylic acid (E-07) | Yield: 85%<br>The synthesis was carried out starting from B-05 analogously to G-01. |
| E-08 | 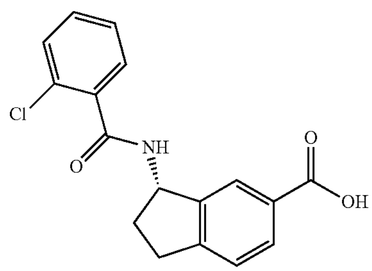 [SMILES: O=C(O)c1ccc2c(c1)[C@@H](NC(=O)c1ccccc1Cl)CC2] | (S)-3-(2-Chlorobenzamido)-2,3-dihydro-1H-indene-5-carboxylic acid (E-08) | Yield: 86%<br>The synthesis was carried out starting from B-06 analogously to E-01. |
| E-09 | 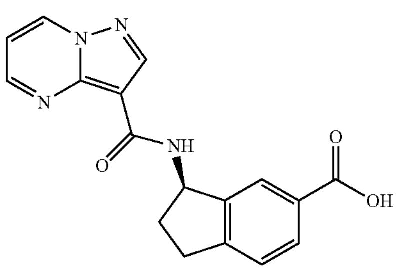 [SMILES: O=C(O)c1ccc2c(c1)[C@H](NC(=O)c1cnn3cccnc13)CC2] | (R)-3-(Pyrazolo[1,5-a]pyrimidine-3-carboxamido)-2,3-dihydro-1H-indene-5-carboxylic acid (E-09) | Yield: 93%<br>The synthesis was carried out starting from B-07 analogously to G-01. |
| E-10 | 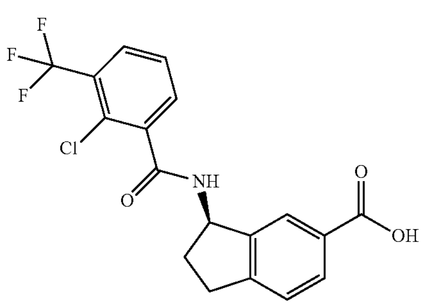 [SMILES: O=C(O)c1ccc2c(c1)[C@H](NC(=O)c1cccc(C(F)(F)F)c1Cl)CC2] | (R)-3-(2-Chloro-3-(trifluoromethyl)benzamido)-2,3-dihydro-1H-indene-5-carboxylic acid (E-10) | Yield: 97%<br>The synthesis was carried out starting from B-08 analogously to G-01. |

-continued

| No. | Structure | Amino acid (E, F & G) | Comments |
|---|---|---|---|
| E-11 | 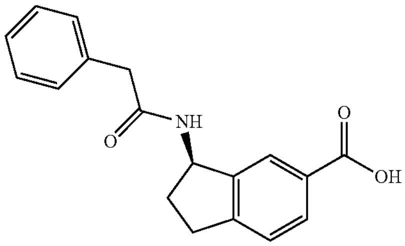 [SMILES: O=C(Cc1ccccc1)N[C@@H]1CCc2ccc(C(=O)O)cc21] | (R)-3-(2-Phenylacetamido)-2,3-dihydro-1H-indene-5-carboxylic acid (E-11) | Yield: 96%<br>The synthesis was carried out starting from B-09 analogously to G-01. |
| E-12 | 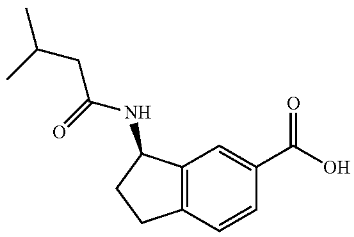 [SMILES: CC(C)CC(=O)N[C@@H]1CCc2ccc(C(=O)O)cc21] | (R)-3-(3-Methylbutanamido)-2,3-dihydro-1H-indene-5-carboxylic acid (E-12) | Yield: 89%<br>The synthesis was carried out starting from B-10 analogously to G-01. |
| E-13 | 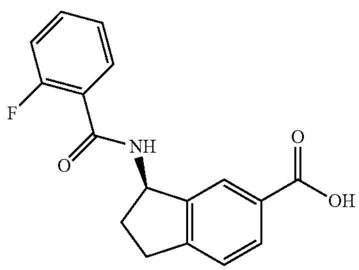 [SMILES: O=C(O)c1ccc2c(c1)[C@H](NC(=O)c1ccccc1F)CC2] | (R)-3-(2-Fluorobenzamido)-2,3-dihydro-1H-indene-5-carboxylic acid (E-13) | Yield: 92%<br>The synthesis was carried out starting from B-11 analogously to G-01. |
| E-14 | 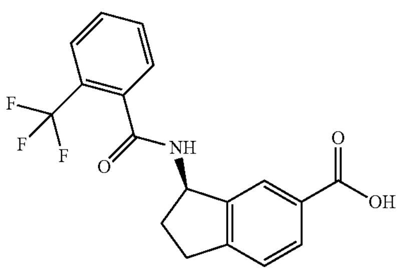 [SMILES: O=C(O)c1ccc2c(c1)[C@H](NC(=O)c1ccccc1C(F)(F)F)CC2] | (R)-3-(2-(Trifluoromethyl)benzamido)-2,3-dihydro-1H-indene-5-carboxylic acid (E-14) | Yield: 70%<br>The synthesis was carried out starting from B-12 analogously to G-01. |
| E-15 | 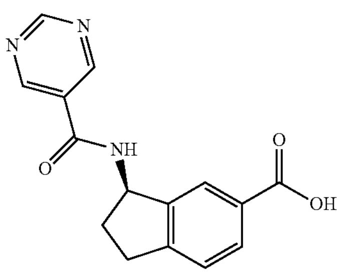 [SMILES: O=C(O)c1ccc2c(c1)[C@H](NC(=O)c1cncnc1)CC2] | (R)-3-(Pyrimidine-5-carboxamido)-2,3-dihydro-1H-indene-5-carboxylic acid (E-15) | Yield: 70%<br>The synthesis was carried out starting from B-13 analogously to G-01. |
| E-16 | 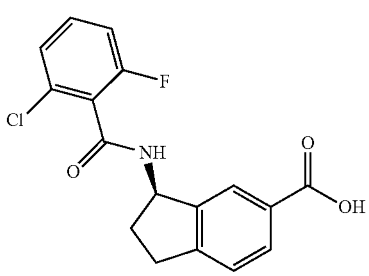 [SMILES: O=C(O)c1ccc2c(c1)[C@H](NC(=O)c1c(F)cccc1Cl)CC2] | (R)-3-(2-Chloro-6-fluorobenzamido)-2,3-dihydro-1H-indene-5-carboxylic acid (E-16) | Yield: 84%<br>The synthesis was carried out starting from B-14 analogously to G-01. |

-continued

| No. | Structure | Amino acid (E, F & G) | Comments |
|---|---|---|---|
| E-17 | 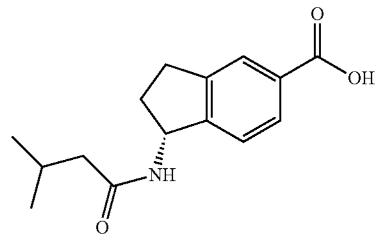 [SMILES: CC(C)CC(=O)N[C@@H]1CCc2cc(C(=O)O)ccc21] | (R)-1-(3-Methylbutanamido)-2,3-dihydro-1H-indene-5-carboxylic acid (E-17) | Yield: 99%<br>The synthesis was carried out starting from B-15 analogously to G-01. |
| E-18 | 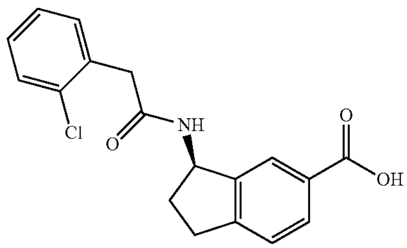 [SMILES: O=C(Cc1ccccc1Cl)N[C@@H]1CCc2ccc(C(=O)O)cc21] | (R)-3-(2-(2-Chlorophenyl)acetamido)-2,3-dihydro-1H-indene-5-carboxylic acid (E-18) | Yield: >99%<br>The synthesis was carried out starting from B-16 analogously to G-01. |
| E-19 | 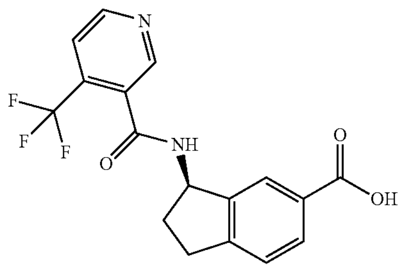 | (R)-3-(4-(Trifluoromethyl)nicotinamido)-2,3-dihydro-1H-indene-5-carboxylic acid (E-19) | Yield: 82%<br>The synthesis was carried out starting from B-17 analogously to G-01 |
| E-20 | 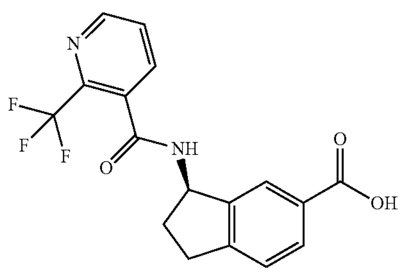 [SMILES: O=C(O)c1ccc2c(c1)[C@H](NC(=O)c1cccnc1C(F)(F)F)CC2] | (R)-3-(2-(Trifluoromethyl)nicotinamido)-2,3-dihydro-1H-indene-5-carboxylic acid (E-20) | Yield: 93%<br>The synthesis was carried out starting from B-18 analogously to G-01 |
| E-21 | 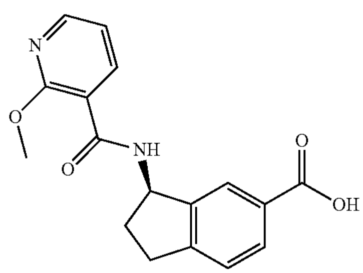 [SMILES: COc1ncccc1C(=O)N[C@@H]1CCc2ccc(C(=O)O)cc21] | (R)-3-(2-Methoxynicotinamido)-2,3-dihydro-1H-indene-5-carboxylic acid (E-21) | Yield: 76%<br>The synthesis was carried out starting from B-19 analogously to G-01 |
| E-22 | 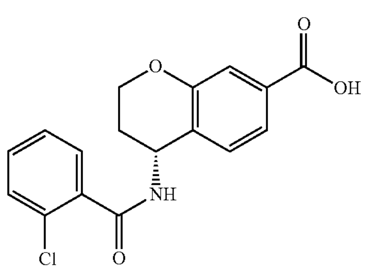 [SMILES: O=C(O)c1ccc2c(c1)OCC[C@H]2NC(=O)c1ccccc1Cl] | (R)-4-(2-Chlorobenzamido)chromane-7-carboxylic acid (E22) | Yield: 96%<br>The synthesis was carried out starting from B-20 analogously to G-01 |

-continued

| No. | Structure | Amino acid (E, F & G) | Comments |
|---|---|---|---|
| E-23 | 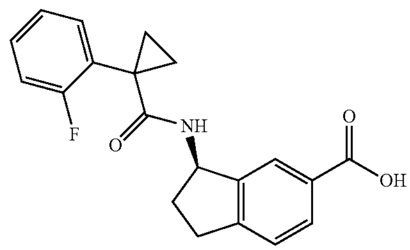 [SMILES: O=C(O)c1ccc2c(c1)[C@H](NC(=O)C1(c3ccccc3F)CC1)CC2] | (R)-3-(1-(2-Fluorophenyl)cyclopropanecarboxamido)-2,3-dihydro-1H-indene-5-carboxylic acid (E-23) | Yield: 93%<br>The synthesis was carried out starting from B-21 analogously to G-01 |
| E-24 | 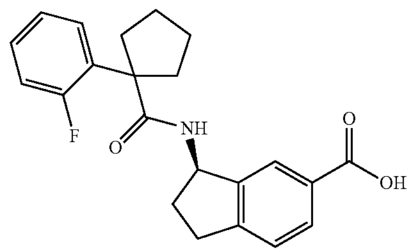 [SMILES: O=C(O)c1ccc2c(c1)[C@H](NC(=O)C1(c3ccccc3F)CCCC1)CC2] | (R)-3-(1-(2-Fluorophenyl)cyclopentanecarboxamido)-2,3-dihydro-1H-indene-5-carboxylic acid (E-24) | Yield: 91%<br>The synthesis was carried out starting from B-22 analogously to G-01 |
| E-25 | 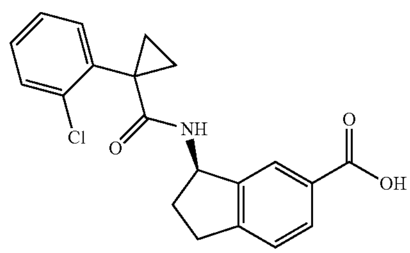 [SMILES: O=C(O)c1ccc2c(c1)[C@H](NC(=O)C1(c3ccccc3Cl)CC1)CC2] | (R)-3-(1-(2-Chlorophenyl)cyclopropanecarboxamido)-2,3-dihydro-1H-indene-5-carboxylic acid (E-25) | Yield: 60%<br>The synthesis was carried out starting from B-23 analogously to G-01 |
| E-26 | 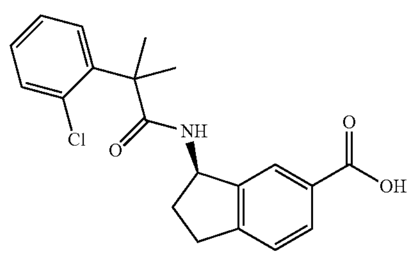 [SMILES: CC(C)(C(=O)N[C@@H]1CCc2ccc(C(=O)O)cc21)c1ccccc1Cl] | (R)-3-(2-(2-Chlorophenyl)-2-methylpropanamido)-2,3-dihydro-1H-indene-5-carboxylic acid (E-26) | Yield: >99%<br>The synthesis was carried out starting from B-24 analogously to G-01 |
| E-27 | 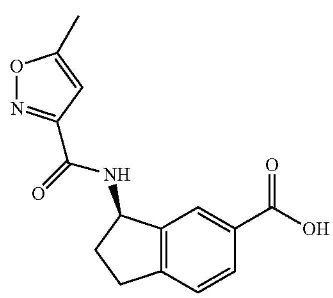 [SMILES: Cc1cc(C(=O)N[C@@H]2CCc3ccc(C(=O)O)cc32)no1] | (R)-3-(5-Methylisoxazole-3-carboxamido)-2,3-dihydro-1H-indene-5-carboxylic acid (E-27) | see below |
| E-29 | 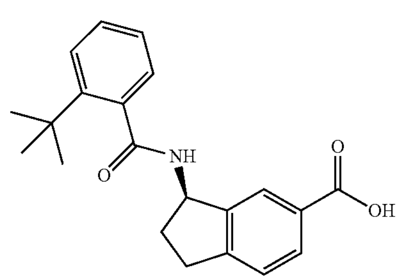 [SMILES: CC(C)(C)c1ccccc1C(=O)N[C@@H]1CCc2ccc(C(=O)O)cc21] | (R)-3-(2-tert-Butylbenzamido)-2,3-dihydro-1H-indene-5-carboxylic acid (E-29) | see below |

-continued

| No. | Structure | Amino acid (E, F & G) | Comments |
|---|---|---|---|
| E-30 | 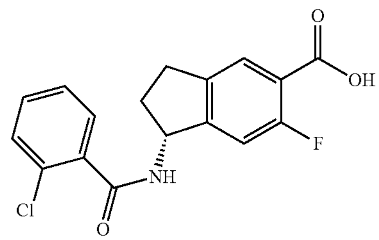 [SMILES: O=C(O)c1cc2c(cc1F)[C@H](NC(=O)c1ccccc1Cl)CC2] | (R)-1-(2-Chlorobenzamido)-6-fluoro-2,3-dihydro-1H-indene-5-carboxylic acid (E-30) | Yield: 92%<br>The synthesis was carried out starting from B-28 analogously to G-01 |
| E-31 | 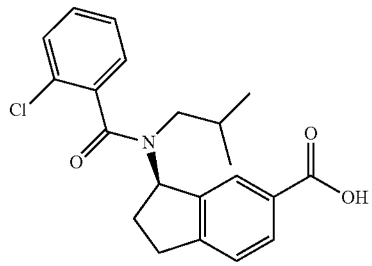 [SMILES: CC(C)CN(C(=O)c1ccccc1Cl)[C@@H]1CCc2ccc(C(=O)O)cc21] | (R)-3-(2-Chloro-N-isobutylbenzamido)-2,3-dihydro-1H-indene-5-carboxylic acid (E-31) | see below |
| E-32 | 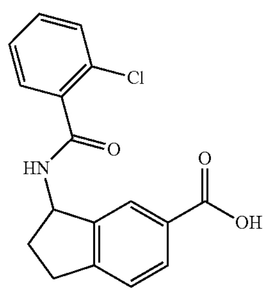 [SMILES: O=C(O)c1ccc2c(c1)C(NC(=O)c1ccccc1Cl)CC2] | 3-[(2-Chloro-benzoyl)amino]-2,3-dihydro-1H-indene-5-carboxylic acid (E-32) | see below |
| E-34 | 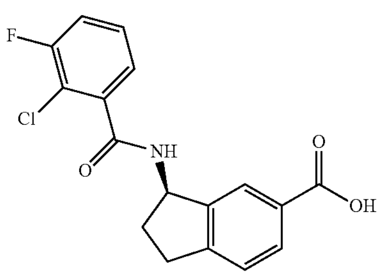 [SMILES: O=C(O)c1ccc2c(c1)[C@H](NC(=O)c1cccc(F)c1Cl)CC2] | (R)-3-(2-Chloro-3-fluorobenzamido)-2,3-dihydro-1H-indene-5-carboxylic acid (E-34) | Yield: 93%<br>The synthesis was carried out starting from B-32 analogously to G-01. |
| E-35 | 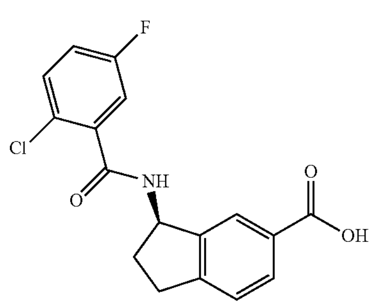 [SMILES: O=C(O)c1ccc2c(c1)[C@H](NC(=O)c1cc(F)ccc1Cl)CC2] | (R)-3-(2-Chloro-5-fluorobenzamido)-2,3-dihydro-1H-indene-5-carboxylic acid (E-35) | Yield: 96%<br>The synthesis was carried out starting from B-33 analogously to G-01. |

-continued

| No. | Structure | Amino acid (E, F & G) | Comments |
|---|---|---|---|
| E-36 | 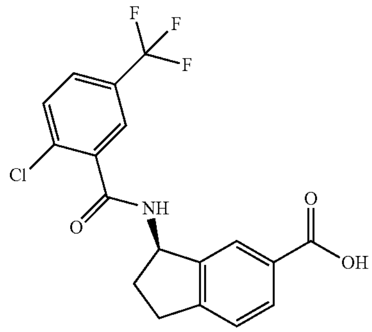 [SMILES: O=C(O)c1ccc2c(c1)[C@H](NC(=O)c1cc(C(F)(F)F)ccc1Cl)CC2] | (R)-3-(2-Chloro-5-(trifluoromethyl)benzamido)-2,3-dihydro-1H-indene-5-carboxylic acid (E-36) | Yield: 91%<br>The synthesis was carried out starting from B-34 analogously to G-01. |
| E-37 | 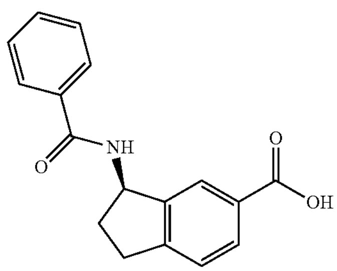 [SMILES: O=C(O)c1ccc2c(c1)[C@H](NC(=O)c1ccccc1)CC2] | (R)-3-Benzamido-2,3-dihydro-1H-indene-5-carboxylic acid (E-37) | Yield: 52%<br>The synthesis was carried out starting from B-35 analogously to G-01. |
| E-38 | 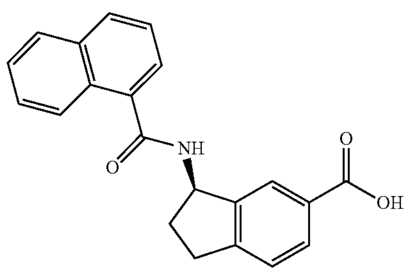 [SMILES: O=C(O)c1ccc2c(c1)[C@H](NC(=O)c1cccc3ccccc13)CC2] | (R)-3-(1-Naphthamido)-2,3-dihydro-1H-indene-5-carboxylic acid (E-38) | see below |
| E-39 | 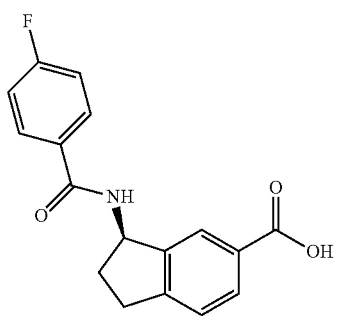 [SMILES: O=C(O)c1ccc2c(c1)[C@H](NC(=O)c1ccc(F)cc1)CC2] | (R)-3-(4-Fluorobenzamido)-2,3-dihydro-1H-indene-5-carboxylic acid (E-39) | Yield: 85%<br>The synthesis was carried out starting from B-37 analogously to G-01. |
| E-40 | 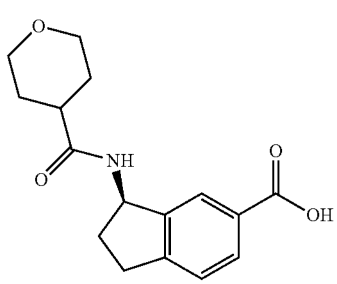 [SMILES: O=C(O)c1ccc2c(c1)[C@H](NC(=O)C1CCOCC1)CC2] | (R)-3-(Tetrahydro-2H-pyran-4-carboxamido)-2,3-dihydro-1H-indene-5-carboxylic acid (E-40) | Yield: 90%<br>The synthesis was carried out starting from B-38 analogously to G-01. |

-continued

| No. | Structure | Amino acid (E, F & G) | Comments |
|---|---|---|---|
| E-41 | 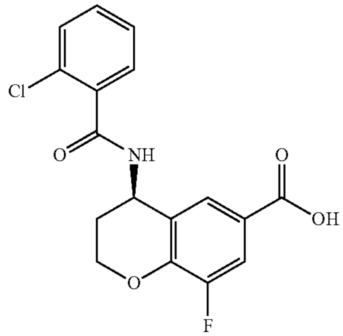 [SMILES: O=C(O)c1cc(F)c2c(c1)[C@H](NC(=O)c1ccccc1Cl)CCO2] | (R)-4-(2-Chlorobenzamido)-8-fluorochromane-6-carboxylic acid (E-41) | Yield: 80%<br>The synthesis was carried out starting from B-39 analogously to G-01. |
| E-42 | 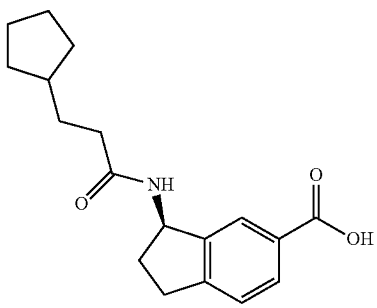 [SMILES: O=C(CCC1CCCC1)N[C@@H]1CCc2ccc(C(=O)O)cc21] | (R)-3-(3-Cyclopentylpropanamido)-2,3-dihydro-1H-indene-5-carboxylic acid (E-42) | Yield: 89%<br>The synthesis was carried out starting from B-40 analogously to G-01. |
| E-43 | 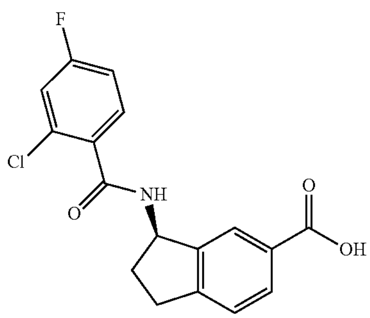 [SMILES: O=C(O)c1ccc2c(c1)[C@H](NC(=O)c1ccc(F)cc1Cl)CC2] | (R)-3-(2-Chloro-4-fluorobenzamido)-2,3-dihydro-1H-indene-5-carboxylic acid (E-43) | Yield: 95%<br>The synthesis was carried out starting from B-41 analogously to G-01. |
| E-44 | 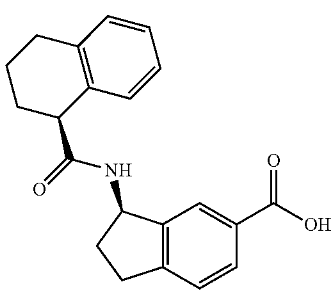 [SMILES: O=C(O)c1ccc2c(c1)[C@H](NC(=O)[C@H]1CCCc3ccccc31)CC2] | (R)-3-((S)-1,2,3,4-Tetrahydronaphthalene-1-carboxamido)-2,3-dihydro-1H-indene-5-carboxylic acid (E-44) | Yield: 99%<br>The synthesis was carried out starting from B-42 analogously to G-01. |
| E-45 | 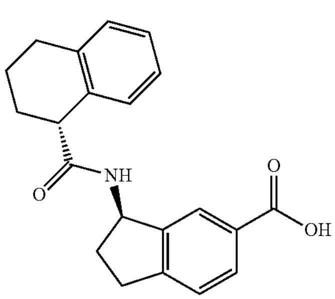 [SMILES: O=C(O)c1ccc2c(c1)[C@H](NC(=O)[C@@H]1CCCc3ccccc31)CC2] | (R)-3-((R)-1,2,3,4-Tetrahydronaphthalene-1-carboxamido)-2,3-dihydro-1H-indene-5-carboxylic acid (E-45) | Yield: 96%<br>The synthesis was carried out starting from B-43 analogously to G-01. |

-continued

| No. | Structure | Amino acid (E, F & G) | Comments |
|---|---|---|---|
| E-46 | 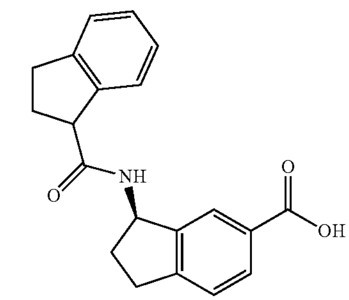 [SMILES: O=C(O)c1ccc2c(c1)[C@H](NC(=O)C1CCc3ccccc31)CC2] | (3R)-3-(2,3-Dihydro-1H-indene-1-carboxamido)-2,3-dihydro-1H-indene-5-carboxylic acid (E-46) | Yield: 91%<br>The synthesis was carried out starting from B-44 analogously to G-01. |
| E-47 | 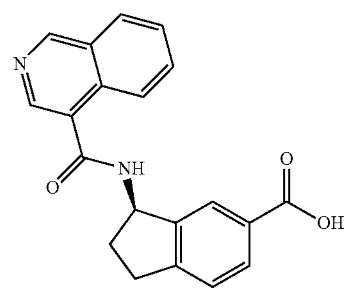 [SMILES: O=C(O)c1ccc2c(c1)[C@H](NC(=O)c1cncc3ccccc13)CC2] | (R)-3-(Isoquinoline-4-carboxamido)-2,3-dihydro-1H-indene-5-carboxylic acid (E-47) | Yield: 71%<br>The synthesis was carried out starting from B-45 analogously to G-01. |
| E-48 | 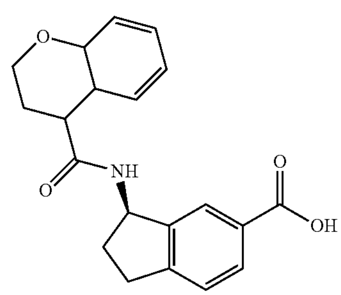 [SMILES: O=C(O)c1ccc2c(c1)[C@H](NC(=O)C1CCOC3C=CC=CC31)CC2] | (3R)-3-(3,4,4a,8a-Tetrahydro-2H-chromene-4-carboxamido)-2,3-dihydro-1H-indene-5-carboxylic acid (E-48) | Yield: 87%<br>The synthesis was carried out starting from B-46 analogously to G-01. |
| E-49 | 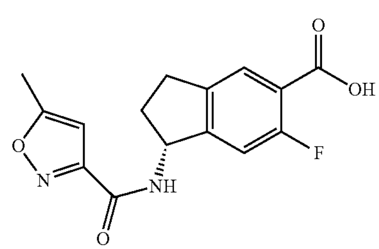 [SMILES: Cc1cc(C(=O)N[C@@H]2CCc3cc(C(=O)O)c(F)cc32)no1] | (R)-6-Fluoro-1-(5-methylisoxazole-3-carboxamido)-2,3-dihydro-1H-indene-5-carboxylic acid (E-49) | Yield: 94%<br>The synthesis was carried out starting from B-47 analogously to G-01. |
| E-50 | 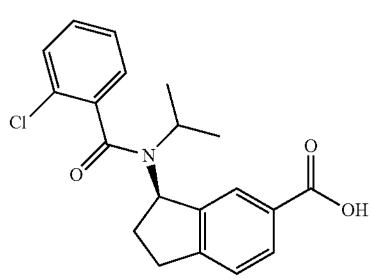 [SMILES: CC(C)N(C(=O)c1ccccc1Cl)[C@@H]1CCc2ccc(C(=O)O)cc21] | (R)-3-(2-Chloro-N-isopropylbenzamido)-2,3-dihydro-1H-indene-5-carboxylic acid (E-50) | Yield: 90%<br>The synthesis was carried out starting from B-48 analogously to G-01. |

-continued

| No. | Structure | Amino acid (E, F & G) | Comments |
|---|---|---|---|
| E-51 | 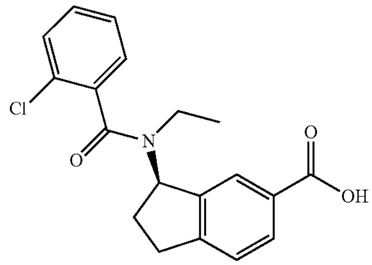 [SMILES: CCN(C(=O)c1ccccc1Cl)[C@@H]1CCc2ccc(C(=O)O)cc21] | (R)-3-(2-Chloro-N-ethylbenzamido)-2,3-dihydro-1H-indene-5-carboxylic acid (E-51) | Yield: 91%<br>The synthesis was carried out starting from B-49 analogously to G-01. |
| E-52 | 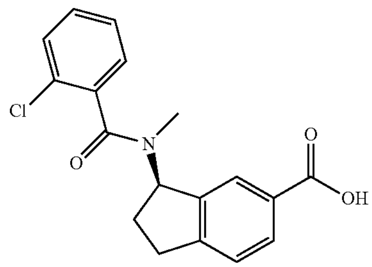 [SMILES: CN(C(=O)c1ccccc1Cl)[C@@H]1CCc2ccc(C(=O)O)cc21] | (R)-3-(2-Chloro-N-methylbenzamido)-2,3-dihydro-1H-indene-5-carboxylic acid (E-52) | Yield: 97%<br>The synthesis was carried out starting from B-50 analogously to G-01. |
| E-53 | 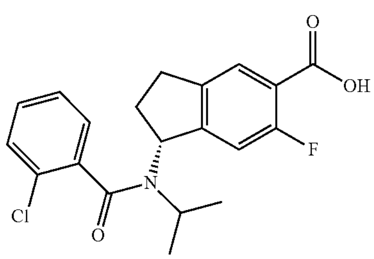 [SMILES: CC(C)N(C(=O)c1ccccc1Cl)[C@@H]1CCc2cc(C(=O)O)c(F)cc21] | (R)-1-(2-Chloro-N-isopropylbenzamido)-6-fluoro-2,3-dihydro-1H-indene-5-carboxylic acid (E-53) | Yield: 96%<br>The synthesis was carried out starting from B-51 analogously to G-01. |
| E-54 | 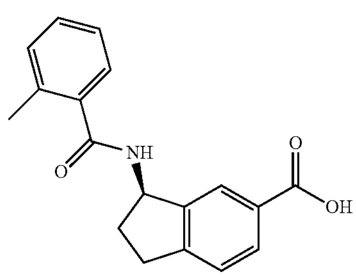 [SMILES: Cc1ccccc1C(=O)N[C@@H]1CCc2ccc(C(=O)O)cc21] | (R)-3-(2-Methylbenzamido)-2,3-dihydro-1H-indene-5-carboxylic acid (E-54) | Yield: 88%<br>The synthesis was carried out starting from B-52 analogously to G-01. |
| E-55 | 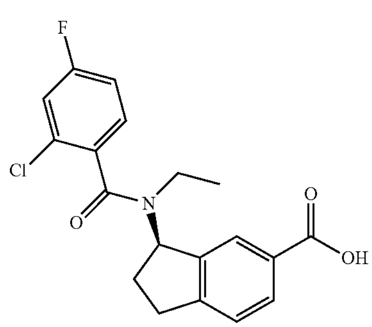 [SMILES: CCN(C(=O)c1ccc(F)cc1Cl)[C@@H]1CCc2ccc(C(=O)O)cc21] | (R)-3-(2-Chloro-N-ethyl-4-fluorobenzamido)-2,3-dihydro-1H-indene-5-carboxylic acid (E-55) | Yield: 91%<br>The synthesis was carried out starting from B-53 analogously to G-01. |

-continued

| No. | Structure | Amino acid (E, F & G) | Comments |
|---|---|---|---|
| E-56 | 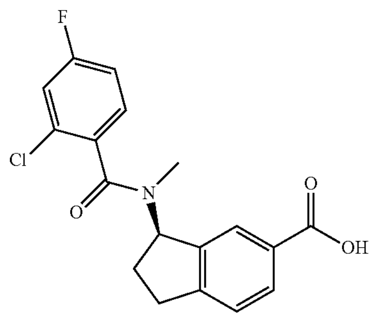 [SMILES: CN(C(=O)c1ccc(F)cc1Cl)[C@@H]1CCc2ccc(C(=O)O)cc21] | (R)-3-(2-Chloro-4-fluoro-N-methylbenzamido)-2,3-dihydro-1H-indene-5-carboxylic acid (E-56) | Yield: 90%<br>The synthesis was carried out starting from B-54 analogously to G-01. |
| E-57 | 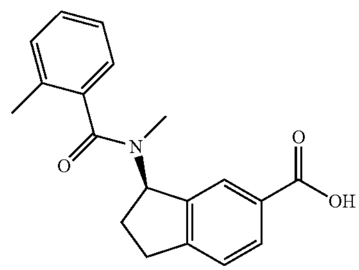 [SMILES: Cc1ccccc1C(=O)N(C)[C@@H]1CCc2ccc(C(=O)O)cc21] | (R)-3-(N,2-Dimethylbenzamido)-2,3-dihydro-1H-indene-5-carboxylic acid (E-57) | Yield: 90%<br>The synthesis was carried out starting from B-55 analogously to G-01. |
| E-58 | 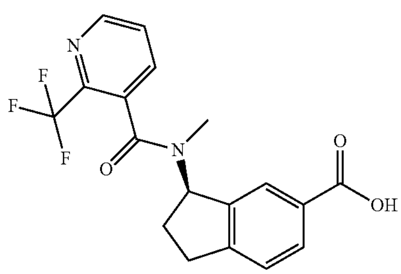 [SMILES: CN(C(=O)c1cccnc1C(F)(F)F)[C@@H]1CCc2ccc(C(=O)O)cc21] | (R)-3-(N-Methyl-2-(trifluoromethyl)nicotinamido)-2,3-dihydro-1H-indene-5-carboxylic acid (E-58) | Yield: >99%<br>The synthesis was carried out starting from B-56 analogously to G-01. |
| E-59 | 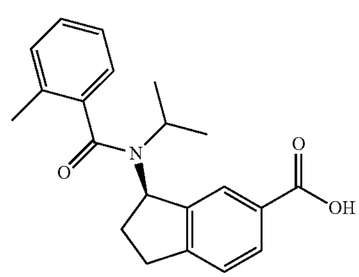 [SMILES: Cc1ccccc1C(=O)N(C(C)C)[C@@H]1CCc2ccc(C(=O)O)cc21] | (R)-3-(N-Isopropyl-2-methylbenzamido)-2,3-dihydro-1H-indene-5-carboxylic acid (E-59) | Yield: 86%<br>The synthesis was carried out starting from B-57 analogously to G-01. |
| E-61 | 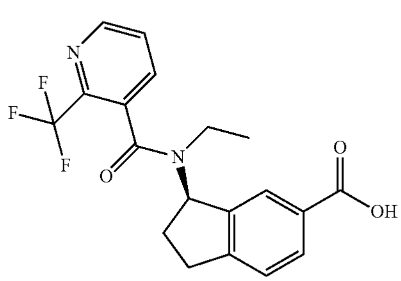 [SMILES: CCN(C(=O)c1cccnc1C(F)(F)F)[C@@H]1CCc2ccc(C(=O)O)cc21] | (R)-3-(N-Ethyl-2-(trifluoromethyl)nicotinamido)-2,3-dihydro-1H-indene-5-carboxylic acid (E-61) | Yield: 99%<br>The synthesis was carried out starting from B-59 analogously to G-01. |

-continued

| No. | Structure | Amino acid (E, F & G) | Comments |
|---|---|---|---|
| E-62 | 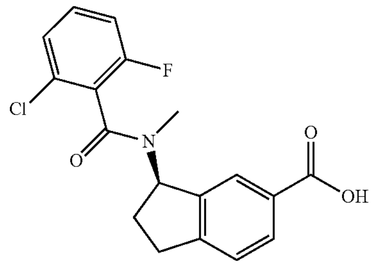 [SMILES: CN(C(=O)c1c(F)cccc1Cl)[C@@H]1CCc2ccc(C(=O)O)cc21] | (R)-3-(2-Chloro-6-fluoro-N-methylbenzamido)-2,3-dihydro-1H-indene-5-carboxylic acid (E-62) | Yield: 91%<br>The synthesis was carried out starting from B-60 analogously to G-01. |
| E-63 | 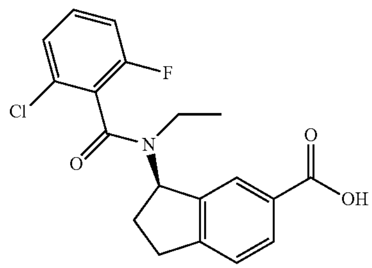 [SMILES: CCN(C(=O)c1c(F)cccc1Cl)[C@@H]1CCc2ccc(C(=O)O)cc21] | (R)-3-(2-Chloro-N-ethyl-6-fluorobenzamido)-2,3-dihydro-1H-indene-5-carboxylic acid (E-63) | Yield: 99%<br>The synthesis was carried out starting from B-61 analogously to G-01. |
| E-65 | 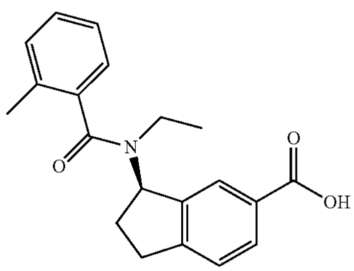 [SMILES: CCN(C(=O)c1ccccc1C)[C@@H]1CCc2ccc(C(=O)O)cc21] | (R)-3-(N-Ethyl-2-methylbenzamido)-2,3-dihydro-1H-indene-5-carboxylic acid (E-65) | Yield: 89%<br>The synthesis was carried out starting from B-63 analogously to G-01. |
| E-68 | 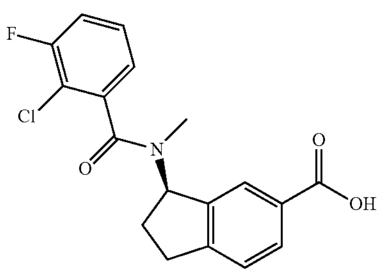 [SMILES: CN(C(=O)c1cccc(F)c1Cl)[C@@H]1CCc2ccc(C(=O)O)cc21] | (R)-Methyl 3-(2-chloro-3-fluoro-N-methylbenzamido)-2,3-dihydro-1H-indene-5-carboxylic acid (E-68) | Yield: 96%<br>The synthesis was carried out starting from B-66 analogously to G-01. |
| E-69 | 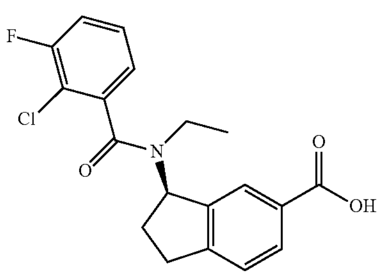 [SMILES: CCN(C(=O)c1cccc(F)c1Cl)[C@@H]1CCc2ccc(C(=O)O)cc21] | (R)-Methyl 3-(2-chloro-N-ethyl-3-fluorobenzamido)-2,3-dihydro-1H-indene-5-carboxylic acid (E-69) | Yield: >99%<br>The synthesis was carried out starting from B-67 analogously to G-01. |

-continued

| No. | Structure | Amino acid (E, F & G) | Comments |
|---|---|---|---|
| E-70 | 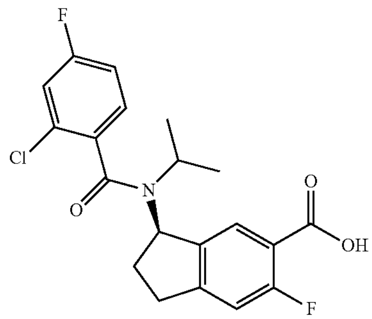 [SMILES: CC(C)N(C(=O)c1ccc(F)cc1Cl)[C@@H]1CCc2cc(F)c(C(=O)O)cc21] | (R)-Methyl 3-(2-chloro-4-fluoro-N-isopropylbenzamido)-6-fluoro-2,3-dihydro-1H-indene-5-carboxylic acid (E-70) | Yield: 87%<br>The synthesis was carried out starting from B-68 analogously to G-01. |
| E-71 | 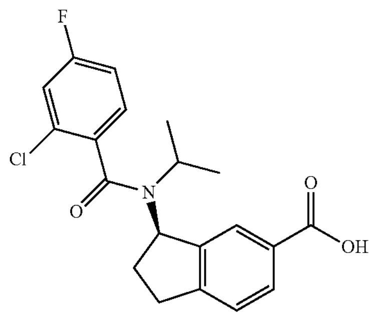 [SMILES: CC(C)N(C(=O)c1ccc(F)cc1Cl)[C@@H]1CCc2ccc(C(=O)O)cc21] | (R)-Methyl 3-(2-chloro-4-fluoro-N-isopropylbenzamido)-2,3-dihydro-1H-indene-5-carboxylic acid (E-71) | Yield: 86%<br>The synthesis was carried out starting from B-69 analogously to G-01. |
| E-74 | 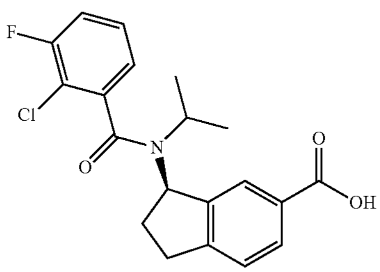 [SMILES: CC(C)N(C(=O)c1cccc(F)c1Cl)[C@@H]1CCc2ccc(C(=O)O)cc21] | (R)-Methyl 3-(2-chloro-3-fluoro-N-isopropylbenzamido)-2,3-dihydro-1H-indene-5-carboxylic acid (E-74) | Yield: 90%<br>The synthesis was carried out starting from B-72 analogously to G-01. |
| E-75 | 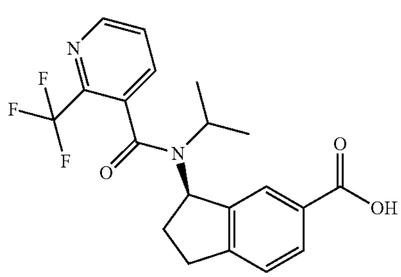 [SMILES: CC(C)N(C(=O)c1cccnc1C(F)(F)F)[C@@H]1CCc2ccc(C(=O)O)cc21] | (R)-Methyl 3-(N-isopropyl-2-(trifluoromethyl)nicotinamido)-2,3-dihydro-1H-indene-5-carboxylic acid (E-75) | Yield: 89%<br>The synthesis was carried out starting from B-73 analogously to G-01. |
| E-76 | 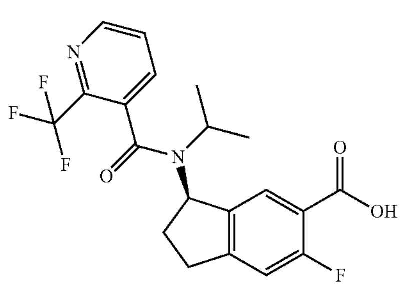 [SMILES: CC(C)N(C(=O)c1cccnc1C(F)(F)F)[C@@H]1CCc2cc(F)c(C(=O)O)cc21] | (R)-Methyl 6-fluoro-3-(N-isopropyl-2-(trifluoromethyl)nicotinamido)-2,3-dihydro-1H-indene-5-carboxylic acid (E-76) | Yield: 80%<br>The synthesis was carried out starting from B-74 analogously to G-01. |

-continued

| No. | Structure | Amino acid (E, F & G) | Comments |
|---|---|---|---|
| E-77 | 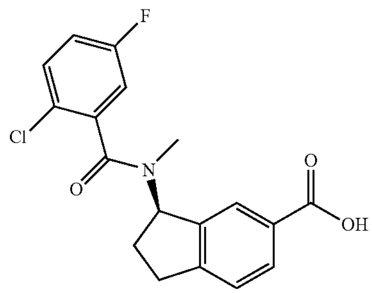 [SMILES: CN(C(=O)c1cc(F)ccc1Cl)[C@@H]1CCc2ccc(C(=O)O)cc21] | (R)-Methyl 3-(2-chloro-5-fluoro-N-methylbenzamido)-2,3-dihydro-1H-indene-5-carboxylic acid (E-77) | Yield: 97%<br>The synthesis was carried out starting from B-75 analogously to G-01. |
| E-78 | 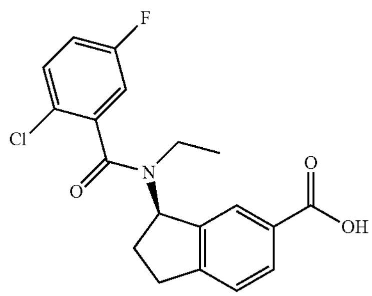 [SMILES: CCN(C(=O)c1cc(F)ccc1Cl)[C@@H]1CCc2ccc(C(=O)O)cc21] | (R)-3-(2-Chloro-N-ethyl-5-fluorobenzamido)-2,3-dihydro-1H-indene-5-carboxylic acid (E-78) | Yield: 99%<br>The synthesis was carried out starting from B-76 analogously to G-01. |
| E-79 | 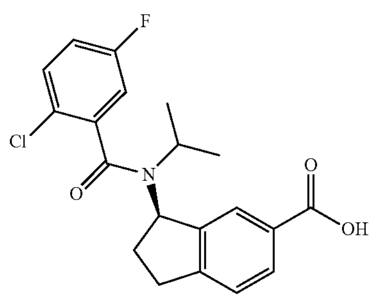 [SMILES: CC(C)N(C(=O)c1cc(F)ccc1Cl)[C@@H]1CCc2ccc(C(=O)O)cc21] | (R)-Methyl 3-(2-chloro-5-fluoro-N-isopropylbenzamido)-2,3-dihydro-1H-indene-5-carboxylic acid (E-79) | Yield: >99%<br>The synthesis was carried out starting from B-77 analogously to G-01. |
| E-80 | 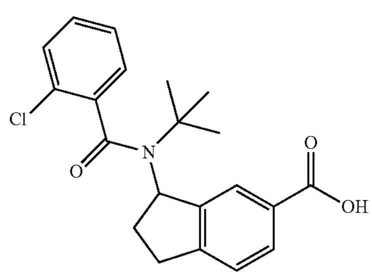 [SMILES: CC(C)(C)N(C(=O)c1ccccc1Cl)C1CCc2ccc(C(=O)O)cc21] | 3-(N-tert-Butyl-2-chlorobenzamido)-2,3-dihydro-1H-indene-5-carboxylic acid (E-80) | Yield: 66%<br>The synthesis was carried out starting from B-78 analogously to E-82. |
| E-81 | 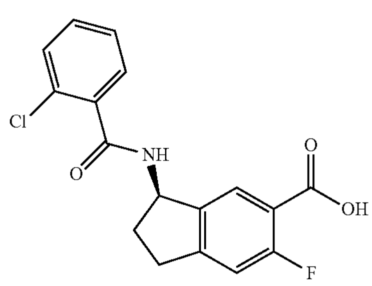 [SMILES: O=C(O)c1cc2c(cc1F)CC[C@H]2NC(=O)c1ccccc1Cl] | (R)-3-(2-Chlorobenzamido)-6-fluoro-2,3-dihydro-1H-indene-5-carboxylic acid (E-81) | Yield: 94%<br>The synthesis was carried out starting from B-79 analogously to E-82. |

-continued

| No. | Structure | Amino acid (E, F & G) | Comments |
|---|---|---|---|
| E-82 | 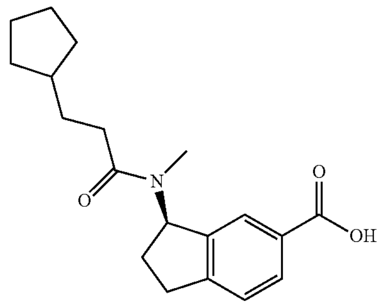 [SMILES: CN(C(=O)CCC1CCCC1)[C@@H]1CCc2ccc(C(=O)O)cc21] | (R)-3-(3-Cyclopentyl-N-methylpropanamido)-2,3-dihydro-1H-indene-5-carboxylic acid (E-82) | see below |
| E-83 | 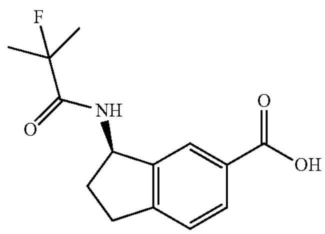 [SMILES: CC(C)(F)C(=O)N[C@@H]1CCc2ccc(C(=O)O)cc21] | (R)-3-(2-Fluoro-2-methylpropanamido)-2,3-dihydro-1H-indene-5-carboxylic acid (E-83) | Yield: 93%<br>The synthesis was carried out starting from B-81 analogously to E-82. |
| E-84 | 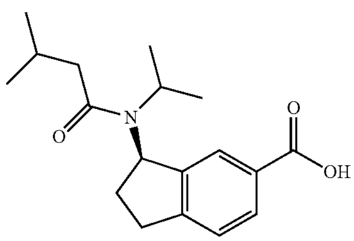 [SMILES: CC(C)CC(=O)N(C(C)C)[C@@H]1CCc2ccc(C(=O)O)cc21] | (R)-3-(N-Isopropyl-3-methylbutanamido)-2,3-dihydro-1H-indene-5-carboxylic acid (E-84) | Yield: 87%<br>The synthesis was carried out starting from B-82 analogously to E-01 Method 2. |
| E-85 | 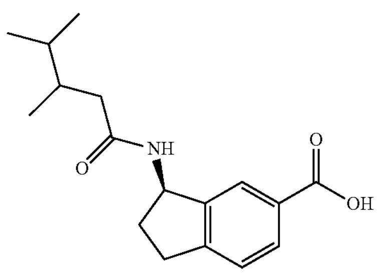 [SMILES: CC(C)C(C)CC(=O)N[C@@H]1CCc2ccc(C(=O)O)cc21] | (3R)-3-(3,4-Dimethylpentanamido)-2,3-dihydro-1H-indene-5-carboxylic acid (E-85) | Yield: 94%<br>The synthesis was carried out starting from B-83 analogously to G-01. |
| E-86 | 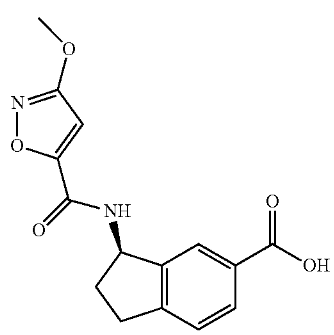 [SMILES: COc1cc(C(=O)N[C@@H]2CCc3ccc(C(=O)O)cc32)on1] | (R)-3-(3-Methoxylsoxazole-5-carboxamido)-2,3-dihydro-1H-indene-5-carboxylic acid (E-86) | Yield: >99%<br>The synthesis was carried out starting from B-84 analogously to G-01. |

-continued

| No. | Structure | Amino acid (E, F & G) | Comments |
|---|---|---|---|
| E-87 | 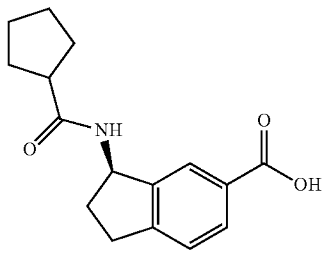 [SMILES: O=C(O)c1ccc2c(c1)[C@H](NC(=O)C1CCCC1)CC2] | (R)-3-(Cyclopentanecarboxamido)-2,3-dihydro-1H-indene-5-carboxylic acid (E-87) | Yield: >99%<br>The synthesis was carried out starting from B-85 analogously to G-01. |
| E-88 | 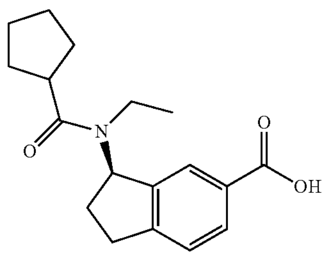 [SMILES: CCN(C(=O)C1CCCC1)[C@@H]1CCc2ccc(C(=O)O)cc21] | (R)-3-(N-Ethylcyclopentanecarboxamido)-2,3-dihydro-1H-indene-5-carboxylic acid (E-88) | Yield: 94%<br>The synthesis was carried out starting from B-86 analogously to G-01. |
| E-89 | 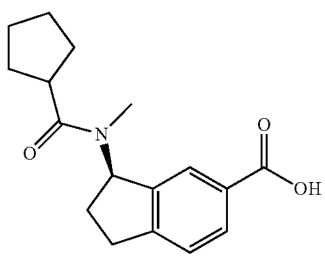 [SMILES: CN(C(=O)C1CCCC1)[C@@H]1CCc2ccc(C(=O)O)cc21] | (R)-3-(N-Methylcyclopentanecarboxamido)-2,3-dihydro-1H-indene-5-carboxylic acid (E-89) | Yield: 91%<br>The synthesis was carried out starting from B-87 analogously to G-01. |
| E-90 | 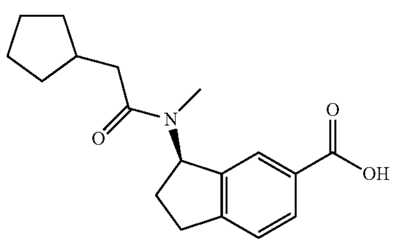 [SMILES: CN(C(=O)CC1CCCC1)[C@@H]1CCc2ccc(C(=O)O)cc21] | (R)-3-(2-Cyclopentyl-N-methylacetamid)-2,3-dihydro-1H-indene-5-carboxylic acid (E-90) | Yield: 99%<br>The synthesis was carried out starting from B-88 analogously to G-01. |
| E-91 | 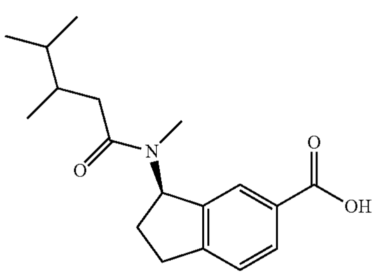 [SMILES: CC(C)C(C)CC(=O)N(C)[C@@H]1CCc2ccc(C(=O)O)cc21] | (3R)-3-(N,3,4-Trimethylpentanamide)-2,3-dihydro-1H-indene-5-carboxylic acid (E-91) | Yield: 95%<br>The synthesis was carried out starting from B-89 analogously to G-01. |
| E-92 | 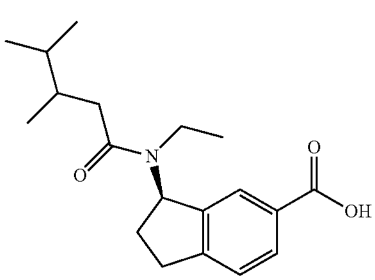 [SMILES: CCN(C(=O)CC(C)C(C)C)[C@@H]1CCc2ccc(C(=O)O)cc21] | (3R)-3-(N-Ethyl-3,4-dimethylpentanamide)-2,3-dihydro-1H-indene-5-carboxylic acid (E-92) | Yield: 85%<br>The synthesis was carried out starting from B-90 analogously to G-01. |

| No. | Structure | Amino acid (E, F & G) | Comments |
|---|---|---|---|
| E-93 | 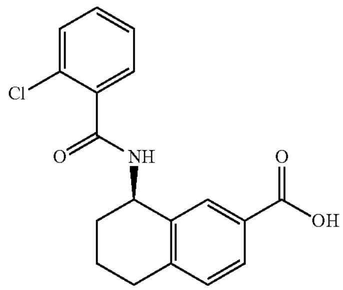 [SMILES: O=C(O)c1ccc2c(c1)[C@H](NC(=O)c1ccccc1Cl)CCC2] | (R)-8-(2-Chlorobenzamide)-5,6,7,8-tetrahydronaphthalene-2-carboxylic acid (E-93) | Yield: 95%<br>The synthesis was carried out starting from B-91 analogously to G-01. |
| E-94 | 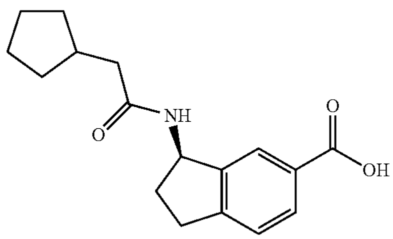 [SMILES: O=C(CC1CCCC1)N[C@@H]1CCc2ccc(C(=O)O)cc21] | (R)-3-(2-Cyclopentylacetamido)-2,3-dihydro-1H-indene-5-carboxylic acid (E-94) | Yield: >99%<br>The synthesis was carried out starting from B-92 analogously to G-01. |
| E-95 | 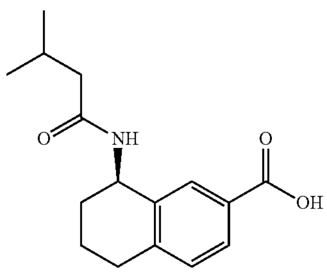 [SMILES: CC(C)CC(=O)N[C@@H]1CCCc2ccc(C(=O)O)cc21] | (R)-8-(3-Methylbutanamide)-5,6,7,8-tetrahydronaphthalene-2-carboxylic acid (E-95) | Yield: 90%<br>The synthesis was carried out starting from B-93 analogously to G-01. |
| E-96 | 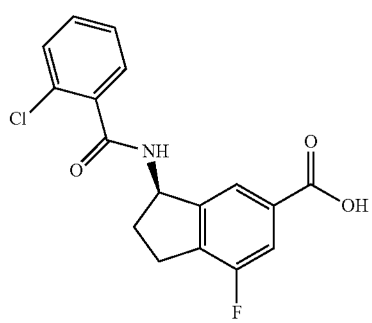 [SMILES: O=C(O)c1cc(F)c2c(c1)[C@H](NC(=O)c1ccccc1Cl)CC2] | (R)-3-(2-Chlorobenzamido)-7-fluoro-2,3-dihydro-1H-indene-5-carboxylic acid (E-96) | Yield: 90%<br>The synthesis was carried out starting from B-94 analogously to E-82. |
| F-01 | 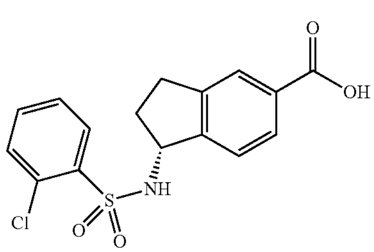 [SMILES: O=C(O)c1ccc2c(c1)CC[C@H]2NS(=O)(=O)c1ccccc1Cl] | (R)-1-(2-Chlorophenylsulfonamido)-2,3-dihydro-1H-indene-5-carboxylic acid (F-01) | Yield: 62%<br>The synthesis was carried out starting from C-01 analogously to G-01 |

-continued

| No. | Structure | Amino acid (E, F & G) | Comments |
|---|---|---|---|
| F-02 | 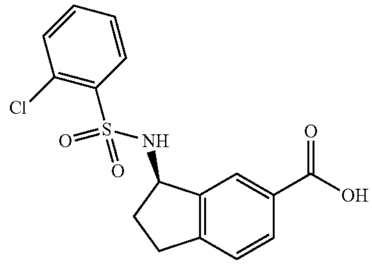 [SMILES: O=C(O)c1ccc2c(c1)[C@H](NS(=O)(=O)c1ccccc1Cl)CC2] | (R)-3-(2-Chlorophenylsulfonamido)-2,3-dihydro-1H-indene-5-carboxylic acid (F-02) | Yield: 81%<br>The synthesis was carried out starting from C-02 analogously to G-01 |
| F-03 | 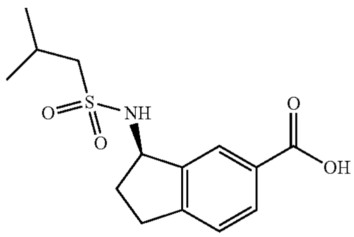 [SMILES: CC(C)CS(=O)(=O)N[C@@H]1CCc2ccc(C(=O)O)cc21] | (R)-3-(2-Methylpropylsulfonamido)-2,3-dihydro-1H-indene-5-carboxylic acid (F-03) | see below |
| F-04 | 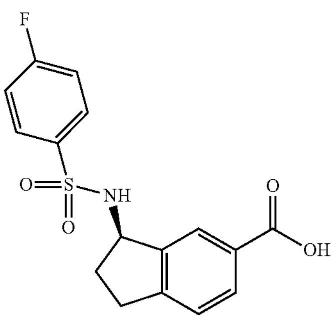 [SMILES: O=C(O)c1ccc2c(c1)[C@H](NS(=O)(=O)c1ccc(F)cc1)CC2] | (R)-Methyl 3-(4-fluorophenylsulfonamido)-2,3-dihydro-1H-indene-5-carboxylic acid (F-04) | Yield: 77%<br>The synthesis was carried out starting from C-04 analogously to G-01. |
| F-05 | 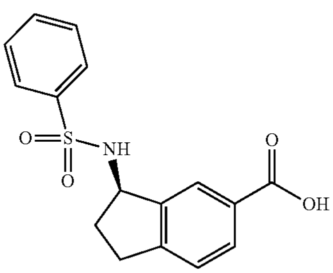 [SMILES: O=C(O)c1ccc2c(c1)[C@H](NS(=O)(=O)c1ccccc1)CC2] | (R)-Methyl 3-(phenylsulfonamido)-2,3-dihydro-1H-indene-5-carboxylic acid (F-05) | Yield: 46%<br>The synthesis was carried out starting from C-05 analogously to G-01. |
| G-01 | 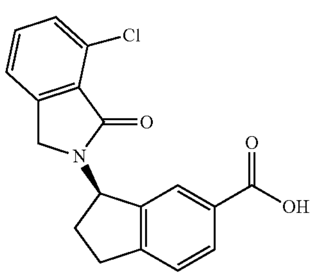 [SMILES: O=C(O)c1ccc2c(c1)[C@H](N1Cc3cccc(Cl)c3C1=O)CC2] | (R)-3-(7-Chloro-1-oxoisoindolin-2-yl)-2,3-dihydro-1H-indene-5-carboxylic acid (G-01) | see below |

-continued

| No. | Structure | Amino acid (E, F & G) | Comments |
|---|---|---|---|
| G-02 | 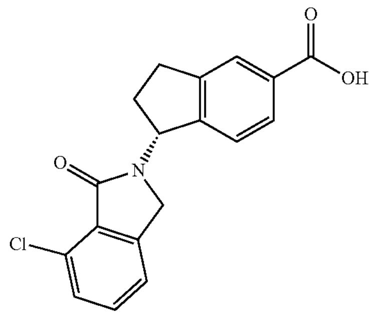 [SMILES: O=C(O)c1ccc2c(c1)CC[C@H]2N1Cc2cccc(Cl)c2C1=O] | (R)-1-(7-Chloro-1-oxoisoindolin-2-yl)-2,3-dihydro-1H-indene-5-carboxylic acid (G-02) | Yield: 91%<br>The synthesis was carried out starting from D-02 analogously to G-01.<br>or<br>Yield: 84% |
| G-03 | 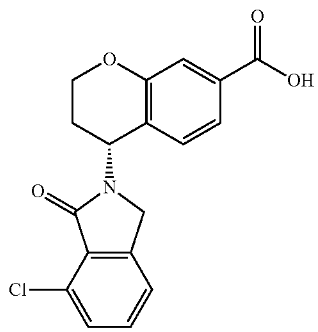 [SMILES: O=C(O)c1ccc2c(c1)OCC[C@H]2N1Cc2cccc(Cl)c2C1=O] | (R)-4-(7-Chloro-1-oxoisoindolin-2-yl)chromane-7-carboxylic acid (G-03) | Yield: 98%<br>The synthesis was carried out starting from D-03 analogously to G-01. |
| G-04 | 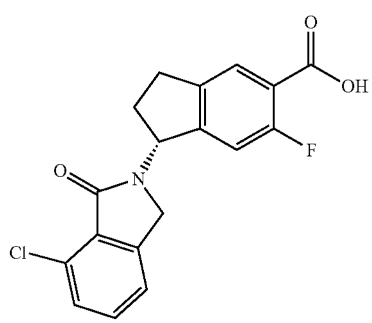 [SMILES: O=C(O)c1cc2c(cc1F)[C@H](N1Cc3cccc(Cl)c3C1=O)CC2] | (R)-1-(7-Chloro-1-oxoisoindolin-2-yl)-6-fluoro-2,3-dihydro-1H-indene-5-carboxylic acid (G-04) | Yield: 94%<br>The synthesis was carried out starting from D-04 analogously to G-01. |
| G-05 | 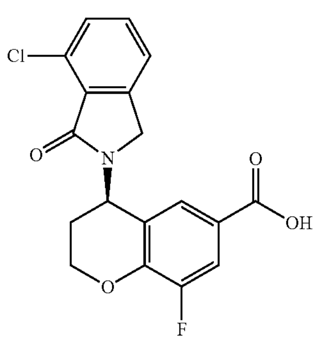 [SMILES: O=C(O)c1cc(F)c2c(c1)[C@H](N1Cc3cccc(Cl)c3C1=O)CCO2] | (R)-4-(7-Chloro-1-oxoisoindolin-2-yl)-8-fluorochromane-6-carboxylic acid (G-05) | see below |

| No. | Structure | Amino acid (E, F & G) | Comments |
|---|---|---|---|
| G-06 | 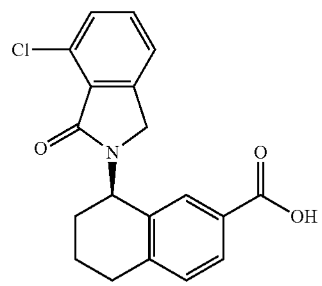 [SMILES: O=C(O)c1ccc2c(c1)[C@H](N1Cc3cccc(Cl)c3C1=O)CCC2] | (R)-8-(7-Chloro-1-oxoisoindolin-2-yl)-5,6,7,8-tetrahydronaphthalene-2-carboxylic acid (G-06) | Yield: 93% The synthesis was carried out starting from D-06 analogously to G-01. |

Note:
In the case of reactions carried out analogously to a described method, the reaction conditions were optionally adapted, in particular in respect of the reagent equiv., the replacement of Et₃N by DIPEA or of magnesium sulfate by sodium sulfate, and the reaction times (these were adapted according to TLC monitoring). If necessary, the produt was purified by column chromatography.

Synthesis of Amino Acid E-01

(3R)-3-[(2-Chloro-benzoyl)amino]-2,3-dihydro-1H-indene-5-carboxylic acid (E-01)

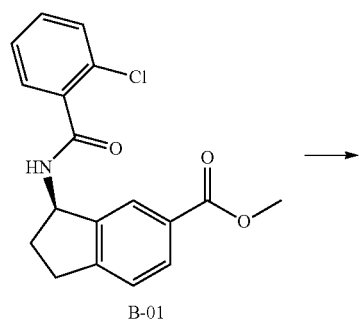

Method 1

LiOH (5 eq) was added to a suspension of (3R)-3-[(2-chloro-benzoyl)amino]-2,3-dihydro-1H-indene-5-carboxylic acid methyl ester (B-01) (8.569 mmol, 1 eq) in methanol (35 ml) and water (8 ml), and the reaction mixture was stirred overnight at 25° C. Methanol was removed in vacuo and the residue was taken up in diethyl ether and water. The phases were separated and the aqueous phase was adjusted to pH 2 with 1N HCl. The aqueous phase was extracted with ethyl acetate (2×) and the combined organic phases were then dried over magnesium sulfate. After concentration, the desired product (3R)-3-[(2-chloro-benzoyl)amino]-2,3-dihydro-1H-indene-5-carboxylic acid (E-01) was obtained. Yield: 93% or
Method 2
LiOH.H₂O (2.7 g, 65.32 mmol, 2.5 eq) in water (35 ml) was added dropwise to a cooled (0° C.) solution of (3R)-3-[(2-chloro-benzoyl)amino]-2,3-dihydro-1H-indene-5-carboxylic acid methyl ester (B-01) (8.6 g, 26.13 mmol, 1 eq) in MeOH:THF (1:1, 70 ml), and stirring was carried out for 3 h at RT. After monitoring by thin-layer chromatography, the reaction solution was concentrated under reduced pressure and the residue was taken up in water (100 ml), adjusted to pH 3 with 1 M HCl and extracted with ethyl acetate (3×200 ml). The combined organic phases were washed with sat. NaCl solution (200 ml), dried over sodium sulfate and concentrated under reduced pressure. Yield: 92% (7.6 g, 24.12 mmol).

Synthesis of Amino Acid E-27

(R)-3-(5-Methylisoxazole-3-carboxamido)-2,3-dihydro-1H-indene-5-carboxylic acid (E-27)

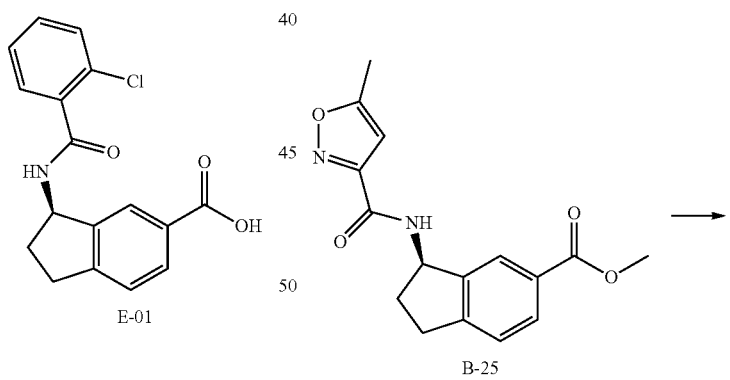

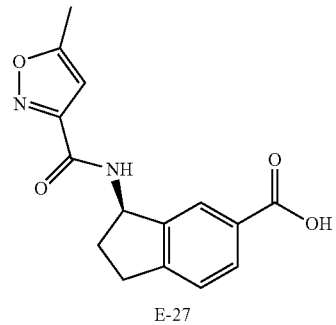

LiOH (3.0 g, 42.66 mmol, 8 eq) in water (30 ml) was added dropwise to a cooled (0° C.) solution of (R)-methyl 3-(5-methylisoxazole-3-carboxamido)-2,3-dihydro-1H-indene-5-carboxylate (B-25) (1.6 g, 5.3 mmol, 1 eq) in MeOH:THF (1:1, 60 ml), and stirring was carried out for 5 h at RT. After monitoring by thin-layer chromatography, the reaction solution was concentrated under reduced pressure and the residue was taken up in water (50 ml), adjusted to pH 2 with KHSO$_4$ and extracted with DCM (2×100 ml). The combined organic phases were washed with sat. NaCl solution (50 ml), dried over sodium sulfate and concentrated under reduced pressure. Yield: 59% (900 mg, 3.14 mmol).

Synthesis of Amino Acid E-29

(R)-3-(2-tert-Butylbenzamido)-2,3-dihydro-1H-indene-5-carboxylic acid (E-29)

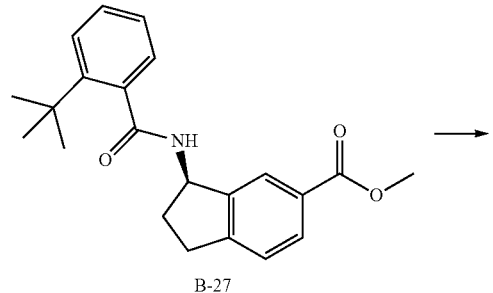

B-27

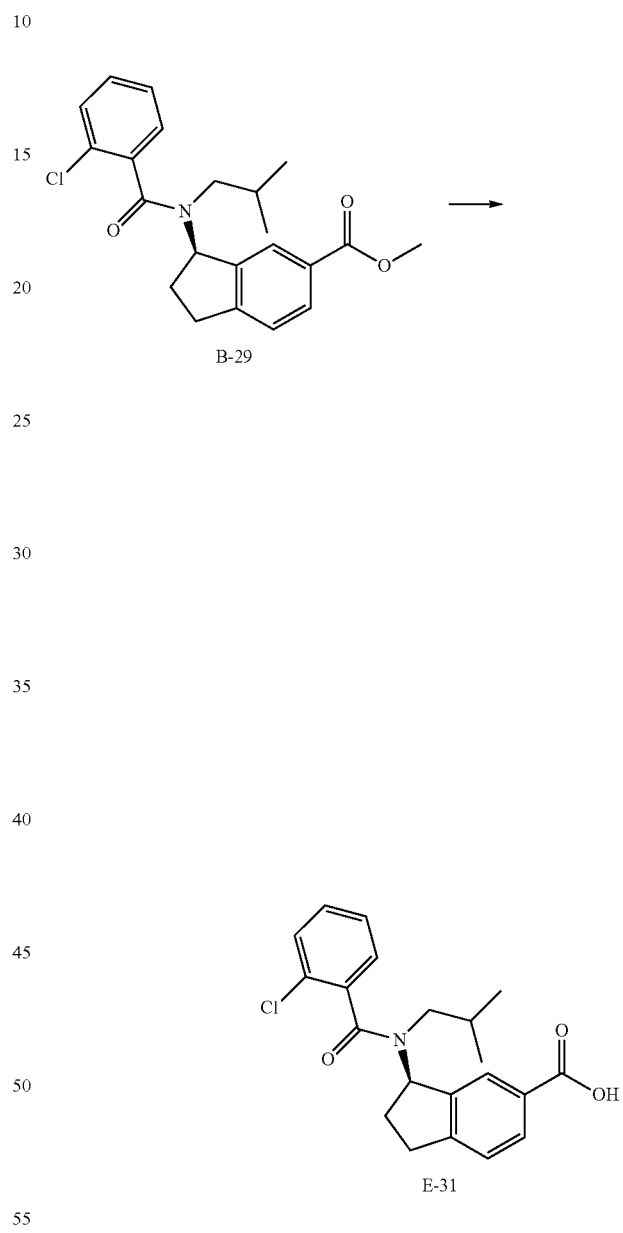

E-29

LiOH.H$_2$O (700 g, 17.0 mmol, 6 eq), dissolved in water (30 ml), was added dropwise to a cooled (0° C.) solution of (R)-methyl 3-(2-tert-butylbenzamido)-2,3-dihydro-1H-indene-5-carboxylate (B-27) (1.0 g, 2.8 mmol, 1 eq) in MeOH: THF (1:1, 60 ml), and stirring was carried out for 4 h at RT. After monitoring by thin-layer chromatography, the reaction solution was reduced under reduced pressure and the residue was taken up in water (50 ml), acidified with KHSO$_4$ solution and extracted with dichloromethane (2×100 ml). The combined organic phases were washed with sat. NaCl solution (50 ml), dried over sodium sulfate and concentrated and dried under reduced pressure. Yield: 900 mg Synthesis of Amino Acid E-31

(R)-3-(2-Chloro-N-isobutylbenzamido)-2,3-dihydro-1H-indene-5-carboxylic acid (E-31)

B-29

E-31

LiOH (173 mg, 4.156 mmol, 2 eq), dissolved in water (12 ml), was added dropwise to an ice-cooled (0° C.) solution of (R)-methyl 3-(2-chloro-N-isobutylbenzamido)-2,3-dihydro-1H-indene-5-carboxylate (B-29) (0.8 g, 2.078 mmol, 1 eq) in MeOH:THF (1:1, 24 ml), and stirring was carried out for 8 h at RT. After monitoring by thin-layer chromatography, the reaction solution was concentrated and the residue was taken up in water (30 ml) and extracted with ethyl acetate (25 ml). The aqueous phase was adjusted to pH 3 with 2 M HCl and extracted with ethyl acetate (2×50 ml). The combined organic phases were washed with sat. NaCl solution (50 ml), dried over sodium sulfate and concentrated under reduced pressure. Yield: 78% (600 mg, 1.62 mmol).

Synthesis of Amino Acid E-32

3-[(2-Chloro-benzoyl)amino]-2,3-dihydro-1H-indene-5-carboxylic acid (E-32)

The synthesis of amino acid E-32 was carried out analogously to the synthesis of amino acid E-01.

Synthesis of Amino Acid E-38

(R)-3-(1-Naphthamido)-2,3-dihydro-1H-indene-5-carboxylic acid (E-38)

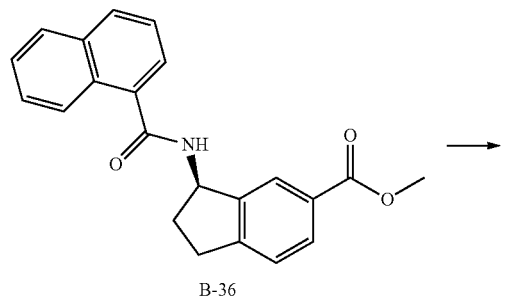

B-36

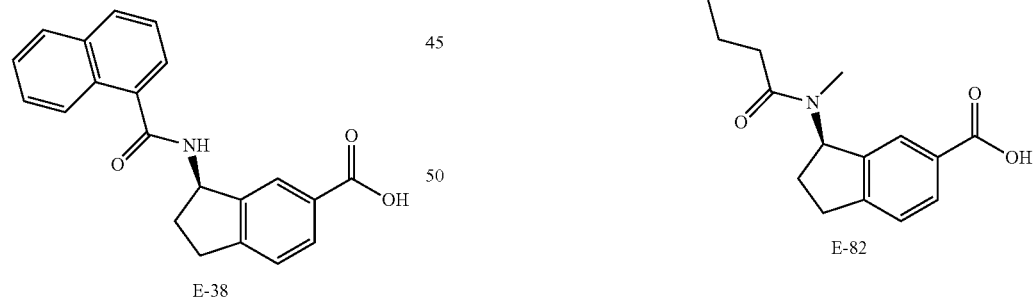

E-38

LiOH.H$_2$O (0.272 g, 3.62 mmol, 5 eq) dissolved in water (0.6 ml) was added dropwise to a cooled (0° C.) solution of (R)-methyl 3-(1-naphthamido)-2,3-dihydro-1H-indene-5-carboxylate (B-36) (0.25 g, 0.724 mmol, 1 eq) in MeOH (3 ml), and the resulting mixture was stirred for 16 h at RT. After monitoring by TLC, further LiOH.H$_2$O (0.272 g, 3.62 mmol, 5 eq) was metered in, and the reaction mixture was heated to 40° C. and stirred for 1 hour. Then the reaction solution was concentrated under reduced pressure, the residue was taken up in water and diethyl ether, and the phases were separated. The aqueous phase was acidified with 1 M HCl and extracted with ethyl acetate. The organic phase was dried over magnesium sulfate and concentrated under reduced pressure. Yield: 96% (0.23 g)

Synthesis of Amino Acid E-82

(R)-3-(3-Cyclopentyl-N-methylpropanamido)-2,3-dihydro-1H-indene-5-carboxylic acid (E-82)

(R)-Methyl 3-(3-cyclopentyl-N-methylpropanamido)-2,3-dihydro-1H-indene-5-carboxylate (B-80) (1.5 g, 4.56 mmol, 1.0 eq.) was dissolved in MeOH:THF:H$_2$O (1:1:1, 24 ml); LiOH H$_2$O (383 mg, 9.118 mmol, 2.0 eq.) was added at 0° C., and the mixture was stirred for 4 hours at RT. After monitoring by TLC, the reaction solution was concentrated under reduced pressure, and the residue was taken up in water (15 ml) and extracted with ethyl acetate (2×20 ml). The aqueous phase was adjusted to pH 1-2 with 3 M HCl solution and extracted with DCM (3×50 ml). The combined org. phases were washed with sat. NaCl solution (50 ml), dried over sodium sulfate and concentrated under reduced pressure, dried. The crude product was used in the next stage without being purified further. Yield: 83% (1.2 g, 0.415 mmol)

Synthesis of Amino Acid F-03

(R)-3-(2-Methylpropylsulfonamido)-2,3-dihydro-1H-indene-5-carboxylic acid (F-03)

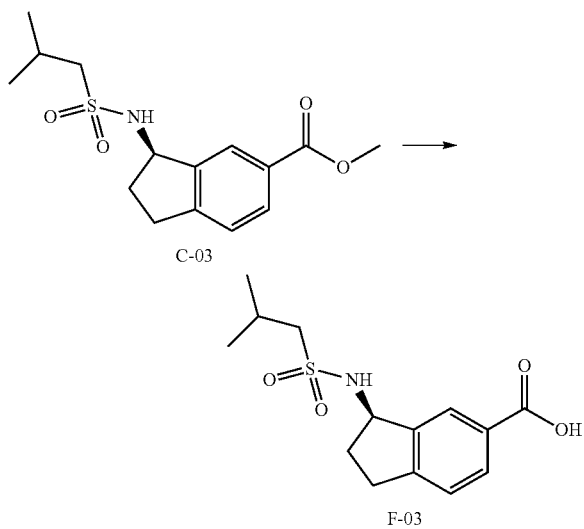

LiOH.H₂O (200 mg, 4.8 mmol, 3 eq) in water (3 ml) was added dropwise to a cooled (0° C.) solution of (R)-methyl 3-(2-methylpropylsulfonamido)-2,3-dihydro-1H-indene-5-carboxylate (C-03) (500 mg, 1.6 mmol, 1 eq) in MeOH:THF (1:1, 12 ml), and stirring was carried out for 6 h at RT. After monitoring by thin-layer chromatography, the reaction solution was concentrated under reduced pressure and the residue was taken up in water (50 ml), adjusted to pH 2 with 2M HCl solution and extracted with dichloromethane (2×80 ml). The combined organic phases were washed with sat. NaCl solution (40 ml), dried over sodium sulfate and concentrated and dried under reduced pressure. Yield: 450 mg Synthesis of Amino Acid G-01

(R)-3-(7-Chloro-1-oxoisoindolin-2-yl)-2,3-dihydro-1H-indene-5-carboxylic acid (G-01)

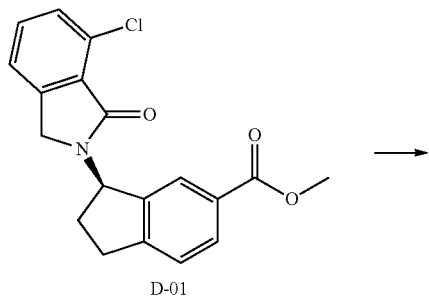

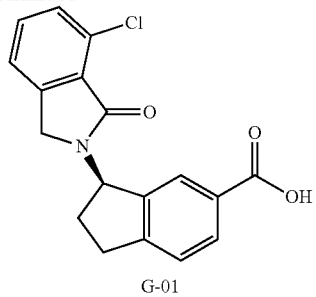

KOH (1 mol/l aq) (2 eq) was added to a suspension of (R)-methyl 3-(7-chloro-1-oxoisoindolin-2-yl)-2,3-dihydro-1H-indene-5-carboxylate (D-01) (0.42 mmol, 1 eq) in a mixture of ethanol (4 ml) and water (1.6 ml). The reaction mixture was stirred overnight at RT. Ethanol was removed in vacuo, and the residue was taken up in diethyl ether and water. The phases were separated, and the aqueous phase was adjusted to pH 3 with 1N HCl. The aqueous phase was extracted with ethyl acetate (3×) and the combined organic phases were dried over sodium sulfate. After concentration, the desired product (R)-3-(7-chloro-1-oxoisoindolin-2-yl)-2,3-dihydro-1H-indene-5-carboxylic acid (G-01) was obtained. Yield: 82%

Synthesis of Amino Acid G-05

(R)-4-(7-Chloro-1-oxoisoindolin-2-yl)-8-fluorochromane-6-carboxylic acid (G-05)

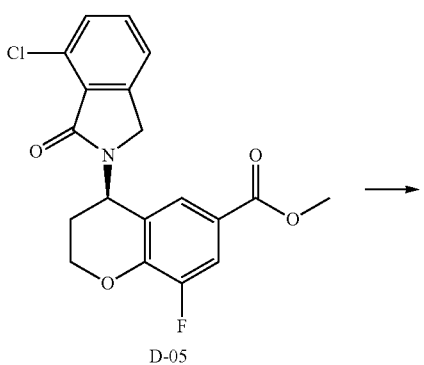

KOH (1 mol/l aq) (2 eq) was added to a suspension of (R)-methyl 4-(7-chloro-1-oxoisoindolin-2-yl)-8-fluorchromane-6-carboxylate (D-05) (0.8 mmol, 1 eq) in a mixture of ethanol (4.6 ml) and water (1.6 ml). The reaction mixture was stirred overnight at RT. Ethanol was removed in vacuo and the residue was taken up in diethyl ether and water. The phases were separated and the aqueous phase was adjusted to pH 3 with 1N HCl. The aqueous phase was extracted with ethyl acetate (3×) and the combined organic phases were dried over sodium sulfate and concentrated under reduced pressure. The crude product was purified by column chromatography (silica gel, ethyl acetate:cyclohexane 1:1). Yield: 62%

B. Amine Structural Units

Overview: Amine Structural Units

| No. | Structure | Amine (AMN) |
|---|---|---|
| AMN-01 | 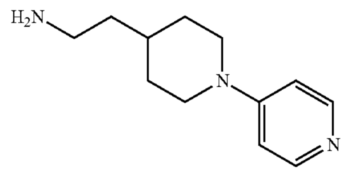 [SMILES: NCCC1CCN(c2ccncc2)CC1] | 2-(1-(Pyridin-4-yl)piperidin-4-yl)ethanamine (AMN-01) see below |
| AMN-03 | 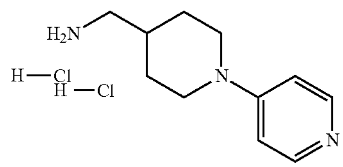 | (1-(Pyridin-4-yl)piperidin-4-yl)methanamine dihydrochloride (AMN-03) see below |
| AMN-04 | 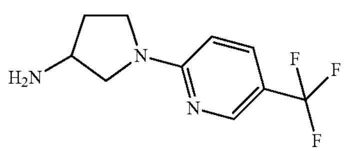 [SMILES: NC1CCN(c2ccc(C(F)(F)F)cn2)C1] | 1-(5-(Trifluoromethyl)pyridin-2-yl)pyrrolidin-3-amine (AMN-04) commercially available from Anthem (Chinglu) (Order No. M1028) |
| AMN-06 | 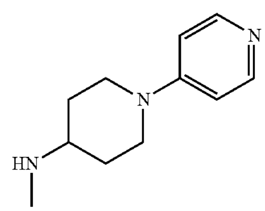 | N-Methyl-1-(pyridin-4-yl)piperidin-4-amine (AMN-06) commercially available from UkrOrgSynthesis (Order No. BBV-5632152) Synthesis-see below |
| AMN-07 | 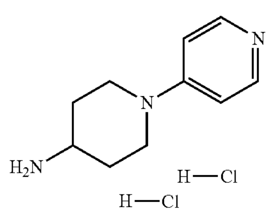 | 1-(Pyridin-4-yl)piperidin-4-amine dihydrochloride (AMN-07) commercially available from ABCR (Order No. AB171113) |
| AMN-09 | 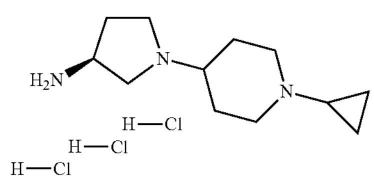 | (S)-1-(1-Cyclopropylpiperidin-4-yl)pyrrolidin-3-amine trihydrochloride (AMN-09) see below |
| AMN-10 | 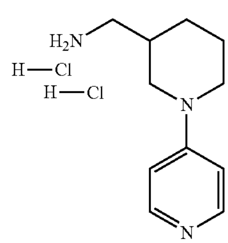 | (1-(Pyridin-4-yl)piperidin-3-yl)methanamine dihydrochloride (AMN-10) see below |

-continued

| No. | Structure | Amine (AMN) |
|---|---|---|
| AMN-13 | 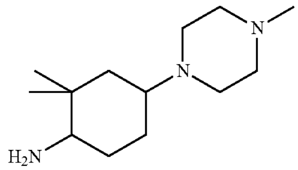 | 2,2-Dimethyl-4-(4-methylpiperazin-1-yl)cyclohexanamine (AMN-13)<br>see below |
| AMN-14 | 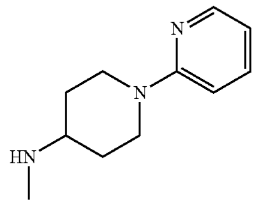 | N-Methyl-1-(pyridin-2-yl)piperidin-4-amine (AMN-14)<br>commercially available from UkrOrgSynthesis<br>(Order No.: BBV-32060162) |
| AMN-15 | 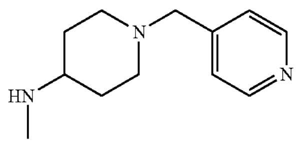 | N-Methyl-1-(pyridin-4-ylmethyl)piperidin-4-amine (AMN-15)<br>commercially available from UkrOrgSynthesis<br>(Order No.: BBV-29386844) |
| AMN-16 | 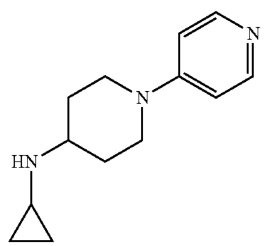 [SMILES: c1cc(N2CCC(NC3CC3)CC2)ccn1] | N-Cyclopropyl-1-(pyridin-4-yl)piperidin-4-amine (AMN-16)<br>commercially available from UkrOrgSynthesis<br>(Order No.: BBV-5632149) |
| AMN-17 | 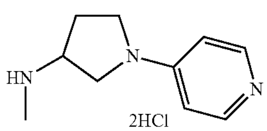 | N-Methyl-1-(pyridin-4-yl)pyrrolidin-3-amine dihydrochloride (AMN-17)<br>see below |
| AMN-18 | 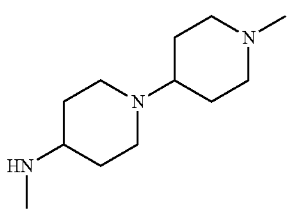 | N,1'-Dimethyl-1,4'-bipiperidin-4-amine (AMN-18)<br>commercially available from UkrOrgSynthesis<br>(Order No.: BBV-15972202) |
| AMN-19 | 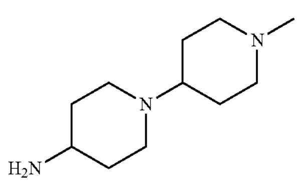 | 1'-Methyl-1,4'-bipiperidin-4-amine (AMN-19)<br>commercially available from UkrOrgSynthesis<br>(Order No.: BBV-25471444) |
| AMN-20 | 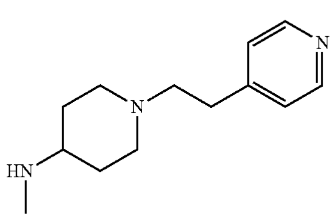 [SMILES: CNC1CCN(CCc2ccncc2)CC1] | N-Methyl-1-(2-(pyridin-4-yl)ethyl)piperidin-4-amine (AMN-20)<br>commercially available from UkrOrgSynthesis<br>(Order No.: BBV-32067238) |

| No. | Structure | Amine (AMN) |
|---|---|---|
| AMN-21 | (structure) HCl | N-Methyl-1-((2-(pyrrolidin-1-yl)pyridin-4-yl)methyl)piperidin-4-amine hydrochloride (AMN-21) see below |
| AMN-22 | (structure) 2xHCl | N-Methyl-1-(1-(2-methylpyridin-4-yl)piperidin-4-yl)methanamine dihydrochloride (AMN-22) Yield: >99% The synthesis was carried out analogously to AMN-17[a]. |
| AMN-23 | (structure) | 1-(4-Methoxyphenyl)-N-methylpiperidin-4-amine (AMN-23) commercially available from UkrOrgSynthesis (Order No.: BBV-15957763) |
| AMN-24 | (structure) | 1-(4-Chlorophenyl)-N-methylpiperidin-4-amine (AMN-24) commercially available from UkrOrgSynthesis (Order No.: BBV-29452985) |
| AMN-25 | (structure) 2HCl | N-Methyl-1-(2-methylpyridin-4-yl)piperidin-4-amine dihydrochloride (AMN-25) Yield: >99% The synthesis was carried out analogously to AMN-17[a]. |
| AMN-26 | (structure) HCl | 2-(1-(2-Methylpyridin-4-yl)piperidin-4-yl)ethanamine hydrochloride (AMN-26) Yield: >99% The synthesis was carried out analogously to AMN-17[a]. |
| AMN-27 | (structure) | 1-(2,6-Dimethylpyrimidin-4-yl)-N-methylpiperidin-4-amine (AMN-27) commercially available from UkrOrgSynthesis (Order No.: BBV-32124101) |

| No. | Structure | Amine (AMN) |
|---|---|---|
| AMN-28 | 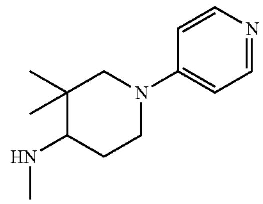 [SMILES: CNC1CCN(c2ccncc2)CC1(C)C] | N,3,3-Trimethyl-1-(pyridin-4-yl)piperidin-4-amine (AMN-28)<br>see below |
| AMN-29 | 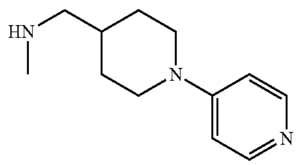 | N-Methyl-1-(1-(pyridin-4-yl)piperidin-4-yl)methanamine (AMN-29)<br>see below |
| AMN-30 | 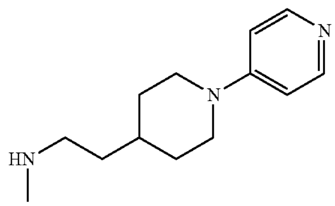 [SMILES: CNCCC1CCN(c2ccncc2)CC1] | N-Methyl-2-(1-(pyridin-4-yl)piperidin-4-yl)ethanamine (AMN-30) |
| AMN-31 | 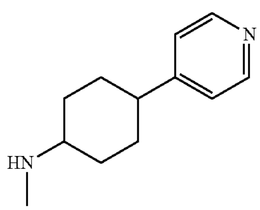 | N-Methyl-4-(pyridin-4-yl)cyclohexanamine (AMN-31)<br>see below |
| AMN-32 | 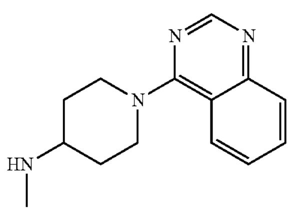 [SMILES: CNC1CCN(c2ncnc3ccccc23)CC1] | N-Methyl-1-(quinazolin-4-yl)piperidin-4-amine (AMN-32)<br>commercially available from BCH Research (Order No.: BCH 305321) |
| AMN-33 | 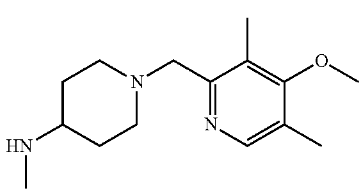 [SMILES: CNC1CCN(Cc2ncc(C)c(OC)c2C)CC1] | 1-((4-Methoxy-3,5-dimethylpyridin-2-yl)methyl)-N-methylpiperidin-4-amine (AMN-33)<br>commercially available from BCH Research (Order No.: BCH 270822) |
| AMN-34 | 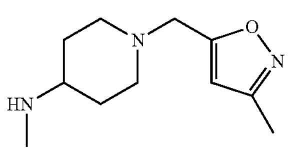 | N-Methyl-1-((3-methylisoxazol-5-yl)methyl)piperidin-4-amine (AMN-34)<br>commercially available from UkrOrgSynthesis (Order No.: BBV-33571853) |
| AMN-35 | 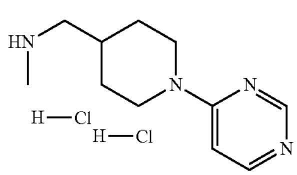 | N-Methyl-1-(1-(pyrimidin-4-yl)piperidin-4-yl)methanamine dihydrochloride (AMN-35)<br>see below |

-continued

| No. | Structure | Amine (AMN) |
|---|---|---|
| AMN-36 | 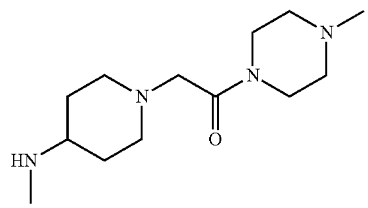 [SMILES: CNC1CCN(CC(=O)N2CCN(C)CC2)CC1] | 2-(4-(Methylamino)piperidin-1-yl)-1-(4-methylpiperazin-1-yl)ethanone (AMN-36) commercially available from BCH Research (Order No.: BCH 270816) |
| AMN-37 | 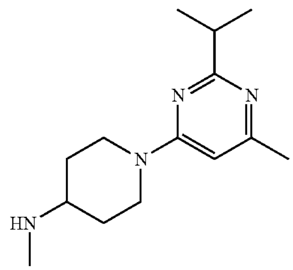 [SMILES: CNC1CCN(c2cc(C)nc(C(C)C)n2)CC1] | 1-(2-Isopropyl-6-methylpyrimidin-4-yl)-N-methylpiperidin-4-amine (AMN-37) commercially available from FCH Group Company (Order No.: FCH 305762) |
| AMN-38 | 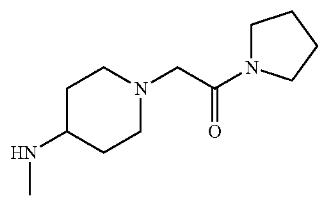 [SMILES: CNC1CCN(CC(=O)N2CCCC2)CC1] | 2-(4-(Methylamino)piperidin-1-yl)-1-(pyrrolidin-1-yl)ethanone (AMN-38) commercially available from UkrOrgSynthesis (Order No.: BBV-29386906) |
| AMN-39 | 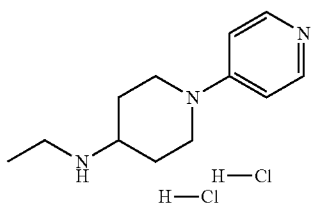 | N-Ethyl-1-(pyridin-4-yl)piperidin-4-amine dihydrochloride (AMN-39) Yield: 83%* The synthesis was carried out analogously to AMN-35. |
| AMN-40 | 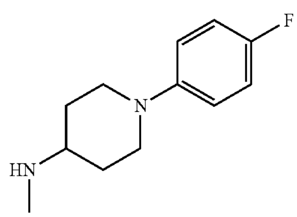 | 1-(4-Fluorophenyl)-N-methylpiperidin-4-amine (AMN-40) commercially available from UkrOrgSynthesis (Order No.: BBV-15958191) |
| AMN-41 | 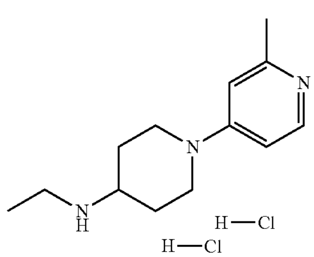 | N-Ethyl-1-(2-methylpyridin-4-yl)piperidin-4-amine dihydrochloride (AMN-41) Yield: 99%* The synthesis was carried out analogously to AMN-35. |
| AMN-42 | 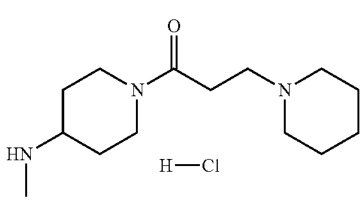 | 1-(4-(Methylamino)piperidin-1-yl)-3-(piperidin-1-yl)propan-1-one hydrochloride (AMN-42) see below |

-continued

| No. | Structure | Amine (AMN) |
|---|---|---|
| AMN-43 | 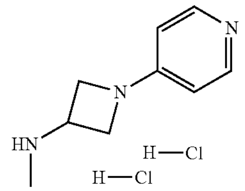 | N-Methyl-1-(pyridin-4-yl)azetidin-3-amine dihydrochloride (AMN-43)<br>Yield: 91%*<br>The synthesis was carried out analogously to AMN-35. |
| AMN-44 | 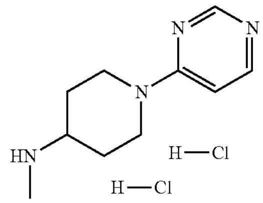 | N-Methyl-1-(pyrimidin-4-yl)piperidin-4-amine dihydrochloride (AMN-44)<br>see below |
| AMN-45 | 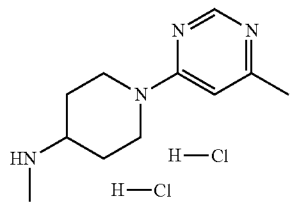 | N-Methyl-1-(6-methylpyrimidin-4-yl)piperidin-4-amine dihydrochloride (AMN-45)<br>commercially available from UkrOrgSynthesis (Order No.: BBV-32576980) |
| AMN-46 | 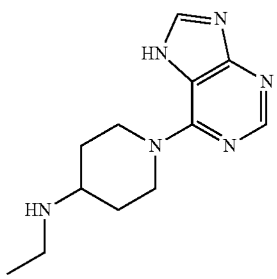 [SMILES: CCNC1CCN(c2ncnc3nc[nH]c23)CC1] | N-Ethyl-1-(7H-purin-6-yl)piperidin-4-amine (AMN-46)<br>commercially available from FCH Group Company (Order No.: FCH305767) |
| AMN-47 | 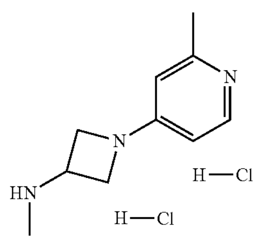 | N-Methyl-1-(2-methylpyridin-4-yl)azetidin-3-amine dihydrochloride (AMN-47)<br>see below |
| AMN-48 | 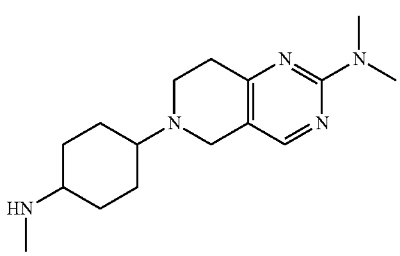 [SMILES: CNC1CCC(N2CCc3nc(N(C)C)ncc3C2)CC1] | N,N-Dimethyl-6-(4-(methylamino)cyclohexyl)-5,6,7,8-tetrahydropyrido[4,3-d]pyrimidin-2-amine (AMN-48)<br>see below |
| AMN-49 | 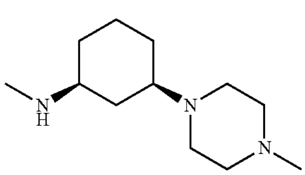 | (1S,3R)-N-Methyl-3-(4-methylpiperazin-1-yl)cyclohexanamine (AMN-49)<br>see below |

| No. | Structure | Amine (AMN) |
|---|---|---|
| AMN-50 | 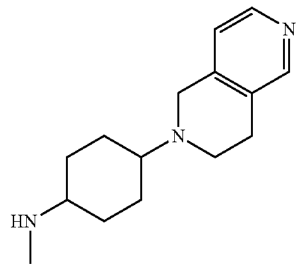 [SMILES: CNC1CCC(N2CCc3cnccc3C2)CC1] | 4-(3,4-Dihydro-2,6-naphthyridin-2(1H)-yl)-N-methylcyclohexanamine (AMN-50)<br>see below |
| AMN-51 | 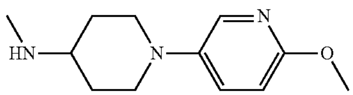 | 1-(6-Methoxypyridin-3-yl)-N-methylpiperidin-4-amine (AMN-51)<br>see below |
| AMN-52 | 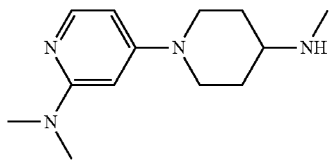 | N,N-Dimethyl-4-(4-(methylamino)piperidin-1-yl)pyridin-2-amine (AMN-52)<br>see below |
| AMN-53 | 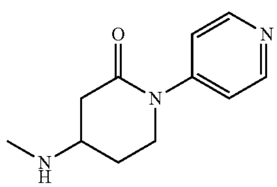 | 4-(Methylamino)-1-(pyridin-4-yl)piperidin-2-one (AMN-53)<br>see below |
| AMN-54 | 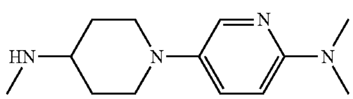 | N,N-Dimethyl-5-(4-(methylamino)piperidin-1-yl)pyridin-2-amine (AMN-54)<br>see below |
| AMN-55 | 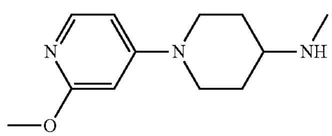 | 1-(2-Methoxypyridin-4-yl)-N-methylpiperidin-4-amine (AMN-55)<br>see below |
| AMN-56 | 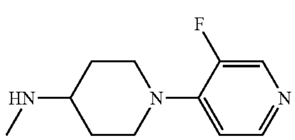 | 1-(3-Fluoropyridin-4-yl)-N-methylpiperidin-4-amine (AMN-56)<br>The synthesis was carried out starting from 4-bromo-2-pyrrolidin-1-yl-pylridine analogously to AMN-54. |
| AMN-57 | 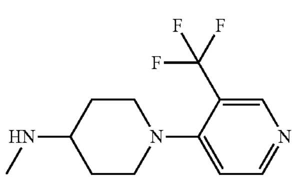 [SMILES: CNC1CCN(c2ccncc2C(F)(F)F)CC1] | N-Methyl-1-(3-(trifluoromethyl)pyridin-4-yl)piperidin-4-amine (AMN-57)<br>The synthesis was carried out starting from 4-chloro-3-(trifluoromethyl)pyridine hydrochloride analogously to AMN-54. |
| AMN-58 | 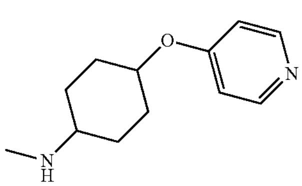 | N-Methyl-4-(pyridin-4-yloxy)cyclohexanamine (AMN-58)<br>see below |

-continued

| No. | Structure | Amine (AMN) |
|---|---|---|
| AMN-59 | 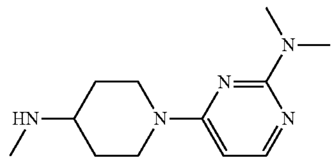 | N,N-Dimethyl-4-(4-(methylamino)piperidin-1-yl)pyrimidin-2-amine (AMN-59)<br>The synthesis was carried out starting from 4-bromo-2-(N,N-dimethylamino)pyrimidine analogously to AMN-54. |
| AMN-60 | 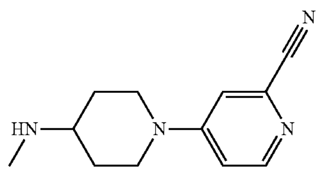 [SMILES: CNC1CCN(c2ccnc(C#N)c2)CC1] | 4-(4-(Methylamino)piperidin-1-yl)picolinonitrile (AMN-60)<br>see below |
| AMN-61 | 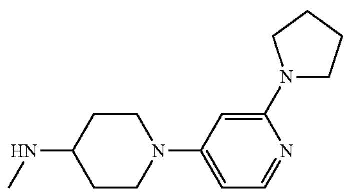 [SMILES: CNC1CCN(c2ccnc(N3CCCC3)c2)CC1] | N-Methyl-1-(2-(pyrrolidin-1-yl)pyridin-4-yl)piperidin-4-amine (AMN-61)<br>The synthesis was carried out starting from 4-chloro-2-methylpyrimidine analogously to AMN-54. |
| AMN-62 | 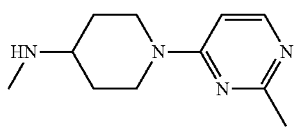 | N-Methyl-1-(2-methylpyrimidin-4-yl)piperidin-4-amine (AMN-62)<br>The synthesis was carried out starting from 4-bromo-3-fluoropyridine analogously to AMN-54. |
| AMN-63 | 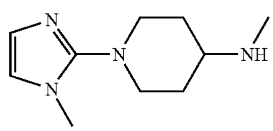 | N-Methyl-1-(1-methyl-1H-imidazol-2-yl)piperidin-4-amine (AMN-63)<br>see below |
| AMN-64 | 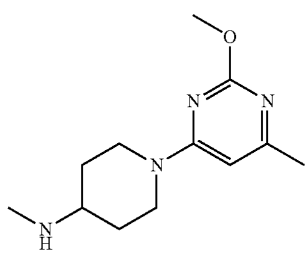 | 1-(2-Methoxy-6-methylpyrimidin-4-yl)-N-methylpiperidin-4-amine (AMN-64)<br>see below |
| AMN-65 | 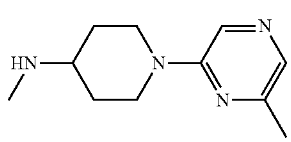 | N-Methyl-1-(6-methylpyrazin-2-yl)piperidin-4-amine (AMN-65)<br>see below |
| AMN-67 | 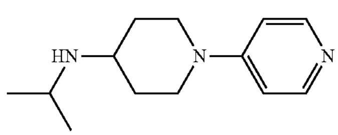 [SMILES: CC(C)NC1CCN(c2ccncc2)CC1] | N-Isopropyl-1-(pyridin-4-yl)piperidin-4-amine (AMN-67)<br>see below |
| AMN-68 | 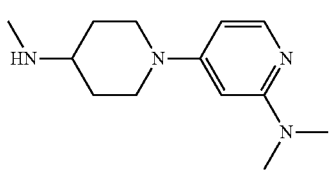 | N,N-Dimethyl-4-(4-(methylamino)cyclohexyl)pyridin-2-amine (AMN-68)<br>see below |

| No. | Structure | Amine (AMN) |
|---|---|---|
| AMN-69 | 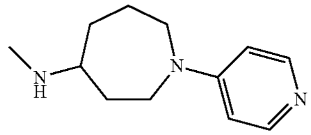 | N-Methyl-1-(pyridin-4-yl)azepan-4-amine (AMN-69) see below |
| AMN-70 | 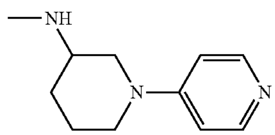 | N-Methyl-1-(pyridin-4-yl)piperidin-3-amine (AMN-70) see below |
| AMN-71 | 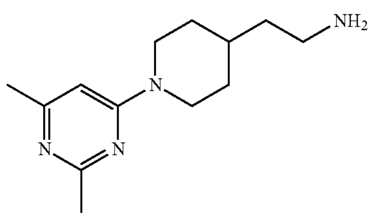 [SMILES: Cc1cc(N2CCC(CCN)CC2)nc(C)n1] | 2-(1-(2,6-Dimethylpyrimidin-4-yl)piperidin-4-yl)ethanamine (AMN-71) see below |
| AMN-72 | 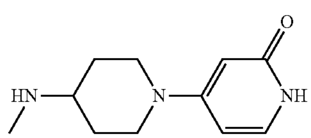 | 4-(4-(Methylamino)piperidin-1-yl)pyridin-2(1H)-one (AMN-72) see below |
| AMN-73 | 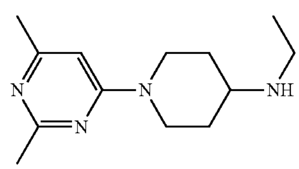 [SMILES: CCNC1CCN(c2cc(C)nc(C)n2)CC1] | 1-(2,6-Dimethylpyrimidin-4-yl)-N-ethylpiperidin-4-amine (AMN-73) see below |

(a)No solid precipitated, therefore the reaction mixture was concentrated completely. The residue was taken up in dichloromethane (2 × 30 ml), the solvent was concentrated and the product was dried in vacuo. Yield of the last stage Synthesis of amine AMN-01

2-(1-(Pyridin-4-yl)piperidin-4-yl)ethanamine (AMN-01)

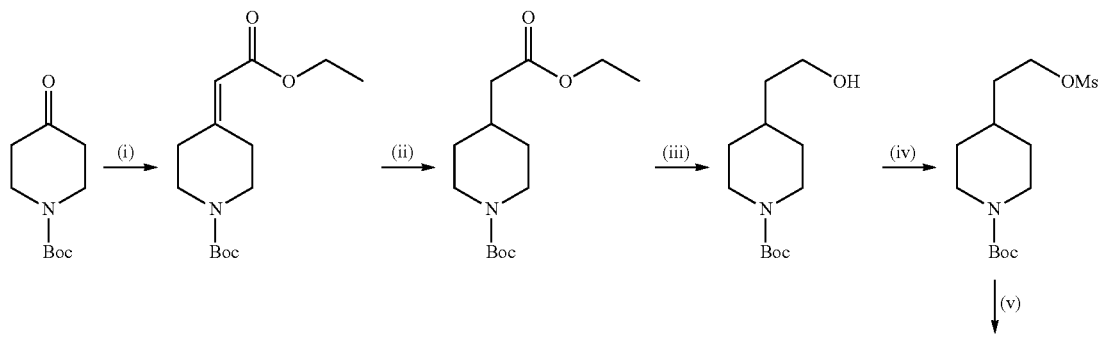

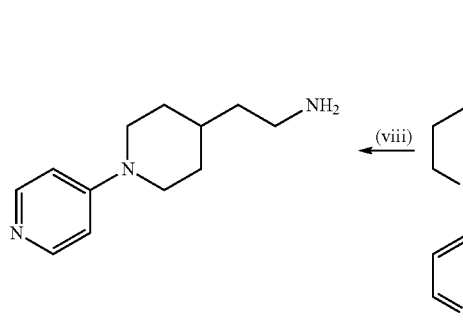

Stage (i): tert-Butyl 4-(2-ethoxy-2-oxoethylidene) piperidine-1-carboxylate

A solution of tert-butyl 4-oxopiperidine-1-carboxylate (10.0 g, 50.25 mmol, 1 eq) in THF (50 ml) was slowly added dropwise to an ice-cold (0° C.) suspension of NaH (1.56 g, 65.32 mmol, 1.3 eq) in THF (50 ml), and stirring was carried out for 30 min. Triethyl phosphonoacetate (12.96 ml, 65.32 mmol, 1.3 eq), dissolved in THF (50 ml), was added and stirring was carried out for 2 h at RT. The reaction mixture was hydrolyzed with water (5 ml) and concentrated. The residue was taken up in water (150 ml) and extracted with ethyl acetate (2×300 ml). The combined organic phases were washed with sat. NaCl solution (200 ml), dried over sodium sulfate and concentrated under reduced pressure. After purification by column chromatography (silica gel, 3% ethyl acetate in hexane), the desired product was obtained in the form of a white solid. Yield: 78% (10.5 g, 39.03 mmol).

Stage (ii): tert-Butyl 4-(2-ethoxy-2-oxoethyl)piperidine-1-carboxylate tert-Butyl 4-(2-ethoxy-2-oxoethylidene)piperidine-1-carboxylate (5.0 g, 18.58 mmol, 1 eq) was dissolved in ethanol (20 ml) and degassed for 30 min with argon. Pd—C (500 mg, 10%) was added and hydrogenation was carried out for 12 h at RT under balloon pressure ($H_2$). After monitoring by thin-layer chromatography, the reaction mixture was filtered off over Celite and washed with ethanol (200 ml), and the filtrate was concentrated under reduced pressure. Yield: 89% (4.5 g, 16.6 mmol).

Stage (iii): tert-Butyl 4-(2-hydroxyethyl)piperidine-1-carboxylate

LAH (819 mg, 21.58 mmol, 1.3 eq) was placed in THF (50 ml) at 0° C.; a solution of tert-butyl 4-(2-ethoxy-2-oxoethyl)piperidine-1-carboxylate (4.5 g, 16.60 mmol, 1 eq) in THF (50 ml) was added dropwise and then stirring was carried out for 1 h at RT. After monitoring by thin-layer chromatography, the reaction mixture was hydrolyzed with sat. sodium sulfate solution (2 ml), filtered over Celite and washed with THF (300 ml). The filtrate was concentrated under reduced pressure and a colourless oil was obtained, which was used in the next stage without being purified and analyzed further. Yield: 92% (3.5 g, 15.28 mmol).

Stage (iv): tert-Butyl 4-(2-(methylsulfonyloxy)ethyl)piperidine-1-carboxylate Methanesulfonic acid chloride (2.5 ml, 32.7 mmol, 1.5 eq) was added to an ice-cooled (0° C.) solution of tert-butyl 4-(2-hydroxyethyl)piperidine-1-carboxylate (5.0 g, 21.8 mmol, 1 eq) and triethylamine (6 ml, 43.6 mmol, 2 eq) in dichloromethane (30 ml), and stirring was carried out for 1 h at RT. After monitoring by thin-layer chromatography, the reaction mixture was diluted with dichloromethane (100 ml), washed with water and sat. NaCl solution (in each case 50 ml), dried over sodium sulfate and concentrated under reduced pressure. A yellow oil was obtained, which was used in the next step without being purified further.

Stage (v): tert-Butyl 4-(2-(dibenzylamino)ethyl)piperidine-1-carboxylate

Dibenzylamine (4.1 ml, 21.24 mmol, 1 eq) was added to a solution of tert-butyl 4-(2-(methyl-sulfonyloxy)ethyl)piperidine-1-carboxylate (6.5 g, 21.24 mmol, 1 eq) and triethylamine (3.2 ml, 23.36 mmol, 1.1 eq) in toluene (100 ml), and refluxing was carried out for 72 h. Then the reaction solution was concentrated and the residue was taken up in dichloromethane (300 ml), washed with water and sat. NaCl solution (in each case 100 ml), dried over sodium sulfate and concentrated under reduced pressure. After purification by column chromatography (silica gel, 5% ethyl acetate in hexane), a yellow solid was obtained. Yield: 67% (5.8 g, 14.21 mmol).

Stage (vi): N,N-Dibenzyl-2-(piperidin-4-yl)ethanamine tert-Butyl 4-(2-(dibenzylamino)ethyl)piperidine-1-carboxylate (5.0 g, 12.25 mmol, 1 eq) was dissolved in dichloromethane (100 ml) and cooled to 0° C. TFA (25 ml) was added dropwise at that temperature and then stirring was carried out for 1 h at RT. After monitoring by thin-layer chromatography, the reaction mixture was concentrated under reduced pressure. The crude product was used in the next stage without being purified further.

Stage (vii): N,N-Dibenzyl-2-(1-(pyridin-4-yl)piperidin-4-yl)ethanamine

N,N-Dibenzyl-2-(piperidin-4-yl)ethanamine (2.4 g, 7.79 mmol, 1 eq) and 4-bromopyridine HBr (1.97 g, 10.12 mmol, 1.3 eq) were dissolved in n-butanol (30 ml) and DIPEA (3.3 ml, 19.47 mmol, 2.5 eq) and the mixture was refluxed for 48 h. After monitoring by thin-layer chromatography, the reaction solution was concentrated under reduced pressure and the residue was taken up in dichloromethane (100 ml), washed with water and sat. NaCl solution (in each case 50 ml), dried over sodium sulfate and concentrated under reduced pressure. After purification by column chromatography (silica gel, 3.5% MeOH in dichloromethane), a white solid was obtained. Yield: 53% (1.6 g, 4.15 mmol).

Stage (viii): 2-(1-(Pyridin-4-yl)piperidin-4-yl)ethanamine (AMN-01)

N,N-Dibenzyl-2-(1-(pyridin-4-yl)piperidin-4-yl)ethanamine (1.4 g, 3.63 mmol, 1 eq) was dissolved in ethanol (80 ml) and degassed for 30 min with nitrogen. 20% Pd(OH)$_2$ (800 mg) was added and hydrogenation was carried out for 48 h at RT under balloon pressure (H$_2$). After monitoring by thin-layer chromatography, the reaction mixture was filtered off over Celite and washed with ethanol (200 ml), and the filtrate was reduced under reduced pressure. Yield: 94% (700 mg, 3.41 mmol).

Synthesis of Amine AMN-03

(1-(Pyridin-4-yl)piperidin-4-yl)methanamine dihydrochloride (AMN-03)

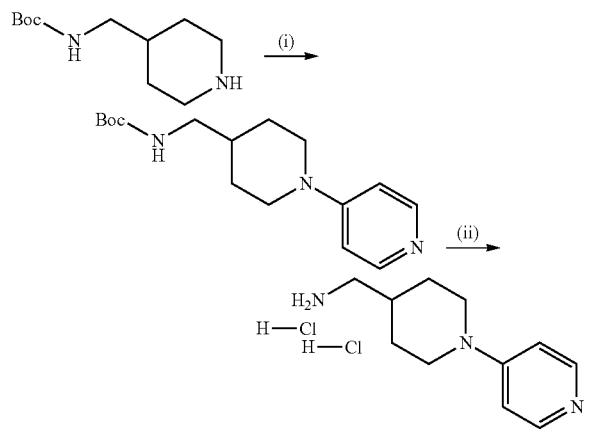

Stage (i): tert-Butyl (1-(pyridin-4-yl)piperidin-4-yl)methylcarbamate

Potassium carbonate (3 eq), L-proline (0.4 eq), CuI (0.2 eq) and 4-bromopyridine (1 eq) were added under a protecting gas atmosphere to a solution of tert-butyl piperidin-4-ylmethyl-carbamate (3 g, 15 mmol) in DMSO. The reaction mixture was heated for 20 h at 100° C. After cooling to room temperature, the mixture was diluted with ethyl acetate and sat. sodium chloride solution and filtered over Celite, and the residue was then washed with ethyl acetate. The phases were separated, dried and concentrated under reduced pressure. The crude product was purified by column chromatography. Yield: 30%

Stage (ii): (1-(Pyridin-4-yl)piperidin-4-yl)methanamine dihydrochloride (AMN-03)

tert-Butyl (1-(pyridin-4-yl)piperidin-4-yl)methylcarbamate (7 g, 24.4 mmol) was dissolved in methanol and cooled in an ice bath; acetyl chloride (8.6 ml, 121.8 mmol) was added and stirring was carried out for 3 h at room temperature. The solvent was removed under reduced pressure and the residue was taken up in water/dichloromethane. The phases were separated, and the aqueous phase was washed with dichloromethane (2×) and dried by freeze drying. Yield: quantitative Synthesis of Amine AMN-06

N-Methyl-1-(pyridin-4-yl)piperidin-4-amine (AMN-06)

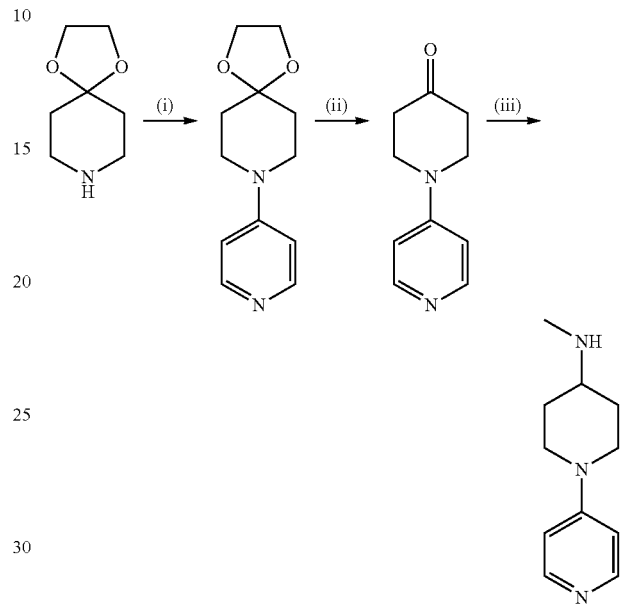

Stage (i): 8-(Pyridin-4-yl)-1,4-dioxa-8-azaspiro[4.5]decane 1,4-Dioxa-8-azaspiro[4.5]decane (10.0 g, 69.9 mmol, 1 eq) and 4-bromopyridine hydrochloride (16.2 g, 83.7 mmol, 1.2 eq) were dissolved in n-butanol (120 ml) and DIPEA (23 ml, 139.8 mmol, 2 eq) and refluxed for 14 h. After monitoring by thin-layer chromatography, the reaction solution was concentrated under reduced pressure. After purification by column chromatography (silica gel, 3% MeOH in dichloromethane), the desired product was obtained in the form of a white solid. Yield: 58% (9.0 g, 40.9 mmol).

Stage (ii): 1-(Pyridin-4-yl)piperidin-4-one 8-(Pyridin-4-yl)-1,4-dioxa-8-azaspiro[4.5]decane was dissolved at 0° C. in ice-cooled concentrated HCl (6 ml) and stirred for 10 min. After monitoring by thin-layer chromatography, the reaction mixture was adjusted to pH 10-12 with 2 M NaOH and extracted with chloroform (3×100 ml). The combined organic phases were washed with sat. NaCl solution (in each case 50 ml), dried over sodium sulfate and concentrated under reduced pressure. The product so obtained was used in the next stage without being purified further.

Stage (iii): N-Methyl-1-(pyridin-4-yl)piperidin-4-amine

Acetic acid (150 μl) was added to a solution of 1-(pyridin-4-yl)piperidin-4-one (450 mg, 2.55 mmol, 1 eq) and methylamine hydrochloride (190 mg, 2.81 mmol, 1.1 eq) in methanol (10 ml), and stirring was carried out for 20 min at RT. Then NaBH₃CN (166 mg, 2.81 mmol, 1.1 eq) was added in portions and stirring was carried out for 16 h at RT. The solvent was concentrated, and the residue was taken up in chloroform (100 ml), washed with sat. K₂CO₃ solution (30 ml) and sat. NaCl solution (30 ml), dried over sodium sulfate and concentrated under reduced pressure. The product (yellow solid) was used in the next stage without being purified further. Yield: 82% (400 mg, 2.09 mmol).

Synthesis of Amine AMN-09

(S)-1-(1-Cyclopropylpiperidin-4-yl)pyrrolidin-3-amine trihydrochloride (AMN-09)

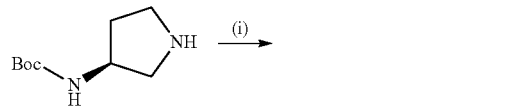

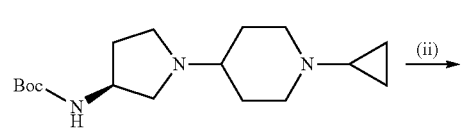

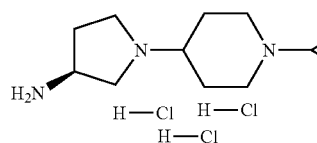

Stage (i): (S)-tert-Butyl 1-(1-cyclopropylpiperidin-4-yl)pyrrolidin-3-ylcarbamate Sodium triacetoxyborohydride (2.874 mmol, 1.07 eq) was added to a solution of (3S)-(−)-(tert-butoxycarbonylamino)pyrrolidine (0.5 g, 2.686 mmol, 1 eq) and 1-cyclopropylpiperidin-4-one (3.062 mmol, 1.14 eq) in dichloromethane (17 ml) and acetic acid (0.25 ml). The resulting reaction mixture was stirred for 16 h at RT. Then 2 N NaOH solution was added and the aqueous phase was extracted with dichloromethane (3×20 ml). The combined organic phases were extracted with sat. NaCl solution, dried over magnesium sulfate and concentrated under reduced pressure. After purification by column chromatography (silica gel, ethyl acetate:ethanol, 10:1), the desired product was obtained. Yield: 98% (0.81 g).

Stage (i): (S)-1-(1-Cyclopropylpiperidin-4-yl)pyrrolidin-3-amine trihydrochloride (AMN-09)

(S)-tert-Butyl 1-(1-cyclopropylpiperidin-4-yl)pyrrolidin-3-ylcarbamate (0.87 g, 2.282 mmol) was dissolved in methanol (4.6 ml), and HCl in methanol (1.25 M, 9.1 ml) was added. The reaction mixture was heated for 3 h at 50° C. and then stirred overnight at RT. The resulting precipitate was filtered off. The filtrate was concentrated to half, and diethyl ether was added. The resulting precipitate was filtered off again. Yield: >99% (0.72 g).

Synthesis of Amine AMN-10

(1-(Pyridin-4-yl)piperidin-3-yl)methanamine dihydrochloride (AMN-10)

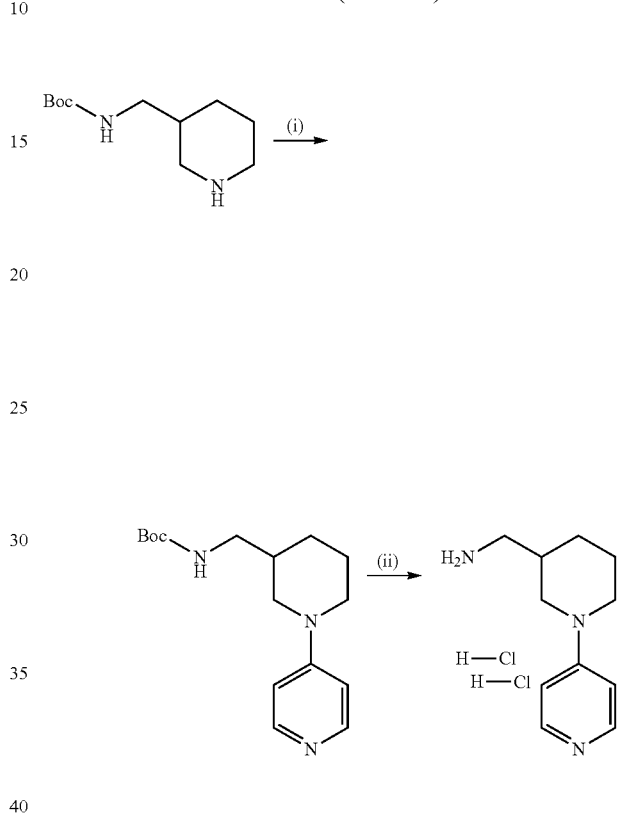

Stage (i): tert-Butyl (1-(pyridin-4-yl)piperidin-3-yl)methylcarbamate (+/−)-3-(Boc-aminomethyl)piperidine (500 mg, 2.335 mmol, 1 eq) and 4-chloropyridine hydrochloride (7.01 mmol, 3 eq) were dissolved in 2-propanol (4.5 ml) and DIPEA (9.4 mmol, 4 eq) and refluxed for 16 h. After monitoring by thin-layer chromatography, the reaction solution was diluted with sat. NaHCO₃ solution and extracted with ethyl acetate (4×20 ml). The combined org. phases were washed with sat. NaCl solution, dried over magnesium sulfate and concentrated. The crude product was purified by column chromatography (silica gel, ethyl acetate:ethanol 10:1+ammonia (25% aq)). Yield: 53%.

Stage (ii): (1-(Pyridin-4-yl)piperidin-3-yl)methanamine dihydrochloride (AMN-10)

tert-Butyl (1-(pyridin-4-yl)piperidin-3-yl)methylcarbamate (0.35 g, 1.2 mmol, 1 eq) was dissolved in ethanol (4 ml), and acetyl chloride (0.42 ml, 6.0 mmol, 5 eq) was added, while cooling with ice. The reaction solution was stirred for 12 h at RT and then diluted with diethyl ether (20 ml). The resulting white solid was filtered off and dried in vacuo. Yield: 79%.

241

Synthesis of Amine AMN-13

2,2-Dimethyl-4-(4-methylpiperazin-1-yl)cyclohexanamine (AMN-13)

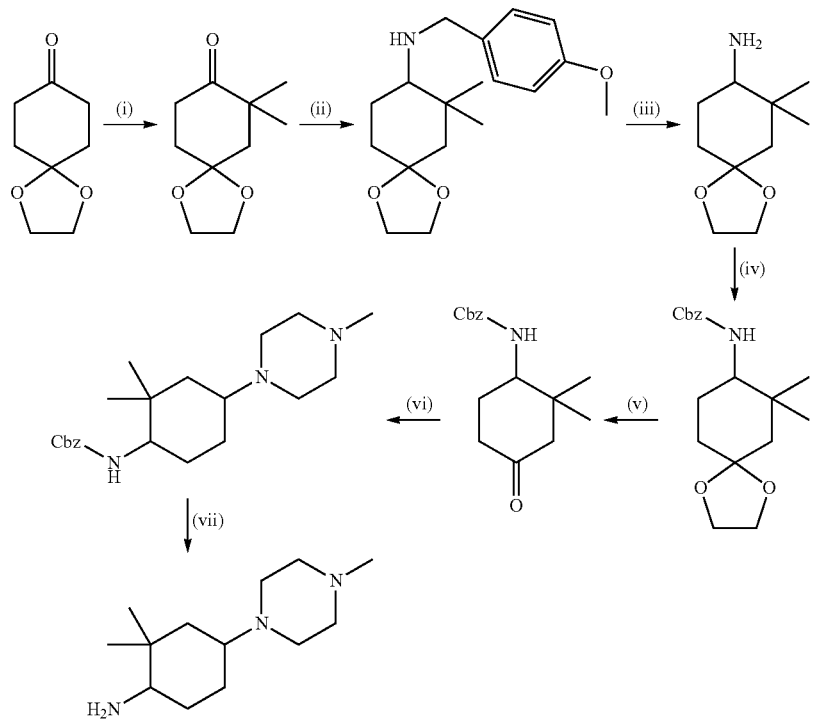

Stage (i):
7,7-Dimethyl-1,4-dioxaspiro[4.5]decan-8-one

A solution of Bu$^t$OK (39.0 g, 352.157 mmol, 2.2 eq) in THF (250 ml) was added dropwise at 0° C. to a solution of 1,4-dioxaspiro[4.5]decan-8-one (25 g, 160.7 mmol, 1 eq) in THF (500 ml). Then methyl iodide (60 ml, 960.43 mmol, 6 eq) was added dropwise at 0° C. and stirring was carried out for 16 h at RT. The reaction mixture was filtered off over Celite, and the filtrate was concentrated under reduced pressure and then purified by column chromatography (silica gel, 3% ethyl acetate in hexane). The desired product was obtained in the form of a light-yellow oil. Yield: 21% (6.18 g, 33.58 mmol).

Stage (ii): N-(4-Methoxybenzyl)-7,7-dimethyl-1,4-dioxaspiro[4.5]decan-8-amine 7,7-Dimethyl-1,4-dioxaspiro[4.5]decan-8-one (2.8 g, 15.217 mmol, 1 eq) and 4-methoxy-benzylamine (2.08 g, 15.217 mmol, 1 eq) were dissolved in dichloromethane (100 ml) and stirred for 3 h at RT. Na(OAc)$_3$BH (9.67 g, 45.65 mmol, 3 eq) was added in portions at 0° C., and stirring was carried out for 20 h at RT. The reaction solution was diluted with dichloromethane (100 ml), washed with water (100 ml) and sat. NaCl solution (100 ml), dried over sodium sulfate and concentrated under reduced pressure. The crude product was purified by column chromatography (Alox neutral, 10% ethyl acetate in hexane). Yield: 46% (2.13 g, 6.98 mmol).

242

Stage (iii):
7,7-Dimethyl-1,4-dioxaspiro[4.5]decan-8-amine

N-(4-Methoxybenzyl)-7,7-dimethyl-1,4-dioxaspiro[4.5]decan-8-amine (2.3 g, 7.54 mmol, 1 eq) was dissolved in MeOH (30 ml); Pd(OH)$_2$ (690 mg) was added, and hydrogenation was carried out for 2 h at RT under balloon pressure (H$_2$). After monitoring by thin-layer chromatography, the reaction mixture was filtered off over Celite and the filtrate was concentrated under reduced pressure. The crude product was purified by column chromatography (Alox neutral, 1% methanol in dichloromethane). The desired product was obtained in the form of a yellow oil. Yield: 72% (1.0 g, 5.41 mmol).

Stage (iv): Benzyl 7,7-dimethyl-1,4-dioxaspiro[4.5]decan-8-ylcarbamate 7,7-Dimethyl-1,4-dioxaspiro[4.5]decan-8-amine (1.3 g, 7.027 mmol, 1 eq) was dissolved in triethylamine (3.89 ml, 28.10 mmol, 4 eq) and dichloromethane (25 ml) and added dropwise at 0° C. to a 50% solution of Cbz-Cl (2.56 ml, 8.432 mmol, 1.2 eq) in toluene, and the mixture was then stirred for 2 h at RT. After monitoring by thin-layer chromatography, the reaction mixture was diluted with dichloromethane (100 ml), washed with water (75 ml), sat. NH$_4$Cl solution (75 ml) and sat. NaCl solution (75 ml), dried over sodium sulfate and concentrated under reduced pressure. After purification by column chromatography (silica gel, 15% ethyl acetate in hexane), the desired product was obtained in the form of a colourless, viscous oil. Yield: 34% (960 mg, 3.0 mmol).

Stage (v): Benzyl 2,2-dimethyl-4-oxocyclohexylcarbamate

2 M HCl (14 ml) was added to a solution of benzyl 7,7-dimethyl-1,4-dioxaspiro[4.5]decan-8-ylcarbamate (1.4 g, 4.3887 mmol, 1 eq) in MeOH (14 ml), and stirring was carried out for 18 h at RT. The solvent was concentrated under reduced pressure and the residue was diluted with water (10 ml) and rendered basic with sat. sodium hydrogen carbonate solution (20 ml). Then extraction with ethyl acetate (2×50 ml) was carried out. The combined organic phases were washed with water (50 ml) and sat. NaCl solution (50 ml), dried over sodium sulfate and concentrated under reduced pressure. The crude product was used in the next step without being purified further. Yield: 91% (1.1 g, 4.0 mmol).

Stage (vi): Benzyl 2,2-dimethyl-4-(4-methylpiperazin-1-yl)cyclohexylcarbamate

N-Methylpiperazine (0.620 ml, 5.6 mmol, 2 eq) was added at 0° C. to a solution of benzyl 2,2-dimethyl-4-oxocyclohexylcarbamate (770 mg, 2.8 mmol, 1 eq) in dichloromethane (15 ml), and stirring was carried out for 2 h at RT. Na(OAc)$_3$BH (1.78 g, 8.4 mmol, 3 eq) was added in portions at 0° C., and stirring was carried out for 18 h at RT. The reaction solution was diluted with dichloromethane (60 ml), washed with water (50 ml) and sat. NaCl solution (50 ml), dried over sodium sulfate and concentrated under reduced pressure. After purification by column chromatography (Alox neutral, 1% MeOH in dichloromethane), a white solid was obtained. Yield: 44% (440 mg, 1.225 mmol).

Stage (vii): 2,2-Dimethyl-4-(4-methylpiperazin-1-yl)cyclohexanamine (AMN-13)

Benzyl 2,2-dimethyl-4-(4-methylpiperazin-1-yl)cyclohexylcarbamate (0.5 g, 1.393 mmol, 1 eq) was dissolved in MeOH (6 ml); Pd(OH)$_2$ (150 mg) was added, and hydrogenation was carried out for 2 h at RT under balloon pressure (H$_2$). After monitoring by thin-layer chromatography, the reaction mixture was filtered off over Celite and the filtrate was concentrated under reduced pressure. The desired product was thus obtained and was used in the next stage without being purified further. Yield: 95% (300 mg, 1.33 mmol).

Synthesis of Amine AMN-17

N-Methyl-1-(pyridin-4-yl)pyrrolidin-3-amine dihydrochloride (AMN-17)

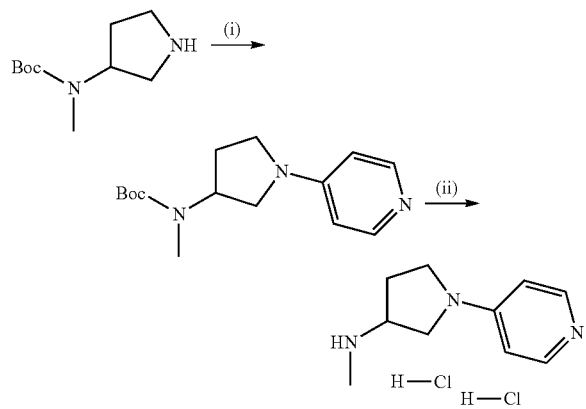

Stage (i): tert-Butyl methyl(1-(pyridin-4-yl)pyrrolidin-3-yl)carbamate 3-(N-Tert-butoxycarbonyl-N-methylamino)pyrrolidine (4.993 mmol, 1 eq) and 4-chloropyridine hydrochloride (14.979 mmol, 3 eq) were dissolved in 2-propanol (15 ml) and DIPEA (19.972 mmol, 4 eq) and refluxed for 16 h. After monitoring by thin-layer chromatography, the reaction solution was diluted with sat. NaHCO$_3$ solution and extracted with ethyl acetate (3×20 ml). The combined org. phases were washed with sat. NaCl solution, dried over magnesium sulfate and concentrated. The crude product was purified by column chromatography (silica gel, ethyl acetate:ethanol 10:1+ammonia (25% aq)). Yield: 61%.

Stage (ii): N-Methyl-1-(pyridin-4-yl)pyrrolidin-3-amine dihydrochloride (AMN-17)

tert-Butyl methyl(1-(pyridin-4-yl)pyrrolidin-3-yl)carbamate (3.028 mmol, 1 eq) was dissolved in ethanol (11 ml), and acetyl chloride (15.14 mmol, 5 eq) was added, while cooling with ice. After stirring for 16 h at RT, a solid precipitated. Ethanol was concentrated slightly, and the precipitate was filtered off, washed with diethyl ether and dried. Yield: 94%.

Synthesis of Amine AMN-21

N-Methyl-1-((2-(pyrrolidin-1-yl)pyridin-4-yl)methyl)piperidin-4-amine hydrochloride (AMN-21)

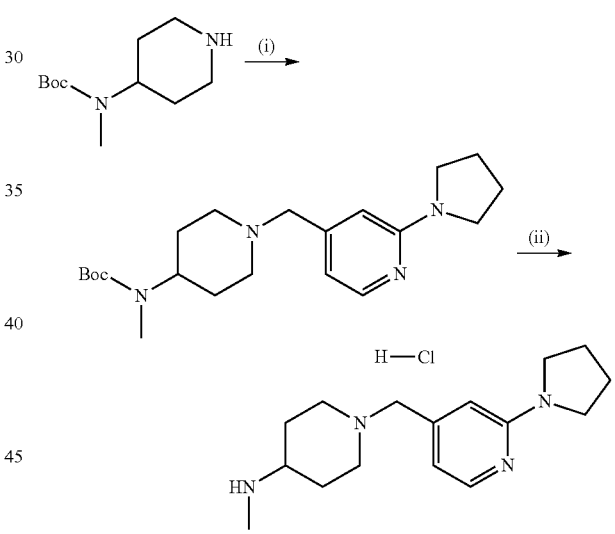

Stage (i): tert-Butyl methyl(1-((2-(pyrrolidin-1-yl)pyridin-4-yl)methyl)piperidin-4-yl)carbamate tert-Butyl methyl(piperidin-4-yl)carbamate (2.333 mmol, 1 eq) and 2-(pyrrolidin-1-yl)-isonicotinaldehyde (2.66 mmol, 1.14 eq) were dissolved in dichloromethane (15 ml), and acetic acid (5.459 mmol, 2.34 eq) and sodium triacetoxyborohydride (3.266 mmol, 1.4 eq) were added. The reaction mixture was stirred for 48 h at RT. When the reaction was complete (TLC monitoring), sat. sodium hydrogen carbonate solution was added to the reaction mixture and the phases were separated. The aqueous phase was extracted with dichloromethane (2×30 ml). The combined organic phases were washed with sat. NaCl solution, dried over sodium sulfate and concentrated. The crude product was purified by column chromatography (silica gel, ethyl acetate:cyclohexane 2:1). Yield: 64%.

Stage (ii): N-Methyl-1-((2-(pyrrolidin-1-yl)pyridin-4-yl)methyl)piperidin-4-amine hydrochloride (AMN-21)

tert-Butyl methyl(1-((2-(pyrrolidin-1-yl)pyridin-4-yl)methyl)piperidin-4-yl)carbamate (1.469 mmol, 1.0 eq) was dissolved in ethanol (5 ml), and acetyl chloride (7.345 mmol, 5 eq) was added, while cooling with ice. The reaction mixture was stirred for 16 h at RT. TLC monitoring showed that the reaction was incomplete. Acetyl chloride (1 eq) was metered in, and the reaction mixture was stirred for 1 h at 50° C. A solid precipitated. Ethanol was concentrated slightly, and the precipitate was filtered off, washed with diethyl ether and dried. Yield: >99%

Synthesis of Amine AMN-27

1-(2,6-Dimethylpyrimidin-4-yl)-N-methylpiperidine-4-amine (AMN-27)

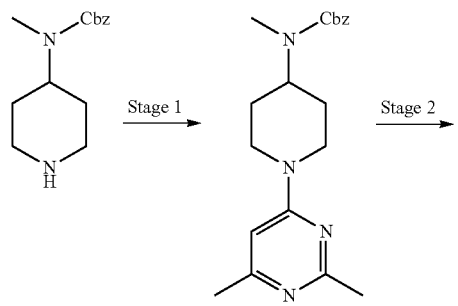

Stage 1: Benzyl 1-(2,6-dimethylpyrimidin-4-yl)piperidin-4-yl(methyl)carbamate A mixture of benzyl methyl(piperidin-4-yl)carbamate (stage 3 AMN-52) (17.24 mmol, 1.0 eq.), 4-chloro-2,6-dimethylpyrimidine (2.94 g, 2068 mmol, 1.2 eq.) and $K_2CO_3$ (4.76 g, 34.48 mmol, 2.0 eq.) in acetone (80 ml) was refluxed for 14 hours. The mixture was concentrated, and the residue was taken up in water (150 ml) and extracted with ethyl acetate (2×200 ml). The combined organic phases were washed with water (150 ml) and sat. NaCl solution (150 ml), dried over sodium sulfate and concentrated under reduced pressure. The crude product was purified by column chromatography (silica gel, 70% ethyl acetate/hexane). Yield: 62% (3.8 g, 10.73 mmol)

Stage 2: 1-(2,6-Dimethylpyrimidin-4-yl)-N-methylpiperidin-4-amine (AMN-27)

Benzyl 1-(2,6-dimethylpyrimidin-4-yl)piperidin-4-yl(methyl)carbamate (3.6 g, 10.169 mmol, 1.0 eq.) was dissolved in MeOH (40 ml) and degassed for 15 min with $N_2$. $Pd(OH)_2$ (800 mg) was then added, and hydrogenation was carried out for 4 hours at room temperature under balloon pressure. After monitoring by TLC, the reaction mixture was filtered over Celite and washed with methanol (100 ml). The filtrate was concentrated under reduced pressure and the crude product was used in the next stage without being purified further. Yield: 95% (2.12 g, 9.636 mmol)

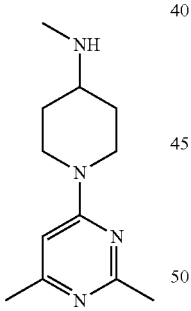

Synthesis of Amine AMN-28

N,3,3-Trimethyl-1-(pyridin-4-yl)piperidin-4-amine (AMN-28)

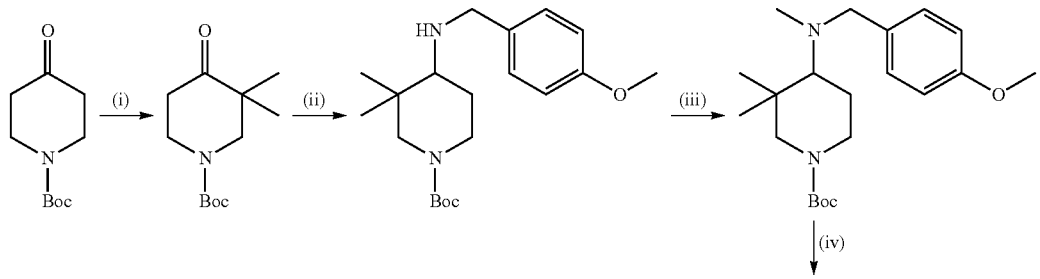

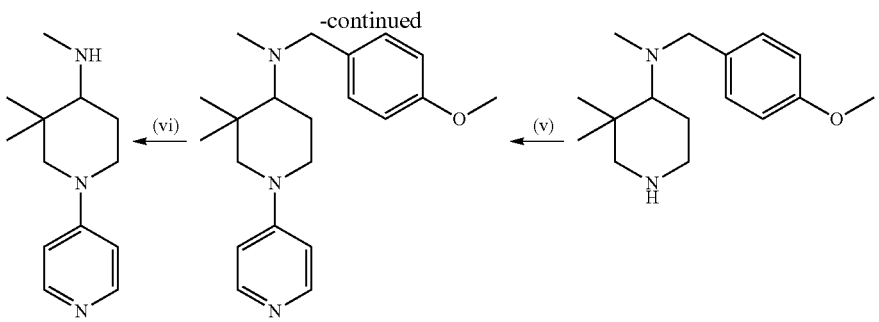

Stage (i): tert-Butyl 3,3-dimethyl-4-oxopiperidine-1-carboxylate

A suspension of Bu'OK (28.0 g, 251.25 mmol, 2.5 eq) in THF was added dropwise at 0° C. to a solution of tert-butyl 4-oxopiperidine-1-carboxylate (20 g, 100.5 mmol, 1 eq) in THF (500 ml), and stirring was carried out for 30 min at RT. Then methyl iodide (15.5 ml, 251.0 mmol, 2.5 eq) was added dropwise, and stirring was carried out for 20 h at RT. The reaction mixture was diluted with ethyl acetate (500 ml), washed with sat. NaCl solution (2×200 ml), dried over sodium sulfate and concentrated under reduced pressure. The crude product was purified by column chromatography (silica gel, 5% ethyl acetate in hexane). Yield: 18% (4 g, 17.6 mmol).

Stage (ii): tert-Butyl 4-(4-methoxybenzylamino)-3,3-dimethylpiperidine-1-carboxylate tert-Butyl 3,3-dimethyl-4-oxopiperidine-1-carboxylate (3.3 g, 14.53 mmol, 1 eq) and 4-methoxybenzylamine (3.98 g, 29.07 mmol, 2 eq) were dissolved in dichloromethane (40 ml), and stirring was carried out for 2 h at RT. The reaction mixture was cooled to 0° C., and Na(OAc)$_3$BH (9.24 g, 43.61 mmol, 3 eq) was added in portions. Then stirring was carried out for 16 h at RT. The reaction mixture was diluted with dichloromethane (150 ml), washed with water and sat. NaCl solution (in each case 100 ml), dried over sodium sulfate and concentrated under reduced pressure. The crude product was purified by column chromatography (Alox neutral, 10% ethyl acetate in hexane) (colourless oil). Yield: 38% (1.948 g, 5.59 mmol).

Stage (iii): tert-Butyl 4-(4-methoxybenzyl)(methyl)amino)-3,3-dimethylpiperidine-1-carboxylate NaH (335 mg, 8.39 mmol, 1.5 eq, 60% in mineral oil) was added to a solution of tert-butyl 4-(4-methoxybenzylamino)-3,3-dimethylpiperidine-1-carboxylate (1.948 g, 5.59 mmol, 1 eq) in DMF (15 ml). Then methyl iodide (525 µl, 8.39 mmol, 1.5 eq) was added at 0° C. and the reaction mixture was stirred for 2 h at RT. Then the reaction mixture was hydrolyzed with ice-water (100 ml) and extracted with ethyl acetate (2×100 ml). The combined organic phases were washed with water and sat. NaCl solution (in each case 100 ml), dried over sodium sulfate and concentrated under reduced pressure. The crude product was purified by column chromatography (silica gel, 10% ethyl acetate in hexane) (colourless liquid).

Stage (iv): N-(4-Methoxybenzyl)-N,3,3-trimethylpiperidin-4-amine tert-Butyl 4-((4-methoxybenzyl)(methyl)amino)-3,3-dimethylpiperidine-1-carboxylate (1.87 g, 5.17 mmol, 1 eq) was dissolved in dichloromethane (4 ml); TFA (4 ml) was added at 0° C., and stirring was carried out for 2 h at RT. The reaction solution was concentrated under reduced pressure, taken up in toluene and dried again. The crude product was used in the next stage without being purified further.

Stage (v): N-(4-Methoxybenzyl)-N,3,3-trimethyl-1-(pyridin-4-yl)piperidin-4-amine N-(4-Methoxybenzyl)-N,3,3-trimethylpiperidin-4-amine (5.17 mmol, 1 eq) and 4-bromopyridine hydrochloride (1.509 g, 7.76 mmol, 1.5 eq) were dissolved in n-butanol (40 ml) and DIPEA (4.26 ml, 25.87 mmol, 5 eq) and refluxed for 16 h. After monitoring by thin-layer chromatography, the reaction solution was concentrated under reduced pressure. After purification by column chromatography (silica gel, 5% MeOH in dichloromethane), the desired product was obtained in the form of a white solid. Yield: 40% (700 mg, 2.06 mmol).

Stage (vi): N,3,3-Trimethyl-1-(pyridin-4-yl)piperidin-4-amine (AMN-28)

A solution of N-(4-methoxybenzyl)-N,3,3-trimethyl-1-(pyridin-4-yl)piperidin-4-amine (320 mg, 0.944 mmol, 1 eq) in MeOH (6 ml) was degassed for 15 min with nitrogen, then Pd(OH)$_2$ (320 mg) was added and hydrogenation was carried out for 5 h at RT under balloon pressure (H$_2$). After monitoring by thin-layer chromatography, the reaction mixture was filtered off over Celite and the filtrate was concentrated under reduced pressure. The crude product so obtained was used in the next stage without being purified further. Yield: 92% (190 mg, 0.867 mmol).

Synthesis of Amine AMN-29

N-Methyl-1-(1-(pyridin-4-yl)piperidin-4-yl)methanamine (AMN-29)

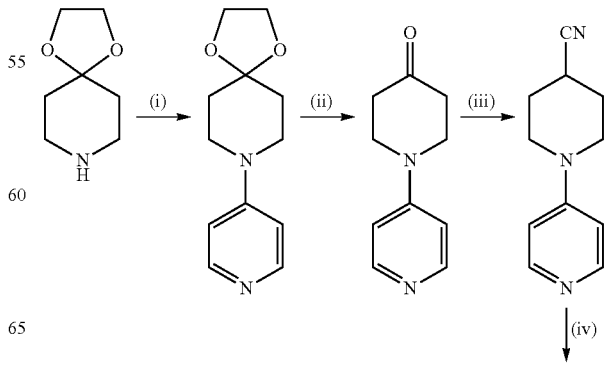

-continued

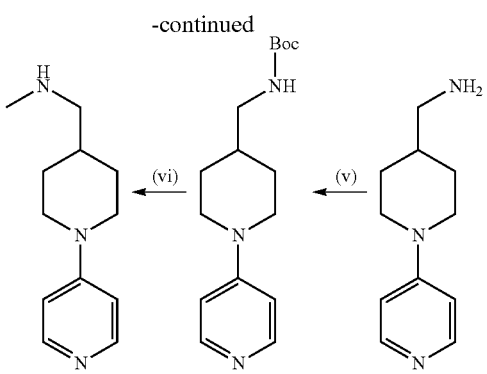

Stage (i): 8-(Pyridin-4-yl)-1,4-dioxa-8-azaspiro[4.5]decane 1,4-Dioxa-8-azaspiro[4.5]decane (10.0 g, 69.9 mmol, 1 eq) and 4-bromopyridine HBr (16.2 g, 83.7 mmol, 1.2 eq) were dissolved in n-butanol (120 ml) and DIPEA (23 ml, 139.8 mmol, 2.0 eq) and refluxed for 14 h. After monitoring by thin-layer chromatography, the reaction solution was concentrated under reduced pressure. After purification by column chromatography (silica gel, 3% MeOH in dichloromethane), the desired product was obtained in the form of a white solid. Yield: 58% (9.0 g, 40.9 mmol).

Stage (ii): 1-(Pyridin-4-yl)piperidin-4-one 8-(Pyridin-4-yl)-1,4-dioxa-8-azaspiro[4.5]decane (2.6 g, 11.82 mmol, 1 eq) was dissolved at 0° C. in ice-cooled concentrated HCl (15 ml), and stirring was carried out for 10 min. After monitoring by thin-layer chromatography, the reaction mixture was adjusted to pH 10-12 with 2 N NaOH and extracted with chloroform (3×100 ml). The combined organic phases were washed with water and sat. NaCl solution (in each case 150 ml), dried over sodium sulfate and reduced under reduced pressure. The product so obtained was used in the next stage without being purified further.

Stage (iii): 1-(Pyridin-4-yl)piperidine-4-carbonitrile $^t$BuOK (2.29 g, 20.45 mmol, 2.5 eq) was added in portions at −5° C. to a solution of 1-(pyridin-4-yl)piperidin-4-one (1.44 g, 8.18 mmol, 1 eq) and TOSMIC (1.91 g, 9.81 mmol, 1.2 eq) in DME (20 ml) and EtOH (0.5 ml), and then stirring was carried out for 2 h at RT. The reaction mixture was hydrolyzed with ice-water (50 ml), extracted with dichloromethane (2×100 ml). The combined organic phases were washed with water and sat. NaCl solution (in each case 100 ml), dried over sodium sulfate and concentrated under reduced pressure. After purification by column chromatography (silica gel, 4% MeOH in dichloromethane), the desired product was obtained in the form of a brown solid. Yield: 34% (530 mg, 2.83 mmol).

Stage (iv): (1-(Pyridin-4-yl)piperidin-4-yl)methanamine

At 0° C., BH$_3$-DMS (1.089 ml, 11.336 mmol, 4 eq) and BF$_3$-Et$_2$O (355 4 2.83 mmol, 1 eq) were added to a solution of 1-(pyridin-4-yl)piperidine-4-carbonitrile (530 mg, 2.83 mmol, 1 eq) in THF (10 ml) and heated for 1 h at boiling temperature. The reaction mixture was hydrolyzed with MeOH (15 ml) and concentrated under reduced pressure. The white solid so obtained was used in the next stage without being purified further. Yield: quantitative Stage (v): tert-Butyl (1-(pyridin-4-yl)piperidin-4-yl)methylcarbamate (1-(Pyridin-4-yl)piperidin-4-yl)methanamine (540 mg, 2.83 mmol, 1 eq) was dissolved in dichloromethane (15 ml) and triethylamine (0.98 ml, 7.06 mmol, 2.5 eq). Then Boc anhydride (725 µl, 3.39 mmol, 1.2 eq) was added at 0° C., with stirring, and stirring was carried out for 2 h. After monitoring by thin-layer chromatography, the reaction mixture was diluted with dichloromethane (70 ml), washed with water (30 ml) and sat. NaCl solution (30 ml), dried over sodium sulfate and concentrated. The crude product was purified by column chromatography (Alox neutral, 1% MeOH in dichloromethane). Yield: 22% (180 mg, 0.618 mmol).

Stage (vi): N-Methyl-1-(1-(pyridin-4-yl)piperidin-4-yl)methanamine (AMN-29)

A solution of tert-butyl (1-(pyridin-4-yl)piperidin-4-yl)methylcarbamate (180 mg, 0.618 mmol, 1 eq) in THF (4 ml) was added dropwise at 0° C. to a suspension of LAH (188 mg, 4.94 mmol, 8 eq) in THF (4 ml) and heated for 16 h at boiling temperature. The reaction mixture was hydrolyzed with H$_2$O:THF (9:1, 2 ml) and 10% NaOH solution (0.4 ml) at 0° C., diluted with THF (25 ml) and stirred for 1 h at RT. The reaction mixture was filtered over Celite and the filtrate was concentrated under reduced pressure. The resulting amine was used in the following stage without being purified further. Yield: 150 mg.

Synthesis of Amine AMN-30

N-Methyl-2-(1-(pyridin-4-yl)piperidin-4-yl)ethanamine (AMN-30)

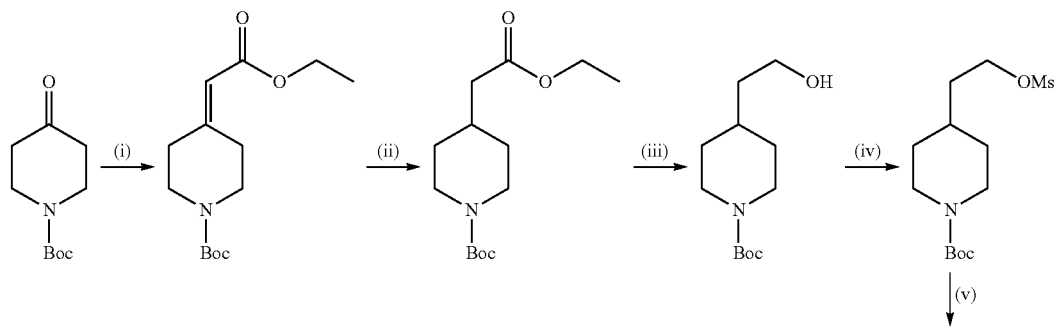

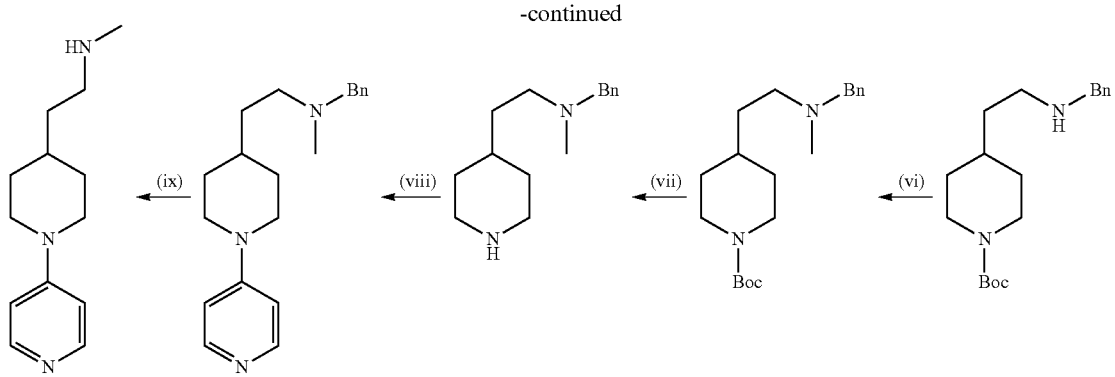

Stage (i): tert-Butyl 4-(2-ethoxy-2-oxoethylidene)piperidine-1-carboxylate

A solution of tert-butyl 4-oxopiperidine-1-carboxylate (10.0 g, 50.25 mmol, 1 eq) in THF (50 ml) was added at 0° C. to a suspension of NaH (1.56 g, 65.32 mmol, 1.3 eq) in THF (50 ml), and stirring was carried out for 30 min. Triethyl phosphoroacetate (12.96 ml, 65.32 mmol, 1.3 eq) in THF (50 ml) was added dropwise, and stirring was carried out for 2 h at RT. The reaction mixture was hydrolyzed with water (5 ml) and concentrated. The residue was taken up in water (150 ml) and extracted with ethyl acetate (2×300 ml). The combined organic phases were washed with sat. NaCl solution (200 ml), dried over sodium sulfate and concentrated under reduced pressure. The crude substance was purified by column chromatography (silica gel, 3% ethyl acetate in hexane) (white solid). Yield: 78% (10.5 g, 39.03 mmol).

Stage (ii): tert-Butyl 4-(2-ethoxy-2-oxoethyl)piperidine-1-carboxylate tert-Butyl 4-(2-ethoxy-2-oxoethylidene)piperidine-1-carboxylate (5.0 g, 18.58 mmol, 1 eq) was dissolved in ethanol (20 ml) and degassed for 30 min with nitrogen. Pd—C (500 mg, 10%) was added, and hydrogenation was carried out for 12 h at RT under balloon pressure ($H_2$). After monitoring by thin-layer chromatography, the reaction mixture was filtered off over Celite and washed with ethanol (200 ml), and the filtrate was concentrated under reduced pressure. Yield: 89% (4.5 g, 16.6 mmol).

Stage (iii): tert-Butyl 4-(2-hydroxyethyl)piperidine-1-carboxylate

LAH (819 mg, 21.58 mmol, 1.3 eq) was placed in THF (50 ml) at 0° C.; a solution of tert-butyl 4-(2-ethoxy-2-oxoethyl)piperidine-1-carboxylate (4.5 g, 16.60 mmol, 1 eq) in THF (50 ml) was added dropwise, and then stirring was carried out for 1 h at RT. After monitoring by thin-layer chromatography, the reaction mixture was hydrolyzed with sat. sodium sulfate solution (2 ml), filtered over Celite and washed with THF (300 ml). The filtrate was concentrated under reduced pressure. A colourless oil was obtained, which was used in the next stage without being purified further. Yield: 92% (3.5 g, 15.28 mmol).

Stage (iv): tert-Butyl 4-(2-(methylsulfonyloxy)ethyl)piperidine-1-carboxylate Methanesulfonic acid chloride (0.41 ml, 6.5 mmol, 1.5 eq) was added to an ice-cooled (0° C.) solution of tert-butyl 4-(2-hydroxyethyl)piperidine-1-carboxylate (1.0 g, 4.37 mmol, 1 eq) and triethylamine (1.2 ml, 8.7 mmol, 2.0 eq) in dichloromethane (10 ml), and stirring was carried out for 1 h at RT. After monitoring by thin-layer chromatography, the reaction mixture was diluted with dichloromethane (75 ml), washed with water and sat. NaCl solution (in each case 30 ml), dried over sodium sulfate and concentrated under reduced pressure. A yellow oil was obtained, which was used in the next step without being purified further.

Stage (v): tert-Butyl 4-(2-(benzylamino)ethyl)piperidine-1-carboxylate

Benzylamine (345 μl, 3.22 mmol, 1.1 eq) was added to a solution of tert-butyl 4-(2-(methyl-sulfonyloxy)ethyl)piperidine-1-carboxylate (0.9 g, 2.93 mmol, 1 eq) and triethylamine (0.8 ml, 5.86 mmol, 2 eq) in toluene (50 ml), and refluxing was carried out for 48 h. After monitoring by thin-layer chromatography, the reaction solution was concentrated and the residue was taken up in ethyl acetate (100 ml), washed with water (30 ml) and sat. NaCl solution (40 ml), dried over sodium sulfate and concentrated under reduced pressure. After purification by column chromatography (silica gel, ethyl acetate), a yellow solid was obtained. Yield: 43% (400 mg, 1.25 mmol).

Stage (vi): tert-Butyl 4-(2-(benzyl(methyl)amino)ethyl)piperidine-1-carboxylate At 0° C., a solution of tert-butyl 4-(2-(benzylamino)ethyl)piperidine-1-carboxylate (400 mg, 1.25 mmol, 1 eq) in THF (10 ml) was added dropwise to a suspension of NaH (110 mg, 2.74 mmol, 1.3 eq, 60% in mineral oil) in DMF (4 ml), and stirring was carried out for 30 min. Then a solution of iodomethane (93 μl, 1.5 mmol, 1.2 eq) in THF (2 ml) was added dropwise at 0° C., and stirring was carried out for 2 h at RT. After monitoring by thin-layer chromatography, the reaction mixture was diluted with water (5 ml) and extracted with ethyl acetate (2×50 ml). The combined organic phases were washed with water and sat. NaCl solution (in each case 50 ml), dried over sodium sulfate and concentrated under reduced pressure. After purification by column chromatography (silica gel, 60% ethyl acetate in hexane), a light-yellow solid was obtained. Yield: 34% (140 mg, 0.42 mmol).

Stage (vii): N-Benzyl-N-methyl-2-(piperidin-4-yl)ethanamine

TFA (2.78 ml) was added dropwise at 0° C. to a solution of tert-butyl 4-(2-(benzyl(methyl)-amino)ethyl)piperidine-1- carboxylate (600 mg, 1.8 mmol, 1 eq) in dichloromethane (30 ml), and stirring was carried out for 1 h at RT. After monitoring by thin-layer chromatography, the reaction mixture was concentrated to dryness. The residue was dissolved in MeOH (50 ml), Amberlyst A-21 ion-exchanger resin (2 g) was added, and stirring was carried out for 30 min. The reaction mixture was filtered and the filtrate was concentrated to dryness under reduced pressure and used in the next stage without being purified further.

Stage (viii): N-Benzyl-N-methyl-2-(1-(pyridin-4-yl)piperidin-4-yl)ethanamine

N-Benzyl-N-methyl-2-(piperidin-4-yl)ethanamine (600 mg, 2.58 mmol, 1 eq) and 4-bromo-pyridine HBr (553 mg, 2.84 mmol, 1.1 eq) were dissolved in n-butanol (15 ml); DIPEA (2.34 ml, 12.9 mmol, 5 eq) was added, and refluxing was carried out for 16 h. After monitoring by thin-layer chromatography, the reaction mixture was concentrated and the residue was purified by column chromatography (Alox 5-7% MeOH in dichloromethane). Yield: 56% (450 mg, 1.45 mmol).

Stage (ix): N-Methyl-2-(1-(pyridin-4-yl)piperidin-4-yl)ethanamine

N-Benzyl-N-methyl-2-(1-(pyridin-4-yl)piperidin-4-yl)ethanamine (1.4 g, 3.63 mmol, 1 eq) was dissolved in MeOH (20 ml) and degassed for 30 min with nitrogen. 20% Pd—(OH)$_2$ (200 mg) was added and hydrogenation was carried out for 2 h at RT under balloon pressure (H$_2$). After monitoring by thin-layer chromatography, the reaction mixture was filtered off over Celite and washed with MeOH (3×25 ml), and the filtrate was concentrated under reduced pressure. Yield: 30% (240 mg, 1.09 mmol).

Synthesis of amine AMN-31

N-Methyl-4-(pyridin-4-yl)cyclohexanamine (AMN-31)

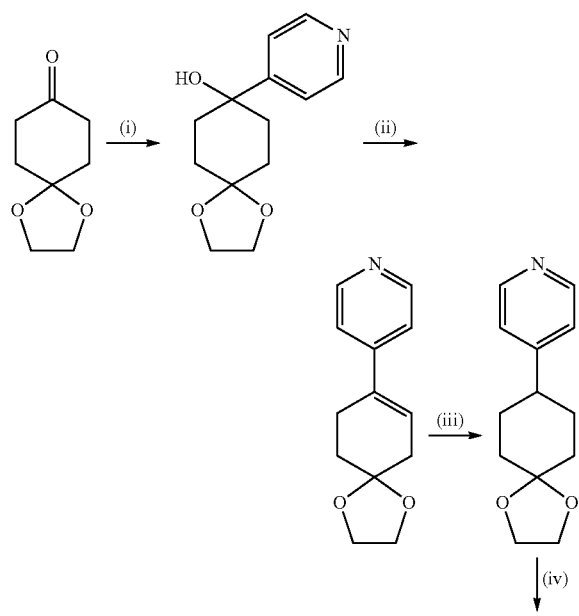

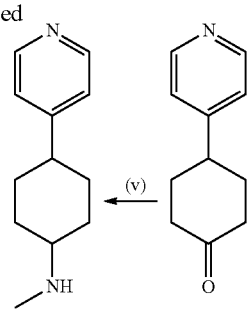

Stage (i): 8-(Pyridin-4-yl)-1,4-dioxaspiro[4.5]decan-8-ol n-BuLi (32 ml, 64.0 mmol, 2 eq, 2 M solution in hexane) was placed in THF (60 ml) and cooled to −78° C. A solution of 4-bromopyridine (6.3 g, 40.0 mmol, 1.25 eq) in THF (50 ml) was slowly added dropwise at that temperature, and stirring was carried out for 1.5 h. A solution of 1,4-dioxaspiro[4.5]decan-8-one (5.0 g, 32.0 mmol, 1 eq) in THF (50 ml) was added likewise at −78° C., and stirring was carried out for 2 h. After monitoring by thin-layer chromatography, the reaction solution was hydrolyzed with water (100 ml), while cooling, and extracted with ethyl acetate (2×200 ml). The combined organic phases were washed with water (100 ml) and sat. NaCl solution (100 ml), dried over sodium sulfate and concentrated under reduced pressure. After purification by column chromatography (silica gel, 2% MeOH in dichloromethane), the desired product was obtained in the form of a light-brown solid. Yield: 64% (6.0 g, 25.53 mmol).

Stage (ii): 4-(1,4-Dioxaspiro[4.5]dec-7-en-8-yl)pyridine

SOCl$_2$ (10.5 ml) was added dropwise at −10° C. to a solution of 8-(pyridin-4-yl)-1,4-dioxa-spiro[4.5]decan-8-ol (6.0 g, 25.5 mmol, 1 eq) in pyridine (50 ml), and stirring was carried out for 15 min. After monitoring by thin-layer chromatography, the reaction mixture was poured carefully onto ice (100 g), neutralized with sat. sodium hydrogen carbonate solution (100 ml) and extracted with dichloromethane (2×150 ml). The combined organic phases were washed with water (100 ml) and sat. NaCl solution (100 ml), dried over sodium sulfate and concentrated under reduced pressure. The crude product was purified by column chromatography (silica gel, 1% MeOH in dichloromethane). Yield: 63% (3.5 g, 16.1 mmol).

Stage (iii): 4-(1,4-Dioxaspiro[4.5]decan-8-yl)pyridine 4-(1,4-Dioxaspiro[4.5]dec-7-en-8-yl)pyridine (3.5 g, 16.1 mmol, 1 eq) was dissolved in MeOH (80 ml) and degassed for 15 min with argon. Pd(OH)$_2$ (1.75 g, 50%) was added, and hydrogenation was carried out for 3 h at RT under balloon pressure (H$_2$). After monitoring by thin-layer chromatography, the reaction mixture was filtered off over Celite and the filtrate was concentrated under reduced pressure. Yield: 84% (3.0 g, 13.6 mmol).

Stage (iv): 4-(Pyridin-4-yl)cyclohexanone

2 M HCl (13.6 ml) was added to a solution of 4-(1,4-dioxaspiro[4.5]decan-8-yl)pyridine (3.0 g, 13.6 mmol, 1 eq) in THF (136 ml), and stirring was carried out for 3 h at RT. The solvent was removed under reduced pressure. The residue was diluted with water (50 ml) and rendered basic with solid sodium hydrogen carbonate. Then extraction with ethyl acetate (2×100 ml) was carried out. The combined organic phases were washed with water (80 ml), dried over sodium sulfate and concentrated under reduced pressure. The desired product was used in the next step without being purified further. Yield: 69% (1.65 g, 9.42 mmol).

Stage (v): N-Methyl-4-(pyridin-4-yl)cyclohexanamine (AMN-31)

Acetic acid (0.2 ml) was added catalytically to an ice-cooled (0° C.) solution of 4-(pyridin-4-yl)cyclohexanone (500 mg, 2.857 mmol, 1 eq) and methylamine hydrochloride (957 mg, 14.28 mmol, 5 eq) in MeOH (10 ml), and stirring was carried out for 1 h at RT. NaCNBH$_3$ (358 mg, 5.714 mmol, 2 eq) was added at 0° C. and stirring was carried out for a further 14 h at RT. The reaction mixture was concentrated, diluted with dichloromethane (100 ml) and washed with sat. sodium hydrogen carbonate solution (60 ml) and sat. NaCl solution (60 ml). The organic phase was dried over sodium sulfate, concentrated under reduced pressure and purified by column chromatography (Alox neutral, 6% MeOH in dichloromethane). The desired amine was obtained in the form of a light-yellow solid. Yield: 27% (150 mg, 1.26 mmol).

Synthesis of amine AMN-35

N-Methyl-1-(1-(pyrimidin-4-yl)piperidin-4-yl)methanamine dihydrochloride (AMN-35)

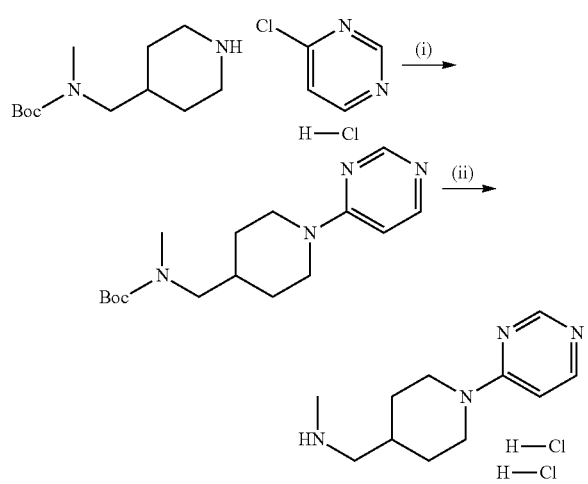

Stage (i): tert-Butyl methyl((1-(pyrimidin-4-yl)piperidin-4-yl)methyl)carbamate tert-Butyl methyl(piperidin-4-ylmethyl)carbamate (1.4 mmol, 1.0 eq) and 4-chloropyridine (4.2 mmol, 3.0 eq) were dissolved in 2-propanol (5 ml) and DIPEA (7.0 mmol. 5.0 eq) and refluxed for 16 hours. After monitoring by TLC, the reaction solution was diluted with ethyl acetate and sat. sodium hydrogen carbonate solution and the phases were separated. The aqueous phase was washed with ethyl acetate. The combined organic phases were dried over magnesium sulfate, concentrated under reduced pressure and purified by column chromatography (silica gel, ethyl acetate:ethanol 10:1+ammonia solution). Yield: 51%

Stage (ii): N-Methyl-1-(1-(pyrimidin-4-yl)piperidin-4-yl)methanamine dihydrochloride (AMN-35)

tert-Butyl methyl((1-(pyrimidin-4-yl)piperidin-4-yl)methyl)carbamate (0.718 mmol, 1 eq) was dissolved in ethanol (2.5 ml), and acetyl chloride (3.59 mmol, 5.0 eq) was added while cooling with ice. The reaction mixture was then stirred for 2 hours at 40° C. and then concentrated. The residue was taken up in a small amount of acetone and a solid was precipitated with diethyl ether. The solid was filtered off, washed with diethyl ether and dried. Yield: >99%

Synthesis of Amine AMN-42

1-(4-(Methylamino)piperidin-1-yl)-3-(piperidin-1-yl)propan-1-one hydrochloride (AMN-42)

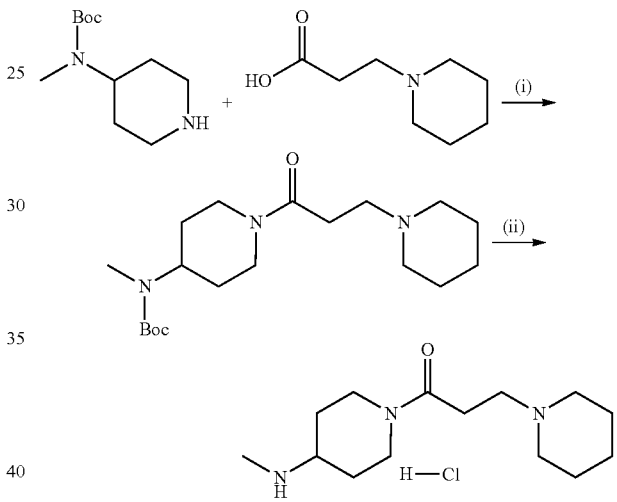

Stage (i): tert-Butyl methyl(1-(3-(piperidin-1-yl)propanoyl)piperidin-4-yl)carbamate 3-(Piperidin-1-yl)propanoic acid (3.183 mmol, 1.0 eq) was dissolved in dichloromethane (40 ml) and DIPEA (7.958 mmol, 2.5 eq) and cooled to 0° C.; EDCI (3.82 mmol, 1.2 eq) and HOBT (0.637 mmol, 0.2 eq) were added and stirring was carried out for 15 hours at RT. The mixture was then cooled to 0° C. again, tert-butyl methyl(piperidin-4-yl)carbamate (3.183 mmol, 1.0 eq) was added, and the reaction mixture was stirred for 16 hours at RT. Then the reaction mixture was diluted with ethyl acetate, washed with 10% ammonium chloride solution, sat. NaHCO$_3$ solution and with sat. NaCl solution, dried over magnesium sulfate and concentrated. The crude product was purified by column chromatography (silica gel, ethyl acetate/ethanol). Yield: 78%

Stage (ii): 1-(4-(Methylamino)piperidin-1-yl)-3-(piperidin-1-yl)propan-1-one hydrochloride (AMN-42)

tert-Butyl methyl(1-(3-(piperidin-1-yl)propanoyl)piperidin-4-yl)carbamate (2.461 mmol, 1 eq) was dissolved in ethanol (9 ml), and acetyl chloride (12.31 mmol, 5.0 eq) was added while cooling with ice. The reaction mixture was stirred for 16 hours at RT and then concentrated. The residue was taken up in a small amount of acetone, and a solid was precipitated by addition of diethyl ether. The solid was filtered off, washed with diethyl ether and dried. Yield: >99%

Synthesis of amine AMN-44

N-Methyl-1-(pyrimidin-4-yl)piperidin-4-amine dihydrochloride (AMN-44)

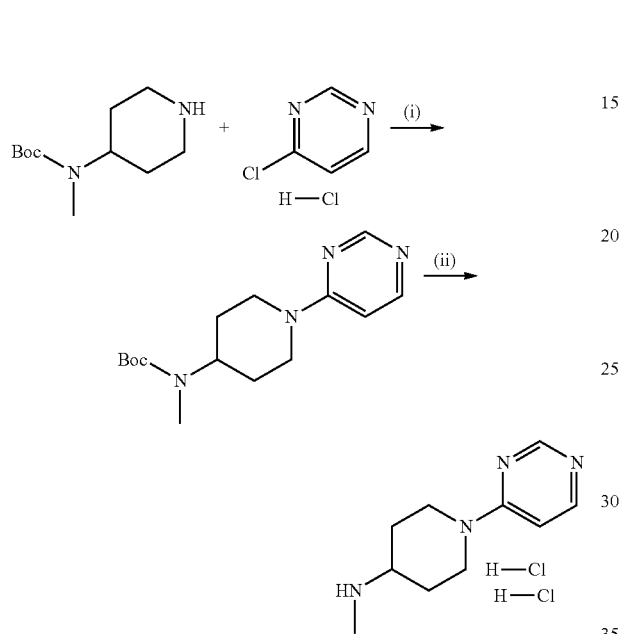

Stage (i): tert-Butyl methyl(1-(pyrimidin-4-yl)piperidin-4-yl)carbamate tert-Butyl methyl(piperidin-4-ylmethyl)carbamate (4.67 mmol, 1.0 eq) and 4-chloropyrimidine hydrochloride (14.0 mmol, 3.0 eq) were dissolved in 2-propanol (18 ml) and DIPEA (23.33 mmol. 5.0 eq) and refluxed for 16 hours. After monitoring by TLC, the reaction solution was diluted with ethyl acetate and sat. sodium hydrogen carbonate solution, and the phases were separated. The aqueous phase was washed with ethyl acetate. The combined organic phases were washed 1× with sat. NaCl solution, dried over magnesium sulfate and concentrated under reduced pressure. The crude product was purified by column chromatography (silica gel, ethyl acetate:ethanol 10:1+ammonia solution). Yield: 78%

Stage (ii): N-Methyl-1-(pyrimidin-4-yl)piperidin-4-amine dihydrochloride (AMN-44)

tert-Butyl methyl(1-(pyrimidin-4-yl)piperidin-4-yl)carbamate (3.63 mmol, 1 eq) was dissolved in ethanol (13 ml), and acetyl chloride (18.13 mmol, 5.0 eq) was added while cooling with ice. The reaction mixture was then stirred for 2 hours at 40° C. The reaction mixture was concentrated under reduced pressure. A white precipitate formed from the concentrated solution. The suspension was diluted with diethyl ether and stirred for 1 hour at RT. Then the precipitate was filtered off with suction, washed with diethyl ether and dried. Yield: 96%

Synthesis of amine AMN-47

N-Methyl-1-(2-methylpyridin-4-yl)azetidin-3-amine dihydrochloride (AMN-47)

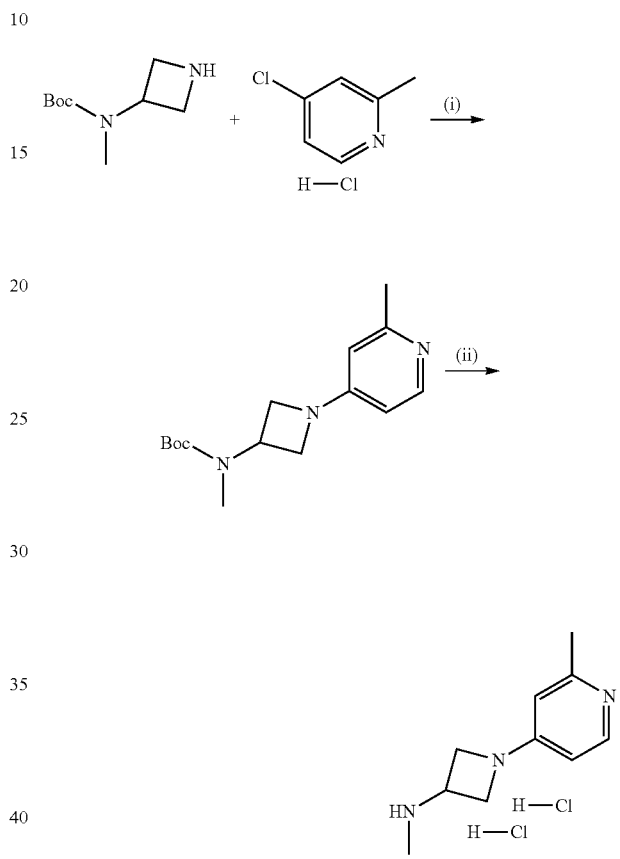

Stage (i): tert-Butyl methyl(1-(2-methylpyridin-4-yl)azetidin-3-yl)carbamate 3-(Boc-methylamino)azetidine (2.74 mmol, 1.0 eq) and 4-chloro-2-methylpyridine HCl (8.21 mmol, 3.0 eq) were dissolved in 2-propanol (5 ml) and DI PEA (13.69 mmol. 5.0 eq) and refluxed for 24 hours. After monitoring by TLC, the reaction solution was diluted with ethyl acetate and sat. sodium hydrogen carbonate solution, and the phases were separated. The aqueous phase was washed with ethyl acetate. The combined organic phases were washed 1× with sat. NaCl solution, dried over magnesium sulfate, concentrated under reduced pressure. The crude product was purified by column chromatography (silica gel, ethyl acetate:ethanol 10:1+ammonia solution). Yield: 51%

Stage (ii): N-Methyl-1-(2-methylpyridin-4-yl)azetidin-3-amine dihydrochloride (AMN-47)

tert-Butyl methyl(1-(2-methylpyridin-4-yl)azetidin-3-yl)carbamate (1.37 mmol, 1 eq) was dissolved in ethanol (5 ml), and acetyl chloride (6.85 mmol, 5.0 eq) was added while cooling with ice. The reaction mixture was then stirred for 2 hours at 40° C. The solvent was removed in vacuo and the residue was dried. Yield: 99%

Synthesis of amine AMN-48

N,N-Dimethyl-6-(4-(methylamino)cyclohexyl)-5,6,7,8-tetrahydropyrido[4,3-d]pyrimidine-2-amine (AMN-48)

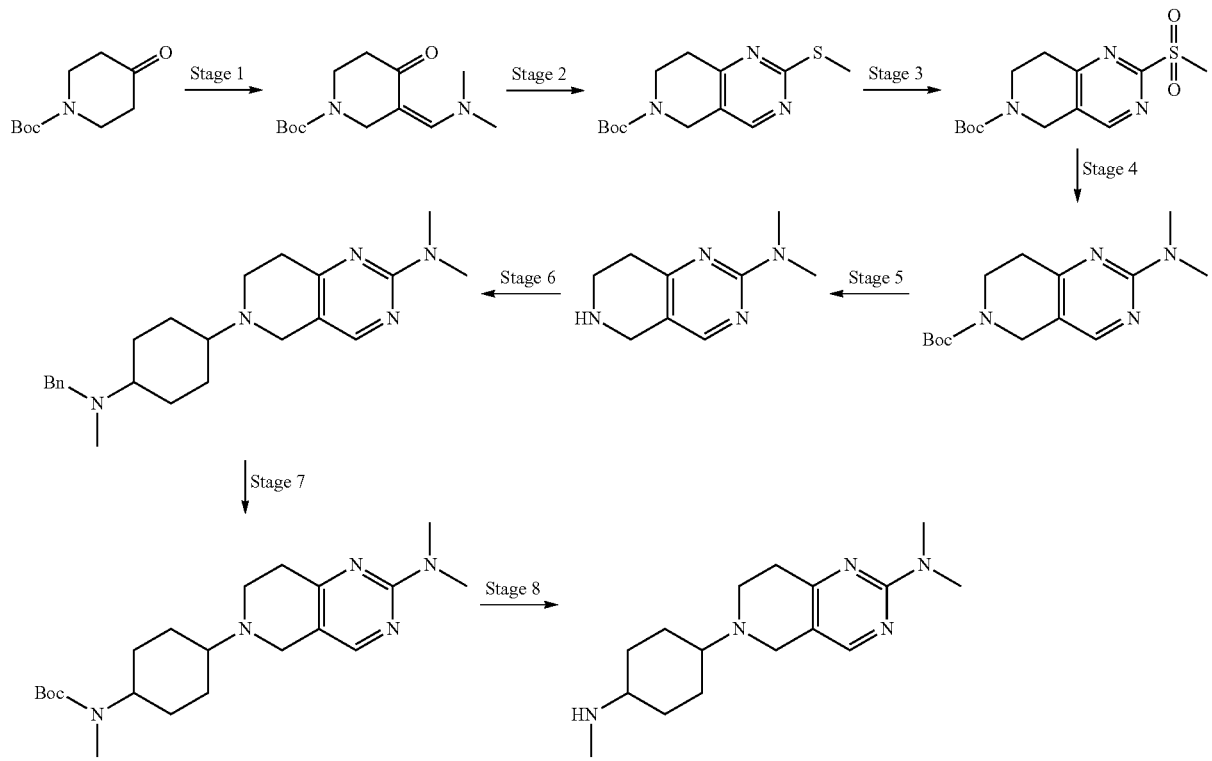

Stage 1: tert-Butyl 3-((dimethylamino)methylene)-4-oxopiperidine-1-carboxylate

A mixture of tert-butyl 4-oxopiperidine-1-carboxylate (20.0 g, 100.38 mmol, 1.0 eq.) and N,N-dimethylformamide dimethylacetal (80 ml) was refluxed for 6 hours. After monitoring by thin-layer chromatography, the reaction mixture was concentrated under reduced pressure and the residue was taken up in DCM (300 ml), washed with water (200 ml) and sat. NaCl solution (200 ml), dried over sodium sulfate, concentrated and purified by column chromatography (silica gel, 2.5% MeOH in DCM). Yield: 40% (10.2 g, 40.16 mmol)

Stage 2: tert-Butyl 2-(methylthio)-7,8-dihydropyrido[4,3-d]pyrimidine-6(5H)-carboxylate S-Methylisothiourea sulfate (16.44 g, 59.06 mmol, 1.5 eq.) and tert-butyl 3-((dimethylamino)-methylene)-4-oxopiperidine-1-carboxylate (10.0 g, 39.37 mmol, 1.0 eq.) were taken up in water (40 ml); 1 M NaOH solution (50 ml) was added and stirring was carried out for 1 hour at 80° C. After monitoring by TLC, the reaction mixture was diluted with water (100 ml) and extracted with DCM (2×150 ml). The combined org. phases were washed with sat. NaCl solution (100 ml), dried over sodium sulfate, concentrated under reduced pressure and purified by column chromatography (silica gel, 25% ethyl acetate in hexane). Yield: 40% (4.5 g, 16.01 mmol)

Stage 3: tert-Butyl 2-(methylsulfonyl)-7,8-dihydropyrido[4,3-d]pyrimidine-6(5H)-carboxylate m-CPBA (37.82 g, 109.60 mmol, 4.0 eq.) was added at 0° C. to a solution of tert-butyl 2-(methylthio)-7,8-dihydropyrido[4,3-d]pyrimidine-6(5H)-carboxylate (7.70 g, 27.40 mmol, 1.0 eq.) in DCM (150 ml), and the mixture was stirred for 4 hours at RT. The reaction mixture was diluted with DCM (200 ml), washed with sat. sodium hydrogen carbonate solution (2×300 ml), water and sat. NaCl solution (in each case 300 ml), dried over sodium sulfate, concentrated under reduced pressure and purified by column chromatography (silica gel, 35% ethyl acetate in hexane). Yield: 32% (2.8 g, 8.95 mmol)

Stage 4: tert-Butyl 2-(dimethylamino)-7,8-dihydropyrido[4,3-d]pyrimidine-6(5H)-carboxylate A mixture of tert-butyl 2-(methylsulfonyl)-7,8-dihydropyrido[4,3-d]pyrimidine-6(5H)-carboxylate (2.8 g, 8.95 mmol, 1.0 eq.), dimethylamine HCl (1.09 g, 13.42 mmol, 1.5 eq.) and DIPEA (4.37 ml, 25.56 mmol, 4.0 eq.) in NMP (6.5 ml) was stirred for 1 hour at 130° C. in a microwave. The reaction mixture was diluted with water (100 ml) and extracted with ethyl acetate (2×150 ml). The combined org. phases were washed with sat. NaCl solution (200 ml), dried over sodium sulfate, concentrated under reduced pressure and purified by column chromatography (silica gel, 18% ethyl acetate in hexane). Yield: 78% (1.95 g, 7.01 mmol)

Stage 5: N,N-Dimethyl-5,6,7,8-tetrahydropyrido[4,3-d]pyrimidin-2-amine tert-Butyl 2-(dimethylamino)-7,8-dihydropyrido[4,3-d]pyrimidine-6(5H)-carboxylate (1.95 g, 7.01 mmol, 1.0 eq.) was dissolved in DCM (20 ml); TFA (5 ml) was added at 0° C., and stirring was carried out for 1 hour at RT. The reaction mixture was concentrated under reduced pressure and dried to yield the TFA salt. The crude product was dissolved in MeOH (25 ml) and rendered basic with Amberlyst A-21. The reaction mixture was filtered, the filtrate was concentrated under reduced pressure, and the crude product so obtained was used in the next stage without being purified further.

Stage 6: 6-(4-(Benzyl(methyl)amino)cyclohexyl)-N,N-dimethyl-5,6,7,8-tetrahydropyrido[4,3-d]pyrimidine-2-amine N,N-Dimethyl-5,6,7,8-tetrahydropyrido[4,3-d]pyrimidine-2-amine (1.0 g, 4.57 mmol, 1.0 eq.) and 4-(benzyl(methyl)amino)cyclohexanone (stage 3 AMN-50) (0.813 g, 4.57 mmol, 1.0 eq.) were dissolved in MeOH (30 ml); one drop of acetic acid was added and stirring was carried out for 2 hours at RT. NaCNBH$_3$ (0.575 g, 9.14 mmol, 2.0 eq.) was added and the mixture was stirred for a further 16 hours at RT. The reaction mixture was concentrated under reduced pressure, and the residue was taken up in DCM (100 ml), washed with sat. sodium hydrogen carbonate solution (2×60 ml) and sat. NaCl solution (60 ml), dried over sodium sulfate, concentrated under reduced pressure and purified by column chromatography (silica gel, 3% MeOH in DCM). Yield: 28% (0.5 g, 1.32 mmol)

Stage 7: tert-Butyl 4-(2-(dimethylamino)-7,8-dihydropyrido[4,3-d]pyrimidin-6(5H)-yl)cyclohexyl(methyl)carbamate 6-(4-(Benzyl(methyl)amino)cyclohexyl)-N,N-dimethyl-5,6,7,8-tetrahydropyrido[4,3-d]pyrimidin-2-amine (500 mg, 1.32 mmol, 1.0 eq.) and Boc anhydride (0.35 ml, 1.58 mmol, 1.2 eq.) were dissolved in ethanol (30 ml) and degassed with argon. Pd(OH)$_2$ (200 mg) was then added and hydrogenation was carried out for 2 hours. After monitoring by TLC, the reaction mixture was filtered, the filtrate was concentrated under reduced pressure and the crude product so obtained was purified by column chromatography (silica gel, 2% MeOH in DCM). Yield: 29% (0.15 g, 0.39 mmol)

Stage 8: N,N-Dimethyl-6-(4-(methylamino)cyclohexyl)-5,6,7,8-tetrahydropyrido[4,3-d]-pyrimidin-2-amine (AMN-48)

tert-Butyl 4-(2-(dimethylamino)-7,8-dihydropyrido[4,3-d]pyrimidin-6(5H)-yl)cyclohexyl-(methyl)carbamate (150 mg, 0.39 mmol, 1.0 eq.) was dissolved in DCM (4 ml); TFA (1 ml) was added at 0° C. and the mixture was then stirred for 1 hour at RT. The reaction mixture was concentrated under reduced pressure and dried to yield the TFA salt. The crude product was rendered basic with Amberlyst A-21 to yield the free amine.

Synthesis of amine AMN-49

(1S,3R)—N-Methyl-3-(4-methylpiperazin-1-yl)cyclohexanamine (AMN-49)

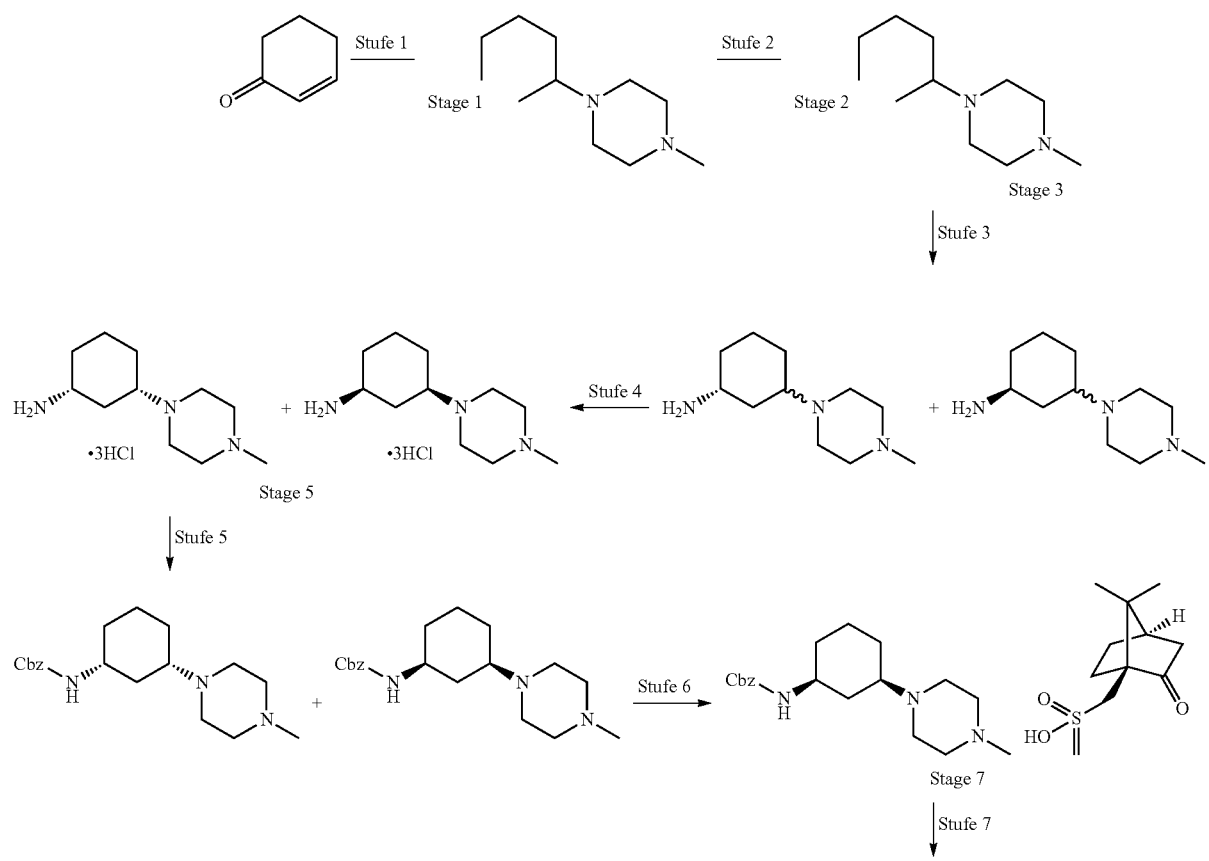

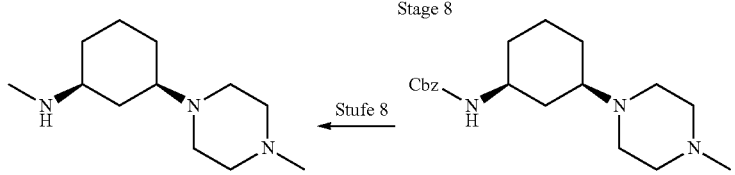

Stage 1 & Stage 2: 3-(4-Methylpiperazin-1-yl)cyclohexanone oxime

N-Methylpiperazine (104.16 g, 1041.6 mmol, 1.0 eq.) was added dropwise to a solution of 2-cyclohexen-1-one (100.0 g, 1041.6 mmol, 1.0 eq.) in ethanol (300 ml), and the resulting mixture was stirred for 5 hours at RT. The reaction solution was diluted with ethanol (600 ml) and cooled to 0° C.; $K_2CO_3$ (172.48 g, 1249.9 mmol, 1.2 eq.) and $NH_2OH \cdot HCl$ (86.7 g, 1249.9 mmol, 1.2 eq.) were added, and the mixture was stirred for 30 minutes at 0° C. and then heated to RT and stirred for a further 16 hours. The reaction mixture was filtered off over Celite and washed with ethanol (500 ml). The filtrate was concentrated under reduced pressure and the residue was taken up in THF (100 ml) and n-hexane (500 ml) and stirred for 3 hours. The resulting solid was filtered off and used in the next stage without being purified further. Yield: 54% (120.0 g, 568.7 mmol)

Stage 3: 3-(4-Methylpiperazin-1-yl)cyclohexanamine

LAH (13015 g, 355.45 mmol, 2.5 eq.) was taken up in THF (600 ml), and 3-(4-methylpiperazin-1-yl)cyclohexanone oxime (30.0 g, 142.18 mmol, 1.0 eq.) was added in portions at 0° C. The reaction mixture was then heated to RT and refluxed for 14 hours. Then it was cooled to 0° C. again, hydrolyzed with 15% NaOH solution (15 ml), filtered off and washed with 10% MeOH in DCM (500 ml). The filtrate was concentrated under reduced pressure and used in the next stage without being purified further. Yield: 67% (19.0 g, 96.44 mmol)

Stage 4: (cis)-3-(4-Methylpiperazin-1-yl)cyclohexanamine tri hydrochloride 3-(4-Methylpiperazin-1-yl)cyclohexanamine (59.0 g, 284.26 mmol) was dissolved in MeOH (70 ml); 7 M ethanolic HCl solution (150 ml) was added, and stirring was carried out for 3 hours at 50° C. The resulting precipitate was filtered off and recrystallised from methanol, and the amine hydrochloride so obtained was dried. Yield: 32% (28.0 g, 91.80 mmol)

Stage 5: (cis)-Benzyl-3-(4-methylpiperazin-1-yl) cyclohexylcarbamate (cis)-3-(4-Methylpiperazin-1-yl)cyclohexanamine trihydrochloride (5.0 g, 16.39 mmol, 1.0 eq.) and $K_2CO_3$ (9.05 g, 65.56 mmol, 4.0 eq.) were dissolved in water (15 ml); a solution of Cbz-Cl (2.85 g, 16.39 mmol, 1.0 eq.) in toluene (25 ml) was added at 0° C., and the reaction mixture was then stirred for 16 hours at RT. The reaction solution was diluted with water (15 ml) and the phases were separated. The org. phase was dried over sodium sulfate, concentrated under reduced pressure and purified by column chromatography (Alox, 1% MeOH in DCM). Yield: 37% (2.0 g, 6.04 mmol)

Stage 6: Benzyl (1S,3R)-3-(4-methylpiperazin-1-yl) cyclohexylcarbamate ((1S,4R)-7,7-dimethyl-2-oxo-bicyclo[2.2.1]heptan-1-yl)methanesulfonate A mixture of (cis)-benzyl-3-(4-methylpiperazin-1-yl)cyclohexylcarbamate (2.0 g, 6.04 mmol, 1.0 eq.), isopropyl acetate (12 ml) and toluene (2.5 ml) was heated for 15 minutes at 65° C. (1S)-(+) Camphorsulfonic acid (700 mg, 3.02 mmol, 0.5 eq.) and water (0.1 ml) were added at RT and the mixture was heated for 3 hours at 75° C. Stirring was then carried out for 3 hours at RT and the mixture was subsequently allowed to stand overnight at RT for crystallization. The resulting precipitate was filtered off and washed with isopropyl acetate (20 ml). For purification, the desired product was recrystallized from ethanol/isopropyl acetate. Yield: 14% (500 mg, 0.888 mmol)

Stage 7: Benzyl (1S,3R)-3-(4-methylpiperazin-1-yl) cyclohexylcarbamate

Benzyl (1S,3R)-3-(4-methylpiperazin-1-yl)cyclohexylcarbamate ((1S,4R)-7,7-dimethyl-2-oxobicyclo[2.2.1]heptan-1-yl)methanesulfonate (30. g, 5.32 mmol, 1.0 eq.) was taken up in toluene (15 ml); a solution of NaOH (0.234 g, 5.852 mmol, 1.1 eq.) in water (15 ml) was added and stirring was carried out for 30 minutes at RT. The reaction mixture was diluted with toluene (15 ml) and the phases were separated. The org. phase was washed with sat. NaCl solution (15 ml), dried over sodium sulfate and concentrated under reduced pressure. Yield: 96% (1.7 g, 5.13 mmol)

Stage 8: (1S,3R)—N-Methyl-3-(4-methylpiperazin-1-yl)cyclohexanamine

Benzyl (1S,3R)-3-(4-methylpiperazin-1-yl)cyclohexylcarbamate (2.0 g, 6.0472 mmol, 1.0 eq.) was dissolved in THF (10 ml) and added dropwise at 0° C. to a suspension of LAH (0.345 g, 9.06 mmol, 1.5 eq.) in THF (30 ml). The reaction mixture was then refluxed for 30 minutes. The reaction mixture was subsequently cooled to 0° C., hydrolyzed with 10% NaOH solution (0.35 ml), filtered off and washed with THF (2×50 ml). The filtrate was concentrated under reduced pressure and dried. Yield: 94% (1.2 g, 5.68 mmol)

Synthesis of amine AMN-50

4-(3,4-Dihydro-2,6-naphthyridin-2(1H)-yl)-N-methylcyclohexanamine (AMN-50)

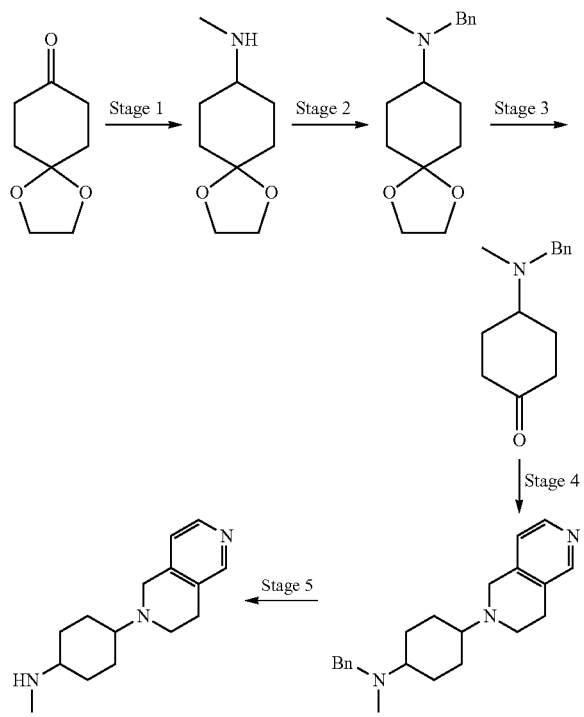

Stage 1: N-Methyl-1,4-dioxaspiro[4.5]decan-8-amine 1,4-Dioxaspiro[4.5]decan-8-one (10.0 g, 64.10 mmol, 1.0 eq.) was dissolved in MeOH (100 ml); AcOH (0.1 ml) and $CH_3NH_2 \cdot HCl$ (8.65 g, 128.21 mmol, 2.0 eq.) were added and stirring was carried out for 2 hours at RT. $NaCNBH_3$ (10.0 g, 160.256 mmol, 2.5 eq.) was added in portions at 0° C. and the mixture was then stirred for 16 hours at RT. The reaction mixture was concentrated under reduced pressure and the residue was purified by column chromatography (Alox, 5% MeOH in DCM). Yield: 54% (6.0 g, 35.08 mmol)

Stage 2: N-Benzyl-N-methyl-1,4-dioxaspiro[4.5]decan-8-amine

N-Methyl-1,4-dioxaspiro[4.5]decan-8-amine (4.0 g, 23.39 mmol, 1.0 eq.) was dissolved in DCM (70 ml); benzaldehyde (2.83 g, 28.07 mmol, 1.2 eq.) and AcOH (0.2 ml) were added and the mixture was stirred for 30 minutes at RT. NaBH(OAc)$_3$ (14.8 g, 70.17 mmol, 3.0 eq.) was added at 0° C. and the reaction mixture was stirred for a further 14 hours at RT. After monitoring by TLC, water (100 ml) was added to the reaction and the phases were separated. The aqueous phase was extracted with 10% MeOH in DCM (2×100 ml). The combined org. phases were washed in succession with water (100 ml) and sat. NaCl solution (100 ml), dried over sodium sulfate, concentrated under reduced pressure and purified by column chromatography (silica gel, 4% MeOH in DCM). Yield: 49% (3.0 g, 11.49 mmol)

Stage 3: 4-(Benzyl(methyl)amino)cyclohexanone

N-Benzyl-N-methyl-1,4-dioxaspiro[4.5]decan-8-amine (1.0 g, 3.83 mmol, 1.0 eq.) was dissolved in MeOH (12 ml); 6 M HCl solution (12 ml) was added at 0° C., and stirring was carried out for 16 hours at RT. After monitoring by TLC, the solvent was removed under reduced pressure and the residue was taken up in water (50 ml), adjusted to pH 8-9 with $NaCHO_3$ (solid) and extracted with DCM (2×50 ml). The combined org. phases were washed with water and sat. NaCl solution (in each case 50 ml), dried over sodium sulfate and concentrated under reduced pressure and dried. The crude product was used in the next stage without being purified further. Yield: 74% (620 mg, 2.857 mmol)

Stage 4: N-Benzyl-4-(3,4-dihydro-2,6-naphthyridin-2(1H)-yl)-N-methylcyclohexanamine 4-(Benzyl(methyl)amino)cyclohexanone (680 mg, 3.133 mmol, 1.0 eq.) and 1,2,3,4-tetrahydro-2,6-naphthyridine dihydrochloride (713 mg, 3.44 mmol, 1.1 eq.) were dissolved in MeOH (20 ml) and the mixture was stirred for 5 hours at RT. Then the solution was cooled to 0° C., $NaCNBH_3$ (393 mg, 3.26 mmol, 2.0 eq.) was added and the mixture was stirred for 16 hours at RT. The reaction solution was concentrated to dryness under reduced pressure and purified by column chromatography (Alox, 1.2% MeOH in DCM). Yield: 38% (400 mg, 1.194 mmol)

Stage 5: 4-(3,4-Dihydro-2,6-naphthyridin-2(1H)-yl)-N-methylcyclohexanamine (AMN-50)

N-Benzyl-4-(3,4-dihydro-2,6-naphthyridin-2(1H)-yl)-N-methylcyclohexanamine (250 mg, 0.746 mmol, 1.0 eq.) was dissolved in MeOH (5 ml) and degassed with $N_2$. Pd(OH)$_2$ (250 mg) was then added and hydrogenation was carried out for 8 hours. After monitoring by TLC, the reaction mixture was filtered over Celite and the filtrate was concentrated under reduced pressure. The crude product so obtained was used in the next stage without being purified further. Yield: 67% (124 mg, 0.506 mmol)

Synthesis of amine AMN-51

1-(6-Methoxypyridin-3-yl)-N-methylpiperidin-4-amine (AMN-51)

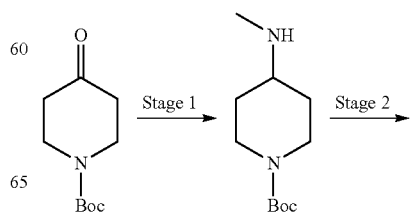

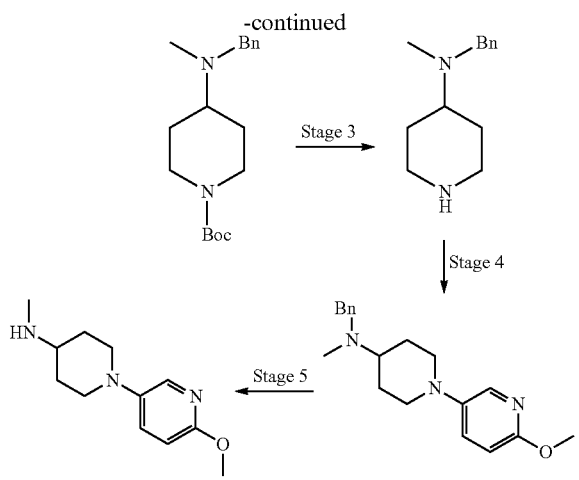

Stage 1: tert-Butyl 4-(methylamino)piperidine-1-carboxylat tert-Butyl 4-oxopiperidine-1-carboxylate (5.0 g, 25.126 mmol, 1.0 eq.) was dissolved in MeOH (50 ml); AcOH (2 drops) and $CH_3NH_2 \cdot HCl$ (2.2 g, 32.663 mmol, 1.3 eq.) were added and stirring was carried out for 2 hours at RT. NaCNBH$_3$ (3.11 g, 50.25 mmol, 2.0 eq.) was added in portions at 0° C. and the mixture was stirred for 14 hours at RT. The reaction mixture was concentrated under reduced pressure and the residue was purified by column chromatography (Alox, 3% MeOH in DCM). Yield: 55% (3.0 g, 14.019 mmol)

Stage 2: tert-Butyl 4-(benzyl(methyl)amino)piperidine-1-carboxylate tert-Butyl 4-(methylamino)piperidine-1-carboxylate (3.0 g, 14.019 mmol, 1.0 eq.) was dissolved in DCM (30 ml); benzaldehyde (1.7 ml, 16.823 mmol, 1.2 eq.) was added and the mixture was stirred for 1 hour at RT. NaBH(OAc)$_3$ (4.81 g, 28.038 mmol, 3.0 eq.) was then added at 0° C. and the reaction mixture was stirred for 14 hours at RT. After monitoring by TLC, DCM (300 ml) was added to the reaction and washing was carried out in succession with sodium hydrogen carbonate solution (100 ml), water (100 ml) and sat. NaCl solution (100 ml). The organic phase was dried over sodium sulfate, concentrated under reduced pressure and purified by column chromatography (silica gel, 1% MeOH in DCM). Yield: 28% (1.2 g, 3.947 mmol)

Stage 3: N-Benzyl-N-methylpiperidin-4-amine tert-Butyl 4-(benzyl(methyl)amino)piperidine-1-carboxylate (1.2 g, 3.947 mmol, 1.0 eq.) was dissolved in DCM (10 ml); TFA (1.2 ml) was added at 0° C. and the mixture was stirred for 2 hours at RT. The reaction mixture was concentrated under reduced pressure, taken up several times in toluene and dried. The crude product was used in the next stage without being purified further.

Stage 4: N-Benzyl-1-(6-methoxypyridin-3-yl)-N-methylpiperidin-4-amine

N-Benzyl-N-methylpiperidin-4-amine (3.947 mmol, 1.0 eq.), 5-bromo-2-methoxypyridine (614 μl, 4.737 mmol, 1.2 eq.) and t-BuONa (757 mg, 7.894 mmol, 2.0 eq.) were dissolved in toluene (12 ml) and degassed with argon. Xantphos (136 mg. 0.237 mmol, 0.06 eq.) and Pd$_2$(dba)$_3$ (72 mg, 0.079 mmol, 0.02 eq.) were then added and the mixture was heated for 4 hours at 90° C. After monitoring by TLC, the reaction mixture was concentrated under reduced pressure and purified by column chromatography (silica gel, 3% MeOH in DCM). Yield: 36% (450 mg, 1.447 mmol)

Stage 5: 1-(6-Methoxypyridin-3-yl)-N-methylpiperidin-4-amine (AMN-51)

N-Benzyl-1-(6-methoxypyridin-3-yl)-N-methylpiperidin-4-amine (450 mg, 1.447 mmol, 1.0 eq.) was dissolved in MeOH (6 ml) and degassed with N$_2$. Pd(OH)$_2$ (225 mg, 50%) was then added and hydrogenation was carried out for 3 hours. After monitoring by TLC, the reaction mixture was filtered over Celite and the filtrate was concentrated under reduced pressure and used in the next stage without being purified further. Yield: 78% (250 mg, 1.13 mmol)

Synthesis of Amine AMN-52

N,N-Dimethyl-4-(4-(methylamino)piperidin-1-yl)pyridin-2-amine (AMN-52)

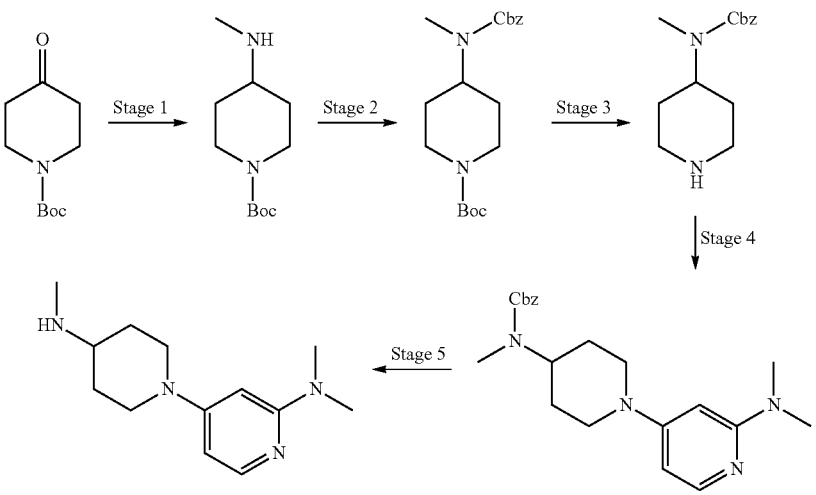

Stage 1: tert-Butyl 4-(methylamino)piperidine-1-carboxylate tert-Butyl 4-oxopiperidine-1-carboxylate (5.0 g, 25.126 mmol, 1.0 eq.) was dissolved in MeOH (50 ml); AcOH (2 drops) and $CH_3NH_2 \cdot HCl$ (2.2 g, 32.663 mmol, 1.3 eq.) were added and stirring was carried out for 2 hours at RT. NaCNBH$_3$ (3.11 g, 50.25 mmol, 2.0 eq.) was added in portions at 0° C. and the mixture was stirred for 14 hours at RT. The reaction mixture was concentrated under reduced pressure and the residue was purified by column chromatography (Alox, 3% MeOH in DCM). Yield: 55% (3.0 g, 14.019 mmol)

Stage 2: tert-Butyl 4-((benzyloxycarbonyl)(methyl)amino)piperidine-1-carboxylate Cbz-Cl (0.393 ml, 2.8 mol, 1.2 eq.) was added to a mixture of tert-butyl 4-(methylamino)-piperidine-1-carboxylate (500 mg, 2.336 mmol, 1.0 eq.) and $K_2CO_3$ (616 mg, 4.67 mmol, 2.0 eq.) in DCM (6 ml), and the mixture was stirred for 14 hours at RT. The reaction mixture was diluted with DCM (100 ml), washed with water and sat. NaCl solution (in each case 40 ml), dried over sodium sulfate, concentrated under reduced pressure and purified by column chromatography (silica gel, 15% ethyl acetate in hexane). Yield: 49% (400 mg, 1.149 mmol)

Stage 3: Benzyl methyl(piperidin-4-yl)carbamate tert-Butyl 4-((benzyloxycarbonyl)(methyl)amino)piperidine-1-carboxylate (0.3 g, 0.682 mmol, 1.0 eq.) was dissolved in DCM (10 ml); TFA (2.5 ml) was added at 0° C. and stirring was carried out for 2 hours at RT. The reaction mixture was concentrated under reduced pressure, taken up several times in toluene and dried. The crude product was used in the next stage without being purified further.

Stage 4: Benzyl 1-(2-(dimethylamino)pyridin-4-yl)piperidin-4-yl(methyl)carbamate Benzyl methyl(piperidin-4-yl)carbamate (0.862 mmol, 1.0 eq.), 4-bromo-N,N-dimethylpyridin-2-amine (173 mg, 0.862 mmol, 1.0 eq.) and t-BuONa (193 mg, 1.72 mmol, 2.0 eq.) were taken up in toluene (10 ml) and degassed with $N_2$. BINAP (26 mg, 0.043 mmol, 0.05 eq.) and $Pd_2(dba)_3$ (39 mg, 0.043 mmol, 0.05 eq.) were then added and the mixture was heated for 16 hours at 80° C. After monitoring by TLC, the reaction mixture was filtered over Celite and the filtrate was concentrated under reduced pressure and purified by column chromatography (silica gel, 4% MeOH in DCM). Yield: 63% (200 mg, 03543 mmol)

Stage 5: N,N-Dimethyl-4-(4-(methylamino)piperidin-1-yl)pyridin-2-amine (AMN-52)

Benzyl 1-(2-(dimethylamino)pyridin-4-yl)piperidin-4-yl(methyl)carbamate (280 mg, 0.76 mmol, 1.0 eq.) was dissolved in MeOH (10 ml) and degassed with $N_2$. Pd(OH)$_2$ (140 mg, 50%) was then added and hydrogenation was carried out for 3 hours. After monitoring by TLC, the reaction mixture was filtered over Celite, the filtrate was concentrated under reduced pressure and the crude product was used in the next stage without being purified further. Yield: 96% (170 mg, 0.726 mmol)

Synthesis of Amine AMN-53

4-(Methylamino)-1-(pyridin-4-yl)piperidin-2-one (AMN-53)

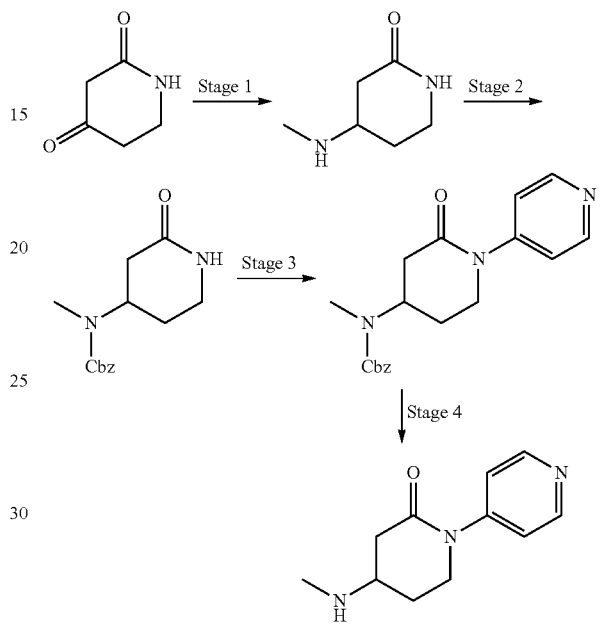

Stage 1: 4-(Methylamino)piperidin-2-one

Piperidine-2,4-dione (2.0 g, 25.126 mmol, 1.0 eq.) was dissolved in MeOH (20 ml); AcOH (0.1 ml) and $CH_3NH_2 \cdot HCl$ (2.37 g, 35.398 mmol, 2.0 eq.) were added and stirring was carried out for 2 hours at RT. NaCNBH$_3$ (3.29 g, 53.097 mmol, 3.0 eq.) was added in portions at 0° C. and the mixture was stirred for 14 hours at RT. After monitoring by TLC, the reaction mixture was filtered, the filtrate was concentrated under reduced pressure and the residue was used in the next stage without being purified further. Yield: 81% (1.814 g, 14.173 mmol)

Stage 2: Benzyl methyl(2-oxopiperidin-4-yl)carbamate

Cbz-Cl (7.2 ml, 21.259 mol, 1.5 eq., 50% solution in toluene) was added at 0° C. to a mixture of 4-(methylamino)piperidin-2-one (1.814 g, 14.173 mmol, 1.0 eq.) and $K_2CO_3$ (3.91 g, 28.346 mmol, 2.0 eq.) in THF (50 ml) and the mixture was stirred for 14 hours at RT. After monitoring by TLC, the reaction mixture was diluted with DCM (300 ml), washed with water and saturated NaCl solution (in each case 150 ml), dried over sodium sulfate, concentrated under reduced pressure and purified by column chromatography (Alox, 1% MeOH in DCM). Yield: 27% (1.0 g, 3.82 mmol)

Stage 3: Benzyl methyl(2-oxo-1-(pyridin-4-yl)piperidin-4-yl)carbamate

Benzyl methyl(2-oxopiperidin-4-yl)carbamate (300 mg, 1.145 mmol, 1.0 eq.), 4-bromopyridine HCl (244 mg, 1.259 mmol, 1.1 eq.) and Cs$_2$CO$_3$ (744 mg, 2.29 mmol, 2.0 eq.) were taken up in toluene and degassed with N$_2$. Xantphos (66 mg, 0.114 mmol, 0.1 eq.) and Pd$_2$(dba)$_3$ (104 mg, 0.114 mmol, 0.1 eq.) were then added and the mixture was heated for 14 hours at 90° C. After monitoring by TLC, the reaction mixture was filtered over Celite and the filtrate was concentrated under reduced pressure and purified by column chromatography (Alox, 1% MeOH in DCM). Yield: 41% (160 mg, 0.472 mmol)

Stage 4: 4-(Methylamino)-1-(pyridin-4-yl)piperidin-2-one (AMN-53)

Benzyl methyl(2-oxo-1-(pyridin-4-yl)piperidin-4-yl)carbamate (300 mg, 0.885 mmol, 1.0 eq.) was dissolved in MeOH and degassed with N$_2$. Pd(OH)$_2$ (240 mg) was then added and hydrogenation was carried out for 4 hours. After monitoring by TLC, the reaction mixture was filtered over Celite, the filtrate was concentrated under reduced pressure and the crude product was purified by column chromatography (Alox, 3% MeOH in DCM). Yield: 77% (140 mg, 0.683 mmol)

Synthesis of Amine AMN-54

N,N-Dimethyl-5-(4-(methylamino)piperidin-1-yl)pyridin-2-amine (AMN-54)

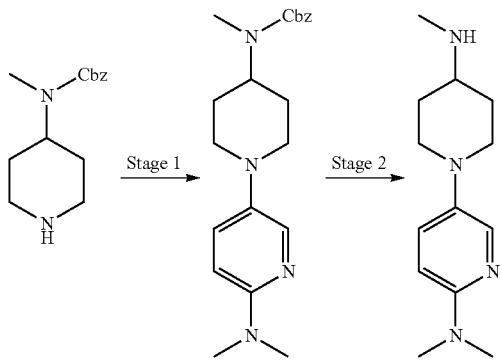 [SMILES: CN(C(=O)OCc1ccccc1)C1CCNCC1 ; CN(C)c1ccc(N2CCC(N(C)C(=O)OCc3ccccc3)CC2)cn1 ; CNC1CCN(c2ccc(N(C)C)nc2)CC1]

Stage 1: Benzyl 1-(6-(dimethylamino)pyridin-3-yl)piperidin-4-yl(methyl)carbamate Benzyl methyl(piperidin-4-yl)carbamate (stage 3 AMN-52) (616 mg, 2.4875 mmol, 1.0 eq.), 5-bromo-2-dimethylaminopyridine (500 mg, 2.4875 mmol, 1.0 eq.) and KOBu$^t$ (557 mg, 4.978 mmol, 2.0 eq.) were taken up in toluene (15 ml) and degassed with N$_2$. BINAP (77 mg, 0.124 mmol, 0.05 eq.) and Pd$_2$(dba)$_3$ (113 mg, 0.124 mmol, 0.05 eq.) were then added and the mixture was heated for 16 hours at 80° C. After monitoring by TLC, the reaction mixture was filtered over Celite and the filtrate was concentrated under reduced pressure and purified by column chromatography (silica gel, 2% MeOH in DCM). Yield: 67% (500 mg, 1.358 mmol)

Stage 2: N,N-Dimethyl-5-(4-(methylamino)piperidin-1-yl)pyridin-2-amine (AMN-54)

Benzyl 1-(6-(dimethylamino)pyridin-3-yl)piperidin-4-yl(methyl)carbamate (400 mg, 1.086 mmol, 1.0 eq.) was dissolved in MeOH (10 ml) and degassed with argon. Pd(OH)$_2$ (200 mg) was then added and hydrogenation was carried out for 3 hours. After monitoring by TLC, the reaction mixture was filtered over Celite, the filtrate was concentrated under reduced pressure and the crude product was used in the next stage without being purified further. Yield: 94% (240 mg, 1.0212 mmol)

Synthesis of Amine AMN-55

1-(2-Methoxypyridin-4-yl)-N-methylpiperidin-4-amine (AMN-55)

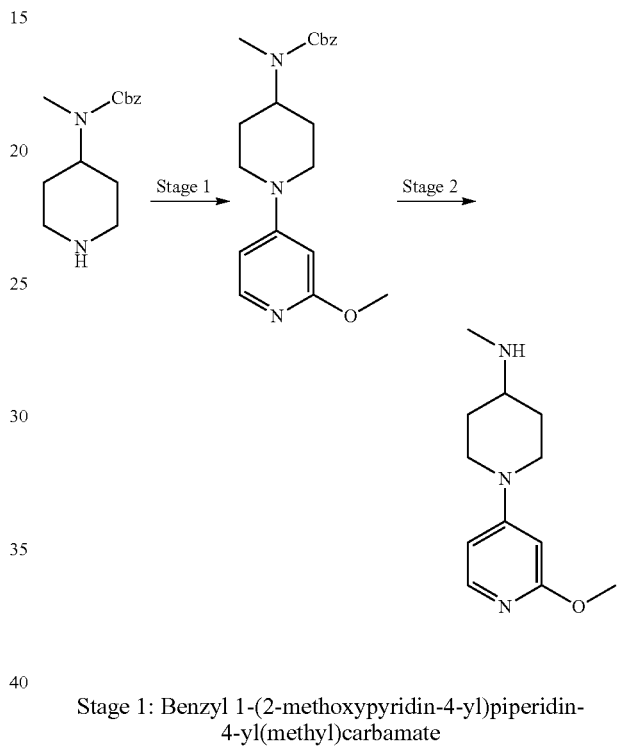

Stage 1: Benzyl 1-(2-methoxypyridin-4-yl)piperidin-4-yl(methyl)carbamate

Benzyl methyl(piperidin-4-yl)carbamate (stage 3 AMN-52) (1.43 mmol, 1.0 eq.), 2-methoxy-4-bromopyridine and BuONa (411 mg, 4.29 mmol, 3.0 eq.) were taken up in toluene (20 ml) and degassed with argon. Xantphos (50 mg, 0.085 mmol, 0.06 eq.) and Pd$_2$(dba)$_3$ (26 mg, 0.028 mmol, 0.02 eq.) were then added and the mixture was heated for 16 hours at 90° C. After monitoring by TLC, the reaction mixture was concentrated and the residue was taken up in DCM (100 ml), washed with water and sat. NaCl solution (50 ml), dried over sodium sulfate and concentrated under reduced pressure. The crude product was purified by column chromatography (silica gel, 0.5% MeOH in DCM). Yield: 51% (260 mg, 0.732 mmol)

Stage 2: 1-(2-Methoxypyridin-4-yl)-N-methylpiperidin-4-amine (AMN-55)

Benzyl 1-(2-methoxypyridin-4-yl)piperidin-4-yl(methyl)carbamate (250 mg, 0.704 mmol, 1.0 eq.) was dissolved in MeOH (20 ml) and degassed with argon. Pd/C (75 mg) was then added and hydrogenation was carried out for 3 hours. After monitoring by TLC, the reaction mixture was filtered over Celite and washed with MeOH (2×20 ml) and the filtrate was concentrated under reduced pressure. The crude product was used in the next stage without being purified further. Yield: 99% (155 mg, 0.701 mmol)

Synthesis of amine AMN-58

N-Methyl-4-(pyridin-4-yloxy)cyclohexanamine (AMN-58)

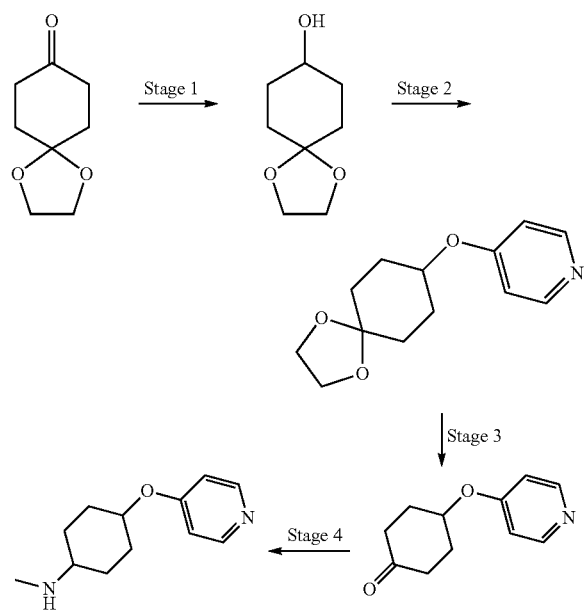

Stage 1: 1,4-Dioxaspiro[4.5]decan-8-ol 1,4-Dioxaspiro[4.5]decan-8-one (5.4 g, 34.571 ml, 1.0 eq.) was dissolved in MeOH (35 ml). NaBH₄ (1.57 g, 41.485 mmol, 1.2 eq.) was added at 0° C. and the mixture was stirred for 1 hour at RT. After monitoring by TLC, the reaction mixture was concentrated and the residue was taken up in water (100 ml) and extracted with DCM (2×150 ml). The combined org. phases were washed with water (150 ml) and sat. NaCl solution (200 ml), dried over sodium sulfate, concentrated under reduced pressure and used in the next stage without being purified further. Yield: 90% (4.9 g, 31.012 mmol)

Stage 2: 4-(1,4-Dioxaspiro[4.5]decan-8-yloxy)pyridine 1,4-Dioxaspiro[4.5]decan-8-ol (4.93 g, 31.202 mmol, 1.0 eq.) was dissolved in DMSO (100 ml); potassium tert-butylate (10.5 g, 93.61 mmol, 3.0 eq.) was added at 0° C. and the mixture was stirred for 1 hour at RT. 4-Bromopyridine HCl (9.1 g, 46.803 mmol, 1.5 eq.) was then added at 0° C. and stirring was carried out for 16 hours at RT. After monitoring by TLC, the reaction mixture was concentrated and the residue was taken up in water (200 ml) and extracted with DCM (2×200 ml). The combined org. phases were washed with water (200 ml) and sat. NaCl solution (250 ml), dried over sodium sulfate, concentrated under reduced pressure and purified by column chromatography (silica gel, 40% ethyl acetate in hexane). Yield: 35% (2.6 g, 11.063 mmol)

Stage 3: 4-(Pyridin-4-yloxy)cyclohexanone 4-(1,4-Dioxaspiro[4.5]decan-8-yloxy)pyridine (1.6 g, 6.808 mmol, 1.0 eq.) was dissolved in MeOH (16 ml). 6 M HCl solution (16 ml) was added at 0° C. to the solution and the mixture was then stirred for 16 hours at RT. After monitoring by TLC, the solvent was removed under reduced pressure and the residue was taken up in water (50 ml), adjusted to pH 9 with NaHCO₃ solution and extracted with DCM (2×75 ml). The combined org. phases were washed with water and sat. NaCl solution (in each case 100 ml), dried over sodium sulfate and concentrated under reduced pressure and dried. The crude product was used in the next stage without being purified further. Yield: 89% (1.15 g, 6.052 mmol)

Stage 4: N-Methyl-4-(pyridin-4-yloxy)cyclohexanamine (AMN-58)

4-(Pyridin-4-yloxy)cyclohexanone (1.15 g, 6.052 mmol, 1.0 eq.) was dissolved in MeOH (15 ml); CH₃NH₂.HCl (490 mg, 7.263 mmol, 1.2 eq.) was added and stirring was carried out for 3 hours at RT. NaCNBH₃ (760 mg, 12.105 mmol, 2.0 eq.) was added in portions at 0° C. and the mixture was stirred for 16 hours at RT. After monitoring by TLC, the reaction mixture was concentrated under reduced pressure and the residue was taken up in water (50 ml) and extracted with 10% MeOH in DCM (2×75 ml). The combined org. phases were dried over sodium sulfate, concentrated and purified by column chromatography (Alox, 3% MeOH in DCM). Yield: 21% (270 mg, 1.310 mmol)

Synthesis of Amine AMN-60

4-(4-(Methylamino)piperidin-1-yl)picolinonitrile (AMN-60)

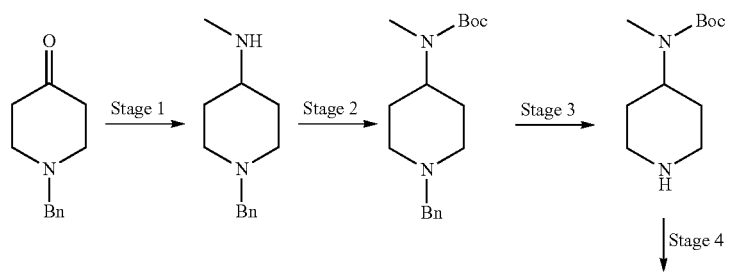

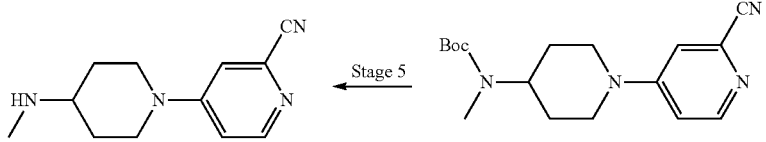

Stage 1: 1-Benzyl-N-methylpiperidin-4-amine

1-Benzylpiperidin-4-one (5.0 g, 26.315 mmol, 1.0 eq.) was dissolved in MeOH (78 ml); AcOH (0.2 ml) and $CH_3NH_2 \cdot HCl$ (2.6 g, 39.47 mmol, 1.5 eq.) were added and stirring was carried out for 2 hours at RT. $NaCNBH_3$ (3.3 g, 52.63 mmol, 2.0 eq.) was then added in portions at 0° C. and the mixture was stirred for 16 hours at RT. The reaction mixture was concentrated under reduced pressure. The residue was taken up in sat. sodium hydrogen carbonate solution (150 ml) and extracted with DCM (2×200 ml). The combined org. phases were dried over sodium sulfate, concentrated and used in the next stage without being purified further. Yield: 92% (5.0 g, 24.509 mmol)

Stage 2: tert-Butyl 1-benzylpiperidin-4-yl(methyl)carbamate

Boc anhydride (6.0 ml, 26.96 mmol, 1.1 eq.) was added at 0° C. to a solution of 1-benzyl-N-methylpiperidin-4-amine (5.0 g, 24.50 mmol, 1.0 eq.) and TEA (10.9 g, 73.50 mmol, 3.0 eq.) in DCM (90 ml) and the mixture was stirred for 16 hours at RT. After monitoring by TLC, the reaction solution was diluted with DCM (250 ml), washed with water and sat. NaCl solution (in each case 100 ml), dried over sodium sulfate, concentrated under reduced pressure and purified by column chromatography (silica gel, 20% ethyl acetate in hexane). Yield: 60% (4.5 g, 14.80 mmol)

Stage 3: tert-Butyl methyl(piperidin-4-yl)carbamate tert-Butyl 1-benzylpiperidin-4-yl(methyl)carbamate (1.0 g, 3.289 mmol, 1.0 eq.) was dissolved in MeOH (15 ml) and degassed with argon. Pd/C (300 mg) was then added and hydrogenation was carried out for 4 hours. After monitoring by TLC, the reaction mixture was filtered over Celite and the filtrate was concentrated under reduced pressure. The crude product was used in the next stage without being purified further. Yield: 85% (600 mg, 2.803 mmol)

Stage 4: tert-Butyl 1-(2-cyanopyridin-4-yl)piperidin-4-yl(methyl)carbamate

A mixture of tert-butyl methyl(piperidin-4-yl)carbamate (465 mg, 2.173 mmol, 1.0 eq.), 4-chloropyridine-2-carbonitrile (300 mg, 2.173 mmol, 1.0 eq.) and $K_2CO_3$ (600 mg, 4.34 mmol, 2.0 eq.) in THF (4 ml) was heated for 48 hours at 100° C. in a pressure vessel. The mixture was filtered and washed with THF (10 ml). The filtrate was concentrated and purified by column chromatography (silica gel, 1% MeOH in DCM). Yield: 44% (300 mg, 0.949 mmol)

Stage 5: 4-(4-(Methylamino)piperidin-1-yl)picolinonitrile (AMN-60)

tert-Butyl 1-(2-cyanopyridin-4-yl)piperidin-4-yl(methyl)carbamate (300 mg, 0.949 mmol, 1.0 eq.) was dissolved in DCM (10 ml); TFA (2 ml) was added at 0° C. and stirring was carried out for 2 hours at RT. The reaction mixture was concentrated under reduced pressure, taken up several times in toluene and dried. The crude product was used in the next stage without being purified further.

Synthesis of amine AMN-63

N-Methyl-1-(1-methyl-1H-imidazol-2-yl)piperidin-4-amine (AMN-63)

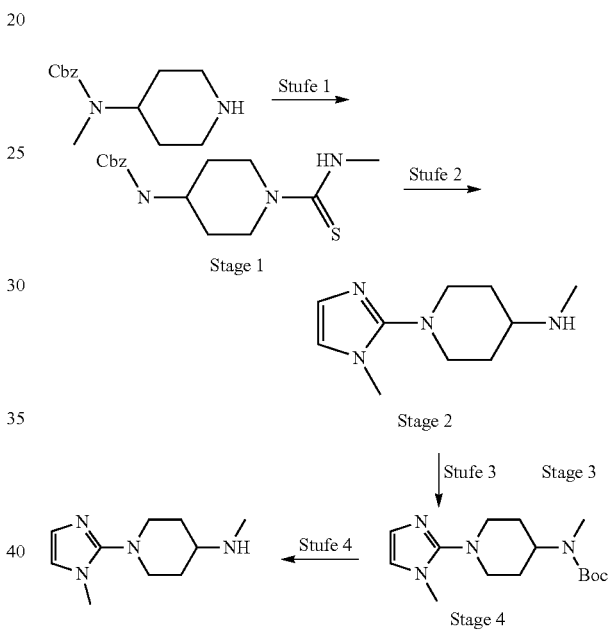

Stage 1: Benzyl methyl(1-(methylcarbamothioyl)piperidin-4-yl)carbamate

A solution of methyl isothiocyanate (500 mg, 6.8493 mmol, 1 eq) in dichloromethane (4 ml) was added dropwise over a period of 5 min to a solution of benzyl methyl(piperidin-4-yl)carbamate (stage 3 AMN-52) (1.7 g, 6.8493 mmol, 1 eq). When the addition was complete, the reaction mixture was stirred for 20 hours at room temperature. Concentration under reduced pressure was then carried out and the crude product was purified by column chromatography (silica gel, 2% methanol in dichloromethane). Yield: 45% (1 g, 3.115 mmol)

Stage 2: N-Methyl-1-(1-methyl-1H-imidazol-2-yl)piperidin-4-amine

A solution of iodomethane (0.22 ml, 3.4267 mmol, 1.1 eq) in methanol (5 ml) was added dropwise over a period of 5 min to a solution of benzyl methyl(1-(methylcarbamothioyl)-piperidin-4-yl)carbamate (1 g, 3.115 mmol, 1 eq) in methanol (10 ml). Stirring was then carried out for 20 h at room temperature. When the reaction was complete according to TLC monitoring, the reaction mixture was concentrated under reduced pressure. The residue was taken up in pyridine (15 ml); aminoacetaldehyde-diethylacetal (455 mg, 3.4267 mmol, 1.1 eq) was added and refluxing was carried out for 10 h. The reaction mixture was concentrated under reduced pressure, 2 N HCl solution (20 ml) was added, and the mixture was refluxed for 5 h. The reaction mixture was concentrated under reduced pressure and dried by removal of toluene by distillation. The crude product was used in the next stage without being purified further. Yield: 1.1 g (5.67 mmol)

Stage 3: tert-Butyl methyl(1-(1-methyl-1H-imidazol-2-yl)piperidin-4-yl)carbamate Boc anhydride (1.4 ml, 6.237 mmol, 1.1 eq) was added dropwise at 0° C. to a solution of N-methyl-1-(1-methyl-1H-imidazol-2-yl)piperidin-4-amine (1.1 g, 5.67 mmol, 1 eq) and TEA (2.4 ml, 17.01 mmol, 3 eq) in dichloromethane (20 ml). The reaction mixture was stirred for 16 h at room temperature. When the reaction was complete according to TLC monitoring, the mixture was diluted with dichloromethane (100 ml), washed with water (100 ml) and saturated sodium chloride solution (100 ml) and dried over sodium sulfate. The solvent was removed by distillation under reduced pressure and the crude product was purified by column chromatography (silica gel, 2% methanol/dichloromethane). The desired product was in the form of a light-yellow solid. Yield: 25% (400 mg, 1.36 mmol)

Stage 4: N-Methyl-1-(1-methyl-1H-imidazol-2-yl)piperidin-4-amine (AMN-63)

Trifluoroacetic acid (1 ml) was added at 0° C. to a solution of tert-butyl methyl(1-(1-methyl-1H-imidazol-2-yl)piperidin-4-yl)carbamate (241 mg, 0.82 mmol, 1 eq) in dichloromethane (5 ml), and the reaction mixture was stirred for 1 h at room temperature. Concentration under reduced pressure was then carried out. The crude product so obtained was used in the next stage without being purified further.

Synthesis of Amine AMN-64

1-(2-Methoxy-6-methylpyrimidin-4-yl)-N-methylpiperidin-4-amine (AMN-64)

Stage 1: 2-Methoxy-6-methylpyrimidin-4(3H)-one

Ca(OH)$_2$ (7.2 g, 97.56 mmol, 1.2 eq) was added at 0° C. to a mixture of O-methylisourea hemisulfate (10 g, 81.3 mmol, 1 eq) and ethyl 3-oxobutanoate (10.5 g, 81.3 mmol, 1 eq) in water (160 ml). Stirring was then carried out for 24 h at room temperature. When the reaction was complete according to TLC monitoring, filtration over Celite was carried out. The filtrate was concentrated under reduced pressure and dried. The desired product was in the form of a white solid and was used in the next stage without being purified further. Yield: 12 g Stage 2: 4-Chloro-2-methoxy-6-methylpyrimidine 2-Methoxy-6-methylpyrimidin-4(3H)-one (12 g, 85.71 mmol, 1 eq) was heated for 30-40 min at 100° C. in POCl$_3$ (85 ml). The reaction mixture was then concentrated and diluted with ice-water (100 ml). The aqueous phase was rendered alkaline (pH~9) with NaHCO$_3$ and extracted with ethyl acetate (2×200 ml). The combined organic phases were washed with saturated sodium chloride solution (100 ml), dried over sodium sulfate and concentrated under reduced pressure. The crude product was purified by column chromatography (silica gel, 2% ethyl acetate/hexane). The desired product was in the form of a light-yellow solid. Yield: 2.3% (300 mg, 1.8987 mmol) after 2 stages Stage 3: Benzyl 1-(2-methoxy-6-methylpyrimidin-4-yl)piperidin-4-yl(methyl)carbamate A mixture of 4-chloro-2-methoxy-6-methylpyrimidine (300 mg, 1.8987 mmol, 1 eq), benzyl methyl(piperidin-4-yl)carbamate (stage 3 AMN-52) (470 mg, 1.8987 mmol, 1 eq) and K$_2$CO$_3$ (523 mg, 3.796 mmol, 2 eq) in acetone (10 ml) was refluxed for 16 h. When the reaction was complete according to TLC monitoring, filtration over Celite was carried out and the filtrate was concentrated under reduced pressure. The crude product was purified by column chromatography (silica gel, 2% methanol/dichloromethane). The desired product was in the form of a light-yellow solid. Yield: 71% (500 mg, 1.3513 mmol)

Stage 4: 1-(2-Methoxy-6-methylpyrimidin-4-yl)-N-methylpiperidin-4-amine (AMN-64)

A solution of benzyl 1-(2-methoxy-6-methylpyrimidin-4-yl)piperidin-4-yl(methyl)carbamate (400 mg, 1.0810 mmol, 1

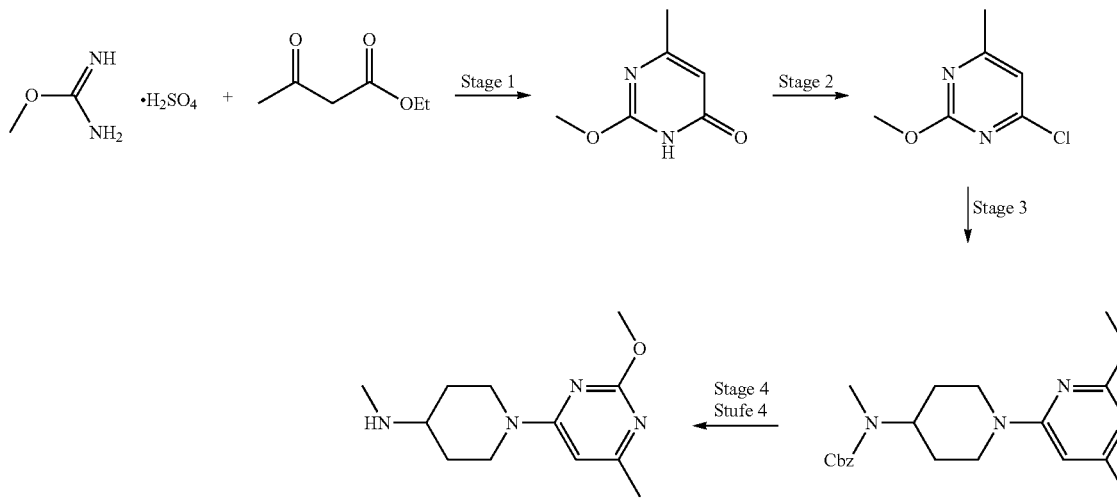

eq) in methanol (6 ml) was degassed for 20 min with argon, and then Pd(OH)$_2$ (200 mg) was added. The reaction mixture was stirred for 3 h at room temperature under a hydrogen atmosphere (balloon), and then the catalyst was filtered off. The filtrate was concentrated under reduced pressure. The crude product so obtained was in the form of a colourless liquid, which was used in the next stage without being purified further. Yield: 94% (240 mg, 1.0169 mmol)

Synthesis of Amine AMN-65

N-Methyl-1-(6-methylpyrazin-2-yl)piperidin-4-amine (AMN-65)

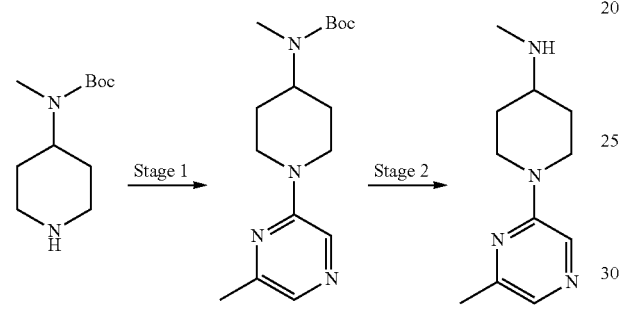

Stage 1: tert-Butyl methyl(1-(6-methylpyrazin-2-yl)piperidin-4-yl)carbamate

KOBu$^t$ (483 mg, 4.32 mmol, 2.5 eq) was added at room temperature to a solution of tert-butyl methyl(piperidin-4-yl)carbamate (stage 3 AMN-60) (370 mg, 1.72 mmol, 1 eq) and 2-chloro-6-methylpyrazine (244 mg, 1.9 mmol, 1.1 eq) in toluene (50 ml) and the mixture was degassed for 30 min with argon. BINAP (64.5 mg, 0.103 mmol, 0.06 eq) and Pd$_2$(dba)$_3$ (31.6 mg, 0.034 mmol, 0.02 eq) were added and the reaction mixture was refluxed for 16 h. After cooling, concentration under reduced pressure was carried out. The residue was taken up in dichloromethane (50 ml) and washed with water (30 ml) and saturated sodium chloride solution (30 ml) and dried over sodium sulfate. The solvent was removed by distillation under reduced pressure and the crude product so obtained was purified by column chromatography (Alox, 0.5% methanol/dichloromethane). The desired product was in the form of a brown solid. Yield: 47% (250 mg, 0.816 mmol)

Stage 2: N-Methyl-1-(6-methylpyrazin-2-yl)piperidin-4-amine (AMN-65)

Trifluoroacetic acid (2 ml) was added at 0° C. to a solution of tert-butyl methyl(1-(6-methylpyrazin-2-yl)piperidin-4-yl)carbamate (250 mg, 0.816 mmol, 1 eq) in dichloromethane (10 ml) and the reaction mixture was stirred for 2 h at room temperature. Concentration under reduced pressure was then carried out. The crude product so obtained was used in the next stage without being purified further.

Synthesis of Amine AMN-67

N-Isopropyl-1-(pyridin-4-yl)piperidin-4-amine (AMN-67)

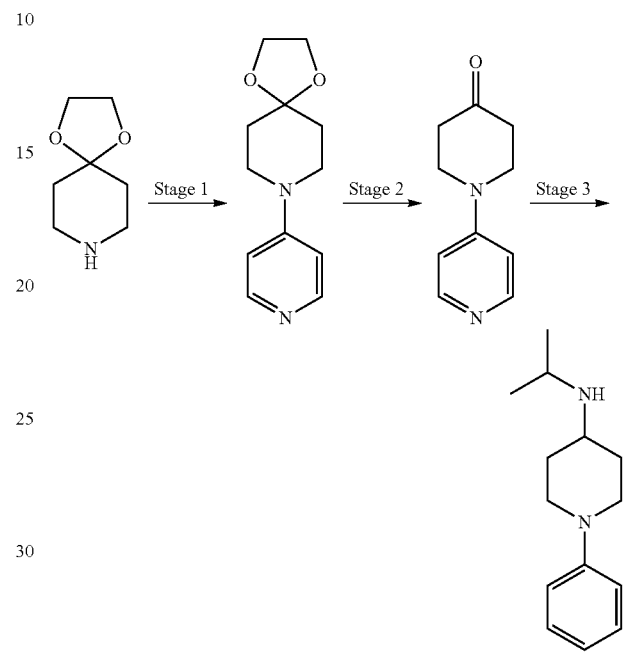

Stage 1: 8-(Pyridin-4-yl)-1,4-dioxa-8-azaspiro[4.5]decane 1,4-Dioxa-8-azaspiro[4.5]decane (5.0 g, 34.9 mmol, 1.0 eq.), 4-bromopyridine HCl (7.46 g, 38.46 mmol, 1.1 eq.) and DIPEA (18.2 ml, 104.7 mmol, 3.0 eq.) were dissolved in n-butanol (100 ml) and refluxed for 36 hours. The reaction solution was concentrated under reduced pressure and purified by column chromatography (Alox, 3% MeOH in DCM). Yield: 91% (7.0 g, 31.81 mmol)

Stage 2: 1-(Pyridin-4-yl)piperidin-4-one 8-(Pyridin-4-yl)-1,4-dioxa-8-azaspiro[4.5]decane (7.0 g, 31.8 mmol, 1.0 eq.) was dissolved at 0° C. in conc. HCl (42 ml) and stirred for 14 hours at RT. After monitoring by TLC, the reaction solution was rendered alkaline with 2 M NaOH solution and extracted with chloroform (250 ml). The org. phase was dried over sodium sulfate and concentrated under reduced pressure. Yield: 80% (4.5 g, 25.56 mmol)

Stage 3: N-Isopropyl-1-(pyridin-4-yl)piperidin-4-amine (AMN-67)

1-(Pyridin-4-yl)piperidin-4-one (1.5 g, 8.52 mmol, 1.0 eq.) was dissolved in MeOH (40 ml); AcOH (0.6 ml) and isopropylamine (1.39 ml, 17.04 mmol, 2.0 eq.) were added and the mixture was stirred for 3 hours at RT. NaCNBH$_3$ (856 mg, 12.78 mmol, 1.5 eq.) was then added in portions at 0° C. and stirring was carried out for a further 14 hours at RT. The reaction mixture was concentrated under reduced pressure and the residue was taken up in water (100 ml) and extracted with DCM (150 ml). The org. phase was washed with sat. NaHCO$_3$ solution (100 ml), dried over sodium sulfate, concentrated and purified by column chromatography (Alox, 2% MeOH in DCM). Yield: 64% (1.2 g, 5.47 mmol)

Synthesis of Amine AMN-68

N,N-Dimethyl-4-(4-(methylamino)cyclohexyl)pyridin-2-amine (AMN-68)

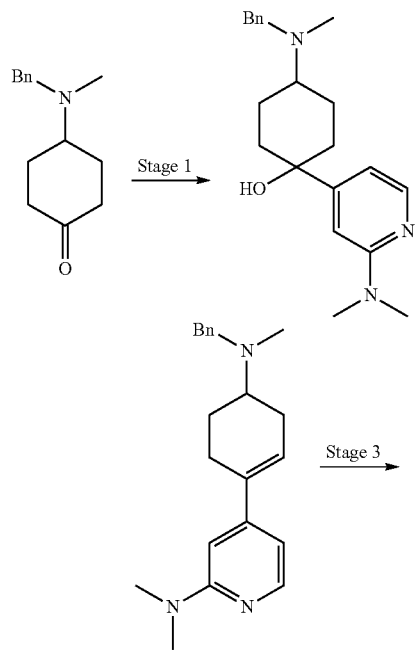

Stage 1: 4-(Benzyl(methyl)amino)-1-(2-(dimethylamino)pyridin-4-yl)cyclohexanol n-BuLi (3 ml, 5.98 mmol, 1.2 eq., 2 M solution in hexane) was added at −78° C. to a solution of 4-bromo-N,N-dimethylpyridin-2-amine (978 mg, 5.23 mmol, 1.05 eq.) in diethyl ether (15 ml) and the mixture was stirred for 45 minutes. A solution of 4-(benzyl(methyl)amino)cyclo-hexanone (stage 3, AMN-50) (1.08 g, 4.9, 8 mmol 1.0 eq.) in diethyl ether (10 ml) was added dropwise thereto at the same temperature. The reaction mixture was stirred for 16 hours at RT and was then hydrolyzed with sat. ammonium chloride solution (30 ml) and extracted with ethyl acetate (3×60 ml). The combined org. phases were washed with sat. NaCl solution (100 ml), dried over sodium sulfate, concentrated and purified by column chromatography (silica gel, 2,5% MeOH in DCM). Yield: 71% (1.20 g, 3.54 mmol)

Stage 2: 4-(4-(Benzyl(methyl)amino)cyclohex-1-enyl)-N,N-dimethylpyridin-2-amine

A mixture of 4-(benzyl(methyl)amino)-1-(2-(dimethylamino)pyridin-4-yl)cyclohexanol (300 mg, 0.88 mmol, 1.0 eq.) and PTSA (1.1 g, 5.31 mmol, 6.0 eq.) in toluene (10 ml) was refluxed for 16 hours. After monitoring by TLC, the mixture was concentrated and the residue was taken up in DCM and washed with sat. NaHCO$_3$ solution (3×30 ml), water (30 ml) and sat. NaCl solution (30 ml). The org. phase was dried over sodium sulfate, concentrated under reduced pressure and purified by column chromatography (silica gel, 3% MeOH in DCM). Yield: 57% (160 mg, 0.50 mmol)

Stage 3: N,N-Dimethyl-4-(4-(methylamino)cyclohexyl)pyridin-2-amine (AMN-68)

4-(4-(Benzyl(methyl)amino)cyclohex-1-enyl)-N,N-dimethylpyridin-2-amine (340 mg, 1.06 mmol, 1.0 eq.) was dissolved in MeOH (10 ml) and degassed with argon. Pd(OH)$_2$ (170 mg) was then added and hydrogenation was carried out for 3 hours. After monitoring by TLC, the reaction mixture was filtered over Celite and the filtrate was concentrated under reduced pressure and purified by column chromatography (Alox, 2% MeOH in DCM). Yield: 71% (175 mg, 0.75 mmol)

Synthesis of Amine AMN-68

N-Methyl-1-(pyridin-4-yl)azepan-4-amine (AMN-69)

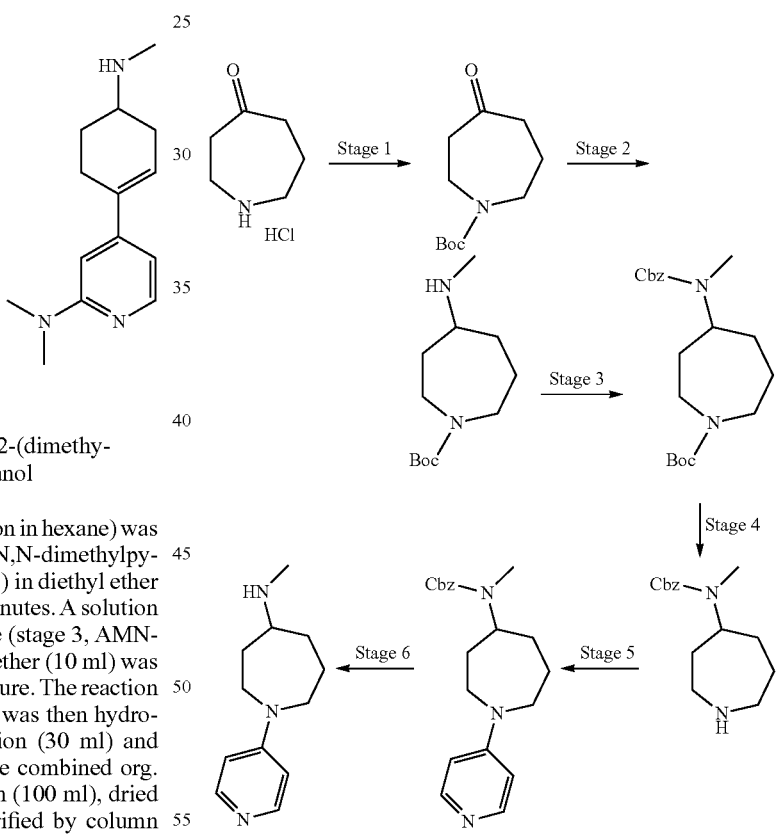

Stage 1: tert-Butyl 4-oxoazepane-1-carboxylat

Azepan-4-one hydrochloride (3.0 g, 20.05 g, 20.16 mmol, 1.0 eq.) was dissolved in DCM (100 ml) and TEA (6.9 ml, 50.1 mmol, 2.5 eq.) and cooled to 0° C.; Boc anhydride (5.1 ml, 24.06 mmol, 1.2 eq.) was added and the mixture was stirred for 16 hours at RT. After monitoring by TLC, the reaction solution was diluted with DCM (100 ml), washed with water (100 ml) and sat. NaCl solution (100 ml), dried over sodium sulfate, concentrated under reduced pressure and used in the next stage without being purified further. Yield: 79% (3.4 g, 15.96 mmol)

Stages 2 to 6: N-Methyl-1-(pyridin-4-yl)azepan-4-amine (AMN-69)

The synthesis was carried out analogously to stages 1 to 5 AMN-54, 4-bromopyridine hydrochloride being used in stage 5.

Synthesis of Amine AMN-70

N-Methyl-1-(pyridin-4-yl)piperidin-3-amine (AMN-70)

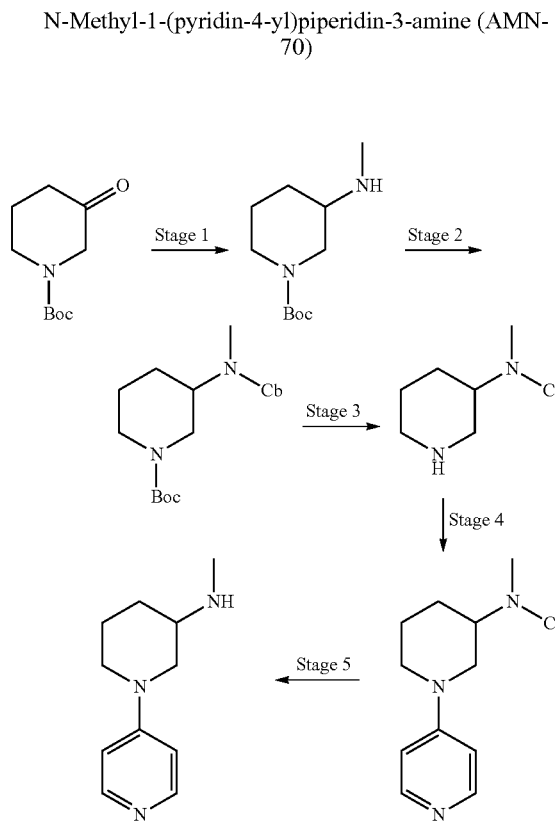

Stages 1 to 3: Benzyl methyl(piperidin-3-yl)carbamate

The synthesis was carried out analogously to stages 1 to 3 AMN-55.

Stage 4: Benzyl methyl(1-(pyridin-4-yl)piperidin-3-yl)carbamate

A mixture of benzyl methyl(piperidin-3-yl)carbamate (6.32 mmol, 1.0 eq.), 4-brompyridine HCl (2.5 g, 12.64 mmol, 2.0 eq.) and DIPEA (5.7 ml, 31.6 mmol, 5.0 eq.) in n-butanol (40 ml) was refluxed for 24 hours. The reaction mixture was concentrated and the residue was taken up in DCM (200 ml) and washed with sat. NaHCO₃ solution (3×100 ml), water (100 ml) and sat. NaCl solution (100 ml). The org. phase was then dried over sodium sulfate, concentrated under reduced pressure and purified by column chromatography (silica gel, 5% MeOH in DCM). Yield: 77% (1.6 g, 4.92 mmol)

Stage 5: N-Methyl-1-(pyridin-4-yl)piperidin-3-amine (AMN-70)

The synthesis was carried out analogously to stage 5 AMN-55.

Synthesis of Amine AMN-71

2-(1-(2,6-Dimethylpyrimidin-4-yl)piperidin-4-yl)ethanamine (AMN-71)

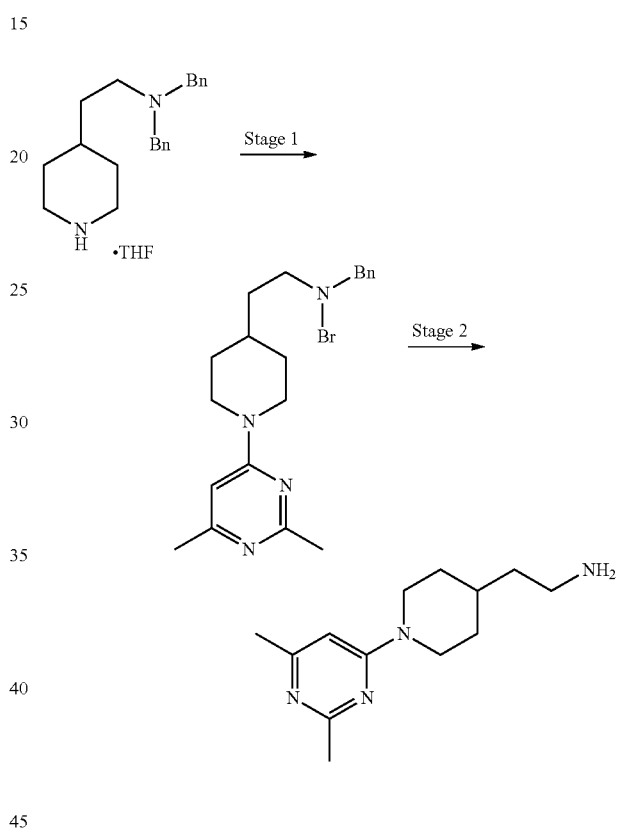

Stage 1: N,N-Dibenzyl-2-(1-(2,6-dimethylpyrimidin-4-yl)piperidin-4-yl)ethanamine A mixture of N,N-dibenzyl-2-(piperidin-4-yl)ethanamine trifluoroacetate (see stage 6 AMN-01) (6.372 mmol, 1.0 eq), 4-chloro-2,6-dimethylpyrimidine (1.17 g, 8.283 mmol, 1.3 eq) and K₂CO₃ (2.64 g, 19.116 mmol, 3.0 eq) in acetone (50 ml) was stirred for 16 hours at boiling temperature. After monitoring by TLC, the mixture was concentrated, diluted with DCM (100 ml) and washed with water (50 ml) and sat. NaCl solution (50 ml). The org. phase was dried over sodium sulfate and concentrated under reduced pressure, and the crude product so obtained was purified by column chromatography (silica gel, 2% MeOH in DCM). Yield: 49% (1.3 g, 3.14 mmol)

Stage 2: 2-(1-(2,6-Dimethylpyrimidin-4-yl)piperidin-4-yl)ethanamine (AMN-71)

A solution of N,N-dibenzyl-2-(1-(2,6-dimethylpyrimidin-4-yl)piperidin-4-yl)ethanamine (700 mg, 1.691 mmol, 1.0 eq) in MeOH (10 ml) was degassed for 30 minutes with nitrogen;

10% Pd(OH)$_2$ (420 mg) was added and hydrogenation was carried out for 12 hours at RT. After monitoring by TLC, the reaction mixture was filtered off over Celite and washed with MeOH (100 ml). The filtrate was concentrated under reduced pressure and dried. Yield: 66% (260 mg, 1.11 mmol)

Synthesis of Amine AMN-72

4-(4-(Methylamino)piperidin-1-yl)pyridin-2(1H)-one (AMN-72)

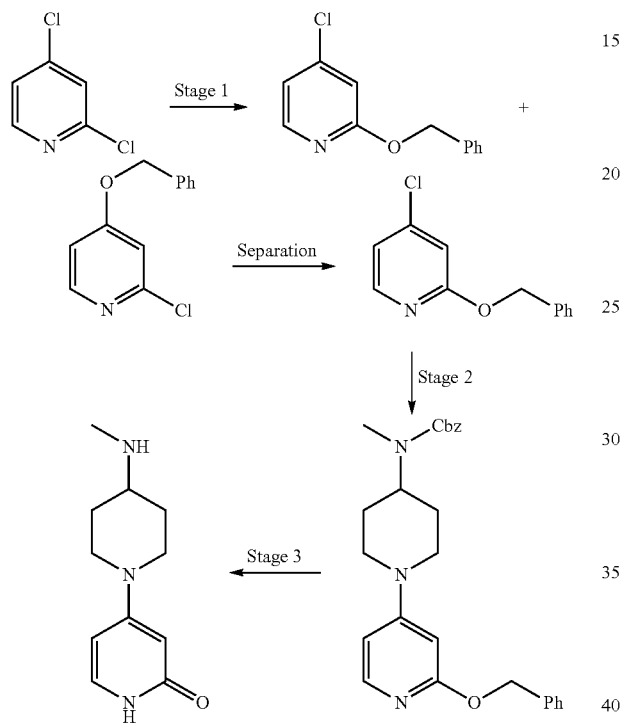

Stage 1: 2-(Benzyloxy)-4-chloropyridine

Benzyl alcohol (1.7 ml, 16.326 mmol, 1.2 eq) was added at 0° C. to a suspension of NaH (1.088 g, 27.21 mmol, 2.0 eq) in THF (50 ml) and the mixture was stirred for 30 minutes. A solution of 2,4-dichloropyridine (2.0 g, 13.605 mmol, 1.0 eq) in THF (10 ml) was added dropwise and stirring was carried out for 2 hours at RT. After monitoring by TLC, the reaction mixture was hydrolyzed with ice-water (60 ml) and extracted with ethyl acetate (2×120 ml). The combined org. phases were washed with sat. NaCl solution (100 ml), dried over sodium sulfate, concentrated under reduced pressure and purified by column chromatography (silica gel, 1% ethyl acetate in hexane). Yield: 27% (800 mg, 3.653 mmol)

Stage 2: Benzyl 1-(2-(benzyloxy)pyridin-4-yl)piperidin-4-yl(methyl)carbamate

A mixture of 2-(benzyloxy)-4-chloropyridine (800 mg, 3.653 mmol, 1.0 eq), benzyl methyl(piperidin-4-yl)carbamate (stage 3 AMN-52) (0.997 g, 4.018 mmol, 1.1 eq) and Cs$_2$CO$_3$ (2.374 g, 7.306 mmol, 2.0 eq) in toluene (10 ml) was degassed for 15 minutes with nitrogen. Pd$_2$(dba)$_3$ (166 mg, 0.182 mmol, 0.05 eq) and Xantphos (105 mg, 0.182 mmol, 0.05 eq) were then added and stirring was carried out for 14 hours at 90° C. After monitoring by TLC, the mixture was diluted with DCM (150 ml), washed with water (70 ml) and sat. NaCl solution (70 ml), dried over sodium sulfate and concentrated under reduced pressure. The crude product was purified by column chromatography (silica gel, 2.0% MeOH in DCM). Yield: 32% (500 mg, 1.160 mmol)

Stage 3: 4-(4-(Methylamino)piperidin-1-yl)pyridin-2 (1H)-one (AMN-72)

A solution of benzyl 1-(2-(benzyloxy)pyridin-4-yl)piperidin-4-yl(methyl)carbamate (400 mg, 1.160 mmol, 1.0 eq) in MeOH (5 ml) was degassed for 15 minutes with nitrogen. Pd(OH)$_2$ (300 mg, 60% w/w) was then added and hydrogenation was carried out for 4 hours at RT. After monitoring by TLC, the reaction mixture was filtered off over Celite, concentrated under reduced pressure and dried. Yield: 87% (210 mg, 1.014 mmol)

Synthesis of Amine AMN-73

1-(2,6-Dimethylpyrimidin-4-yl)-N-ethylpiperidin-4-amine (AMN-73)

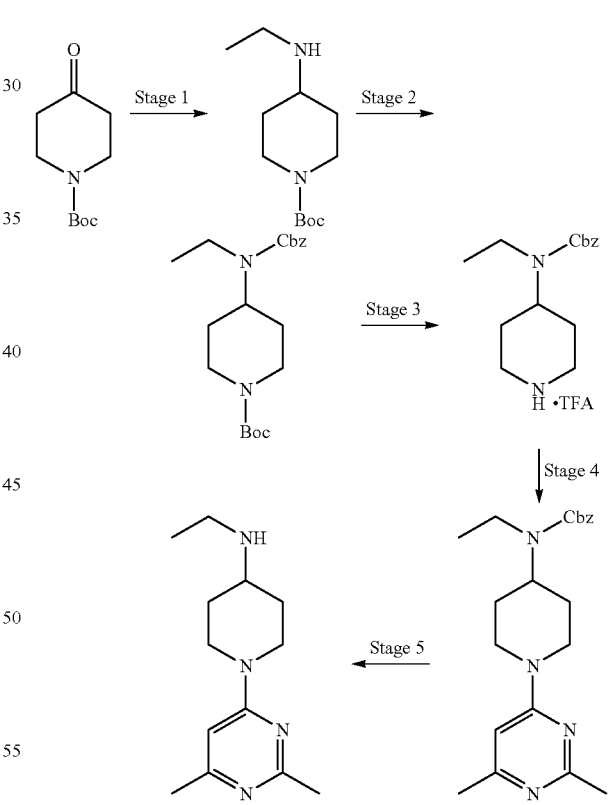

Stage 1: tert-Butyl 4-(ethylamino)piperidine-1-carboxylate

Ethylamine HCl (6.14 g, 75.376 mmol, 1.5 eq) and tert-butyl 4-oxopiperidine-1-carboxylate (10.0 g, 50.25 mmol, 1.0 eq) were dissolved in MeOH (200 ml); acetic acid (0.2 ml) was added and stirring was carried out for 2 hours at RT. NaBH$_3$CN (6.3 g, 100.50 ml, 2.0 eq) was then added in portions at 0° C. and the mixture was stirred for 14 hours at RT. The reaction mixture was concentrated and the residue was taken up in sat. sodium hydrogen carbonate solution (150 ml) and extracted with DCM (2×400 ml). The combined org. phases were washed with sat. NaCl solution (200 ml), dried over sodium sulfate and concentrated under reduced pressure. The crude product was purified by column chromatography (silica gel, 1% MeOH in DCM). Yield: 70% (8.0 g, 35.08 mmol)

Stage 2: tert-Butyl 4-((benzyloxycarbonyl)(ethyl) amino)piperidine-1-carboxylate A 50% Cbz-Cl-toluene solution (20.87 ml, 61.40 mmol, 2.0 eq) was added dropwise at 0° C. to a mixture of tert-butyl 4-(ethylamino)piperidine-1-carboxylate (7.0 g, 30.70 mmol, 1.0 eq) and K$_2$CO$_3$ (12.71 g, 92.10 mmol, 3.0 eq) in DCM (100 ml) and the mixture was stirred for 14 hours at RT. The reaction mixture was diluted with DCM (200 ml), washed with water (100 ml) and sat. NaCl solution (100 ml), dried over sodium sulfate, concentrated under reduced pressure and purified by column chromatography (silica gel, 20% ethyl acetate in hexane). Yield: 63% (7.0 g, 19.33 mmol)

Stage 3: Benzyl ethyl(piperidin-4-yl)carbamate trifluoroacetate

TFA (2.5 ml) was added at 0° C. to a solution of tert-butyl 4-((benzyloxycarbonyl)(ethyl)-amino)piperidine-1-carboxylate (1.5 g, 414 mmol, 1.0 eq) in DCM (10 ml) and the mixture was stirred for 2 hours at RT. After monitoring by TLC, the reaction mixture was concentrated under reduced pressure and dried. The crude product was used in the next stage without being purified further.

Stage 4: Benzyl 1-(2,6-dimethylpyrimidin-4-yl)piperidin-4-yl(ethyl)carbamate

A mixture of benzyl ethyl(piperidin-4-yl)carbamate trifluoroacetate (4.14 mmol, 1.0 eq), 4-chloro-2,6-dimethylpyrimidine (0.706 g, 4.97 mmol, 1.2 eq) and K$_2$CO$_3$ (1.14 g, 8.28 mmol, 2.0 eq) in acetone (20 ml) was stirred for 14 hours at boiling temperature. After monitoring by TLC, the mixture was concentrated, diluted with DCM (200 ml), washed with water (80 ml) and sat. NaCl solution (80 ml), dried over sodium sulfate and concentrated under reduced pressure. The crude product was purified by column chromatography (silica gel, 2.0% MeOH in DCM). Yield: 63% (960 mg, 2.60 mmol)

Stage 5: 1-(2,6-Dimethylpyrimidin-4-yl)-N-ethylpiperidin-4-amine (AMN-73)

A solution of benzyl 1-(2,6-dimethylpyrimidin-4-yl)piperidin-4-yl(ethyl)carbamate (960 mg, 2.6 mmol, 1.0 eq) in MeOH (40 ml) was degassed for 15 minutes with nitrogen; Pd(OH)$_2$ (480 mg) was added and hydrogenation was carried out for 1 hour at RT. After monitoring by TLC, the reaction mixture was filtered off over Celite and washed with MeOH (100 ml) and the filtrate was concentrated under reduced pressure and dried. Yield: 66% (400 mg, 1.709 mmol)

C. Single Substance Syntheses
General Method for the Synthesis of the Illustrative Compounds (H)

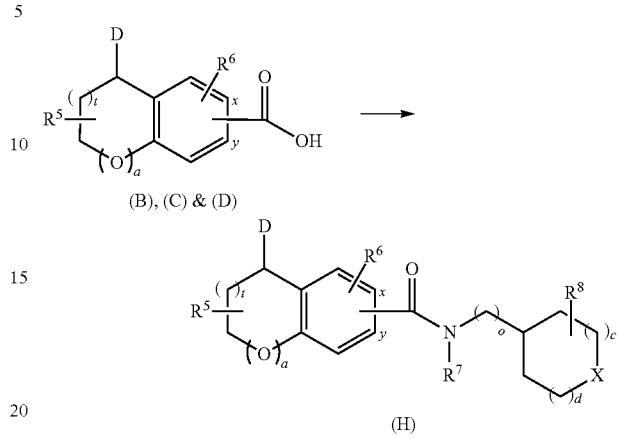

1) Synthesis of the Illustrative Compounds
General Working Procedure 1 (GWP-1):
The carboxylic acid (1 eq) was dissolved in dichloromethane, and N-ethyldiisopropylamine (from 2.5 to 5.0 eq) was added at 0° C. N-Ethyl-N'-3-(dimethylamino)-propyl-carbodiimide hydrochloride (1.2 eq) and 1-hydroxybenzotriazole hydrate (0.2 eq) were added at 0° C. and the reaction mixture was stirred for 15 min at RT. It was cooled to 0° C. again, the amine (1 eq) was added, and stirring was carried out for from 16 h to 2.5 days at RT. When the reaction was complete (TLC monitoring), the reaction mixture was diluted with ethyl acetate. The organic phase was washed with 10% NH$_4$Cl solution, sat. NaHCO$_3$ solution and sat. NaCl solution, dried over sodium sulfate or magnesium sulfate and filtered off. The solvent was concentrated and the residue was purified by column chromatography (silica gel, ethyl acetate/ethanol/ammonia (25% aq) or ethyl acetate/cyclohexane).
General Working Procedure 2 (GWP-2):
HATU (1-1.5 eq) and DIPEA (2.0-4.0 eq) were added to an ice-cooled solution or suspension of the carboxylic acid (1 eq) in dichloromethane, and stirring was carried out for from 15 to 30 min. The amine (1 eq) was dissolved in dichloromethane and added dropwise to the reaction solution, and the reaction mixture was stirred for 12-16 h at RT. The reaction solution was diluted with dichloromethane, washed with sat. sodium hydrogen carbonate solution, sat. ammonium chloride solution, water and sat. NaCl solution, dried over sodium sulfate and concentrated under reduced pressure. After purification by column chromatography (silica gel, MeOH in dichloromethane), the desired product was obtained.
General Working Procedure 3 (GWP-3):
EDCI (1.5 eq), HOBt or HOAt (1 eq) and DIPEA (4 eq) were added to an ice-cooled solution or suspension of the carboxylic acid (1 eq) in dichloromethane, and stirring was carried out for 15 min. The amine (1 eq), dissolved in dichloromethane, was added to the reaction solution, and stirring was carried out for 16 h at RT. The reaction solution was diluted with dichloromethane, washed with sat. sodium hydrogen carbonate solution, sat. ammonium chloride solution, water and sat. NaCl solution, dried over sodium sulfate and concentrated under reduced pressure. After purification by column chromatography (silica gel, MeOH in dichloromethane), the desired product was obtained.

General Working Procedure 4 (GWP-4):
HATU (1-1.5 eq) and DIPEA (2.0-4.0 eq) were added to an ice-cooled solution or suspension of the carboxylic acid (1 eq) in tetrahydrofuran, and stirring was carried out for from 15 to 30 min. The amine (1 eq) was added to the reaction solution, and the reaction mixture was stirred for 16 h at RT. The reaction solution was diluted with ethyl acetate, washed with sat. sodium hydrogen carbonate solution, sat. ammonium chloride solution and sat. NaCl solution, dried over magnesium sulfate and concentrated under reduced pressure. After purification by column chromatography (silica gel, ethyl acetate/cyclohexane), the desired product was obtained.

General Working Procedure 5 (GWP-5):
The carboxylic acid (1.0 eq.) was dissolved in THF; at 0° C., DIPEA (2.5-4.0 eq.) and HATU (1.0-1.5 äq.) were added and stirring was carried out for 15 minutes. The amine (1.0-1.1 eq.) dissolved in THF was then added and the mixture was stirred for 16 hours at RT. The reaction solution was concentrated and the residue was taken up in DCM and washed in succession with sat. ammonium chloride solution, sat. sodium hydrogen carbonate solution, water and sat. NaCl solution. The org. phase was then dried over sodium sulfate, concentrated under reduced pressure and purified by column chromatography (silica gel or Alox, MeOH/DCM).

TABLE

| Example No. | Name | Structure | Amino acid (ACI) | Amine (AMN) | Synthesis according to | Yield | Comments |
|---|---|---|---|---|---|---|---|
| H-01 | 3-[(2-Chloro-benzoyl)amino]-N-[2-(1-pyridin-4-yl-piperidin-4-yl)-ethyl]-2,3-dihydro-1H-indene-5-carboxylic acid amide (H-01) | 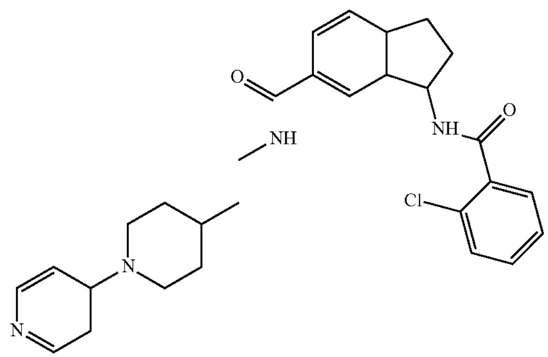 | 3-[(2-Chloro-benzoyl)amino]-2,3-dihydro-1H-indene-5-carboxylic acid (E-32) | 2-(1-(Pyridin-4-yl)piperidin-4-yl)ethanamine (AMN-01) | GWP-3 | 35% | |
| H-03 | (3R)-3-[(2-Chloro-benzoyl)amino]-N-[(1-pyridin-4-yl-piperidin-4-yl)-methyl]-2,3-dihydro-1H-indene-5-carboxylic acid amide (H-03) | 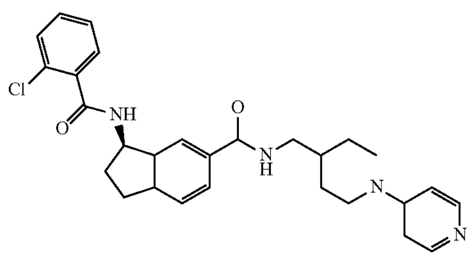 [SMILES: CCC(CCNC1C=CN=CC1)CNC(O)C1=CC2C(C=C1)CC[C@H]2NC(=O)c1ccccc1Cl] | (3R)-3-[(2-Chloro-benzoyl)amino]-2,3-dihydro-1H-indene-5-carboxylic acid (E-01) | (1-(Pyridin-4-yl)piperidin-4-yl)methanamine dihydrochloride (AMN-03) | GWP-1 | 72% | Reaction time 7d |

TABLE-continued

| Example No. | Structure | Name | Amino acid (ACI) | Amine (AMN) | Synthesis according to | Yield | Comments |
|---|---|---|---|---|---|---|---|
| H-04 | 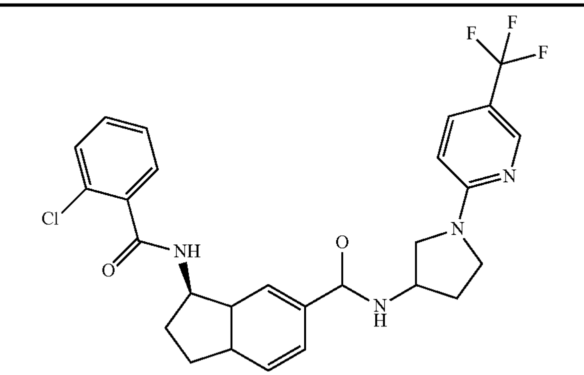 | (3R)-3-[(2-Chloro-benzoyl)amino]-N-[1-[5-(trifluoromethyl)-pyridin-2-yl]-pyrrolidin-3-yl]-2,3-dihydro-1H-indene-5-carboxylic acid amide (H-04) | (3R)-3-[(2-Chloro-benzoyl)amino]-2,3-dihydro-1H-indene-5-carboxylic acid (E-01) | 1-(5-(Trifluoromethyl)pyridin-2-yl)pyrrolidin-3-amine (AMN-04) | GWP-1 | 73% | |
| H-06 | 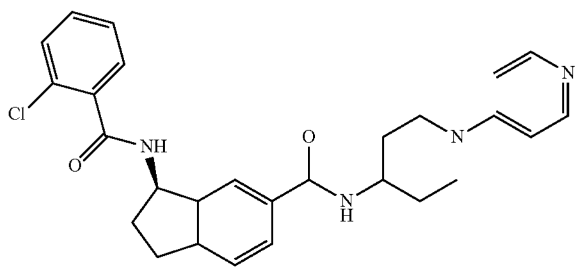 [SMILES: C=C/N=C\C=C\NCCC(CC)NC(O)C1=CC2C(C=C1)CC[C@H]2NC(=O)c1ccccc1Cl] | (3R)-3-[(2-Chloro-benzoyl)amino]-N-methyl-N-(1-pyridin-4-yl-piperidin-4-yl)-2,3-dihydro-1H-indene-5-carboxylic acid amide (H-06) | (3R)-3-[(2-Chloro-benzoyl)amino]-2,3-dihydro-1H-indene-5-carboxylic acid (E-01) | N-Methyl-1-(pyridin-4-yl)piperidin-4-amine (AMN-06) | GWP-1 | 86% | |
| H-07 | 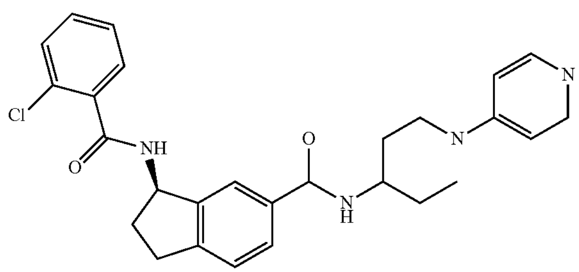 [SMILES: CCC(CCNC1=CCNC=C1)NC(O)c1ccc2c(c1)[C@H](NC(=O)c1ccccc1Cl)CC2] | (3R)-3-[(2-Chloro-benzoyl)amino]-N-(1-pyridin-4-yl-piperidin-4-yl)-2,3-dihydro-1H-indene-5-carboxylic acid amide (H-07) | (3R)-3-[(2-Chloro-benzoyl)amino]-2,3-dihydro-1H-indene-5-carboxylic acid (E-01) | 1-(Pyridin-4-yl)piperidin-4-amine dihydrochloride (AMN-07) | GWP-1 | 41% | |

TABLE-continued

| Example No. | Structure | Name | Amino acid (ACI) | Amine (AMN) | Synthesis according to | Yield | Comments |
|---|---|---|---|---|---|---|---|
| H-09 | 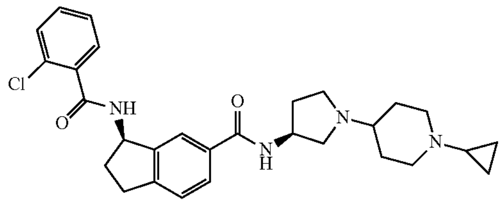 [SMILES: O=C(N[C@H]1CCN(C2CCN(C3CC3)CC2)C1)c1ccc2c(c1)[C@H](NC(=O)c1ccccc1Cl)CC2] | (3R)-3-[(2-Chloro-benzoyl)amino]-N-[(3S)-1-(1-cyclopropyl-piperidin-4-yl)-pyrrolidin-3-yl]-2,3-dihydro-1H-indene-5-carboxylic acid amide (H-09) | (3R)-3-[(2-Chloro-benzoyl)amino]-2,3-dihydro-1H-indene-5-carboxylic acid (E-01) | (S)-1-(1-Cyclopropylpiperidin-4-yl)pyrrolidin-3-amine trihydrochloride (AMN-09) | GWP-1 | 83% | |
| H-10 | 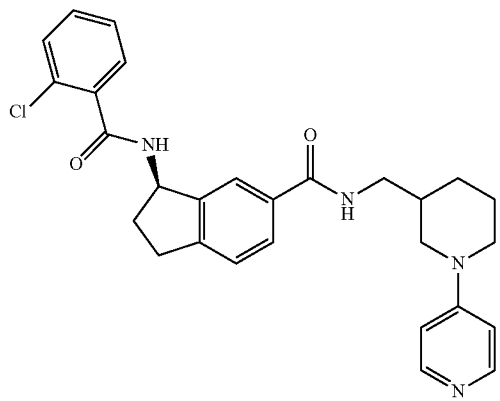 [SMILES: O=C(NCC1CCCN(c2ccncc2)C1)c1ccc2c(c1)[C@H](NC(=O)c1ccccc1Cl)CC2] | (3R)-3-[(2-Chloro-benzoyl)amino]-N-[(1-pyridin-4-yl-piperidin-3-yl)-methyl]-2,3-dihydro-1H-indene-5-carboxylic acid amide (H-10) | (3R)-3-[(2-Chloro-benzoyl)amino]-2,3-dihydro-1H-indene-5-carboxylic acid (E-01) | (1-(Pyridin-4-yl)piperidin-3-yl)methanamine dihydrochloride (AMN-10) | GWP-1 | 86% | |

TABLE-continued

| Example No. | Name | Structure | Amino acid (ACI) | Amine (AMN) | Synthesis according to | Yield | Comments |
|---|---|---|---|---|---|---|---|
| H-11 | (1R)-1-(4-Chloro-3-oxo-1,2-dihydro-isoindol-2-yl)-N-methyl-N-(1-pyridin-4-yl-piperidin-4-yl)-2,3-dihydro-1H-indene-5-carboxylic acid amide (H-11) | 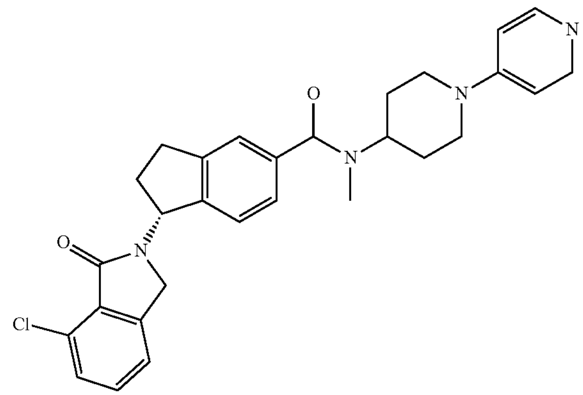 [SMILES: CN(C1CCN(C2=CCNC=C2)CC1)C(O)c1ccc2c(c1)CC[C@H]2N1Cc2cccc(Cl)c2C1=O] | (R)-1-(7-Chloro-1-oxoisoindolin-2-yl)-2,3-dihydro-1H-indene-5-carboxylic acid (G-02) | N-Methyl-1-(pyridin-4-yl)piperidin-4-amine (AMN-06) | GWP-1 | 93% | |
| H-12 | (3R)-3-(4-Chloro-3-oxo-1,2-dihydro-isoindol-2-yl)-N-methyl-N-(1-pyridin-4-yl-piperidin-4-yl)-2,3-dihydro-1H-indene-5-carboxylic acid amide (H-12) | 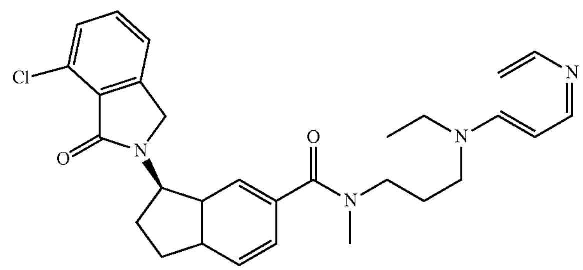 [SMILES: C=C/N=C\C=C\N(CC)CCCN(C)C(=O)C1=CC2C(C=C1)CC[C@H]2N1Cc2cccc(Cl)c2C1=O] | (R)-3-(7-Chloro-1-oxoisoindolin-2-yl)-2,3-dihydro-1H-indene-5-carboxylic acid (G-01) | N-Methyl-1-(pyridin-4-yl)piperidin-4-amine (AMN-06) | GWP-1 | 75% | |
| H-14 | (3R)-3-[(2-Chloro-benzoyl)amino]-N-[2,2-dimethyl-4-(4-methyl-piperazin-1-yl)-cyclohexyl]-2,3-dihydro-1H-indene-5-carboxylic acid amide (H-14) | 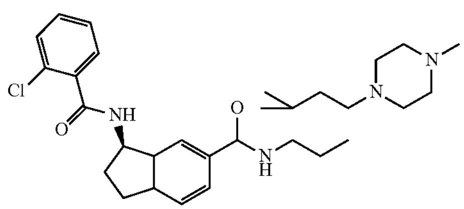 | (3R)-3-[(2-Chloro-benzoyl)amino]-2,3-dihydro-1H-indene-5-carboxylic acid (E-01) | 2,2-Dimethyl-4-(4-methylpiperazin-1-yl)cyclohexanamine (AMN-13) | GWP-3 | 26% (150 mg, 0.286 mmol) | |

TABLE-continued

| Example No. | Name | Structure | Amino acid (ACI) | Amine (AMN) | Synthesis according to | Yield | Comments |
|---|---|---|---|---|---|---|---|
| H-15 | (3R)-3-[(2-Chloro-benzoyl)amino]-N-[2-(1-pyridin-4-yl-piperidin-4-yl)-ethyl]-2,3-dihydro-1H-indene-5-carboxylic acid amide (H-15) | 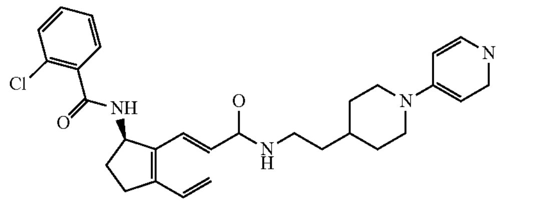 [SMILES: C=CC1=C(/C=C/C(O)NCCC2CCN(C3=CCNC=C3)CC2)[C@H](NC(=O)c2ccccc2Cl)CC1] | (3R)-3-[(2-Chloro-benzoyl)amino]-2,3-dihydro-1H-indene-5-carboxylic acid (E-01) | 2-(1-(Pyridin-4-yl)piperidin-4-yl)ethanamine (AMN-01) | GWP-3 | 43% (550 mg, 1.09 mmol) | |
| H-16 | (1R)-1-[[(2-Chlorophenyl)sulfonyl]amino]-N-methyl-N-(1-pyridin-4-yl-piperidin-4-yl)-2,3-dihydro-1H-indene-5-carboxylic acid amide (H-16) | 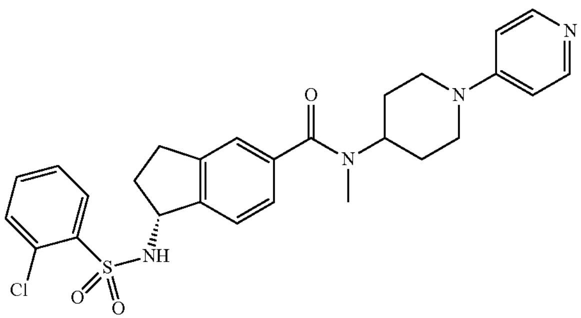 [SMILES: CN(C(=O)c1ccc2c(c1)CC[C@H]2NS(=O)(=O)c1ccccc1Cl)C1CCN(c2ccncc2)CC1] | (R)-1-(2-Chlorophenylsulfonamido)-2,3-dihydro-1H-indene-5-carboxylic acid (F-01) | N-Methyl-1-(pyridin-4-yl)piperidin-4-amine (AMN-06) | GWP-1 | 63% | |
| H-17 | (1R)-1-[(2-Chloro-benzoyl)amino]-N-methyl-N-(1-pyridin-4-yl-piperidin-4-yl)-2,3-dihydro-1H-indene-5-carboxylic acid amide (H-17) | 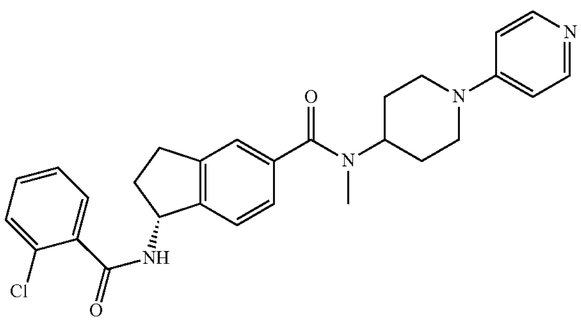 [SMILES: CN(C(=O)c1ccc2c(c1)CC[C@H]2NC(=O)c1ccccc1Cl)C1CCN(c2ccncc2)CC1] | (R)-1-(2-Chlorobenzamido)-2,3-dihydro-1H-indene-5-carboxylic acid (E-02) | N-Methyl-1-(pyridin-4-yl)piperidin-4-amine (AMN-06) | GWP-1 | 88% | |

| Example No. | Name | Structure | Amino acid (ACI) | Amine (AMN) | Synthesis according to | Yield | Comments |
|---|---|---|---|---|---|---|---|
| H-18 | (3R)-3-(Cyclobutanecarbonylamino)-N-methyl-N-(1-pyridin-4-yl-piperidin-4-yl)-2,3-dihydro-1H-indene-5-carboxylic acid amide (H-18) | 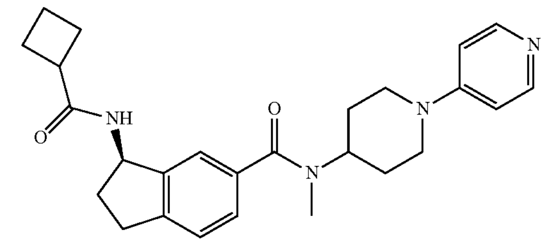 [SMILES: CN(C(=O)c1ccc2c(c1)[C@H](NC(=O)C1CCC1)CC2)C1CCN(c2ccncc2)CC1] | (R)-3-(Cyclobutanecarboxamido)-2,3-dihydro-1H-indene-5-carboxylic acid (E-05) | N-Methyl-1-(pyridin-4-yl)piperidin-4-amine (AMN-06) | GWP-1 | 90% | |
| H-19 | (3R)-3-(2,2-Dimethyl-propanoylamino)-N-methyl-N-(1-pyridin-4-yl-piperidin-4-yl)-2,3-dihydro-1H-indene-5-carboxylic acid amide (H-19) | 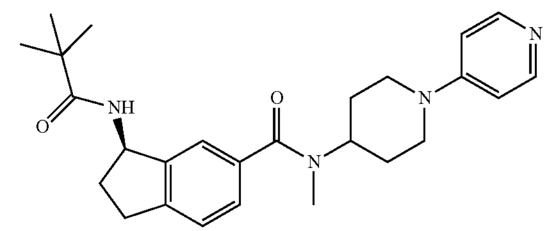 [SMILES: CN(C(=O)c1ccc2c(c1)[C@H](NC(=O)C(C)(C)C)CC2)C1CCN(c2ccncc2)CC1] | (R)-3-Pivalamido-2,3-dihydro-1H-indene-5-carboxylic acid (E-06) | N-Methyl-1-(pyridin-4-yl)piperidin-4-amine (AMN-06) | GWP-1 | 80% | |
| H-20 | (4R)-4-[(2-Chloro-benzoyl)amino]-N-methyl-N-(1-pyridin-4-yl-piperidin-4-yl)-3,4-dihydro-2H-chromene-6-carboxylic acid amide (H-20) | 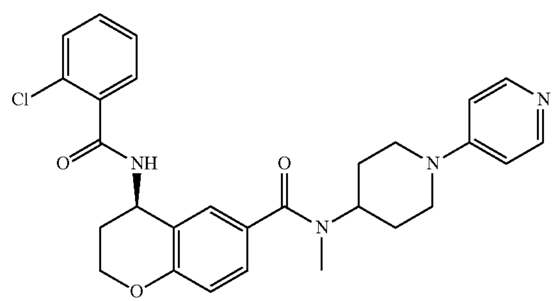 [SMILES: CN(C(=O)c1ccc2c(c1)[C@H](NC(=O)c1ccccc1Cl)CCO2)C1CCN(c2ccncc2)CC1] | (R)-4-(2-Chlorobenzamido)chromane-6-carboxylic acid (E-07) | N-Methyl-1-(pyridin-4-yl)piperidin-4-amine (AMN-06) | GWP-1 | 70% | |

TABLE-continued

| Example No. | Structure | Name | Amino acid (ACI) | Amine (AMN) | Synthesis according to | Yield | Comments |
|---|---|---|---|---|---|---|---|
| H-21 | 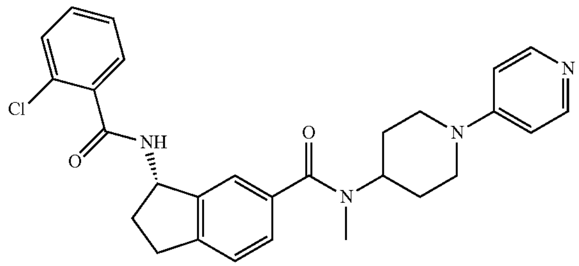 [SMILES: CN(C(=O)c1ccc2c(c1)[C@@H](NC(=O)c1ccccc1Cl)CC2)C1CCN(c2ccncc2)CC1] | (3S)-3-[(2-Chloro-benzoyl)amino]-N-methyl-N-(1-pyridin-4-yl-piperidin-4-yl)-2,3-dihydro-1H-indene-5-carboxylic acid amide (H-21) | (S)-3-(2-Chlorobenzamido)-2,3-dihydro-1H-indene-5-carboxylic acid (E-08) | N-Methyl-1-(pyridin-4-yl)piperidin-4-amine (AMN-06) | GWP-1 | 86% | |
| H-22 | 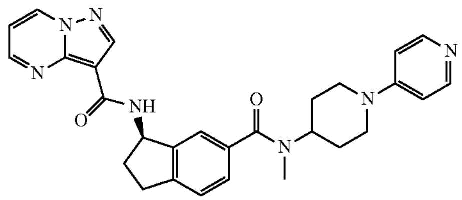 [SMILES: CN(C(=O)c1ccc2c(c1)[C@H](NC(=O)c1cnn3cccnc13)CC2)C1CCN(c2ccncc2)CC1] | N-[(1R)-6-[Methyl-[(1-pyridin-4-yl-piperidin-4-yl)-carbamoyl]]-2,3-dihydro-1H-indene-1-yl]-pyrazolo[1,5-a]pyrimidine-3-carboxylic acid amide (H-22) | (R)-3-(Pyrazolo[1,5-a]pyrimidine-3-carboxamido)-2,3-dihydro-1H-indene-5-carboxylic acid (E-09) | N-Methyl-1-(pyridin-4-yl)piperidin-4-amine (AMN-06) | GWP-1 | 56% | |
| H-23 | 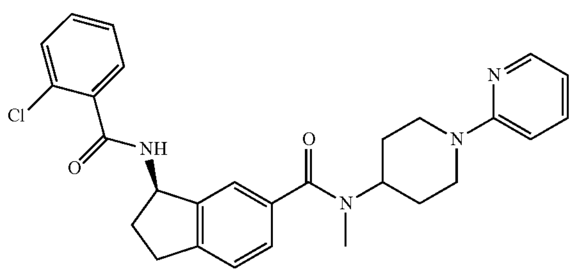 [SMILES: CN(C(=O)c1ccc2c(c1)[C@H](NC(=O)c1ccccc1Cl)CC2)C1CCN(c2ccccn2)CC1] | (3R)-3-[(2-Chloro-benzoyl)amino]-N-methyl-N-(1-pyridin-2-yl-piperidin-4-yl)-2,3-dihydro-1H-indene-5-carboxylic acid amide (H-23) | (3R)-3-[(2-Chloro-benzoyl)amino]-2,3-dihydro-1H-indene-5-carboxylic acid (E-01) | N-Methyl-1-(pyridin-2-yl)piperidin-4-amine (AMN-14) | GWP-1 | 64% | |

| Example No. | Structure | Name | Amino acid (ACI) | Amine (AMN) | Synthesis according to | Yield | Comments |
|---|---|---|---|---|---|---|---|
| H-24 | 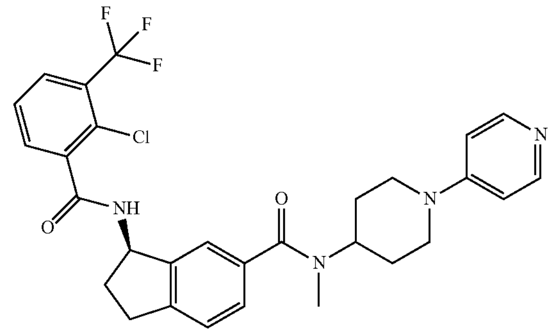 [SMILES: CN(C(=O)c1ccc2c(c1)[C@H](NC(=O)c1cccc(C(F)(F)F)c1Cl)CC2)C1CCN(c2ccncc2)CC1] | (3R)-3-[[2-Chloro-3-(trifluoromethyl)benzoyl]amino]-N-methyl-N-(1-pyridin-4-yl-piperidin-4-yl)-2,3-dihydro-1H-indene-5-carboxylic acid amide (H-24) | (R)-3-(2-Chloro-3-(trifluoromethyl)benzamido)-2,3-dihydro-1H-indene-5-carboxylic acid (E-10) | N-Methyl-1-(pyridin-4-yl)pipendin-4-amine (AMN-06) | GWP-1 | 75% | |
| H-25 | 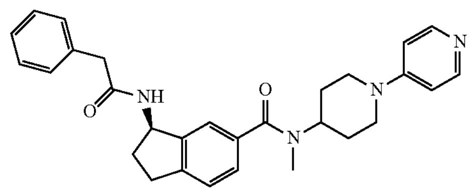 [SMILES: CN(C(=O)c1ccc2c(c1)[C@H](NC(=O)Cc1ccccc1)CC2)C1CCN(c2ccncc2)CC1] | (3R)-N-Methyl-3-[(2-phenyl-acetyl)amino]-N-(1-pyridin-4-yl-piperidin-4-yl)-2,3-dihydro-1H-indene-5-carboxylic acid amide (H-25) | (R)-3-(2-Phenylacetamido)-2,3-dihydro-1H-indene-5-carboxylic acid (E-11) | N-Methyl-1-(pyridin-4-yl)pipendin-4-amine (AMN-06) | GWP-1 | 71% | |
| H-26 | 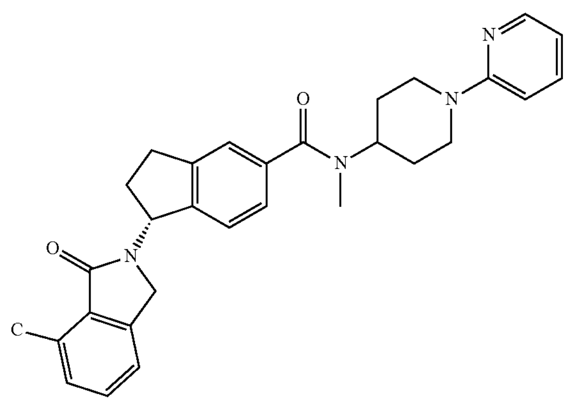 [SMILES: Cc1cccc2c1C(=O)N([C@@H]1CCc3cc(C(=O)N(C)C4CCN(c5ccccn5)CC4)ccc31)C2] | (1R)-1-(4-Chloro-3-oxo-1,2-dihydro-isoindol-2-yl)-N-methyl-N-(1-pyridin-2-yl-piperidin-4-yl)-2,3-dihydro-1H-indene-5-carboxylic acid amide (H-26) | (R)-1-(7-Chloro-1-oxoisoindolin-2-yl)-2,3-dihydro-1H-indene-5-carboxylic acid (G-02) | N-Methyl-1-(pyridin-2-yl)pipendin-4-amine (AMN-14) | GWP-1 | 22% | |

TABLE-continued

| Example No. | Structure | Name | Amino acid (ACI) | Amine (AMN) | Synthesis according to | Yield | Comments |
|---|---|---|---|---|---|---|---|
| H-27 | 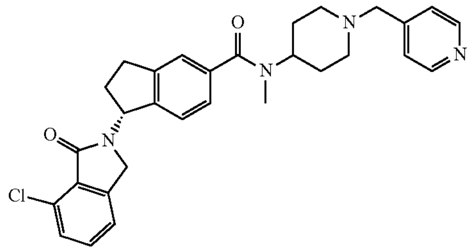 [SMILES: CN(C(=O)c1ccc2c(c1)CC[C@H]2N1Cc2cccc(Cl)c2C1=O)C1CCN(Cc2ccncc2)CC1] | (1R)-1-(4-Chloro-3-oxo-1,2-dihydro-isoindol-2-yl)-N-methyl-N-[1-(pyridin-4-yl-methyl)-piperidin-4-yl]-2,3-dihydro-1H-indene-5-carboxylic acid amide (H-27) | (R)-1-(7-Chloro-1-oxoisoindolin-2-yl)-2,3-dihydro-1H-indene-5-carboxylic acid (G-02) | N-Methyl-1-(pyridin-4-ylmethyl)piperidin-4-amine (AMN-15) | GWP-1 | 26% | |
| H-28 | 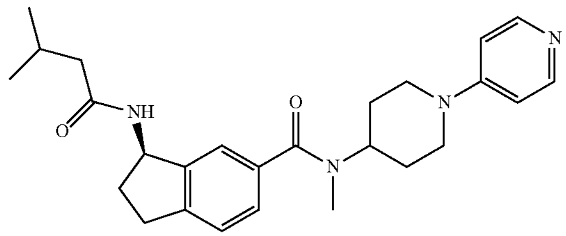 [SMILES: CC(C)CC(=O)N[C@@H]1CCc2ccc(C(=O)N(C)C3CCN(c4ccncc4)CC3)cc21] | (3R)-N-Methyl-3-(3-methylbutanoylamino)-N-(1-pyridin-4-yl-piperidin-4-yl)-2,3-dihydro-1H-indene-5-carboxylic acid amide (H-28) | (R)-3-(3-Methylbutanamido)-2,3-dihydro-1H-indene-5-carboxylic acid (E-12) | N-Methyl-1-(pyridin-4-yl)piperidin-4-amine (AMN-06) | GWP-1 | 72% | |
| H-29 | 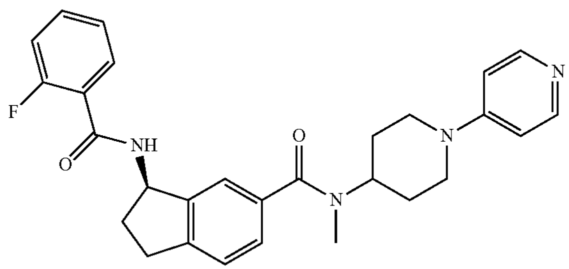 [SMILES: CN(C(=O)c1ccc2c(c1)[C@H](NC(=O)c1ccccc1F)CC2)C1CCN(c2ccncc2)CC1] | (3R)-3-[(2-Fluoro-benzoyl)amino]-N-methyl-N-(1-pyridin-4-yl-piperidin-4-yl)-2,3-dihydro-1H-indene-5-carboxylic acid amide (H-29) | (R)-3-(2-Fluorobenzamido)-2,3-dihydro-1H-indene-5-carboxylic acid (E-13) | N-Methyl-1-(pyridin-4-yl)piperidin-4-amine (AMN-06) | GWP-1 | 58% | |
| H-30 | 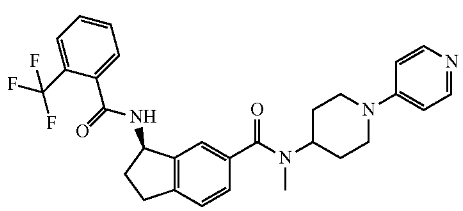 [SMILES: CN(C(=O)c1ccc2c(c1)[C@H](NC(=O)c1ccccc1C(F)(F)F)CC2)C1CCN(c2ccncc2)CC1] | (3R)-N-Methyl-N-(1-pyridin-4-yl-piperidin-4-yl)-3-[[2-(trifluoromethyl)benzoyl]amino]-2,3-dihydro-1H-indene-5-carboxylic acid amide (H-30) | (R)-3-(2-(Trifluoromethyl)benzamido)-2,3-dihydro-1H-indene-5-carboxylic acid (E-14) | N-Methyl-1-(pyridin-4-yl)piperidin-4-amine (AMN-06) | GWP-1 | 86% | |

TABLE-continued

| Example No. | Structure | Name | Amino acid (ACI) | Amine (AMN) | Synthesis according to | Yield | Comments |
|---|---|---|---|---|---|---|---|
| H-31 | 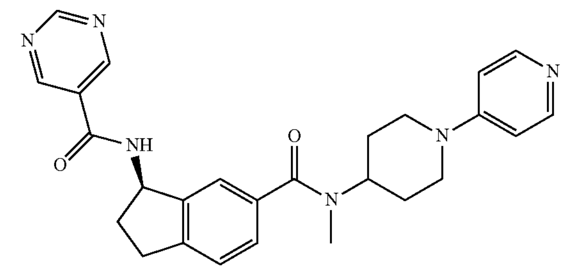 [SMILES: CN(C(=O)c1ccc2c(c1)[C@H](NC(=O)c1cncnc1)CC2)C1CCN(c2ccncc2)CC1] | N-[(1R)-6-[Methyl-(1-pyridin-4-yl-piperidin-4yl)carbamoyl]-2,3-dihydro-1H-inden-1-yl]-pyrimidine-5-carboxylic acid amide (H-31) | (R)-3-(Pyrimidine-5-carboxamido)-2,3-dihydro-1H-indene-5-carboxylic acid (E-15) | N-Methyl-1-(pyridin-4-yl)piperidin-4-amine (AMN-06) | GWP-1 | 29% | |
| H-32 | 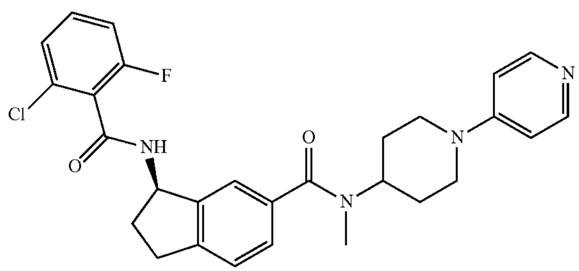 [SMILES: CN(C(=O)c1ccc2c(c1)[C@H](NC(=O)c1c(F)cccc1Cl)CC2)C1CCN(c2ccncc2)CC1] | (3R)-3-[(2-Chloro-6-fluorobenzoyl)amino]-N-methyl-N-(1-pyridin-4-yl-piperidin-4-yl)-2,3-dihydro-1H-indene-5-carboxylic acid amide (H-32) | (R)-3-(2-Chloro-6-fluorobenzamido)-2,3-dihydro-1H-indene-5-carboxylic acid (E-16) | N-Methyl-1-(pyridin-4-yl)piperidin-4-amine (AMN-06) | GWP-1 | 88% | |
| H-33 | 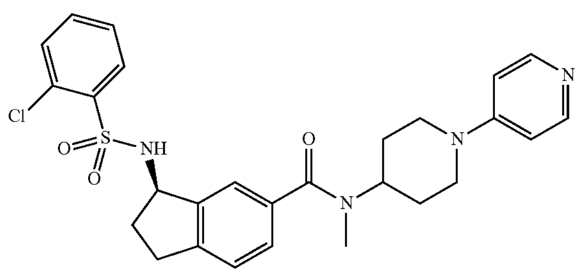 [SMILES: CN(C(=O)c1ccc2c(c1)[C@H](NS(=O)(=O)c1ccccc1Cl)CC2)C1CCN(c2ccncc2)CC1] | (3R)-3-[[(2-Chlorophenyl)sulfonyl]amino]-N-methyl-N-(1-pyridin-4-yl-piperidin-4-yl)-2,3-dihydro-1H-indene-5-carboxylic acid amide (H-33) | (R)-3-(2-Chlorophenylsulfonamido)-2,3-dihydro-1H-indene-5-carboxylic acid (F-02) | N-Methyl-1-(pyridin-4-yl)piperidin-4-amine dihydrochloride (AMN-06) | GWP-1 | 89% | |

| Example No. | Structure | Name | Amino acid (ACI) | Amine (AMN) | Synthesis according to | Yield | Comments |
|---|---|---|---|---|---|---|---|
| H-34 | 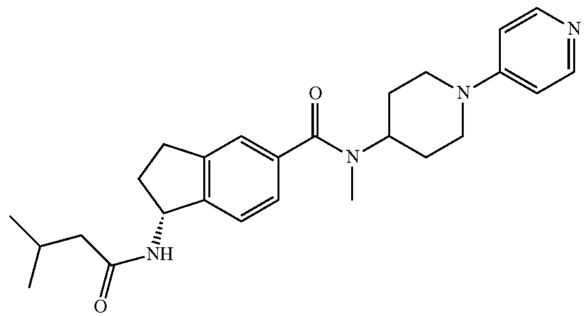 [SMILES: CC(C)CC(=O)N[C@@H]1CCc2cc(C(=O)N(C)C3CCN(c4ccncc4)CC3)ccc21] | (1R)-N-Methyl-1-(3-methyl-butanoylamino)-N-(1-pyridin-4-yl-piperidin-4-yl)-2,3-dihydro-1H-indene-5-carboxylic acid amide (H-34) | (R)-1-(3-Methylbutanamido)-2,3-dihydro-1H-indene-5-carboxylic acid (E-17) | N-Methyl-1-(pyridin-4-yl)piperidin-4-amine (AMN-06) | GWP-1 | 71% | |
| H-35 | 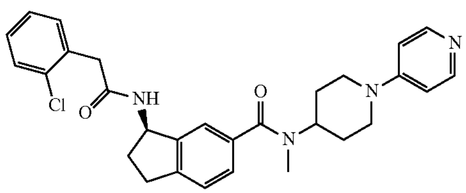 [SMILES: CN(C(=O)c1ccc2c(c1)[C@H](NC(=O)Cc1ccccc1Cl)CC2)C1CCN(c2ccncc2)CC1] | (3R)-3-[[2-(2-Chlorophenyl)-acetyl]amino]-N-methyl-N-(1-pyridin-4-yl-piperidin-4-yl)-2,3-dihydro-1H-indene-5-carboxylic acid amide (H-35) | (R)-3-(2-Chlorophenyl)acetamido)-2,3-dihydro-1H-indene-5-carboxylic acid (E-18) | N-Methyl-1-(pyridin-4-yl)piperidin-4-amine (AMN-06) | GWP-1 | 74% | |
| H-36 | 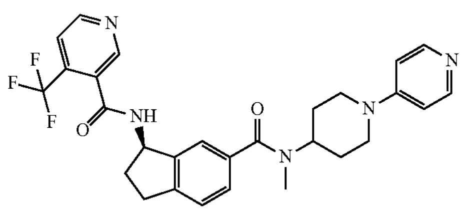 [SMILES: CN(C(=O)c1ccc2c(c1)[C@H](NC(=O)c1cnccc1C(F)(F)F)CC2)C1CCN(c2ccncc2)CC1] | N-[(1R)-6-[Methyl-(1-pyridin-4-yl-piperidin-4-yl)-carbamoyl]-2,3-dihydro-1H-inden-1-yl]-4-(trifluoromethyl)-pyridine-3-carboxylic acid amide (H-36) | (R)-3-(4-(Trifluoromethyl)nicotinamido)-2,3-dihydro-1H-indene-5-carboxylic acid (E-19) | N-Methyl-1-(pyridin-4-yl)piperidin-4-amine (AMN-06) | GWP-1 | 85% | |
| H-37 | 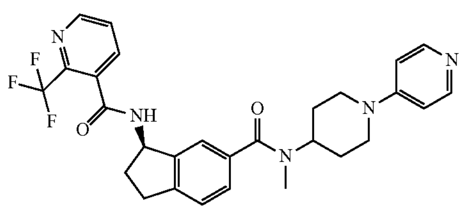 [SMILES: CN(C(=O)c1ccc2c(c1)[C@H](NC(=O)c1cccnc1C(F)(F)F)CC2)C1CCN(c2ccncc2)CC1] | N-[(1R)-6-[Methyl-(1-pyridin-4-yl-piperidin-4-yl)-carbamoyl]-2,3-dihydro-1H-inden-1-yl]-2-(trifluoromethyl)-pyridine-3-carboxylic acid amide (H-37) | (R)-3-(2-(Trifluoromethyl)nicotinamido)-2,3-dihydro-1H-indene-5-carboxylic acid (E-20) | N-Methyl-1-(pyridin-4-yl)piperidin-4-amine (AMN-06) | GWP-1 | 72% | |

TABLE-continued

| Example No. | Structure | Name | Amino acid (ACI) | Amine (AMN) | Synthesis according to | Yield | Comments |
|---|---|---|---|---|---|---|---|
| H-38 | 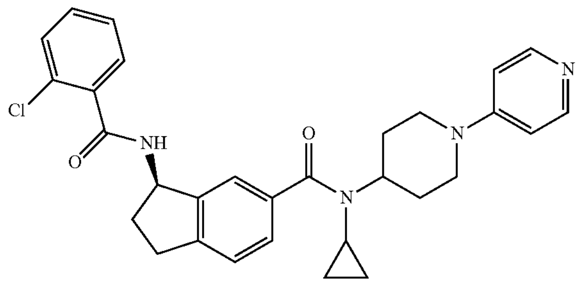 [SMILES: O=C(N[C@@H]1CCc2ccc(C(=O)N(C3CC3)C3CCN(c4ccncc4)CC3)cc21)c1ccccc1Cl] | (3R)-3-[(2-Chloro-benzoyl)amino]-N-cyclopropyl-N-(1-pyridin-4-yl-piperidin-4-yl)-2,3-dihydro-1H-indene-5-carboxylic acid amide (H-38) | (3R)-3-[(2-Chloro-benzoyl)amino]-2,3-dihydro-1H-indene-5-carboxylic acid (E-01) | N-Cyclopropyl-1-(pyridin-4-yl)piperidin-4-amine (AMN-16) | GWP-1 | 49% | |
| H-39 | 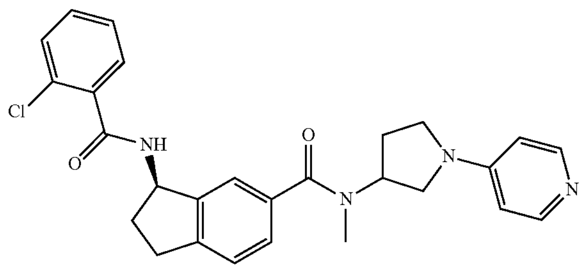 [SMILES: CN(C(=O)c1ccc2c(c1)[C@H](NC(=O)c1ccccc1Cl)CC2)C1CCN(c2ccncc2)C1] | (3R)-3-[(2-Chloro-benzoyl)amino]-N-methyl-N-(1-pyridin-4-yl-pyrrolidin-3-yl)-2,3-dihydro-1H-indene-5-carboxylic acid amide (H-39) | (3R)-3-[(2-Chloro-benzoyl)amino]-2,3-dihydro-1H-indene-5-carboxylic acid (E-01) | N-Methyl-1-(pyridin-4-yl)pyrrolidin-3-amine dihydrochloride (AMN-17) | GWP-1 | 71% | |
| H-40 | 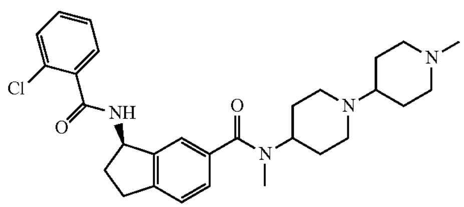 [SMILES: CN1CCC(N2CCC(N(C)C(=O)c3ccc4c(c3)[C@H](NC(=O)c3ccccc3Cl)CC4)CC2)CC1] | (3R)-3-[(2-Chloro-benzoyl)amino]-N-methyl-N-[1-(1-methyl-piperidin-4-yl)-piperidin-4-yl]-2,3-dihydro-1H-indene-5-carboxylic acid amide (H-40) | (3R)-3-[(2-Chloro-benzoyl)amino]-2,3-dihydro-1H-indene-5-carboxylic acid (E-01) | N,1-Dimethyl-1,4-bipiperidin-4-amine (AMN-18) | GWP-1 | 33% | |

TABLE-continued

| Example No. | Structure | Name | Amino acid (ACI) | Amine (AMN) | Synthesis according to | Yield | Comments |
|---|---|---|---|---|---|---|---|
| H-41 | 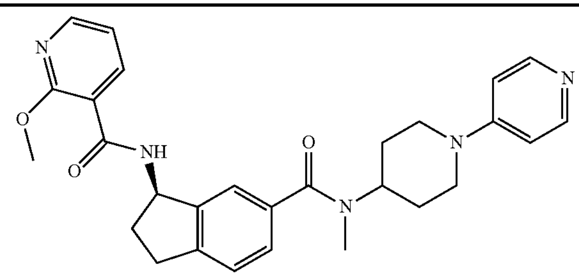 | 2-Methoxy-N-[(1R)-6-[methyl-(1-pyridin-yl-piperidin-4yl)-carbamoyl]-2,3-dihydro-1H-inden-1-yl]-pyridine-3-carboxylic acid amide (H-41) | R-3-(2-Methoxynicotinamido)-2,3-dihydro-1H-indene-5-carboxylic acid (E-21) | N-Methyl-1-(pyridin-4-yl)piperidin-4-amine (AMN-06) | GWP-1 | 77% | |
| H-42 | 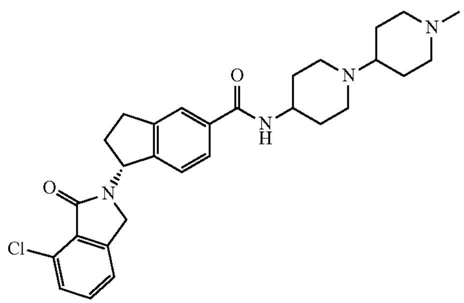 [SMILES: CN1CCC(N2CCC(NC(=O)c3ccc4c(c3)CC[C@H]4N3Cc4cccc(Cl)c4C3=O)CC2)CC1] | (1R)-1-(4-Chloro-3-oxo-1,2-dihydro-isoindol-2-yl)-N-[1-(1-methyl-piperidin-4-yl)-piperidin-4-yl]-2,3-dihydro-1H-indene-5-carboxylic acid amide (H-42) | (R)-1-(7-Chloro-1-oxoisoindolin-2-yl)-2,3-dihydro-1H-indene-5-carboxylic acid (G-02) | 1'-Methyl-1,4'-bipiperidin-4-amine (AMN-19) | GWP-1 | 38% | |
| H-43 | 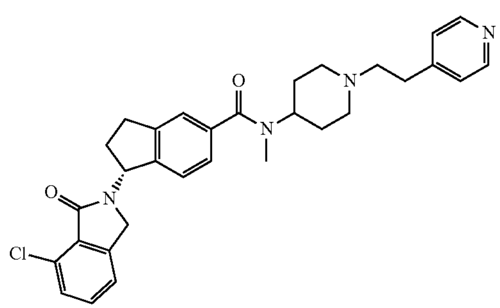 [SMILES: CN(C(=O)c1ccc2c(c1)CC[C@H]2N1Cc2cccc(Cl)c2C1=O)C1CCN(CCc2ccncc2)CC1] | (1R)-1-(4-Chloro-3-oxo-1,2-dihydro-isoindol-2-yl)-N-methyl-N-[1-(2-pyridin-4-yl-ethyl)-piperidin-4-yl]-2,3-dihydro-1H-Indene-5-carboxylic acid amide (H-43) | (R)-1-(7-Chloro-1-oxoisoindolin-2-yl)-2,3-dihydro-1H-indene-5-carboxylic acid (G-02) | N-Methyl-1-(2-(pyridin-4-yl)ethyl)piperidin-4-amine (AMN-20) | GWP-1 | >99% | |

| Example No. | Structure | Name | Amino acid (ACI) | Amine (AMN) | Synthesis according to | Yield | Comments |
|---|---|---|---|---|---|---|---|
| H-44 | 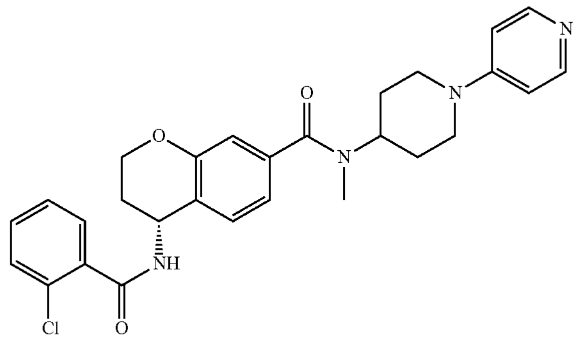 [SMILES: CN(C(=O)c1ccc2c(c1)OCC[C@H]2NC(=O)c1ccccc1Cl)C1CCN(c2ccncc2)CC1] | (4R)-4-[(2-Chloro-benzoyl)amino]-N-methyl-N-(1-pyridin-4-yl-piperidin-4-yl)-3,4-dihydro-2H-chromene-7-carboxylic acid amide (H-44) | (R)-4-(2-Chlorobenzamido)chromane-7-carboxylic acid (E22) | N-Methyl-1-(pyridin-4-yl)piperidin-4-amine (AMN-06) | GWP-1 | 92% | |
| H-45 | 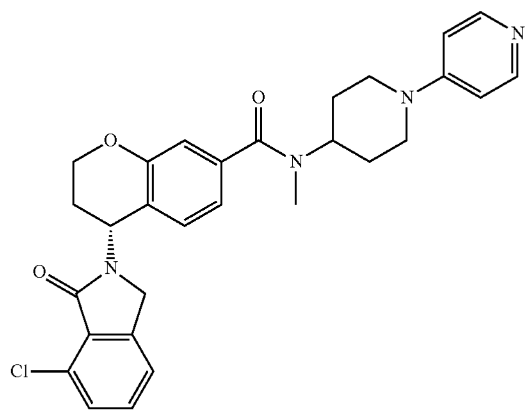 [SMILES: CN(C(=O)c1ccc2c(c1)OCC[C@H]2N1Cc2cccc(Cl)c2C1=O)C1CCN(c2ccncc2)CC1] | (4R)-4-(4-Chloro-3-oxo-1,2-dihydro-isoindol-2-yl)-N-methyl-N-(1-pyridin-4-yl-piperidin-4-yl)-3,4-dihydro-2H-chromene-7-carboxylic acid amide (H-45) | (R)-4-(7-Chloro-1-oxoisoindolin-2-yl)chromane-7-carboxylic acid (G-03) | N-Methyl-1-(pyridin-4-yl)piperidin-4-amine (AMN-06) | GWP-1 | 67% | |
| H-46 | 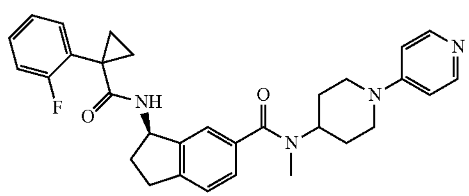 [SMILES: CN(C(=O)c1ccc2c(c1)[C@H](NC(=O)C1(c3ccccc3F)CC1)CC2)C1CCN(c2ccncc2)CC1] | (3R)-3-[[1-(2-Fluorophenyl)-cyclopropanecarbonyl]amino]-N-methyl-N-(1-pyridin-4-yl-piperidin-4-yl)-2,3-dihydro-1H-indene-5-carboxylic acid amide (H-46) | (R)-3-(1-(2-Fluorophenyl)cyclopropane-carboxamido)-2,3-dihydro-1H-indene-5-carboxylic acid (E-23) | N-Methyl-1-(pyridin-4-yl)piperidin-4-amine (AMN-06) | GWP-1 | 62% | |

| Example No. | Structure | Name | Amino acid (ACI) | Amine (AMN) | Synthesis according to | Yield | Comments |
|---|---|---|---|---|---|---|---|
| H-47 | 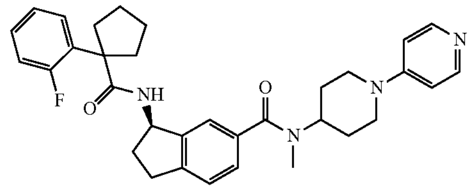 [SMILES: CN(C(=O)c1ccc2c(c1)[C@H](NC(=O)C1(c3ccccc3F)CCCC1)CC2)C1CCN(c2ccncc2)CC1] | (3R)-3-[[1-(2-Fluorophenyl)-cyclopentanecarbonyl]amino]-N-methyl-N-(1-pyridin-4-yl-piperidin-4-yl)-2,3-dihydro-1H-indene-5-carboxylic acid amide (H-47) | (R)-3-(1-(2-Fluorophenyl)cyclopentane-carboxamido)-2,3-dihydro-1H-indene-5-carboxylic acid (E-24) | N-Methyl-1-(pyridin-4-yl)piperidin-4-amine (AMN-06) | GWP-1 | 78% | |
| H-48 | 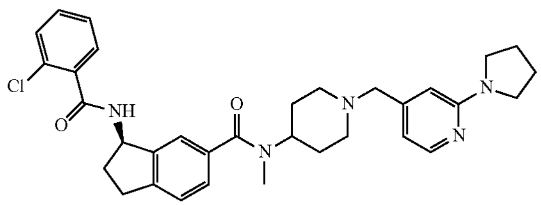 [SMILES: CN(C(=O)c1ccc2c(c1)[C@H](NC(=O)c1ccccc1Cl)CC2)C1CCN(Cc2ccnc(N3CCCC3)c2)CC1] | (3R)-3-[(2-Chloro-benzoyl)amino]-N-methyl-N-[1-[(2-pyrrolidin-1-yl-pyridin-4-yl)methyl]-piperidin-4-yl]-2,3-dihydro-1H-indene-5-carboxylic acid amide (H-48) | (3R)-3-[(2-Chloro-benzoyl)amino]-2,3-dihydro-1H-indene-5-carboxylic acid (E-01) | N-Methyl-1-((2-(pyrrolidin-1-yl)pyridin-4-yl)methyl)piperidin-4-amine hydrochloride (AMN-21) | GWP-1 | 40% | |
| H-49 | 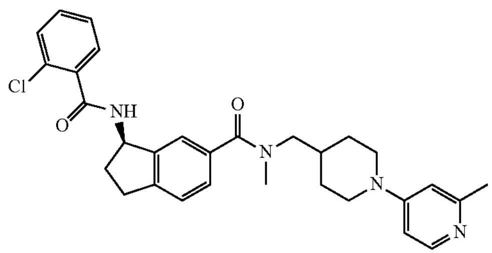 [SMILES: Cc1cc(N2CCC(CN(C)C(=O)c3ccc4c(c3)[C@H](NC(=O)c3ccccc3Cl)CC4)CC2)ccn1] | (3R)-3-[(2-Chloro-benzoyl)amino]-N-methyl-N-[[1-(2-methyl-pyridin-4-yl)piperidin-4-yl]methyl]-2,3-dihydro-1H-indene-5-carboxylic acid amide (H-49) | (3R)-3-[(2-Chloro-benzoyl)amino]-2,3-dihydro-1H-indene-5-carboxylic acid (E-01) | N-Methyl-1-(1-(2-methylpyridin-4-yl)piperidin-4-yl)methanamine dihydrochloride (AMN-22) | GWP-1 | 66% | |
| H-50 | 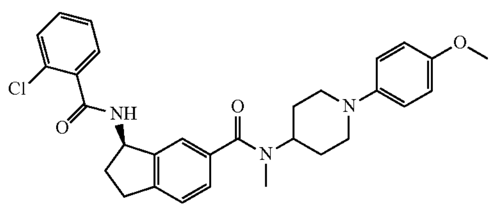 [SMILES: COc1ccc(N2CCC(N(C)C(=O)c3ccc4c(c3)[C@H](NC(=O)c3ccccc3Cl)CC4)CC2)cc1] | (3R)-3-[(2-Chloro-benzoyl)amino]-N-[1-(4-methoxyphenyl)-piperidin-4-yl]-N-methyl-2,3-dihydro-1H-indene-5-carboxylic acid amide (H-50) | (3R)-3-[(2-Chloro-benzoyl)amino]-2,3-dihydro-1H-indene-5-carboxylic acid (E-01) | 1-(4-Methoxyphenyl)-N-methylpiperidin-4-amine (AMN-23) | GWP-1 | 89% | |

| Example No. | Structure | Name | Amino acid (ACI) | Amine (AMN) | Synthesis according to | Yield | Comments |
|---|---|---|---|---|---|---|---|
| H-51 | 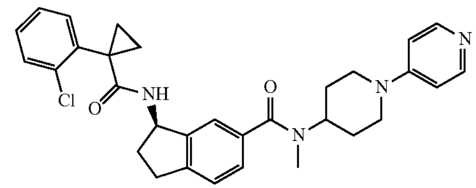 [SMILES: CN(C(=O)c1ccc2c(c1)[C@H](NC(=O)C1(c3ccccc3Cl)CC1)CC2)C1CCN(c2ccncc2)CC1] | (3R)-3-[[1-(2-Chlorophenyl)-cyclopropanecarbonyl]amino]-N-methyl-N-(1-pyridin-4-yl-piperidin-4-yl)-2,3-dihydro-1H-indene-5-carboxylic acid amide (H-51) | (R)-3-(1-(2-Chlorophenyl)cyclopropane-carboxamido)-2,3-dihydro-1H-indene-5-carboxylic acid (E-25) | N-Methyl-1-(pyridin-4-yl)piperidin-4-amine (AMN-06) | GWP-1 | 95% | |
| H-52 | 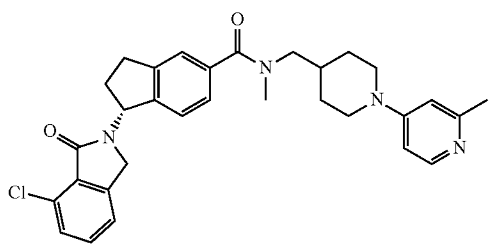 [SMILES: Cc1cc(N2CCC(CN(C)C(=O)c3ccc4c(c3)CC[C@H]4N3Cc4cccc(Cl)c4C3=O)CC2)ccn1] | (1R)-1-(4-Chloro-3-oxo-1,2-dihydro-isoindol-2-yl)-N-methyl-N-[[1-(2-methyl-pyridin-4-yl)-piperidin-4-yl]-methyl]-2,3-dihydro-1H-indene-5-carboxylic acid amide (H-52) | (R)-1-(7-Chloro-1-oxoisoindolin-2-yl)-2,3-dihydro-1H-indene-5-carboxylic acid (G-02) | N-Methyl-1-(1-(2-methylpyridin-4-yl)piperidin-4-yl)methanamine dihydrochloride (AMN-22) | GWP-1 | 41% | |
| H-53 | 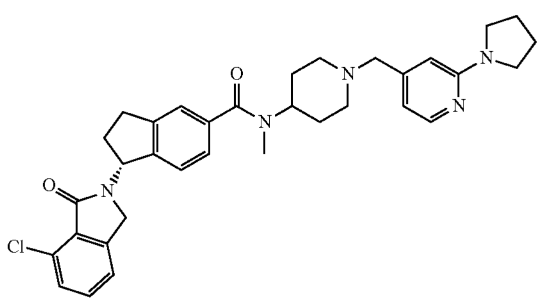 [SMILES: CN(C(=O)c1ccc2c(c1)CC[C@H]2N1Cc2cccc(Cl)c2C1=O)C1CCN(Cc2ccnc(N3CCCC3)c2)CC1] | (1R)-1-(4-Chloro-3-oxo-1,2-dihydro-isoindol-2-yl)-N-methyl-N-[1-[(2-pyrrolidin-1-yl-pyridin-4-yl)-methyl]-piperidin-4-yl]-2,3-dihydro-1H-indene-5-carboxylic acid amide (H-53) | (R)-1-(7-Chloro-1-oxoisoindolin-2-yl)-2,3-dihydro-1H-indene-5-carboxylic acid (G-02) | N-Methyl-1-(2-(pyrrolidin-1-yl)pyridin-4-yl)methyl)piperidin-4-amine hydrochloride (AMN-21) | GWP-1 | 28% | |
| H-54 | 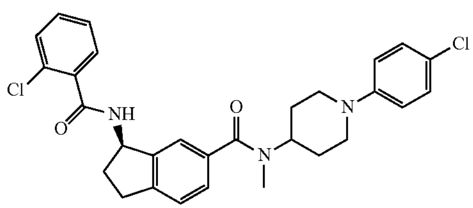 [SMILES: CN(C(=O)c1ccc2c(c1)[C@H](NC(=O)c1ccccc1Cl)CC2)C1CCN(c2ccc(Cl)cc2)CC1] | (3R)-3-[(2-Chloro-benzoyl)amino]-N-[1-(4-chlorophenyl)-piperidin-4-yl]-N-methyl-2,3-dihydro-1H-indene-5-carboxylic acid amide (H-54) | (3R)-3-[(2-Chloro-benzoyl)amino]-2,3-dihydro-1H-indene-5-carboxylic acid (E-01) | 1-(4-Chlorophenyl)-N-methylpiperidin-4-amine (AMN-24) | GWP-1 | 84% | |

| Example No. | Structure | Name | Amino acid (ACI) | Amine (AMN) | Synthesis according to | Yield | Comments |
|---|---|---|---|---|---|---|---|
| H-55 | 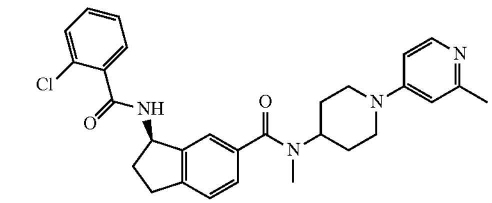 | (3R)-3-[(2-Chloro-benzoyl)amino]-N-methyl-N-[1-(2-methyl-pyridin-4-yl)-piperidin-4-yl]-2,3-dihydro-1H-indene-5-carboxylic acid amide (H-55) | (3R)-3-[(2-Chloro-benzoyl)amino]-2,3-dihydro-1H-indene-5-carboxylic acid (E-01) | N-Methyl-1-(2-methylpyridin-4-yl)piperidin-4-amine dihydrochloride (AMN-25) | GWP-1 | 71% | |
| H-56 | 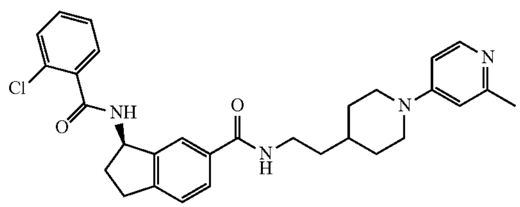 [SMILES: Cc1cc(N2CCC(CCNC(=O)c3ccc4c(c3)[C@H](NC(=O)c3ccccc3Cl)CC4)CC2)ccn1] | (3R)-3-[(2-Chloro-benzoyl)amino]-N-[2-[1-(2-methyl-pyridin-4-yl)-piperidin-4-yl]-ethyl]-2,3-dihydro-1H-indene-5-carboxylic acid amide (H-56) | (3R)-3-[(2-Chloro-benzoyl)amino]-2,3-dihydro-1H-indene-5-carboxylic acid (E-01) | 2-(1-(2-Methylpyridin-4-yl)piperidin-4-yl)ethanamine hydrochloride (AMN-26) | GWP-1 | 41% | |
| H-57 | 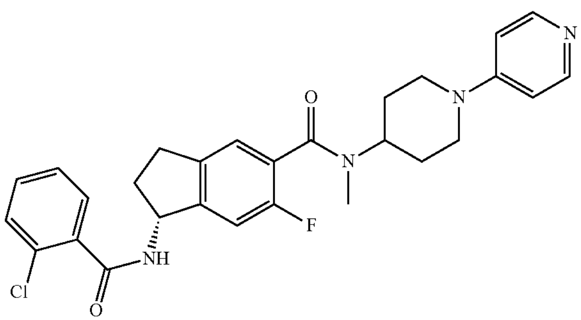 [SMILES: CN(C(=O)c1cc2c(cc1F)[C@H](NC(=O)c1ccccc1Cl)CC2)C1CCN(c2ccncc2)CC1] | (1R)-1-[(2-Chloro-benzoyl)amino]-6-fluoro-N-methyl-N-(1-pyridin-4-yl-piperidin-4-yl)-2,3-dihydro-1H-indene-5-carboxylic acid amide (H-57) | (R)-1-(2-Chlorobenzamido)-6-fluoro-2,3-dihydro-1H-indene-5-carboxylic acid (E-30) | N-Methyl-1-(pyridin-4-yl)piperidin-4-amine (AMN-06) | GWP-1 | 85% | |
| H-58 | 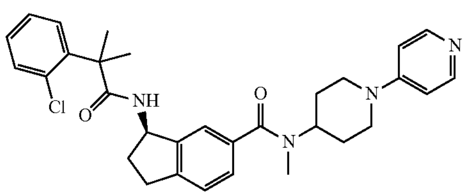 [SMILES: CN(C(=O)c1ccc2c(c1)[C@H](NC(=O)C(C)(C)c1ccccc1Cl)CC2)C1CCN(c2ccncc2)CC1] | (3R)-3-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide (H-58) | (R)-3-(2-(2-Chlorophenyl)-2-methylpropanamido)-2,3-dihydro-1H-indene-5-carboxylic acid (E-26) | N-Methyl-1-(pyridin-4-yl)piperidin-4-amine (AMN-06) | GWP-1 | 74% | |

TABLE-continued

| Example No. | Structure | Name | Amino acid (ACI) | Amine (AMN) | Synthesis according to | Yield | Comments |
|---|---|---|---|---|---|---|---|
| H-59 | 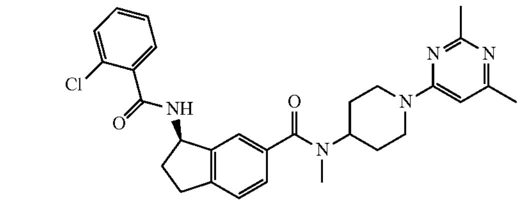 | (3R)-3-[(2-Chloro-benzoyl)amino]-N-[1-(2,6-dimethyl-pyrimidin-4-yl)-piperidin-4-yl]-N-methyl-2,3-dihydro-1H-indene-5-carboxylic acid amide (H-59) | (3R)-3-[(2-Chloro-benzoyl)amino]-2,3-dihydro-1H-indene-5-carboxylic acid (E-01) | 1-(2,6-Dimethylpyrimidin-4-yl)-N-methylpiperidin-4-amine (AMN-27) | GWP-1 | 81% | |
| H-60 | 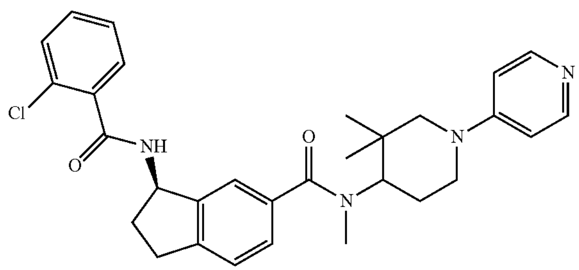 [SMILES: CN(C(=O)c1ccc2c(c1)[C@H](NC(=O)c1ccccc1Cl)CC2)C1CCN(c2ccncc2)CC1(C)C] | (3R)-3-[(2-Chloro-benzoyl)amino]-N-(3,3-dimethyl-1-pyridin-4-yl-piperidin-4-yl)-N-methyl-2,3-dihydro-1H-indene-5-carboxylic acid amide (H-60) | (3R)-3-[(2-Chloro-benzoyl)amino]-2,3-dihydro-1H-indene-5-carboxylic acid (E-01) | N,3,3-Trimethyl-1-(pyridin-4-yl)piperidin-4-amine (AMN-28) | GWP-3 | 29% (130 mg, 0.251 mmol) | |
| H-61 | 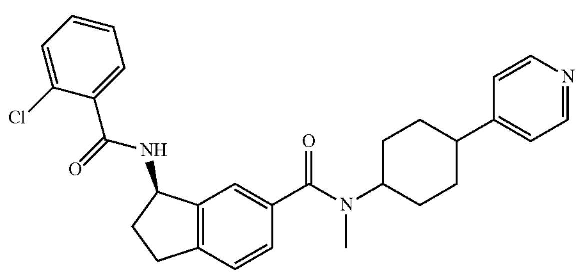 | (3R)-3-[(2-Chloro-benzoyl)amino]-N-methyl-N-(4-pyridin-4-yl-cyclohexyl)-2,3-dihydro-1H-indene-5-carboxylic acid amide (H61) | (3R)-3-[(2-Chloro-benzoyl)amino]-2,3-dihydro-1H-indene-5-carboxylic acid (E-01) | N-Methyl-4-(pyridin-4-yl)cyclohexanamine (AMN-31) | GWP-2 | 32% (150 mg, 0.308 mmol) | |

TABLE-continued

| Example No. | Structure | Name | Amino acid (ACI) | Amine (AMN) | Synthesis according to | Yield | Comments |
|---|---|---|---|---|---|---|---|
| H-62 | 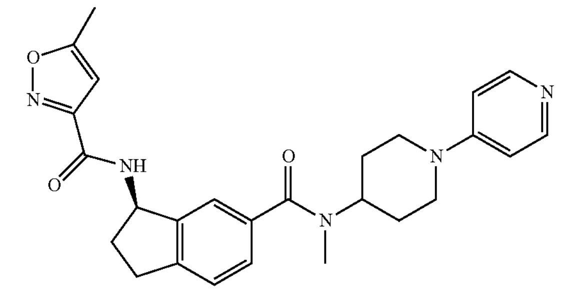 | 5-Methyl-N-[(1R)-6-[methyl-(1-pyridin-4-yl-piperidin-4-yl)carbamoyl]-2,3-dihydro-1H-inden-1-yl]-isoxazole-3-carboxylic acid amide (H-62) | (R)-3-(5-Methylisoxazole-3-carboxamido)-2,3-dihydro-1H-indene-5-carboxylic acid (E-27) | N-Methyl-1-(pyridin-4-yl)piperidin-4-amine (AMN-06) | GWP-2 | 37% (120 mg, 0.26 mmol). | |
| H-63 | 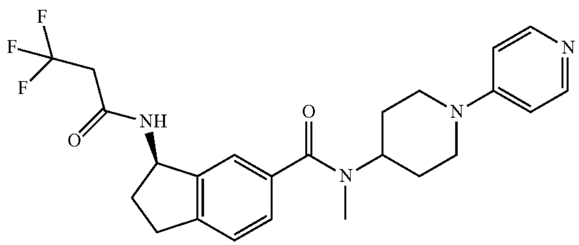 [SMILES: CN(C(=O)c1ccc2c(c1)[C@H](NC(=O)CC(F)(F)F)CC2)C1CCN(c2ccncc2)CC1] | (3R)-N-Methyl-N-(1-pyridin-4-yl-piperidin-4-yl)-3-(3,3,3-trifluoro-propanoylamino)-2,3-dihydro-1H-indene-5-carboxylic acid amide (H-63) | | | | | see below |
| H-64 | 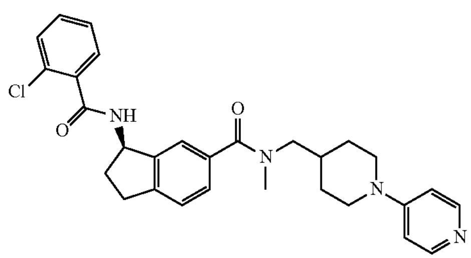 [SMILES: CN(CC1CCN(c2ccncc2)CC1)C(=O)c1ccc2c(c1)[C@H](NC(=O)c1ccccc1Cl)CC2] | (3R)-3-[(2-Chloro-benzoyl)amino]-N-methyl-N-[(1-pyridin-4-yl-piperidin-4-yl)methyl]-2,3-dihydro-1H-indene-5-carboxylic acid amide (H-64) | (3R)-3-[(2-Chloro-benzoyl)amino]-2,3-dihydro-1H-indene-5-carboxylic acid (E-01) | N-Methyl-1-(1-(pyridin-4-yl)piperidin-4-yl)methanamine (AMN-29) | GWP-3 | 35% (130 mg, 0.258 mmol) | |

| Example No. | Structure | Name | Amino acid (ACI) | Amine (AMN) | Synthesis according to | Yield | Comments |
|---|---|---|---|---|---|---|---|
| H-65 | 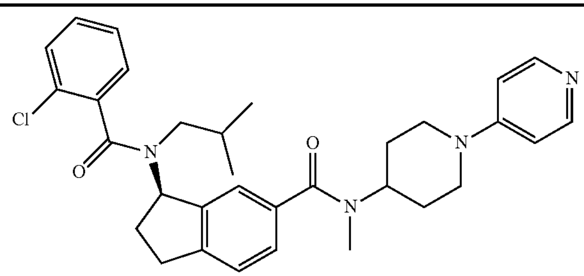 | (3R)-3-[(2-Chloro-benzoyl)-(2-methyl-propyl)-amino]-N-methyl-N-(1-pyridin-4-yl-piperidin-4-yl)-2,3-dihydro-1H-indene-5-carboxylic acid amide (H-65) | (R)-3-(2-Chloro-N-isobutylbenzamido)-2,3-dihydro-1H-indene-5-carboxylic acid (E-31) | N-Methyl-1-(pyridin-4-yl)piperidin-4-amine (AMN-06) | GWP-2 | 27% (120 mg, 0.22 mmol) | |
| H-66 | 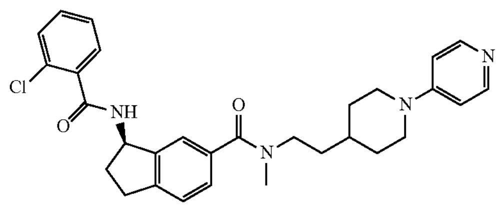 [SMILES: CN(CCC1CCN(c2ccncc2)CC1)C(=O)c1ccc2c(c1)[C@H](NC(=O)c1ccccc1Cl)CC2] | (3R)-3-[(2-Chloro-benzoyl)amino]-N-methyl-N-[2-(1-pyridin-4-yl-piperidin-4-yl)-ethyl]-2,3-dihydro-1H-indene-5-carboxylic acid amide (H-66) | (3R)-3-[(2-Chloro-benzoyl)amino]-2,3-dihydro-1H-indene-5-carboxylic acid (E-01) | N-Methyl-2-(1-(pyridin-4-yl)piperidin-4-yl)ethanamine (AMN-30) | GWP-2 | 19% (100 mg, 0.194 mmol) | |
| H-67 | 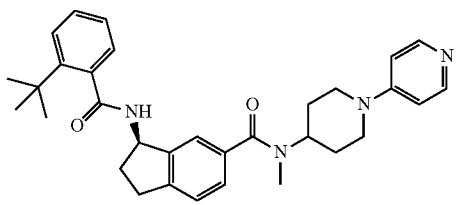 [SMILES: CN(C(=O)c1ccc2c(c1)[C@H](NC(=O)c1ccccc1C(C)(C)C)CC2)C1CCN(c2ccncc2)CC1] | (3R)-3-[(2-tert-Butyl-benzoyl)amino]-N-methyl-N-(1-pyridin-4-yl-piperidin-4-yl)-2,3-dihydro-1H-indene-5-carboxylic acid amide (H-67) | (R)-3-(2-tert-Butylbenzamido)-2,3-dihydro-1H-indene-5-carboxylic acid (E-29) | N-Methyl-1-(pyridin-4-yl)piperidin-4-amine (AMN-06) | GWP-2 | 40% (270 mg, 0.529 mmol) | |
| H-68 | 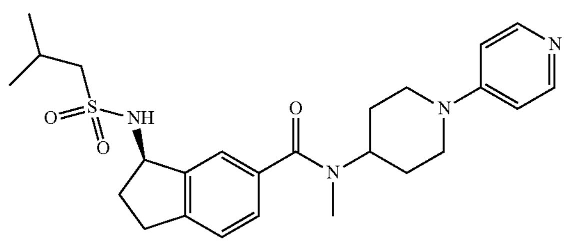 [SMILES: CC(C)CS(=O)(=O)N[C@@H]1CCc2ccc(C(=O)N(C)C3CCN(c4ccncc4)CC3)cc21] | (3R)-N-Methyl-3-[(2-methyl-propylsulfonyl)amino]-N-(1-pyridin-4-yl-piperidin-4-yl)-2,3-dihydro-1H-indene-5-carboxylic acid amide (H-68) | (R)-3-(2-Methylpropylsulfonamido)-2,3-dihydro-1H-indene-5-carboxylic acid (F-03) | N-Methyl-1-(pyridin-4-yl)piperidin-4-amine (AMN-06) | GWP-2 | 53% (250 mg, 0.53 mmol) | |

| Example No. | Structure | Name | Amino acid (ACI) | Amine (AMN) | Synthesis according to | Yield | Comments |
|---|---|---|---|---|---|---|---|
| H-69 | 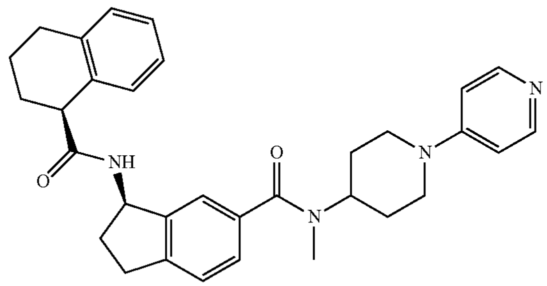 [SMILES: CN(C(=O)c1ccc2c(c1)[C@H](NC(=O)[C@H]1CCCc3ccccc31)CC2)C1CCN(c2ccncc2)CC1] | (1S)-N-[(1R)-6-[Methyl-(1-pyridin-4-yl-piperidin-4-yl)-carbamoyl]-2,3-dihydro-1H-inden-1-yl]-1,2,3,4-tetrahydro-naphthalene-1-carboxylic acid amide (H-69) | (R)-3-((S)-1,2,3,4-Tetrahydronaphthalene-1-carboxamido)-2,3-dihydro-1H-indene-5-carboxylic acid (E-44) | N-Methyl-1-(pyridin-4-yl)piperidin-4-amine (AMN-06) | GWP-1 | 65% | |
| H-70 | 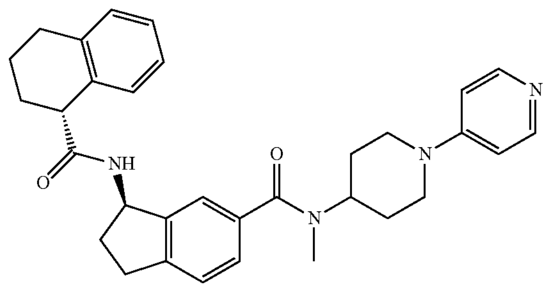 [SMILES: CN(C(=O)c1ccc2c(c1)[C@H](NC(=O)[C@@H]1CCCc3ccccc31)CC2)C1CCN(c2ccncc2)CC1] | N-[(1R)-6-[Methyl-(1-pyridin-4-yl-piperidin-4-yl)-carbamoyl]-2,3-dihydro-1H-inden-1-yl]-1,2,3,4-tetrahydro-naphthalene-1-carboxylic acid amide (H-70) | (R)-3-((R)-1,2,3,4-Tetrahydronaphthalene-1-carboxamido)-2,3-dihydro-1H-indene-5-carboxylic acid (E-45) | N-Meth-1-(pyridin-4-yl)piperidin-4-amine (AMN-06) | GWP-1 | 58% | |
| H-71 | 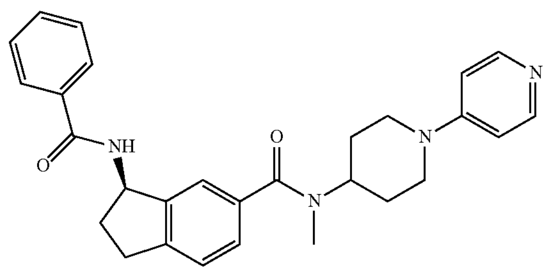 [SMILES: CN(C(=O)c1ccc2c(c1)[C@H](NC(=O)c1ccccc1)CC2)C1CCN(c2ccncc2)CC1] | (3R)-3-Benzoylamino-N-methyl-N-(1-pyridin-4-yl-piperidin-4-yl)-2,3-dihydro-1H-indene-5-carboxylic acid amide (H-71) | (R)-3-Benzamido-2,3-dihydro-1H-indene-5-carboxylic acid (E-37) | N-Methyl-1-(pyridin-4-yl)piperidin-4-amine (AMN-06) | GWP-1 | 79% | |

TABLE-continued

| Example No. | Structure | Name | Amino acid (ACI) | Amine (AMN) | Synthesis according to | Yield | Comments |
|---|---|---|---|---|---|---|---|
| H-72 | 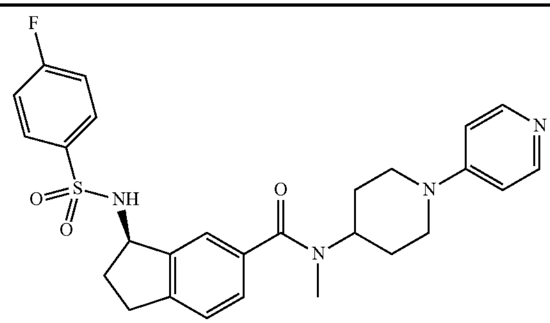 | (3R)-3-[[(4-Fluorophenyl)sulfonyl]amino]-N-methyl-N-(1-pyridin-4-yl-piperidin-4-yl)-2,3-dihydro-1H-indene-5-carboxylic acid amide (H-72) | (R)-Methyl 3-(4-fluorophenylsulfonamido)-2,3-dihydro-1H-indene-5-carboxylic acid (F-04) | N-Methyl-1-(pyridin-4-yl)piperidin-4-amine (AMN-06) | GWP-1 | 71% | |
| H-73 | 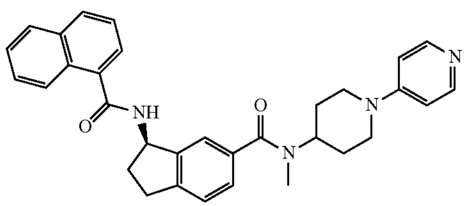 [SMILES: CN(C(=O)c1ccc2c(c1)[C@H](NC(=O)c1cccc3ccccc13)CC2)C1CCN(c2ccncc2)CC1] | N-[(1R)-6-[Methyl-(1-pyridin-4-yl-piperidin-4-yl)-carbamoyl]-2,3-dihydro-1H-Inden-1-yl]-naphthalene-1-carboxylic acid amide (H-73) | (R)-3-(1-Naphthamido)-2,3-dihydro-1H-indene-5-carboxylic acid (E-38) | N-Methyl-1-(pyridin-4-yl)piperidin-4-amine (AMN-06) | GWP-1 | 85% | |
| H-74 | 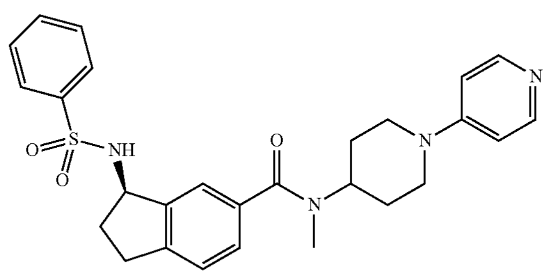 [SMILES: CN(C(=O)c1ccc2c(c1)[C@H](NS(=O)(=O)c1ccccc1)CC2)C1CCN(c2ccncc2)CC1] | (3R)-3-(Benzenesulfonamido)-N-methyl-N-(1-pyridin-4-yl-piperidin-4-yl)-2,3-dihydro-1H-indene-5-carboxylic acid amide (H-74) | (R)-Methyl 3-(phenylsulfonamido)-2,3-dihydro-1H-indene-5-carboxylic acid (F-05) | N-Methyl-1-(pyridin-4-yl)piperidin-4-amine (AMN-06) | GWP-1 | 84% | |

TABLE-continued

| Example No. | Structure | Name | Amino acid (ACI) | Amine (AMN) | Synthesis according to | Yield | Comments |
|---|---|---|---|---|---|---|---|
| H-75 | 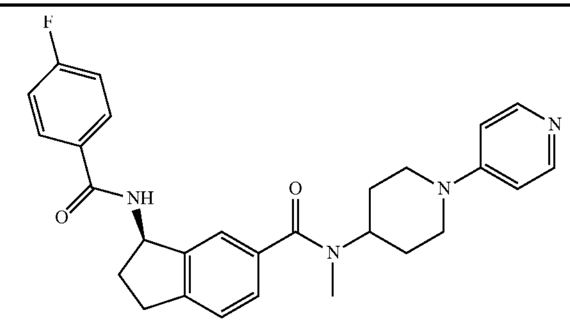 | (3R)-3-[(4-Fluoro-benzoyl)amino]-N-methyl-N-(1-pyridin-4-yl-piperidin-4-yl)-2,3-dihydro-1H-indene-5-carboxylic acid amide (H-75) | (R)-3-(4-Fluorobenzamido)-2,3-dihydro-1H-indene-5-carboxylic acid (E-39) | N-Methyl-1-(pyridin-4-yl)piperidin-4-amine (AMN-06) | GWP-1 | 95% | |
| H-76 | 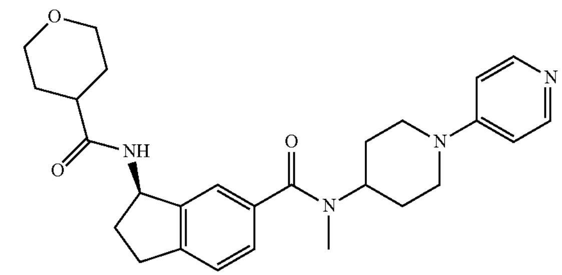 [SMILES: CN(C(=O)c1ccc2c(c1)[C@H](NC(=O)C1CCOCC1)CC2)C1CCN(c2ccncc2)CC1] | N-[(1R)-6-[Methyl-(1-pyridin-4-yl-piperidin-4-yl)-carbamoyl]-1H-yl]-2,3-dihydro-1H-yl)-1-2,3-tetrahydro-pyran-4-carboxylic acid amide (H-76) | (R)-3-(Tetrahydro-2H-pyran-4-carboxamido)-2,3-dihydro-1H-indene-5-carboxylic acid (E-40) | N-Methyl-1-(pyridin-4-yl)piperidin-4-amine (AMN-06) | GWP-1 | 44% | |
| H-77 | 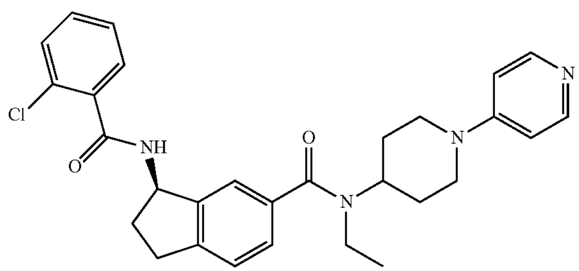 [SMILES: CCN(C(=O)c1ccc2c(c1)[C@H](NC(=O)c1ccccc1Cl)CC2)C1CCN(c2ccncc2)CC1] | (3R)-3-[(2-Chloro-benzoyl)amino]-N-ethyl-N-(1-pyridin-4-yl-piperidin-4-yl)-2,3-dihydro-1H-indene-5-carboxylic acid amide (H-77) | (3R)-3-[(2-Chloro-benzoyl)amino]-2,3-dihydro-1H-indene-5-carboxylic acid (E-01) | N-Ethyl-1-(pyridin-4-yl)piperidin-4-amine dihydrochloride (AMN-39) | GWP-1 | 72% | |

| Example No. | Structure | Name | Amino acid (ACI) | Amine (AMN) | Synthesis according to | Yield | Comments |
|---|---|---|---|---|---|---|---|
| H-78 | 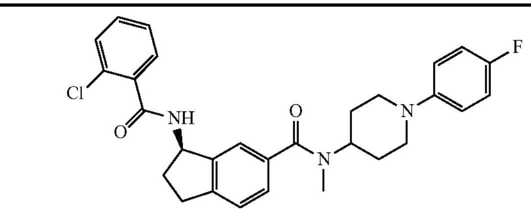 | (3R)-3-[(2-Chloro-benzoyl)amino]-N-[1-(4-fluorophenyl)-pipendin-4-yl]-N-methyl-2,3-dihydro-1H-indene-5-carboxylic acid amide (H-78) | (3R)-3-[(2-Chloro-benzdyl)amino]-2,3-dihydro-1H-indene-5-carboxylic acid (E-01) | 1-(4-Fluorophenyl)-N-methylpiperidin-4-amine (AMN-40) | GWP-1 | 46% | |
| H-79 | 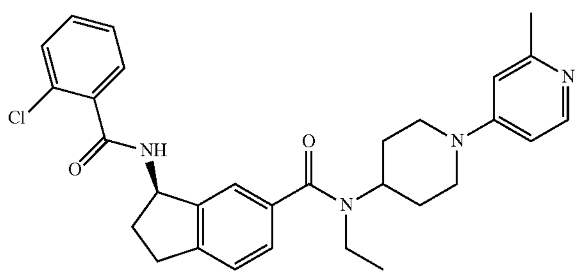 [SMILES: CCN(C(=O)c1ccc2c(c1)[C@H](NC(=O)c1ccccc1Cl)CC2)C1CCN(c2ccnc(C)c2)CC1] | (3R)-3-[(2-Chloro-benzoyl)amino]-N-ethyl-N-[1-(2-methyl-pyridin-4-yl)-piperidin-4-yl]-2,3-dihydro-1H-indene-5-carboxylic acid amide (H-79) | (3R)-3-[(2-Chloro-benzoyl)amino]-2,3-dihydro-1H-indene-5-carboxylic acid (E-01) | N-Ethyl-1-(2-methylpyridin-4-yl)piperidin-4-amine dihydrochloride (AMN-41) | GWP-1 | 8% | |
| H-80 | 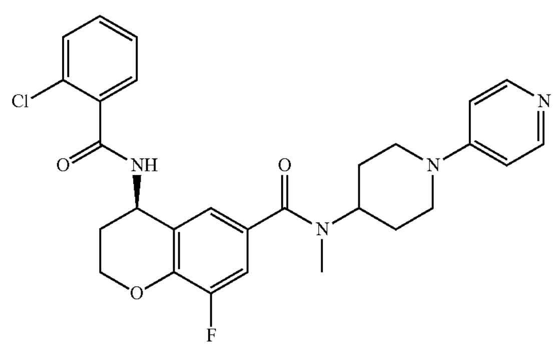 [SMILES: CN(C(=O)c1cc(F)c2c(c1)[C@H](NC(=O)c1ccccc1Cl)CCO2)C1CCN(c2ccncc2)CC1] | (4R)-4-[(2-Chloro-benzoyl)amino]-8-fluoro-N-methyl-N-(1-pyridin-4-yl)-piperidin-4-yl)-3,4-dihydro-2H-chromene-6-carboxylic acid amide (H-80) | (R)-4-(2-Chlorobenzamido)-8-fluorochromane-6-carboxylic acid (E-41) | N-Methyl-1-(pyridin-4-yl)piperidin-4-amine (AMN-06) | GWP-1 | 76% | |

| Example No. | Structure | Name | Amino acid (ACI) | Amine (AMN) | Synthesis according to | Yield | Comments |
|---|---|---|---|---|---|---|---|
| H-81 | 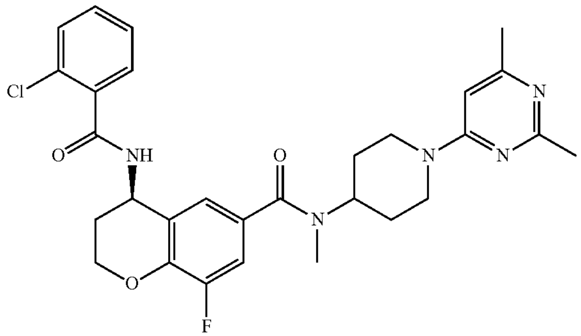 [SMILES: Cc1cc(N2CCC(N(C)C(=O)c3cc(F)c4c(c3)[C@H](NC(=O)c3ccccc3Cl)CCO4)CC2)nc(C)n1] | (4R)-4-[[2-Chloro-benzoyl)amino]-N-[1-(2,6-dimethyl-pyrimidin-4-yl)-piperidin-4-yl]-8-fluoro-N-methyl-3,4-dihydro-2H-chromene-6-carboxylic acid amide (H-81) | (R)-4-(2-Chlorobenzamido)-8-fluorochromane-6-carboxylic acid (E-41) | 1-(2,6-Dimethylpyrimidin-4-yl)-N-methylpiperidin-4-amine (AMN-27) | GWP-1 | 82% | |
| H-82 | 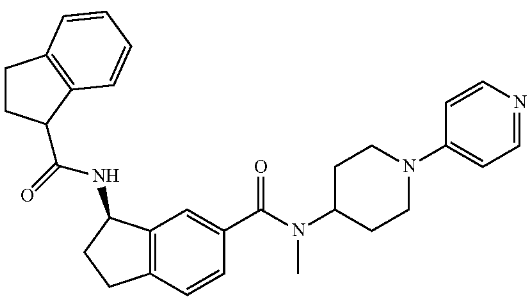 [SMILES: CN(C(=O)c1ccc2c(c1)[C@H](NC(=O)C1CCc3ccccc31)CC2)C1CCN(c2ccncc2)CC1] | (3R)-3-(2,3-Dihydro-1H-inden-1-carbonylamino)-N-methyl-N-(1-pyridin-4-yl-piperidin-4-yl)-2,3-dihydro-1H-indene-5-carboxylic acid amide (H-82) | (3R)-3-(2,3-Dihydro-1H-inden-1-carboxamido)-2,3-dihydro-1H-indene-5-carboxylic acid (E-46) | N-Methyl-1-(pyridin-4-yl)piperidin-4-amine (AMN-06) | GWP-1 | 88% | |
| H-83 | 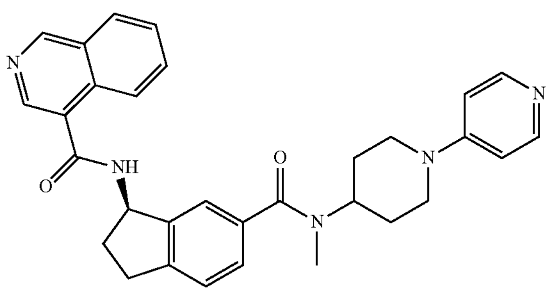 [SMILES: CN(C(=O)c1ccc2c(c1)[C@H](NC(=O)c1cncc3ccccc13)CC2)C1CCN(c2ccncc2)CC1] | N-[(1R)-6-[Methyl-(1-pyridin-4-yl-piperidin-4-yl)carbamoyl]-2,3-dihydro-1H-inden-1-yl]-isoquinoline-4-carboxylic acid amide (H-83) | (R)-3-(Isoquinoline-4-carboxamido)-2,3-dihydro-1H-indene-5-carboxylic acid (E-47) | N-Methyl-1-(pyridin-4-yl)piperidin-4-amine (AMN-06) | GWP-1 | 77% | |

TABLE-continued

| Example No. | Structure | Name | Amino acid (ACI) | Amine (AMN) | Synthesis according to | Yield | Comments |
|---|---|---|---|---|---|---|---|
| H-84 | 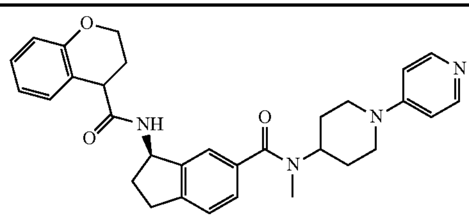 | N-[(1R)-6-[Methyl-(1-pyridin-4-yl-piperidin-4-yl)-carbamoyl]-2,3-dihydro-1H-inden-1-yl]-3,4-dihydro-2H-chromene-4-carboxylic acid amide (H-84) | (3R)-3-(3,4,4a,8a-Tetrahydro-2H-chromene-4-carboxamido)-2,3-dihydro-1H-indene-5-carboxylic acid (E-48) | N-Methyl-1-(pyridin-4-yl)piperidin-4-amine (AMN-06) | GWP-1 | 78% | |
| H-85 | 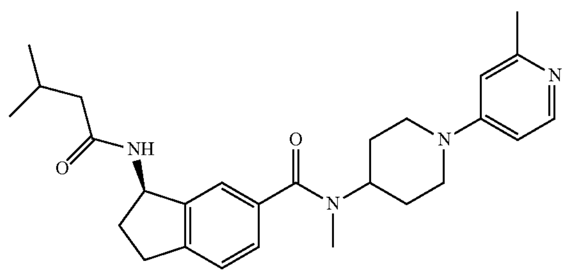 [SMILES: Cc1cc(N2CCC(N(C)C(=O)c3ccc4c(c3)[C@H](NC(=O)CC(C)C)CC4)CC2)ccn1] | (3R)-N-Methyl-3-(3-methyl-butanoylamino)-N-[1-(2-methyl-pyridin-4-yl)-piperidin-4-yl]-2,3-dihydro-1H-indene-5-carboxylic acid amide (H-85) | (R)-3-(3-Methylbutanamido)-2,3-dihydro-1H-indene-5-carboxylic acid (E-12) | N-Methyl-1-(2-methylpyridin-4-yl)piperidin-4-amine dihydrochloride (AMN-25) | GWP-1 | 87% | |
| H-86 | 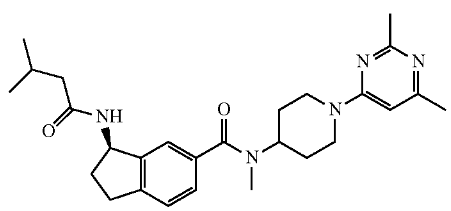 [SMILES: Cc1cc(N2CCC(N(C)C(=O)c3ccc4c(c3)[C@H](NC(=O)CC(C)C)CC4)CC2)nc(C)n1] | (3R)-N-[1-(2,6-Dimethyl-pyrimidin-4-yl)-piperidin-4-yl]-N-methyl-3-(3-methyl-butanoylamino)-2,3-dihydro-1H-indene-5-carboxylic acid amide (H-86) | (R)-3-(3-Methylbutanamido)-2,3-dihydro-1H-indene-5-carboxylic acid (E-12) | 1-(2,6-Dimethylpyrimidin-4-yl)-N-methylpiperidin-4-amine (AMN-27) | GWP-1 | 68% | |

TABLE-continued

| Example No. | Structure | Name | Amino acid (ACI) | Amine (AMN) | Synthesis according to | Yield | Comments |
|---|---|---|---|---|---|---|---|
| H-87 | 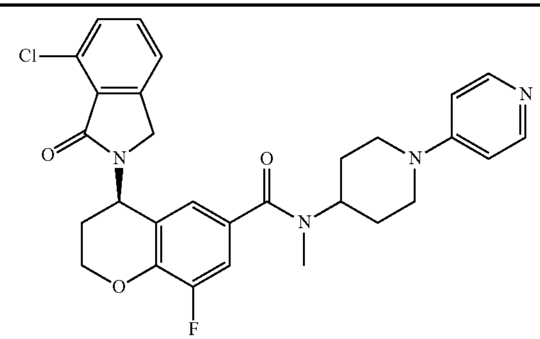 | (4R)-4-(4-Chloro-3-oxo-1,2-dihydro-isoindol-2-yl)-8-fluoro-N-methyl-N-(1-pyridin-4-yl-piperidin-4-yl)-3,4-dihydro-2H-chromene-6-carboxylic acid amide (H-87) | (R)-4-(7-Chloro-1-oxoisoindolin-2-yl)-8-fluorochromane-6-carboxylic acid (G-05) | N-Methyl-1-(pyridin-4-yl)piperidin-4-amine (AMN-06) | GWP-1 | 13% | |
| H-88 | 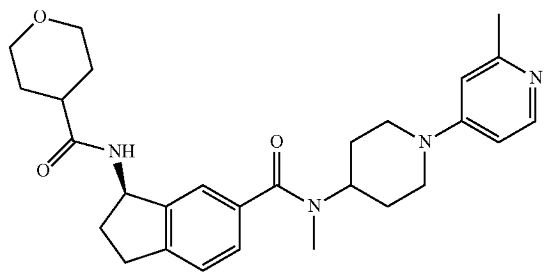 [SMILES: Cc1cc(N2CCC(N(C)C(=O)c3ccc4c(c3)[C@H](NC(=O)C3CCOCC3)CC4)CC2)ccn1] | N-[(1R)-6-[Methyl-[1-(2-methyl-pyridin-4-yl)-piperidin-4-yl]-carbamoyl]-2,3-dihydro-1H-inden-1-yl]-tetrahydro-pyran-4-carboxylic acid amide (H-88) | (R)-3-(Tetrahydro-2H-pyran-4-carboxamido)-2,3-dihydro-1H-indene-5-carboxylic acid (E-40) | N-Methyl-1-(2-methylpyridin-4-yl)piperidin-4-amine dihydrochloride (AMN-25) | GWP-1 | 28% | |
| H-89 | 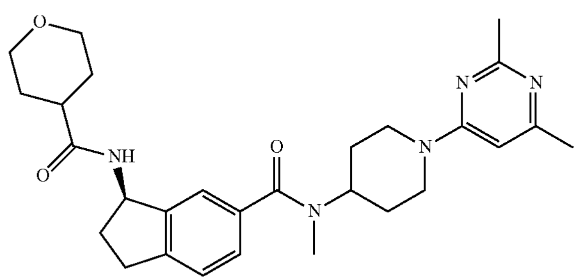 [SMILES: Cc1cc(N2CCC(N(C)C(=O)c3ccc4c(c3)[C@H](NC(=O)C3CCOCC3)CC4)CC2)nc(C)n1] | N-[(1R)-6-[[1-(2,6-Dimethyl-pyrimidin-4-yl)-piperidin-4-yl]-methyl-carbamoyl]-2,3-dihydro-1H-inden-1-yl]-tetrahydro-pyran-4-carboxylic acid amide (H-89) | (R)-3-(Tetrahydro-2H-pyran-4-carboxamido)-2,3-dihydro-1H-indene-5-carboxylic acid (E-40) | 1-(2,6-Dimethylpyrimidin-4-yl)-N-methylpiperidin-4-amine (AMN-27) | GWP-1 | 75% | |

TABLE-continued

| Example No. | Structure | Name | Amino acid (ACI) | Amine (AMN) | Synthesis according to | Yield | Comments |
|---|---|---|---|---|---|---|---|
| H-90 | 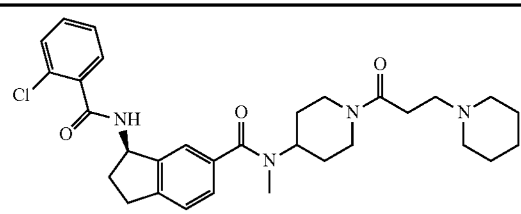 | (3R)-3-[(2-Chloro-benzoyl)amino]-N-methyl-N-[1-(3-piperidin-1-yl-propanoyl)-piperidin-4-yl]-2,3-dihydro-1H-indene-5-carboxylic acid amide (H-90) | (3R)-3-[(2-Chloro-benzoyl)amino]-2,3-dihydro-1H-indene-5-carboxylic acid (E-01) | 1-(4-(Methylamino)piperidin-1-yl)-3-(piperidin-1-yl)propan-1-one hydrochloride (AMN-42) | GWP-1 | 76% | |
| H-91 | 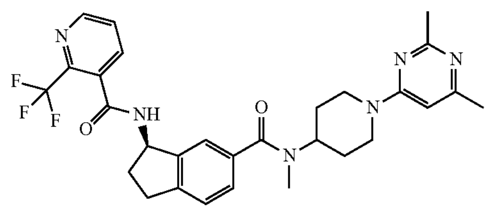 [SMILES: Cc1cc(N2CCC(N(C)C(=O)c3ccc4c(c3)[C@H](NC(=O)c3cccnc3C(F)(F)F)CC4)CC2)nc(C)n1] | N-[(1R)-6-[[1-(2,6-Dimethyl-pyrimidin-4-yl)-piperidin-4-yl]methyl-carbamoyl]-2,3-dihydro-1H-inden-1-yl]-2-(trifluoromethyl)-pyridine-3-carboxylic acid amide (H-91) | (R)-3-(2-(Trifluoromethyl)nicotinamido)-2,3-dihydro-1H-indene-5-carboxylic acid (E-20) | 1-(2,6-Dimethylpyrimidin-4-yl)-N-methylpiperidin-4-amine (AMN-27) | GWP-1 | 78% | |
| H-92 | 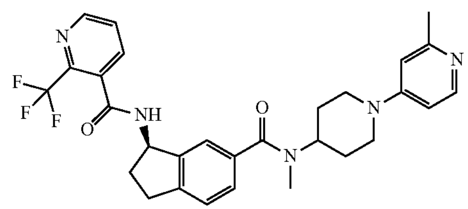 [SMILES: Cc1cc(N2CCC(N(C)C(=O)c3ccc4c(c3)[C@H](NC(=O)c3cccnc3C(F)(F)F)CC4)CC2)ccn1] | N-[(1R)-6-[Methyl-[1-(2-methyl-pyridin-4-yl)-piperidin-4-yl]carbamoyl]-2,3-dihydro-1H-inden-1-yl]-2-(trifluoromethyl)-pyridine-3-carboxylic acid amide (H-92) | (R)-3-(2-(Trifluoromethyl)nicotinamido)-2,3-dihydro-1H-indene-5-carboxylic acid (E-20) | N-Methyl-1-(2-methylpyridin-4-yl)piperidin-4-amine dihydrochloride (AMN-25) | GWP-1 | 80% | |
| H-93 | 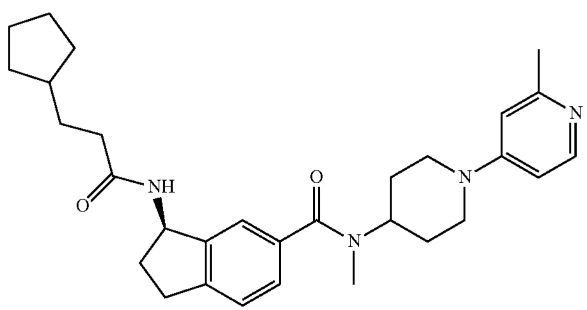 [SMILES: Cc1cc(N2CCC(N(C)C(=O)c3ccc4c(c3)[C@H](NC(=O)CCC3CCCC3)CC4)CC2)ccn1] | (3R)-3-(3-Cyclopentyl-propanoylamino)-N-methyl-N-[1-(2-methyl-pyridin-4-yl)-piperidin-4-yl]-2,3-dihydro-1H-indene-5-carboxylic acid amide (H-93) | (R)-3-(3-Cyclopentylpropanamido)-2,3-dihydro-1H-indene-5-carboxylic acid (E-42) | N-Methyl-1-(2-methylpyridin-4-yl)piperidin-4-amine dihydrochloride (AMN-25) | GWP-1 | 73% | |

| Example No. | Structure | Name | Amino acid (ACI) | Amine (AMN) | Synthesis according to | Yield | Comments |
|---|---|---|---|---|---|---|---|
| H-94 | 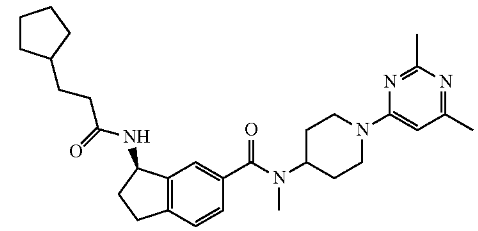 [SMILES: Cc1cc(N2CCC(N(C)C(=O)c3ccc4c(c3)[C@H](NC(=O)CCC3CCCC3)CC4)CC2)nc(C)n1] | (3R)-3-(3-Cyclopentyl-propanoylamino)-N-[1-(2,6-dimethyl-pyrimidin-4-yl)-piperidin-4-yl]-N-methyl-2,3-dihydro-1H-indene-5-carboxylic acid amide (H-94) | (R)-3-(3-Cyclopentyl)propanamido)-2,3-dihydro-1H-indene-5-carboxylic acid (E-42) | 1-(2,6-Dimethylpyrimidin-4-yl)-N-methylpipendin-4-amine (AMN-27) | GWP-1 | >99% | |
| H-95 | 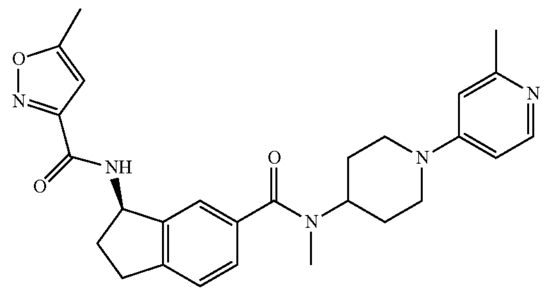 [SMILES: Cc1cc(N2CCC(N(C)C(=O)c3ccc4c(c3)[C@H](NC(=O)c3cc(C)on3)CC4)CC2)ccn1] | 5-Methyl-N-[(1R)-6-[methyl-[1-(2-methyl-pyridin-4-yl)-piperidin-4-yl]-carbamoyl]-2,3-dihydro-1H-inden-1-yl]-isoxazole-3-carboxylic acid amide (H-95) | (R)-3-(5-Methylisoxazole-3-carboxamido)-2,3-dihydro-1H-indene-5-carboxylic acid (E-27) | N-Methyl-1-(2-methylpyridin-4-yl)piperidin-4-amine dihydrochloride (AMN-25) | GWP-1 | 67% | |
| H-96 | 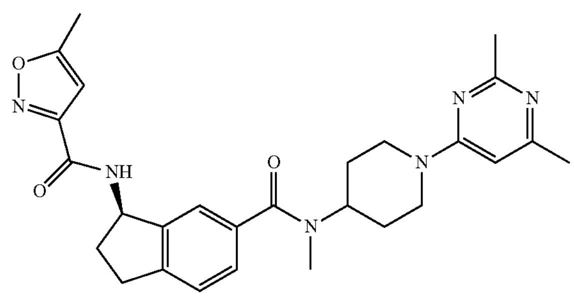 [SMILES: Cc1cc(N2CCC(N(C)C(=O)c3ccc4c(c3)[C@H](NC(=O)c3cc(C)on3)CC4)CC2)nc(C)n1] | N-[(1R)-6-[[1-(2,6-Dimethyl-pyrimidin-4-yl)-piperidin-4-yl]-methyl-carbamoyl]-2,3-dihydro-1H-inden-1-yl]-5-methyl-isoxazole-3-carboxylic acid amide (H-96) | (R)-3-(5-Methylisoxazole-3-carboxamido)-2,3-dihydro-1H-indene-5-carboxylic acid (E-27) | 1-(2,6-Dimethylpyrimidin-4-yl)-N-methylpiperidin-4-amine (AMN-27) | GWP-1 | 88% | |

| Example No. | Structure | Name | Amino acid (ACI) | Amine (AMN) | Synthesis according to | Yield | Comments |
|---|---|---|---|---|---|---|---|
| H-98 | 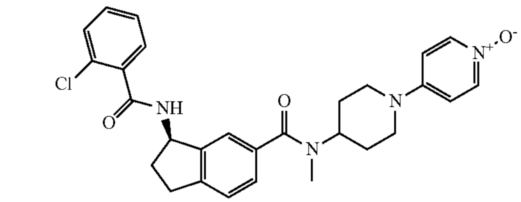 [SMILES: CN(C(=O)c1ccc2c(c1)[C@H](NC(=O)c1ccccc1Cl)CC2)C1CCN(c2cc[n+]([O-])cc2)CC1] | (3R)-3-[(2-Chloro-benzoyl)amino]-N-methyl-N-[1-(1-oxido-pyridin-1-ium-4-yl)-piperidin-4-yl]-2,3-dihydro-1H-indene-5-carboxylic acid amide (H-98) | | | | | see below |
| H-99 | 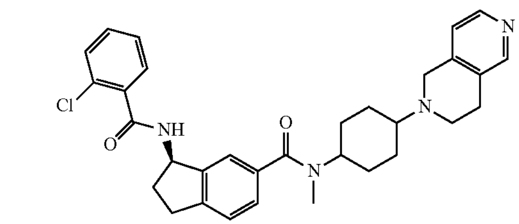 [SMILES: CN(C(=O)c1ccc2c(c1)[C@H](NC(=O)c1ccccc1Cl)CC2)C1CCC(N2CCc3cnccc3C2)CC1] | (3R)-3-[(2-Chloro-benzoyl)amino]-N-methyl-N-[4-(1,2,3,4-tetrahydro-[2,6]naphthyridin-2-yl)-cyclohexyl]-2,3-dihydro-1H-indene-5-carboxylic acid amide (H-99) | (3R)-3-[(2-Chloro-benzoyl)amino]-2,3-dihydro-1H-indene-5-carboxylic acid (E-01) | 4-(3,4-Dihydro-2,6-naphthyridin-2(1H)-yl)-N-methylcyclohexanamine (AMN-50) | GWP-5 | 21% (60 mg, 0.11 mmol) | |
| H-100 | 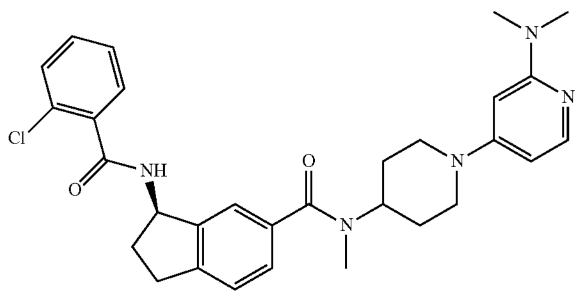 [SMILES: CN(C)c1cc(N2CCC(N(C)C(=O)c3ccc4c(c3)[C@H](NC(=O)c3ccccc3Cl)CC4)CC2)ccn1] | (3R)-3-[(2-Chloro-benzoyl)amino]-N-[1-(2-dimethylamino-pyridin-4-yl)-piperidin-4-yl]-N-methyl-2,3-dihydro-1H-indene-5-carboxylic acid amide (H-100) | (3R)-3-[(2-Chloro-benzoyl)amino]-2,3-dihydro-1H-indene-5-carboxylic acid (E-01) | N,N-Dimethyl-4-(4-(methylamino)piperidin-1-yl)pyridin-2-amine (AMN-52) | GWP-5 | 35% (120 mg, 0.225 mmol). | |
| H-101 | 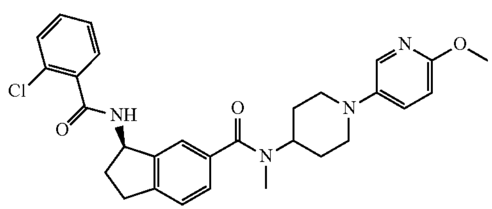 [SMILES: COc1ccc(N2CCC(N(C)C(=O)c3ccc4c(c3)[C@H](NC(=O)c3ccccc3Cl)CC4)CC2)cn1] | (3R)-3-[(2-Chloro-benzoyl)amino]-N-[1-(6-methoxy-pyridin-3-yl)-piperidin-4-yl]-N-methyl-2,3-dihydro-1H-indene-5-carboxylic acid amide (H-101) | (3R)-3-[(2-Chloro-benzoyl)amino]-2,3-dihydro-1H-indene-5-carboxylic acid (E-01) | 1-(6-Methoxypyridin-3-yl)-N-methylpiperidin-4-amine (AMN-51) | GWP-2 | 16% (95 mg, 0.183 mmol) | |

| Example No. | Structure | Name | Amino acid (ACI) | Amine (AMN) | Synthesis according to | Yield | Comments |
|---|---|---|---|---|---|---|---|
| H-102 | 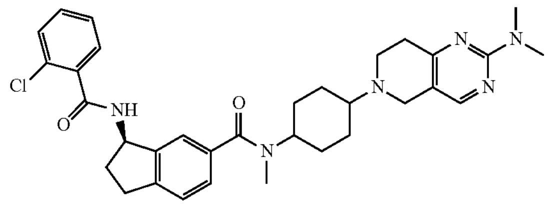 [SMILES: CN(C)c1ncc2c(n1)CCN(C1CCC(N(C)C(=O)c3ccc4c(c3)[C@H](NC(=O)c3ccccc3Cl)CC4)CC1)C2] | (3R)-3-[(2-Chloro-benzoyl)amino]-N-[4-(2-dimethylamino-5,6,7,8-tetrahydro-pyrido[4,3-d]pyrimidin-6-yl)-cyclohexyl]-N-methyl-2,3-dihydro-1H-indene-5-carboxylic acid amide (H-102) | (3R)-3-[(2-Chloro-benzoyl)amino]-2,3-dihydro-1H-indene-5-carboxylic acid (E-01) | N,N-Dimethyl-6-(4-(methylamino)cyclohexyl)-5,6,7,8-tetrahydropyrido[4,3-d]pyrimidin-2-amine (AMN-48) | GWP-2 | 60% (110 mg, 0.187 mmol) | |
| H-103 | 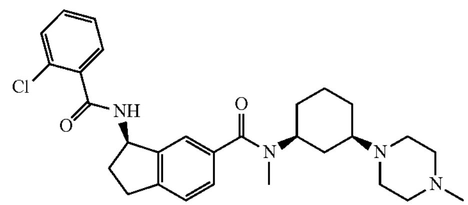 [SMILES: CN1CCN([C@@H]2CCC[C@H](N(C)C(=O)c3ccc4c(c3)[C@H](NC(=O)c3ccccc3Cl)CC4)C2)CC1] | (3R)-3-[(2-Chloro-benzoyl)amino]-N-methyl-N-[(1S,3R)-3-(4-methyl-piperazin-1-yl)-cyclohexyl]-2,3-dihydro-1H-indene-5-carboxylic acid amide (H-103) | (3R)-3-[(2-Chloro-benzoyl)amino]-2,3-dihydro-1H-indene-5-carboxylic acid (E-01) | (1S,3R)-N-Methyl-3-(4-methylpiperazin-1-yl)cyclohexanamine (AMN-49) | GWP-5 | 28% (120 mg, 0.2362 mmol) | |
| H-104 | 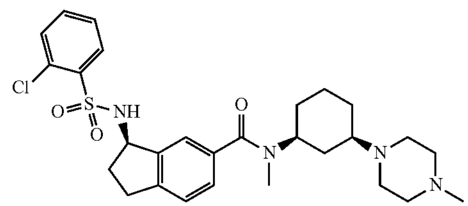 [SMILES: CN1CCN([C@@H]2CCC[C@H](N(C)C(=O)c3ccc4c(c3)[C@H](NS(=O)(=O)c3ccccc3Cl)CC4)C2)CC1] | (3R)-3-[(2-Chlorophenyl)sulfonyl]amino]-N-methyl-N-[(1S,3R)-3-(4-methyl-piperazin-1-yl)-cyclohexyl]-2,3-dihydro-1H-indene-5-carboxylic acid amide (H-104) | (R)-3-(2-Chlorophenylsulfonamido)-2,3-dihydro-1H-indene-5-carboxylic acid (F-02) | (1S,3R)-N-Methyl-3-(4-methylpiperazin-1-yl)cyclohexanamine (AMN-49) | GWP-5 | 25% (100 mg, 0.1838 mmol) | |
| H-110 | 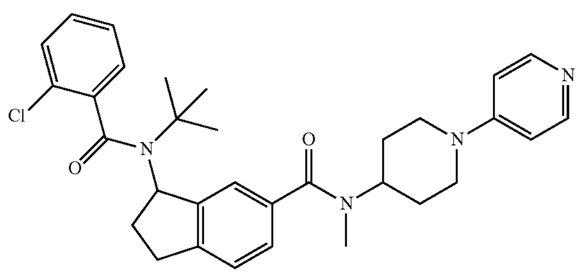 [SMILES: CN(C(=O)c1ccc2c(c1)C(N(C(=O)c1ccccc1Cl)C(C)(C)C)CC2)C1CCN(c2ccncc2)CC1] | 3-[tert-Butyl-(2-chloro-benzoyl)-amino]-N-methyl-N-(1-pyridin-4-yl-piperidin-4-yl)-2,3-dihydro-1H-indene-5-carboxylic acid amide (H-110) | 3-(N-tert-Butyl-2-chlorobenzamido)-2,3-dihydro-1H-indene-5-carboxylic acid (E-80) | N-Methyl-1-(pyridin-4-yl)piperidin-4-amine (AMN-06) | GWP-5 | 36% (130 mg, 0.2385 mmol) | |

TABLE-continued

| Example No. | Structure | Name | Amino acid (ACI) | Amine (AMN) | Synthesis according to | Yield | Comments |
|---|---|---|---|---|---|---|---|
| H-111 | 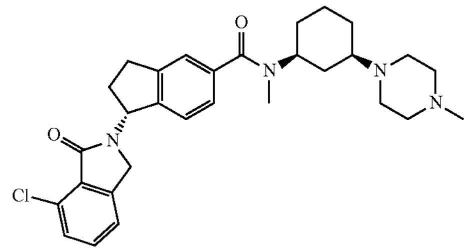 [SMILES: CN1CCN([C@@H]2CCC[C@H](N(C)C(=O)c3ccc4c(c3)CC[C@H]4N3Cc4cccc(Cl)c4C3=O)C2)CC1] | (1R)-1-(4-Chloro-3-oxo-1,2-dihydro-isoindol-2-yl)-N-methyl-N-[(1S,3R)-3-(4-methyl-piperazin-1-yl)-cyclohexyl]-2,3-dihydro-1H-indene-5-carboxylic acid amide (H-111) | (R)-1-(7-Chloro-1-oxoisoindolin-2-yl)-2,3-dihydro-1H-indene-5-carboxylic acid (G-02) | (1S,3R)-N-Methyl-3-(4-methylpiperazin-1-yl)cyclohexanamine (AMN-49) | GWP-5 | 36% (130 mg, 0.250 mmol) | |
| H-112 | 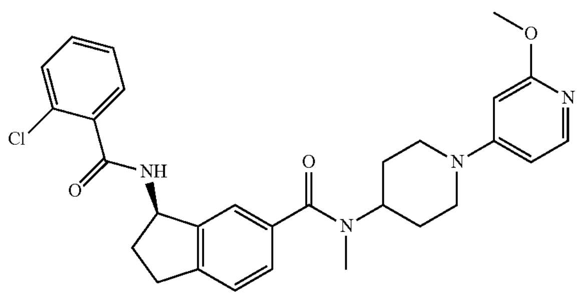 [SMILES: COc1cc(N2CCC(N(C)C(=O)c3ccc4c(c3)[C@H](NC(=O)c3ccccc3Cl)CC4)CC2)ccn1] | (3R)-3-[(2-Chloro-benzoyl)amino]-N-[1-(2-methoxy-pyridin-4-yl)-piperidin-4-yl]-N-methyl-2,3-dihydro-1H-indene-5-carboxylic acid amide (H-112) | (3R)-3-[(2-Chloro-benzoyl)amino]-2,3-dihydro-1H-indene-5-carboxylic acid (E-01) | 1-(2-Methoxypyridin-4-yl)-N-methylpiperidin-4-amine (AMN-55) | GWP-5 | 53% (200 mg, 0.386 mmol) | |
| H-113 | 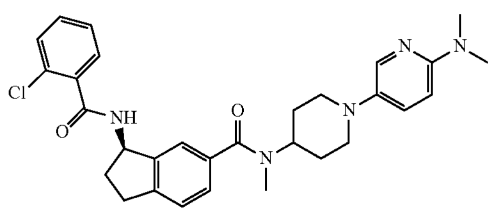 [SMILES: CN(C)c1ccc(N2CCC(N(C)C(=O)c3ccc4c(c3)[C@H](NC(=O)c3ccccc3Cl)CC4)CC2)cn1] | (3R)-3-[(2-Chloro-benzoyl)amino]-N-[1-(6-dimethylamino-pyridin-3-yl)-piperidin-4-yl]-N-methyl-2,3-dihydro-1H-indene-5-carboxylic acid amide (H-113) | (3R)-3-[(2-Chloro-benzoyl)amino]-2,3-dihydro-1H-indene-5-carboxylic acid (E-01) | N,N-Dimethyl-5-(4-(methylamino)piperidin-1-yl)pyridin-2-amine (AMN-54) | GWP-5 | 60% (210 mg, 0.395 mmol) | |
| H-114 | 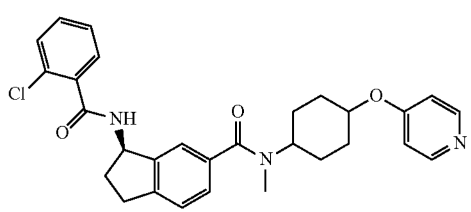 [SMILES: CN(C(=O)c1ccc2c(c1)[C@H](NC(=O)c1ccccc1Cl)CC2)C1CCC(Oc2ccncc2)CC1] | (3R)-3-[(2-Chloro-benzoyl)amino]-N-methyl-N-(4-pyridin-4-yloxy-cyclohexyl)-2,3-dihydro-1H-indene-5-carboxylic acid amide (H-114) | (3R)-3-[(2-Chloro-benzoyl)amino]-2,3-dihydro-1H-indene-5-carboxylic acid (E-01) | N-Methyl-4-(pyridin-4-yloxy)cyclohexanamine (AMN-58) | GWP-5 | 62% (300 mg, 0.596 mmol) | |

TABLE-continued

| Example No. | Structure | Name | Amino acid (ACI) | Amine (AMN) | Synthesis according to | Yield | Comments |
|---|---|---|---|---|---|---|---|
| H-115 | 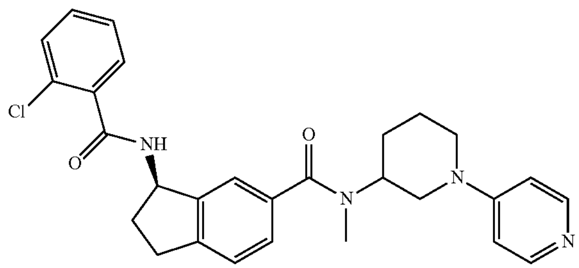 [SMILES: CN(C(=O)c1ccc2c(c1)[C@H](NC(=O)c1ccccc1Cl)CC2)C1CCCN(c2ccncc2)C1] | (3R)-3-[(2-Chloro-benzoyl)amino]-N-methyl-N-(1-pyridin-4-yl-piperidin-3-yl)-2,3-dihydro-1H-indene-5-carboxylic acid amide (H-115) | (3R)-3-[(2-Chloro-benzoyl)amino]-2,3-dihydro-1H-indene-5-carboxylic acid (E-01) | N-Methyl-1-(pyridin-4-yl)piperidin-3-amine (AMN-70) | GWP-2 | 60% 142 mg, 0.29 mmol | |
| H-116 | 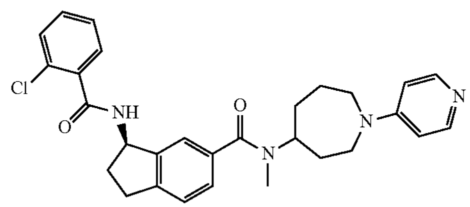 [SMILES: CN(C(=O)c1ccc2c(c1)[C@H](NC(=O)c1ccccc1Cl)CC2)C1CCCN(c2ccncc2)CC1] | (3R)-3-[(2-Chloro-benzoyl)amino]-N-methyl-N-(1-pyridin-4-yl-azepan-4-yl)-2,3-dihydro-1H-indene-5-carboxylic acid amide (H-116) | (3R)-3-[(2-Chloro-benzoyl)amino]-2,3-dihydro-1H-indene-5-carboxylic acid (E-01) | N-Methyl-1-(pyridin-4-yl)azepan-4-amine (AMN-69) | GWP-5 | 27% (200 mg, 0.398 mmol) | |
| H-117 | 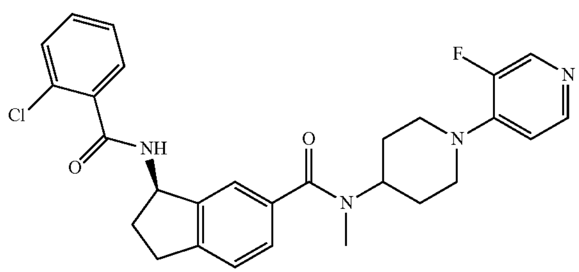 [SMILES: CN(C(=O)c1ccc2c(c1)[C@H](NC(=O)c1ccccc1Cl)CC2)C1CCN(c2ccncc2F)CC1] | (3R)-3-[(2-Chloro-benzoyl)amino]-N-[1-(3-fluoro-pyridin-4-yl)-piperidin-4-yl]-N-methyl-2,3-dihydro-1H-indene-5-carboxylic acid amide (H-117) | (3R)-3-[(2-Chloro-benzoyl)amino]-2,3-dihydro-1H-indene-5-carboxylic acid (E-01) | 1-(3-Fluoropyridin-4-yl)-N-methylpiperidin-4-amine (AMN-56) | GWP-5 | 56% (200 mg, 0.395 mmol) | |

| Example No. | Structure | Name | Amino acid (ACI) | Amine (AMN) | Synthesis according to | Yield | Comments |
|---|---|---|---|---|---|---|---|
| H-118 | 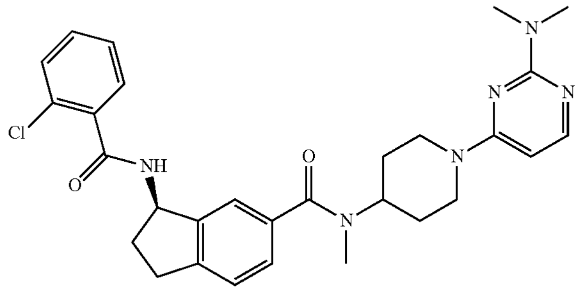 [SMILES: CN(C)c1nccc(N2CCC(N(C)C(=O)c3ccc4c(c3)[C@H](NC(=O)c3ccccc3Cl)CC4)CC2)n1] | (3R)-N-[1-(2-dimethylamino-pyrimidin-4-yl)-piperidin-4-yl]-3-[(2-Chloro-benzoyl)amino]-N-methyl-2,3-dihydro-1H-indene-5-carboxylic acid amide (H-118) | (3R)-3-[(2-Chloro-benzoyl)amino]-2,3-dihydro-1H-indene-5-carboxylic acid (E-01) | N,N-Dimethyl-4-(4-(methylamino)piperidin-1-yl)pyrimidin-2-amine (AMN-59) | GWP-2 | 51% (176 mg, 0.33 mmol) | |
| H-119 | 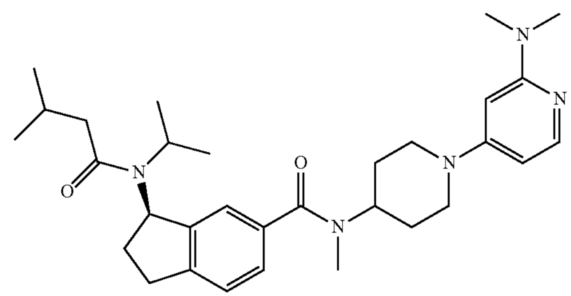 [SMILES: CC(C)CC(=O)N(C(C)C)[C@@H]1CCc2ccc(C(=O)N(C)C3CCN(c4ccnc(N(C)C)c4)CC3)cc21] | (3R)-N-[1-(2-Dimethylamino-pyrimidin-4-yl)-pipendin-4-yl]-3-[isopropyl-(3-methyl-butanoyl)-amino]-N-methyl-2,3-dihydro-1H-indene-5-carboxylic acid amide (H-119) | (R)-3-(N-Isopropyl-3-methylbutanamido)-2,3-dihydro-1H-Indene-5-carboxylic acid (E-84) | N,N-Dimethyl-4-(4-(methylamino)piperidin-1-yl)pyridin-2-amine (AMN-52) | GWP-5 | 44% (150 mg, 0.289 mmol) | |
| H-120 | 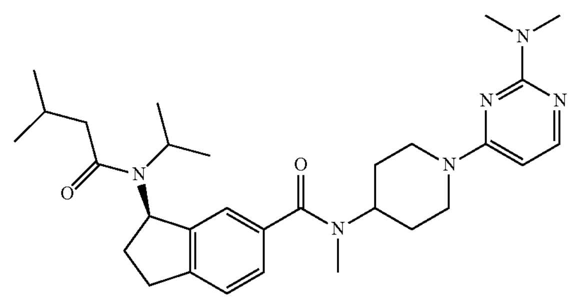 [SMILES: CC(C)CC(=O)N(C(C)C)[C@@H]1CCc2ccc(C(=O)N(C)C3CCN(c4ccnc(N(C)C)n4)CC3)cc21] | (3R)-N-[1-(2-Dimethylamino-pyrimidin-4-yl)-pipendin-4-yl]-3-[isopropyl-(3-methyl-butanoyl)-amino]-N-methyl-2,3-dihydro-1H-indene-5-carboxylic acid amide (H-120) | (R)-3-(N-Isopropyl-3-methylbutanamido)-2,3-dihydro-1H-Indene-5-carboxylic acid (E-84) | N,N-Dimethyl-4-(4-(methylamino)piperidin-1-yl)pyrimidin-2-amine (AMN-59) | GWP-5 | 28% (140 mg, 0.269 mmol) | |

| Example No. | Structure | Name | Amino acid (ACI) | Amine (AMN) | Synthesis according to | Yield | Comments |
|---|---|---|---|---|---|---|---|
| H-122 | 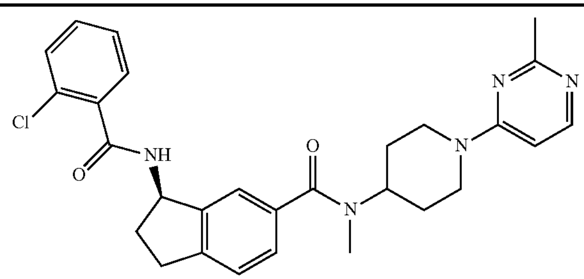 | (3R)-3-[(2-Chloro-benzoyl)amino]-N-methyl-N-[1-(2-methyl-pyrimidin-4-yl)-piperidin-4-yl]-2,3-dihydro-1H-indene-5-carboxylic acid amide (H-122) | (3R)-3-[(2-Chloro-benzoyl)amino]-2,3-dihydro-1H-indene-5-carboxylic acid (E-01) | N-Methyl-1-(2-methylpyrimidin-4-yl)piperidin-4-amine (AMN-62) | GWP-2 | 65% (210 mg, 0.417 mmol) | |
| H-123 | 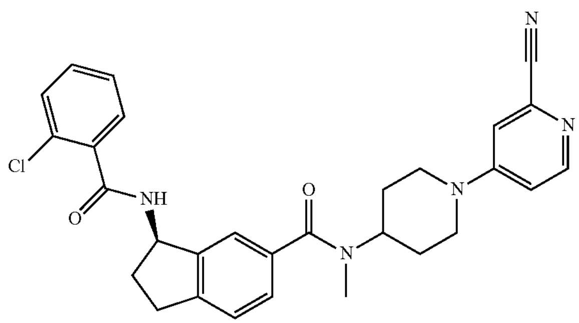 [SMILES: CN(C(=O)c1ccc2c(c1)[C@H](NC(=O)c1ccccc1Cl)CC2)C1CCN(c2ccnc(C#N)c2)CC1] | (3R)-3-[(2-Chloro-benzoyl)amino]-N-[1-(2-cyano-pyridin-4-yl)-piperidin-4-yl]-N-methyl-2,3-dihydro-1H-indene-5-carboxylic acid amide (H-123) | (3R)-3-[(2-Chloro-benzoyl)amino]-2,3-dihydro-1H-indene-5-carboxylic acid (E-01) | 4-(4-(Methylamino)piperidin-1-yl)picolinonitrile (AMN-60) | GWP-5 | 76% (250 mg, 0.486 mmol) | |
| H-124 | 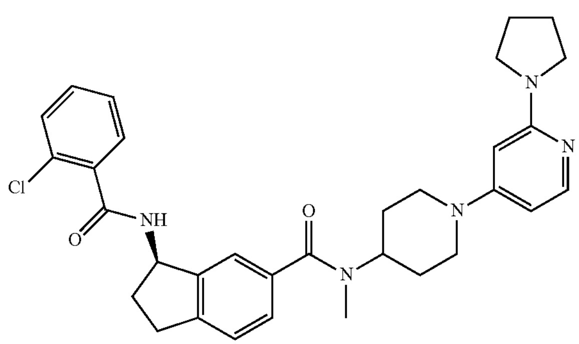 [SMILES: CN(C(=O)c1ccc2c(c1)[C@H](NC(=O)c1ccccc1Cl)CC2)C1CCN(c2ccnc(N3CCCC3)c2)CC1] | (3R)-3-[(2-Chloro-benzoyl)amino]-N-methyl-N-[1-(2-pyrrolidin-1-yl-pyridin-4-yl)-piperidin-4-yl]-2,3-dihydro-1H-indene-5-carboxylic acid amide (H-124) | (3R)-3-[(2-Chloro-benzoyl)amino]-2,3-dihydro-1H-indene-5-carboxylic acid (E-01) | N-Methyl-1-(2-(pyrrolidin-1-yl)pyridin-4-yl)piperidin-4-amine (AMN-61) | GWP-5 | 34% (120 mg, 0.215 mmol) | |

| Example No. | Structure | Name | Amino acid (ACI) | Amine (AMN) | Synthesis according to | Yield | Comments |
|---|---|---|---|---|---|---|---|
| H-125 | 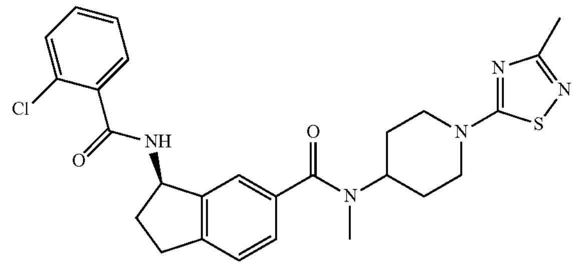 [SMILES: Cc1nsc(N2CCC(N(C)C(=O)c3ccc4c(c3)[C@H](NC(=O)c3ccccc3Cl)CC4)CC2)n1] | (3R)-3-[(2-Chloro-benzoyl)amino]-N-methyl-N-[1-(3-methyl-[1,2,4]thiadiazol-5-yl)-piperidin-4-yl]-2,3-dihydro-1H-indene-5-carboxylic acid amide (H-125) | | | | | see below |
| H-126 | 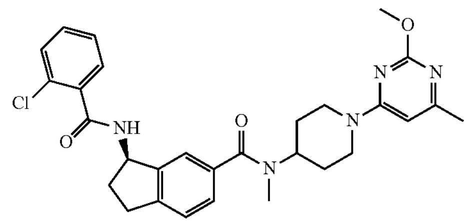 | (3R)-3-[(2-Chloro-benzoyl)amino]-N-[1-(2-methoxy-6-methyl-pyrimidin-4-yl)-piperidin-4-yl]-N-methyl-2,3-dihydro-1H-indene-5-carboxylic acid amide (H-126) | (3R)-3-[(2-Chloro-benzoyl)amino]-2,3-dihydro-1H-indene-5-carboxylic acid (E-01) | 1-(2-Methoxy-6-methylpyrimidin-4-yl)-N-methylpiperidin-4-amine (AMN-64) | GWP-5 | 74% (250 mg, 0.4690 mmol) | |
| H-127 | 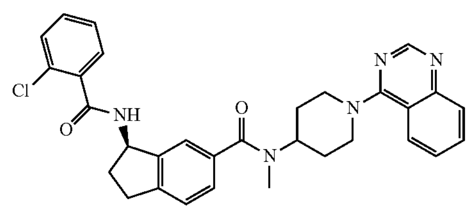 [SMILES: CN(C(=O)c1ccc2c(c1)[C@H](NC(=O)c1ccccc1Cl)CC2)C1CCN(c2ncnc3ccccc23)CC1] | (3R)-3-[(2-Chloro-benzoyl)amino]-N-methyl-N-(1-quinazolin-4-yl-piperidin-4-yl)-2,3-dihydro-1H-indene-5-carboxylic acid amide (H-127) | (3R)-3-[(2-Chloro-benzoyl)amino]-2,3-dihydro-1H-indene-5-carboxylic acid (E-01) | N-Methyl-1-(quinazolin-4-yl)piperidin-4-amine (AMN-32) | GWP-1 | 78% | |
| H-128 | 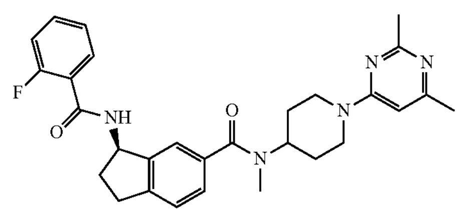 [SMILES: Cc1cc(N2CCC(N(C)C(=O)c3ccc4c(c3)[C@H](NC(=O)c3ccccc3F)CC4)CC2)nc(C)n1] | (3R)-N-[1-(2,6-Dimethyl-pyrimidin-4-yl)-piperidin-4-yl]-3-[(2-fluoro-benzoyl)amino]-N-methyl-2,3-dihydro-1H-indene-5-carboxylic acid amide (H-128) | (R)-3-(2-Fluorobenzamido)-2,3-dihydro-1H-indene-5-carboxylic acid (E-13) | 1-(2,6-Dimethylpyrimidin-4-yl)-N-methylpiperidin-4-amine (AMN-27) | GWP-1 | 56% | |

| Example No. | Structure | Name | Amino acid (ACI) | Amine (AMN) | Synthesis according to | Yield | Comments |
|---|---|---|---|---|---|---|---|
| H-129 | 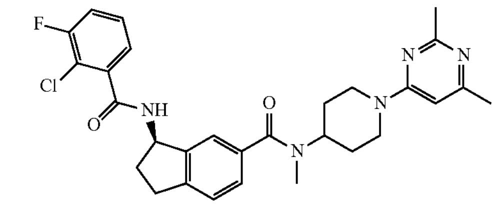 [SMILES: Cc1cc(N2CCC(N(C)C(=O)c3ccc4c(c3)[C@H](NC(=O)c3cccc(F)c3Cl)CC4)CC2)nc(C)n1] | (3R)-3-[(2-Chloro-3-fluoro-benzoyl)amino]-N-[1-(2,6-dimethyl-pyrimidin-4-yl)-piperidin-4-yl]-N-methyl-2,3-dihydro-1H-indene-5-carboxylic acid amide (H-129) | (R)-3-(2-Chloro-3-fluorobenzamido)-2,3-dihydro-1H-indene-5-carboxylic acid (E-34) | 1-(2,6-Dimethylpyrimidin-4-yl)-N-methylpiperidin-4-amine (AMN-27) | GWP-1 | 68% | |
| H-130 | 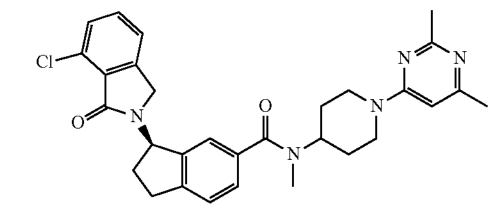 [SMILES: Cc1cc(N2CCC(N(C)C(=O)c3ccc4c(c3)[C@H](N3Cc5cccc(Cl)c5C3=O)CC4)CC2)nc(C)n1] | (3R)-3-(4-Chloro-3-oxo-1,2-dihydro-isoindol-2-yl)-N-[1-(2,6-dimethyl-pyrimidin-4-yl)-piperidin-4-yl]-N-methyl-2,3-dihydro-1H-indene-5-carboxylic acid amide (H-130) | (R)-3-(7-Chloro-1-oxoisoindolin-2-yl)-2,3-dihydro-1H-indene-5-carboxylic acid (G-01) | 1-(2,6-Dimethylpyrimidin-4-yl)-N-methylpiperidin-4-amine (AMN-27) | GWP-1 | 70% | |
| H-131 | 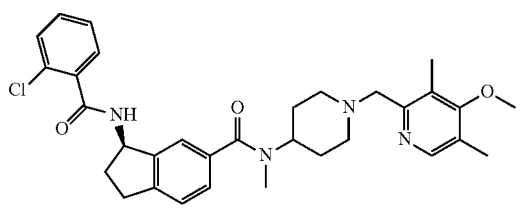 [SMILES: COc1c(C)cnc(CN2CCC(N(C)C(=O)c3ccc4c(c3)[C@H](NC(=O)c3ccccc3Cl)CC4)CC2)c1C] | (3R)-3-[(2-Chloro-benzoyl)amino]-N-[1-[(4-methoxy-3,5-dimethyl-pyridin-2-yl)-methyl]-piperidin-4-yl]-N-methyl-2,3-dihydro-1H-indene-5-carboxylic acid amide (H-131) | (3R)-3-[(2-Chloro-benzoyl)amino]-2,3-dihydro-1H-indene-5-carboxylic acid (E-01) | 1-((4-Methoxy-3,5-dimethylpyridin-2-yl)methyl)-N-methylpiperidin-4-amine (AMN-33) | GWP-1 | 51% | |
| H-132 | 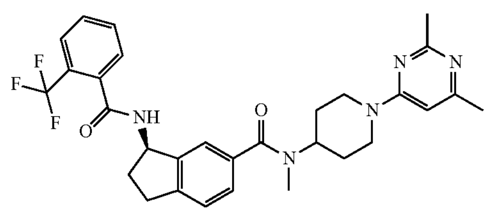 [SMILES: Cc1cc(N2CCC(N(C)C(=O)c3ccc4c(c3)[C@H](NC(=O)c3ccccc3C(F)(F)F)CC4)CC2)nc(C)n1] | (3R)-N-[1-(2,6-Dimethyl-pyrimidin-4-yl)-piperidin-4-yl]-N-methyl-3-[[2-(trifluoromethyl)-benzoyl]amino]-2,3-dihydro-1H-indene-5-carboxylic acid amide (H-132) | (R)-3-(2-(Trifluoromethyl)benzamido)-2,3-dihydro-1H-indene-5-carboxylic acid (E-14) | 1-(2,6-Dimethylpyrimidin-4-yl)-N-methylpiperidin-4-amine (AMN-27) | GWP-1 | 78% | |

| Example No. | Structure | Name | Amino acid (ACI) | Amine (AMN) | Synthesis according to | Yield | Comments |
|---|---|---|---|---|---|---|---|
| H-133 | 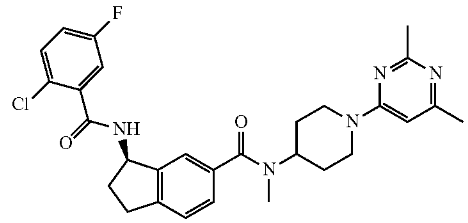 [SMILES: Cc1cc(N2CCC(N(C)C(=O)c3ccc4c(c3)[C@H](NC(=O)c3cc(F)ccc3Cl)CC4)CC2)nc(C)n1] | (3R)-3-[(2-Chloro-5-fluoro-benzoyl)amino]-N-[1-(2,6-dimethyl-pyrimidin-4-yl)-piperidin-4-yl]-N-methyl-2,3-dihydro-1H-indene-5-carboxylic acid amide (H-133) | (R)-3-(2-Chloro-5-fluorobenzamido)-2,3-dihydro-1H-indene-5-carboxylic acid (E-35) | 1-(2,6-Dimethylpyrimidin-4-yl)-N-methylpiperidin-4-amine (AMN-27) | GWP-1 | 88% | |
| H-134 | 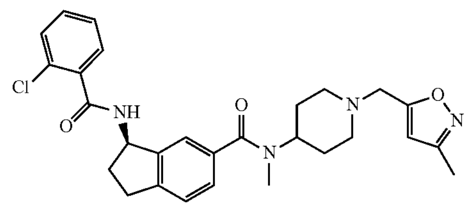 [SMILES: Cc1cc(CN2CCC(N(C)C(=O)c3ccc4c(c3)[C@H](NC(=O)c3ccccc3Cl)CC4)CC2)on1] | (3R)-3-[(2-Chloro-benzoyl)amino]-N-methyl-N-[1-[(3-methyl-isoxazol-5-yl)-methyl]-piperidin-4-yl]-2,3-dihydro-1H-indene-5-carboxylic acid amide (H-134) | (3R)-3-[(2-Chloro-benzoyl)amino]-2,3-dehydro-1H-indene-5-carboxylic acid (E-01) | N-Methyl-1-(3-methylisoxazol-5-yl)methyl)piperidin-4-amine AMN-34) | GWP-1 | 75% | |
| H-135 | 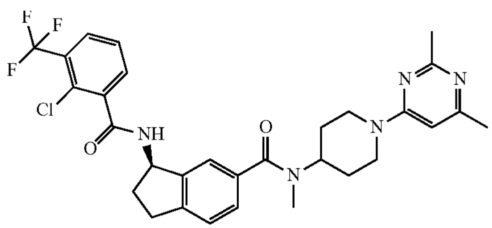 [SMILES: Cc1cc(N2CCC(N(C)C(=O)c3ccc4c(c3)[C@H](NC(=O)c3cccc(C(F)(F)F)c3Cl)CC4)CC2)nc(C)n1] | (3R)-3-[[2-Chloro-3-(trifluoromethyl)-benzoyl]amino]-N-[1-(2,6-dimethyl-pyrimidin-4-yl)-piperidin-4-yl]-N-methyl-2,3-dihydro-1H-indene-5-carboxylic acid amide (H-135) | (R)-3-(2-Chloro-3-(trifluoromethyl)benzamido)-2,3-dihydro-1H-indene-5-carboxylic acid (E-10) | 1-(2,6-Dimethylpyrimidin-4-yl)-N-methylpiperidin-4-amine (AMN-27) | GWP-1 | 98% | |
| H-136 | 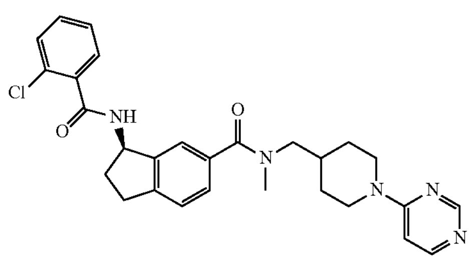 [SMILES: CN(CC1CCN(c2ccncn2)CC1)C(=O)c1ccc2c(c1)[C@H](NC(=O)c1ccccc1Cl)CC2] | (3R)-3-[(2-Chloro-benzoyl)amino]-N-methy-N-[(1-pyrimidin-4-yl-piperidin-4-yl)-methyl]-2,3-dihydro-1H-indene-5-carboxylic acid amide (H-136) | (3R)-3-[(2-Chloro-benzoyl)amino]-2,3-dihydro-1H-indene-5-carboxylic acid (E-01) | N-Methyl-1-(1-(pyridin-4-yl)piperidin-4-yl)methanamine dihydrochloride (AMN-35) | GWP-1 | 65% | |

| Example No. | Structure | Name | Amino acid (ACI) | Amine (AMN) | Synthesis according to | Yield | Comments |
|---|---|---|---|---|---|---|---|
| H-137 | 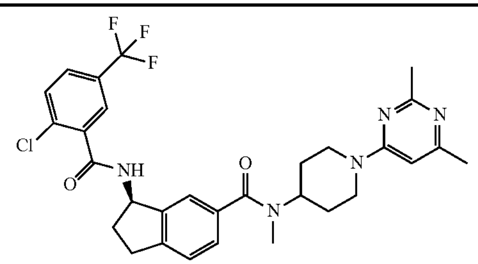 | (3R)-3-[[2-Chloro-5-(trifluoromethyl)benzoyl]amino]-N-[1-(2,6-dimethyl-pyrimidin-4-yl)-piperidin-4-yl]-N-methyl-2,3-dihydro-1H-indene-5-carboxylic acid amide (H-137) | (R)-3-(2-Chloro-5-(trifluoromethyl)benzamido)-2,3-dihydro-1H-indene-5-carboxylic acid (E-36) | 1-(2,6-Dimethylpyrimidin-4-yl)-N-methylpiperidin-4-amine (AMN-27) | GWP-1 | 86% | |
| H-138 | 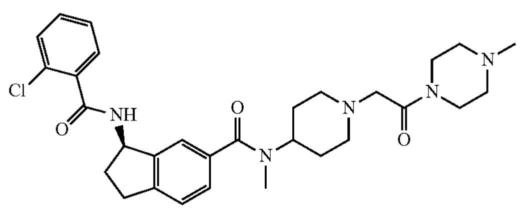 [SMILES: CN1CCN(C(=O)CN2CCC(N(C)C(=O)c3ccc4c(c3)[C@H](NC(=O)c3ccccc3Cl)CC4)CC2)CC1] | (3R)-3-[(2-Chloro-benzoyl)amino]-N-methyl-N-[1-[2-(4-methyl-piperazin-1-yl)-2-oxo-ethyl]-piperidin-4-yl]-2,3-dihydro-1H-indene-5-carboxylic acid amide (H-138) | (3R)-3-[(2-Chloro-benzoyl)amino]-2,3-dihydro-1H-indene-5-carboxylic acid (E-01) | 2-(4-(Methylamino)piperidin-1-yl)-1-(4-methylpiperazin-1-yl)ethanone (AMN-36) | GWP-1 | 76% | |
| H-139 | 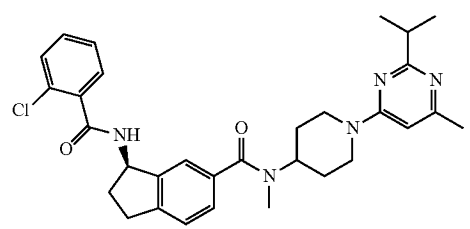 | (3R)-3-[(2-Chloro-benzoyl)amino]-N-[1-(2-isopropyl-6-methyl-pyrimidin-4-yl)-piperidin-4-yl]-N-methyl-2,3-dihydro-1H-indene-5-carboxylic acid amide (H-139) | (3R)-3-[(2-Chloro-benzoyl)amino]-2,3-dihydro-1H-indene-5-carboxylic acid (E-01) | 1-(2-Isopropyl-6-methylpyrimidin-4-yl)-N-methylpiperidin-4-amine (AMN-37) | GWP-1 | 84% | |
| H-140 | 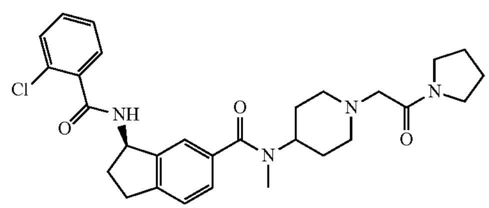 [SMILES: CN(C(=O)c1ccc2c(c1)[C@H](NC(=O)c1ccccc1Cl)CC2)C1CCN(CC(=O)N2CCCC2)CC1] | (3R)-3-[(2-Chloro-benzoyl)amino]-N-methyl-N-[1-(2-oxo-2-pyrrolidin-1-yl-ethyl)-piperidin-4-yl]-2,3-dihydro-1H-indene-5-carboxylic acid amide (H-140) | (3R)-3-[(2-Chloro-benzoyl)amino]-2,3-dihydro-1H-indene-5-carboxylic acid (E-01) | 2-(4-(Methylamino)piperidin-1-yl)-1-(pyrrolidin-1-yl)ethanone (AMN-38) | GWP-1 | 72% | |

| Example No. | Structure | Name | Amino acid (ACI) | Amine (AMN) | Synthesis according to | Yield | Comments |
|---|---|---|---|---|---|---|---|
| H-141 | 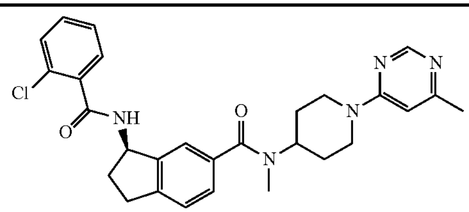 | (3R)-3-[(2-Chloro-benzoyl)amino]-N-methyl-N-[1-(6-methyl-pyrimidin-4-yl)-piperidin-4-yl]-2,3-dihydro-1H-indene-5-carboxylic acid amide (H-141) | (3R)-3-[(2-Chloro-benzoyl)amino]-2,3-dihydro-1H-indene-5-carboxylic acid (E-01) | N-Methyl-1-(6-methylpyrimidin-4-yl)piperidin-4-amine dihydrochloride (AMN-45) | GWP-1 | 79% | |
| H-142 | 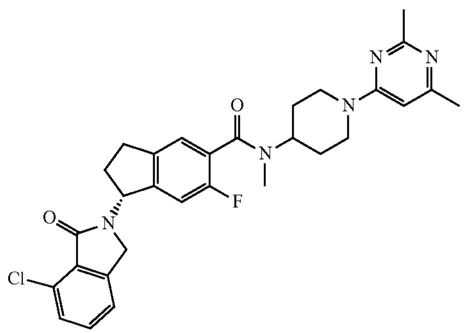 [SMILES: Cc1cc(N2CCC(N(C)C(=O)c3cc4c(cc3F)[C@H](N3Cc5cccc(Cl)c5C3=O)CC4)CC2)nc(C)n1] | (1R)-1-(4-Chloro-3-oxo-1,2-dihydro-isoindol-2-yl)-N-[1-(2,6-dimethyl-pyrimidin-4-yl)-piperidin-4-yl]-6-fluoro-N-methyl-2,3-dihydro-1H-indene-5-carboxylic acid amide (H-142) | (R)-1-(7-Chloro-1-oxoisoindolin-2-yl)-6-fluoro-2,3-dihydro-1H-indene-5-carboxylic acid (G-04) | 1-(2,6-Dimethylpyrimidin-4-yl)-N-methylpiperidin-4-amine (AMN-27) | GWP-1 | 70% | |
| H-143 | 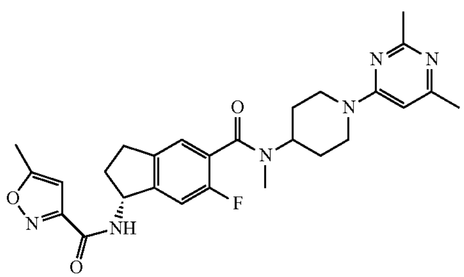 [SMILES: Cc1cc(N2CCC(N(C)C(=O)c3cc4c(cc3F)[C@H](NC(=O)c3cc(C)on3)CC4)CC2)nc(C)n1] | N-[(1R)-5-[[1-(2,6-Dimethyl-pyrimidin-4-yl)-piperidin-4-yl]-methyl-carbamoyl]-6-fluoro-2,3-dihydro-1H-inden-1-yl]-5-methyl-isoxazole-3-carboxylic acid amide (H-143) | (R)-6-Fluoro-1-(5-methylisoxazole-3-carboxamido)-2,3-dihydro-1H-indene-5-carboxylic acid (E-49) | 1-(2,6-Dimethylpyrimidin-4-yl)-N-methylpiperidin-4-amine (AMN-27) | GWP-1 | 60% | |

| Example No. | Structure | Name | Amino acid (ACI) | Amine (AMN) | Synthesis according to | Yield | Comments |
|---|---|---|---|---|---|---|---|
| H-144 | 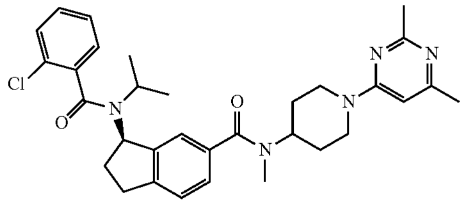 [SMILES: Cc1cc(N2CCC(N(C)C(=O)c3ccc4c(c3)[C@H](N(C(=O)c3ccccc3Cl)C(C)C)CC4)CC2)nc(C)n1] | (3R)-3-[(2-Chloro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide (H-144) | (R)-3-(2-Chloro-N-isopropylbenzamido)-2,3-dihydro-1H-indene-5-carboxylic acid (E-50) | 1-(2,6-Dimethylpyrimidin-4-yl)-N-methylpiperidin-4-amine (AMN-27) | GWP-1 | 79% | |
| H-145 | 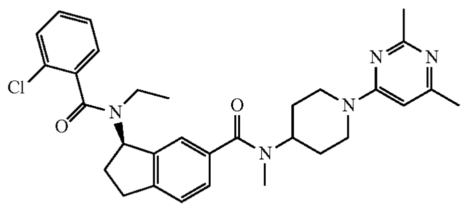 [SMILES: CCN(C(=O)c1ccccc1Cl)[C@@H]1CCc2ccc(C(=O)N(C)C3CCN(c4cc(C)nc(C)n4)CC3)cc21] | (3R)-3-[(2-Chloro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide (H-145) | (R)-3-(2-Chloro-N-ethylbenzamido)-2,3-dihydro-1H-indene-5-carboxylic acid (E-51) | 1-(2,6-Dimethylpyrimidin-4-yl)-N-methylpiperidin-4-amine (AMN-27) | GWP-1 | 67% | |
| H-146 | 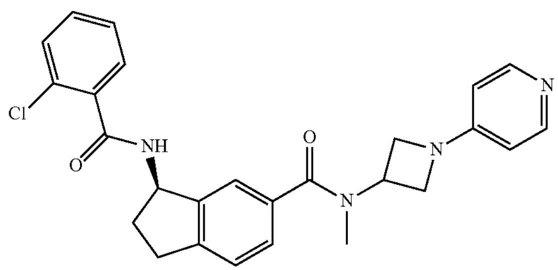 [SMILES: CN(C(=O)c1ccc2c(c1)[C@H](NC(=O)c1ccccc1Cl)CC2)C1CN(c2ccncc2)C1] | (3R)-3-[(2-Chloro-benzoyl)amino]-N-methyl-N-(1-pyridin-4-yl-azetidin-3-yl)-2,3-dihydro-1H-indene-5-carboxylic acid amide (H-146) | (3R)-3-[(2-Chloro-benzoyl)amino]-2,3-dihydro-1H-indene-5-carboxylic acid (E-01) | N-Methyl-1-(pyridin-4-yl)azetidin-3-amine dihydrochloride (AMN-43) | GWP-1 | 87% | |
| H-147 | 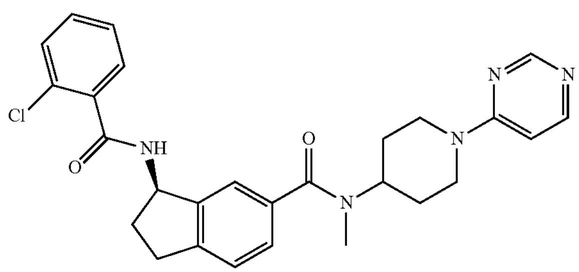 [SMILES: CN(C(=O)c1ccc2c(c1)[C@H](NC(=O)c1ccccc1Cl)CC2)C1CCN(c2ccncn2)CC1] | (3R)-3-[(2-Chloro-benzoyl)amino]-N-methyl-N-(1-pyrimidin-4-yl-piperidin-4-yl)-2,3-dihydro-1H-indene-5-carboxylic acid amide (H-147) | (3R)-3-[(2-Chloro-benzoyl)amino]-2,3-dihydro-1H-indene-5-carboxylic acid (E-01) | N-Methyl-1-(pyrimidin-4-yl)piperidin-4-amine dihydrochloride (AMN-44) | GWP-1 | 86% | |

TABLE-continued

| Example No. | Structure | Name | Amino acid (ACI) | Amine (AMN) | Synthesis according to | Yield | Comments |
|---|---|---|---|---|---|---|---|
| H-148 | 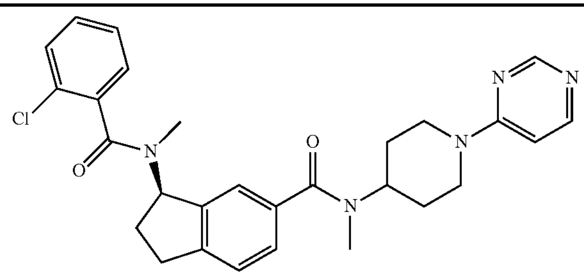 | (3R)-3-[(2-Chloro-benzoyl)-methyl-amino]-N-methyl-N-(1-pyrimidin-4-yl-piperidin-4-yl)-2,3-dihydro-1H-indene-5-carboxylic acid amide (H-148) | (R)-3-(2-Chloro-N-methylbenzamido)-2,3-dihydro-1H-indene-5-carboxylic acid (E-52) | N-Methyl-1-(pyrimidin-4-yl)piperidin-4-amine dihydrochloride (AMN-44) | GWP-1 | 48% | |
| H-149 | 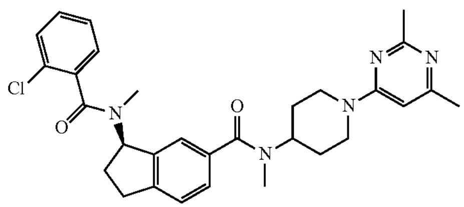 [SMILES: Cc1cc(N2CCC(N(C)C(=O)c3ccc4c(c3)[C@H](N(C)C(=O)c3ccccc3Cl)CC4)CC2)nc(C)n1] | (3R)-3-[(2-Chloro-benzoyl)-methyl-amino]-N-[1-(2,6-dimethyl-pyrimidin-4-yl)-piperidin-4-yl]-N-methyl-2,3-dihydro-1H-indene-5-carboxylic acid amide (H-149) | (R)-3-(2-Chloro-N-methylbenzamido)-2,3-dihydro-1H-indene-5-carboxylic acid (E-52) | 1-(2,6-Dimethylpyrimidin-4-yl)-N-methylpiperidin-4-amine (AMN-27) | GWP-1 | 62% | |
| H-150 | 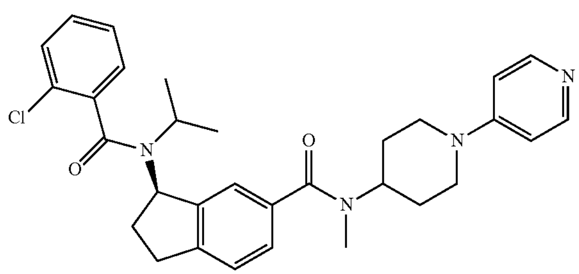 [SMILES: CC(C)N(C(=O)c1ccccc1Cl)[C@@H]1CCc2ccc(C(=O)N(C)C3CCN(c4ccncc4)CC3)cc21] | (3R)-3-[(2-Chloro-benzoyl)-isopropyl-amino]-N-methyl-N-(1-pyridin-4-yl-piperidin-4-yl)-2,3-dihydro-1H-indene-5-carboxylic acid amide (H-150) | (R)-3-(2-Chloro-N-isopropylbenzamido)-2,3-dihydro-1H-indene-5-carboxylic acid (E-50) | N-Methyl-1-(pyridin-4-yl)piperidin-4-amine (AMN-06) | GWP-1 | 40% | |

TABLE-continued

| Example No. | Name | Structure | Amino acid (ACI) | Amine (AMN) | Synthesis according to | Yield | Comments |
|---|---|---|---|---|---|---|---|
| H-151 | (1R)-1-[(2-Chloro-benzoyl)amino]-N-[1-(2,6-dimethyl-pyrimidin-4-yl)-piperidin-4-yl]-6-fluoro-N-methyl-2,3-dihydro-1H-indene-5-carboxylic acid amide (H-151) | 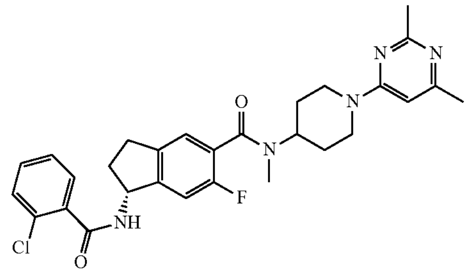 [SMILES: Cc1cc(N2CCC(N(C)C(=O)c3cc4c(cc3F)[C@H](NC(=O)c3ccccc3Cl)CC4)CC2)nc(C)n1] | (R)-1-(2-Chlorobenzamido)-6-fluoro-2,3-dihydro-1H-indene-5-carboxylic acid (E-30) | 1-(2,6-Dimethylpyrimidin-4-yl)-N-methylpiperidin-4-amine (AMN-27) | GWP-1 | 80% | |
| H-152 | (1R)-1-[(2-Chloro-benzoyl)amino]-6-fluoro-N-methyl-N-[1-(6-methyl-pyrimidin-4-yl)-piperidin-4-yl]-2,3-dihydro-1H-indene-5-carboxylic acid amide (H-152) | 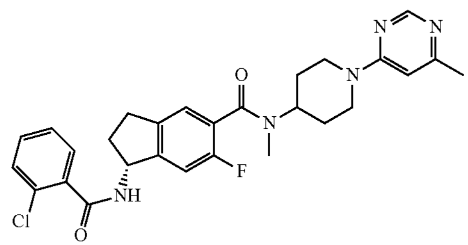 [SMILES: Cc1cc(N2CCC(N(C)C(=O)c3cc4c(cc3F)[C@H](NC(=O)c3ccccc3Cl)CC4)CC2)ncn1] | (R)-1-(2-Chlorobenzamido)-6-fluoro-2,3-dihydro-1H-indene-5-carboxylic acid (E-30) | N-Methyl-1-(6-methylpyrimidin-4-yl)piperidin-4-amine dihydrochloride (AMN-45) | GWP-1 | 87% | |
| H-153 | (3R)-3-[(2-Chloro-benzoyl)-methyl-amino]-N-methyl-N-(1-pyridin-4-yl-piperidin-4-yl)-2,3-dihydro-1H-indene-5-carboxylic acid amide (H-153) | 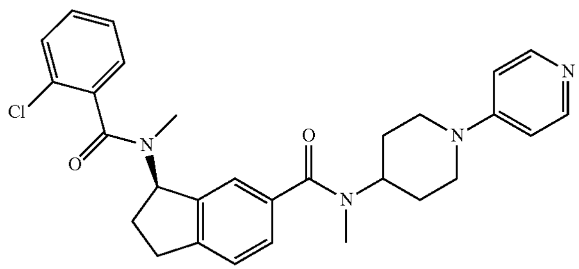 [SMILES: CN(C(=O)c1ccc2c(c1)[C@H](N(C)C(=O)c1ccccc1Cl)CC2)C1CCN(c2ccncc2)CC1] | (R)-3-(2-Chloro-N-methylbenzamido)-2,3-dihydro-1H-indene-5-carboxylic acid (E-52) | N-Methyl-1-(pyridin-4-yl)piperidin-4-amine (AMN-06) | GWP-1 | 57% | |

TABLE-continued

| Example No. | Structure | Name | Amino acid (ACI) | Amine (AMN) | Synthesis according to | Yield | Comments |
|---|---|---|---|---|---|---|---|
| H-155 | 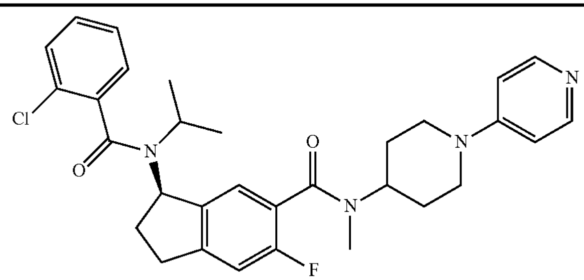 | (3R)-3-[(2-Chloro-benzoyl)-isopropyl-amino]-6-fluoro-N-methyl-N-(1-pyridin-4-yl-piperidin-4-yl)-2,3-dihydro-1H-indene-5-carboxylic acid amide (H-155) | (R)-3-(2-Chloro-N-isopropylbenzamido)-2,3-dihydro-1H-indene-5-carboxylic acid (E-50) | N-Methyl-1-(pyridin-4-yl)piperidin-4-amine (AMN-06) | GWP-1 | 78% | |
| H-156 | 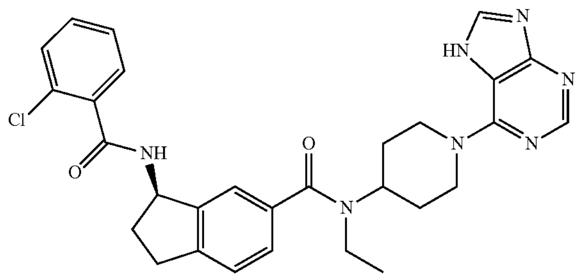 [SMILES: CCN(C(=O)c1ccc2c(c1)[C@H](NC(=O)c1ccccc1Cl)CC2)C1CCN(c2ncnc3nc[nH]c23)CC1] | (3R)-3-[(2-Chloro-benzoyl)amino]-N-ethyl-N-[1-(7H-purin-6-yl)-piperidin-4-yl]-2,3-dihydro-1H-indene-5-carboxylic acid amide (H-156) | (3R)-3-[(2-Chloro-benzoyl)amino]-2,3-dihydro-1H-indene-5-carboxylic acid (E-01) | N-Ethyl-1-(7H-purin-6-yl)piperidin-4-amine (AMN-46) | GWP-4 | 62% | |
| H-158 | 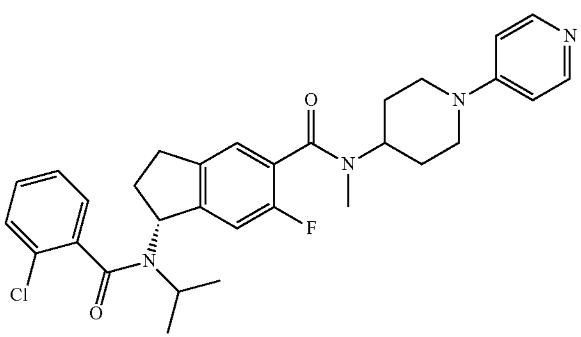 [SMILES: CC(C)N(C(=O)c1ccccc1Cl)[C@@H]1CCc2cc(C(=O)N(C)C3CCN(c4ccncc4)CC3)c(F)cc21] | (1R)-1-[(2-Chloro-benzoyl)isopropyl-amino]-6-fluoro-N-methyl-N-(1-pyridin-4-yl-piperidin-4-yl)-2,3-dihydro-1H-indene-5-carboxylic acid amide (H-158) | (R)-1-(2-Chloro-N-isopropylbenzamido)-6-fluoro-2,3-dihydro-1H-indene-5-carboxylic acid (E-53) | N-Methyl-1-(pyridin-4-yl)piperidin-4-amine (AMN-06) | GWP-1 | 68% | |

| Example No. | Structure | Name | Amino acid (ACI) | Amine (AMN) | Synthesis according to | Yield | Comments |
|---|---|---|---|---|---|---|---|
| H-160 | 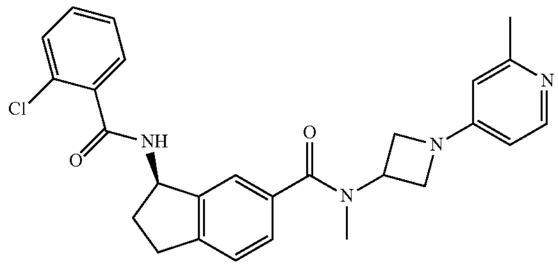 [SMILES: Cc1cc(N2CC(N(C)C(=O)c3ccc4c(c3)[C@H](NC(=O)c3ccccc3Cl)CC4)C2)ccn1] | (3R)-3-[(2-Chloro-benzoyl)amino]-N-methyl-N-[1-(2-methyl-pyridin-4-yl)-azetidin-3-yl]-2,3-dihydro-1H-indene-5-carboxylic acid amide (H-160) | (3R)-3-[(2-Chloro-benzoyl)amino]-2,3-dihydro-1H-indene-5-carboxylic acid (E-01) | N-Methyl-1-(2-methylpyridin-4-yl)azetidin-3-amine dihydrochloride (AMN-47) | GWP-1 | 96% | |
| H-161 | 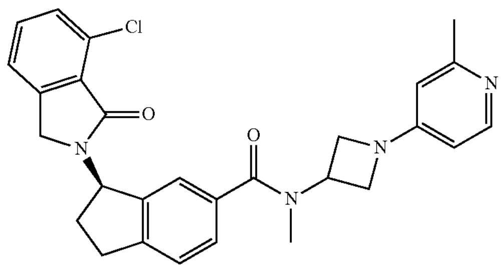 [SMILES: Cc1cc(N2CC(N(C)C(=O)c3ccc4c(c3)[C@H](N3Cc5cccc(Cl)c5C3=O)CC4)C2)ccn1] | (3R)-3-(4-Chloro-3-oxo-1,2-dihydro-isoindol-2-yl)-N-methyl-N-[1-(2-methyl-pyridin-4-yl)-azetidin-3-yl]-2,3-dihydro-1H-indene-5-carboxylic acid amide (H-161) | (R)-3-(7-Chloro-1-oxoisoindolin-2-yl)-2,3-dihydro-1H-indene-5-carboxylic acid (G-01) | N-Methyl-1-(2-methylpyridin-4-yl)azetidin-3-amine dihydrochloride (AMN-47) | GWP-1 | 90% | |
| H-162 | 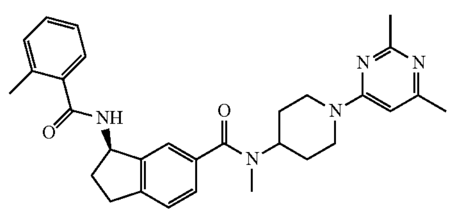 | (3R)-N-[1-(2,6-Dimethyl-pyrimidin-4-yl)-piperidin-4-yl]-N-methyl-3-[(2-methyl-benzoyl)amino]-2,3-dihydro-1H-indene-5-carboxylic acid amide (H-162) | (R)-3-(2-Methylbenzamido)-2,3-dihydro-1H-indene-5-carboxylic acid (E-54) | 1-(2,6-Dimethylpyrimidin-4-yl)-N-methylpiperidin-4-amine (AMN-27) | GWP-1 | 87% | |
| H-163 | 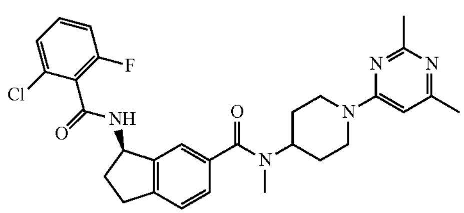 [SMILES: Cc1cc(N2CCC(N(C)C(=O)c3ccc4c(c3)[C@H](NC(=O)c3c(F)cccc3Cl)CC4)CC2)nc(C)n1] | (3R)-3-[(2-Chloro-6-fluorobenzoyl)amino]-N-[1-(2,6-dimethyl-pyrimidin-4-yl)-piperidin-4-yl]-N-methyl-2,3-dihydro-1H-indene-5-carboxylic acid amide (H-163) | (R)-3-(2-Chloro-6-fluorobenzamido)-2,3-dihydro-1H-indene-5-carboxylic acid (E-16) | 1-(2,6-Dimethylpyrimidin-4-yl)-N-methylpiperidin-4-amine (AMN-27) | GWP-1 | 68% | |

| Example No. | Structure | Name | Amino acid (ACI) | Amine (AMN) | Synthesis according to | Yield | Comments |
|---|---|---|---|---|---|---|---|
| H-164 | 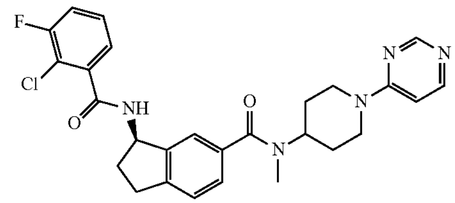 [SMILES: CN(C(=O)c1ccc2c(c1)[C@H](NC(=O)c1cccc(F)c1Cl)CC2)C1CCN(c2ccncn2)CC1] | (3R)-3-[(2-Chloro-3-fluoro-benzoyl)amino]-N-methyl-N-(1-pyrimidin-4-yl-piperidin-4-yl)-2,3-dihydro-1H-indene-5-carboxylic acid amide (H-164) | (R)-3-(2-Chloro-3-fluorobenzamido)-2,3-dihydro-1H-indene-5-carboxylic acid (E-34) | N-Methyl-1-(pyrimidin-4-yl)piperidin-4-amine dihydrochloride (AMN-44) | GWP-1 | 78% | |
| H-165 | 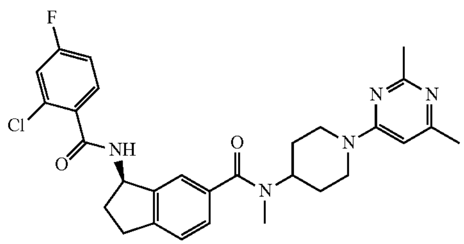 [SMILES: Cc1cc(N2CCC(N(C)C(=O)c3ccc4c(c3)[C@H](NC(=O)c3ccc(F)cc3Cl)CC4)CC2)nc(C)n1] | (3R)-3-[(2-Chloro-4-fluoro-benzoyl)amino]-N-[1-(2,6-dimethyl-pyrimidin-4-yl)-piperidin-4-yl]-N-methyl-2,3-dihydro-1H-indene-5-carboxylic acid amide (H-165) | (R)-3-(2-Chloro-4-fluorobenzamido)-2,3-dihydro-1H-indene-5-carboxylic acid (E-43) | 1-(2,6-Dimethylpyrimidin-4-yl)-N-methylpiperidin-4-amine (AMN-27) | GWP-1 | 71% | |
| H-166 | 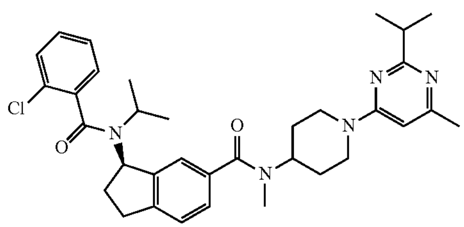 [SMILES: Cc1cc(N2CCC(N(C)C(=O)c3ccc4c(c3)[C@H](N(C(=O)c3ccccc3Cl)C(C)C)CC4)CC2)nc(C(C)C)n1] | (3R)-3-[(2-Chloro-benzoyl)-isopropyl-amino]-N-[1-(2-isopropyl-6-methyl-pyrimidin-4-yl)-piperidin-4-yl]-N-methyl-2,3-dihydro-1H-indene-5-carboxylic acid amide (H-166) | (R)-3-(2-Chloro-N-isopropylbenzamido)-2,3-dihydro-1H-indene-5-carboxylic acid (E-50) | 1-(2-Isopropyl-6-methylpyrimidin-4-yl)-N-methylpiperidin-4-amine (AMN-37) | GWP-1 | 30% | |
| H-167 | 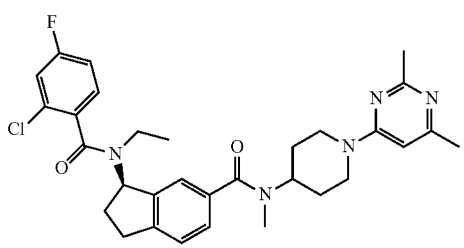 [SMILES: CCN(C(=O)c1ccc(F)cc1Cl)[C@@H]1CCc2ccc(C(=O)N(C)C3CCN(c4cc(C)nc(C)n4)CC3)cc21] | (3R)-3-[(2-Chloro-4-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide (H-167) | (R)-3-(2-Chloro-N-ethyl-4-fluorobenzamido)-2,3-dihydro-1H-indene-5-carboxylic acid (E-55) | 1-(2,6-Dimethylpyrimidin-4-yl)-N-methylpiperidin-4-amine (AMN-27) | GWP-1 | 60% | |

| Example No. | Structure | Name | Amino acid (ACI) | Amine (AMN) | Synthesis according to | Yield | Comments |
|---|---|---|---|---|---|---|---|
| H-168 | 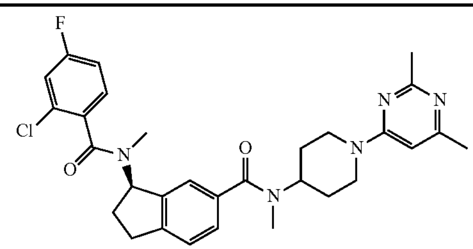 | (3R)-3-[(2-Chloro-4-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide (H-168) | (R)-3-(2-Chloro-4-fluoro-N-methylbenzamido)-2,3-dihydro-1H-indene-5-carboxylic acid (E-56) | 1-(2,6-Dimethylpyrimidin-4-yl)-N-methylpiperidin-4-amine (AMN-27) | GWP-1 | 55% | |
| H-169 | 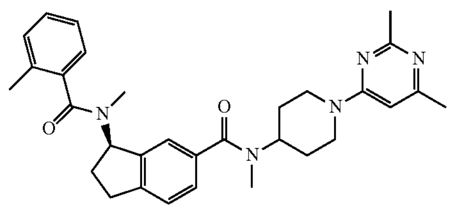 | (3R)-N-[1-(2,6-Dimethyl-pyrimidin-4-yl)-piperidin-4-yl]-N-methyl-3-[methyl-(2-methyl-benzoyl)-amino]-2,3-dihydro-1H-indene-5-carboxylic acid amide (H-169) | (R)-3-(N,2-Dimethylbenzamido)-2,3-dihydro-1H-indene-5-carboxylic acid (E-57) | 1-(2,6-Dimethylpyrimidin-4-yl)-N-methylpiperidin-4-amine (AMN-27) | GWP-1 | 69% | |
| H-170 | 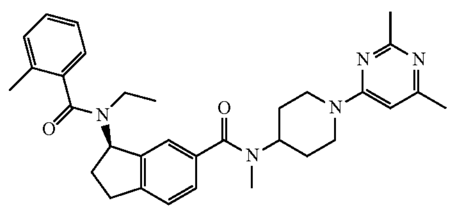 | (3R)-N-[1-(2,6-Dimethyl-pyrimidin-4-yl)-piperidin-4-yl]-3-[ethyl-(2-methyl-benzoyl)-amino]-N-methyl-2,3-dihydro-1H-indene-5-carboxylic acid amide (H-170) | (R)-3-(N-Ethyl-2-methylbenzamido)-2,3-dihydro-1H-indene-5-carboxylic acid (E-65) | 1-(2,6-Dimethylpyrimidin-4-yl)-N-methylpiperidin-4-amine(AMN-27) | GWP-1 | 70% | |
| H-171 | 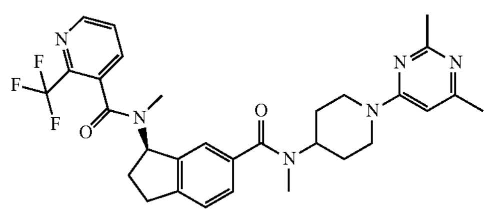 [SMILES: Cc1cc(N2CCC(N(C)C(=O)c3ccc4c(c3)[C@H](N(C)C(=O)c3cccnc3C(F)(F)F)CC4)CC2)nc(C)n1] | N-[(1R)-6-[[1-(2,6-Dimethyl-pyrimidin-4-yl)-piperidin-4-yl]-methyl-carbamoyl]-2,3-dihydro-1H-inden-1-yl]-N-methyl-2-(trifluoromethyl)pyridine-3-carboxylic acid amide (H-171) | (R)-3-(N-Methyl-2-(trifluoromethyl)nicotinamido)-2,3-dihydro-1H-indene-5-carboxylic acid (E-58) | 1-(2,6-Dimethylpyrimidin-4-yl)-N-methylpiperidin-4-amine (AMN-27) | GWP-1 | 71% | |

TABLE-continued

| Example No. | Structure | Name | Amino acid (ACI) | Amine (AMN) | Synthesis according to | Yield | Comments |
|---|---|---|---|---|---|---|---|
| H-172 | 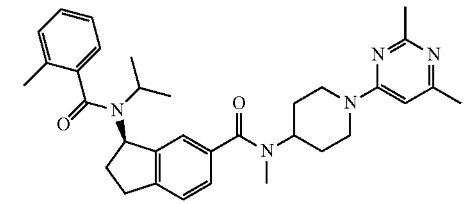 | (3R)-N-[1-(2,6-Dimethyl-pyrimidin-4-yl)-piperidin-4-yl]-3-[isopropyl-(2-methyl-benzoyl)-amino]-N-methyl-2,3-dihydro-1H-indene-5-carboxylic acid amide (H-172) | (R)-3-(N-Isopropyl-2-methylbenzamido)-2,3-dihydro-1H-indene-5-carboxylic acid (E-59) | 1-(2,6-Dimethylpyrimidin-4-yl)-N-methylpiperidin-4-amine (AMN-27) | GWP-1 | 62% | |
| H-174 | 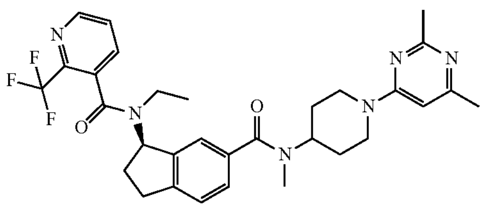 [SMILES: CCN(C(=O)c1cccnc1C(F)(F)F)[C@@H]1CCc2ccc(C(=O)N(C)C3CCN(c4cc(C)nc(C)n4)CC3)cc21] | N-[(1R)-6-[[1-(2,6-Dimethyl-pyrimidin-4-yl)-piperidin-4-yl]-methyl-carbamoyl]-2,3-dihydro-1H-inden-1-yl]-N-ethyl-2-(trifluoromethyl)-pyridine-3-carboxylic acid amide (H-174) | (R)-3-(N-Ethyl-2-(trifluoromethyl)nicotinamido)-2,3-dihydro-1H-indene-5-carboxylic acid (E-61) | 1-(2,6-Dimethylpyrimidin-4-yl)-N-methylpiperidin-4-amine (AMN-27) | GWP-1 | 71% | |
| H-175 | 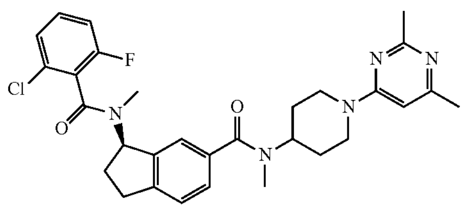 [SMILES: Cc1cc(N2CCC(N(C)C(=O)c3ccc4c(c3)[C@H](N(C)C(=O)c3c(F)cccc3Cl)CC4)CC2)nc(C)n1] | (3R)-3-[(2-Chloro-6-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide (H-175) | (R)-3-(2-Chloro-6-fluoro-N-methylbenzamido)-2,3-dihydro-1H-indene-5-carboxylic acid (E-62) | 1-(2,6-Dimethylpyrimidin-4-yl)-N-methylpiperidin-4-amine (AMN-27) | GWP-1 | 63% | |
| H-176 | 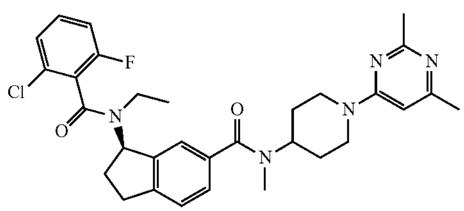 [SMILES: CCN(C(=O)c1c(F)cccc1Cl)[C@@H]1CCc2ccc(C(=O)N(C)C3CCN(c4cc(C)nc(C)n4)CC3)cc21] | (3R)-3-[(2-Chloro-6-fluoro-benzoyl)-ethyl-amino]-N-[4-(2,6-dimethyl-pyrimidin-4-yl)-cyclohexyl]-N-methyl-2,3-dihydro-1H-indene-5-carboxylic acid amide (H-176) | (R)-3-(2-Chloro-N-ethyl-6-fluorobenzamido)-2,3-dihydro-1H-indene-5-carboxylic acid (E-63) | 1-(2,6-Dimethylpyrimidin-4-yl)-N-methylpiperidin-4-amine (AMN-27) | GWP-1 | 54% | |

| Example No. | Structure | Name | Amino acid (ACI) | Amine (AMN) | Synthesis according to | Yield | Comments |
|---|---|---|---|---|---|---|---|
| H-178 | 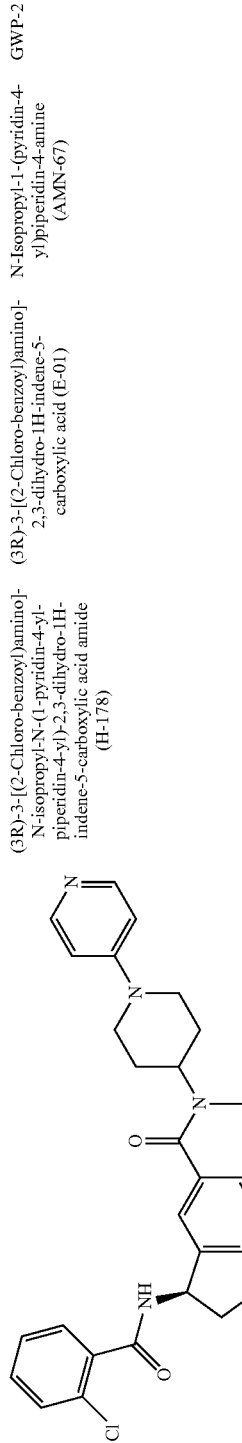 | (3R)-3-[(2-Chloro-benzoyl)amino]-N-isopropyl-N-(1-pyridin-4-yl-piperidin-4-yl)-2,3-dihydro-1H-indene-5-carboxylic acid amide (H-178) | (3R)-3-[(2-Chloro-benzoyl)amino]-2,3-dihydro-1H-indene-5-carboxylic acid (E-01) | N-Isopropyl-1-(pyridin-4-yl)piperidin-4-amine (AMN-67) | GWP-2 | 9% (75 mg, 0.145 mmol) | |
| H-179 | 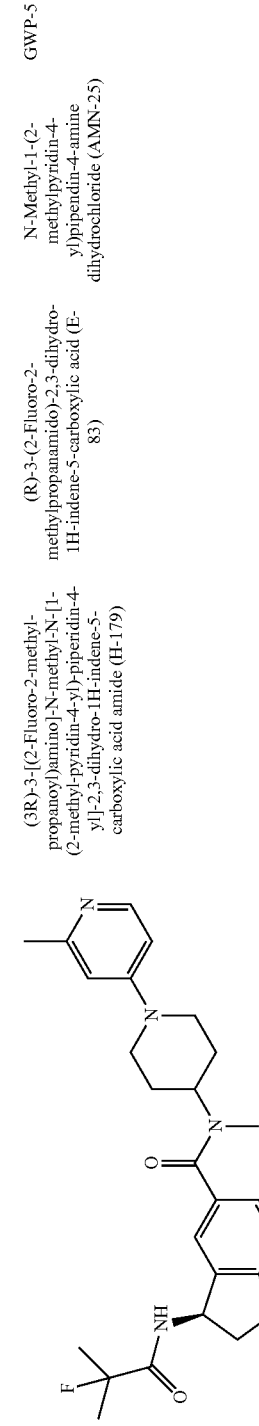 | (3R)-3-[(2-Fluoro-2-methyl-propanoyl)amino]-N-methyl-N-[1-(2-methyl-pyridin-4-yl)-piperidin-4-yl]-2,3-dihydro-1H-indene-5-carboxylic acid amide (H-179) | (R)-3-(2-Fluoro-2-methylpropanamido)-2,3-dihydro-1H-indene-5-carboxylic acid (E-83) | N-Methyl-1-(2-methylpyridin-4-yl)pipendin-4-amine dihydrochloride (AMN-25) | GWP-5 | 85% (250 mg, 0.553 mmol) | |
| H-180 | 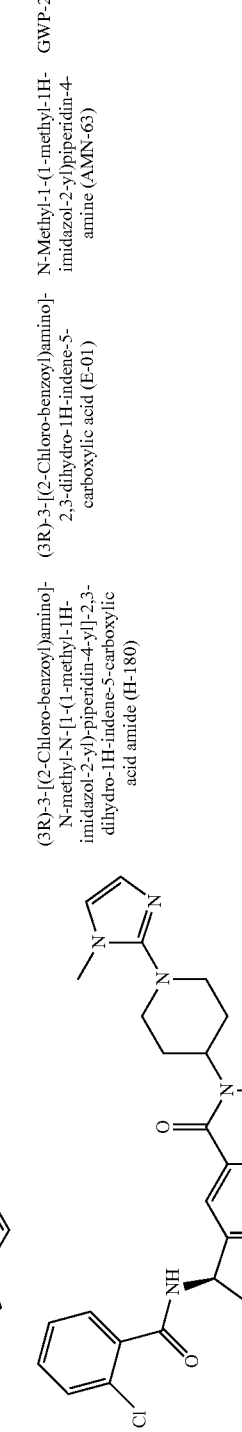 | (3R)-3-[(2-Chloro-benzoyl)amino]-N-methyl-N-[1-(1-methyl-1H-imidazol-2-yl)-piperidin-4-yl]-2,3-dihydro-1H-indene-5-carboxylic acid amide (H-180) | (3R)-3-[(2-Chloro-benzoyl)amino]-2,3-dihydro-1H-indene-5-carboxylic acid (E-01) | N-Methyl-1-(1-methyl-1H-imidazol-2-yl)piperidin-4-amine (AMN-63) | GWP-2 | 64% (200 mg, 0.407 mmol) | |

| Example No. | Structure | Name | Amino acid (ACI) | Amine (AMN) | Synthesis according to | Yield | Comments |
|---|---|---|---|---|---|---|---|
| H-181 | 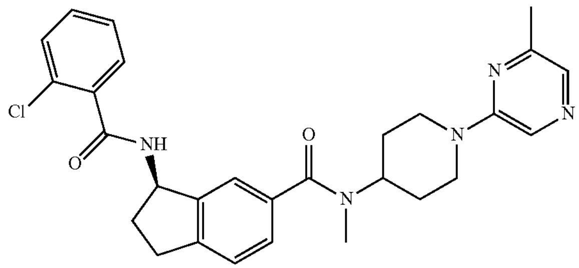 [SMILES: Cc1cncc(N2CCC(N(C)C(=O)c3ccc4c(c3)[C@H](NC(=O)c3ccccc3Cl)CC4)CC2)n1] | (3R)-3-[(2-Chloro-benzoyl)amino]-N-methyl-N-[1-(6-methyl-pyrazin-2-yl)piperidin-4-yl]-2,3-dihydro-1H-indene-5-carboxylic acid amide (H-181) | (3R)-3-[(2-Chloro-benzoyl)amino]-2,3-dihydro-1H-indene-5-carboxylic acid (E-01) | N-Methyl-1-(6-methylpyrazin-2-yl)piperidin-4-amine (AMN-65) | GWP-5 | 37%, (150 mg, 0.298 mmol) | |
| H-182 | 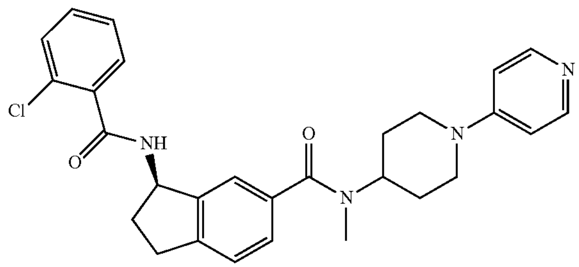 [SMILES: CN(C(=O)c1ccc2c(c1)[C@H](NC(=O)c1ccccc1Cl)CC2)C1CCN(c2ccncc2)CC1] | (3R)-3-[(2-Chloro-benzoyl)amino]-N-methyl-N-(2-oxo-1-pyridin-4-yl-piperidin-4-yl)-2,3-dihydro-1H-indene-5-carboxylic acid amide (H-182) | (3R)-3-[(2-Chloro-benzoyl)amino]-2,3-dihydro-1H-indene-5-carboxylic acid (E-01) | 4-(Methylamino)-1-(pyridin-4-yl)piperidin-2-one (AMN-53) | GWP-2 | 37% (90 mg, 0.179 mmol) | |
| H-183 | 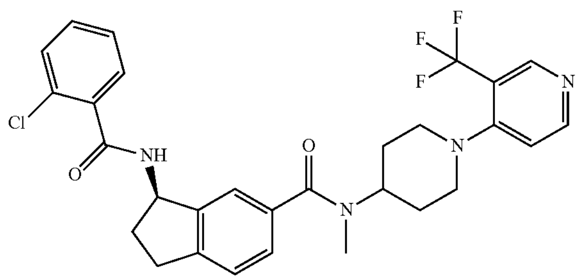 [SMILES: CN(C(=O)c1ccc2c(c1)[C@H](NC(=O)c1ccccc1Cl)CC2)C1CCN(c2ccncc2C(F)(F)F)CC1] | (3R)-3-[(2-Chloro-benzoyl)amino]-N-methyl-N-[1-[3-(trifluoromethyl)-pyridin-4-yl]-piperidin-4-yl]-2,3-dihydro-1H-indene-5-carboxylic acid amide (H-183) | (3R)-3-[(2-Chloro-benzoyl)amino]-2,3-dihydro-1H-indene-5-carboxylic acid (E-01) | N-Methyl-1-(3-(trifluoromethyl)pyridin-4-yl)piperidin-4-amine (AMN-57) | GWP-2 | 61% (195 mg, 0.35 mmol) | |

TABLE-continued

| Example No. | Structure | Name | Amino acid (ACI) | Amine (AMN) | Synthesis according to | Yield | Comments |
|---|---|---|---|---|---|---|---|
| H-184 | 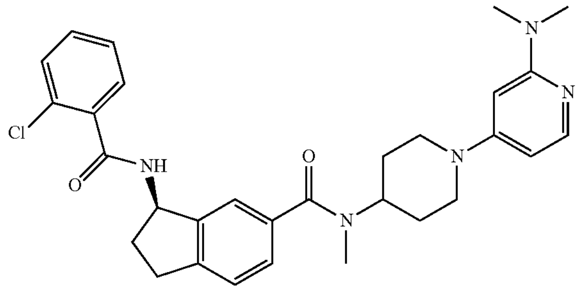 [SMILES: CN(C)c1cc(N2CCC(N(C)C(=O)c3ccc4c(c3)[C@H](NC(=O)c3ccccc3Cl)CC4)CC2)ccn1] | (3R)-3-[(2-Chloro-benzoyl)amino]-N-[4-(2-dimethylamino-pyridin-4-yl)cyclohexyl]-N-methyl-2,3-dihydro-1H-indene-5-carboxylic acid amide (H-184) | (3R)-3-[(2-Chloro-benzoyl)amino]-2,3-dihydro-1H-indene-5-carboxylic acid (E-01) | N,N-Dimethyl-4-(4-(methylamino)cyclohexyl)pyridin-2-amine (AMN-68) | GWP-2 | 46% (170 mg, 0.32 mmol) | |
| H-185 | 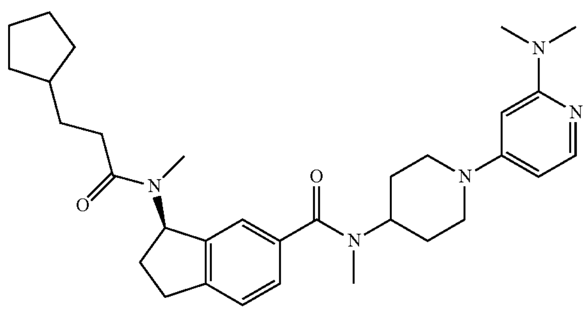 [SMILES: CN(C)c1cc(N2CCC(N(C)C(=O)c3ccc4c(c3)[C@H](N(C)C(=O)CCC3CCCC3)CC4)CC2)ccn1] | (3R)-3-(3-Cyclopentyl-propanoyl-methyl-amino)-N-[1-(2-dimethylamino-pyridin-4-yl)-piperidin-4-yl]-N-methyl-2,3-dihydro-1H-indene-5-carboxylic acid amide (H-185) | (R)-3-(3-Cyclopentyl-N-methylpropanamido)-2,3-dihydro-1H-indene-5-carboxylic acid (E-82) | N,N-Dimethyl-4-(4-(methylamino)piperidin-1-yl)pyridin-2-amine (AMN-52) | GWP-5 | 26% (110 mg, 0.207 mmol) | |
| H-186 | 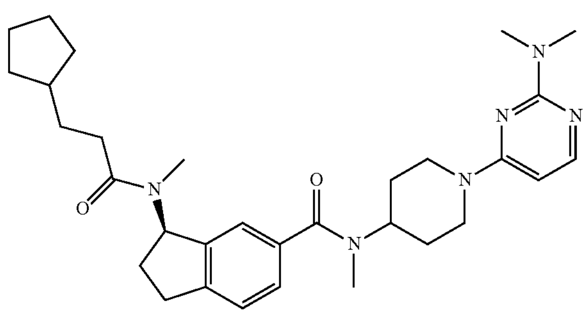 [SMILES: CN(C)c1nccc(N2CCC(N(C)C(=O)c3ccc4c(c3)[C@H](N(C)C(=O)CCC3CCCC3)CC4)CC2)n1] | (3R)-3-(3-Cyclopentyl-propanoyl-methyl-amino)-N-[1-(2-dimethylamino-pyrimidin-4-yl)-piperidin-4-yl]-N-methyl-2,3-dihydro-1H-indene-5-carboxylic acid amide (H-186) | (R)-3-(3-Cyclopentyl-N-methylpropanamido)-2,3-dihydro-1H-indene-5-carboxylic acid (E-82) | N,N-Dimethyl-4-(4-(methylamino)piperidin-1-yl)pyrimidin-2-amine (AMN-59) | GWP-5 | 37% (110 mg, 0.20 mmol) | |

TABLE-continued

| Example No. | Structure | Name | Amino acid (ACI) | Amine (AMN) | Synthesis according to | Yield | Comments |
|---|---|---|---|---|---|---|---|
| H-188 | 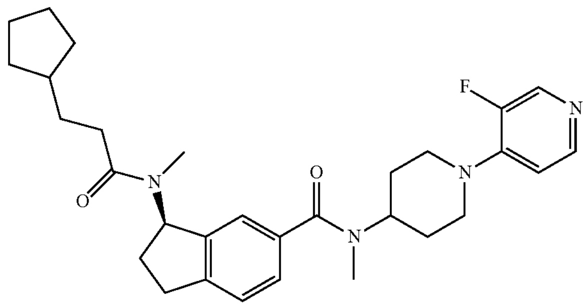 [SMILES: CN(C(=O)c1ccc2c(c1)[C@H](N(C)C(=O)CCC1CCCC1)CC2)C1CCN(c2ccncc2F)CC1] | (3R)-3-(3-Cyclopentyl-propanoyl-methyl-amino)-N-[1-(3-fluoro-pyridin-4-yl)-piperidin-4-yl]-N-methyl-2,3-dihydro-1H-indene-5-carboxylic acid amide (H-188) | (R)-3-(3-Cyclopentyl-N-methylpropanamido)-2,3-dihydro-1H-indene-5-carboxylic acid (E-82) | 1-(3-Fluoropyridin-4-yl)-N-methlpiperidin-4-amine (AMN-56) | GWP-5 | 21% (130 mg, 0.256 mmol) | |
| H-191 | 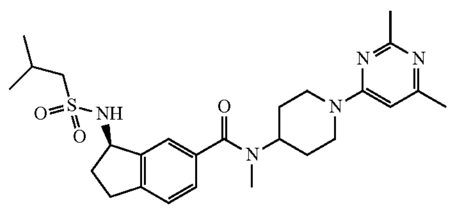 [SMILES: Cc1cc(N2CCC(N(C)C(=O)c3ccc4c(c3)[C@H](NS(=O)(=O)CC(C)C)CC4)CC2)nc(C)n1] | (3R)-N-[1-(2,6-Dimethyl-pyrimidin-4-yl)-piperidin-4-yl]-N-methyl-3-[(2-methyl-propylsulfonyl)amino]-2,3-dihydro-1H-indene-5-carboxylic acid amide (H-191) | (R)-3-(2-Methylpropylsulfonamido)-2,3-dihydro-1H-indene-5-carboxylic acid (F-03) | 1-(2,6-Dimethylpyrimidin-4-yl)-N-methylpiperidin-4-amine (AMN-27) | GWP-2 | 36% (130 mg, 0.26 mmol) | |
| H-195 | 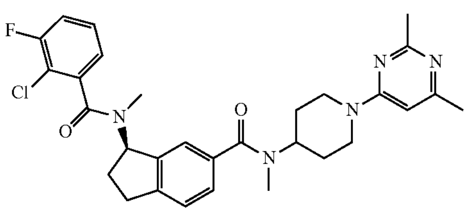 [SMILES: Cc1cc(N2CCC(N(C)C(=O)c3ccc4c(c3)[C@H](N(C)C(=O)c3cccc(F)c3Cl)CC4)CC2)nc(C)n1] | (3R)-3-[(2-Chloro-3-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide (H-195) | (R)-Methyl 3-(2-chloro-3-fluoro-N-methylbenzamido)-2,3-dihydro-1H-indene-5-carboxylic acid (E-68) | 1-(2,6-Dimethylpyrimidin-4-yl)-N-methylpiperidin-4-amine (AMN-27) | GWP-1 | 69% | |
| H-196 | 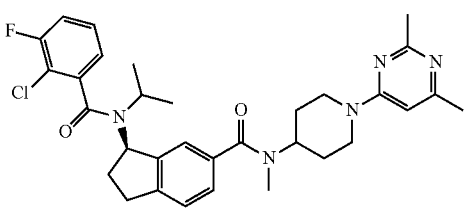 [SMILES: Cc1cc(N2CCC(N(C)C(=O)c3ccc4c(c3)[C@H](N(C(=O)c3cccc(F)c3Cl)C(C)C)CC4)CC2)nc(C)n1] | (3R)-3-[(2-Chloro-3-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide (H-196) | (R)-Methyl 3-(2-chloro-3-fluoro-N-isopropylbenzamido)-2,3-dihydro-1H-indene-5-carboxylic acid (E-74) | 1-(2,6-Dimethylpyrimidin-4-yl)-N-methylpiperidin-4-amine (AMN-27) | GWP-1 | 39% | |

TABLE-continued

| Example No. | Structure | Name | Amino acid (ACI) | Amine (AMN) | Synthesis according to | Yield | Comments |
|---|---|---|---|---|---|---|---|
| H-197 | 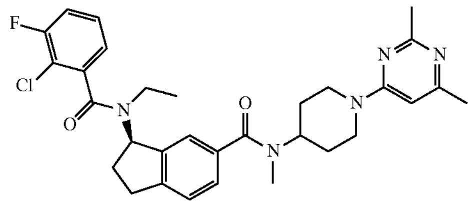 [SMILES: CCN(C(=O)c1cccc(F)c1Cl)[C@@H]1CCc2ccc(C(=O)N(C)C3CCN(c4cc(C)nc(C)n4)CC3)cc21] | (3R)-3-[(2-Chloro-3-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide (H-197) | (R)-Methyl 3-(2-chloro-N-ethyl-3-fluorobenzamido)-2,3-dihydro-1H-indene-5-carboxylic acid (E-69) | 1-(2,6-Dimethylpyrimidin-4-yl)-N-methylpiperidin-4-amine (AMN-27) | GWP-1 | 51% | |
| H-198 | 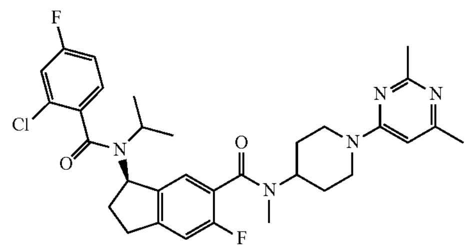 [SMILES: Cc1cc(N2CCC(N(C)C(=O)c3cc4c(cc3F)CC[C@H]4N(C(=O)c3ccc(F)cc3Cl)C(C)C)CC2)nc(C)n1] | (3R)-3-[(2-Chloro-4-fluoro-benzoyl)-isopropyl-amino]-N-[1-(2,6-dimethyl-pyrimidin-4-yl)-piperidin-4-yl]-6-fluoro-N-methyl-2,3-dihydro-1H-indene-5-carboxylic acid amide (H-198) | (R)-Methyl 3-(2-chloro-4-fluoro-N-isopropylbenzamido)-6-fluoro-2,3-dihydro-1H-indene-5-carboxylic acid (E-70) | 1-(2,6-Dimethylpyrimidin-4-yl)-N-methylpiperidin-4-amine (AMN-27) | GWP-1 | 79% | |
| H-199 | 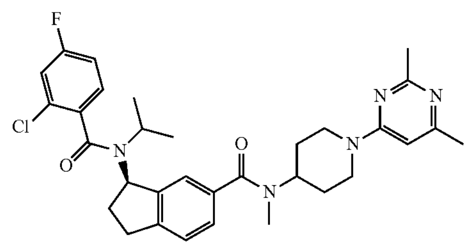 [SMILES: Cc1cc(N2CCC(N(C)C(=O)c3ccc4c(c3)[C@H](N(C(=O)c3ccc(F)cc3Cl)C(C)C)CC4)CC2)nc(C)n1] | (3R)-3-[(2-Chloro-4-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide (H-199) | (R)-Methyl 3-(2-chloro-4-fluoro-N-isopropylbenzamido)-2,3-dihydro-1H-indene-5-carboxylic acid (E-71) | 1-(2,6-Dimethylpyrimidin-4-yl)-N-methylpiperidin-4-amine (AMN-27) | GWP-1 | 73% | |
| H-202 | 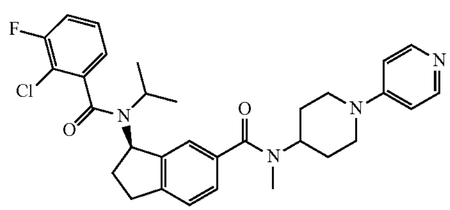 [SMILES: CC(C)N(C(=O)c1cccc(F)c1Cl)[C@@H]1CCc2ccc(C(=O)N(C)C3CCN(c4ccncc4)CC3)cc21] | (3R)-3-[(2-Chloro-3-fluoro-benzoyl)-isopropyl-amino]-N-methyl-N-(1-pyridin-4-yl-piperidin-4-yl)-2,3-dihydro-1H-indene-5-carboxylic acid amide (H-202) | (R)-Methyl 3-(2-chloro-3-fluoro-N-isopropylbenzamido)-2,3-dihydro-1H-indene-5-carboxylic acid (E-74) | N-Methyl-1-(pyridin-4-yl)piperidin-4-amine (AMN-06) | GWP-1 | 87% | |

TABLE-continued

| Example No. | Structure | Name | Amino acid (ACI) | Amine (AMN) | Synthesis according to | Yield | Comments |
|---|---|---|---|---|---|---|---|
| H-203 | 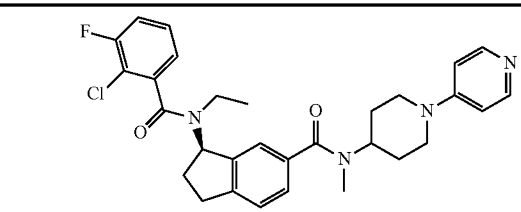 | (3R)-3-[(2-Chloro-3-fluoro-benzoyl)ethyl-amino]-N-methyl-N-(1-pyridin-4-yl-piperidin-4-yl)-2,3-dihydro-1H-indene-5-carboxylic acid amide (H-203) | (R)-Methyl 3-(2-chloro-N-ethyl-3-fluorobenzamido)-2,3-dihydro-1H-indene-5-carboxylic acid (E-69) | N-Methyl-1-(pyridin-4-yl)piperidin-4-amine (AMN-06) | GWP-1 | 71% | |
| H-204 | 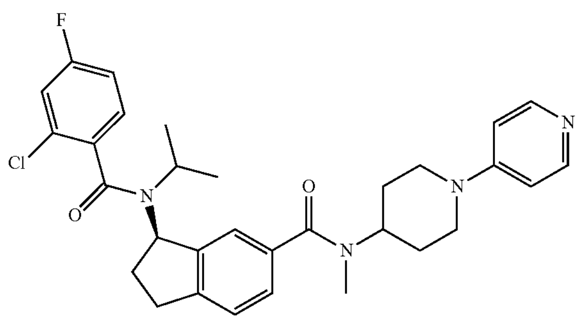 [SMILES: CC(C)N(C(=O)c1ccc(F)cc1Cl)[C@@H]1CCc2ccc(C(=O)N(C)C3CCN(c4ccncc4)CC3)cc21] | (3R)-3-[(2-Chloro-4-fluoro-benzoyl)-isopropyl-amino]-N-methyl-N-(1-pyridin-4-yl-piperidin-4-yl)-2,3-dihydro-1H-indene-5-carboxylic acid amide (H-204) | (R)-Methyl 3-(2-chloro-4-fluoro-N-isopropylbenzamido)-2,3-dihydro-1H-indene-5-carboxylic acid (E-71) | N-Methyl-1-(pyridin-4-yl)piperidin-4-amine (AMN-06) | GWP-1 | 78% | |
| H-205 | 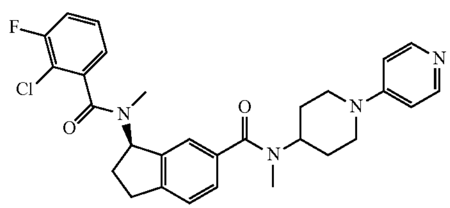 [SMILES: CN(C(=O)c1ccc2c(c1)[C@H](N(C)C(=O)c1cccc(F)c1Cl)CC2)C1CCN(c2ccncc2)CC1] | (3R)-3-[(2-Chloro-3-fluoro-benzoyl)-methyl-amino]-N-methyl-N-(1-pyridin-4-yl-piperidin-4-yl)-2,3-dihydro-1H-indene-5-carboxylic acid amide (H-205) | (R)-Methyl 3-(2-chloro-3-fluoro-N-methylbenzamido)-2,3-dihydro-1H-indene-5-carboxylic acid (E-68) | N-Methyl-1-(pyridin-4-yl)piperidin-4-amine (AMN-06) | GWP-1 | 80% | |

| Example No. | Structure | Name | Amino acid (ACI) | Amine (AMN) | Synthesis according to | Yield | Comments |
|---|---|---|---|---|---|---|---|
| H-206 | 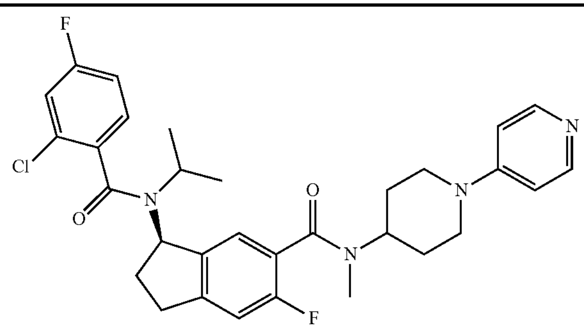 | (3R)-3-[(2-Chloro-4-fluoro-benzoyl)-isopropyl-amino]-6-fluoro-N-methyl-N-(1-pyridin-4-yl-piperidin-4-yl)-2,3-dihydro-1H-indene-5-carboxylic acid amide (H-206) | (R)-Methyl 3-(2-chloro-4-fluoro-N-isopropylbenzamido)-6-fluoro-2,3-dihydro-1H-indene-5-carboxylic acid (E-70) | N-Methyl-1-(pyridin-4-yl)piperidin-4-amine (AMN-06) | GWP-1 | 69% | |
| H-207 | 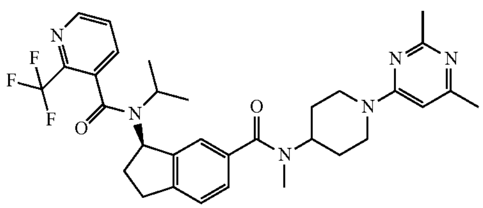 [SMILES: Cc1cc(N2CCC(N(C)C(=O)c3ccc4c(c3)[C@H](N(C(=O)c3cccnc3C(F)(F)F)C(C)C)CC4)CC2)nc(C)n1] | N-[(1R)-6-1-(2,6-Dimethyl-pyrimidin-4-yl)-piperidin-4-yl]-methyl-carbamoyl]-2,3-dihydro-1H-inden-1-yl]-N-isopropyl-2-(trifluoromethyl)-pyridine-3-carboxylic acid amide (H-207) | (R)-Methyl 3-(N-isopropyl-2-(trifluoromethyl)nicotinamido)-2,3-dihydro-1H-indene-5-carboxylic acid (E-75) | 1-(2,6-Dimethylpyrimidin-4-yl)-N-methylpiperidin-4-amine (AMN-27) | GWP-1 | 79% | |
| H-208 | 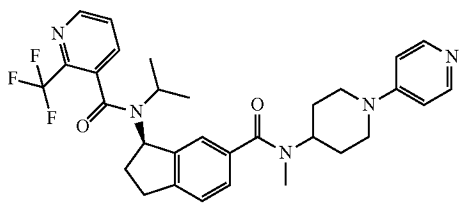 [SMILES: CC(C)N(C(=O)c1cccnc1C(F)(F)F)[C@@H]1CCc2ccc(C(=O)N(C)C3CCN(c4ccncc4)CC3)cc21] | N-Isopropyl-N-[((1R)-6-[methyl-(1-pyridin-4-yl-piperidin-4-yl)-carbamoyl]-2,3-dihydro-1H-inden-1-yl]-2-(trifluoromethyl)-pyridine-3-carboxylic acid amide (H-208) | (R)-Methyl 3-(N-isopropyl-2-(trifluoromethyl)nicotinamido)-2,3-dihydro-1H-indene-5-carboxylic acid (E-75) | N-Methyl-1-(pyridin-4-yl)pipendin-4-amine (AMN-06) | GWP-1 | 76% | |
| H-209 | 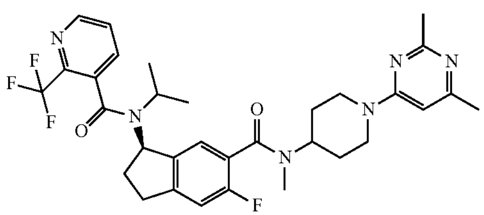 [SMILES: Cc1cc(N2CCC(N(C)C(=O)c3cc4c(cc3F)CC[C@H]4N(C(=O)c3cccnc3C(F)(F)F)C(C)C)CC2)nc(C)n1] | N-[(1R)-6-[[1-(2,6-Dimethyl-pyrimidin-4-yl)-piperidin-4-yl]-metyl-carbamoyl]-5-fluoro-2,3-dihydro-1H-inden-1-yl]-N-isopropyl-2-(trifluoromethyl)-pyridine-3-carboxylic acid amide (H-209) | (R)-Methyl 6-fluoro-3-(N-isopropyl-2-(trifluoromethyl)nicotinamido)-2,3-dihydro-1H-indene-5-carboxylic acid (E-76) | 1-(2,6-Dimethylpyrimidin-4-yl)-N-methylpiperidin-4-amine (AMN-27) | GWP-1 | 67% | |

| Example No. | Structure | Name | Amino acid (ACI) | Amine (AMN) | Synthesis according to | Yield | Comments |
|---|---|---|---|---|---|---|---|
| H-210 | 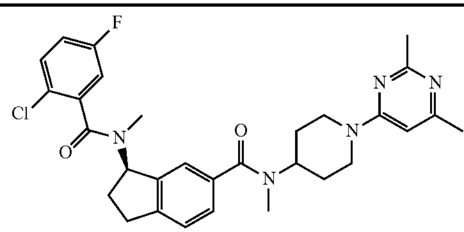 | (3R)-3-[(2-Chloro-5-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide (H-210) | (R)-Methyl 3-(2-chloro-5-fluoro-N-methylbenzamido)-2,3-dihydro-1H-indene-5-carboxylic acid (E-77) | 1-(2,6-Dimethylpyrimidin-4-yl)-N-methylpiperidin-4-amine (AMN-27) | GWP-1 | 87% | stirred for 5 days |
| H-211 | 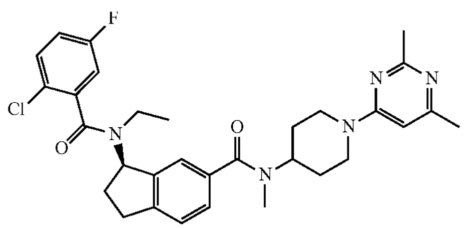 [SMILES: CCN(C(=O)c1cc(F)ccc1Cl)[C@@H]1CCc2ccc(C(=O)N(C)C3CCN(c4cc(C)nc(C)n4)CC3)cc21] | (3R)-3-[(2-Chloro-5-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide (H-211) | (R)-3-(2-Chloro-N-ethyl-5-fluorobenzamido)-2,3-dihydro-1H-indene-5-carboxylic acid (E-78) | 1-(2,6-Dimethylpyrimidin-4-yl)-N-methylpiperidin-4-amine (AMN-27) | GWP-1 | 30% | |
| H-212 | 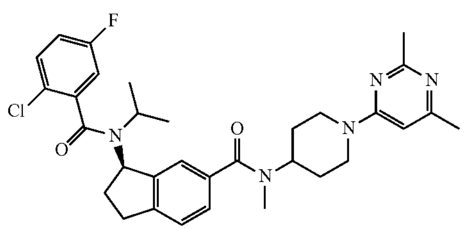 [SMILES: Cc1cc(N2CCC(N(C)C(=O)c3ccc4c(c3)[C@H](N(C(=O)c3cc(F)ccc3Cl)C(C)C)CC4)CC2)nc(C)n1] | (3R)-3-[(2-Chloro-5-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide (H-212) | (R)-Methyl 3-(2-chloro-5-fluoro-N-isopropylbenzamido)-2,3-dihydro-1H-indene-5-carboxylic acid (E-79) | 1-(2,6-Dimethylpyrimidin-4-yl)-N-methylpiperidin-4-amine (AMN-27) | GWP-1 | 75% | |
| H-213 | 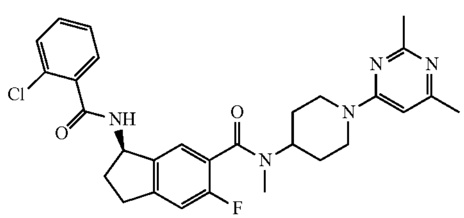 [SMILES: Cc1cc(N2CCC(N(C)C(=O)c3cc4c(cc3F)CC[C@H]4NC(=O)c3ccccc3Cl)CC2)nc(C)n1] | (3R)-3-[(2-Chlorobenzoyl)amino]-N-[1-(2,6-dimethyl-pyrimidin-4-yl)-piperidin-4-yl]-6-fluoro-N-methyl-2,3-dihydro-1H-indene-5-carboxylic acid amide (H-213) | (R)-3-(2-Chlorobenzamido)-6-fluoro-2,3-dihydro-1H-indene-5-carboxylic acid (E-81) | 1-(2,6-Dimethylpyrimidin-4-yl)-N-methylpiperidin-4-amine (AMN-27) | GWP-2 | 57% (250 mg, 0.467 mmol) | |

TABLE-continued

| Example No. | Structure | Name | Amino acid (ACI) | Amine (AMN) | Synthesis according to | Yield | Comments |
|---|---|---|---|---|---|---|---|
| H-214 | 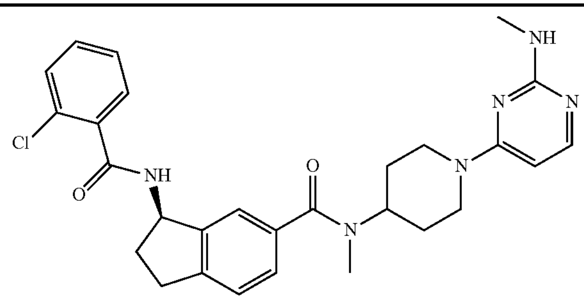 | (3R)-3-[(2-Chloro-benzoyl)amino]-N-methyl-N-[1-(2-methylamino-pyrimidin-4-yl)-piperidin-4-yl]-2,3-dihydro-1H-indene-5-carboxylic acid amide (H-214) | | | | | see below |
| H-215 | 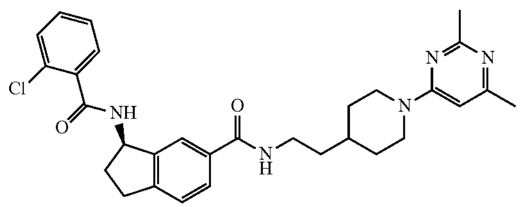 [SMILES: Cc1cc(N2CCC(CCNC(=O)c3ccc4c(c3)[C@H](NC(=O)c3ccccc3Cl)CC4)CC2)nc(C)n1] | (3R)-3-[(2-Chloro-benzoyl)amino]-N-[2-[1-(2,6-dimethyl-pyrimidin-4-yl)-piperidin-4-yl]-ethyl]-2,3-dihydro-1H-indene-5-carboxylic acid amide (H-215) | (3R)-3-[(2-Chloro-benzoyl)amino]-2,3-dihydro-1H-indene-5-carboxylic acid (E-01) | 2-(1-(2,6-Dimethylpyrimidin-4-yl)piperidin-4-yl)ethanamine (AMN-71) | GWP-5 | 44% (250 mg, 0.470 mmol) | |
| H-216 | 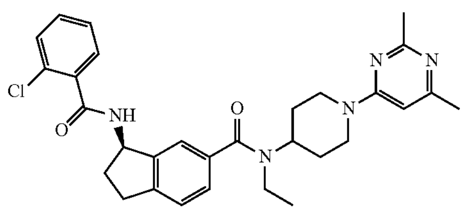 | (3R)-3-[(2-Chloro-benzoyl)amino]-N-[1-(2,6-dimethyl-pyrimidin-4-yl)-piperidin-4-yl]-N-ethyl-2,3-dihydro-1H-indene-5-carboxylic acid amide (H-216) | (3R)-3-[(2-Chloro-benzoyl)amino]-2,3-dihydro-1H-indene-5-carboxylic acid (E-01) | 1-(2,6-Dimethylpyrimidin-4-yl)-N-ethylpiperidin-4-amine (AMN-73) | GWP-2 | 40% (170 mg, 0.32 mmol) | |
| H-217 | 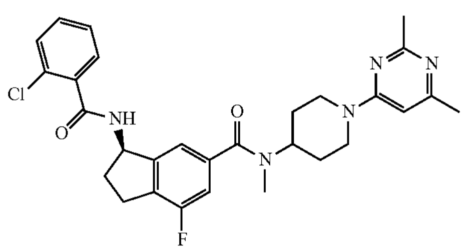 [SMILES: Cc1cc(N2CCC(N(C)C(=O)c3cc(F)c4c(c3)[C@H](NC(=O)c3ccccc3Cl)CC4)CC2)nc(C)n1] | (3R)-3-[(2-Chloro-benzoyl)amino]-N-[1-(2,6-dimethylpyrimidin-4-yl]-7-fluoro-N-methyl-2,3-dihydro-1H-indene-5-carboxylic acid amide (H-217) | (R)-3-(2-Chlorobenzamido)-7-fluoro-2,3-dihydro-1H-indene-5-carboxylic acid (E-96) | 1-(2,6-Dimethylpyrimidin-4-yl)-N-methylpiperidin-4-amine (AMN-27) | GWP-2 | 42% (170 mg, 0.317 mmol) | |

TABLE-continued

| Example No. | Name | Structure | Amino acid (ACI) | Amine (AMN) | Synthesis according to | Yield | Comments |
|---|---|---|---|---|---|---|---|
| H-219 | (3R)-3-[(2-Chloro-benzoyl)amino]-N-methyl-N-[1-(2-oxo-1H-pyridin-4-yl)piperidin-4-yl]-2,3-dihydro-1H-indene-5-carboxylic acid amide (H-219) | 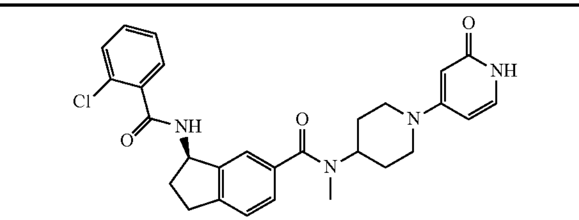 | (3R)-3-[(2-Chloro-benzoyl)amino]-2,3-dihydro-1H-indene-5-carboxylic acid (E-01) | 4-(4-(Methylamino)piperidin-1-yl)pyridin-2(1H)-one (AMN-72) | GWP-5 | 45% (230 mg, 0.456 mmol) | |
| H-220 | (3R)-3-[(2-Chloro-6-fluoro-benzoylyethyl-amino]-N-methyl-N-(1-pyridin-4-yl-piperidin-4-yl)-2,3-dihydro-1H-indene-5-carboxylic acid amide (H-220) | 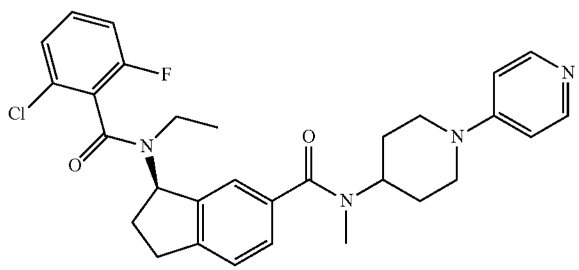 [SMILES: CCN(C(=O)c1c(F)cccc1Cl)[C@@H]1CCc2ccc(C(=O)N(C)C3CCN(c4ccncc4)CC3)cc21] | (R)-3-(2-Chloro-N-ethyl-6-fluorobenzamido)-2,3-dihydro-1H-indene-5-carboxylic acid (E-63) | N-Methyl-1-(pyridin-4-yl)piperidin-4-amine (AMN-06) | GWP-1 | 56% | |
| H-221 | (3R)-3-[(2-Chloro-5-fluoro-benzoyl)ethyl-amino]-N-methyl-N-(1-pyridin-4-yl-pipendin-4-yl)-2,3-dihydro-1H-indene-5-carboxylic acid amide (H-221) | 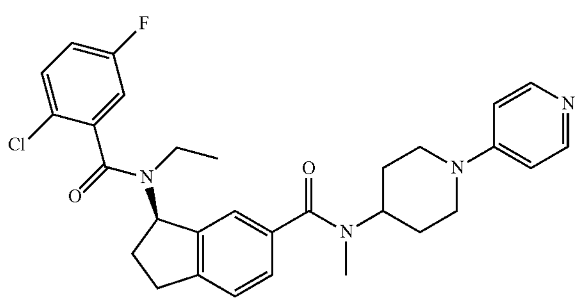 [SMILES: CCN(C(=O)c1cc(F)ccc1Cl)[C@@H]1CCc2ccc(C(=O)N(C)C3CCN(c4ccncc4)CC3)cc21] | (R)-3-(2-Chloro-N-ethyl-5-fluorobenzamido)-2,3-dihydro-1H-indene-5-carboxylic acid (E-78) | N-Methyl-1-(pyridin-4-yl)piperidin-4-amine (AMN-06) | GWP-1 | 68% | |

| Example No. | Structure | Name | Amino acid (ACI) | Amine (AMN) | Synthesis according to | Yield | Comments |
|---|---|---|---|---|---|---|---|
| H-222 | 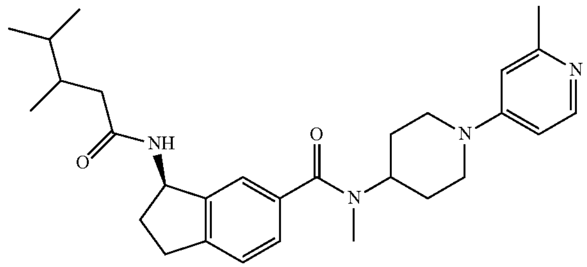 [SMILES: Cc1cc(N2CCC(N(C)C(=O)c3ccc4c(c3)[C@H](NC(=O)CC(C)C(C)C)CC4)CC2)ccn1] | (3R)-3-(3,4-Dimethyl-pentanoylamino)-N-methyl-N-[1-(2-methyl-pyridin-4-yl)-piperidin-4-yl]-2,3-dihydro-1H-indene-5-carboxylic acid amide (H-222) | (3R)-3-(3,4-Dimethylpentanamido)-2,3-dihydro-1H-indene-5-carboxylic acid (E-85) | N-Methyl-1-(2-methylpyridin-4-yl)piperidin-4-amine dihydrochloride (AMN-25) | GWP-1 | 79% | |
| H-223 | 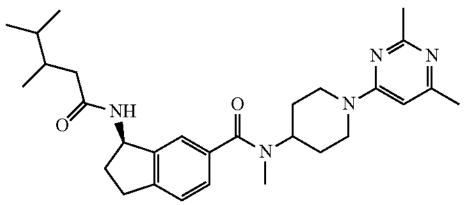 [SMILES: Cc1cc(N2CCC(N(C)C(=O)c3ccc4c(c3)[C@H](NC(=O)CC(C)C(C)C)CC4)CC2)nc(C)n1] | (3R)-3-(3,4-Dimethyl-pentanoylamino)-N-[1-(2,6-dimethyl-pyrimidin-4-yl)-piperidin-4-yl]-N-methyl-2,3-dihydro-1H-indene-5-carboxylic acid amide (H-223) | (3R)-3-(3,4-Dimethylpentanamido)-2,3-dihydro-1H-indene-5-carboxylic acid (E-85) | 1-(2,6-Dimethylpyrimidin-4-yl)-N-methylpiperidin-4-amine (AMN-27) | GWP-1 | 86% | |
| H-224 | 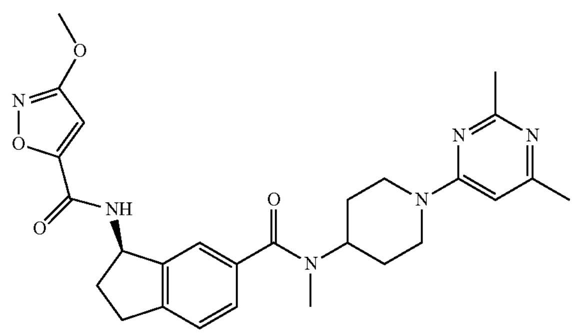 [SMILES: COc1cc(C(=O)N[C@@H]2CCc3ccc(C(=O)N(C)C4CCN(c5cc(C)nc(C)n5)CC4)cc32)on1] | N-[(1R)-6-[[1-(2,6-Dimethyl-pyrimidin-4-yl)-piperidin-4-yl]-methyl-carbamoyl]-2,3-dihydro-1H-inden-1-yl]-3-methoxy-isoxazole-5-carboxylic acid amide (H-224) | (R)-3-(3-Methoxyisoxazole-5-carboxamido)-2,3-dihydro-1H-indene-5-carboxylic acid (E-86) | 1-(2,6-Dimethylpyrimidin-4-yl)-N-methylpiperidin-4-amine (AMN-27) | GWP-1 | 43% | |

TABLE-continued

| Example No. | Structure | Name | Amino acid (ACI) | Amine (AMN) | Synthesis according to | Yield | Comments |
|---|---|---|---|---|---|---|---|
| H-225 | 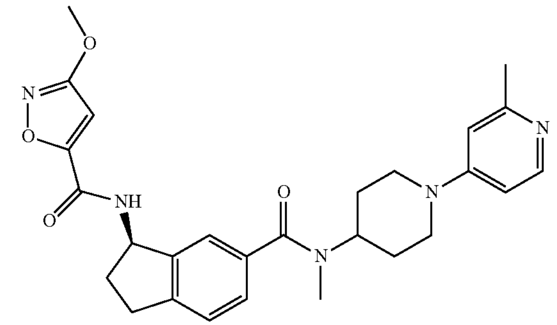 [SMILES: COc1cc(C(=O)N[C@@H]2CCc3ccc(C(=O)N(C)C4CCN(c5ccnc(C)c5)CC4)cc32)on1] | 3-Methoxy-N-[(1R)-6-[methyl-[1-(2-methyl-pyridin-4-yl)-piperidin-4-yl]-carbamoyl]-2,3-dihydro-1H-inden-1-yl]-isoxazole-5-carboxylic acid amide (H-225) | (R)-3-(3-Methoxyisoxazole-5-carboxamido)-2,3-dihydro-1H-indene-5-carboxylic acid (E-86) | N-Methyl-1-(2-methylpyridin-4-yl)piperidin-4-amine dihydrochloride (AMN-25) | GWP-1 | 35% | |
| H-226 | 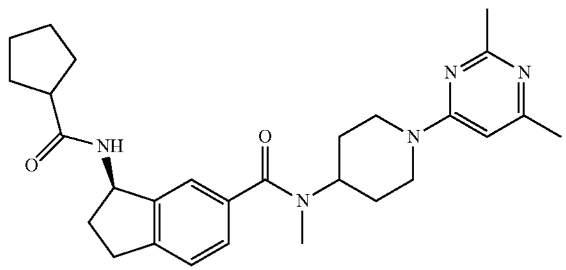 [SMILES: Cc1cc(N2CCC(N(C)C(=O)c3ccc4c(c3)[C@H](NC(=O)C3CCCC3)CC4)CC2)nc(C)n1] | (3R)-3-(Cyclopentanecarbonylamino)-N-[1-(2,6-dimethyl-pyrimidin-4-yl)-piperidin-4-yl]-N-methyl-2,3-dihydro-1H-indene-5-carboxylic acid amide (H-226) | (R)-3-(Cyclopentanecarboxamido)-2,3-dihydro-1H-indene-5-carboxylic acid (E-87) | 1-(2,6-Dimethylpyrimidin-4-yl)-N-methylpiperidin-4-amine (AMN-27) | GWP-1 | 84% | |
| H-227 | 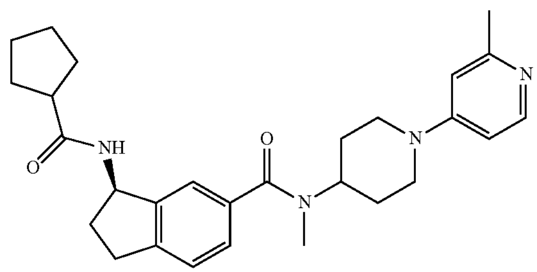 [SMILES: Cc1cc(N2CCC(N(C)C(=O)c3ccc4c(c3)[C@H](NC(=O)C3CCCC3)CC4)CC2)ccn1] | (3R)-3-(Cyclopentanecarbonylamino)-N-methyl-N-[1-(2-methyl-pyridin-4-yl)-piperidin-4-yl]-2,3-dihydro-1H-indene-5-carboxylic acid amide (H-227) | (R)-3-(Cyclopentanecarboxamido)-2,3-dihydro-1H-indene-5-carboxylic acid (E-87) | N-Methyl-1-(2-methylpyridin-4-yl)piperidin-4-amine dihydrochloride (AMN-25) | GWP-1 | 75% | |

TABLE-continued

| Example No. | Structure | Name | Amino acid (ACI) | Amine (AMN) | Synthesis according to | Yield | Comments |
|---|---|---|---|---|---|---|---|
| H-228 | 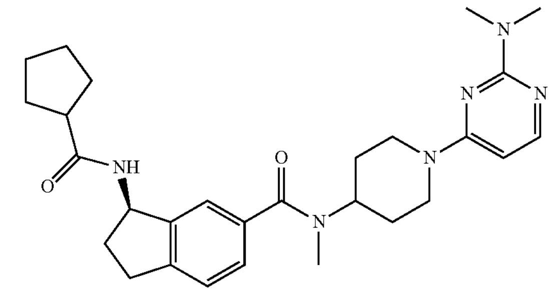 [SMILES: CN(C)c1nccc(N2CCC(N(C)C(=O)c3ccc4c(c3)[C@H](NC(=O)C3CCCC3)CC4)CC2)n1] | (3R)-3-(Cyclopentanecarbonylamino)-N-[1-(2-dimethylamino-pyrimidin-4-yl)-piperidin-4-yl]-N-methyl-2,3-dihydro-1H-indene-5-carboxylic acid amide (H-228) | (R)-3-(Cyclopentanecarboxamido)-2,3-dihydro-1H-indene-5-carboxylic acid (E-87) | N,N-Dimethyl-4-(4-(methylamino)piperidin-1-yl)pyrimidin-2-amine (AMN-59) | GWP-1 | 69% | |
| H-229 | 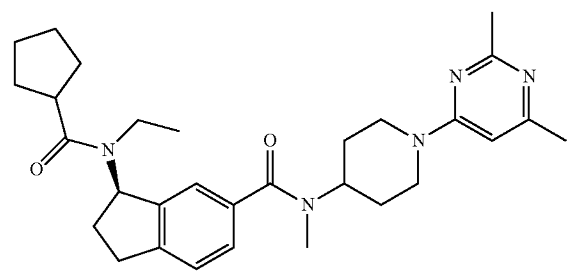 [SMILES: CCN(C(=O)C1CCCC1)[C@@H]1CCc2ccc(C(=O)N(C)C3CCN(c4cc(C)nc(C)n4)CC3)cc21] | (3R)-3-(Cyclopentanecarbonyl-ethyl-amino)-N-[1-(2,6-dimethyl-pyrimidin-4-yl)-piperidin-4-yl]-N-methyl-2,3-dihydro-1H-indene-5-carboxylic acid amide (H-229) | (R)-3-(N-Ethylcyclopentanecarboxamido)-2,3-dihydro-1H-indene-5-carboxylic acid (E-88) | 1-(2,6-Dimethylpyrimidin-4-yl)-N-methylpiperidin-4-amine (AMN-27) | GWP-1 | 92% | |
| H-230 | 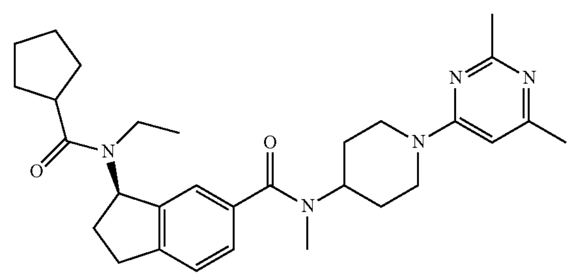 [SMILES: CCN(C(=O)C1CCCC1)[C@@H]1CCc2ccc(C(=O)N(C)C3CCN(c4cc(C)nc(C)n4)CC3)cc21] | (3R)-3-(Cyclopentanecarbonyl-methyl-amino)-N-[1-(2,6-dimethyl-pyrimidin-4-yl)-piperidin-4-yl]-N-methyl-2,3-dihydro-1H-indene-5-carboxylic acid amide (H-230) | (R)-3-(N-Methylcyclopentanecarboxamido)-2,3-dihydro-1H-indene-5-carboxylic acid (E-89) | 1-(2,6-Dimethylpyrimidin-4-yl)-N-methylpiperidin-4-amine (AMN-27) | GWP-1 | 56% | |

| Example No. | Structure | Name | Amino acid (ACI) | Amine (AMN) | Synthesis according to | Yield | Comments |
|---|---|---|---|---|---|---|---|
| H-231 | 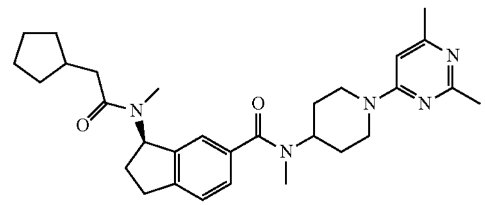 [SMILES: Cc1cc(N2CCC(N(C)C(=O)c3ccc4c(c3)[C@H](N(C)C(=O)CC3CCCC3)CC4)CC2)nc(C)n1] | (3R)-3-[(2-Cyclopentyl-acetyl)-methyl-amino]-N-[1-(2,6-dimethyl-pyrimidin-4-yl)-piperidin-4-yl]-N-methyl-2,3-dihydro-1H-indene-5-carboxylic acid amide (H-231) | (R)-3-(2-Cyclopentyl-N-methylacetamide)-2,3-dihydro-1H-indene-5-carboxylic acid (E-90) | 1-(2,6-Dimethylpyrimidin-4-yl)-N-methylpiperidin-4-amine (AMN-27) | GWP-1 | 60% | |
| H-232 | 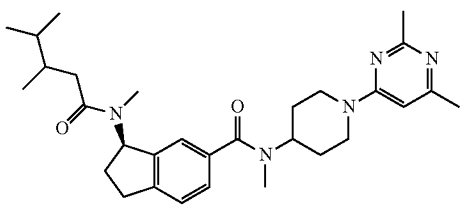 [SMILES: Cc1cc(N2CCC(N(C)C(=O)c3ccc4c(c3)[C@H](N(C)C(=O)CC(C)C(C)C)CC4)CC2)nc(C)n1] | (3R)-3-(3,4-Dimethyl-pentanoyl-methyl-amino)-N-[1-(2,6-dimethyl-pyrimidin-4-yl)-piperidin-4-yl]-N-methyl-2,3-dihydro-1H-indene-5-carboxylic acid amide (H-232) | (3R)-3-(N,3,4-Trimethylpentanamide)-2,3-dihydro-1H-indene-5-carboxylic acid (E-91) | 1-(2,6-Dimethylpyrimidin-4-yl)-N-methylpiperidin-4-amine (AMN-27) | GWP-1 | 86% | |
| H-233 | 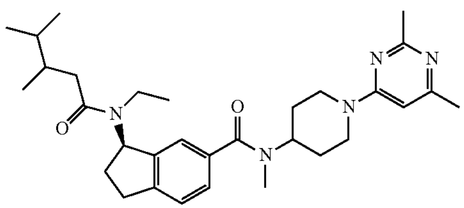 [SMILES: CCN(C(=O)CC(C)C(C)C)[C@@H]1CCc2ccc(C(=O)N(C)C3CCN(c4cc(C)nc(C)n4)CC3)cc21] | (3R)-3-(3,4-Dimethyl-pentanoyl-ethyl-amino)-N-[1-(2,6-dimethyl-pyrimidin-4-yl)-piperidin-4-yl]-N-methyl-2,3-dihydro-1H-indene-5-carboxylic acid amide (H-233) | (3R)-3-(N-Ethyl-3,4-dimethylpentanamide)-2,3-dihydro-1H-indene-5-carboxylic acid (E-92) | 1-(2,6-Dimethylpyrimidin-4-yl)-N-methylpiperidin-4-amine (AMN-27) | GWP-1 | 77% | |
| H-234 | 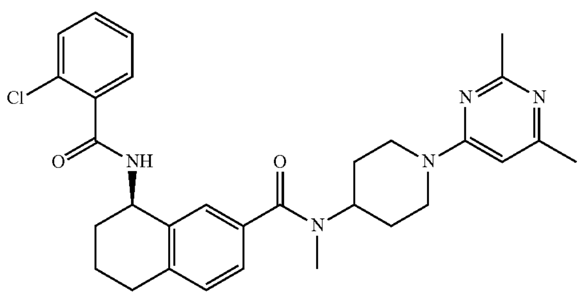 [SMILES: Cc1cc(N2CCC(N(C)C(=O)c3ccc4c(c3)[C@H](NC(=O)c3ccccc3Cl)CCC4)CC2)nc(C)n1] | (8R)-8-[(2-Chloro-benzoyl)amino]-N-[1-(2,6-dimethyl-pyrimidin-4-yl)-piperidin-4-yl]-N-methyl-5,6,7,8-tetrahydro-naphthalene-2-carboxylic acid amide (H-234) | (R)-8-(2-Chlorobenzamide)-5,6,7,8-tetrahydronaphthalene-2-carboxylic acid (E-93) | 1-(2,6-Dimethylpyrimidin-4-yl)-N-methylpipendin-4-amine (AMN-27) | GWP-1 | 81% | |

| Example No. | Structure | Name | Amino acid (ACI) | Amine (AMN) | Synthesis according to | Yield | Comments |
|---|---|---|---|---|---|---|---|
| H-235 | 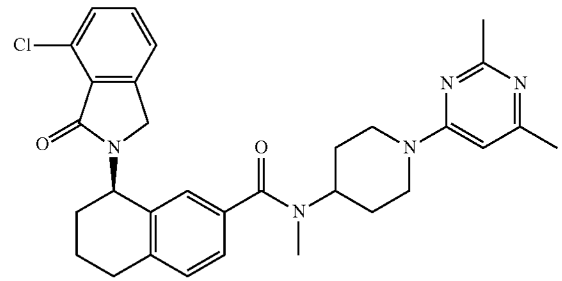 [SMILES: Cc1cc(N2CCC(N(C)C(=O)c3ccc4c(c3)[C@H](N3Cc5cccc(Cl)c5C3=O)CCC4)CC2)nc(C)n1] | (8R)-8-(4-Chloro-3-oxo-1,2-dihydro-isoindol-2-yl)-N-[1-(2,6-dimethyl-pyrimidin-4-yl)-piperidin-4-yl]-N-methyl-5,6,7,8-tetrahydro-naphthalene-2-carboxylic acid amide (H-235) | (R)-8-(7-Chloro-1-oxoisoindolin-2-yl)-5,6,7,8-tetrahydronaphthalene-2-carboxylic acid (G-06) | 1-(2,6-Dimethylpyrimidin-4-yl)-N-methylpiperidin-4-amine (AMN-27) | GWP-1 | 84% | |
| H-236 | 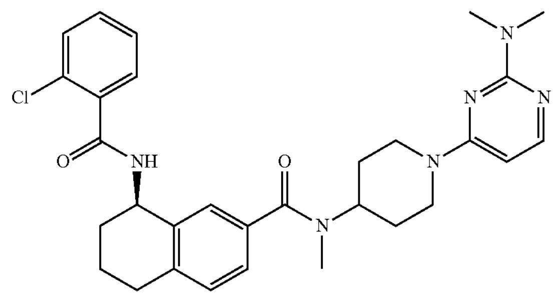 [SMILES: CN(C)c1nccc(N2CCC(N(C)C(=O)c3ccc4c(c3)[C@H](NC(=O)c3ccccc3Cl)CCC4)CC2)n1] | (8R)-8-[(2-Chloro-benzoyl)amino]-N-[1-(2-dimethylamino-pyrimidin-4-yl)-piperidin-4-yl]-N-methyl-5,6,7,8-tetrahydro-naphthalene-2-carboxylic acid amide (H-236) | (R)-8-(2-Chlorobenzamide)-5,6,7,8-tetrahydronaphthalene-2-carboxylic acid (E-93) | N,N-Dimethyl-4-(4-(methylamino)piperidin-1-yl)pyrimidin-2-amine (AMN-59) | GWP-1 | 90% | |
| H-237 | 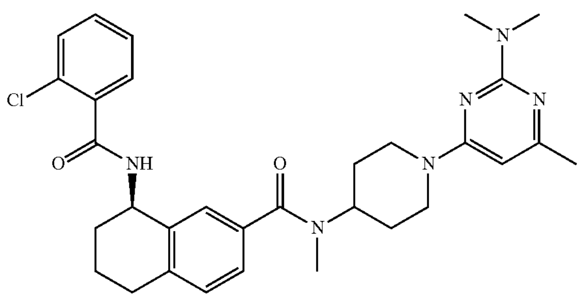 [SMILES: Cc1cc(N2CCC(N(C)C(=O)c3ccc4c(c3)[C@H](NC(=O)c3ccccc3Cl)CCC4)CC2)nc(N(C)C)n1] | (8R)-8-[(2-Chloro-benzoyl)amino]-N-[1-(2-dimethylamino-6-methyl-pyrimidin-4-yl)-piperidin-4-yl]-N-methyl-5,6,7,8-tetrahydro-naphthalene-2-carboxylic acid amide (H-237) | (R)-8-(2-Chlorobenzamide)-5,6,7,8-tetrahydronaphthalene-2-carboxylic acid (E-93) | Boc-deprotected amines Lib-02_AMN03 | GWP-1 | 88% | |

TABLE-continued

| Example No. | Structure | Name | Amino acid (ACI) | Amine (AMN) | Synthesis according to | Yield | Comments |
|---|---|---|---|---|---|---|---|
| H-238 | 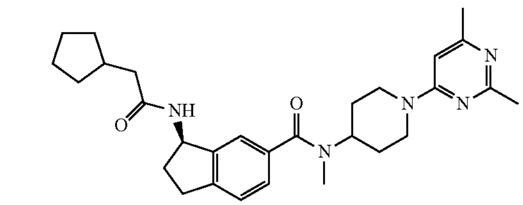 [SMILES: Cc1cc(N2CCC(N(C)C(=O)c3ccc4c(c3)[C@H](NC(=O)CC3CCCC3)CC4)CC2)nc(C)n1] | (3R)-3-[(2-Cyclopentyl-acetyl)amino]-N-[1-(2,6-dimethyl-pyrimidin-4-yl)-piperidin-4-yl]-N-methyl-2,3-dihydro-1H-indene-5-carboxylic acid amide (H-238) | (R)-3-(2-Cyclopentylacetamido)-2,3-dihydro-1H-indene-5-carboxylic acid (E-94) | 1-(2,6-Dimethylpyrimidin-4-yl)-N-methylpiperidin-4-amine (AMN-27) | GWP-1 | 36% | |
| H-239 | 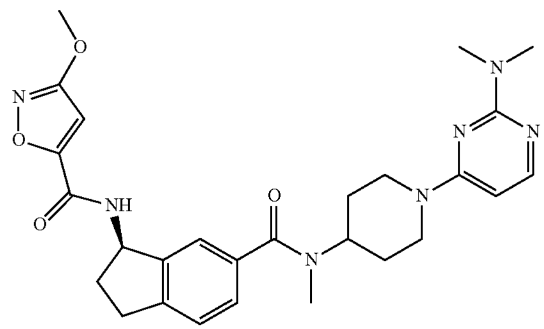 [SMILES: COc1cc(C(=O)N[C@@H]2CCc3ccc(C(=O)N(C)C4CCN(c5ccnc(N(C)C)n5)CC4)cc32)on1] | N-[(1R)-6-[[1-(2-Dimethylamino-pyrimidin-4-yl)-piperidin-4-yl]-methyl-carbamoyl]-2,3-dihydro-1H-inden-1-yl]-3-methoxy-isoxazole-5-carboxylic acid amide (H-239) | (R)-3-(3-Methoxyisoxazole-5-carboxamido)-2,3-dihydro-1H-indene-5-carboxylic acid (E-86) | N,N-Dimethyl-4-(4-(methylamino)piperidin-1-yl)pyrimidin-2-amine (AMN-59) | GWP-1 | 78% | |
| H-240 | 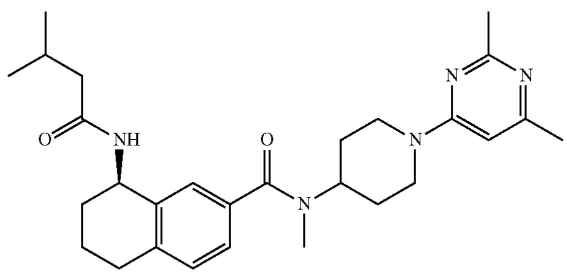 [SMILES: Cc1cc(N2CCC(N(C)C(=O)c3ccc4c(c3)[C@H](NC(=O)CC(C)C)CCC4)CC2)nc(C)n1] | (8R)-N-[1-(2,6-Dimethyl-pyrimidin-4-yl)-piperidin-4-yl]-N-methyl-8-(3-methyl-butanoylamino)-5,6,7,8-tetrahydro-naphthalene-2-carboxylic acid amide (H-240) | (R)-8-(3-Methylbutanamide)-5,6,7,8-tetrahydronaphthalene-2-carboxylic acid (E-95) | 1-(2,6-Dimethylpyrimidin-4-yl)-N-methylpiperidin-4-amine (AMN-27) | GWP-1 | 86% | |

TABLE-continued

| Example No. | Structure | Name | Amino acid (ACI) | Amine (AMN) | Synthesis according to | Yield | Comments |
|---|---|---|---|---|---|---|---|
| H-241 | 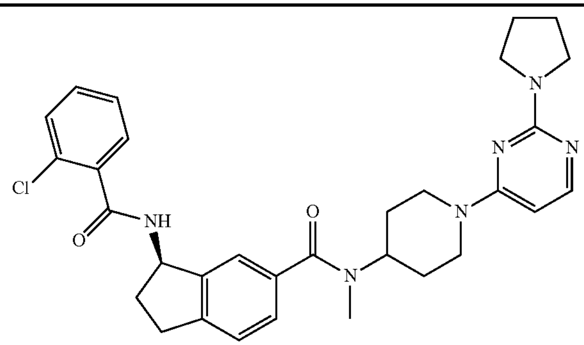 | (3R)-3-[(2-Chloro-benzoyl)amino]-N-methyl-N-[1-(2-pyrrolidin-1-yl-pyrimidin-4-yl)-piperidin-4-yl]-2,3-dihydro-1H-indene-5-carboxylic acid amide (H-241) | (3R)-3-[(2-Chloro-benzoyl)amino]-2,3-dihydro-1H-indene-5-carboxylic acid (E-01) | Boc-deprotected amine Lib-02_AMN02 | GWP-1 | 73% | |
| H-242 | 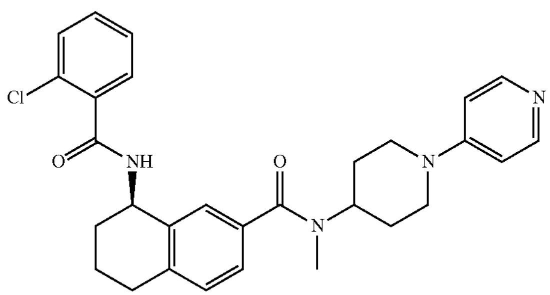 [SMILES: CN(C(=O)c1ccc2c(c1)[C@H](NC(=O)c1ccccc1Cl)CCC2)C1CCN(c2ccncc2)CC1] | (8R)-8-[(2-Chloro-benzoyl)amino]-N-methyl-N-(1-pyridin-4-yl-pipendin-4-yl)-5,6,7,8-tetrahydro-naphthalene-2-carboxylic acid amide (H-242) | (R)-8-(2-Chlorobenzamide)-5,6,7,8-tetrahydronaphthalene-2-carboxylic acid (E-93) | N-Methyl-1-(pyridin-4-yl)piperidin-4-amine (AMN-06) | GWP-1 | 79% | |
| H-243 | 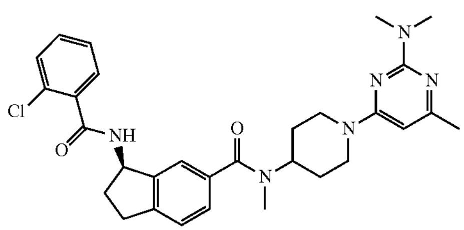 [SMILES: Cc1cc(N2CCC(N(C)C(=O)c3ccc4c(c3)[C@H](NC(=O)c3ccccc3Cl)CC4)CC2)nc(N(C)C)n1] | (3R)-3-[(2-Chloro-benzoyl)amino]-N-[1-(2-dimethylamino-6-methyl-pyrimidin-4-yl)-pipendin-4-yl]-N-methyl-2,3-dihydro-1H-indene-5-carboxylic acid amide (H-243) | (3R)-3-[(2-Chloro-benzoyl)amino]-2,3-dihydro-1H-indene-5-carboxylic acid (E-01) | Boc-deprotected amine Lib-02_AMN03 | GWP-1 | 92% | |

TABLE-continued

| Example No. | Structure | Name | Amino acid (ACI) | Amine (AMN) | Synthesis according to | Yield | Comments |
|---|---|---|---|---|---|---|---|
| H-244 | ![structure] | (3R)-N-[1-(2-Amino-pyrimidin-4-yl)-piperidin-4-yl]-3-[(2-chloro-benzoyl)amino]-N-methyl-2,3-dihydro-1H-indene-5-carboxylic acid amide (H-244) | | | | | see below |

Synthesis of the dihydroindene derivatives (H)
*a* Typical batch size: 0.15–0.7 mmol.

Synthesis of Illustrative Compound H-63

(3R)—N-Methyl-N-(1-pyridin-4-yl-piperidin-4-yl)-3-(3,3,3-trifluoro-propanoylamino)-2,3-dihydro-1H-indene-5-carboxylic acid amide (H-63)

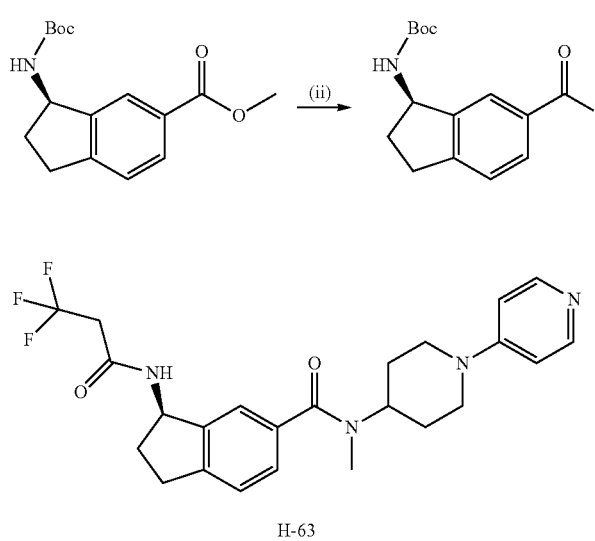
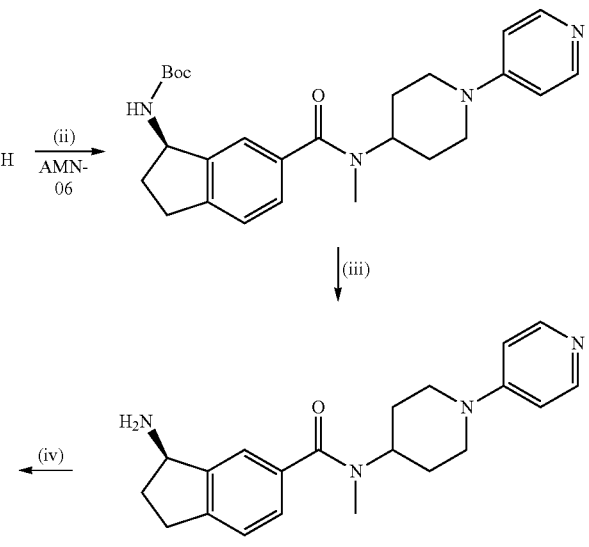

Stage (i): (R)-3-(tert-Butoxycarbonylamino)-2,3-dihydro-1H-indene-5-carboxylic acid LiOH (647 mg, 15.42 mmol, 3 eq), dissolved in water (8 ml), was added dropwise to an ice-cooled (0° C.) solution of (R)-methyl 3-(tert-butoxycarbonylamino)-2,3-dihydro-1H-indene-5-carboxylate (stage (ii) product of A-07) (1.5 g, 5.15 mmol, 1 eq) in MeOH:THF (1:1, 16 ml), and stirring was carried out for 6 h at RT. After monitoring by thin-layer chromatography, the reaction solution was concentrated and the residue was taken up in water (20 ml) and adjusted to pH 3 with NaHSO$_3$. The acidic, aqueous phase was extracted with ethyl acetate (2×150 ml), washed with sat. NaCl solution (2×50 ml), dried over sodium sulfate and concentrated under reduced pressure. Yield: 70% (1.0 g, 3.61 mmol).

Stage (ii): (R)-tert-Butyl 6-(methyl(1-(pyridin-4-yl)piperidin-4-yl)carbamoyl)-2,3-dihydro-1H-inden-1-ylcarbamate HATU (0.795 g, 2.09 mmol, 1 eq) and DIPEA (350 μA 2.04 mmol, 2.5 eq) were added to an ice-cooled solution of (R)-3-(tert-butoxycarbonylamino)-2,3-dihydro-1H-indene-5-carboxylic acid (368 mg, 2.09 mmol, 1 eq) in THF (5 ml), and stirring was carried out for 30 min. N-Methyl-1-(pyridin-4-yl)piperidin-4-amine (AMN-06) (400 mg, 2.09 mmol, 1 eq) was dissolved in THF (5 ml) and added dropwise to the reaction solution, and stirring was carried out for 16 h at RT. The reaction solution was diluted with dichloromethane (100 ml), washed with sat. sodium hydrogen carbonate solution (50 ml), sat. ammonium chloride solution (50 ml), water (50 ml) and sat. NaCl solution (50 ml), dried over sodium sulfate and concentrated under reduced pressure. After purification by column chromatography (silica gel, 0.5% MeOH in dichloromethane), the desired product was obtained in the form of a yellowish solid. Yield: 64% (600 mg, 1.33 mmol).

Stage (iii): (R)-3-Amino-N-methyl-N-(1-(pyridin-4-yl)piperidin-4-yl)-2,3-dihydro-1H-indene-5-carboxamide TFA (1 ml) was added dropwise at 0° C. to a solution of (R)-tert-butyl 6-(methyl(1-(pyridin-4-yl)piperidin-4-yl)carbamoyl)-2,3-dihydro-1H-inden-1-ylcarbamate (0.2 g, 0.44 mmol, 1 eq) in dichloromethane (5 ml), and stirring was carried out for 1 h at RT. Then the solvent was concentrated under reduced pressure. The residue was taken up in dichloromethane and concentrated again. Then the TFA salt was stirred for 1 h with Amberlyst-21 in MeOH (10 ml) and filtered. The filtrate was concentrated under reduced pressure and used in the next stage without being purified further.

Stage (iv): (3R)—N-Methyl-N-(1-pyridin-4-yl-piperidin-4-yl)-3-(3,3,3-trifluoropropanoyl-amino)-2,3-dihydro-1H-indene-5-carboxylic acid amide (H-63)

HATU (168 mg, 0.44 mmol, 1 eq) and DIPEA (200 μl, 1.1 mmol, 2.5 eq) were added to an ice-cooled solution of 3,3,3-trifluoropropionic acid (67.5 mg, 0.528 mmol, 1.2 eq) in THF (5 ml), and the mixture was stirred for 30 min. (R)-3-Amino-N-methyl-N-(1-(pyridin-4-yl)piperidin-4-yl)-2,3-dihydro-1H-indene-5-carboxamide (154 mg, 0.44 mmol, 1 eq) was dissolved in THF (2 ml) and added dropwise to the reaction solution, and stirring was carried out for 16 h at RT. The reaction solution was diluted with dichloromethane (100 ml), washed with sat. sodium hydrogen carbonate solution (40 ml), sat. ammonium chloride solution (40 ml), water (40 ml) and sat. NaCl solution (40 ml), dried over sodium sulfate and concentrated under reduced pressure. After purification by column chromatography (silica gel, 5% MeOH in dichlo-

Synthesis of Illustrative Compound H-98

(3R)-3-[(2-Chloro-benzoyl)amino]-N-methyl-N-[1-(1-oxido-pyridin-1-ium-4-yl)-piperidin-4-yl]-2,3-dihydro-1H-indene-5-carboxylic acid amide (H-98)

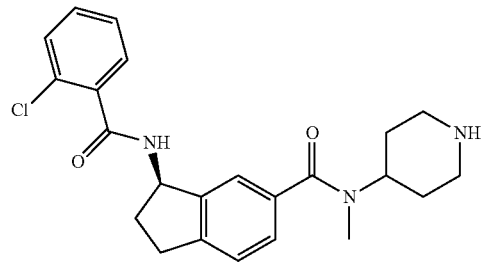

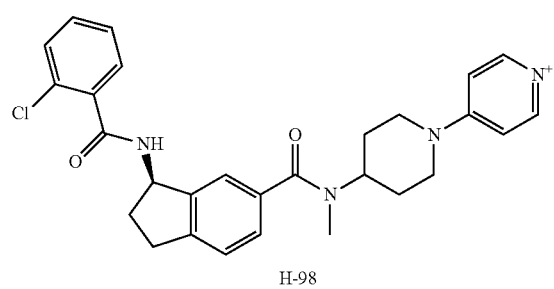

H-98

A mixture of (R)-3-(2-chlorobenzamido)-N-methyl-N-(piperidin-4-yl)-2,3-dihydro-1H-indene-5-carboxamide (see stage 2 illustrative compound H-214) (200 mg, 0.486 mmol, 1 eq), 4-chloropyridine N-oxide (63 mg, 0.486 mmol, 1 eq) and DIPEA (0.210 ml, 1.215 mmol, 2.5 eq) in ethanol (10 ml) was heated for 72 h at 130° C. in a pressure vessel. The reaction mixture was concentrated under reduced pressure and the crude product was then prepurified by column chromatography (Alox, 1% methanol/dichloromethane). It was then further purified by means of preparative TLC. The desired product was in the form of a white solid. Yield: 18% (90 mg, 0.178 mmol) The indicated yield is based on 2 combined batches of size 200 mg

Synthesis of Illustrative Compound H-125

(3R)-3-[(2-Chloro-benzoyl)amino]-N-methyl-N-[1-(3-methyl-[1,2,4]thiadiazol-5-yl)-piperidin-4-yl]-2,3-dihydro-1H-indene-5-carboxylic acid amide (H-125)

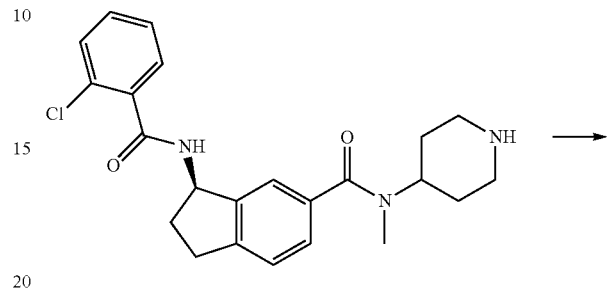

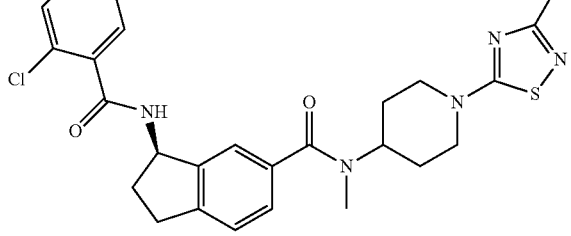

H-125

A mixture of (R)-3-(2-chlorobenzamido)-N-methyl-N-(piperidin-4-yl)-2,3-dihydro-1H-indene-5-carboxamide (see stage 2 illustrative compound H-214) (230 mg, 0.559 mmol, 1 eq), 5-chloro-3-methyl-1,2,4-thiadiazole (83 mg, 0.615 mmol, 1.1 eq) and $Cs_2CO_3$ (363 mg, 1.118 mmol, 2 eq) in dioxane (10 ml) was heated for 2 h at 80° C. When the reaction was complete according to TLC monitoring, the reaction mixture was concentrated under reduced pressure. The residue was taken up in dichloromethane (50 ml), washed with water (30 ml) and saturated sodium chloride solution (30 ml) and dried over sodium sulfate. The solvent was removed by distillation under reduced pressure and the crude product was purified by column chromatography (Alox, 0.5% methanol/dichloromethane). The desired product was in the form of a white solid. Yield: 59% (170 mg, 0.333 mmol)

Synthesis of Illustrative Compound H-214

(3R)-3-[(2-Chloro-benzoyl)amino]-N-methyl-N-[1-(2-methylamino-pyrimidin-4-yl)-piperidin-4-yl]-2,3-dihydro-1H-indene-5-carboxylic acid amide (H-214)

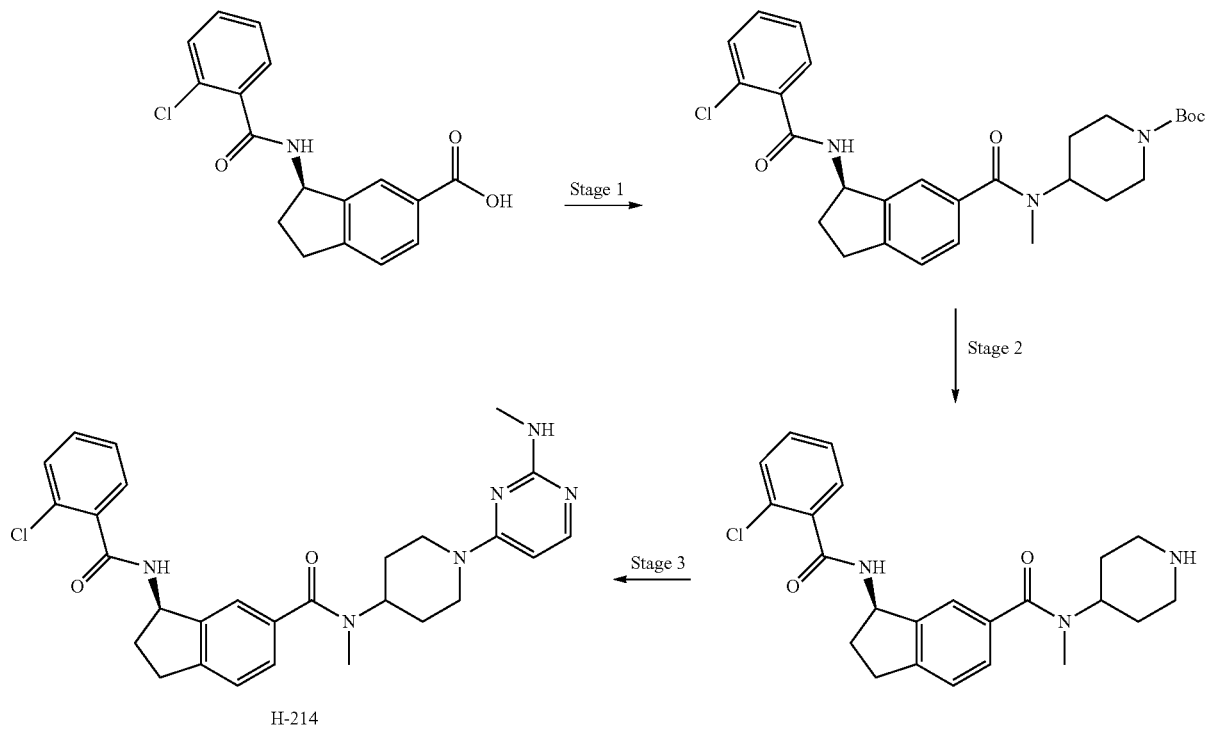

H-214

Stage 1: (R)-tert-Butyl 4-(3-(2-chlorobenzamido)-N-methyl-2,3-dihydro-1H-indene-5-carboxamido)piperidine-1-carboxylate DIPEA (0.28 ml, 1.585 mmol, 2.5 eq) and HATU (240 mg, 0.634 mmol, 1 eq) were added to a suspension, cooled to 0° C., of (3R)-3-[(2-chloro-benzoyl)amino]-2,3-dihydro-1H-indene-5-carboxylic acid (E-01) (200 mg, 0.634 mmol, 1 eq) in THF (5 ml). The reaction mixture was stirred for 15 min, and then a solution of tert-butyl 4-(methylamino)piperidine-1-carboxylate (135 mg, 0.634 mmol, 1 eq) in THF (3 ml) was added and stirring was carried out for 16 h at room temperature. The reaction mixture was concentrated under reduced pressure, diluted with dichloromethane (50 ml) and washed with saturated ammonium chloride solution (30 ml), water (30 ml) and saturated sodium chloride solution (30 ml). Drying over sodium sulfate and concentration under reduced pressure were then carried out. The crude product was purified by column chromatography (silica gel, 2% methanol/dichloromethane) to yield the desired product in the form of a white solid. Yield: 92% (300 mg, 0.587 mmol)

Stage 2: (R)-3-(2-Chlorobenzamido)-N-methyl-N-(piperidin-4-yl)-2,3-dihydro-1H-indene-5-carboxamide (R)-tert-Butyl 4-(3-(2-chlorobenzamido)-N-methyl-2,3-dihydro-1H-indene-5-carboxamido)-piperidine-1-carboxylate (300 mg, 0.587 mmol, 1 eq) was dissolved in dichloromethane (10 ml). The solution was cooled to 0° C., and trifluoroacetic acid (2 ml) was added dropwise. The reaction mixture was stirred for 1 h at room temperature and then concentrated under reduced pressure. The residue was taken up in dichloromethane (100 ml), washed with saturated sodium hydrogen carbonate solution and saturated sodium chloride solution (in each case 50 ml), dried over sodium sulfate and concentrated under reduced pressure. The desired product was in the form of a brown solid and was used in the next stage without being purified further. Yield: 95% (230 mg, 0.559 mmol)

Stage 3: (3R)-3-[(2-Chloro-benzoyl)amino]-N-methyl-N-[1-(2-methylamino-pyrimidin-4-yl)-piperidin-4-yl]-2,3-dihydro-1H-indene-5-carboxylic acid amide (H-214)

A mixture of (R)-3-(2-chlorobenzamido)-N-methyl-N-(piperidin-4-yl)-2,3-dihydro-1H-indene-5-carboxamide (400 mg, 0.973 mmol, 1 eq), (4-chloropyrimidin-2-yl)methylamine (280 mg, 1.946 mmol, 2 eq) and DIPEA (0.33 ml, 1.946 mmol, 2 eq) in dioxane (10 ml) was refluxed for 16 h. When the reaction was complete according to TLC monitoring, concentration under reduced pressure was carried out and the residue was taken up in dichloromethane (100 ml) and washed with water (40 ml) and saturated sodium chloride solution (40 ml). The organic phase was dried over sodium sulfate and concentrated under reduced pressure. The crude product was purified by column chromatography (silica gel, 6% methanol in dichloromethane). The desired product was in the form of a white solid. Yield: 49% (250 mg, 0.482 mmol)

Synthesis of Illustrative Compound H-244

(3R)—N-[1-(2-Amino-pyrimidin-4-yl)-piperidin-4-yl]-3-[(2-chloro-benzoyl)amino]-N-methyl-2,3-dihydro-1H-indene-5-carboxylic acid amide (H-244)

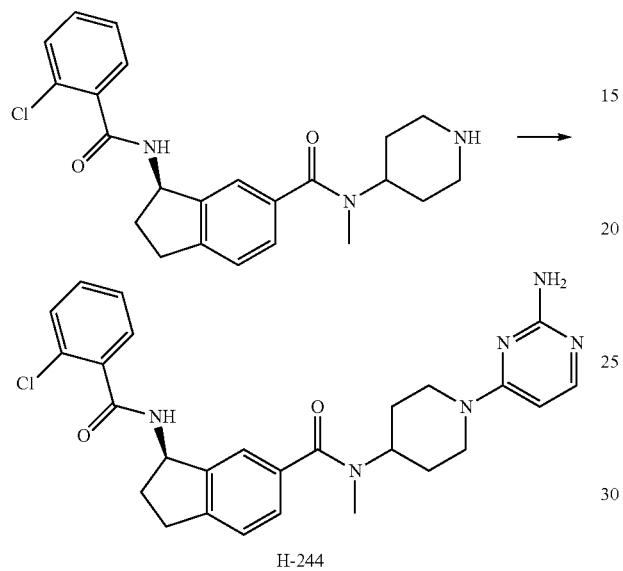

H-244

A mixture of (R)-3-(2-chlorobenzamido)-N-methyl-N-(piperidin-4-yl)-2,3-dihydro-1H-indene-5-carboxamide (stage 2H-214) (200 mg, 0.486 mmol, 1.0 eq), 4-chloro-pyrimidin-2-ylamine (94 mg, 0.728 mmol, 1.5 eq) and DIPEA (0.125 ml, 0.728 mmol, 1.5 eq) in dioxane (10 ml) was refluxed for 16 h. When the reaction was complete according to TLC monitoring, concentration under reduced pressure was carried out, and the reside was taken up in dichloromethane (50 ml) and washed with water (30 ml) and saturated sodium chloride solution (30 ml). The organic phase was dried over sodium sulfate and concentrated under reduced pressure. The crude product was purified by column chromatography (silica gel, 6% methanol in dichloromethane). Yield: 45% (110 mg, 0.267 mmol)

Analytical Data—Single Substances

Method 1:
Equipment and methods for HPLC-MS analysis: HPLC: Waters Alliance 2795 with PDA Waters 2998; MS: Micromass Quattro Micro™ API; column: Waters Atlantis® T3, 3 μm, 100 Å, 2.1×30 mm; column temperature: 40° C., eluent A: purified water+0.1% formic acid; eluent B: acetonitrile (gradient grade)+0.1% formic acid; gradient: 0% B to 100% B in 8.8 min, 100% B for 0.4 min, 100% B to 0% B in 0.01 min, 0% B for 0.8 min; flow: 1.0 ml/min; ionization: ES+, 25 V; batch: 100 μl/min 70% methanol+0.2% formic acid; UV: 200-400 nm.

or

Method 2:
Equipment and Methods for LC/MS Analysis: Hardware: coupled Agilent 1290 Infinity UHPLC-TOF system; LC module: MTP-Handler: Agilent, model BenchCel 2R; thermostatted autoinjector: Agilent, model G4226A; column oven: Agilent, model G1316C; DAD: Agilent, model G4212A; binary pump: Agilent, model G4220A. Time Of Flight mass spectrometer: Agilent 6224; ion source: Dual ESI; Column: manufacturer: Waters; type: Acquity HPLC HSS T3 1.8 μm (Part No. 186003538); dimensions: 2.1×50 mm; Eluents: eluent A: water from Millipore ultrapure water system: Milli-Q Integral 3+0.1% formic acid; eluent B: acetonitrile, Merck KGaA: LiChrosolv Hypergrade for LC-MS (1.00029.9010)+0.1% formic acid; formic acid: Merck KGaA: Suprapur 98-100% (1.11670.1000); LC method: flow: 2.5 ml/min; run time: 1.2 min; gradient: start 2% B, 1 min 100% B, 1.09 min 100% B, 1.11 min 2% B, 1.2 min 2% B stop; column temperature: 80° C.; UV: 190-400 nm; MS method: ion polarity: positive; gas temperature: 325° C.; gas flow: 10 ml/min

| Example No. | [M+] found | R.t. [min] |
| --- | --- | --- |
| H-01 | 503.3 | 2.9 min |
| H-03 | 489.0 | 2.8 min |
| H-04 | 529.0 | 3.5 min |
| H-06 | 489.1 | 2.6 min |
| H-07 | 475.1 | 2.6 min |
| H-09 | 507.24 | 1.49 min |
| H-10 | 489.0 | 2.6 min |
| H-11 | 501.0 | 3.0 min |
| H-12 | 501.0 | 3.0 min |
| H-14 | 523.1 | 2.1 min |
| H-15 | 503.0 | 3.1 min |
| H-16 | 525.0 | 3.0 min |
| H-17 | 489.0 | 2.6 min |
| H-18 | 433.1 | 2.5 min |
| H-19 | 435.1 | 2.6 min |
| H-20 | 505.0 | 2.6 min |
| H-21 | 489.0 | 2.6 min |
| H-22 | 496.1 | 2.7 min |
| H-23 | 489.0 | 2.7 min |
| H-24 | 557.0 | 3.1 min |
| H-25 | 469.1 | 2.7 min |
| H-26 | 501.0 | 3.0 min |
| H-27 | 515.0 | 2.7 min |
| H-28 | 435.1 | 2.5 min |
| H-29 | 473.1 | 2.8 min |
| H-30 | 523.1 | 2.8 min |
| H-31 | 457.1 | 2.3 min |
| H-32 | 507.0 | 2.8 min |
| H-33 | 525.0 | 3.1 min |
| H-34 | 435.1 | 2.5 min |
| H-35 | 503.0 | 3.0 min |
| H-36 | 524.0 | 2.6 min |
| H-37 | 524.0 | 2.5 min |
| H-38 | 515.0 | 3.1 min |
| H-39 | 475.2 | 2.0 + 2.1 min |
| H-40 | 509.3 | 1.3 min |
| H-41 | 486.15 | 2.8 min |
| H-42 | 507.1 | 2.3 min |
| H-43 | 529.2 | 2.3 min |
| H-44 | 505.2 | 2.6 min |
| H-45 | 517.1 | 2.9 min |
| H-46 | 513.2 | 3.2 min |
| H-47 | 541.2 | 3.4 min |
| H-48 | 545.2 | 3.0 min |
| H-49 | 517.2 | 2.4 min |
| H-50 | 518.2 | 3.1 min |
| H-51 | 529.2 | 3.3 min |
| H-52 | 529.2 | 5.0 min |
| H-53 | 584.2 | 2.5 min |
| H-54 | 522.1 | 4.7 min |
| H-55 | 503.2 | 2.9 min |
| H-56 | 517.2 | 3.2 min |
| H-57 | 507.2 | 2.8 min |
| H-58 | 531.2 | 3.2 min |
| H-59 | 518.2 | 3.0 min |
| H-60 | 517.0 | 3.0 min |
| H-61 | 488.0 | 2.8 min |
| H-62 | 460.1 | 2.6 min |
| H-63 | 461.0 | 2.4 min |

-continued

| Example No. | [M+] found | R.t. [min] |
|---|---|---|
| H-64 | 503.0 | 2.9 min |
| H-65 | 545.1 | 3.7 min |
| H-66 | 517.0 | 3.1 min |
| H-67 | 511.2 | 5.1 min |
| H-68 | 471.2 | 2.9 min |
| H-69 | 509.3 | 3.2 min |
| H-70 | 509.3 | 3.2 min |
| H-71 | 455.2 | 2.5 min |
| H-72 | 509.2 | 4.5 min |
| H-73 | 505.2 | 2.9 min |
| H-74 | 491.2 | 2.8 min |
| H-75 | 473.2 | 2.7 min |
| H-76 | 463.3 | 2.2 min |
| H-77 | 503.2 | 2.7 min |
| H-78 | 506.2 | 4.1 min |
| H-79 | 517.2 | 2.9 min |
| H-80 | 523.2 | 2.6 min |
| H-81 | 552.2 | 2.8 min |
| H-82 | 495.2 | 4.4 + 4.5 min |
| H-83 | 506.2 | 2.5 min |
| H-84 | 511.2 | 2.8 + 3.0 min |
| H-85 | 449.2 | 2.6 min |
| H-86 | 464.2 | 2.7 min |
| H-87 | 535.1 | 2.8 min |
| H-88 | 477.2 | 2.4 min |
| H-89 | 492.3 | 2.4 min |
| H-90 | 551.3 | 2.7 min |
| H-91 | 553.2 | 2.8 min |
| H-92 | 538.2 | 2.7 min |
| H-93 | 489.2 | 3.2 min |
| H-94 | 504.3 | 3.3 min |
| H-95 | 474.2 | 2.8 min |
| H-96 | 489.2 | 2.7 min |
| H-98 | 505.2 | 4.3 min |
| H-99 | 543.3 | 2.3 min |
| H-100 | 532.2 | 3.2 min |
| H-101 | 519.2 | 3.6 min |
| H-102 | 587.3 | 2.8 min |
| H-103 | 509.2 | 2.3 min |
| H-104 | 545.2 | 2.6 min |
| H-110 | 545.2 | 3.6 min |
| H-111 | 521.2 | 2.7 min |
| H-112 | 519.2 | 2.9 min |
| H-113 | 532.2 | 3.0 min |
| H-114 | 504.2 | 2.9 min |
| H-115 | 489.1 | 2.8 min |
| H-116 | 503.2 | 2.6 min |
| H-117 | 507.1 | 2.9 min |
| H-118 | 533.2 | 3.2 min |
| H-119 | 520.3 | 3.7 min |
| H-120 | 521.3 | 3.7 min |
| H-122 | 504.1 | 3.0 min |
| H-123 | 514.1 | 3.6 min |
| H-124 | 558.2 | 3.5 min |
| H-125 | 510.1 | 3.8 min |
| H-126 | 531.2 | 3.1 min |
| H-127 | 540.1 | 3.1 min |
| H-128 | 502.2 | 3.0 min |
| H-129 | 536.1 | 3.0 min |
| H-130 | 530.1 | 3.2 min |
| H-131 | 561.2 | 3.1 min |
| H-132 | 552.2 | 3.1 min |
| H-133 | 536.1 | 3.1 min |
| H-134 | 507.1 | 2.6 min |
| H-135 | 586.1 | 3.4 min |
| H-136 | 504.1 | 2.9 min |
| H-137 | 586.1 | 3.5 min |
| H-138 | 552.2 | 2.0 min |
| H-139 | 546.2 | 3.4 min |
| H-140 | 523.1 | 2.7 min |
| H-141 | 504.1 | 2.9 min |
| H-142 | 548.1 | 3.3 min |
| H-143 | 507.2 | 3.0 min |
| H-144 | 560.2 | 3.8 min |
| H-145 | 546.2 | 3.6 min |
| H-146 | 461.1 | 2.7 min |
| H-147 | 490.1 | 2.78 min |
| H-148 | 504.2 | 3.3 min |

-continued

| Example No. | [M+] found | R.t. [min] |
|---|---|---|
| H-149 | 532.2 | 3.5 min |
| H-150 | 351.2 | 3.7 min |
| H-151 | 536.2 | 3.3 min |
| H-152 | 522.2 | 3.1 min |
| H-153 | 503.2 | 3.4 min |
| H-155 | 549.1 | 3.6 min |
| H-156 | 544.1 | 3.5 min |
| H-158 | 549.1 | 3.6 min |
| H-160 | 475.1 | 3.0 min |
| H-161 | 487.1 | 3.3 min |
| H-162 | 498.2 | 3.0 min |
| H-163 | 536.1 | 2.9 min |
| H-164 | 508.1 | 2.8 min |
| H-165 | 536.1 | 3.1 min |
| H-166 | 588.2 | 4.0 min |
| H-167 | 564.1 | 3.5 min |
| H-168 | 550.1 | 3.3 min |
| H-169 | 512.2 | 3.3 min |
| H-170 | 526.2 | 3.4 min |
| H-171 | 567.2 | 3.0 min |
| H-172 | 540.2 | 3.6 min |
| H-174 | 581.1 | 3.2 min |
| H-175* | 550.2 | 0.51 min |
| H-176* | 564.3 | 0.54 min |
| H-178 | 517.5 | 2.4 min |
| H-179 | 453.4 | 1.6 min |
| H-180 | 492.4 | 1.6 min |
| H-181 | 504.4 | 2.6 min |
| H-182 | 503.0 | 2.8 min |
| H-183 | 557.1 | 3.4 min |
| H-184 | 531.1 | 3.4 min |
| H-185 | 532.3 | 3.9 min |
| H-186 | 533.3 | 3.9 min |
| H-188 | 507.1 | 3.5 min |
| H-191* | 500.3 | 0.47 min |
| H-195* | 550.2 | 0.49 min |
| H-196* | 578.3 | 0.55 min |
| H-197* | 564.3 | 0.52 min |
| H-198* | 596.3 | 0.55 min |
| H-199* | 578.3 | 0.55 min |
| H-202* | 549.2 | 0.53 min |
| H-203* | 535.2 | 0.50 min |
| H-204* | 549.2 | 0.53 min |
| H-205* | 521.2 | 0.47 min |
| H-206* | 567.2 | 0.54 min |
| H-207* | 595.3 | 0.56 min |
| H-208* | 566.3 | 0.53 min |
| H-209* | 613.3 | 0.57 min |
| H-210* | 550.2 | 0.51 min |
| H-211* | 564.3 | 0.53 min |
| H-212* | 578.3 | 0.56 min |
| H-213* | 536.2 | 0.47 min |
| H-214* | 519.2 | 0.46 min |
| H-215* | 532.2 | 0.45 min |
| H-216* | 532.2 | 0.45 min |
| H-217* | 536.1 | 0.44 min |
| H-219* | 505.2 | 0.45 min |
| H-220* | 535.2 | 0.48 min |
| H-221* | 535.2 | 0.48 min |
| H-222* | 477.3 | 0.45 min |
| H-223* | 492.3 | 0.46 min |
| H-224* | 505.3 | 0.38 min |
| H-225* | 490.2 | 0.37 min |
| H-226* | 476.3 | 0.41 min |
| H-227* | 461.3 | 0.39 min |
| H-228* | 491.3 | 0.43 min |
| H-229* | 504.3 | 0.47 min |
| H-230* | 490.3 | 0.45 min |
| H-244 | 505.2 | 0.42 min |

*according to method 2

Library Syntheses

Library No. 1

1) Synthesis of the Amine Structural Units CC_AMN
Overview:

| CC_AMN. | Structure | Name (CC_AMN) |
|---|---|---|
| CC_AMN-01 | 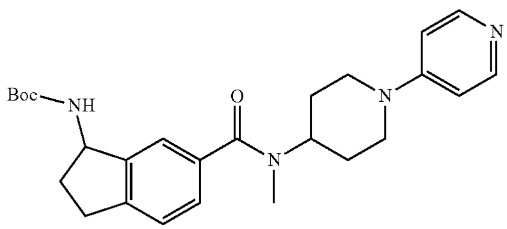 [SMILES: CN(C(=O)c1ccc2c(c1)C(NC(=O)OC(C)(C)C)CC2)C1CCN(c2ccncc2)CC1] | 3-Amino-N-methyl-N-(1-pyridin-4-yl-piperidin-4-yl)-2,3-dihydro-1H-indene-5-carboxylic acid amide (CC_AMN-01) |
| CC_AMN-02 | 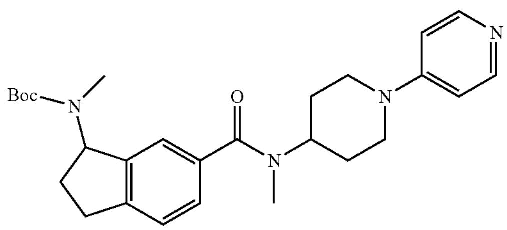 [SMILES: CN(C(=O)c1ccc2c(c1)C(N(C)C(=O)OC(C)(C)C)CC2)C1CCN(c2ccncc2)CC1] | N-Methyl-3-methylamino-N-(1-pyridin-4-yl-piperidin-4-yl)-2,3-dihydro-1H-indene-5-carboxylic acid amide (CC_AMN-02) |
| CC_AMN-03 | 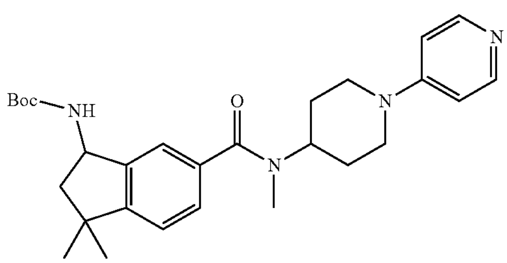 [SMILES: CN(C(=O)c1ccc2c(c1)C(NC(=O)OC(C)(C)C)CC2(C)C)C1CCN(c2ccncc2)CC1] | 3-Amino-N,1,1-trimethyl-N-(1-pyridin-4-yl-piperidin-4-yl)-2,3-dihydro-indene-5-carboxylic acid amide (CC_AMN-03) |
| CC_AMN-04 | 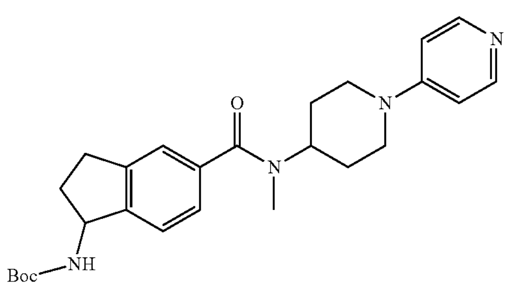 [SMILES: CN(C(=O)c1ccc2c(c1)CCC2NC(=O)OC(C)(C)C)C1CCN(c2ccncc2)CC1] | 1-Amino-N-methyl-N-(1-pyridin-4-yl-piperidin-4-yl)-2,3-dihydro-1H-indene-5-carboxylic acid amide (CC_AMN-04) |
| CC_AMN-05 | 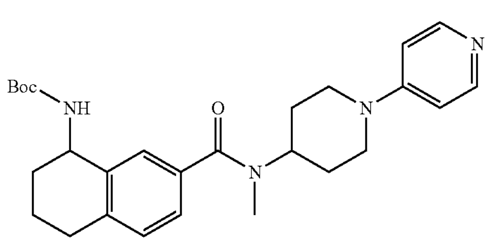 [SMILES: CN(C(=O)c1ccc2c(c1)C(NC(=O)OC(C)(C)C)CCC2)C1CCN(c2ccncc2)CC1] | 8-Amino-N-methyl-N-(1-pyridin-4-yl-piperidin-4-yl)-5,6,7,8-tetrahydro-naphthalene-2-carboxylic acid amide (CC_AMN-05) |

| CC_AMN. | Structure | Name (CC_AMN) |
|---|---|---|
| CC_AMN-06 | 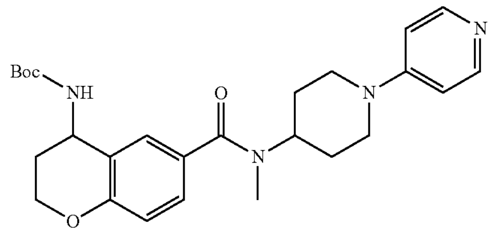 [SMILES: CN(C(=O)c1ccc2c(c1)C(NC(=O)OC(C)(C)C)CCO2)C1CCN(c2ccncc2)CC1] | 4-Amino-N-methyl-N-(1-pyridin-4-yl-piperidin-4-yl)-3,4-dihydro-2H-chromene-6-carboxylic acid amide (CC_AMN-06) |
| CC_AMN-07 | 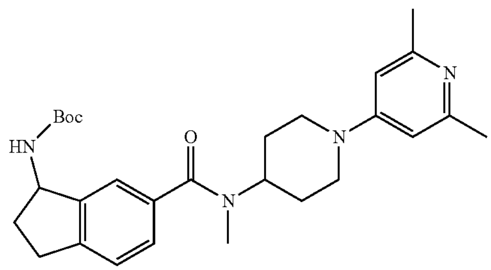 [SMILES: Cc1cc(N2CCC(N(C)C(=O)c3ccc4c(c3)C(NC(=O)OC(C)(C)C)CC4)CC2)cc(C)n1] | 3-Amino-N-[1-(2,6-dimethyl-pyridin-4-yl)-piperidin-4-yl]-N-methyl-2,3-dihydro-1H-indene-5-carboxylic acid amide (CC_AMN-07) |
| CC_AMN-08 | 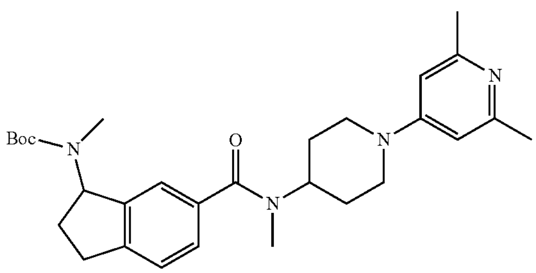 [SMILES: Cc1cc(N2CCC(N(C)C(=O)c3ccc4c(c3)C(N(C)C(=O)OC(C)(C)C)CC4)CC2)cc(C)n1] | N-[1-(2,6-Dimethyl-pyridin-4-yl)-piperidin-4-yl]-N-methyl-3-methylamino-2,3-dihydro-1H-indene-5-carboxylic acid amide (CC_AMN-08) |
| CC_AMN-09 | 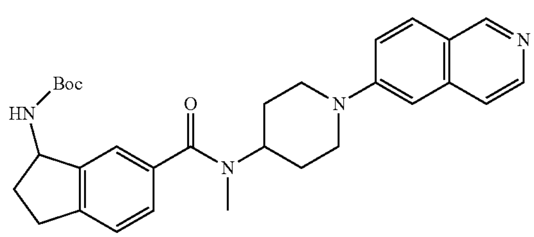 [SMILES: CN(C(=O)c1ccc2c(c1)C(NC(=O)OC(C)(C)C)CC2)C1CCN(c2ccc3cnccc3c2)CC1] | 3-Amino-N-(1-isoquinolin-6-yl-piperidin-4-yl)-N-methyl-2,3-dihydro-1H-indene-5-carboxylic acid amide (CC_AMN-09) |
| CC_AMN-11 | 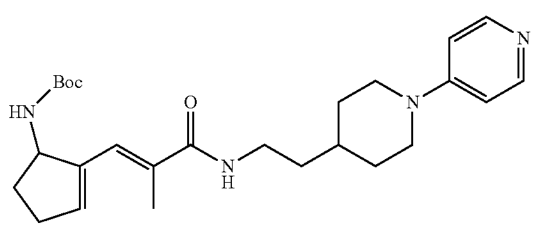 [SMILES: C/C(=C\C1=CCCC1NC(=O)OC(C)(C)C)C(=O)NCCC1CCN(c2ccncc2)CC1] | 3-Amino-N-[2-(1-pyridin-4-yl-piperidin-4-yl)-ethyl]-2,3-dihydro-1H-indene-5-carboxylic acid amide (CC_AMN-11) |

Syntheses of Structural Units

Synthesis of CC_AMN-01: 3-Amino-N-methyl-N-(1-pyridin-4-yl-piperidin-4-yl)-2,3-dihydro-1H-indene-5-carboxylic acid amide (CC_AMN-01)

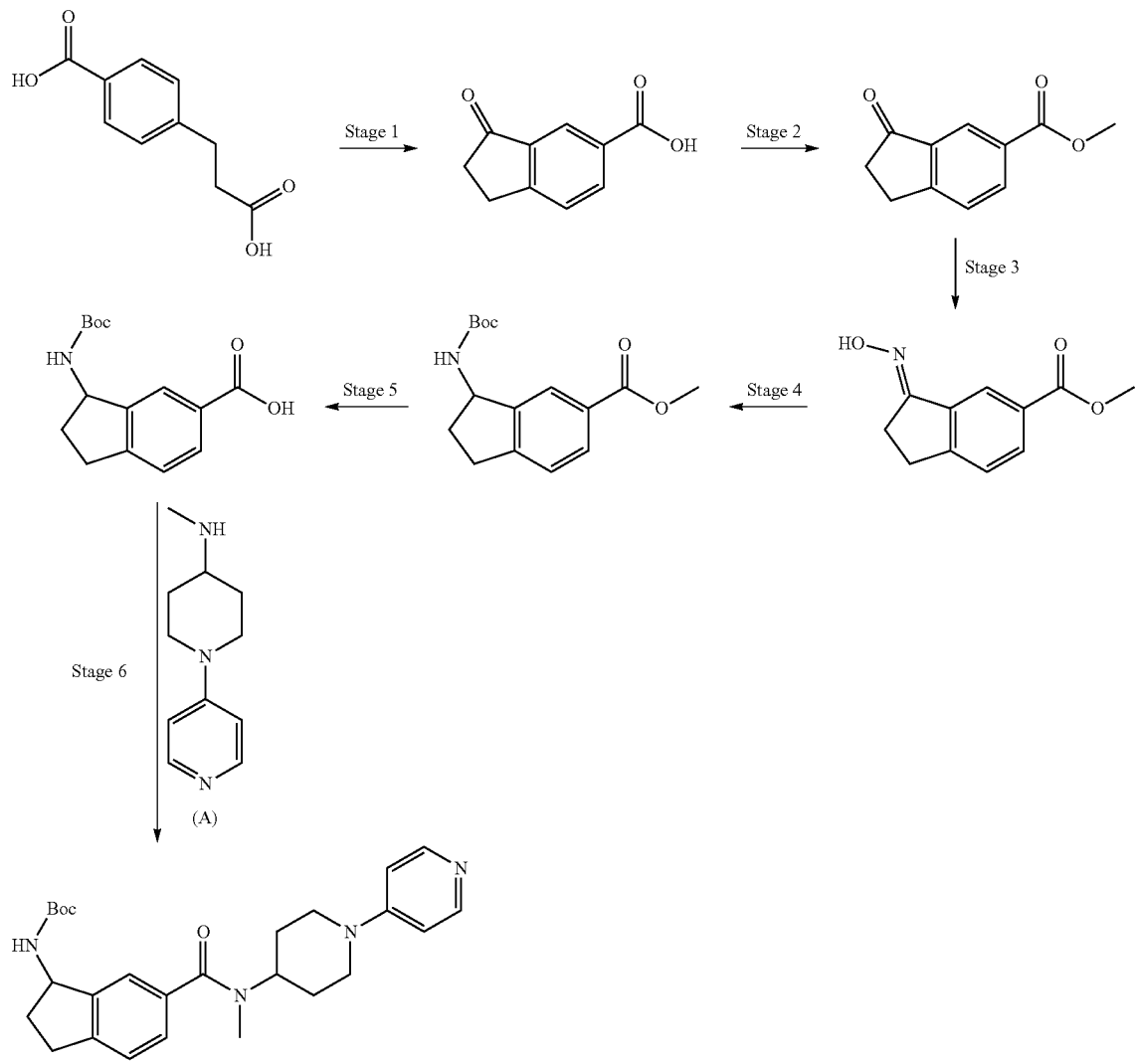

Stage 1:
In a round-bottomed flask, 3-(4-carboxyphenyl)propionic acid (50 g, 0.2577 mol), AlCl$_3$ (240 g, 1.804 mol) and sodium chloride (24 g, 10% wt of AlCl$_3$) were mixed and heated for 1 hour at 190° C. The reaction mixture was cooled to 100° C. and poured carefully onto ice. The reaction mixture was acidified with 6M HCl (1200 ml) and extracted with ethyl acetate (4×800 ml). The combined org. phases were washed with water and sat. NaCl solution, dried over sodium sulfate and concentrated under reduced pressure. The crude product (15 g, 33%) was used in the next stage without being purified further. Yield: 33% (15 g, 0.035 mol).

Stage 2:
The product from stage 1 (4 g, 0.022 mol) was dissolved in methanol (100 ml); conc. sulfuric acid (0.5 ml) was added and refluxing was carried out for 12 hours. After monitoring by thin-layer chromatography, the reaction solution was concentrated to dryness and the crude product was purified by column chromatography. A white solid was obtained. Yield: 58% (2.5 g, 0.012 mol).

Stage 3:
The product from stage 2 (2.5 g, 0.022 mol) was dissolved in methanol (50 ml). Hydroxylamine HCl (2.72 g, 0.0394 mol) and sodium acetate (6.4 g, 0.0786 mol) were added at RT and heating was carried out for 2 h at boiling temperature. After monitoring by thin-layer chromatography, the methanol was concentrated and the residue was taken up in ethyl acetate, washed with water and sat. NaCl solution, dried over sodium sulfate and concentrated to dryness. The crude product was used in the next stage without being purified further. Yield: 90% (2.5 g, 0.0198 mol).

Stage 4:
The product from stage 3 (21 g, 0.1024 mol) was dissolved in ethanol (300 ml), then water (52 ml) and conc. HCl (105 ml) were added and stirring was carried out for 15 minutes. Zn powder (40.17 g, 0.1024 mol) was added to the reaction solution, while cooling with ice, and heating was carried out for 1 hour at boiling temperature. After cooling to RT, the suspension was filtered over Celite and washed with ethanol. The filtrate was concentrated under reduced pressure, taken up in toluene and again concentrated to dryness. The resulting crude amine (100 g) was taken up in 1,4-dioxane (300 ml) and cooled to 0° C., and TEA (67 ml, 0.66 mol) was added. Then Boc anhydride (70 g, 0.3165 mol) was added and stirring was carried out for 12 hours at RT. The reaction solution was concentrated and the residue was taken up in water (1.01) and ethyl acetate (1.51). The phases were separated and the org. phase was washed with water and sat. NaCl solution, dried over sodium sulfate and concentrated under reduced pressure. The crude product was purified by column chromatography. Yield: 53% (16 g, 0.054 mol).

Stage 5:

The product from stage 4 (21 g, 0.0721 mol) was taken up in THF-methanol-water (6:4:1) (110 ml) and cooled to 0° C.; LiOH H$_2$O (16.3 g, 0.32 mol) was added in portions, and stirring was carried out for 8 hours at RT. The reaction mixture was concentrated to dryness and the residue was taken up in a little water and washed with diethyl ether. The aqueous phase was acidified at 0° C. with 10% citric acid solution. The resulting white precipitate was filtered off, washed with water and dried for 24 hours at 60° C. in vacuo. Yield: 77% (15 g, 0.0555 mol).

Stage 6:

TFA (2 ml) was added at 0° C. to a solution of Boc-protected amine (0.3 g, 0.0009 mol) in DCM (10 ml), and stirring was carried out for 1 hour at RT. The reaction mixture was concentrated to dryness and the crude amine was obtained in the form of the TFA salt, which was used further without being purified. The acid from stage 5 (0.25 g, 0.0009 mol) was dissolved in DCM (10 ml); EDCI (0.25 g, 0.0035 mol) and HOBT (0.18 g, 0.0035 mol) were added, and the mixture was cooled to 0° C. After addition of DIPEA (0.74 ml, 0.00451 mol), the reaction solution was stirred for 10 minutes. The TFA salt was dissolved in DCM (10 ml) and added dropwise to the reaction solution, and stirring was carried out for 16 hours at RT. The reaction solution was diluted with water and extracted with ethyl acetate (3×10 ml). The combined org. phases were washed with water and sat. NaCl solution, dried over sodium sulfate and concentrated. The crude product was purified by column chromatography. Yield: 71% (0.29 g, 0.00064 mol).

Synthesis of Intermediate A

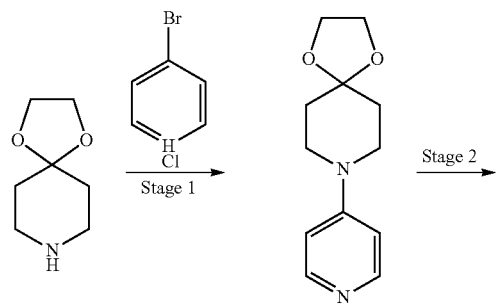

Stage 1:

1,4-Dioxa-8-azaspiro-(4,5)-decane (20 g, 0.139 mol) was dissolved in toluene (2 ml/mmol), and potassium tert-butylate (26.71 g, 0.278 mol) was added. 4-Bromopyridine HBr (29.91 g, 0.1529 mol) was added and the reaction solution was degassed with argon. After addition of X-PHOS (3.31 g, 0.00695 mol, 0.05 eq.) and Pd(OAC)2 (1.56 g, 0.00695 mol, 0.05 eq.), the reaction mixture was heated for 10 hours at 120° C. Then it was diluted with ethyl acetate (200 ml) and the resulting precipitate was filtered off over Celite. The filtrate was concentrated under reduced pressure and purified by column chromatography (silica gel 100-200, 2% methanol in DCM). Yield: 52.32% (16 g, 0.0727 mol).

Stage 2:

The product from stage 1 (29 g, 0.131 mol, 1.0 eq.) was taken up in 6M HCl (400 ml) and heated for 3 hours at 100° C. After cooling to RT, the reaction solution was rendered basic with 6M NaOH (300 ml) and washed with ethyl acetate (5×200 ml). The combined org. phases were dried over sodium sulfate and concentrated under reduced pressure. The crude product was used in the next stage without being purified further. Yield: 88.61% (20.43 g, 0.116 mol).

Stage 3:

The product from stage 2 (20.43 g, 0.116 mol, 1.0 eq.) was dissolved in methanol. Then acetic acid (6.62 ml, 0.116 mol, 1.0 eq.), methylamine HCl (8.5 g, 0.126 mol, 1.09 eq.) and, in portions, sodium cyanoborohydride (7.87 g, 0.125 mol, 1.08 eq.) were added and stirring was carried out for 17 hours at RT. The reaction mixture was concentrated and the residue was taken up in sat. aqueous potassium carbonate solution (300 ml) and dichloromethane (200 ml). The phases were separated and the org. phase was dried over sodium sulfate and concentrated to dryness under reduced pressure. The crude product was used in the next stage without being purified further. Yield: 81.24% (18 g, 0.0942 mol).

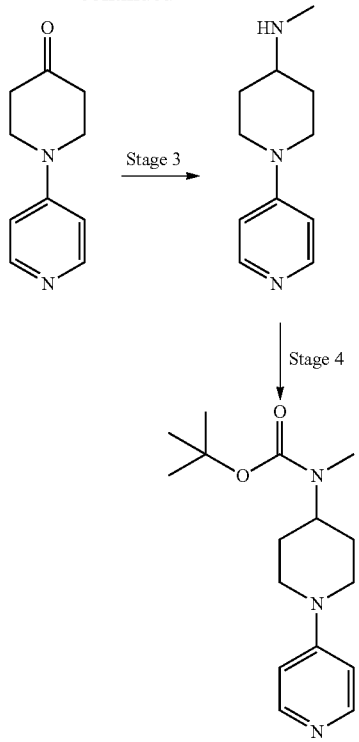

Stage 4:

The product from stage 3 (17.76 g, 0.0929 mol, 1.0 eq.) was dissolved in DCM (276 ml), and TEA (0.139 mol, 1.5 eq.) and Boc anhydride (24.06 g, 0.1104 mol, 1.2 eq.) were added at 0° C. The reaction mixture was stirred overnight at RT, then diluted with DCM (300 ml), washed with water and sat. NaCl solution (in each case 200 ml), dried over sodium sulfate and concentrated. The crude product was purified by column chromatography (silica gel 100-200, 2% methanol in DCM). Yield: 72% (19.3 g, 0.066 mol).

Synthesis of CC_AMN-02: N-Methyl-3-methylamino-N-(1-pyridin-4-yl-piperidin-4-yl)-2,3-dihydro-1H-indene-5-carboxylic acid amide (CC_AMN-02)

purified by column chromatography (ethyl acetate/hexane). Yield: 77% (15 g, 0.0555 mol).

Stage 6:

The product from stage 5 (2 g, 6.55 mmol) was taken up in THF-methanol-water (6:4:1) (110 ml) and cooled to 0° C.; LiOH H$_2$O (1.31 g, 30 mmol) was added in portions and stirring was carried out for 8 hours at RT. The reaction mixture was concentrated to dryness and the residue was taken up in a little water and washed with diethyl ether. The aqueous phase was acidified at 0° C. with HCl solution. The resulting white precipitate was filtered off, washed with water and dried for 24 hours at 60° C. in vacuo. Yield: 99%.

Stage 7:

TFA (3 ml) was added at 0° C. to a solution of Boc-protected amine (1.2 g, 0.0041 mol) in DCM (20 ml), and stirring was carried out for 16 hours at RT. The reaction mixture was

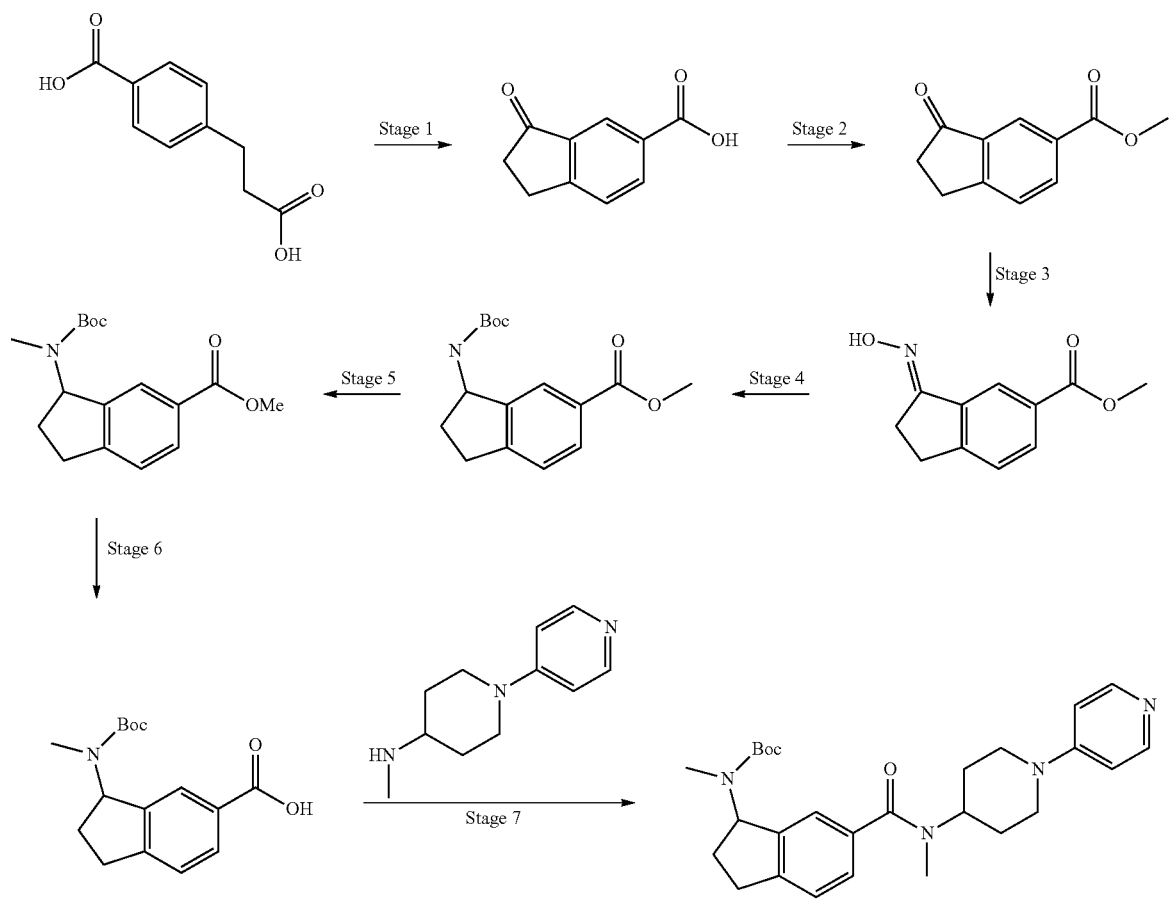

Stage 1 to Stage 4:

See CC_AMN-01

Stage 5:

The Boc-protected amino ester (3.4 g, 11.68 mmol) was dissolved in DMF (60 ml); NaH (1.4 g, 30 mmol, 60% in mineral oil) was added at 0° C. and stirring was carried out for 2 hours at RT. Then the reaction mixture was cooled to 0° C. again and iodomethane (2.19 ml, 30 mmol) was added dropwise. The reaction mixture was stirred for 16 hours at RT, hydrolyzed with ice and diluted with water. Then extraction with ethyl acetate was carried out. The org. phase was washed with water and sat. NaCl solution, dried over sodium sulfate and concentrated under reduced pressure. The crude product was concentrated to dryness and the crude amine was obtained in the form of the TFA salt, which was used further without being purified. The acid from stage 6 (1.0 g, 0.0034 mol) was dissolved in DCM (30 ml); EDCI (0.97 g, 0.0051 mol) and HOBT (0.6 g, 0.0051 mol) were added, and the mixture was cooled to 0° C. After addition of DIPEA (3.0 ml, 0.17 mol), the reaction solution was stirred for 10 minutes. The TFA salt was dissolved in DCM (10 ml) and added dropwise to the reaction solution, and stirring was carried out for 16 hours at RT. The reaction solution was diluted with water and extracted with ethyl acetate (3×20 ml). The combined org. phases were washed with water and sat. NaCl solution, dried over sodium sulfate and concentrated. The crude product was purified by column chromatography. Yield: 46% (0.75 g, 0.00160 mol).

Synthesis of CC_AMN-03: 3-Amino-N,1,1-trimethyl-N-(1-pyridin-4-yl-piperidin-4-yl)-2,3-dihydro-indene-5-carboxylic acid amide (CC_AMN-03)

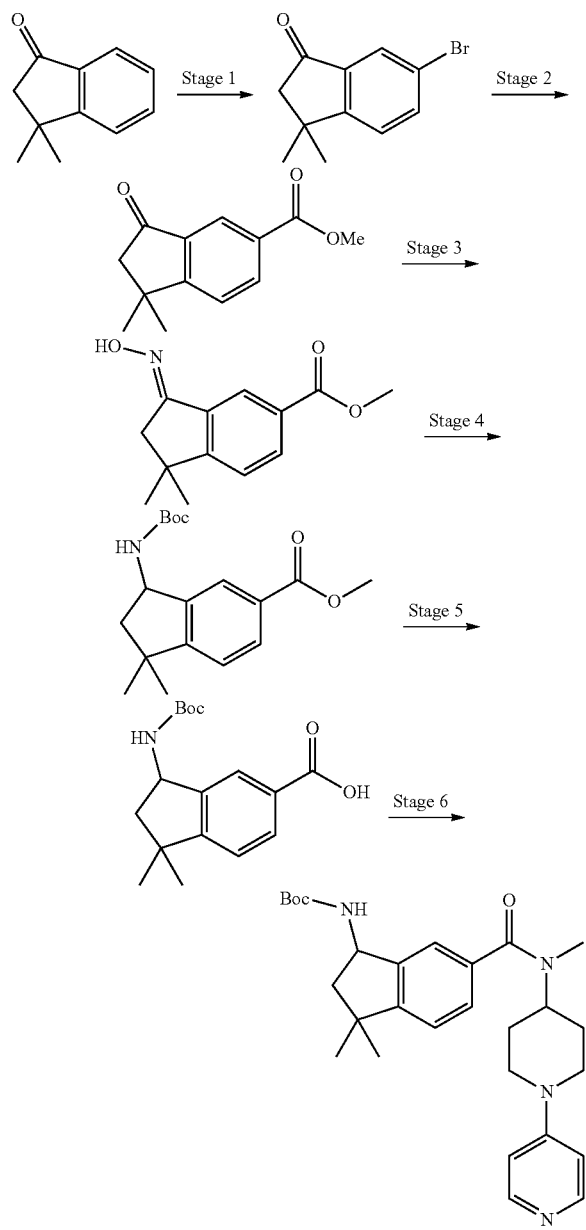

Stage 1:
Bromine (0.6 g, 0.00375 mol) was added at 100° C. to a mixture of AlCl₃ (1.04 g, 0.0078 mol) and 3,3-dimethyl-indan-1-one (0.5 g, 0.0031 mol), and heating was carried out for 40-45 minutes at 100° C. The reaction mixture was hydrolyzed with ice and extracted with ethyl acetate (3×50 ml). The combined org. phases were dried over sodium sulfate, concentrated under reduced pressure and purified by column chromatography. Yield: 26% (0.2 g, 0.0020 mol).

Stage 2:
The product from stage 1 (0.1 g, 0.00418 mol) was dissolved in DMSO (5 ml) and methanol (4 ml); TEA was added, and degassing was carried out for 15 minutes with argon. Then palladium acetate (0.004 g, 0.0002 mol) and DPPP (1,3-bis-diphenylphosphinopropane) (0.008 g, 0.0002 mol) were added and degassing was carried out for 30 minutes with CO. The reaction mixture was stirred for 2 hours at 65° C. under CO balloon pressure. Then the methanol was concentrated and the residue was diluted with water and extracted with diethyl ether. The org. phase was dried over sodium sulfate and concentrated. Yield: 44% (0.04 g).

Stage 3:
The product from stage 2 (4.3 g, 0.0197 mol) was dissolved in methanol (75 ml). Hydroxylamine HCl (3.4 g, 0.0493 mol) and sodium acetate (8.0 g, 0.0983 mol) were added at RT, and heating was carried out for 2 hours at 80° C. After monitoring by thin-layer chromatography, the methanol was concentrated and the residue was taken up in ethyl acetate, washed with water and sat. NaCl solution, dried over sodium sulfate and concentrated to dryness. The crude product was used in the next stage without being purified further.

Stage 4:
The product from stage 3 (4 g, 0.0171 mol) was dissolved in ethanol (20 ml), then water (10 ml) and conc. HCl (20 ml) were added and stirring was carried out for 15 minutes. Zn powder (6.6 g, 0.103 mol) was added to the reaction solution and heating was carried out for 1 hour at boiling temperature. After cooling to RT, the suspension was filtered over Celite and the filtrate was concentrated to dryness under reduced pressure. The resulting crude amine (6 g) was taken up in 1,4-dioxane (100 ml) and cooled to 5-10° C., and TEA (3.3 ml, 0.0328 mol) was added. Then Boc anhydride (6.0 g, 0.0273 mol) was added and stirring was carried out for 12 hours at RT. The reaction solution was concentrated and the residue was taken up in water and ethyl acetate. The phases were separated and the org. phase was washed with water and sat. NaCl solution, dried over sodium sulfate and concentrated under reduced pressure. The crude product was purified by column chromatography. Yield: 51% (2.8 g, 0.00875 mol).

Stage 5:
The product from stage 4 (2.8 g, 0.00875 mol) was taken up in THF-methanol-water (6:4:1) and cooled to 0° C.; LiOH H₂O (1.47 g, 0.035 mol) was added in portions and stirring was carried out for 20 hours at RT. The reaction mixture was concentrated to dryness and the residue was taken up in a little water and washed with diethyl ether. The aqueous phase was acidified at 0° C. with 10% citric acid solution. Extraction with ethyl acetate was carried out, and the org. phase was washed with water and sat. NaCl solution, dried over sodium sulfate and concentrated to dryness. Yield: 55% (1.5 g, 0.0049 mol).

Stage 6:
TFA (2 ml) was added at 0° C. to a solution of Boc-protected amine (0.3 g, 0.0012 mol) in DCM (10 ml), and stirring was carried out for 1 hour at RT. The reaction mixture was concentrated to dryness and the crude amine was obtained in the form of the TFA salt, which was used further without being purified. The acid from stage 5 (0.25 g, 0.0008 mol) was dissolved in DCM (10 ml); EDCI (0.23 g, 0.002 mol) and HOBT (0.16 g, 0.002 mol) were added, and the mixture was cooled to 0° C. After addition of DIPEA (0.5 ml, 0.004 mol), the reaction solution was stirred for 10 minutes. The TFA salt was dissolved in DCM (10 ml) and added dropwise to the reaction mixture, and stirring was carried out for 16 hours at RT. The reaction solution was diluted with water and extracted with ethyl acetate (3×10 ml). The combined org.

phases were washed with water and sat. NaCl solution, dried over sodium sulfate and concentrated. The crude product was purified by column chromatography. Yield: 69% (0.27 g, 0.00056 mol).

Synthesis of CC_AMN-04: 1-Amino-N-methyl-N-(1-pyridin-4-yl-piperidin-4-yl)-2,3-dihydro-1H-indene-5-carboxylic acid amide (CC_AMN-04)

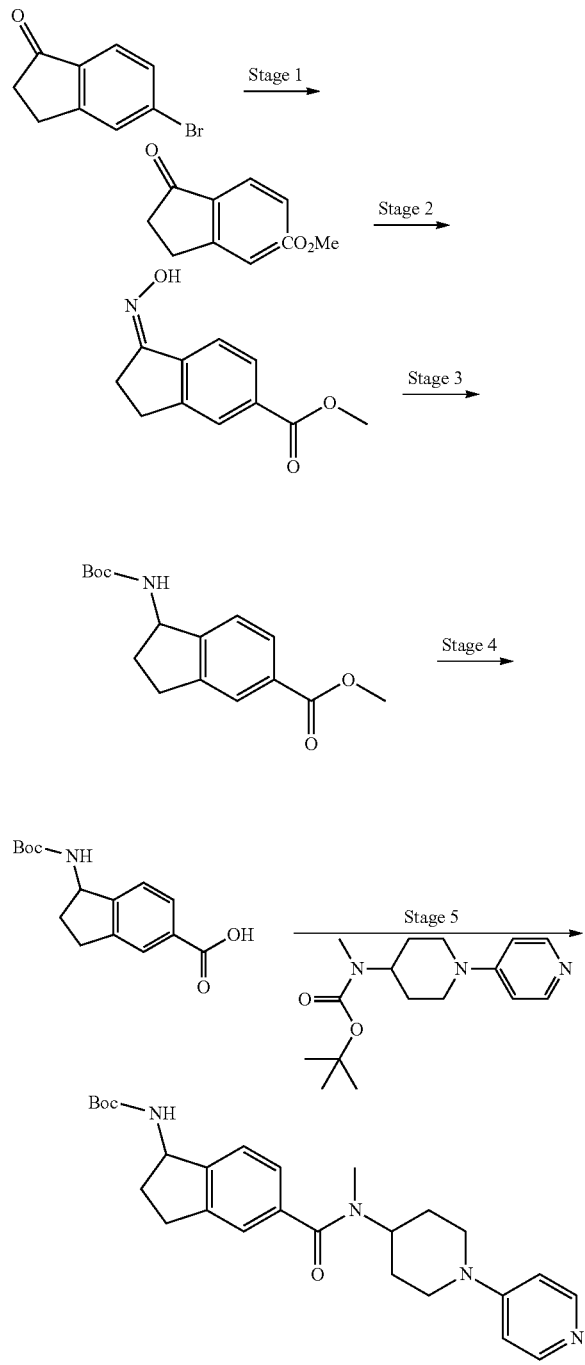

Stage 1:
The bromine starting material (1.0 g, 0.0047 mol) was dissolved in DMSO (56 ml) and methanol (45 ml); TEA (1.45 ml, 0.0104 mol, 2.2 eq.) was added and degassing was carried out with carbon monoxide. Then palladium acetate (42.5 mg, 0.000189 mol, 0.04 eq.) and DPPP (77.25 mg, 0.000189 mol, 0.04 eq.) were added and degassing was carried out for 2 hours with CO. Then the methanol was concentrated and the residue was diluted with water and extracted with diethyl ether. The org. phase was dried over sodium sulfate, concentrated and purified by column chromatography. Yield: 66% (600 mg, 0.0031 mol).

Stage 2:
The product from stage 1 (2.5 g, 0.0131 mol) was dissolved in methanol (50 ml). Hydroxyl-amine HCl (2.72 g, 0.0394 mol, 3.0 eq.) and sodium acetate (6.4 g, 0.0786 mol) were added at RT and heating was carried out for 2 hours at boiling temperature. The methanol was concentrated and the residue was taken up in ethyl acetate, washed with water and sat. NaCl solution, dried over sodium sulfate and concentrated to dryness. The crude product was used in the next stage without being purified further. Yield: 90%.

Stage 3:
The product from stage 2 (7.0 g, 0.034 mol) was dissolved in ethanol (100 ml), then water (52 ml) and conc. HCl (35 ml) were added and stirring was carried out for 15 minutes. Zn powder (13.3 g, 0.204 mol) was added to the reaction solution, while cooling, and heating was carried out for 1 hour at boiling temperature. After cooling to RT, the suspension was filtered over Celite and washed with ethanol, the filtrate was concentrated under reduced pressure and the residue was taken up in toluene and concentrated to dryness again. The resulting crude amine was taken up in 1,4-dioxane (100 ml) and cooled to 0° C., and TEA (22.3 ml, 0.22 mol, 6.0 eq.) was added. Then Boc anhydride (23.3 g, 0.1055 mol, 3.0 eq.) was added and stirring was carried out for 12 hours at RT. The reaction solution was concentrated and the residue was taken up in water (300 ml) and ethyl acetate (500 ml). The phases were separated and the org. phase was washed with water and sat. NaCl solution, dried over sodium sulfate and concentrated under reduced pressure. The crude product was purified by column chromatography. Yield: 53% (5.3 mol).

Stage 4:
The product from stage 3 (5.25 g, 0.018 mol) was taken up in THF-methanol-water (6:4:1) (27.6 ml) and cooled to 0° C.; LiOH H₂O (3.4 g, 0.08 mol, 4.0 eq.) was added in portions and stirring was carried out for 8 hours at RT. The reaction mixture was concentrated to dryness and the residue was taken up in a little water and acidified at 0° C. with 10% citric acid solution. The resulting precipitate was filtered off, washed with water and dried. Yield: 75% (3.75 g, 0.013 mol).

Stage 5:
TFA (20 ml) was added at 0° C. to a solution of intermediate A (3.3 g, 0.0173 mol) in DCM (100 ml), and stirring was carried out for 1 hour at RT. The reaction mixture was concentrated to dryness, and the crude amine was obtained in the form of the TFA salt, which was used further without being purified. The acid from stage 4 (4.0 g, 0.0009 mol) was dissolved in DCM (50 ml); EDCI (4.12 g, 0.0216 mol) and HOBT (2.91 g, 0.0216 mol) were added and the mixture was cooled to 0° C. After addition of DIPEA (12.9 ml, 0.072 mol), the reaction solution was stirred for 10 minutes. The TFA salt was dissolved in DCM (50 ml) and added dropwise to the reaction solution, and stirring was carried out for 16 hours at RT. The reaction solution was diluted with water and extracted with ethyl acetate (3×100 ml). The combined org. phases were washed with water and sat. NaCl solution, dried over sodium sulfate and concentrated. The crude product was purified by column chromatography. Yield: 89% (5.8 g, 0.0128 mol).

Synthesis of CC_AMN-05: 8-Amino-N-methyl-N-(1-pyridin-4-yl-piperidin-4-yl)-5,6,7,8-tetrahydro-naphthalene-2-carboxylic acid amide (CC_AMN-05)

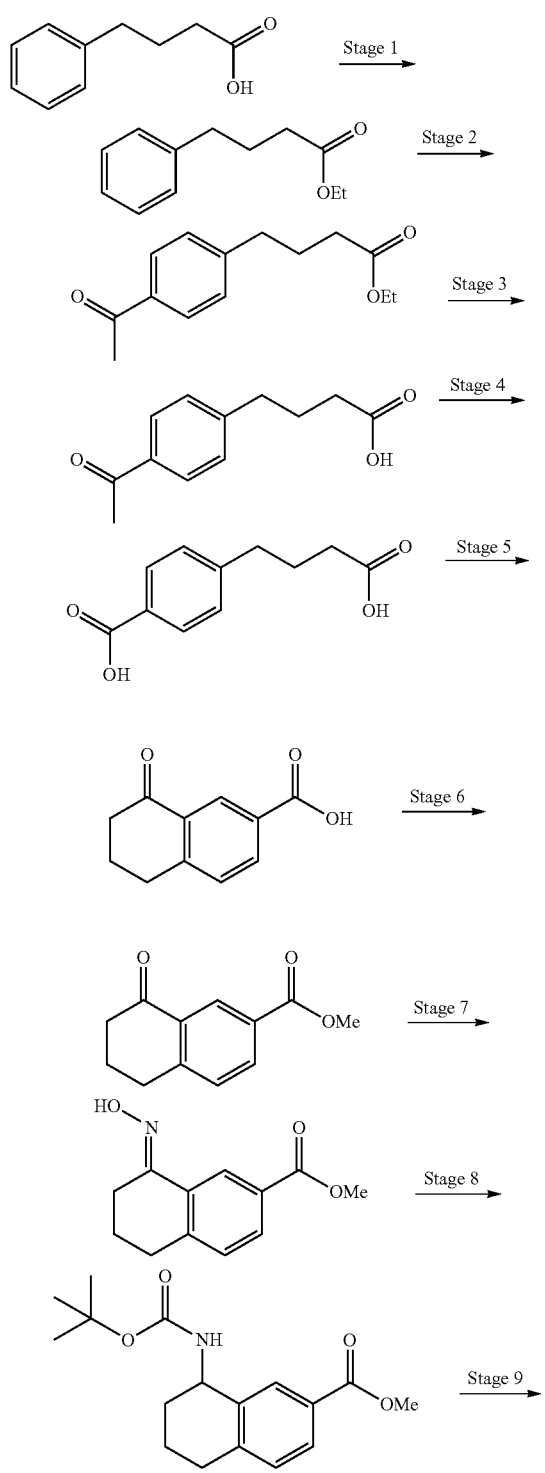

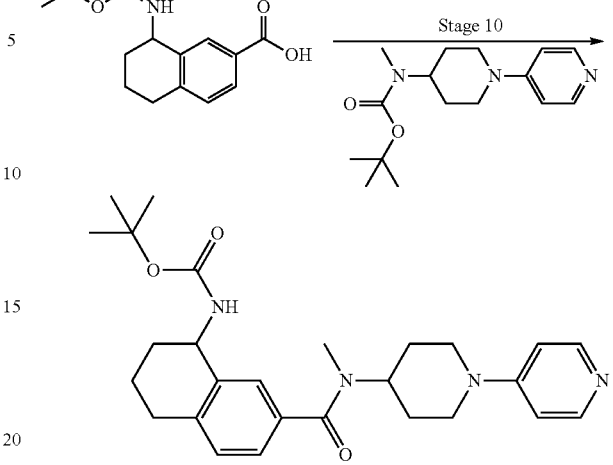

Stage 1:
Conc. sulfuric acid (0.4 ml) was added to a solution of 4-phenylbutanoic acid (25.0 g, 0.1522 mol, 1 eq.) in ethanol (80 ml), and heating was carried out for 5 hours at boiling temperature. The ethanol was concentrated and the residue was taken up in water (250 ml) and extracted with ethyl acetate (3×400 ml). The combined org. phases were washed with water (300 ml) and sat. NaCl solution (200 ml), dried over sodium sulfate and concentrated under reduced pressure. Yield: 81.2% (22 g, 0.12359 mol).

Stage 2:
A solution of the product from stage 1 (35.0 g, 0.1832 mol, 1.0 eq.) in dichloromethane (600 ml) was added dropwise to a solution of $AlCl_3$ (107.9 g, 0.8099 mol, 4.42 eq.) and acetyl chloride (24 ml, 29.7 g, 0.379 mol, 2.07 eq.) in dichloromethane (600 ml), and stirring was carried out for 15 minutes at RT. Then the reaction mixture was added to cooled conc. HCl solution (400 ml) and extracted with DCM (3×500 ml). The combined org. phases were washed with water (400 ml) and sat. NaCl solution (300 ml), dried over sodium sulfate and concentrated under reduced pressure. Yield: 91.3% (39 g, 0.16645 mol).

Stage 3:
The product from stage 2 (20.0 g, 0.0854 mol, 1.0 eq.) was taken up in THF (427 ml), methanol (200 ml) and water (200 ml); $LiOH \cdot H_2O$ (10.7 g, 0.2564 mol, 3.0 eq.) was added in portions, and stirring was carried out for 16 hours at RT. The reaction mixture was concentrated to dryness and the residue was taken up in water (400 ml) and washed with diethyl ether. The aqueous phase was adjusted to pH 2 with 2M HCl and the resulting precipitate was filtered off, washed with water and dried in vacuo. Yield: 96.5% (18.0 g, 0.08242 mol).

Stage 4:
A mixture of aqueous sodium hypochloride solution (15%, 350.6 ml, 0.24765 mol) and NaOH solution (50%, 182.75 ml) was heated to 55° C. Then the acid from stage 3 (17 g, 0.08252 mol, 1.0 eq.) was added in portions, the temperature being between 60-70° C. The reaction mixture was stirred for 20 hours at 55° C., cooled to RT and hydrolyzed with aqueous sodium bisulfite solution (25%, 350.6 ml). Then it was acidified with conc. HCl solution and the resulting precipitate was filtered off, washed with water (3×100 ml) and dried. Yield: 49.52% (8.5 g, 0.04086 mol).

Stage 5:
In a round-bottomed flask, the acid from stage 4 (14.0 g, 0.0373 mol, 1 eq.), $AlCl_3$ (64.62 g, 0.4846 mol, 7.2 eq.) and sodium chloride (6.642 g, 0.11165 mol, 1.68 eq.) were mixed and heated for 1 hour at 190° C. The hot reaction mixture was poured carefully onto ice (200 g). The reaction mixture was acidified with 6M HCl (560 ml) and extracted with ethyl acetate (5×600 ml). The combined org. phases were washed with water (500 ml) and sat. NaCl solution (200 ml), dried over sodium sulfate and concentrated under reduced pressure. The crude product (15 g, 33%) was used in the next stage without being purified further. Yield: 70.38% (9.0 g, 0.04736 mol).

Stage 6:
The product from stage 5 (17.5 g, 0.0921 mol, 1.0 eq.) was dissolved in methanol (644 ml); conc. sulfuric acid (0.5 ml) was added, and refluxing was carried out for 16 hours. After monitoring by thin-layer chromatography, the reaction solution was concentrated to dryness and the residue was taken up in water (200 ml) and extracted with ethyl acetate (3×300 ml). The combined org. phases were washed with water (300 ml) and sat. NaCl solution (100 ml), dried over sodium sulfate and concentrated under reduced pressure. The crude product was purified by column chromatography (silica gel 100-200, 10% ethyl acetate in hexane). Yield: 53.22% (10.0 g, 0.04901 mol).

Stage 7:
The product from stage 6 (10.0 g, 0.0529 mol, 1.0 eq.) was dissolved in methanol (208 ml). Hydroxylamine HCl (10.82 g, 0.1557 mol, 3.0 eq.) and sodium acetate (25.54 g, 0.3114 mol, 6.0 eq.) were added at RT, and heating was carried out for 2 hours at boiling temperature. After monitoring by thin-layer chromatography, the methanol was concentrated and the residue was taken up in water (200 ml) and extracted with ethyl acetate (2×300 ml). The combined org. phases were washed with water (200 ml) and sat. NaCl solution (100 ml), dried over sodium sulfate and concentrated to dryness. The crude product was used in the next stage without being purified further. Yield: 96.77% (11.0 g, 0.05022 mol).

Stage 8:
The product from stage 7 (11.0 g, 0.05022 mol, 1.0 eq.) was dissolved in ethanol (102 ml); then HCl solution (100 ml, 50%) and Zn powder (19.58 g, 0.3013 mol, 6.0 eq.) were added and stirring was carried out for 20 minutes. The suspension was filtered over Celite and washed with ethanol (50 ml). The filtrate was concentrated to dryness under reduced pressure. The resulting crude amine was taken up in 1,4-dioxane (200 ml) and cooled to 0° C., and TEA (20.5 ml, 0.1506 mol, 3.0 eq.) was added. Then Boc anhydride (13.14 g, 0.0602 mol, 1.2 eq.) was added and stirring was carried out for 14 hours at RT. The reaction solution was concentrated and the residue was taken up in water (200 ml) and ethyl acetate (2×300 ml). The phases were separated and the org. phase was washed with water and sat. NaCl solution, dried over sodium sulfate and concentrated under reduced pressure. The crude product was purified by column chromatography (silica gel 100-200, 10% ethyl acetate in hexane). Yield: 47% (7.8 g, 0.02422 mol).

Stage 9:
The product from stage 8 (7.8 g, 0.02557 mol, 1.0 eq.) was taken up in THF-methanol-water (6:4:1) (179 ml) and cooled to 0° C.; LiOH $H_2O$ (4.3 g, 0.10229 mol, 4.0 eq.) was added in portions, and stirring was carried out for 16 hours at RT. The reaction mixture was concentrated to dryness and the residue was taken up in water (100 ml) and washed with diethyl ether (70 ml). The aqueous phase was adjusted to pH 2 with 10% citric acid solution. The resulting white precipitate was filtered off, washed with water and dried in vacuo. Yield: 91.38% (6.8 g, 0.02336 mol).

Stage 10:
The acid from stage 9 (4.0 g, 0.01374 mol, 1.0 eq.) was dissolved in DCM (60 ml); EDCI (3.94 g, 0.02061 mol, 1.5 eq.) and HOBT (1.8549 g, 0.01374 mol, 1.0 eq.) were added, and the mixture was cooled to 0° C. After addition of DIPEA (13.72 ml, 0.07935 mol, 2.5 eq.), the reaction solution was stirred for 20 minutes. Intermediate A (2.625 g, 0.01374 mol, 1.0 eq.) dissolved in DCM (36 ml) was added at 0-5° C. and the reaction solution was stirred for 14 hours at RT. The reaction solution was diluted with DCM (300 ml) and washed with sat. ammonium chloride solution (2×100 ml), sat. sodium hydrogen carbonate solution (100 ml), water (100 ml) and sat. NaCl solution (50 ml), dried over sodium sulfate and concentrated under reduced pressure. The crude product was purified by column chromatography (silica gel 100-200, 8% methanol in DCM). Yield: 68.3% (4.5 g, 0.0093847 mol).

Synthesis of CC_AMN-06: 4-Amino-N-methyl-N-(1-pyridin-4-yl-piperidin-4-yl)-3,4-dihydro-2H-chromene-6-carboxylic acid amide (CC_AMN-06)

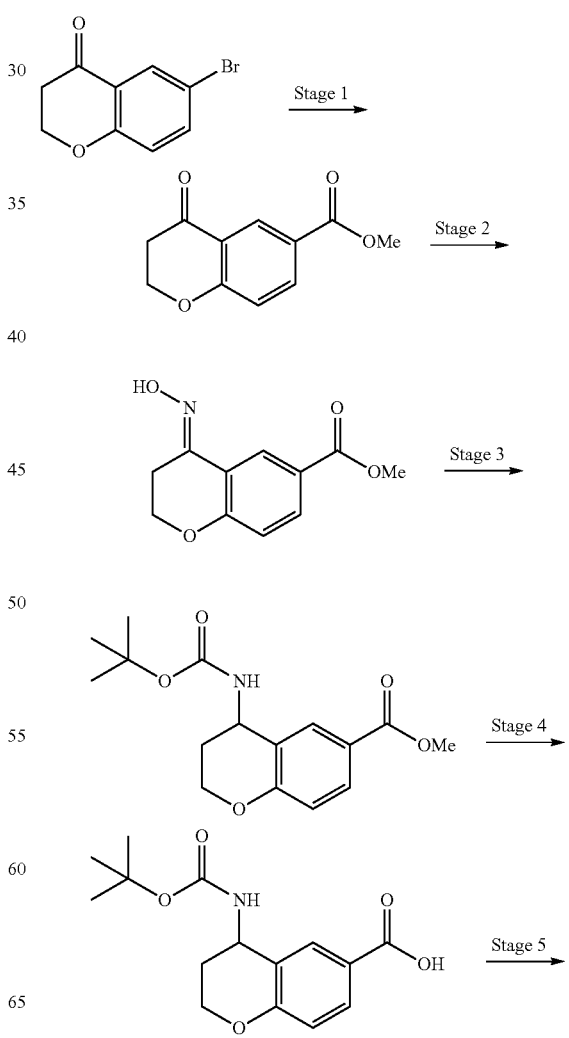

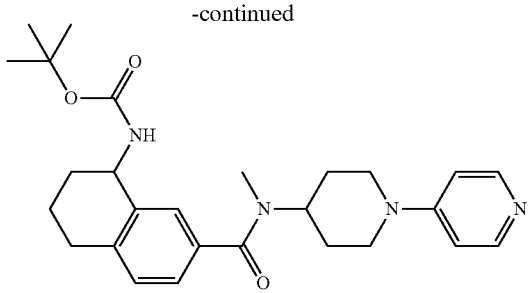

Stage 1:
6-Bromochroman-4-one (1.0 g, 0.0044 mol) was dissolved in DMSO (56 ml) and methanol (45 ml); TEA (1.35 ml, 0.0096 mol, 2.2 eq.) was added, and degassing was carried out with carbon monoxide. Then palladium acetate (39.7 mg, 0.000176 mol, 0.04 eq.) and DPPP (72.31 mg, 0.000176 mol, 0.04 eq.) were added and degassing was carried out for 2 hours with CO. Then the methanol was concentrated and the residue was diluted with water and extracted with diethyl ether. The org. phase was dried over sodium sulfate, concentrated and purified by column chromatography. Yield: 66% (600 mg, 0.0029 mol).

Stage 2:
The product from stage 1 (0.85 g, 0.0041 mol) was dissolved in methanol (15 ml). Hydroxyl-amine HCl (0.085 g, 0.0123 mol, 3.0 eq.) and sodium acetate (2.03 g, 0.0247 mol, 6.0 eq.) were added at RT and heating was carried out for 2 hours at boiling temperature. The methanol was concentrated and the residue was taken up in ethyl acetate, washed with water and sat. NaCl solution, dried over sodium sulfate and concentrated to dryness. The crude product was used in the next stage without being purified further. Yield: 93% (0.85 g, 0.0038 mol).

Stage 3:
The product from stage 2 (0.85 g, 0.0038 mol) was dissolved in ethanol (10 ml), then water (5 ml) and conc. HCl (3.5 ml) were added and stirring was carried out for 15 minutes. Zn powder (1.49 g, 0.023 mol, 6.0 eq.) was added to the reaction solution, while cooling, and heating was carried out for 1 hour at boiling temperature. After cooling to RT, the suspension was filtered over Celite and washed with ethanol, the filtrate was concentrated under reduced pressure, and the residue was taken up in toluene and again concentrated to dryness. The resulting crude amine was taken up in 1,4-dioxane (100 ml) and cooled to 0° C., and TEA (3.21 ml, 0.0230 mol, 6.0 eq.) was added. Then Boc anhydride (2.51 g, 0.0155 mol, 3.0 eq.) was added and stirring was carried out for 12 hours at RT. The reaction solution was concentrated and the residue was taken up in water (300 ml) and ethyl acetate (500 ml). The phases were separated and the org. phase was washed with water and sat. NaCl solution, dried over sodium sulfate and concentrated under reduced pressure. The crude product was purified by column chromatography. Yield: 72% (0.085 g, 0.0027 mol).

Stage 4:
The product from stage 3 (0.85 g, 0.00276 mol) was taken up in THF-methanol-water (6:4:1) (10 ml) and cooled to 0° C.; LiOH H₂O (0.465 g, 0.011 mol, 4.0 eq.) was added in portions and stirring was carried out for 8 hours at RT. The reaction mixture was concentrated to dryness and the residue was taken up in a little water and acidified at 0° C. with 10% citric acid solution. The resulting precipitate was filtered off, washed with water and dried. Yield: 90% (0.073 g, 0.00249 mol).

Stage 5:
TFA (20 ml) was added at 0° C. to a solution of intermediate A (3.3 g, 0.0173 mol) in DCM (100 ml), and stirring was carried out for 1 hour at RT. The reaction mixture was concentrated to dryness and the crude amine was obtained in the form of the TFA salt, which was used further without being purified. The acid from stage 4 (4.0 g, 0.0009 mol) was dissolved in DCM (50 ml); EDCI (4.12 g, 0.0216 mol) and HOBT (2.91 g, 0.0216 mol) were added, and the mixture was cooled to 0° C. After addition of DI PEA (12.9 ml, 0.072 mol), the reaction solution was stirred for 10 minutes. The TFA salt was dissolved in DCM (50 ml) and added dropwise to the reaction solution, and stirring was carried out for 16 hours at RT. The reaction solution was diluted with water and extracted with ethyl acetate (3×100 ml). The combined org. phases were washed with water and sat. NaCl solution, dried over sodium sulfate and concentrated. The crude product was purified by column chromatography. Yield: 89% (5.8 g, 0.0128 mol).

Synthesis of CC_AMN-07: 3-Amino-N-[1-(2,6-dimethyl-pyridin-4-yl)-piperidin-4-yl]-N-methyl-2,3-dihydro-1H-indene-5-carboxylic acid amide (CC_AMN-07)

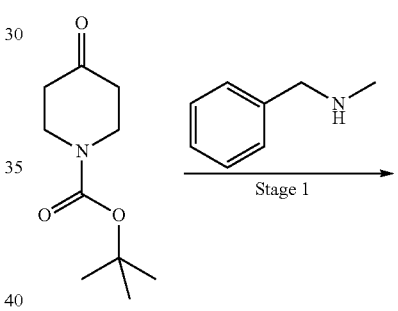

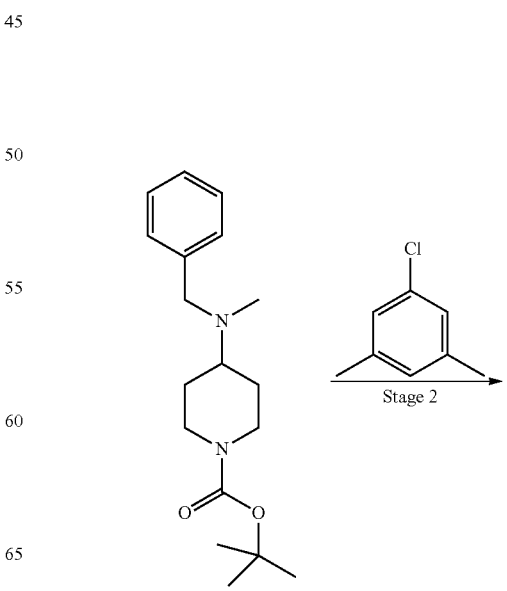

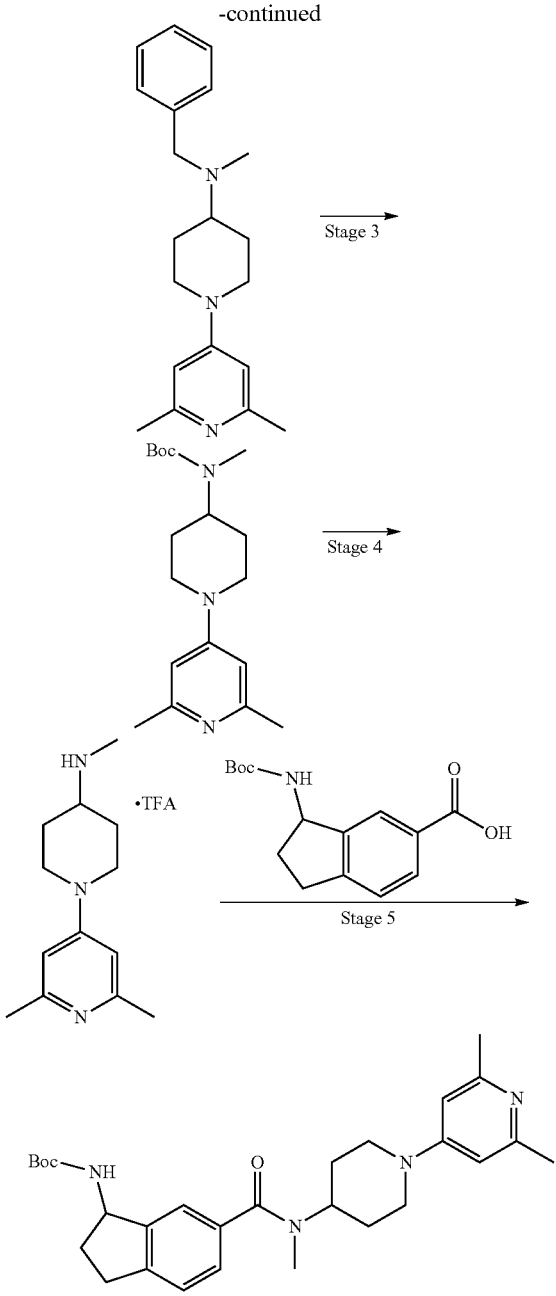

Stage 1:
AcOH (1.5 ml, 0.025 mol, 1.0 eq.) was added dropwise at 0° C. to a solution of N-Boc-4-piperidone (5.0 g, 0.025 mol, 1.0 eq.) and N-methylbenzylamine (6.5 ml, 0.05 mol, 2.0 eq.) in THF (80 ml), and stirring was carried out for 30 minutes. Then NaBH(OAc)$_3$ (8.0 g, 0.038 mol, 1.5 eq.) was added in portions and stirring was carried out for 3 days. The reaction mixture was hydrolyzed with NaHCO$_3$ solution (100 ml), concentrated in vacuo and extracted with ethyl acetate. The org. phase was washed with sat. NaCl solution (2×50 ml), dried over sodium sulfate, concentrated under reduced pressure and purified by column chromatography (silica gel 100-200, 15% ethyl acetate in hexane). Yield: 6.96 g (0.023 mol, 91%).

Stage 2:
The product of stage 1 (19.2 g, 0.063 mol, 1.0 eq.) was dissolved in TFA:DCM (1:4, 600 ml), and stirring was carried out for 3 hours at RT. The reaction mixture was dried in vacuo and used directly. The Boc-deprotected component (12.9 g, 0.063 mol, 1.0 eq.) and 4-chloro-2,6-dimethylpyridine (8.94 g, 0.063 mol, 1.0 eq.) were dissolved in ethanol (45 ml); TEA (27 ml, 0.191 mol, 3.03 eq.) was added and heating was carried out for 20 hours, in a closed vessel, at 120° C. The reaction mixture was concentrated and the residue was purified by column chromatography (silica gel 100-200, 5% MeOH in DCM). Yield: 10 g (0.032 mol, 51%).

Stage 3:
The product from stage 2 (10 g, 0.032 mol) was dissolved in MeOH (300 ml) and degassed with argon; 10% Pd—C (10 mol %) was added and hydrogenation was carried out overnight under a H$_2$ atmosphere. The reaction mixture was filtered over Celite and the filtrate was concentrated to dryness (crude amine, 7 g). The crude amine (7 g, 0.032 mol, 1.0 eq.) was dissolved in DCM (120 ml), and TEA (8.91 ml, 0.064 mol, 2.0 eq.) and Boc anhydride (10.26 ml, 0.048 mol, 1.5 eq.) were added dropwise. The reaction mixture was stirred overnight at RT, then diluted with DCM and washed with water (2×50 ml). The org. phase was washed with sat. NaCl solution (2×40 ml), dried over sodium sulfate and concentrated. The crude product was purified by column chromatography (silica gel, 10% MeOH in DCM). Yield: 7 g (0.022 mol, 68.7%).

Stages 4 & 5:
A solution of the Boc-protected amine (7.0 g, 0.022 mol, 1 eq.) just obtained in TFA/DCM (1:4, 300 ml) was stirred for 3 hours at RT. The reaction mixture was concentrated to dryness and the crude amine was obtained in the form of the TFA salt, which was used further directly. The corresponding acid (4.5 g, 0.016 mol) was dissolved in DCM (40 ml); EDCI (3.1 g, 0.0162 mol, 1.5 eq.) and HOBT (2.19 g, 0.0169 mol, 1.5 eq.) were added and the mixture was cooled to 0° C. After addition of DIPEA (8.95 ml, 0.054 mol, 5.0 eq.), the reaction solution was stirred for 30 minutes at RT. The amine (2.84 g, 0.0129 mol, 1.2 eq.) was dissolved in DCM (25 ml) and added dropwise to the reaction solution, and stirring was carried out for 16 hours at RT. The reaction solution was diluted with DCM (40 ml), washed with sat. ammonium chloride solution (2×15 ml), water (2×15 ml) and sat. NaCl solution (2×15 ml), dried over sodium sulfate and concentrated. The crude product was purified by column chromatography. Yield: 77% (4.0 g, 0.0083 mol).

Synthesis of CC_AMN-08: N-[1-(2,6-Dimethyl-pyridin-4-yl)-piperidin-4-yl]-N-methyl-3-methylamino-2,3-dihydro-1H-indene-5-carboxylic acid amide (CC_AMN-08)

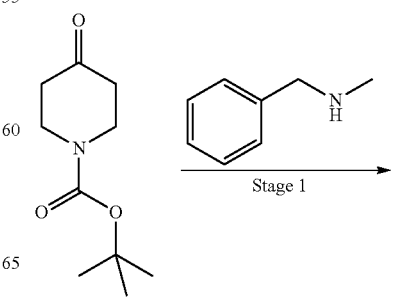

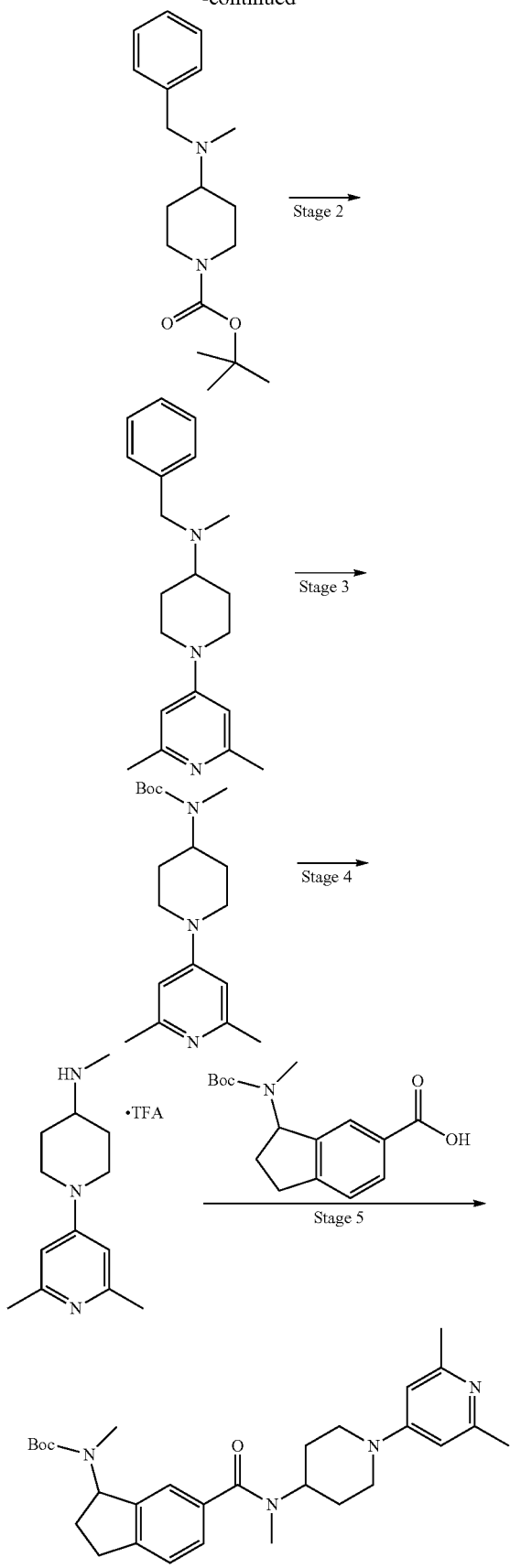

Stage 1:

AcOH (1.5 ml, 0.025 mol, 1.0 eq.) was added dropwise at 0° C. to a solution of N-Boc-4-piperidone (5.0 g, 0.025 mol, 1.0 eq.) and N-methylbenzylamine (6.5 ml, 0.05 mol, 2.0 eq.) in THF (80 ml), and stirring was carried out for 30 minutes. Then NaBH(OAc)$_3$ (8.0 g, 0.038 mol, 1.5 eq.) was added in portions and stirring was carried out for 3 days. The reaction mixture was hydrolyzed with NaHCO$_3$ solution (100 ml), concentrated in vacuo and extracted with ethyl acetate. The org. phase was washed with sat. NaCl solution (2×50 ml), dried over sodium sulfate, concentrated under reduced pressure and purified by column chromatography (silica gel 100-200, 15% ethyl acetate in hexane). Yield: 6.96 g (0.023 mol, 91%).

Stage 2:

The product of stage 1 (19.2 g, 0.063 mol, 1.0 eq.) was dissolved in TFA:DCM (1:4, 600 ml), and stirring was carried out for 3 hours at RT. The reaction mixture was dried in vacuo and used directly. The Boc-deprotected component (12.9 g, 0.063 mol, 1.0 eq.) and 4-chloro-2,6-dimethylpyridine (8.94 g, 0.063 mol, 1.0 eq.) were dissolved in ethanol (45 ml); TEA (27 ml, 0.191 mol, 3.03 eq.) was added, and heating was carried out for 20 hours (in a closed vessel) at 120° C. The reaction mixture was concentrated and the residue was purified by column chromatography (silica gel 100-200, 5% MeOH in DCM). Yield: 10 g (0.032 mol, 51%).

Stage 3:

The product from stage 2 (10 g, 0.032 mol) was dissolved in MeOH (300 ml) and degassed with argon; 10% Pd—C (10 mol %) was added and hydrogenation was carried out overnight under a H$_2$ atmosphere. The reaction mixture was filtered over Celite and the filtrate was concentrated to dryness (crude amine, 7 g). The crude amine (7 g, 0.032 mol, 1.0 eq.) was dissolved in DCM (120 ml), and TEA (8.91 ml, 0.064 mol, 2.0 eq.) and Boc anhydride (10.26 ml, 0.048 mol, 1.5 eq.) were added dropwise. The reaction mixture was stirred overnight at RT, then diluted with DCM and washed with water (2×50 ml). The org. phase was washed with sat. NaCl solution (2×40 ml), dried over sodium sulfate and concentrated. The crude product was purified by column chromatography (silica gel, 10% MeOH in DCM). Yield: 7 g (0.022 mol, 68.7%).

Stages 4 & 5:

A solution of the Boc-protected amine (3.15 g, 0.0098 mol, 1.0 eq.) in TFA/DCM (1:4, 100 ml) was stirred for 3 hours at RT. The reaction mixture was concentrated to dryness and the crude amine was obtained in the form of the TFA salt, which was used further directly. The corresponding acid (2.4 g, 0.0082 mol) was dissolved in DCM (30 ml); EDCI (2.36 g, 0.012 mol, 1.5 eq.) and HOBT (1.67 g, 0.012 mol, 1.5 eq.) were added and the mixture was cooled to 0° C. After addition of DIPEA (6.81 ml, 0.041 mol, 5.0 eq.), the reaction solution was stirred for 30 minutes at RT. The amine TFA salt (1.2 eq.) was dissolved in DCM (20 ml) and added dropwise at 0° C. to the reaction solution, and stirring was carried out for 16 hours at RT. The reaction solution was diluted with DCM (30 ml), washed with sat. sodium hydrogen carbonate solution (2×10 ml), sat. ammonium chloride solution (2×10 ml), water (2×10 ml) and sat. NaCl solution (2×10 ml), dried over sodium Synthesis of CC_AMN-09: 3-Amino-N-(1-isoquinolin-6-yl-piperidin-4-yl)-N-methyl-2,3-dihydro-1H-indene-5-carboxylic acid amide (CC_AMN-09)

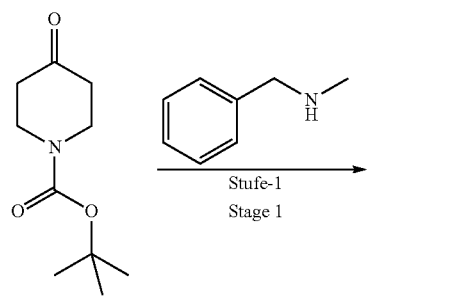

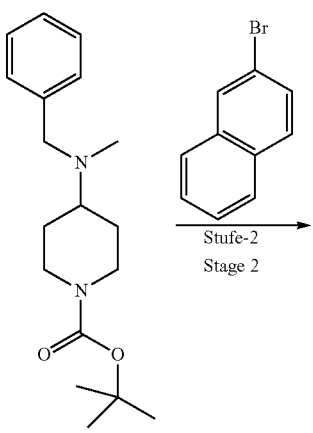

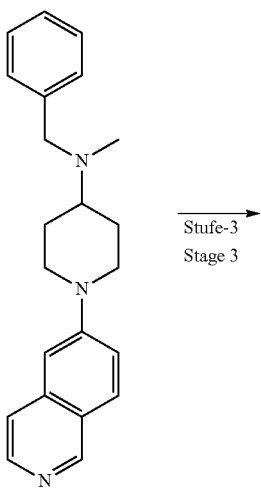

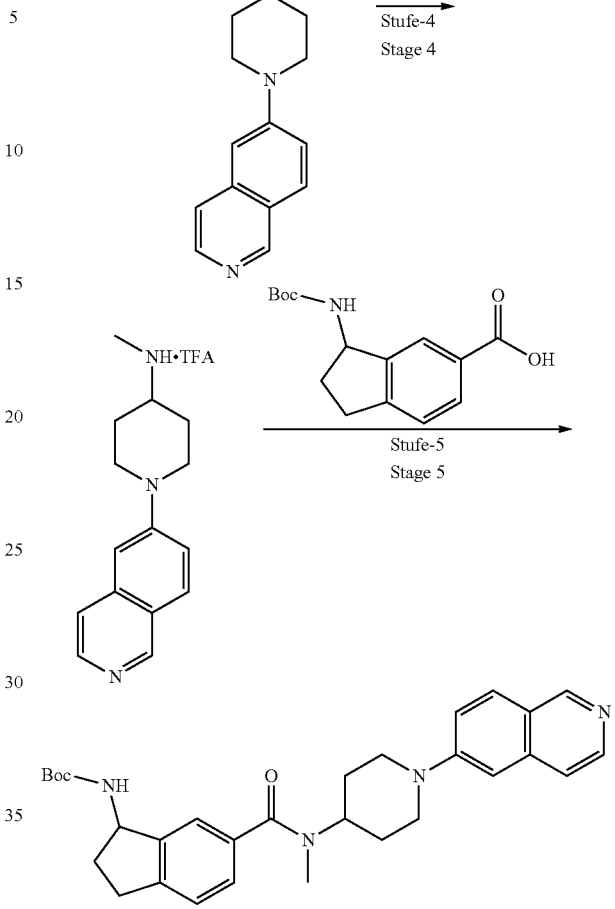

Stage 1:
AcOH (1.5 ml, 0.025 mol, 1.0 eq.) was added dropwise at 0° C. to a solution of N-Boc-4-piperidone (5.0 g, 0.025 mol, 1.0 eq.) and N-methylbenzylamine (6.5 ml, 0.05 mol, 2.0 eq.) in THF (80 ml), and stirring was carried out for 30 minutes. Then NaBH(OAc)₃ (8.0 g, 0.038 mol, 1.5 eq.) was added in portions and stirring was carried out for 3 days. The reaction mixture was hydrolyzed with NaHCO₃ solution (100 ml), concentrated in vacuo and extracted with ethyl acetate. The org. phase was washed with sat. NaCl solution (2×50 ml), dried over sodium sulfate, concentrated under reduced pressure and purified by column chromatography (silica gel 100-200, 15% ethyl acetate in hexane). Yield: 6.96 g (0.023 mol, 91%).

Stage 2:
The product of stage 1 (6.64 g, 0.022 mol, 1.0 eq.) was dissolved in TFA:DCM (1:4, 300 ml), and stirring was carried out for 3 hours at RT. The reaction mixture was dried in vacuo and used directly. The Boc-deprotected component (4.46 g, 0.022 mol, 1.0 eq.) and 6-bromoisoquinoline (5.0 g, 0.024 mol, 1.1 eq.) were dissolved in toluene (100 ml); sodium triacetoxyborohydride (4.33 g, 0.044 mol, 2.0 eq.) was added and degassing was carried out for 15 minutes with argon. X-Phos (0.52 g, 0.0011 mol, 0.05 eq.) and Pd(OAc)₂ (0.25 g, 0.0011 mol, 0.05 eq.) were added to the reaction mixture, and heating was carried out for 16 hours at 120° C. The reaction mixture was diluted with DCM (100 ml) and filtered off over sulfate and concentrated. The crude product was purified by column chromatography. Yield: 77% (3.1 g, 0.0063 mol).

Celite, and the filtrate was concentrated and purified by column chromatography (silica gel 100-200, 5% MeOH in DCM). Yield: 5.8 g (0.017 mol, 88.8%).

Stage 3:

The product from stage 2 (8.5 g, 0.026 mol) was dissolved in MeOH (300 ml) and degassed with argon; 10% Pd—C (10 mol %) was added and hydrogenation was carried out overnight under a H₂ atmosphere. The reaction mixture was filtered over Celite and the filtrate was concentrated to dryness (crude amine, 6.3 g). The crude amine (6.3 g, 0.026 mol, 1.0 eq.) was dissolved in DCM (200 ml), and TEA (7.3 ml, 0.052 mol, 2.0 eq.) and Boc anhydride (8.4 ml, 0.039 mol, 1.5 eq.) were added dropwise. The reaction mixture was stirred overnight at RT, then diluted with DCM and washed with water (2×50 ml). The org. phase was washed with sat. NaCl solution (2×40 ml), dried over sodium sulfate and concentrated. The crude product was purified by column chromatography (silica gel, 5% MeOH in DCM). Yield: 3 g (0.009 mol, 46.1%).

Stages 4 & 5:

A solution of Boc-protected amine (2.95 g, 0.009 mol, 1.2 eq.) in TFA/DCM (1:4, 100 ml) was stirred for 3 hours at RT. The reaction mixture was concentrated to dryness and the crude amine was obtained in the form of the TFA salt, which was used further directly. The corresponding acid (2.0 g, 0.0072 mol) was dissolved in DCM (30 ml); EDCI (2.06 g, 0.0108 mol, 1.5 eq.) and HOBT (1.46 g, 0.0108 mol, 1.5 eq.) were added and the mixture was cooled to 0° C. After addition of DIPEA (5.97 ml, 0.036 mol, 5.0 eq.), the reaction solution was stirred for 30 minutes at RT. The amine TFA salt (2.08 g, 0.0086 mol, 1.2 eq.) was dissolved in DCM (20 ml) and added dropwise at 0° C. to the reaction solution, and stirring was carried out for 16 hours at RT. The reaction solution was diluted with DCM (30 ml), washed with sat. sodium hydrogen carbonate solution (2×100 ml), sat. ammonium chloride solution (2×100 ml), water (2×100 ml) and sat. NaCl solution (2×100 ml), dried over sodium sulfate and concentrated. The crude product was purified by column chromatography. Yield: 94% (3.4 g, 0.0068 mol).

Synthesis of CC_AMN-11: 3-Amino-N-[2-(1-pyridin-4-yl-piperidin-4-yl)-ethyl]-2,3-dihydro-1H-indene-5-carboxylic acid amide (CC_AMN-11)

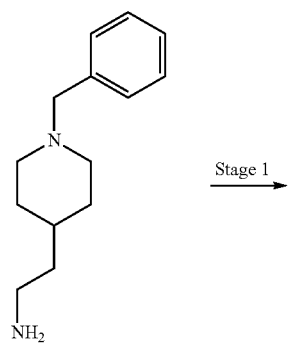

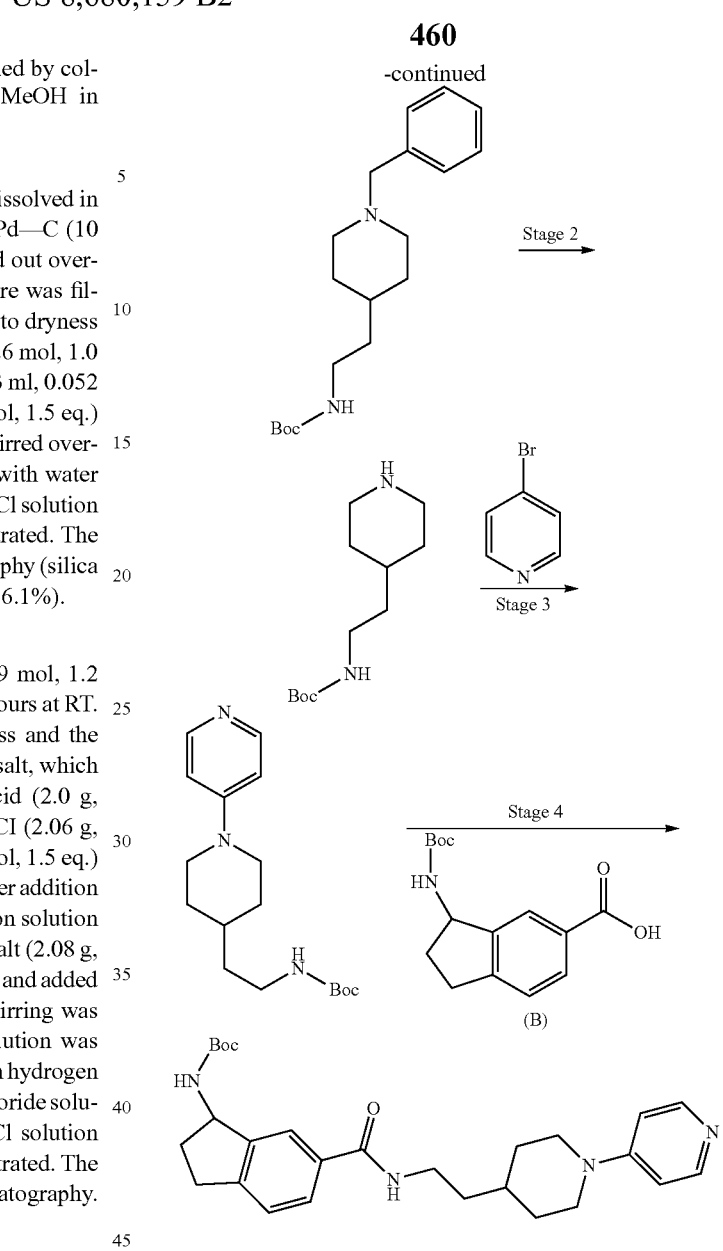

Stage 1:

To a solution of 1-benzyl-4-(2-aminoethyl)piperidine (20 g, 0.0916 mol) in DCM (460 ml) there was added at 0° C. DIPEA (2.0 eq.) followed by Boc anhydride (1.2 eq.), and stirring was carried out for 14 hours at RT. The reaction solution was diluted with DCM and washed with water and sat. NaCl solution, dried over sodium sulfate and concentrated under reduced pressure. The crude product was purified by column chromatography (silica gel, 2% methanol in DCM). Yield: 72% (30.7 g, 500652 mol).

Stage 2:

The product from stage 1 (10 g, 0.0314 mol) was dissolved in methanol (500 ml); acetic acid (2 ml) was added and degassing was carried out with argon. Then 10% Pd—C (5 g) was added and the reaction solution was hydrogenated for 16 hours at normal pressure. After monitoring by thin-layer chromatography, the reaction mixture was filtered off over Celite and washed with methanol, and the filtrate was concentrated under reduced pressure and used in the next stage without being purified further. Yield: 7 g (quantitative).

Stage 3:
The product from stage 2 (9.5 g, 0.04166 mol) was dissolved in DMSO (50 ml); potassium carbonate (3.0 eq.), L-proline (0.4 eq.), CuI (0.2 eq.) and 4-bromopyridine HBr (1 eq.) were added, and stirring was carried out for 14 hours at 150° C. under protecting gas. After monitoring by thin-layer chromatography, the reaction solution was cooled to RT, diluted with ethyl acetate and sat. NaCl solution and filtered off over Celite. The residue was washed with ethyl acetate and the filtrate was washed with water and sat. NaCl solution, dried over sodium sulfate and concentrated under reduced pressure. The crude product was purified by column chromatography (5% methanol in DCM). Yield: 56% (7.1 g, 0.0233 mol).

Stage 4:
A solution of Boc-protected amine (7.5 g, 0.02459 mol) in DCM (600 ml) was cooled to 0° C.; TFA (150 ml) was added, and stirring was carried out for 3 hours at RT. The reaction mixture was concentrated to dryness and the crude amine (in the form of the TFA salt) was reacted further directly. The corresponding acid (B) (6.81 g, 0.02459 mol) was dissolved in DCM (100 ml); HATU (18.69 g, 0.04918 mol) was added, the mixture was cooled to 0° C., DIPEA (12.85 ml, 0.07377 mol) was added, and stirring was carried out for 10 minutes. The crude amine and DIPEA (4.2 ml, 0.02459 mol) dissolved in DCM (50 ml) were added dropwise and the reaction solution was stirred for 16 hours at RT. Then it was diluted with water and extracted with ethyl acetate (3×100 ml). The combined org. phases were washed with water and sat. NaCl solution, dried over sodium sulfate and concentrated. The crude product was purified by column chromatography. Yield: 18% (2 g, 0.00442 mol).

2) Synthesis of the Acids (CC_ACI), Sulfonic Acid Chlorides (CC_SCI) and Isocyanates (CC_ICN)

Overview:

| CC_AMN, CC_SCI, CC_ICN. | Structure | Name |
|---|---|---|
| CC_ACI-01 | 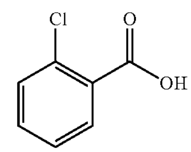 | 2-Chloro-benzoic acid (CC_ACI-01) |
| CC_ACI-02 | 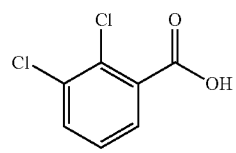 [SMILES: O=C(O)c1cccc(Cl)c1Cl] | 2,3-Dichloro-benzoic acid (CC_ACI-02) |
| CC_ACI-03 | 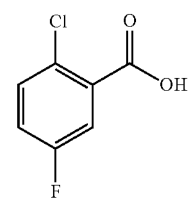 [SMILES: O=C(O)c1cc(F)ccc1Cl] | 2-Chloro-5-fluoro-benzoic acid (CC_ACI-03) |
| CC_ACI-04 | 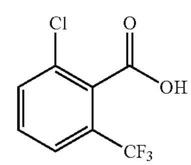 | 2-Chloro-6-(trifluoromethyl)-benzoic acid (CC_ACI-04) |
| CC_ACI-05 | 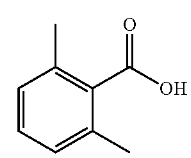 | 2,6-Dimethyl-benzoic acid (CC_ACI-05) |
| CC_ACI-06 | 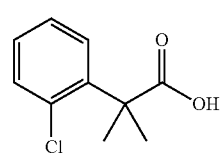 | 2-(2-Chlorophenyl)-2-methyl-propionic acid (CC_ACI-06) |

-continued

| CC_AMN, CC_SCI, CC_ICN. | Structure | Name |
|---|---|---|
| CC_ACl-07 | | Cyclohexanecarboxylic acid (CC_ACI-07) |
| CC_ACI-08 | 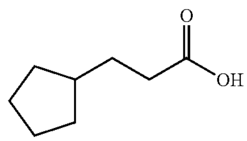 | 3-Cyclopentyl-propionic acid (CC_ACI-08) |
| CC_ACI-09 | 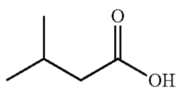 | 3-Methyl-butyric acid (CC_ACI-09) |
| CC_ACI-10 | 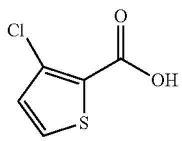 | 3-Chloro-thiophene-2-carboxylic acid (CC_ACI-10) |
| CC_ACI-11 | 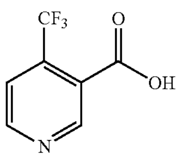 [SMILES: O=C(O)c1cnccc1C(F)(F)F] | 4-(Trifluoromethyl)-pyridine-3-carboxylic acid (CC_ACI-11) |
| CC_ACI-12 | 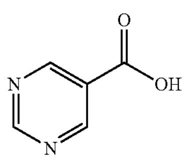 | Pyrimidine-5-carboxylic acid (CC_ACI-12) |
| CC_SCL-01 | 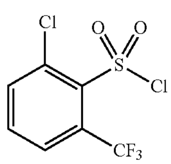 [SMILES: O=S(=O)(Cl)c1c(Cl)cccc1C(F)(F)F] | 2-Chloro-6-(trifluoromethyl)-benzenesulfonyl chloride (CC_SCL-01) |
| CC_SCL-02 | 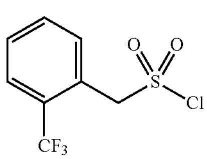 [SMILES: O=S(=O)(Cl)Cc1ccccc1C(F)(F)F] | [2-(Trifluoromethyl)-phenyl]-methanesulfonyl chloride (CC_SCL-02) |
| CC_SCL-03 | 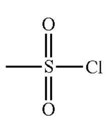 | Methanesulfonyl chloride |
| CC_SCL-04 | 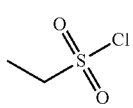 | Ethanesulfonyl chloride |
| CC_SCL-05 | 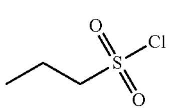 | Propane-1-sulfonyl chloride |

-continued

| CC_AMN, CC_SCI, CC_ICN. | Structure | Name |
|---|---|---|
| CC_SCL-06 | 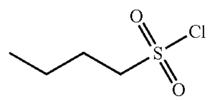 | Butane-1-sulfonyl chloride |
| CC_SCL-07 | 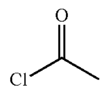 | Acetyl chloride |
| CC_SCL-08 | 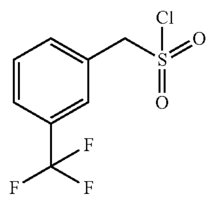 [SMILES: O=S(=O)(Cl)Cc1cccc(C(F)(F)F)c1] | [3-(Trifluoromethyl)phenyl]-methanesulfonyl chloride |
| CC_SCL-09 | 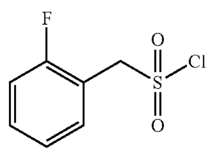 [SMILES: O=S(=O)(Cl)Cc1ccccc1F] | (2-Fluorophenyl)-methanesulfonyl chloride |
| CC_SCL-10 | 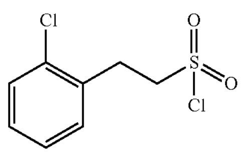 [SMILES: O=S(=O)(Cl)CCc1ccccc1Cl] | 2-(2-Chlorophenyl)-ethanesulfonyl chloride |
| CC_SCL-11 | 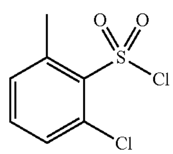 | 2-Chloro-6-methyl-benzenesulfonyl chloride |
| CC_SCL-12 | 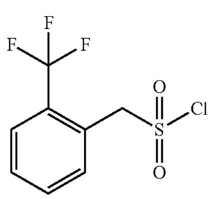 [SMILES: O=S(=O)(Cl)Cc1ccccc1C(F)(F)F] | [2-(Trifluoromethyl)-phenyl]-methanesulfonyl chloride |
| CC_SCL-13 | 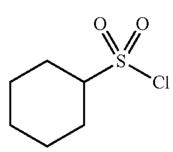 | Cyclohexanesulfonyl chloride |
| CC_ICN-01 | 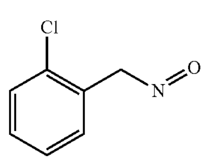 | 1-Chloro-2-(isocyanato-methyl)-benzene (CC_ICN-01) |

-continued
| CC_AMN, CC_SCI, CC_ICN. | Structure | Name |
|---|---|---|
| CC_ICN-02 | 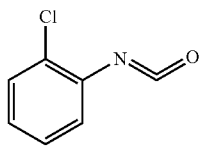 | 1-Chloro-2-isocyanato-benzene |
| CC_ICN-03 | 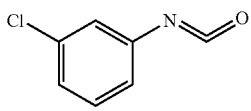 | 1-Chloro-3-isocyanato-benzene |
| CC_ICN-04 | 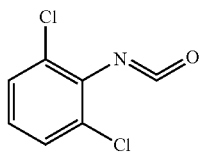 [SMILES: O=C=Nc1c(Cl)cccc1Cl] | 1,3-Dichloro-2-isocyanato-benzene |
| CC_ICN-05 | 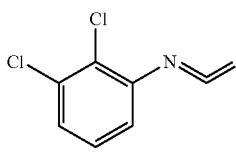 | 1,2-Dichloro-3-isocyanato-benzene |
| CC_ICN-06 | 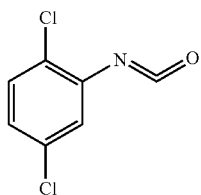 [SMILES: O=C=Nc1cc(Cl)ccc1Cl] | 1,4-Dichloro-2-isocyanato-benzene |
| CC_ICN-07 | 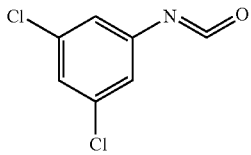 [SMILES: O=C=Nc1cc(Cl)cc(Cl)c1] | 1,3-Dichloro-5-isocyanato-benzene |
| CC_ICN-08 | 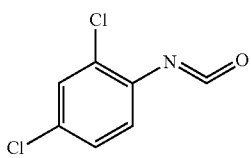 [SMILES: O=C=Nc1ccc(Cl)cc1Cl] | 2,4-Dichloro-1-isocyanato-benzene |
| CC_ICN-09 | 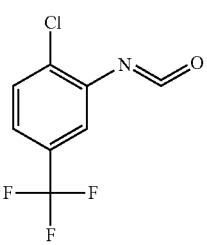 [SMILES: O=C=Nc1cc(C(F)(F)F)ccc1Cl] | 1-Chloro-2-isocyanato-4-(trifluoromethyl)-benzene |

-continued

| CC_AMN, CC_SCI, CC_ICN. | Structure | Name |
|---|---|---|
| CC_ICN-10 | 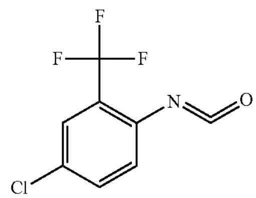 [SMILES: O=C=Nc1ccc(Cl)cc1C(F)(F)F] | 4-Chloro-1-isocyanato-2-(trifluoromethyl)-benzene |
| CC_ICN-11 | 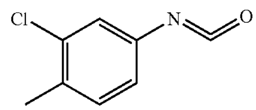 | 2-Chloro-4-isocyanato-1-methyl-benzene |
| CC_ICN-12 | 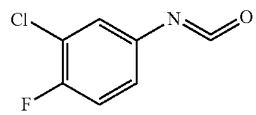 [SMILES: O=C=Nc1ccc(F)c(Cl)c1] | 2-Chloro-1-fluoro-4-isocyanate-benzene |
| CC_ICN-13 | 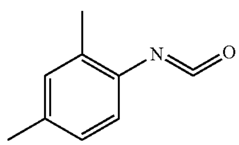 | 1-Isocyanato-2,4-dimethyl-benzene |
| CC_ICN-14 | 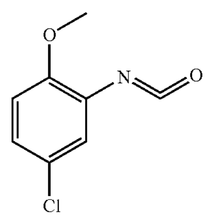 | 4-Chloro-2-isocyanato-1-methoxy-benzene |
| CC_ICN-15 | 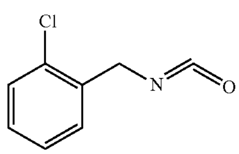 [SMILES: O=C=NCc1ccccc1Cl] | 1-Chloro-2-(isocyanato-methyl)-benzene |
| CC_ICN-16 | 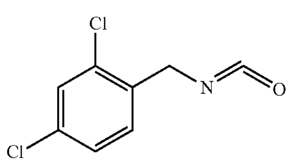 [SMILES: O=C=NCc1ccc(Cl)cc1Cl] | 2,4-Dichloro-1-(isocyanato-methyl)-benzene |
| CC_ACL-01 | 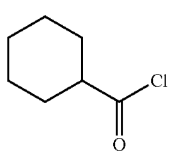 | Cyclohexanecarbonyl chloride |
| CC_ACL-02 | 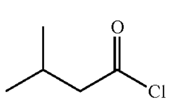 | 3-Methyl-butyryl chloride |
| CC_ACL-03 | 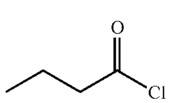 | Butyryl chloride |

| CC_AMN, CC_SCI, CC_ICN. | Structure | Name |
|---|---|---|
| CC_ACL-04 | 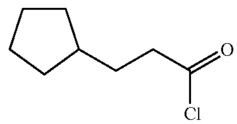 | 3-Cyclopentyl-propionyl chloride |
| CC_ACL-05 | 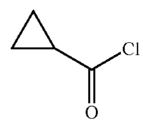 | Cyclopropanecarbonyl chloride |
| CC_ACL-06 | 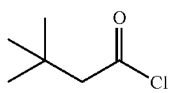 | 3,3-Dimethyl-butyryl chloride |
| CC_ACL-07 | 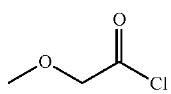 | 2-Methoxy-acetyl chloride |

All the CC_ACIs, CC_SCIs & CC_ICNs shown above are available commercially.

3) Parallel Synthesis of Dihydroindenes
General:

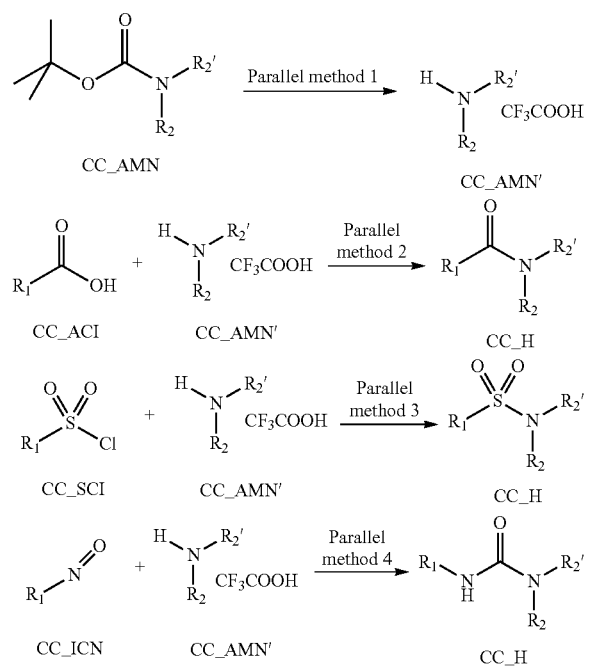

According to the above scheme, the amine structural units CC_AMN' were prepared from the Boc-protected amines CC_AMN according to parallel method 1. The amine trifluoroacetic acid salts CC_AMN' so obtained were reacted in a parallel synthesis, according to parallel method 2, with the acids CC_ACI to give amidic products CC_H. CC_AMN' were reacted in a parallel synthesis, according to parallel method 3, with the sulfonyl chlorides SCI_CC to give sulfonylated products CC_H. CC_AMN' were reacted in a parallel synthesis, according to parallel method 4, with the isocyanates CC_ICN to give ureas CC_H. The correlation of products (CC_H) with the structural units used (CC_ACI, CC_SCI, CC_ICN and AMN) is to be found in the synthesis matrix. The crude products of the parallel synthesis were analyzed by HPLC-MS and then purified by means of reverse phase HPLC-MS. The identity of the products could be determined by analytical HPLC-MS measurements. The crude products of the parallel synthesis were purified by column chromatography. The identity of the products could be determined by analytical HPLC-MS measurements (see HPLC-MS data).

Parallel Method 1: Boc Deprotection

20% trifluoroacetic acid in dichloromethane (10 ml/mol) was added at 0° C. to the corresponding Boc-protected amine (1 eq., CC_AMN). The resulting reaction mixture was stirred for 4 h at 25° C. The progress of the reaction was monitored by means of thin-layer chromatography. Then the solvent was removed under reduced pressure and drying was carried out carefully in order to eliminate traces of trifluoroacetic acid. The crude product so obtained was used for the synthesis of the libraries without being purified further.

Parallel Method 2: Amide Formation

HATU (2 eq.) was added at 0° C. to a dichloromethane solution (3 ml/mmol) of the acid structural unit CC_ACI (1 eq.), and stirring was carried out for 15 min. In a further round-bottomed flask, a dichloromethane solution (1 ml/mmol) of the Boc-deprotected amine structural unit CC_AMN' (1.5 eq.) was cooled in an ice bath; DIPEA (3 eq.) was added, and the mixture was then added at 0° C. to the acid structural unit. The reaction mixture was stirred for 16 h at room temperature and finally diluted with dichloromethane. The organic phase was washed in succession with aqueous NH$_4$Cl solution, Na$_2$CO$_3$ solution and sat. NaCl solution, dried over sodium sulfate and concentrated under reduced pressure. The crude product was purified via a Biotage parallel purification system. Some compounds were purified manually by column chromatography over neutral aluminium oxide with methanol/dichloromethane as eluent. A few compounds were purified by prep. HPLC using an aqueous ammonia method.

Parallel Method 3: Sulfonylation

At 0° C., diisopropylethylamine (3 eq.) was added dropwise to a suspension of CC_AMN' (1.5 eq.) in dichloromethane (1 ml/mmol), and stirring was carried out for a further 15 minutes. Then the sulfonyl chloride (CC_SCl) (1 eq.) in dichloromethane (3 ml/mmol) was added at 0° C., and the reaction mixture was stirred for 12 h at room temperature. The reaction mixture was diluted with dichloromethane, and the organic phase was washed in succession with water, aqueous sat. $Na_2CO_3$ solution and sat. NaCl solution, dried over sodium sulfate and concentrated under reduced pressure. The crude product was purified via a Biotage parallel purification system. Some compounds were purified manually by column chromatography over neutral aluminium oxide with methanol/dichloromethane as eluent. A few compounds were purified by prep. HPLC using an aqueous ammonia method.

Parallel Method 4: Urea Formation

At 0° C., diisopropylethylamine (0.5 eq.) was added dropwise to a suspension of the corresponding isocyanate CC_ICN (1 eq.) in dichloromethane (3 ml/mmol), and stirring was carried out for a further 15 minutes. Then the Boc-deprotected amine (CC_AMN') (1.5 eq.) in dichloromethane (1 ml/mmol) was added at 0° C., and cooling was carried out in an ice bath. Then the isocyanate (CC_ICN) (1 eq.) in dichloromethane (3 ml/mmol) was added at 0° C., and the reaction mixture was stirred for 16 h at room temperature. The reaction mixture was diluted with dichloromethane, and the organic phase was washed in succession with aqueous sat. $Na_2CO_3$ solution, water and sat. NaCl solution, dried over sodium sulfate and concentrated under reduced pressure. The crude product was purified via a Biotage purification system.

Examples & Synthesis Matrix:

| Example No. | Name | ACI_CC | Amine (AMN_CC) | Method No. |
|---|---|---|---|---|
| CC_H-01 | 3-Chloro-N-[6-[2-(1-pyridin-4-yl-piperidin-4-yl)-ethyl-carbamoyl]-2,3-dihydro-1H-inden-1-yl]-thiophene-2-carboxylic acid amide | 3-Chloro-thiophene-2-carboxylic acid (CC_ACI-10) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-02 | 3-[[(2-Chlorophenyl)-methyl-carbamoyl]amino]-N-[2-(1-pyridin-4-yl-piperidin-4-yl)-ethyl]-2,3-dihydro-1H-indene-5-carboxylic acid amide | 1-Chloro-2-(isocyanato-methyl)-benzene (CC_ICN-01) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-03 | 8-[(2,3-Dichloro-benzoyl)amino]-N-methyl-N-(1-pyridin-4-yl-piperidin-4-yl)-5,6,7,8-tetrahydro-naphthalene-2-carboxylic acid amide | 2,3-Dichloro-benzoic acid (CC_ACI-02) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-04 | 8-[(2-Chloro-5-fluoro-benzoyl)amino]-N-methyl-N-(1-pyridin-4-yl-piperidin-4-yl)-5,6,7,8-tetrahydro-naphthalene-2-carboxylic acid amide | 2-Chloro-5-fluoro-benzoic acid (CC_ACI-03) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-05 | 8-(Cyclohexanecarbonylamino)-N-methyl-N-(1-pyridin-4-yl-piperidin-4-yl)-5,6,7,8-tetrahydro-naphthalene-2-carboxylic acid amide | Cyclohexanecarboxylic acid (CC_ACI-07) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-06 | 8-(3-Cyclopentyl-propanoylamino)-N-methyl-N-(1-pyridin-4-yl-piperidin-4-yl)-5,6,7,8-tetrahydro-naphthalene-2-carboxylic acid amide | 3-Cyclopentyl-propionic acid (CC_ACI-08) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-07 | 3-Chloro-N-[7-[methyl-(1-pyridin-4-yl-piperidin-4-yl)-carbamoyl]-1,2,3,4-tetrahydro-naphthalen-1-yl]-thiophene-2-carboxylic acid amide | 3-Chloro-thiophene-2-carboxylic acid (CC_ACI-10) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-08 | N-[7-[Methyl-(1-pyridin-4-yl-piperidin-4-yl)-carbamoyl]-1,2,3,4-tetrahydro-naphthalen-1-yl]-pyrimidine-5-carboxylic acid amide | Pyrimidine-5-carboxylic acid (CC_ACI-12) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-09 | 8-[(2,6-Dimethyl-benzoyl)amino]-N-methyl-N-(1-pyridin-4-yl-piperidin-4-yl)-5,6,7,8-tetrahydro-naphthalene-2-carboxylic acid amide | 2,6-Dimethyl-benzoic acid (CC_ACI-05) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-10 | N-[7-[Methyl-(1-pyridin-4-yl-piperidin-4-yl)-carbamoyl]-1,2,3,4-tetrahydro-naphthalen-1-yl]-4-(trifluoromethyl)-pyridine-3-carboxylic acid amide | 4-(Trifluoromethyl)-pyridine-3-carboxylic acid (CC_ACI-11) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-11 | 8-[[2-Chloro-6-(trifluoromethyl)-benzoyl]amino]-N-methyl-N-(1-pyridin-4-yl-piperidin-4-yl)-5,6,7,8-tetrahydro-naphthalene-2-carboxylic acid amide | 2-Chloro-6-(trifluoromethyl)-benzoic acid (CC_ACI-04) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-12 | N-[3,3-Dimethyl-6-[methyl-(1-pyridin-4-yl-piperidin-4-yl)-carbamoyl]-1,2-dihydro-inden-1-yl]-4-(trifluoromethyl)-pyridine-3-carboxylic acid amide | 4-(Trifluoromethyl)-pyridine-3-carboxylic acid (CC_ACI-11) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-13 | 3-Chloro-N-[5-[methyl-(1-pyridin-4-yl-piperidin-4-yl)-carbamoyl]-2,3-dihydro-1H-inden-1-yl]-thiophene-2-carboxylic acid amide | 3-Chloro-thiophene-2-carboxylic acid (CC_ACI-10) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-14 | 3-(Cyclohexanecarbonylamino)-N,1,1-trimethyl-N-(1-pyridin-4-yl-piperidin-4-yl)-2,3-dihydro-indene-5-carboxylic acid amide | Cyclohexanecarboxylic acid (CC_ACI-07) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |

| Example No. | Name | ACI_CC | Amine (AMN_CC) | Method No. |
|---|---|---|---|---|
| CC_H-15 | 3-[[(2-Chlorophenyl)-methyl-carbamoyl]amino]-N,1,1-trimethyl-N-(1-pyridin-4-yl-piperidin-4-yl)-2,3-dihydro-indene-5-carboxylic acid amide | 1-Chloro-2-(isocyanato-methyl)-benzene (CC_ICN-01) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-16 | 8-[[[2-Chloro-6-(trifluoromethyl)-phenyl]sulfonyl]amino]-N-methyl-N-(1-pyridin-4-yl-piperidin-4-yl)-5,6,7,8-tetrahydro-naphthalene-2-carboxylic acid amide | 2-Chloro-6-(trifluoromethyl)-benzene sulfonyl chloride (CC_SCL-01) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-17 | 3-[[2-Chloro-6-(trifluoromethyl)-benzoyl]amino]-N,1,1-trimethyl-N-(1-pyridin-4-yl-piperidin-4-yl)-2,3-dihydro-indene-5-carboxylic acid amide | 2-Chloro-6-(trifluoromethyl)-benzoic acid (CC_ACI-04) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-18 | 3-(3-Cyclopentyl-propanoylamino)-N,1,1-trimethyl-N-(1-pyridin-4-yl-piperidin-4-yl)-2,3-dihydro-indene-5-carboxylic acid amide | 3-Cyclopentyl-propionic acid (CC_ACI-08) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-19 | 3-[(2,3-Dichloro-benzoyl)amino]-N,1,1-trimethyl-N-(1-pyridin-4-yl-piperidin-4-yl)-2,3-dihydro-indene-5-carboxylic acid amide | 2,3-Dichloro-benzoic acid (CC_ACI-02) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-20 | 3-Chloro-N-[3,3-dimethyl-6-[methyl-(1-pyridin-4-yl-piperidin-4-yl)-carbamoyl]-1,2-dihydro-inden-1-yl]-thiophene-2-carboxylic acid amide | 3-Chloro-thiophene-2-carboxylic acid (CC_ACI-10) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-21 | 3-[(2-Chloro-5-fluoro-benzoyl)amino]-N,1,1-trimethyl-N-(1-pyridin-4-yl-piperidin-4-yl)-2,3-dihydro-indene-5-carboxylic acid amide | 2-Chloro-5-fluoro-benzoic acid (CC_ACI-03) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-22 | N-[3,3-Dimethyl-6-[methyl-(1-pyridin-4-yl-piperidin-4-yl)-carbamoyl]-1,2-dihydro-inden-1-yl]-pyrimidine-5-carboxylic acid amide | Pyrimidine-5-carboxylic acid (CC_ACI-12) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-23 | 3-[(2-Chloro-benzoyl)amino]-N,1,1-trimethyl-N-(1-pyridin-4-yl-piperidin-4-yl)-2,3-dihydro-indene-5-carboxylic acid amide | 2-Chloro-benzoic acid (CC_ACI-01) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-24 | 3-[(2-Chloro-benzoyl)amino]-N-methyl-N-(1-pyridin-4-yl-piperidin-4-yl)-2,3-dihydro-1H-indene-5-carboxylic acid amide | 2-Chloro-benzoic acid (CC_ACI-01) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-25 | 3-[(2,3-Dichloro-benzoyl)-methyl-amino]-N-methyl-N-(1-pyridin-4-yl-piperidin-4-yl)-2,3-dihydro-1H-indene-5-carboxylic acid amide | 2,3-Dichloro-benzoic acid (CC_ACI-02) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-26 | 3-[(2-Chloro-5-fluoro-benzoyl)amino]-N-methyl-N-(1-pyridin-4-yl-piperidin-4-yl)-2,3-dihydro-1H-indene-5-carboxylic acid amide | 2-Chloro-5-fluoro-benzoic acid (CC_ACI-03) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-27 | 3-[(2-Chloro-5-fluoro-benzoyl)-methyl-amino]-N-methyl-N-(1-pyridin-4-yl-piperidin-4-yl)-2,3-dihydro-1H-indene-5-carboxylic acid amide | 2-Chloro-5-fluoro-benzoic acid (CC_ACI-03) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-28 | N-Methyl-3-[methyl-(3-methyl-butanoyl)-amino]-N-(1-pyridin-4-yl-piperidin-4-yl)-2,3-dihydro-1H-indene-5-carboxylic acid amide | 3-Methyl-butyric acid (CC_ACI-09) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-29 | 3-Chloro-N-[6-[methyl-(1-pyridin-4-yl-piperidin-4-yl)-carbamoyl]-2,3-dihydro-1H-inden-1-yl]-thiophene-2-carboxylic acid amide | 3-Chloro-thiophene-2-carboxylic acid (CC_ACI-10) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-30 | 3-Chloro-N-methyl-N-[6-[methyl-(1-pyridin-4-yl-piperidin-4-yl)-carbamoyl]-2,3-dihydro-1H-inden-1-yl]-thiophene-2-carboxylic acid amide | 3-Chloro-thiophene-2-carboxylic acid (CC_ACI-10) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-31 | N-[6-[Methyl-(1-pyridin-4-yl-piperidin-4-yl)-carbamoyl]-2,3-dihydro-1H-inden-1-yl]-4-(trifluoromethyl)-pyridine-3-carboxylic acid amide | 4-(Trifluoromethyl)-pyridine-3-carboxylic acid (CC_ACI-11) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-32 | N-Methyl-N-[6-[methyl-(1-pyridin-4-yl-piperidin-4-yl)-carbamoyl]-2,3-dihydro-1H-inden-1-yl]-4-(trifluoromethyl)-pyridine-3-carboxylic acid amide | 4-(Trifluoromethyl)-pyridine-3-carboxylic acid (CC_ACI-11) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-33 | 4-[(2-Chloro-benzoyl)amino]-N-methyl-N-(1-pyridin-4-yl-piperidin-4-yl)-3,4-dihydro-2H-chromene-6-carboxylic acid amide | 2-Chloro-benzoic acid (CC_ACI-01) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |

-continued

| Example No. | Name | ACI_CC | Amine (AMN_CC) | Method No. |
|---|---|---|---|---|
| CC_H-34 | 3-[(2-Chloro-benzoyl)amino]-N-[2-(1-pyridin-4-yl-piperidin-4-yl)-ethyl]-2,3-dihydro-1H-indene-5-carboxylic acid amide | 2-Chloro-benzoic acid (CC_ACI-01) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-35 | 4-[(2,3-Dichloro-benzoyl)amino]-N-methyl-N-[1-pyridin-4-yl-piperidin-4-yl]-3,4-dihydro-2H-chromene-6-carboxylic acid amide | 2,3-Dichloro-benzoic acid (CC_ACI-02) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-36 | 3-[(2-Chloro-5-fluoro-benzoyl)amino]-N-[2-(1-pyridin-4-yl-piperidin-4-yl)-ethyl]-2,3-dihydro-1H-indene-5-carboxylic acid amide | 2-Chloro-5-fluoro-benzoic acid (CC_ACI-03) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-37 | N-[6-[2-(1-Pyridin-4-yl-piperidin-4-yl)-ethyl]-carbamoyl]-2,3-dihydro-1H-inden-1-yl]-4-(trifluoromethyl)-pyridine-3-carboxylic acid amide | 4-(Trifluoromethyl)-pyridine-3-carboxylic acid (CC_ACI-11) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-38 | 4-(Cyclohexanecarbonylamino)-N-methyl-N-(1-pyridin-4-yl-piperidin-4-yl)-3,4-dihydro-2H-chromene-6-carboxylic acid amide | Cyclohexanecarboxylic acid (CC_ACI-07) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-39 | N-Methyl-4-(3-methyl-butanoylamino)-N-(1-pyridin-4-yl-piperidin-4-yl)-3,4-dihydro-2H-chromene-6-carboxylic acid amide | 3-Methyl-butyric acid (CC_ACI-09) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-40 | 4-[(3-Chloro-thiophene-2-carbonyl)amino]-N-methyl-N-(1-pyridin-4-yl-piperidin-4-yl)-3,4-dihydro-2H-chromene-6-carboxylic acid amide | 3-Chloro-thiophene-2-carboxylic acid (CC_ACI-10) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-41 | N-Methyl-3-(3-methyl-butanoylamino)-N-(1-pyridin-4-yl-piperidin-4-yl)-2,3-dihydro-1H-indene-5-carboxylic acid amide | 3-Methyl-butyric acid (CC_ACI-09) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-42 | N-[6-[Methyl-(1-pyridin-4-yl-piperidin-4-yl)-carbamoyl]-3,4-dihydro-2H-chromen-4-yl]-4-(trifluoromethyl)-pyridine-3-carboxylic acid amide | 4-(Trifluoromethyl)-pyridine-3-carboxylic acid (CC_ACI-11) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-43 | N,1,1-Trimethyl-3-(3-methyl-butanoylamino)-N-(1-pyridin-4-yl-piperidin-4-yl)-2,3-dihydro-indene-5-carboxylic acid amide | 3-Methyl-butyric acid (CC_ACI-09) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-44 | 3-[[[(2-Chlorophenyl)-methyl-carbamoyl]amino]-N-methyl-N-(1-pyridin-4-yl-piperidin-4-yl)-2,3-dihydro-1H-indene-5-carboxylic acid amide | 1-Chloro-2-(isocyanato-methyl)-benzene (CC_ICN-01) | 3-Amino-N-methyl-N-(1-pyridin-4-yl-piperidin-4-yl)-2,3-dihydro-1H-indene-5-carboxylic acid amide (CC_AMN-01) | No. 1 & No. 4 |
| CC_H-45 | N-Methyl-N-[6-[methyl-(1-pyridin-4-yl-piperidin-4-yl)-carbamoyl]-2,3-dihydro-1H-inden-1-yl]-pyrimidine-5-carboxylic acid amide | Pyrimidine-5-carboxylic acid (CC_ACI-12) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-46 | N-Methyl-3-[methyl-[[2-(trifluoromethyl)-phenyl]-methylsulfonyl]-amino]-N-(1-pyridin-4-yl-piperidin-4-yl)-2,3-dihydro-1H-indene-5-carboxylic acid amide | [2-(Trifluoromethyl)-phenyl]-methane sulfonyl chloride (CC_SCL-02) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-47 | 4-[[[2-Chloro-6-(trifluoromethyl)-phenyl]sulfonyl]amino]-N-methyl-N-(1-pyridin-4-yl-piperidin-4-yl)-3,4-dihydro-2H-chromene-6-carboxylic acid amide | 2-Chloro-6-(trifluoromethyl)-benzene sulfonyl chloride (CC_SCL-01) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-48 | N-[6-[Methyl-(1-pyridin-4-yl-piperidin-4-yl)-carbamoyl]-2,3-dihydro-1H-inden-1-yl]-pyrimidine-5-carboxylic acid amide | Pyrimidine-5-carboxylic acid (CC_ACI-12) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-49 | 4-(3-Cyclopentyl-propanoylamino)-N-methyl-N-(1-pyridin-4-yl-piperidin-4-yl)-3,4-dihydro-2H-chromene-6-carboxylic acid amide | 3-Cyclopentyl-propionic acid (CC_ACI-08) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-50 | 3-[[[2-Chloro-6-(trifluoromethyl)-phenyl]sulfonyl]amino]-N-[2-(1-pyridin-4-yl-piperidin-4-yl)-ethyl]-2,3-dihydro-1H-indene-5-carboxylic acid amide | 2-Chloro-6-(trifluoromethyl)-benzene sulfonyl chloride (CC_SCL-01) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 3 |
| CC_H-51 | 3-[[[(2-Chlorophenyl)-methyl-carbamoyl]-methyl-amino]-N-methyl-N-(1-pyridin-4-yl-piperidin-4-yl)-2,3-dihydro-1H-indene-5-carboxylic acid amide | 1-Chloro-2-(isocyanato-methyl)-benzene (CC_ICN-01) | N-Methyl-3-methylamino-N-(1-pyridin-4-yl-piperidin-4-yl)-2,3-dihydro-1H-indene-5-carboxylic acid amide (CC_AMN-02) | No. 1 & No. 4 |
| CC_H-52 | 3-[(2,3-Dichloro-benzoyl)amino]-N-(1-isoquinolin-6-yl-piperidin-4-yl)-N-methyl-2,3-dihydro-1H-indene-5-carboxylic acid amide | 2,3-Dichloro-benzoic acid (CC_ACI-02) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |

| Example No. | Name | ACI_CC | Amine (AMN_CC) | Method No. |
|---|---|---|---|---|
| CC_H-54 | 3-[[[2-Chloro-6-(trifluoromethyl)-phenyl]sulfonyl]amino]-N-methyl-N-(1-pyridin-4-yl-piperidin-4-yl)-2,3-dihydro-1H-indene-5-carboxylic acid amide | 2-Chloro-6-(trifluoromethyl)-benzene sulfonyl chloride (CC_SCL-01) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-55 | N-(1-Isoquinolin-6-yl-piperidin-4-yl)-N-methyl-3-[[[2-(trifluoromethyl)-phenyl]-methylsulfonyl]amino]-2,3-dihydro-1H-indene-5-carboxylic acid amide | [2-(Trifluoromethyl)-phenyl]-methane sulfonyl chloride (CC_SCL-02) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-56 | N-Methyl-N-(1-pyridin-4-yl-piperidin-4-yl)-4-[[[2-(trifluoromethyl)-phenyl]-methylsulfonyl]amino]-3,4-dihydro-2H-chromene-6-carboxylic acid amide | [2-(Trifluoromethyl)-phenyl]-methane sulfonyl chloride (CC_SCL-02) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-57 | 4-[[(2-Chlorophenyl)-methyl-carbamoyl]amino]-N-methyl-N-(1-pyridin-4-yl-piperidin-4-yl)-3,4-dihydro-2H-chromene-6-carboxylic acid amide | 1-Chloro-2-(isocyanato-methyl)-benzene (CC_ICN-01) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-58 | 1-(Cyclohexanecarbonylamino)-N-methyl-N-(1-pyridin-4-yl-piperidin-4-yl)-2,3-dihydro-1H-indene-5-carboxylic acid amide | Cyclohexanecarboxylic acid (CC_ACI-07) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-59 | 3-(3-Cyclopentyl-propanoylamino)-N-methyl-N-(1-pyridin-4-yl-piperidin-4-yl)-2,3-dihydro-1H-indene-5-carboxylic acid amide | 3-Cyclopentyl-propionic acid (CC_ACI-08) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-60 | N-[6-[(1-Isoquinolin-6-yl-piperidin-4-yl)-methyl-carbamoyl]-2,3-dihydro-1H-inden-1-yl]-4-(trifluoromethyl)-pyridine-3-carboxylic acid amide | 4-(Trifluoromethyl)-pyridine-3-carboxylic acid (CC_ACI-11) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-61 | N-Methyl-N-(1-pyridin-4-yl-piperidin-4-yl)-1-[[[2-(trifluoromethyl)-phenyl]-methylsulfonyl]amino]-2,3-dihydro-1H-indene-5-carboxylic acid amide | [2-(Trifluoromethyl)-phenyl]-methane sulfonyl chloride (CC_SCL-02) | 1-Amino-N-methyl-N-(1-pyridin-4-yl-piperidin-4-yl)-2,3-dihydro-1H-indene-5-carboxylic acid amide (CC_AMN-04) | No. 1 & No. 3 |
| CC_H-62 | 3-[[2-Chloro-6-(trifluoromethyl)-benzoyl]amino]-N-(1-isoquinolin-6-yl-piperidin-4-yl)-N-methyl-2,3-dihydro-1H-indene-5-carboxylic acid amide | 2-Chloro-6-(trifluoromethyl)-benzoic acid (CC_ACI-04) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-63 | 4-[(2-Chloro-5-fluoro-benzoyl)amino]-N-methyl-N-(1-pyridin-4-yl-piperidin-4-yl)-3,4-dihydro-2H-chromene-6-carboxylic acid amide | 2-Chloro-5-fluoro-benzoic acid (CC_ACI-03) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-64 | 1-[(2-Chloro-5-fluoro-benzoyl)amino]-N-methyl-N-(1-pyridin-4-yl-piperidin-4-yl)-2,3-dihydro-1H-indene-5-carboxylic acid amide | 2-Chloro-5-fluoro-benzoic acid (CC_ACI-03) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-65 | 1-(3-Cyclopentyl-propanoylamino)-N-methyl-N-(1-pyridin-4-yl-piperidin-4-yl)-2,3-dihydro-1H-indene-5-carboxylic acid amide | 3-Cyclopentyl-propionic acid (CC_ACI-08) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-66 | 1-[(2,6-Dimethyl-benzoyl)amino]-N-methyl-N-(1-pyridin-4-yl-piperidin-4-yl)-2,3-dihydro-1H-indene-5-carboxylic acid amide | 2,6-Dimethyl-benzoic acid (CC_ACI-05) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-67 | 1-[(2,3-Dichloro-benzoyl)amino]-N-methyl-N-(1-pyridin-4-yl-piperidin-4-yl)-2,3-dihydro-1H-indene-5-carboxylic acid amide | 2,3-Dichloro-benzoic acid (CC_ACI-02) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-68 | 1-[(2-Chloro-benzoyl)amino]-N-methyl-N-(1-pyridin-4-yl-piperidin-4-yl)-2,3-dihydro-1H-indene-5-carboxylic acid amide | 2-Chloro-benzoic acid (CC_ACI-01) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-69 | 3-(Cyclohexanecarbonyl-methyl-amino)-N-methyl-N-(1-pyridin-4-yl-piperidin-4-yl)-2,3-dihydro-1H-indene-5-carboxylic acid amide | Cyclohexanecarboxylic acid (CC_ACI-07) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-70 | 3-(3-Cyclopentyl-propanoyl-methyl-amino)-N-methyl-N-(1-pyridin-4-yl-piperidin-4-yl)-2,3-dihydro-1H-indene-5-carboxylic acid amide | 3-Cyclopentyl-propionic acid (CC_ACI-08) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-71 | 4-[(2,6-Dimethyl-benzoyl)amino]-N-methyl-N-(1-pyridin-4-yl-piperidin-4-yl)-3,4-dihydro-2H-chromene-6-carboxylic acid amide | 2,6-Dimethyl-benzoic acid (CC_ACI-05) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-72 | 4-[[2-Chloro-6-(trifluoromethyl)-benzoyl]amino]-N-methyl-N-(1-pyridin-4-yl-piperidin-4-yl)-3,4-dihydro-2H-chromene-6-carboxylic acid amide | 2-Chloro-6-(trifluoromethyl)-benzoic acid (CC_ACI-04) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |

-continued

| Example No. | Name | ACI_CC | Amine (AMN_CC) | Method No. |
|---|---|---|---|---|
| CC_H-73 | 8-[(2-Chloro-benzoyl)amino]-N-methyl-N-(1-pyridin-4-yl-piperidin-4-yl)-5,6,7,8-tetrahydro-naphthalene-2-carboxylic acid amide | 2-Chloro-benzoic acid (CC_ACI-01) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-74 | 3-[(2,3-Dichloro-benzoyl)amino]-N-[2-(1-pyridin-4-yl-piperidin-4-yl)-ethyl]-2,3-dihydro-1H-indene-5-carboxylic acid amide | 2,3-Dichloro-benzoic acid (CC_ACI-02) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-75 | 3-[(2-Chloro-benzoyl)amino]-N-(1-isoquinolin-6-yl-piperidin-4-yl)-N-methyl-2,3-dihydro-1H-indene-5-carboxylic acid amide | 2-Chloro-benzoic acid (CC_ACI-01) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-76 | 3-[(2-Chloro-5-fluoro-benzoyl)amino]-N-(1-isoquinolin-6-yl-piperidin-4-yl)-N-methyl-2,3-dihydro-1H-indene-5-carboxylic acid amide | 2-Chloro-5-fluoro-benzoic acid (CC_ACI-03) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-77 | 3-(Cyclohexanecarbonylamino)-N-(1-isoquinolin-6-yl-piperidin-4-yl)-N-methyl-2,3-dihydro-1H-indene-5-carboxylic acid amide | Cyclohexanecarboxylic acid (CC_ACI-07) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-78 | 3-(3-Cyclopentyl-propanoylamino)-N-(1-isoquinolin-6-yl-piperidin-4-yl)-N-methyl-2,3-dihydro-1H-indene-5-carboxylic acid amide | 3-Cyclopentyl-propionic acid (CC_ACI-08) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-79 | N-(1-Isoquinolin-6-yl-piperidin-4-yl)-N-methyl-3-(3-methyl-butanoylamino)-2,3-dihydro-1H-indene-5-carboxylic acid amide | 3-Methyl-butyric acid (CC_ACI-09) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-80 | 3-Chloro-N-[6-[(1-isoquinolin-6-yl-piperidin-4-yl)-methyl-carbamoyl]-2,3-dihydro-1H-inden-1-yl]-thiophene-2-carboxylic acid amide | 3-Chloro-thiophene-2-carboxylic acid (CC_ACI-10) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-81 | 3-(Cyclohexanecarbonyl-methyl-amino)-N-[1-(2,6-dimethyl-pyridin-4-yl)-piperidin-4-yl]-N-methyl-2,3-dihydro-1H-indene-5-carboxylic acid amide | Cyclohexanecarboxylic acid (CC_ACI-07) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-82 | 3-[(2-Chloro-5-fluoro-benzoyl)-methyl-amino]-N-[1-(2,6-dimethyl-pyridin-4-yl)-piperidin-4-yl]-N-methyl-2,3-dihydro-1H-indene-5-carboxylic acid amide | 2-Chloro-5-fluoro-benzoic acid (CC_ACI-03) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-83 | 3-[(2,3-Dichloro-benzoyl)-methyl-amino]-N-[1-(2,6-dimethyl-pyridin-4-yl)-piperidin-4-yl]-N-methyl-2,3-dihydro-1H-indene-5-carboxylic acid amide | 2,3-Dichloro-benzoic acid (CC_ACI-02) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-84 | 3-(3-Cyclopentyl-propanoyl-methyl-amino)-N-[1-(2,6-dimethyl-pyridin-4-yl)-piperidin-4-yl]-N-methyl-2,3-dihydro-1H-indene-5-carboxylic acid amide | 3-Cyclopentyl-propionic acid (CC_ACI-08) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-85 | 3-[(2,6-Dimethyl-benzoyl)amino]-N,1,1-trimethyl-N-(1-pyridin-4-yl-piperidin-4-yl)-2,3-dihydro-indene-5-carboxylic acid amide | 2,6-Dimethyl-benzoic acid (CC_ACI-05) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-86 | N-6-[[1-(2,6-Dimethyl-pyridin-4-yl)-piperidin-4-yl]-methyl-carbamoyl]-2,3-dihydro-1H-inden-1-yl]-N-methyl-4-(trifluoromethyl)-pyridine-3-carboxylic acid amide | 4-(Trifluoromethyl)-pyridine-3-carboxylic acid (CC_ACI-11) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-87 | 3-[(2-Chloro-benzoyl)-methyl-amino]-N-[1-(2,6-dimethyl-pyridin-4-yl)-piperidin-4-yl]-N-methyl-2,3-dihydro-1H-indene-5-carboxylic acid amide | 2-Chloro-benzoic acid (CC_ACI-01) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-88 | 3-Chloro-N-[6-[[1-(2,6-dimethyl-pyridin-4-yl)-piperidin-4-yl]-methyl-carbamoyl]-2,3-dihydro-1H-inden-1-yl]-N-methyl-thiophene-2-carboxylic acid amide | 3-Chloro-thiophene-2-carboxylic acid (CC_ACI-10) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-89 | N,1,1-Trimethyl-N-(1-pyridin-4-yl-piperidin-4-yl)-3-[[[2-(trifluoromethyl)-phenyl]-methylsulfonyl]amino]-2,3-dihydro-indene-5-carboxylic acid amide | [2-(Trifluoromethyl)-phenyl]-methane sulfonyl chloride (CC_SCL-02) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-90 | N-[1-(2,6-Dimethyl-pyridin-4-yl)-piperidin-4-yl]-N-methyl-3-[methyl-(3-methyl- | 3-Methyl-butyric acid (CC_ACI-09) | N-[1-(2,6-Dimethyl-pyridin-4-yl)-piperidin-4-yl]-N-methyl-3- | No. 1 & No. 2 |

| Example No. | Name | ACI_CC | Amine (AMN_CC) | Method No. |
|---|---|---|---|---|
| | butanoyl)-amino]-2,3-dihydro-1H-indene-5-carboxylic acid amide | | methylamino-2,3-dihydro-1H-indene-5-carboxylic acid amide (CC_AMN-08) | |
| CC_H-91 | 3-[(2,6-Dimethyl-benzoyl)-methyl-amino]-N-[1-(2,6-dimethyl-pyridin-4-yl)-piperidin-4-yl]-N-methyl-2,3-dihydro-1H-indene-5-carboxylic acid amide | 2,6-Dimethyl-benzoic acid (CC_ACI-05) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-92 | N-[6-[[1-(2,6-Dimethyl-pyridin-4-yl)-piperidin-4-yl]-methyl-carbamoyl]-2,3-dihydro-1H-inden-1-yl]-N-methyl-pyrimidine-5-carboxylic acid amide | Pyrimidine-5-carboxylic acid (CC_ACI-12) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 2 |
| CC_H-93 | 3-[[[2-Chloro-6-(trifluoromethyl)-phenyl]sulfonyl]amino]-N,1,1-trimethyl-N-(1-pyridin-4-yl-piperidin-4-yl)-2,3-dihydro-indene-5-carboxylic acid amide | 2-Chloro-6-(trifluoromethyl)-benzene sulfonyl chloride (CC_SCL-01) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-94 | 8-[[[(2-Chlorophenyl)-methyl-carbamoyl]amino]-N-methyl-N-(1-pyridin-4-yl-piperidin-4-yl)-5,6,7,8-tetrahydro-naphthalene-2-carboxylic acid amide | 1-Chloro-2-(isocyanato-methyl)-benzene (CC_ICN-01) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-95 | 3-[[2-(2-Chlorophenyl)-2-methyl-propanoyl]amino]-N,1,1-trimethyl-N-(1-pyridin-4-yl-piperidin-4-yl)-2,3-dihydro-indene-5-carboxylic acid amide | 2-(2-Chlorophenyl)-2-methyl-propionic acid (CC_ACI-06) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 2 |
| CC_H-96 | 3-[(2,3-Dichloro-benzoyl)amino]-N-[1-(2,6-dimethyl-pyridin-4-yl)-piperidin-4-yl]-N-methyl-2,3-dihydro-1H-indene-5-carboxylic acid amide | 2,3-Dichloro-benzoic acid (CC_ACI-02) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-97 | 4-[[2-(2-Chlorophenyl)-2-methyl-propanoyl]amino]-N-methyl-N-(1-pyridin-4-yl-piperidin-4-yl)-3,4-dihydro-2H-chromene-6-carboxylic acid amide | 2-(2-Chlorophenyl)-2-methyl-propionic acid (CC_ACI-06) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-98 | 3-[[2-(2-Chlorophenyl)-2-methyl-propanoyl]amino]-N-(1-isoquinolin-6-yl-piperidin-4-yl)-N-methyl-2,3-dihydro-1H-indene-5-carboxylic acid amide | 2-(2-Chlorophenyl)-2-methyl-propionic acid (CC_ACI-06) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-99 | 3-[(2-Chloro-benzoyl)amino]-N-[1-(2,6-dimethyl-pyridin-4-yl)-piperidin-4-yl]-N-methyl-2,3-dihydro-1H-indene-5-carboxylic acid amide | 2-Chloro-benzoic acid (CC_ACI-01) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-100 | 1-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide | 2-(2-Chlorophenyl)-2-methyl-propionic acid (CC_ACI-06) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-101 | 3-(3-Cyclopentyl-propanoylamino)-N-[2-(1-pyridin-4-yl-piperidin-4-yl)-ethyl]-2,3-dihydro-1H-indene-5-carboxylic acid amide | 3-Cyclopentyl-propionic acid (CC_ACI-08) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-102 | 8-[[2-(2-Chlorophenyl)-2-methyl-propanoyl]amino]-N-methyl-N-(1-pyridin-4-yl-piperidin-4-yl)-5,6,7,8-tetrahydro-naphthalene-2-carboxylic acid amide | 2-(2-Chlorophenyl)-2-methyl-propionic acid (CC_ACI-06) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-103 | 3-[[2-(2-Chlorophenyl)-2-methyl-propanoyl]amino]-N-[2-(1-pyridin-4-yl-piperidin-4-yl)-ethyl]-2,3-dihydro-1H-indene-5-carboxylic acid amide | 2-(2-Chlorophenyl)-2-methyl-propionic acid (CC_ACI-06) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-104 | 3-[[[(2-Chlorophenyl)-methyl-carbamoyl]amino]-N-(1-isoquinolin-6-yl-piperidin-4-yl)-N-methyl-2,3-dihydro-1H-indene-5-carboxylic acid amide | 1-Chloro-2-(isocyanato-methyl)-benzene (CC_ICN-01) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-105 | 3-[(2,6-Dimethyl-benzoyl)amino]-N-[2-(1-pyridin-4-yl-piperidin-4-yl)-ethyl]-2,3-dihydro-1H-indene-5-carboxylic acid amide | 2,6-Dimethyl-benzoic acid (CC_ACI-05) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-106 | 3-[(2-Chloro-benzoyl)-methyl-amino]-N-methyl-N-(1-pyridin-4-yl-piperidin-4-yl)-2,3-dihydro-1H-indene-5-carboxylic acid amide | 2-Chloro-benzoic acid (CC_ACI-01) | N-Methyl-3-methylamino-N-(1-pyridin-4-yl-piperidin-4-yl)-2,3-dihydro-1H-indene-5-carboxylic acid amide (CC_AMN-02) | No. 1 & No. 2 |
| CC_H-107 | 3-[[2-Chloro-6-(trifluoromethyl)-benzoyl]amino]-N-[1-(2,6-dimethyl-pyridin-4-yl)-piperidin-4-yl]-N-methyl-2,3-dihydro-1H-indene-5-carboxylic acid amide | 2-Chloro-6-(trifluoromethyl)-benzoic acid (CC_ACI-04) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-108 | 3-[[2-Chloro-6-(trifluoromethyl)-benzoyl]-methyl-amino]-N-[1-(2,6-dimethyl-pyridin-4-yl)-piperidin-4-yl]-N-methyl-2,3-dihydro- | 2-Chloro-6-(trifluoromethyl)-benzoic acid (CC_ACI-04) | N-[1-(2,6-Dimethyl-pyridin-4-yl)-piperidin-4-yl]-N-methyl-3-methylamino-2,3-dihydro-1H- | No. 1 & No. 2 |

| Example No. | Name | ACI_CC | Amine (AMN_CC) | Method No. |
|---|---|---|---|---|
| | 1H-indene-5-carboxylic acid amide | | indene-5-carboxylic acid amide (CC_AMN-08) | |
| CC_H-109 | 3-Chloro-N-[6-[[1-(2,6-dimethyl-pyridin-4-yl)-piperidin-4-yl]-methyl-carbamoyl]-2,3-dihydro-1H-inden-1-yl]-thiophene-2-carboxylic acid amide | 3-Chloro-thiophene-2-carboxylic acid (CC_ACI-10) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-110 | N-[5-[Methyl-(1-pyridin-4-yl-piperidin-4-yl)-carbamoyl]-2,3-dihydro-1H-inden-1-yl]-4-(trifluoromethyl)-pyridine-3-carboxylic acid amide | 4-(Trifluoromethyl)-pyridine-3-carboxylic acid (CC_ACI-11) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-111 | 3-[[[2-Chloro-6-(trifluoromethyl)-phenyl]sulfonyl]amino]-N-[1-(2,6-dimethyl-pyridin-4-yl)-piperidin-4-yl]-N-methyl-2,3-dihydro-1H-indene-5-carboxylic acid amide | 2-Chloro-6-(trifluoromethyl)-benzene sulfonyl chloride (CC_SCL-01) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-112 | N-[6-[[1-(2,6-Dimethyl-pyridin-4-yl)-piperidin-4-yl]-methyl-carbamoyl]-2,3-dihydro-1H-inden-1-yl]-4-(trifluoromethyl)-pyridine-3-carboxylic acid amide | 4-(Trifluoromethyl)-pyridine-3-carboxylic acid (CC_ACI-11) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-113 | N-Methyl-1-(3-methyl-butanoylamino)-N-(1-pyridin-4-yl-piperidin-4-yl)-2,3-dihydro-1H-indene-5-carboxylic acid amide | 3-Methyl-butyric acid (CC_ACI-09) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-114 | N-[6-[2-(1-Pyridin-4-yl-piperidin-4-yl)-ethyl-carbamoyl]-2,3-dihydro-1H-inden-1-yl]-pyrimidine-5-carboxylic acid amide | Pyrimidine-5-carboxylic acid (CC_ACI-12) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-115 | 3-[(2,6-Dimethyl-benzoyl)amino]-N-[1-(2,6-dimethyl-pyridin-4-yl)-piperidin-4-yl]-N-methyl-2,3-dihydro-1H-indene-5-carboxylic acid amide | 2,6-Dimethyl-benzoic acid (CC_ACI-05) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-116 | 3-(Cyclohexanecarbonylamino)-N-[2-(1-pyridin-4-yl-piperidin-4-yl)-ethyl]-2,3-dihydro-1H-indene-5-carboxylic acid amide | Cyclohexanecarboxylic acid (CC_ACI-07) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-117 | 3-[(2,3-Dichloro-benzoyl)amino]-N-methyl-N-(1-pyridin-4-yl-piperidin-4-yl)-2,3-dihydro-1H-indene-5-carboxylic acid amide | 2,3-Dichloro-benzoic acid (CC_ACI-02) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-118 | N-[6-[[1-(2,6-Dimethyl-pyridin-4-yl)-piperidin-4-yl]-methyl-carbamoyl]-2,3-dihydro-1H-inden-1-yl]-pyrimidine-5-carboxylic acid amide | Pyrimidine-5-carboxylic acid (CC_ACI-12) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-119 | 3-[(2-Chloro-5-fluoro-benzoyl)amino]-N-[1-(2,6-dimethyl-pyridin-4-yl)-piperidin-4-yl]-N-methyl-2,3-dihydro-1H-indene-5-carboxylic acid amide | 2-Chloro-5-fluoro-benzoic acid (CC_ACI-03) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-120 | 3-(3-Cyclopentyl-propanoylamino)-N-[1-(2,6-dimethyl-pyridin-4-yl)-piperidin-4-yl]-N-methyl-2,3-dihydro-1H-indene-5-carboxylic acid amide | 3-Cyclopentyl-propionic acid (CC_ACI-08) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-121 | N-[1-(2,6-Dimethyl-pyridin-4-yl)-piperidin-4-yl]-N-methyl-3-[[[2-(trifluoromethyl)-phenyl]-methylsulfonyl]amino]-2,3-dihydro-1H-indene-5-carboxylic acid amide | [2-(Trifluoromethyl)-phenyl]-methane sulfonyl chloride (CC_SCL-02) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-122 | N-[1-(2,6-Dimethyl-pyridin-4-yl)-piperidin-4-yl]-N-methyl-3-(3-methyl-butanoylamino)-2,3-dihydro-1H-indene-5-carboxylic acid amide | 3-Methyl-butyric acid (CC_ACI-09) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-123 | 3-(Cyclohexanecarbonylamino)-N-[1-(2,6-dimethyl-pyridin-4-yl)-piperidin-4-yl]-N-methyl-2,3-dihydro-1H-indene-5-carboxylic acid amide | Cyclohexanecarboxylic acid (CC_ACI-07) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-124 | N-[6-[Methyl-(1-pyridin-4-yl-piperidin-4-yl)-carbamoyl]-3,4-dihydro-2H-chromen-4-yl]-pyrimidine-5-carboxylic acid amide | Pyrimidine-5-carboxylic acid (CC_ACI-12) | 4-Amino-N-methyl-N-(1-pyridin-4-yl-piperidin-4-yl)-3,4-dihydro-2H-chromene-6-carboxylic acid amide (CC_AMN-06) | No. 1 & No. 2 |
| CC_H-125 | N-Methyl-N-(1-pyridin-4-yl-piperidin-4-yl)-8-[[[2-(trifluoromethyl)-phenyl]- | [2-(Trifluoromethyl)-phenyl]-methane sulfonyl chloride | 8-Amino-N-methyl-N-(1-pyridin-4-yl-piperidin-4-yl)-5,6,7,8-tetrahydro- | No. 1 & No. 3 |

| Example No. | Name | ACI_CC | Amine (AMN_CC) | Method No. |
|---|---|---|---|---|
| | methylsulfonyl]amino]-5,6,7,8-tetrahydro-naphthalene-2-carboxylic acid amide | (CC_SCL-02) | naphthalene-2-carboxylic acid amide (CC_AMN-05) | |
| CC_H-126 | 1-[[[(2-Chlorophenyl)-methyl-carbamoyl]amino]-N-methyl-N-(1-pyridin-4-yl-piperidin-4-yl)-2,3-dihydro-1H-indene-5-carboxylic acid amide | 1-Chloro-2-(isocyanato-methyl)-benzene (CC_ICN-01) | 1-Amino-N-methyl-N-(1-pyridin-4-yl-piperidin-4-yl)-2,3-dihydro-1H-indene-5-carboxylic acid amide (CC_AMN-04) | No. 1 & No. 4 |
| CC_H-127 | 1-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide | 2-Chloro-6-(trifluoromethyl)-benzoic acid (CC_ACI-04) | 1-Amino-N-methyl-N-(1-pyridin-4-yl-piperidin-4-yl)-2,3-dihydro-1H-indene-5-carboxylic acid amide (CC_AMN-04) | No. 1 & No. 2 |
| CC_H-128 | N-[2-(1-Pyridin-4-yl-piperidin-4-yl)-ethyl]-3-[[[2-(trifluoromethyl)-phenyl]-methylsulfonyl]amino]-2,3-dihydro-1H-indene-5-carboxylic acid amide | [2-(Trifluoromethyl)-phenyl]-methane sulfonyl chloride (CC_SCL-02) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 3 |
| CC_H-129 | N-[1-(2,6-Dimethyl-pyridin-4-yl)-piperidin-4-yl]-N-methyl-3-[methyl-[[2-(trifluoromethyl)-phenyl]-methylsulfonyl]-amino]-2,3-dihydro-1H-indene-5-carboxylic acid amide | [2-(Trifluoromethyl)-phenyl]-methane sulfonyl chloride (CC_SCL-02) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-130 | N-[6-[(1-Isoquinolin-6-yl-piperidin-4-yl)-methyl-carbamoyl]-2,3-dihydro-1H-inden-1-yl]-pyrimidine-5-carboxylic acid amide | Pyrimidine-5-carboxylic acid (CC_ACI-12) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-131 | 3-[[2-(2-Chlorophenyl)-2-methyl-propanoyl]amino]-N-[1-(2,6-dimethyl-pyridin-4-yl)-piperidin-4-yl]-N-methyl-2,3-dihydro-1H-indene-5-carboxylic acid amide | 2-(2-Chlorophenyl)-2-methyl-propionic acid (CC_ACI-06) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 2 |
| CC_H-132 | 3-(3-Methyl-butanoylamino)-N-[2-(1-pyridin-4-yl-piperidin-4-yl)-ethyl]-2,3-dihydro-1H-indene-5-carboxylic acid amide | 3-Methyl-butyric acid (CC_ACI-09) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-133 | 3-[(2,6-Dimethyl-benzoyl)amino]-N-(1-isoquinolin-6-yl-piperidin-4-yl)-N-methyl-2,3-dihydro-1H-indene-5-carboxylic acid amide | 2,6-Dimethyl-benzoic acid (CC_ACI-05) | 3-Amino-N-(1-isoquinolin-6-yl-piperidin-4-yl)-N-methyl-2,3-dihydro-1H-indene-5-carboxylic acid amide (CC_AMN-09) | No. 1 & No. 2 |
| CC_H-134 | 3-[[[2-Chloro-6-(trifluoromethyl)-phenyl]sulfonyl]-methyl-amino]-N-[1-(2,6-dimethyl-pyridin-4-yl)-piperidin-4-yl]-N-methyl-2,3-dihydro-1H-indene-5-carboxylic acid amide | 2-Chloro-6-(trifluoromethyl)-benzene sulfonyl chloride (CC_SCL-01) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-135 | N-Methyl-8-(3-methyl-butanoylamino)-N-(1-pyridin-4-yl-piperidin-4-yl)-5,6,7,8-tetrahydro-naphthalene-2-carboxylic acid amide | 3-Methyl-butyric acid (CC_ACI-09) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 2 |
| CC_H-136 | 3-[[2-Chloro-6-(trifluoromethyl)-benzoyl]amino]-N-[2-(1-pyridin-4-yl-piperidin-4-yl)-ethyl]-2,3-dihydro-1H-indene-5-carboxylic acid amide | 2-Chloro-6-(trifluoromethyl)-benzoic acid (CC_ACI-04) | 3-Amino-N-[2-(1-pyridin-4-yl-piperidin-4-yl)-ethyl]-2,3-dihydro-1H-indene-5-carboxylic acid amide (CC_AMN-11) | No. 1 & No. 2 |
| CC_H-137 | 3-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide | 2-Chloro-6-(trifluoromethyl)-benzoic acid (CC_ACI-04) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-138 | 3-[(2,6-Dimethyl-benzoyl)amino]-N-methyl-N-(1-pyridin-4-yl-piperidin-4-yl)-2,3-dihydro-1H-indene-5-carboxylic acid amide | 2,6-Dimethyl-benzoic acid (CC_ACI-05) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-139 | 3-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide | 2-(2-Chlorophenyl)-2-methyl-propionic acid (CC_ACI-06) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-140 | 3-(Cyclohexanecarbonylamino)-N-methyl-N-(1-pyridin-4-yl-piperidin-4-yl)-2,3-dihydro-1H-indene-5-carboxylic acid amide | Cyclohexanecarboxylic acid (CC_ACI-07) | 3-Amino-N-methyl-N-(1-pyridin-4-yl-piperidin-4-yl)-2,3-dihydro-1H-indene-5-carboxylic acid amide (CC_AMN-01) | No. 1 & No. 2 |
| CC_H-141 | N-Methyl-N-(1-pyridin-4-yl-piperidin-4-yl)-3-[[[2-(trifluoromethyl)-phenyl]-methylsulfonyl]amino]-2,3-dihydro-1H-indene-5-carboxylic acid amide | [2-(Trifluoromethyl)-phenyl]-methane sulfonyl chloride (CC_SCL-02) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-142 | 3-[[[(2-Chlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide | 1-Chloro-2-(isocyanato-methyl)-benzene (CC_ICN-01) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-143 | 1-[[[2-Chloro-6-(trifluoromethyl)-phenyl]sulfonyl]amino]-N-methyl-N-(1- | 2-Chloro-6-(trifluoromethyl)-benzene sulfonyl chloride | 1-Amino-N-methyl-N-(1-pyridin-4-yl-piperidin-4-yl)-2,3-dihydro-1H- | No. 1 & No. 3 |

-continued

| Example No. | Name | ACL_CC | Amine (AMN_CC) | Method No. |
|---|---|---|---|---|
| | pyridin-4-yl-piperidin-4-yl)-2,3-dihydro-1H-indene-5-carboxylic acid amide | (CC_SCL-01) | indene-5-carboxylic acid amide (CC_AMN-04) | |
| CC_H-200 | 3-[(2-Chloro-5-fluoro-benzoyl)amino]-N-methyl-N-(1-pyridin-4-yl-piperidin-4-yl)-2,3-dihydro-1H-indene-5-carboxylic acid amide (CC_H-200) | 2-Chloro-5-fluoro-benzoyl chloride (CC_ACL-09) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-201 | 3-[[2-Chloro-5-(trifluoromethyl)-benzoyl]amino]-N-methyl-N-(1-pyridin-4-yl-piperidin-4-yl)-2,3-dihydro-1H-indene-5-carboxylic acid amide (CC_H-201) | 2-Chloro-5-(trifluoromethyl)-benzoyl chloride (CC_ACL-10) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-202 | 3-[(2-Chloro-6-fluoro-3-methyl-benzoyl)amino]-N-methyl-N-(1-pyridin-4-yl-piperidin-4-yl)-2,3-dihydro-1H-indene-5-carboxylic acid amide (CC_H-202) | 2-Chloro-6-fluoro-3-methyl-benzoyl chloride (CC_ACL-11) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-203 | 3-[(2,5-Dichloro-benzoyl)amino]-N-methyl-N-(1-pyridin-4-yl-piperidin-4-yl)-2,3-dihydro-1H-indene-5-carboxylic acid amide (CC_H-203) | 2,5-Dichloro-benzoyl chloride (CC_ACL-12) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-204 | 3-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide (CC_H-204) | 2-Chloro-6-(trifluoromethyl)-benzoyl chloride (CC_ACL-13) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-205 | 3-(Cyclopropanecarbonylamino)-N-methyl-N-(1-pyridin-4-yl-piperidin-4-yl)-2,3-dihydro-1H-indene-5-carboxylic acid amide (CC_H-205) | Cyclopropanecarbonyl chloride (CC_ACL-05) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-206 | 3-(3,3-Dimethyl-butanoylamino)-N-methyl-N-(1-pyridin-4-yl-piperidin-4-yl)-2,3-dihydro-1H-indene-5-carboxylic acid amide (CC_H-206) | 3,3-Dimethyl-butyryl chloride (CC_ACL-06) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-207 | 3-[(2-Methoxy-acetyl)amino]-N-methyl-N-(1-pyridin-4-yl-piperidin-4-yl)-2,3-dihydro-1H-indene-5-carboxylic acid amide (CC_H-207) | 2-Methoxy-acetyl chloride (CC_ACL-07) | 3-Amino-N-methyl-N-(1-pyridin-4-yl-piperidin-4-yl)-2,3-dihydro-1H-indene-5-carboxylic acid amide (CC_AMN-01) | No. 1 & No. 3 |
| CC_H-208 | 3-[(2-Chloro-5-fluoro-benzoyl)-methyl-amino]-N-methyl-N-(1-pyridin-4-yl-piperidin-4-yl)-2,3-dihydro-1H-indene-5-carboxylic acid amide (CC_H-208) | 2-Chloro-5-fluoro-benzoyl chloride (CC_ACL-09) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-209 | 3-[(2-Chloro-6-fluoro-3-methyl-benzoyl)-methyl-amino]-N-methyl-N-(1-pyridin-4-yl-piperidin-4-yl)-2,3-dihydro-1H-indene-5-carboxylic acid amide (CC_H-209) | 2-Chloro-6-fluoro-3-methyl-benzoyl chloride (CC_ACL-11) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-210 | 3-[(2,5-Dichloro-benzoyl)-methyl-amino]-N-methyl-N-(1-pyridin-4-yl-piperidin-4-yl)-2,3-dihydro-1H-indene-5-carboxylic acid amide (CC_H-210) | 2,5-Dichloro-benzoyl chloride (CC_ACL-12) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-211 | 3-(Cyclohexanecarbonyl-methyl-amino)-N-methyl-N-(1-pyridin-4-yl-piperidin-4-yl)-2,3-dihydro-1H-indene-5-carboxylic acid amide (CC_H-211) | Cyclohexanecarbonyl chloride (CC_ACL-01) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-212 | 3-(Cyclopropanecarbonyl-methyl-amino)-N-methyl-N-(1-pyridin-4-yl-piperidin-4-yl)-2,3-dihydro-1H-indene-5-carboxylic acid amide (CC_H-212) | Cyclopropanecarbonyl chloride (CC_ACL-05) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-213 | 3-(3,3-Dimethyl-butanoyl-methyl-amino)-N-methyl-N-(1-pyridin-4-yl-piperidin-4-yl)-2,3-dihydro-1H-indene-5-carboxylic acid amide (CC_H-213) | 3,3-Dimethyl-butyryl chloride (CC_ACL-06) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-214 | 3-[(2-Methoxy-acetyl)-methyl-amino]-N-methyl-N-(1-pyridin-4-yl-piperidin-4-yl)-2,3-dihydro-1H-indene-5-carboxylic acid amide (CC_H-214) | 2-Methoxy-acetyl chloride (CC_ACL-07) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-215 | 3-(Acetyl-methyl-amino)-N-methyl-N-(1-pyridin-4-yl-piperidin-4-yl)-2,3-dihydro-1H-indene-5-carboxylic acid amide (CC_H-215) | Acetyl chloride (CC_SCL-07) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-216 | 3-[[2-Chloro-3-(trifluoromethyl)-benzoyl]-methyl-amino]-N-methyl-N-(1-pyridin-4-yl-piperidin-4-yl)-2,3-dihydro-1H-indene-5-carboxylic acid amide (CC_H-216) | 2-Chloro-3-(trifluoromethyl)-benzoyl chloride (CC_ACL-08) | N-Methyl-3-methylamino-N-(1-pyridin-4-yl-piperidin-4-yl)-2,3-dihydro-1H-indene-5-carboxylic acid amide (CC_AMN-02) | No. 1 & No. 3 |
| CC_H-217 | 3-[[(2-Chlorophenyl)-carbamoyl]-methyl-amino]-N-methyl-N-(1-pyridin-4-yl-piperidin-4-yl)-2,3-dihydro-1H-indene-5-carboxylic acid amide (CC_H-217) | 1-Chloro-2-isocyanato-benzene (CC_ICN-02) | N-Methyl-3-methylamino-N-(1-pyridin-4-yl-piperidin-4-yl)-2,3-dihydro-1H-indene-5-carboxylic acid amide (CC_AMN-02) | No. 1 & No. 4 |
| CC_H-218 | 3-[[(3-Chlorophenyl)-carbamoyl]-methyl-amino]-N-methyl-N-(1-pyridin-4-yl- | 1-Chloro-3-isocyanato-benzene (CC_ICN-03) | N-Methyl-3-methylamino-N-(1-pyridin-4-yl-piperidin-4-yl)-2,3- | No. 1 & No. 4 |

-continued

| Example No. | Name | ACL_CC | Amine (AMN_CC) | Method No. |
|---|---|---|---|---|
| | piperidin-4-yl)-2,3-dihydro-1H-indene-5-carboxylic acid amide (CC_H-218) | | dihydro-1H-indene-5-carboxylic acid amide (CC_AMN-02) | |
| CC_H-219 | 3-[[(2,6-Dichloro-phenyl)-carbamoyl]-methyl-amino]-N-methyl-N-(1-pyridin-4-yl-piperidin-4-yl)-2,3-dihydro-1H-indene-5-carboxylic acid amide (CC_H-219) | 1,3-Dichloro-2-isocyanato-benzene (CC_ICN-04) | N-Methyl-3-methylamino-N-(1-pyridin-4-yl-piperidin-4-yl)-2,3-dihydro-1H-indene-5-carboxylic acid amide (CC_AMN-02) | No. 1 & No. 4 |
| CC_H-220 | 3-[[(2,3-Dichloro-phenyl)-carbamoyl]-methyl-amino]-N-methyl-N-(1-pyridin-4-yl-piperidin-4-yl)-2,3-dihydro-1H-indene-5-carboxylic acid amide (CC_H-220) | 1,2-Dichloro-3-isocyanato-benzene (CC_ICN-05) | N-Methyl-3-methylamino-N-(1-pyridin-4-yl-piperidin-4-yl)-2,3-dihydro-1H-indene-5-carboxylic acid amide (CC_AMN-02) | No. 1 & No. 4 |
| CC_H-221 | 3-[[(2,5-Dichloro-phenyl)-carbamoyl]-methyl-amino]-N-methyl-N-(1-pyridin-4-yl-piperidin-4-yl)-2,3-dihydro-1H-indene-5-carboxylic acid amide (CC_H-221) | 1,4-Dichloro-2-isocyanato-benzene (CC_ICN-06) | N-Methyl-3-methylamino-N-(1-pyridin-4-yl-piperidin-4-yl)-2,3-dihydro-1H-indene-5-carboxylic acid amide (CC_AMN-02) | No. 1 & No. 4 |
| CC_H-222 | 3-[(2-Chloro-5-fluoro-benzoyl)amino]-N,1,1-trimethyl-N-(1-pyridin-4-yl-piperidin-4-yl)-2,3-dihydro-indene-5-carboxylic acid amide (CC_H-222) | 2-Chloro-5-fluoro-benzoyl chloride (CC_ACL-09) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-223 | 3-[[2-Chloro-5-(trifluoromethyl)-benzoyl]amino]-N,1,1-trimethyl-N-(1-pyridin-4-yl-piperidin-4-yl)-2,3-dihydro-indene-5-carboxylic acid amide (CC_H-223) | 2-Chloro-5-(trifluoromethyl)-benzoyl chloride (CC_ACL-10) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-224 | 3-[(2-Chloro-6-fluoro-3-methyl-benzoyl)amino]-N,1,1-trimethyl-N-(1-pyridin-4-yl-piperidin-4-yl)-2,3-dihydro-indene-5-carboxylic acid amide (CC_H-224) | 2-Chloro-6-fluoro-3-methyl-benzoyl chloride (CC_ACL-11) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-225 | 3-[[2-Chloro-6-(trifluoromethyl)-benzoyl]amino]-N,1,1-trimethyl-N-(1-pyridin-4-yl-piperidin-4-yl)-2,3-dihydro-indene-5-carboxylic acid amide (CC_H-225) | 2-Chloro-6-(trifluoromethyl)-benzoyl chloride (CC_ACL-13) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-226 | 3-(Cyclopropanecarbonylamino)-N,1,1-trimethyl-N-(1-pyridin-4-yl-piperidin-4-yl)-2,3-dihydro-indene-5-carboxylic acid amide (CC_H-226) | Cyclopropanecarbonyl chloride (CC_ACL-05) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-227 | 3-(3,3-Dimethyl-butanoylamino)-N,1,1-trimethyl-N-(1-pyridin-4-yl-piperidin-4-yl)-2,3-dihydro-indene-5-carboxylic acid amide (CC_H-227) | 3,3-Dimethyl-butyryl chloride (CC_ACL-06) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-228 | 3-[(2-Methoxy-acetyl)amino]-N,1,1-trimethyl-N-(1-pyridin-4-yl-piperidin-4-yl)-2,3-dihydro-indene-5-carboxylic acid amide (CC_H-228) | 2-Methoxy-acetyl chloride (CC_ACL-07) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-229 | 3-Acetylamino-N,1,1-trimethyl-N-(1-pyridin-4-yl-piperidin-4-yl)-2,3-dihydro-indene-5-carboxylic acid amide (CC_H-229) | Acetyl chloride (CC_SCL-07) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-230 | 3-[[(2-Chloro-6-methyl-phenyl)sulfonyl]amino]-N,1,1-trimethyl-N-(1-pyridin-4-yl-piperidin-4-yl)-2,3-dihydro-indene-5-carboxylic acid amide (CC_H-230) | 2-Chloro-6-methyl-benzenesulfonyl chloride (CC_SCL-11) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-231 | 3-[[2-Chloro-3-(trifluoromethyl)-benzoyl]amino]-N,1,1-trimethyl-N-(1-pyridin-4-yl-piperidin-4-yl)-2,3-dihydro-indene-5-carboxylic acid amide (CC_H-231) | 2-Chloro-3-(trifluoromethyl)-benzoyl chloride (CC_ACL-08) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 3 |
| CC_H-232 | 3-[[(2-Chlorophenyl)-carbamoyl]amino]-N,1,1-trimethyl-N-(1-pyridin-4-yl-piperidin-4-yl)-2,3-dihydro-indene-5-carboxylic acid amide (CC_H-232) | 1-Chloro-2-isocyanato-benzene (CC_ICN-02) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-233 | 3-[[(3-Chlorophenyl)-carbamoyl]amino]-N,1,1-trimethyl-N-(1-pyridin-4-yl-piperidin-4-yl)-2,3-dihydro-indene-5-carboxylic acid amide (CC_H-233) | 1-Chloro-3-isocyanato-benzene (CC_ICN-03) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-234 | 3-[[(2,6-Dichloro-phenyl)-carbamoyl]amino]-N,1,1-trimethyl-N-(1-pyridin-4-yl-piperidin-4-yl)-2,3-dihydro-indene-5-carboxylic acid amide (CC_H-234) | 1,3-Dichloro-2-isocyanato-benzene (CC_ICN-04) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-235 | 3-[[(2,3-Dichloro-phenyl)-carbamoyl]amino]-N,1,1-trimethyl-N-(1-pyridin-4-yl-piperidin-4-yl)-2,3-dihydro-indene-5-carboxylic acid amide (CC_H-235) | 1,2-Dichloro-3-isocyanato-benzene (CC_ICN-05) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |

-continued

| Example No. | Name | ACL_CC | Amine (AMN_CC) | Method No. |
|---|---|---|---|---|
| CC_H-236 | 3-[[(2,5-Dichloro-phenyl)-carbamoyl]amino]-N,1,1-trimethyl-N-(1-pyridin-4-yl-piperidin-4-yl)-2,3-dihydro-indene-5-carboxylic acid amide (CC_H-236) | 1,4-Dichloro-2-isocyanato-benzene (CC_ICN-06) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-237 | 3-[[(3,5-Dichloro-phenyl)-carbamoyl]amino]-N,1,1-trimethyl-N-(1-pyridin-4-yl-piperidin-4-yl)-2,3-dihydro-indene-5-carboxylic acid amide (CC_H-237) | 1,3-Dichloro-5-isocyanato-benzene (CC_ICN-07) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-238 | 3-[[(2,4-Dichlorophenyl)-carbamoyl]amino]-N,1,1-trimethyl-N-(1-pyridin-4-yl-piperidin-4-yl)-2,3-dihydro-indene-5-carboxylic acid amide (CC_H-238) | 2,4-Dichloro-1-isocyanato-benzene (CC_ICN-08) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-239 | 3-[[[2-Chloro-5-(trifluoromethyl)-phenyl]-carbamoyl]amino]-N,1,1-trimethyl-N-(1-pyridin-4-yl-piperidin-4-yl)-2,3-dihydro-indene-5-carboxylic acid amide (CC_H-239) | 1-Chloro-2-isocyanato-4-(trifluoromethyl)-benzene (CC_ICN-09) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-240 | 3-[[[4-Chloro-2-(trifluoromethyl)-phenyl]-carbamoyl]amino]-N,1,1-trimethyl-N-(1-pyridin-4-yl-piperidin-4-yl)-2,3-dihydro-indene-5-carboxylic acid amide (CC_H-240) | 4-Chloro-1-isocyanato-2-(trifluoromethyl)-benzene (CC_ICN-10) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-241 | 3-[[(3-Chloro-4-methyl-phenyl)-carbamoyl]amino]-N,1,1-trimethyl-N-(1-pyridin-4-yl-piperidin-4-yl)-2,3-dihydro-indene-5-carboxylic acid amide (CC_H-241) | 2-Chloro-4-isocyanato-1-methyl-benzene (CC_ICN-11) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-242 | 3-[[(3-Chloro-4-fluoro-phenyl)-carbamoyl]amino]-N,1,1-trimethyl-N-(1-pyridin-4-yl-piperidin-4-yl)-2,3-dihydro-indene-5-carboxylic acid amide (CC_H-242) | 2-Chloro-1-fluoro-4-isocyanato-benzene (CC_ICN-12) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-243 | 3-[[(2,4-Dimethyl-phenyl)-carbamoyl]amino]-N,1,1-trimethyl-N-(1-pyridin-4-yl-piperidin-4-yl)-2,3-dihydro-indene-5-carboxylic acid amide (CC_H-243) | 1-Isocyanato-2,4-dimethyl-benzene (CC_ICN-13) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-244 | 3-[[(5-Chloro-2-methoxy-phenyl)-carbamoyl]amino]-N,1,1-trimethyl-N-(1-pyridin-4-yl-piperidin-4-yl)-2,3-dihydro-indene-5-carboxylic acid amide (CC_H-244) | 4-Chloro-2-isocyanato-1-methoxy-benzene (CC_ICN-14) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-245 | 3-[[(2-Chlorophenyl)-methyl-carbamoyl]amino]-N,1,1-trimethyl-N-(1-pyridin-4-yl-piperidin-4-yl)-2,3-dihydro-indene-5-carboxylic acid amide (CC_H-245) | 1-Chloro-2-(isocyanato-methyl)-benzene (CC_ICN-15) | 3-Amino-N,1,1-trimethyl-N-(1-pyridin-4-yl-piperidin-4-yl)-2,3-dihydro-indene-5-carboxylic acid amide (CC_AMN-03) | No. 1 & No. 4 |
| CC_H-246 | 8-[(2-Chloro-5-fluoro-benzoyl)amino]-N-methyl-N-(1-pyridin-4-yl-piperidin-4-yl)-5,6,7,8-tetrahydro-naphthalene-2-carboxylic acid amide (CC_H-246) | 2-Chloro-5-fluoro-benzoyl chloride (CC_ACL-09) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-247 | 8-[[2-Chloro-5-(trifluoromethyl)-benzoyl]amino]-N-methyl-N-(1-pyridin-4-yl-piperidin-4-yl)-5,6,7,8-tetrahydro-naphthalene-2-carboxylic acid amide (CC_H-247) | 2-Chloro-5-(trifluoromethyl)-benzoyl chloride (CC_ACL-10) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-248 | 8-[(2-Chloro-6-fluoro-3-methyl-benzoyl)amino]-N-methyl-N-(1-pyridin-4-yl-piperidin-4-yl)-5,6,7,8-tetrahydro-naphthalene-2-carboxylic acid amide (CC_H-248) | 2-Chloro-6-fluoro-3-methyl-benzoyl chloride (CC_ACL-11) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-249 | 8-[[2-Chloro-6-(trifluoromethyl)-benzoyl]amino]-N-methyl-N-(1-pyridin-4-yl-piperidin-4-yl)-5,6,7,8-tetrahydro-naphthalene-2-carboxylic acid amide (CC_H-249) | 2-Chloro-6-(trifluoromethyl)-benzoyl chloride (CC_ACL-13) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-250 | 8-(Cyclopropanecarbonylamino)-N-methyl-N-(1-pyridin-4-yl-piperidin-4-yl)-5,6,7,8-tetrahydro-naphthalene-2-carboxylic acid amide (CC_H-250) | Cyclopropanecarbonyl chloride (CC_ACL-05) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-251 | 8-(3,3-Dimethyl-butanoylamino)-N-methyl-N-(1-pyridin-4-yl-piperidin-4-yl)-5,6,7,8-tetrahydro-naphthalene-2-carboxylic acid amide (CC_H-251) | 3,3-Dimethyl-butyryl chloride (CC_ACL-06) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |

-continued

| Example No. | Name | ACI_CC | Amine (AMN_CC) | Method No. |
|---|---|---|---|---|
| CC_H-252 | 8-[(2-Methoxy-acetyl)amino]-N-methyl-N-(1-pyridin-4-yl-piperidin-4-yl)-5,6,7,8-tetrahydro-naphthalene-2-carboxylic acid amide (CC_H-252) | 2-Methoxy-acetyl chloride (CC_ACL-07) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-253 | 8-Acetylamino-N-methyl-N-(1-pyridin-4-yl-piperidin-4-yl)-5,6,7,8-tetrahydro-naphthalene-2-carboxylic acid amide (CC_H-253) | Acetyl chloride (CC_SCL-07) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-254 | 8-[[2-Chloro-3-(trifluoromethyl)-benzoyl]amino]-N-methyl-N-(1-pyridin-4-yl-piperidin-4-yl)-5,6,7,8-tetrahydro-naphthalene-2-carboxylic acid amide (CC_H-254) | 2-Chloro-3-(trifluoromethyl)-benzoyl chloride (CC_ACL-08) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-255 | 8-[[(2-Chlorophenyl)-carbamoyl]amino]-N-methyl-N-(1-pyridin-4-yl-piperidin-4-yl)-5,6,7,8-tetrahydro-naphthalene-2-carboxylic acid amide (CC_H-255) | 1-Chloro-2-isocyanato-benzene (CC_ICN-02) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-256 | 8-[[(3-Chlorophenyl)-carbamoyl]amino]-N-methyl-N-(1-pyridin-4-yl-piperidin-4-yl)-5,6,7,8-tetrahydro-naphthalene-2-carboxylic acid amide (CC_H-256) | 1-Chloro-3-isocyanato-benzene (CC_ICN-03) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-257 | 8-[[(2,6-Dichloro-phenyl)-carbamoyl]amino]-N-methyl-N-(1-pyridin-4-yl-piperidin-4-yl)-5,6,7,8-tetrahydro-naphthalene-2-carboxylic acid amide (CC_H-257) | 1,3-Dichloro-2-isocyanato-benzene (CC_ICN-04) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-258 | 8-[[(2,3-Dichloro-phenyl)-carbamoyl]amino]-N-methyl-N-(1-pyridin-4-yl-piperidin-4-yl)-5,6,7,8-tetrahydro-naphthalene-2-carboxylic acid amide (CC_H-258) | 1,2-Dichloro-3-isocyanato-benzene (CC_ICN-05) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-259 | 8-[[(2,5-Dichloro-phenyl)-carbamoyl]amino]-N-methyl-N-(1-pyridin-4-yl-piperidin-4-yl)-5,6,7,8-tetrahydro-naphthalene-2-carboxylic acid amide (CC_H-259) | 1,4-Dichloro-2-isocyanato-benzene (CC_ICN-06) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-260 | 8-[[(3,5-Dichloro-phenyl)-carbamoyl]amino]-N-methyl-N-(1-pyridin-4-yl-piperidin-4-yl)-5,6,7,8-tetrahydro-naphthalene-2-carboxylic acid amide (CC_H-260) | 1,3-Dichloro-5-isocyanato-benzene (CC_ICN-07) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-261 | 8-[[[2-Chloro-5-(trifluoromethyl)-phenyl]-carbamoyl]amino]-N-methyl-N-(1-pyridin-4-yl-piperidin-4-yl)-5,6,7,8-tetrahydro-naphthalene-2-carboxylic acid amide (CC_H-261) | 1-Chloro-2-isocyanato-4-(trifluoromethyl)-benzene (CC_ICN-09) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-262 | 8-[[(2,4-Dichlorophenyl)-carbamoyl]amino]-N-methyl-N-(1-pyridin-4-yl-piperidin-4-yl)-5,6,7,8-tetrahydro-naphthalene-2-carboxylic acid amide (CC_H-262) | 2,4-Dichloro-1-isocyanato-benzene (CC_ICN-08) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-263 | 8-[[[4-Chloro-2-(trifluoromethyl)-phenyl]-carbamoyl]amino]-N-methyl-N-(1-pyridin-4-yl-piperidin-4-yl)-5,6,7,8-tetrahydro-naphthalene-2-carboxylic acid amide (CC_H-263) | 4-Chloro-1-isocyanato-2-(trifluoromethyl)-benzene (CC_ICN-10) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-264 | 8-[[(3-Chloro-4-methyl-phenyl)-carbamoyl]amino]-N-methyl-N-(1-pyridin-4-yl-piperidin-4-yl)-5,6,7,8-tetrahydro-naphthalene-2-carboxylic acid amide (CC_H-264) | 2-Chloro-4-isocyanato-1-methyl-benzene (CC_ICN-11) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-265 | 8-[[(3-Chloro-4-fluoro-phenyl)-carbamoyl]amino]-N-methyl-N-(1-pyridin-4-yl-piperidin-4-yl)-5,6,7,8-tetrahydro-naphthalene-2-carboxylic acid amide (CC_H-265) | 2-Chloro-1-fluoro-4-isocyanato-benzene (CC_ICN-12) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-266 | 8-[[(2,4-Dimethyl-phenyl)-carbamoyl]amino]-N-methyl-N-(1-pyridin-4-yl-piperidin-4-yl)-5,6,7,8-tetrahydro-naphthalene-2-carboxylic acid amide (CC_H-266) | 1-Isocyanato-2,4-dimethyl-benzene (CC_ICN-13) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-267 | 8-[[(5-Chloro-2-methoxy-phenyl)-carbamoyl]amino]-N-methyl-N-(1-pyridin-4-yl-piperidin-4-yl)-5,6,7,8-tetrahydro-naphthalene-2-carboxylic acid amide (CC_H-267) | 4-Chloro-2-isocyanato-1-methoxy-benzene (CC_ICN-14) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |

-continued

| Example No. | Name | ACL_CC | Amine (AMN_CC) | Method No. |
|---|---|---|---|---|
| CC_H-268 | 8-[[(2-Chlorophenyl)-methyl-carbamoyl]amino]-N-methyl-N-(1-pyridin-4-yl-piperidin-4-yl)-5,6,7,8-tetrahydro-naphthalene-2-carboxylic acid amide (CC_H-268) | 1-Chloro-2-(isocyanato-methyl)-benzene (CC_ICN-15) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-269 | 8-[[(2,4-Dichlorophenyl)-methyl-carbamoyl]amino]-N-methyl-N-(1-pyridin-4-yl-piperidin-4-yl)-5,6,7,8-tetrahydro-naphthalene-2-carboxylic acid amide (CC_H-269) | 2,4-Dichloro-1-(isocyanato-methyl)-benzene (CC_ICN-16) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 4 |
| CC_H-270 | 8-[(Cyclohexylsulfonyl)amino]-N-methyl-N-(1-pyridin-4-yl-piperidin-4-yl)-5,6,7,8-tetrahydro-naphthalene-2-carboxylic acid amide (CC_H-270) | Cyclohexanesulfonyl chloride (CC_SCL-13) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-271 | N-Methyl-8-(3-methyl-butanoylamino)-N-(1-pyridin-4-yl-piperidin-4-yl)-5,6,7,8-tetrahydro-naphthalene-2-carboxylic acid amide (CC_H-271) | 3-Methyl-butyryl chloride (CC_ACL-02) | 8-Amino-N-methyl-N-(1-pyridin-4-yl-piperidin-4-yl)-5,6,7,8-tetrahydro-naphthalene-2-carboxylic acid amide (CC_AMN-05) | No. 1 & No. 3 |
| CC_H-272 | 4-[[2-Chloro-5-(trifluoromethyl)-benzoyl]amino]-N-methyl-N-(1-pyridin-4-yl-piperidin-4-yl)-3,4-dihydro-2H-chromene-6-carboxylic acid amide (CC_H-272) | 2-Chloro-5-(trifluoromethyl)-benzoyl chloride (CC_ACL-10) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-273 | 4-[(2-Chloro-6-fluoro-3-methyl-benzoyl)amino]-N-methyl-N-(1-pyridin-4-yl-piperidin-4-yl)-3,4-dihydro-2H-chromene-6-carboxylic acid amide (CC_H-273) | 2-Chloro-6-fluoro-3-methyl-benzoyl chloride (CC_ACL-11) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-274 | 4-(Cyclopropanecarbonylamino)-N-methyl-N-(1-pyridin-4-yl-piperidin-4-yl)-3,4-dihydro-2H-chromene-6-carboxylic acid amide (CC_H-274) | Cyclopropanecarbonyl chloride (CC_ACL-05) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-275 | 4-(3,3-Dimethyl-butanoylamino)-N-methyl-N-(1-pyridin-4-yl-piperidin-4-yl)-3,4-dihydro-2H-chromene-6-carboxylic acid amide (CC_H-275) | 3,3-Dimethyl-butyryl chloride (CC_ACL-06) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-276 | 4-[(2-Methoxy-acetyl)amino]-N-methyl-N-(1-pyridin-4-yl-piperidin-4-yl)-3,4-dihydro-2H-chromene-6-carboxylic acid amide (CC_H-276) | 2-Methoxy-acetyl chloride (CC_ACL-07) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-277 | 4-Acetylamino-N-methyl-N-(1-pyridin-4-yl-piperidin-4-yl)-3,4-dihydro-2H-chromene-6-carboxylic acid amide (CC_H-277) | Acetyl chloride (CC_SCL-07) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-278 | 4-[[(2-Chloro-6-methyl-phenyl)sulfonyl]amino]-N-methyl-N-(1-pyridin-4-yl-piperidin-4-yl)-3,4-dihydro-2H-chromene-6-carboxylic acid amide (CC_H-278) | 2-Chloro-6-methyl-benzenesulfonyl chloride (CC_SCL-11) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-279 | 4-[[2-Chloro-3-(trifluoromethyl)-benzoyl]amino]-N-methyl-N-(1-pyridin-4-yl-piperidin-4-yl)-3,4-dihydro-2H-chromene-6-carboxylic acid amide (CC_H-279) | 2-Chloro-3-(trifluoromethyl)-benzoyl chloride (CC_ACL-08) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-280 | 4-[[(2-Chlorophenyl)-carbamoyl]amino]-N-methyl-N-(1-pyridin-4-yl-piperidin-4-yl)-3,4-dihydro-2H-chromene-6-carboxylic acid amide (CC_H-280) | 1-Chloro-2-isocyanato-benzene (CC_ICN-02) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-281 | 4-[[(3-Chlorophenyl)-carbamoyl]amino]-N-methyl-N-(1-pyridin-4-yl-piperidin-4-yl)-3,4-dihydro-2H-chromene-6-carboxylic acid amide (CC_H-281) | 1-Chloro-3-isocyanato-benzene (CC_ICN-03) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-282 | 4-[[(2,3-Dichloro-phenyl)-carbamoyl]amino]-N-methyl-N-(1-pyridin-4-yl-piperidin-4-yl)-3,4-dihydro-2H-chromene-6-carboxylic acid amide (CC_H-282) | 1,2-Dichloro-3-isocyanato-benzene (CC_ICN-05) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-283 | 4-[[(2,5-Dichloro-phenyl)-carbamoyl]amino]-N-methyl-N-(1-pyridin-4-yl-piperidin-4-yl)-3,4-dihydro-2H-chromene-6-carboxylic acid amide (CC_H-283) | 1,4-Dichloro-2-isocyanato-benzene (CC_ICN-06) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-284 | 4-[[(3,5-Dichloro-phenyl)-carbamoyl]amino]-N-methyl-N-(1-pyridin-4-yl-piperidin-4-yl)-3,4-dihydro-2H-chromene-6-carboxylic acid amide (CC_H-284) | 1,3-Dichloro-5-isocyanato-benzene (CC_ICN-07) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |

-continued

| Example No. | Name | ACL_CC | Amine (AMN_CC) | Method No. |
|---|---|---|---|---|
| CC_H-285 | 4-[[[2-Chloro-5-(trifluoromethyl)-phenyl]-carbamoyl]amino]-N-methyl-N-(1-pyridin-4-yl-piperidin-4-yl)-3,4-dihydro-2H-chromene-6-carboxylic acid amide (CC_H-285) | 1-Chloro-2-isocyanato-4-(trifluoromethyl)-benzene (CC_ICN-09) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-286 | 4-[[(2,4-Dichlorophenyl)-carbamoyl]amino]-N-methyl-N-(1-pyridin-4-yl-piperidin-4-yl)-3,4-dihydro-2H-chromene-6-carboxylic acid amide (CC_H-286) | 2,4-Dichloro-1-isocyanato-benzene (CC_ICN-08) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-287 | 4-[[[4-Chloro-2-(trifluoromethyl)-phenyl]-carbamoyl]amino]-N-methyl-N-(1-pyridin-4-yl-piperidin-4-yl)-3,4-dihydro-2H-chromene-6-carboxylic acid amide (CC_H-287) | 4-Chloro-1-isocyanato-2-(trifluoromethyl)-benzene (CC_ICN-10) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-288 | 4-[[(3-Chloro-4-methyl-phenyl)-carbamoyl]amino]-N-methyl-N-(1-pyridin-4-yl-piperidin-4-yl)-3,4-dihydro-2H-chromene-6-carboxylic acid amide (CC_H-288) | 2-Chloro-4-isocyanato-1-methyl-benzene (CC_ICN-11) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-289 | 4-[[(3-Chloro-4-fluoro-phenyl)-carbamoyl]amino]-N-methyl-N-(1-pyridin-4-yl-piperidin-4-yl)-3,4-dihydro-2H-chromene-6-carboxylic acid amide (CC_H-289) | 2-Chloro-1-fluoro-4-isocyanato-benzene (CC_ICN-12) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-290 | 4-[[(2,4-Dimethyl-phenyl)-carbamoyl]amino]-N-methyl-N-(1-pyridin-4-yl-piperidin-4-yl)-3,4-dihydro-2H-chromene-6-carboxylic acid amide (CC_H-290) | 1-Isocyanato-2,4-dimethyl-benzene (CC_ICN-13) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-291 | 4-[[(5-Chloro-2-methoxy-phenyl)-carbamoyl]amino]-N-methyl-N-(1-pyridin-4-yl-piperidin-4-yl)-3,4-dihydro-2H-chromene-6-carboxylic acid amide (CC_H-291) | 4-Chloro-2-isocyanato-1-methoxy-benzene (CC_ICN-14) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-292 | 4-[[(2-Chlorophenyl)-methyl-carbamoyl]amino]-N-methyl-N-(1-pyridin-4-yl-piperidin-4-yl)-3,4-dihydro-2H-chromene-6-carboxylic acid amide (CC_H-292) | 1-Chloro-2-(isocyanato-methyl)-benzene (CC_ICN-15) | 4-Amino-N-methyl-N-(1-pyridin-4-yl-piperidin-4-yl)-3,4-dihydro-2H-chromene-6-carboxylic acid amide (CC_AMN-06) | No. 1 & No. 4 |
| CC_H-293 | N-Methyl-4-(3-methyl-butanoylamino)-N-(1-pyridin-4-yl-piperidin-4-yl)-3,4-dihydro-2H-chromene-6-carboxylic acid amide (CC_H-293) | 3-Methyl-butyryl chloride (CC_ACL-02) | 4-Amino-N-methyl-N-(1-pyridin-4-yl-piperidin-4-yl)-3,4-dihydro-2H-chromene-6-carboxylic acid amide (CC_AMN-06) | No. 1 & No. 3 |
| CC_H-294 | 3-[(2-Chloro-5-fluoro-benzoyl)amino]-N-[1-(2,6-dimethyl-pyridin-4-yl)-piperidin-4-yl]-N-methyl-2,3-dihydro-1H-indene-5-carboxylic acid amide (CC_H-294) | 2-Chloro-5-fluoro-benzoyl chloride (CC_ACL-09) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-295 | 3-[(2-Chloro-6-fluoro-3-methyl-benzoyl)amino]-N-[1-(2,6-dimethyl-pyridin-4-yl)-piperidin-4-yl]-N-methyl-2,3-dihydro-1H-indene-5-carboxylic acid amide (CC_H-295) | 2-Chloro-6-fluoro-3-methyl-benzoyl chloride (CC_ACL-11) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-296 | 3-[(2,5-Dichloro-benzoyl)amino]-N-[1-(2,6-dimethyl-pyridin-4-yl)-piperidin-4-yl]-N-methyl-2,3-dihydro-1H-indene-5-carboxylic acid amide (CC_H-296) | 2,5-Dichloro-benzoyl chloride (CC_ACL-12) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-297 | 3-(Cyclohexanecarbonylamino)-N-[1-(2,6-dimethyl-pyridin-4-yl)-piperidin-4-yl]-N-methyl-2,3-dihydro-1H-indene-5-carboxylic acid amide (CC_H-297) | Cyclohexanecarbonyl chloride (CC_ACL-01) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-298 | 3-(Cyclopropanecarbonylamino)-N-[1-(2,6-dimethyl-pyridin-4-yl)-piperidin-4-yl]-N-methyl-2,3-dihydro-1H-indene-5-carboxylic acid amide (CC_H-298) | Cyclopropanecarbonyl chloride (CC_ACL-05) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-299 | 3-(3,3-Dimethyl-butanoylamino)-N-[1-(2,6-dimethyl-pyridin-4-yl)-piperidin-4-yl]-N-methyl-2,3-dihydro-1H-indene-5-carboxylic acid amide (CC_H-299) | 3,3-Dimethyl-butyryl chloride (CC_ACL-06) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-300 | N-[1-(2,6-Dimethyl-pyridin-4-yl)-piperidin-4-yl]-3-[(2-methoxy-acetyl)amino]-N-methyl-2,3-dihydro-1H-indene-5-carboxylic acid amide (CC_H-300) | 2-Methoxy-acetyl chloride (CC_ACL-07) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-301 | 3-Acetylamino-N-[1-(2,6-dimethyl-pyridin-4-yl)-piperidin-4-yl]-N-methyl-2,3-dihydro- | Acetyl chloride (CC_SCL-07) | 3-Amino-N-[1-(2,6-dimethyl-pyridin-4-yl)-piperidin-4-yl]-N-methyl-2,3- | No. 1 & No. 3 |

-continued

| Example No. | Name | ACI_CC | Amine (AMN_CC) | Method No. |
|---|---|---|---|---|
| | 1H-indene-5-carboxylic acid amide (CC_H-301) | | dihydro-1H-indene-5-carboxylic acid amide (CC_AMN-07) | |
| CC_H-302 | N-[1-(2,6-Dimethyl-pyridin-4-yl)-piperidin-4-yl]-N-methyl-3-[[[2-(trifluoromethyl)-phenyl]-methylsulfonyl]amino]-2,3-dihydro-1H-indene-5-carboxylic acid amide (CC_H-302) | [2-(Trifluoromethyl)-phenyl]-methanesulfonyl chloride (CC_SCL-12) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-303 | 3-[[2-Chloro-3-(trifluoromethyl)-benzoyl]amino]-N-[1-(2,6-dimethyl-pyridin-4-yl)-piperidin-4-yl]-N-methyl-2,3-dihydro-1H-indene-5-carboxylic acid amide (CC_H-303) | 2-Chloro-3-(trifluoromethyl)-benzoyl chloride (CC_ACL-08) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-304 | 3-[[(2-Chlorophenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-304) | 1-Chloro-2-isocyanato-benzene (CC_ICN-02) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-305 | 3-[[(3-Chlorophenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-305) | 1-Chloro-3-isocyanato-benzene (CC_ICN-03) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-306 | 3-[[(2,6-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-306) | 1,3-Dichloro-2-isocyanato-benzene (CC_ICN-04) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-307 | 3-[[(2,3-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-307) | 1,2-Dichloro-3-isocyanato-benzene (CC_ICN-05) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-308 | 3-[[(2,5-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-308) | 1,4-Dichloro-2-isocyanato-benzene (CC_ICN-06) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-309 | 3-[[(3,5-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-309) | 1,3-Dichloro-5-isocyanato-benzene (CC_ICN-07) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-310 | 3-[[(2,4-Dichlorophenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-310) | 2,4-Dichloro-1-isocyanato-benzene (CC_ICN-08) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-311 | 3-[[[2-Chloro-5-(trifluoromethyl)-phenyl]-carbamoyl]amino]-N-[1-(2,6-dimethyl-pyridin-4-yl)-piperidin-4-yl]-N-methyl-2,3-dihydro-1H-indene-5-carboxylic acid amide (CC_H-311) | 1-Chloro-2-isocyanato-4-(trifluoromethyl)-benzene (CC_ICN-09) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-312 | 3-[[[4-Chloro-2-(trifluoromethyl)-phenyl]-carbamoyl]amino]-N-[1-(2,6-dimethyl-pyridin-4-yl)-piperidin-4-yl]-N-methyl-2,3-dihydro-1H-indene-5-carboxylic acid amide (CC_H-312) | 4-Chloro-1-isocyanato-2-(trifluoromethyl)-benzene (CC_ICN-10) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-313 | 3-[[(3-Chloro-4-methyl-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-313) | 2-Chloro-4-isocyanato-1-methyl-benzene (CC_ICN-11) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-314 | 3-[[(3-Chloro-4-fluoro-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-314) | 2-Chloro-1-fluoro-4-isocyanato-benzene (CC_ICN-12) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-315 | 3-[[(5-Chloro-2-methoxy-phenyl)-carbamoyl]amino]-N-[1-(2,6-dimethyl-pyridin-4-yl)-piperidin-4-yl]-N-methyl-2,3-dihydro-1H-indene-5-carboxylic acid amide (CC_H-315) | 4-Chloro-2-isocyanato-1-methoxy-benzene (CC_ICN-14) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-316 | 3-[[(2-Chlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide (CC_H-316) | 1-Chloro-2-(isocyanato-methyl)-benzene (CC_ICN-15) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 4 |
| CC_H-317 | 3-[[(2,4-Dichlorophenyl)-methyl-carbamoyl]amino]-N-[1-(2,6-dimethyl- | 2,4-Dichloro-1-(isocyanato-methyl)-benzene (CC_ICN-16) | 3-Amino-N-[1-(2,6-dimethyl-pyridin-4-yl)-piperidin-4-yl]-N-methyl-2,3- | |

-continued

| Example No. | Name | ACL_CC | Amine (AMN_CC) | Method No. |
|---|---|---|---|---|
| | pyridin-4-yl)-piperidin-4-yl]-N-methyl-2,3-dihydro-1H-indene-5-carboxylic acid amide (CC_H-317) | | dihydro-1H-indene-5-carboxylic acid amide (CC_AMN-07) | |
| CC_H-318 | N-[1-(2,6-Dimethyl-pyridin-4-yl)-piperidin-4-yl]-N-methyl-3-(3-methyl-butanoylamino)-2,3-dihydro-1H-indene-5-carboxylic acid amide (CC_H-318) | 3-Methyl-butyryl chloride (CC_ACL-02) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-319 | 3-(Butanoylamino)-N-[1-(2,6-dimethyl-pyridin-4-yl)-piperidin-4-yl]-N-methyl-2,3-dihydro-1H-indene-5-carboxylic acid amide (CC_H-319) | Butyryl chloride (CC_ACL-03) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-320 | 3-(3-Cyclopentyl-propanoylamino)-N-[1-(2,6-dimethyl-pyridin-4-yl)-piperidin-4-yl]-N-methyl-2,3-dihydro-1H-indene-5-carboxylic acid amide (CC_H-320) | 3-Cyclopentyl-propionyl chloride (CC_ACL-04) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-321 | N-[1-(2,6-Dimethyl-pyridin-4-yl)-piperidin-4-yl]-3-[(ethylsulfonyl)amino]-N-methyl-2,3-dihydro-1H-indene-5-carboxylic acid amide (CC_H-321) | Ethanesulfonyl chloride (CC_SCL-04) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-322 | N-[1-(2,6-Dimethyl-pyridin-4-yl)-piperidin-4-yl]-N-methyl-3-[[[3-(trifluoromethyl)phenyl]-methylsulfonyl]amino]-2,3-dihydro-1H-indene-5-carboxylic acid amide (CC_H-322) | [3-(Trifluoromethyl)phenyl]-methanesulfonyl chloride (CC_SCL-08) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-323 | N-[1-(2,6-Dimethyl-pyridin-4-yl)-piperidin-4-yl]-3-[[(2-fluorophenyl)-methylsulfonyl]amino]-N-methyl-2,3-dihydro-1H-indene-5-carboxylic acid amide (CC_H-323) | (2-Fluorophenyl)-methanesulfonyl chloride (CC_SCL-09) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-324 | 3-[[2-(2-Chlorophenyl)-ethylsulfonyl]amino]-N-[1-(2,6-dimethyl-pyridin-4-yl)-piperidin-4-yl]-N-methyl-2,3-dihydro-1H-indene-5-carboxylic acid amide (CC_H-324) | 2-(2-Chlorophenyl)-ethanesulfonyl chloride (CC_SCL-10) | 3-Amino-N-[1-(2,6-dimethyl-pyridin-4-yl)-piperidin-4-yl]-N-methyl-2,3-dihydro-1H-indene-5-carboxylic acid amide (CC_AMN-07) | No. 1 & No. 3 |
| CC_H-325 | 3-[(2-Chloro-5-fluoro-benzoyl)-methyl-amino]-N-[1-(2,6-dimethyl-pyridin-4-yl)-piperidin-4-yl]-N-methyl-2,3-dihydro-1H-indene-5-carboxylic acid amide (CC_H-325) | 2-Chloro-5-fluoro-benzoyl chloride (CC_ACL-09) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-326 | 3-[[2-Chloro-5-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide (CC_H-326) | 2-Chloro-5-(trifluoromethyl)-benzoyl chloride (CC_ACL-10) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-327 | 3-[(2-Chloro-6-fluoro-3-methyl-benzoyl)-methyl-amino]-N-[1-(2,6-dimethyl-pyridin-4-yl)-piperidin-4-yl]-N-methyl-2,3-dihydro-1H-indene-5-carboxylic acid amide (CC_H-327) | 2-Chloro-6-fluoro-3-methyl-benzoyl chloride (CC_ACL-11) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-328 | 3-[(2,5-Dichloro-benzoyl)-methyl-amino]-N-[1-(2,6-dimethyl-pyridin-4-yl)-piperidin-4-yl]-N-methyl-2,3-dihydro-1H-indene-5-carboxylic acid amide (CC_H-328) | 2,5-Dichloro-benzoyl chloride (CC_ACL-12) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-329 | 3-[[2-Chloro-6-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide (CC_H-329) | 2-Chloro-6-(trifluoromethyl)-benzoyl chloride (CC_ACL-13) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-330 | 3-(Cyclohexanecarbonyl-methyl-amino)-N-[1-(2,6-dimethyl-pyridin-4-yl)-piperidin-4-yl]-N-methyl-2,3-dihydro-1H-indene-5-carboxylic acid amide (CC_H-330) | Cyclohexanecarbonyl chloride (CC_ACL-01) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-331 | 3-(Cyclopropanecarbonyl-methyl-amino)-N-[1-(2,6-dimethyl-pyridin-4-yl)-piperidin-4-yl]-N-methyl-2,3-dihydro-1H-indene-5-carboxylic acid amide (CC_H-331) | Cyclopropanecarbonyl chloride (CC_ACL-05) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-332 | 3-(3,3-Dimethyl-butanoyl-methyl-amino)-N-[1-(2,6-dimethyl-pyridin-4-yl)-piperidin-4-yl]-N-methyl-2,3-dihydro-1H-indene-5-carboxylic acid amide (CC_H-332) | 3,3-Dimethyl-butyryl chloride (CC_ACL-06) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-333 | N-[1-(2,6-Dimethyl-pyridin-4-yl)-piperidin-4-yl]-3-[(2-methoxy-acetyl)-methyl-amino]- | 2-Methoxy-acetyl chloride (CC_ACL-07) | N-[1-(2,6-Dimethyl-pyridin-4-yl)-piperidin-4-yl]-N-methyl-3- | No. 1 & No. 3 |

-continued

| Example No. | Name | ACL_CC | Amine (AMN_CC) | Method No. |
|---|---|---|---|---|
| | N-methyl-2,3-dihydro-1H-indene-5-carboxylic acid amide (CC_H-333) | | methylamino-2,3-dihydro-1H-indene-5-carboxylic acid amide (CC_AMN-08) | |
| CC_H-334 | 3-(Acetyl-methyl-amino)-N-[1-(2,6-dimethyl-pyridin-4-yl)-piperidin-4-yl]-N-methyl-2,3-dihydro-1H-indene-5-carboxylic acid amide (CC_H-334) | Acetyl chloride (CC_SCL-07) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-335 | 3-[[(2-Chloro-6-methyl-phenyl)sulfonyl]-methyl-amino]-N-[1-(2,6-dimethyl-pyridin-4-yl)-piperidin-4-yl]-N-methyl-2,3-dihydro-1H-indene-5-carboxylic acid amide (CC_H-335) | 2-Chloro-6-methyl-benzenesulfonyl chloride (CC_SCL-11) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-336 | 3-[[(2-Chlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-336) | 1-Chloro-2-isocyanato-benzene (CC_ICN-02) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-337 | 3-[[(3-Chlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-337) | 1-Chloro-3-isocyanato-benzene (CC_ICN-03) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-338 | 3-[[(2,6-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-338) | 1,3-Dichloro-2-isocyanato-benzene (CC_ICN-04) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-339 | 3-[[(2,3-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-339) | 1,2-Dichloro-3-isocyanato-benzene (CC_ICN-05) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-340 | 3-[[(2,5-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-340) | 1,4-Dichloro-2-isocyanato-benzene (CC_ICN-06) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-341 | 3-[[(3,5-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-341) | 1,3-Dichloro-5-isocyanato-benzene (CC_ICN-07) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-342 | 3-[[(2,4-Dichlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-342) | 2,4-Dichloro-1-isocyanato-benzene (CC_ICN-08) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-343 | 3-[[[2-Chloro-5-(trifluoromethyl)-phenyl]-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-343) | 1-Chloro-2-isocyanato-4-(trifluoromethyl)-benzene (CC_ICN-09) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-344 | 3-[[[4-Chloro-2-(trifluoromethyl)-phenyl]-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-344) | 4-Chloro-1-isocyanato-2-(trifluoromethyl)-benzene (CC_ICN-10) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-345 | 3-[[(3-Chloro-4-methyl-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-345) | 2-Chloro-4-isocyanato-1-methyl-benzene (CC_ICN-11) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-346 | 3-[[(3-Chloro-4-fluoro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-346) | 2-Chloro-1-fluoro-4-isocyanato-benzene (CC_ICN-12) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-347 | 3-[[(2,4-Dimethyl-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-347) | 1-Isocyanato-2,4-dimethyl-benzene (CC_ICN-13) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-348 | 3-[[(5-Chloro-2-methoxy-phenyl)-carbamoyl]-methyl-amino]-N-[1-(2,6-dimethyl-pyridin-4-yl)-piperidin-4-yl]-N- | 4-Chloro-2-isocyanato-1-methoxy-benzene (CC_ICN-14) | N-[1-(2,6-Dimethyl-pyridin-4-yl)-piperidin-4-yl]-N-methyl-3-methylamino-2,3-dihydro-1H- | No. 1 & No. 4 |

-continued

| Example No. | Name | ACL_CC | Amine (AMN_CC) | Method No. |
|---|---|---|---|---|
| | methyl-2,3-dihydro-1H-indene-5-carboxylic acid amide (CC_H-348) | | indene-5-carboxylic acid amide (CC_AMN-08) | |
| CC_H-349 | 3-[[(2-Chlorophenyl)-methyl-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-349) | 1-Chloro-2-(isocyanato-methyl)-benzene (CC_ICN-15) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-350 | 3[[(2,4-Dichlorophenyl)-methyl-carbamoyl]-methyl-amino]-N-[1-(2,6-dimethyl-pyridin-4-yl)-piperidin-4-yl]-N-methyl-2,3-dihydro-1H-indene-5-carboxylic acid amide (CC_H-350) | 2,4-Dichloro-1-(isocyanato-methyl)-benzene (CC_ICN-16) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 4 |
| CC_H-351 | N-[1-(2,6-Dimethyl-pyridin-4-yl)-piperidin-4-yl]-N-methyl-3-(methyl-methylsulfonyl-amino)-2,3-dihydro-1H-indene-5-carboxylic acid amide (CC_H-351) | Methanesulfonyl chloride (CC_SCL-03) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-352 | N-[1-(2,6-Dimethyl-pyridin-4-yl)-piperidin-4-yl]-N-methyl-3-[methyl-(3-methyl-butanoyl)-amino]-2,3-dihydro-1H-indene-5-carboxylic acid amide (CC_H-352) | 3-Methyl-butyryl chloride (CC_ACL-02) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-353 | 3-(Butanoyl-methyl-amino)-N-[1-(2,6-dimethyl-pyridin-4-yl)-piperidin-4-yl]-N-methyl-2,3-dihydro-1H-indene-5-carboxylic acid amide (CC_H-353) | Butyryl chloride (CC_ACL-03) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-354 | 3-(3-Cyclopentyl-propanoyl-methyl-amino)-N-[1-(2,6-dimethyl-pyridin-4-yl)-piperidin-4-yl]-N-methyl-2,3-dihydro-1H-indene-5-carboxylic acid amide (CC_H-354) | 3-Cyclopentyl-propionyl chloride (CC_ACL-04) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-355 | N-[1-(2,6-Dimethyl-pyridin-4-yl)-piperidin-4-yl]-N-methyl-3-[methyl-[[3-(trifluoromethyl)phenyl]-methylsulfonyl]-amino]-2,3-dihydro-1H-indene-5-carboxylic acid amide (CC_H-355) | [3-(Trifluoromethyl)phenyl]-methanesulfonyl chloride (CC_SCL-08) | N-[1-(2,6-Dimethyl-pyridin-4-yl)-piperidin-4-yl]-N-methyl-3-methylamino-2,3-dihydro-1H-indene-5-carboxylic acid amide (CC_AMN-08) | No. 1 & No. 3 |
| CC_H-356 | 3-[(2-Chloro-5-fluoro-benzoyl)amino]-N-(1-isoquinolin-6-yl-piperidin-4-yl)-N-methyl-2,3-dihydro-1H-indene-5-carboxylic acid amide (CC_H-356) | 2-Chloro-5-fluoro-benzoyl chloride (CC_ACL-09) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-357 | 3-[[2-Chloro-5-(trifluoromethyl)-benzoyl]amino]-N-(1-isoquinolin-6-yl-piperidin-4-yl)-N-methyl-2,3-dihydro-1H-indene-5-carboxylic acid amide (CC_H-357) | 2-Chloro-5-(trifluoromethyl)-benzoyl chloride (CC_ACL-10) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-358 | 3-[(2-Chloro-6-fluoro-3-methyl-benzoyl)amino]-N-(1-isoquinolin-6-yl-piperidin-4-yl)-N-methyl-2,3-dihydro-1H-indene-5-carboxylic acid amide (CC_H-358) | 2-Chloro-6-fluoro-3-methyl-benzoyl chloride (CC_ACL-11) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-359 | 3-[(2,5-Dichloro-benzoyl)amino]-N-(1-isoquinolin-6-yl-piperidin-4-yl)-N-methyl-2,3-dihydro-1H-indene-5-carboxylic acid amide (CC_H-359) | 2,5-Dichloro-benzoyl chloride (CC_ACL-12) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-360 | 3-(Cyclohexanecarbonylamino)-N-(1-isoquinolin-6-yl-piperidin-4-yl)-N-methyl-2,3-dihydro-1H-indene-5-carboxylic acid amide (CC_H-360) | Cyclohexanecarbonyl chloride (CC_ACL-01) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-361 | 3-(Cyclopropanecarbonylamino)-N-(1-isoquinolin-6-yl-piperidin-4-yl)-N-methyl-2,3-dihydro-1H-indene-5-carboxylic acid amide (CC_H-361) | Cyclopropanecarbonyl chloride (CC-ACL-05) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-362 | 3-(3,3-Dimethyl-butanoylamino)-N-(1-isoquinolin-6-yl-piperidin-4-yl)-N-methyl-2,3-dihydro-1H-indene-5-carboxylic acid amide (CC_H-362) | 3,3-Dimethyl-butyryl chloride (CC-ACL-06) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-363 | N-(1-Isoquinolin-6-yl-piperidin-4-yl)-3-[(2-methoxy-acetyl)amino]-N-methyl-2,3-dihydro-1H-indene-5-carboxylic acid amide (CC_H-363) | 2-Methoxy-acetyl chloride (CC_ACL-07) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-364 | 3-[[2-Chloro-3-(trifluoromethyl)-benzoyl]amino]-N-(1-isoquinolin-6-yl-piperidin-4-yl)-N-methyl-2,3-dihydro-1H-indene-5-carboxylic acid amide (CC_H-364) | 2-Chloro-3-(trifluoromethyl)-benzoyl chloride (CC_ACL-08) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |

-continued

| Example No. | Name | ACL_CC | Amine (AMN_CC) | Method No. |
|---|---|---|---|---|
| CC_H-365 | 3-[[(2-Chlorophenyl)-carbamoyl]amino]-N-(1-isoquinolin-6-yl-piperidin-4-yl)-N-methyl-2,3-dihydro-1H-indene-5-carboxylic acid amide (CC_H-365) | 1-Chloro-2-isocyanato-benzene (CC_ICN-02) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-366 | 3-[[(2,6-Dichloro-phenyl)-carbamoyl]amino]-N-(1-isoquinolin-6-yl-piperidin-4-yl)-N-methyl-2,3-dihydro-1H-indene-5-carboxylic acid amide (CC_H-366) | 1,3-Dichloro-2-isocyanato-benzene (CC_ICN-04) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-367 | 3-[[(2,3-Dichloro-phenyl)-carbamoyl]-amino]-N-(1-isoquinolin-6-yl-piperidin-4-yl)-N-methyl-2,3-dihydro-1H-indene-5-carboxylic acid amide (CC_H-367) | 1,2-Dichloro-3-isocyanato-benzene (CC_ICN-05) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-368 | 3-[[(2,5-Dichloro-phenyl)-carbamoyl]-amino]-N-(1-isoquinolin-6-yl-piperidin-4-yl)-N-methyl-2,3-dihydro-1H-indene-5-carboxylic acid amide (CC_H-368) | 1,4-Dichloro-2-isocyanato-benzene (CC_ICN-06) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-369 | 3-[[(2,4-Dichlorophenyl)-carbamoyl]amino]-N-(1-isoquinolin-6-yl-piperidin-4-yl)-N-methyl-2,3-dihydro-1H-indene-5-carboxylic acid amide (CC_H-369) | 2,4-Dichloro-1-isocyanato-benzene (CC_ICN-08) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-370 | 3-[[[2-Chloro-5-(trifluoromethyl)-phenyl]-carbamoyl]amino]-N-(1-isoquinolin-6-yl-piperidin-4-yl)-N-methyl-2,3-dihydro-1H-indene-5-carboxylic acid amide (CC_H-370) | 1-Chloro-2-isocyanato-4-(trifluoromethyl)-benzene (CC_ICN-09) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-371 | 3-[[[4-Chloro-2-(trifluoromethyl)-phenyl]-carbamoyl]amino]-N-(1-isoquinolin-6-yl-piperidin-4-yl)-N-methyl-2,3-dihydro-1H-indene-5-carboxylic acid amide (CC_H-371) | 4-Chloro-1-isocyanato-2-(trifluorometyl)-benzene (CC_ICN-10) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-372 | 3-[[(3-Chloro-4-fluoro-phenyl)-carbamoyl]amino]-N-(1-isoquinolin-6-yl-piperidin-4-yl)-N-methyl-2,3-dihydro-1H-indene-5-carboxylic acid amide (CC_H-372) | 2-Chloro-1-fluoro-4-isocyanato-benzene (CC_ICN-12) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-373 | 3-[[(2,4-Dimethyl-phenyl)-carbamoyl]amino]-N-(1-isoquinolin-6-yl-piperidin-4-yl)-N-methyl-2,3-dihydro-1H-indene-5-carboxylic acid amide (CC_H-373) | 1-Isocyanato-2,4-dimethyl-benzene (CC_ICN-13) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-374 | 3-[[(5-Chloro-2-methoxy-phenyl)-carbamoyl]amino]-N-(1-isoquinolin-6-yl-piperidin-4-yl)-N-methyl-2,3-dihydro-1H-indene-5-carboxylic acid amide (CC_H-374) | 4-Chloro-2-isocyanato-1-methoxy-benzene (CC_ICN-14) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-375 | 3-[[(2-Chlorophenyl)-methyl-carbamoyl]amino]-N-(1-isoquinolin-6-yl-piperidin-4-yl)-N-methyl-2,3-dihydro-1H-indene-5-carboxylic acid amide (CC_H-375) | 1-Chloro-2-(isocyanato-methyl)-benzene (CC_ICN-15) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-376 | 3-[[(2,4-Dichlorophenyl)-methyl-carbamoyl]amino]-N-(1-isoquinolin-6-yl-piperidin-4-yl)-N-methyl-2,3-dihydro-1H-indene-5-carboxylic acid amide (CC_H-376) | 2,4-Dichloro-1-(isocyanato-methyl)-benzene (CC_ICN-16) | 3-Amino-N-(1-isoquinolin-6-yl-piperidin-4-yl)-N-methyl-2,3-dihydro-1H-indene-5-carboxylic acid amide (CC_AMN-09) | No. 1 & No. 4 |
| CC_H-377 | N-(1-Isoquinolin-6-yl-piperidin-4-yl)-3-(methansulfonamido)-N-methyl-2,3-dihydro-1H-indene-5-carboxylic acid amide (CC_H-377) | Methanesulfonyl chloride (CC_SCL-03) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-378 | N-(1-Isoquinolin-6-yl-piperidin-4-yl)-N-methyl-3-[(propylsulfonyl)amino]-2,3-dihydro-1H-indene-5-carboxylic acid amide (CC_H-378) | Propane-1-sulfonyl chloride (CC_SCL-05) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-379 | N-(1-Isoquinolin-6-yl-piperidin-4-yl)-N-methyl-3-(3-methyl-butanoylamino)-2,3-dihydro-1H-indene-5-carboxylic acid amide (CC_H-379) | 3-Methyl-butyryl chloride (CC_ACL-02) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-380 | 3-(Butanoylamino)-N-(1-isoquinolin-6-yl-piperidin-4-yl)-N-methyl-2,3-dihydro-1H-indene-5-carboxylic acid amide (CC_H-380) | Butyryl chloride (CC_ACL-03) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-381 | 3-(3-Cyclopentyl-propanoylamino)-N-(1-isoquinolin-6-yl-piperidin-4-yl)-N-methyl-2,3-dihydro-1H-indene-5-carboxylic acid amide (CC_H-381) | 3-Cyclopentyl-propionyl chloride (CC_ACL-04) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |

-continued

| Example No. | Name | ACI_CC | Amine (AMN_CC) | Method No. |
|---|---|---|---|---|
| CC_H-382 | 3-[(Ethylsulfonyl)amino]-N-(1-isoquinolin-6-yl-piperidin-4-yl)-N-methyl-2,3-dihydro-1H-indene-5-carboxylic acid amide (CC_H-382) | Ethanesulfonyl chloride (CC_SCL-04) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-383 | N-(1-Isoquinolin-6-yl-piperidin-4-yl)-N-methyl-3-[[[3-(trifluoromethyl)phenyl]-methylsulfonyl]amino]-2,3-dihydro-1H-indene-5-carboxylic acid amide (CC_H-383) | [3-(Trifluoromethyl)phenyl]-methanesulfonyl chloride (CC_SCL-08) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |
| CC_H-384 | 3-[[(2-Fluorophenyl)-methylsulfonyl]amino]-N-(1-isoquinolin-6-yl-piperidin-4-yl)-N-methyl-2,3-dihydro-1H-indene-5-carboxylic acid amide (CC_H-384) | (2-Fluorophenyl)-methanesulfonyl chloride (CC_SCL-09) | 3-Amino-N-(1-isoquinolin-6-yl-piperidin-4-yl)-N-methyl-2,3-dihydro-1H-indene-5-carboxylic acid amide (CC_AMN-09) | No. 1 & No. 3 |

Analytical and Biological Data:
Representative Examples with % Inhibition ≥50% on Human B1R at 10 μM:

| Entry No. | [M+] found | R.t. [min] | Purity, UV_254 [%] | % Inhibition (r-B1R) at 10 μM | % Inhibition (h-B1R) at 10 μM |
|---|---|---|---|---|---|
| CC_H-03 | Yes | 0.5 | 100 | 103 | 99 |
| CC_H-04 | Yes | 0.478 | 96.35 | 104 | 99 |
| CC_H-05 | Yes | 0.48 | 95.04 | 103 | 98 |
| CC_H-06 | Yes | 0.508 | 97.15 | 104 | 100 |
| CC_H-07 | Yes | 0.492 | 96.89 | 103 | 99 |
| CC_H-08 | Yes | 0.39 | 98.37 | 104 | 99 |
| CC_H-09 | Yes | 0.482 | 94.28 | 103 | 99 |
| CC_H-11 | Yes | 0.503 | 97.52 | 103 | 99 |
| CC_H-12 | Yes | 0.48 | 100 | 104 | 100 |
| CC_H-13 | Yes | 0.463 | 95.21 | 78 | 100 |
| CC_H-14 | Yes | 0.508 | 94.66 | 104 | 99 |
| CC_H-15 | Yes | 0.51 | 94.2 | 101 | 99 |
| CC_H-16 | Yes | 0.53 | 100 | 104 | 99 |
| CC_H-17 | Yes | 0.528 | 100 | 104 | 98 |
| CC_H-18 | Yes | 0.54 | 100 | 102 | 99 |
| CC_H-19 | Yes | 0.53 | 100 | 100 | 100 |
| CC_H-20 | Yes | 0.52 | 100 | 104 | 99 |
| CC_H-21 | Yes | 0.508 | 98.67 | 104 | 99 |
| CC_H-22 | Yes | 0.418 | 97.93 | 90 | 97 |
| CC_H-23 | Yes | 0.498 | 91.51 | 104 | 99 |
| CC_H-24 | Yes | 0.448 | 96.25 | 105 | 100 |
| CC_H-25 | Yes | 0.51 | 97 | 104 | 98 |
| CC_H-26 | Yes | 0.452 | 95.62 | 103 | 100 |
| CC_H-27 | Yes | 0.488 | 96.38 | 104 | 100 |
| CC_H-28 | Yes | 0.46 | 97.82 | 103 | 99 |
| CC_H-29 | Yes | 0.468 | 100 | 103 | 99 |
| CC_H-30 | Yes | 0.48 | 97.17 | 104 | 99 |
| CC_H-32 | Yes | 0.45 | 94.98 | 105 | 97 |
| CC_H-33 | Yes | 0.43 | 97.27 | 104 | 98 |
| CC_H-34 | Yes | 0.472 | 92.52 | 104 | 99 |
| CC_H-35 | Yes | 0.46 | 96.38 | 104 | 97 |
| CC_H-36 | Yes | 0.482 | 98.62 | 104 | 99 |
| CC_H-37 | Yes | 0.45 | 96.56 | 104 | 93 |
| CC_H-38 | Yes | 0.442 | 100 | 104 | 99 |
| CC_H-39 | Yes | 0.402 | 95.92 | 104 | 99 |
| CC_H-40 | Yes | 0.45 | 100 | 100 | 95 |
| CC_H-41 | Yes | 0.42 | 94.77 | 104 | 100 |
| CC_H-42 | Yes | 0.41 | 96.09 | 104 | 99 |
| CC_H-43 | Yes | 0.47 | 97.8 | 105 | 100 |
| CC_H-44 | Yes | 0.46 | 99.04 | 104 | 100 |
| CC_H-45 | Yes | 0.38 | 96.63 | 88 | 96 |
| CC_H-46 | Yes | 0.54 | 98.6 | 104 | 99 |
| CC_H-47 | Yes | 0.497 | 97.1 | 104 | 99 |
| CC_H-48 | Yes | 0.36 | 88.83 | 78 | 96 |
| CC_H-49 | Yes | 0.472 | 98.45 | 102 | 99 |
| CC_H-50 | Yes | 0.533 | 96.89 | 101 | 100 |
| CC_H-51 | Yes | 0.488 | 97.04 | 90 | 99 |
| CC_H-52 | Yes | 0.52 | 100 | 98 | 99 |
| CC_H-54 | Yes | 0.512 | 100 | 104 | 100 |
| CC_H-55 | Yes | 0.55 | 98.46 | 96 | 99 |
| CC_H-57 | Yes | 0.44 | 99.14 | 101 | 100 |
| CC_H-58 | Yes | 0.458 | 85.33 | 77 | 96 |
| CC_H-59 | Yes | 0.49 | 94.5 | 103 | 99 |
| CC_H-61 | Yes | 0.504 | 87.96 | 80 | 100 |
| CC_H-62 | Yes | 0.52 | 100 | 101 | 84 |
| CC_H-63 | Yes | 0.44 | 98.31 | 103 | 99 |
| CC_H-64 | Yes | 0.45 | 92.84 | 87 | 100 |
| CC_H-65 | Yes | 0.49 | 81.7 | 48 | 98 |
| CC_H-66 | Yes | 0.455 | 85.3 | 86 | 99 |
| CC_H-67 | Yes | 0.48 | 76.24 | 98 | 100 |
| CC_H-68 | Yes | 0.44 | 93.52 | 87 | 96 |
| CC_H-69 | Yes | 0.49 | 93.12 | 104 | 99 |
| CC_H-70 | Yes | 0.53 | 97.49 | 103 | 100 |
| CC_H-71 | Yes | 0.486 | 90.7 | | 84 |
| CC_H-72 | Yes | 0.51 | 95.38 | | 93 |
| CC_H-73 | Yes | 0.515 | 100 | | 100 |
| CC_H-74 | Yes | 0.555 | 98.49 | | 96 |
| CC_H-75 | Yes | 0.539 | 97.57 | | 99 |
| CC_H-76 | Yes | 0.547 | 93.43 | | 100 |
| CC_H-77 | Yes | 0.549 | 98.84 | | 99 |
| CC_H-78 | Yes | 0.579 | 99.24 | | 100 |
| CC_H-79 | Yes | 0.507 | 99.22 | | 99 |
| CC_H-80 | Yes | 0.561 | 98.23 | | 98 |
| CC_H-81 | Yes | 0.574 | 95.74 | | 100 |
| CC_H-82 | Yes | 0.568 | 100 | | 100 |
| CC_H-83 | Yes | 0.595 | 100 | | 100 |
| CC_H-84 | Yes | 0.61 | 100 | | 100 |
| CC_H-85 | Yes | 0.56 | 89.57 | | 99 |
| CC_H-86 | Yes | 0.523 | 98.73 | | 95 |
| CC_H-87 | Yes | 0.558 | 95.4 | | 100 |
| CC_H-88 | Yes | 0.561 | 92.25 | | 100 |
| CC_H-89 | Yes | 0.61 | 94.41 | | 100 |
| CC_H-90 | Yes | 0.537 | 98.48 | | 100 |
| CC_H-91 | Yes | 0.573 | 89.8 | | 99 |
| CC_H-92 | Yes | 0.45 | 100 | | 98 |
| CC_H-93 | Yes | 0.61 | 97.87 | | 100 |
| CC_H-94 | Yes | 0.526 | 97.86 | | 100 |
| CC_H-95 | Yes | 0.594 | 99.22 | | 100 |
| CC_H-96 | Yes | 0.558 | 100 | | 100 |
| CC_H-97 | Yes | 0.524 | 98.61 | | 92 |
| CC_H-98 | Yes | 0.585 | 100 | | 92 |
| CC_H-99 | Yes | 0.524 | 99.04 | | 100 |
| CC_H-100 | Yes | 0.544 | 95.47 | | 77 |
| CC_H-101 | Yes | 0.567 | 98.86 | | 100 |
| CC_H-102 | Yes | 0.562 | 93.5 | | 99 |
| CC_H-103 | Yes | 0.57 | 100 | | 89 |
| CC_H-104 | Yes | 0.551 | 96.2 | | 100 |
| CC_H-105 | Yes | 0.54 | 94.58 | | 90 |
| CC_H-106 | Yes | 0.52 | 98.9 | | 100 |
| CC_H-107 | Yes | 0.561 | 91.92 | | 97 |
| CC_H-108 | Yes | 0.59 | 97.39 | | 91 |
| CC_H-109 | Yes | 0.545 | 100 | | 100 |

| Entry No. | [M+] found | R.t. [min] | Purity, UV_254 [%] | % Inhibition (r-B1R) at 10 μM | % Inhibition (h-B1R) at 10 μM |
|---|---|---|---|---|---|
| CC_H-111 | Yes | 0.597 | 93.63 | | 100 |
| CC_H-112 | Yes | 0.496 | 98.69 | | 100 |
| CC_H-115 | Yes | 0.54 | 97.2 | | 99 |
| CC_H-116 | Yes | 0.53 | 100 | | 92 |
| CC_H-118 | Yes | 0.438 | 96.84 | | 89 |
| CC_H-119 | Yes | 0.531 | 97.79 | | 100 |
| CC_H-120 | Yes | 0.568 | 97.47 | | 100 |
| CC_H-121 | Yes | 0.589 | 93.29 | | 100 |
| CC_H-122 | Yes | 0.491 | 97.92 | | 100 |
| CC_H-123 | Yes | 0.534 | 96.46 | | 100 |
| CC_H-124 | Yes | 0.383 | 100 | | 68 |
| CC_H-125 | Yes | 0.582 | 100 | | 100 |
| CC_H-126 | Yes | 0.502 | 98.74 | | 100 |
| CC_H-127 | Yes | 0.515 | 95.81 | | 95 |
| CC_H-128 | Yes | 0.581 | 100 | | 99 |
| CC_H-129 | Yes | 0.62 | 100 | | 100 |
| CC_H-130 | Yes | 0.452 | 100 | | 81 |
| CC_H-131 | Yes | 0.573 | 96.79 | | 99 |
| CC_H-132 | Yes | 0.487 | 97.88 | | 99 |
| CC_H-133 | Yes | 0.548 | 95.56 | | 90 |
| CC_H-134 | Yes | 0.631 | 96.94 | | 100 |
| CC_H-135 | Yes | 0.482 | 82.65 | | 100 |
| CC_H-136 | Yes | 0.551 | 92.64 | | 100 |
| CC_H-137 | Yes | 0.522 | 96.25 | | 96 |
| CC_H-138 | Yes | 0.5 | 97.31 | | 98 |
| CC_H-139 | Yes | 0.537 | 95.87 | | 98 |
| CC_H-140 | Yes | 0.497 | 94.32 | | 100 |
| CC_H-141 | Yes | 0.557 | 100 | | 100 |
| CC_H-142 | Yes | 0.538 | 91.66 | | 100 |
| CC_H-143 | Yes | 0.626 | 1.11 | | 100 |
| CC_H-200 | Yes | | 100 | 111 | |
| CC_H-201 | Yes | | 99.26 | 111 | |
| CC_H-202 | Yes | | 100 | 111 | |
| CC_H-203 | Yes | | 100 | 111 | |
| CC_H-204 | Yes | | 90.41 | 110 | |
| CC_H-205 | Yes | | 97.52 | 98 | |
| CC_H-206 | Yes | | 100 | 109 | |
| CC_H-207 | Yes | | 95.43 | 89 | |
| CC_H-208 | Yes | | 95.97 | 111 | |
| CC_H-209 | Yes | | 51.88 | 112 | |
| CC_H-210 | Yes | | 98.91 | 112 | |
| CC_H-211 | Yes | | 100 | 108 | |
| CC_H-212 | Yes | | 98.38 | 108 | |
| CC_H-213 | Yes | | 98.88 | 110 | |
| CC_H-215 | Yes | | 94.67 | 65 | |
| CC_H-216 | Yes | | 97.8 | 110 | |
| CC_H-217 | Yes | | 100 | 94 | |
| CC_H-218 | Yes | | 99.17 | 109 | |
| CC_H-219 | Yes | | 98.15 | 86 | |
| CC_H-220 | Yes | | 100 | 107 | |
| CC_H-221 | Yes | | 99.22 | 67 | |
| CC_H-222 | Yes | | 94.9 | 110 | |
| CC_H-223 | Yes | | 96.53 | 109 | |
| CC_H-224 | Yes | | 80.67 | 110 | |
| CC_H-225 | Yes | | 76.4 | 112 | |
| CC_H-226 | Yes | | 97.6 | 99 | |
| CC_H-227 | Yes | | 98.84 | 112 | |
| CC_H-228 | Yes | | 96.43 | 107 | |
| CC_H-229 | Yes | | 99.4 | 104 | |
| CC_H-230 | Yes | | 94.73 | 110 | |
| CC_H-231 | Yes | | 94.7 | 111 | |
| CC_H-232 | Yes | | 97.75 | 96 | |
| CC_H-233 | Yes | | 92.34 | 63 | |
| CC_H-234 | Yes | | 98.66 | 108 | |
| CC_H-235 | Yes | | 100 | 65 | |
| CC_H-236 | Yes | | 98.58 | 52 | |
| CC_H-242 | Yes | | 99.35 | 52 | |
| CC_H-245 | Yes | | 86.52 | 107 | |
| CC_H-246 | Yes | | 94.35 | 112 | |
| CC_H-247 | Yes | | 100 | 112 | |
| CC_H-248 | Yes | | 93.56 | 111 | |
| CC_H-249 | Yes | | 87.73 | 110 | |
| CC_H-250 | Yes | | 97.43 | 103 | |
| CC_H-251 | Yes | | 95.84 | 111 | |
| CC_H-252 | Yes | | 95.15 | 107 | |
| CC_H-253 | Yes | | 98.92 | 110 | |
| CC_H-254 | Yes | | 98.6 | 111 | |
| CC_H-255 | Yes | | 97.09 | 104 | |
| CC_H-256 | Yes | | 100 | 96 | |
| CC_H-257 | Yes | | 95.9 | 107 | |
| CC_H-258 | Yes | | 98.18 | 106 | |
| CC_H-259 | Yes | | 96.21 | 100 | |
| CC_H-260 | Yes | | 100 | 61 | |
| CC_H-261 | Yes | | 99.3 | 103 | |
| CC_H-262 | Yes | | 98.95 | 82 | |
| CC_H-265 | Yes | | 96.06 | 105 | |
| CC_H-266 | Yes | | 94.07 | 63 | |
| CC_H-268 | Yes | | 95.91 | 110 | |
| CC_H-269 | Yes | | 97.8 | 109 | |
| CC_H-270 | Yes | | 85.99 | 110 | |
| CC_H-271 | Yes | | 98.72 | 109 | |
| CC_H-272 | Yes | | 98.15 | 112 | |
| CC_H-273 | Yes | | 96.89 | 112 | |
| CC_H-274 | Yes | | 92.72 | 91 | |
| CC_H-275 | Yes | | 98 | 111 | |
| CC_H-276 | Yes | | 97.37 | 51 | |
| CC_H-277 | Yes | | 99 | 100 | |
| CC_H-278 | Yes | | 98.42 | 103 | |
| CC_H-279 | Yes | | 96.26 | 111 | |
| CC_H-280 | Yes | | 99.07 | 91 | |
| CC_H-281 | Yes | | 98.77 | 99 | |
| CC_H-282 | Yes | | 98.8 | 102 | |
| CC_H-283 | Yes | | 99.39 | 106 | |
| CC_H-285 | Yes | | 98.96 | 75 | |
| CC_H-286 | Yes | | 99.2 | 87 | |
| CC_H-288 | Yes | | 100 | 69 | |
| CC_H-289 | Yes | | 94.84 | 77 | |
| CC_H-292 | Yes | | 94.73 | 102 | |
| CC_H-293 | Yes | | 97.69 | 109 | |
| CC_H-294 | Yes | | 95.18 | 111 | |
| CC_H-295 | Yes | | 97.1 | 111 | |
| CC_H-296 | Yes | | 98.89 | 112 | |
| CC_H-297 | Yes | | 98.53 | 110 | |
| CC_H-298 | Yes | | 100 | 101 | |
| CC_H-299 | Yes | | 99.26 | 110 | |
| CC_H-300 | Yes | | 98.33 | 103 | |
| CC_H-302 | Yes | | 99.2 | 112 | |
| CC_H-303 | Yes | | 100 | 112 | |
| CC_H-304 | Yes | | 99.14 | 98 | |
| CC_H-305 | Yes | | 96.1 | 109 | |
| CC_H-306 | Yes | | 99.4 | 107 | |
| CC_H-307 | Yes | | 100 | 91 | |
| CC_H-308 | Yes | | 100 | 96 | |
| CC_H-310 | Yes | | 99.01 | 101 | |
| CC_H-311 | Yes | | 100 | 80 | |
| CC_H-312 | Yes | | 99.24 | 92 | |
| CC_H-314 | Yes | | 98.1 | 81 | |
| CC_H-315 | Yes | | 100 | 72 | |
| CC_H-316 | Yes | | 97.49 | 106 | |
| CC_H-317 | Yes | | 97.85 | 110 | |
| CC_H-318 | Yes | | 96.48 | 111 | |
| CC_H-319 | Yes | | 98.91 | 106 | |
| CC_H-320 | Yes | | 89.3 | 110 | |
| CC_H-321 | Yes | | 84.37 | 65 | |
| CC_H-322 | Yes | | 74.37 | 84 | |
| CC_H-323 | Yes | | 96.47 | 110 | |
| CC_H-324 | Yes | | 97.13 | 108 | |
| CC_H-325 | Yes | | 99.07 | 112 | |
| CC_H-326 | Yes | | 100 | 112 | |
| CC_H-327 | Yes | | 52.96 | 112 | |
| CC_H-328 | Yes | | 98.77 | 111 | |
| CC_H-329 | Yes | | 100 | 111 | |
| CC_H-330 | Yes | | 99 | 111 | |
| CC_H-331 | Yes | | 99.22 | 104 | |
| CC_H-332 | Yes | | 98.42 | 111 | |
| CC_H-333 | Yes | | 100 | 84 | |
| CC_H-335 | Yes | | 100 | 110 | |
| CC_H-336 | Yes | | 97.16 | 97 | |
| CC_H-337 | Yes | | 100 | 110 | |
| CC_H-339 | Yes | | 100 | 92 | |
| CC_H-341 | Yes | | 100 | 95 | |
| CC_H-342 | Yes | | 100 | 107 | |

515

-continued

| Entry No. | [M+] found | R.t. [min] | Purity, UV_254 [%] | % Inhibition (r-B1R) at 10 μM | % Inhibition (h-B1R) at 10 μM |
|---|---|---|---|---|---|
| CC_H-343 | Yes | | 100 | 67 | |
| CC_H-344 | Yes | | 99.23 | 90 | |
| CC_H-346 | Yes | | 100 | 70 | |
| CC_H-347 | Yes | | 96.63 | 57 | |
| CC_H-349 | Yes | | 98.6 | 80 | |
| CC_H-350 | Yes | | 100 | 108 | |
| CC_H-352 | Yes | | 100 | 110 | |
| CC_H-353 | Yes | | 99.35 | 84 | |
| CC_H-354 | Yes | | 100 | 110 | |
| CC_H-355 | Yes | | 100 | 96 | |
| CC_H-356 | Yes | | 100 | 109 | |
| CC_H-357 | Yes | | 100 | 110 | |
| CC_H-358 | Yes | | 100 | 111 | |
| CC_H-359 | Yes | | 99.15 | 110 | |
| CC_H-360 | Yes | | 100 | 109 | |
| CC_H-361 | Yes | | 99.31 | 110 | |
| CC_H-362 | Yes | | 100 | 110 | |
| CC_H-363 | Yes | | 100 | 89 | |

516

-continued

| Entry No. | [M+] found | R.t. [min] | Purity, UV_254 [%] | % Inhibition (r-B1R) at 10 μM | % Inhibition (h-B1R) at 10 μM |
|---|---|---|---|---|---|
| CC_H-364 | Yes | | 100 | 111 | |
| CC_H-365 | Yes | | 100 | 64 | |
| CC_H-366 | Yes | | 100 | 92 | |
| CC_H-375 | Yes | | 98.71 | 91 | |
| CC_H-376 | Yes | | 100 | 77 | |
| CC_H-378 | Yes | | 98.72 | 101 | |
| CC_H-379 | Yes | | 100 | 110 | |
| CC_H-380 | Yes | | 90.01 | 103 | |
| CC_H-381 | Yes | | 99.43 | 109 | |
| CC_H-383 | Yes | | 97.75 | 50 | |
| CC_H-384 | Yes | | 100 | 109 | |

Library No. 2

1) Synthesis of Amine Structural Units CC_AMN

Overview:

| CC_AMN. | Structure | Name (CC_AMN) |
|---|---|---|
| Lib-02_AMN01 | 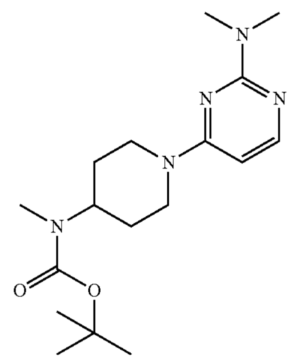 | N-[1-(2-Dimethylamino-pyrimidin-4-yl)-piperidin-4-yl]-N-methyl-carbamic acid tert-butyl ester (Lib-02_AMN01) |
| Lib-02_AMN02 | 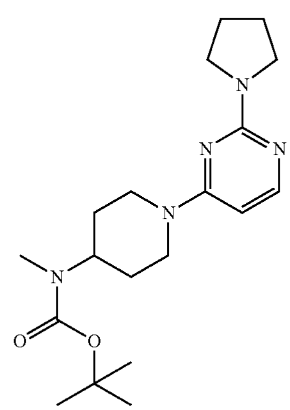 [SMILES: CN(C(=O)OC(C)(C)C)C1CCN(c2ccnc(N3CCCC3)n2)CC1] | N-Methyl-N-[1-(2-pyrrolidin-1-yl-pyrimidin-4-yl)-piperidin-4-yl]-carbamic acid tert-butyl ester (Lib-02_AMN02) |

-continued

| CC_AMN. | Structure | Name (CC_AMN) |
|---|---|---|
| Lib-02_AMN03 | 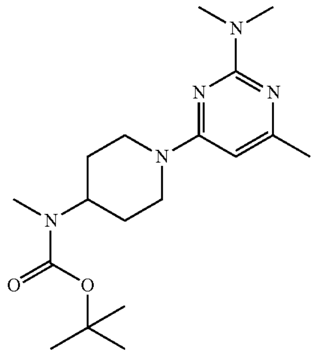 | N-[1-(2-Dimethylamino-6-methyl-pyrimidin-4-yl)-piperidin-4-yl]-N-methyl-carbamic acid tert-butyl ester (Lib-02_AMN03) |
| Lib-02_AMN08 | 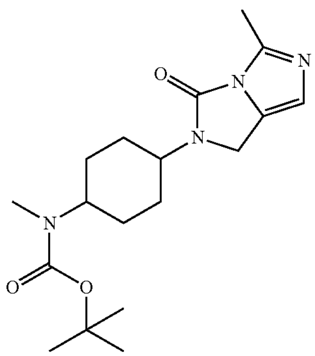 [SMILES: Cc1ncc2n1C(=O)N(C1CCC(N(C)C(=O)OC(C)(C)C)CC1)C2] | N-Methyl-N-[4-(5-methyl-3-oxo-1,2-dihydro-imidazo[5,1-e]imidazol-2-yl)-cyclohexyl]-carbamic acid tert-butyl ester (Lib-02_AMN08) |
| Lib-02_AMN09 | 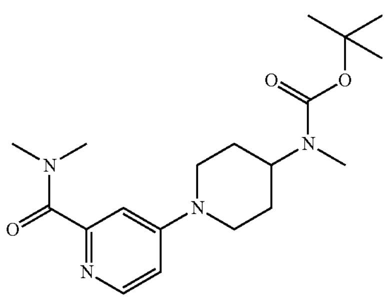 [SMILES: CN(C)C(=O)c1cc(N2CCC(N(C)C(=O)OC(C)(C)C)CC2)ccn1] | N-[1-[2-(Dimethyl-carbamoyl)-pyridin-4-yl]-piperidin-4-yl]-N-methyl-carbamic acid tert-butyl ester (Lib-02_AMN09) |
| Lib-02_AMN10 | 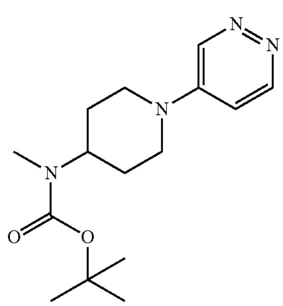 [SMILES: CN(C(=O)OC(C)(C)C)C1CCN(c2ccnnc2)CC1] | N-Methyl-N-(1-pyridazin-4-yl-piperidin-4-yl)-carbamic acid tert-butyl ester (Lib-02_AMN10) |
| Lib-02_AMN12 | 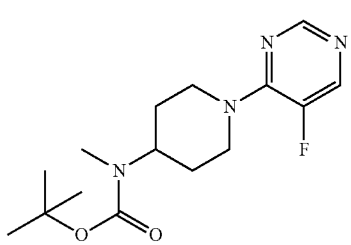 [SMILES: CN(C(=O)OC(C)(C)C)C1CCN(c2ncncc2F)CC1] | N-[1-(5-Fluoro-pyrimidin-4-yl)-piperidin-4-yl]-N-methyl-carbamic acid tert-butyl ester (Lib-02_AMN12) |

-continued

| CC_AMN. | Structure | Name (CC_AMN) |
|---|---|---|
| Lib-02_AMN13 | 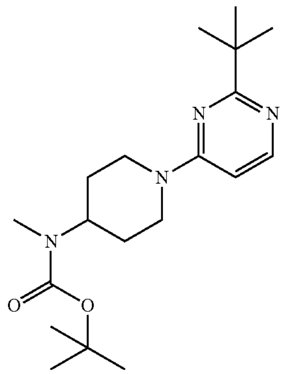 [SMILES: CN(C(=O)OC(C)(C)C)C1CCN(c2ccnc(C(C)(C)C)n2)CC1] | N-[1-(2-tert-Butyl-pyrimidin-4-yl)-piperidin-4-yl]-N-methyl-carbamic acid tert-butyl ester (Lib-02_AMN13) |
| Lib-02_AMN14 | 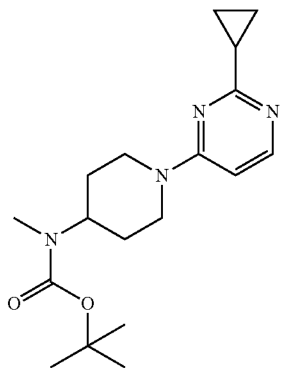 [SMILES: CN(C(=O)OC(C)(C)C)C1CCN(c2ccnc(C3CC3)n2)CC1] | N-[1-(2-Cyclopropyl-pyrimidin-4-yl)-piperidin-4-yl]-N-methyl-carbamic acid tert-butyl ester (Lib-02_AMN14) |
| Lib-02_AMN15 | 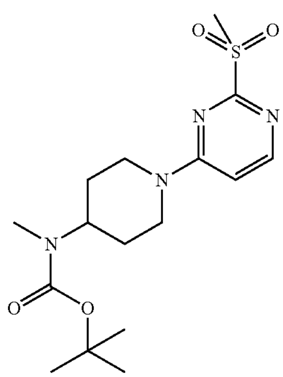 [SMILES: CN(C(=O)OC(C)(C)C)C1CCN(c2ccnc(S(C)(=O)=O)n2)CC1] | N-Methyl-N-[1-(2-methylsulfonyl-pyrimidin-4-yl)-piperidin-4-yl]-carbamic acid tert-butyl ester (Lib-02_AMN15) |

Syntheses of the Structural Units

Synthesis of Lib-02_AMN01: N-[1-(2-Dimethylamino-pyrimidin-4-yl)-piperidin-4-yl]-N-methyl-carbamic acid tert-butyl ester (Lib-02_AMN01)

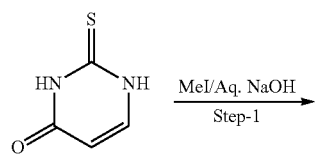

-continued

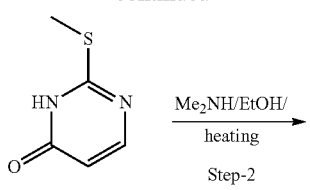

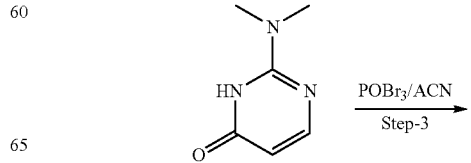

-continued

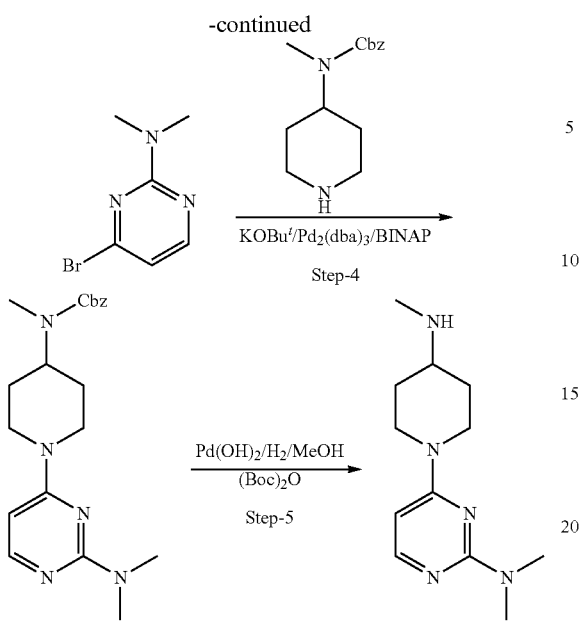

Step 1: 2-Thiouracil (15 g; 0.117 mol) was dissolved in aqueous sodium hydroxide solution (9.3 g of NaOH in 82 ml of water); methyl iodide (8.2 ml; 0.131 mol) was added and stirring was carried out for 16 h at room temperature. The reaction mixture was acidified with glacial acetic acid (20 ml), and the white precipitate was filtered off with suction, washed several times with cold water and dried. Yield: 72.28% (12 g; 0.0084 mol)

Step 2: N,N-Dimethylamine solution in THF (2 mol/l; 52 ml; 0.104 mol) was placed in a pressure vessel. The product from step 1 (12 g; 0.084 mol) was added and stirring was carried out for 16 h at 100° C. After cooling to room temperature, concentration under reduced pressure was carried out and the solid so obtained was washed with ethyl acetate (100 ml) and dried in vacuo. The desired product (white solid) was used in the next step without being purified. Yield: 76% (9 g; 0.064 mol)

Step 3: The product from step 2 (3.6 g; 0.025 mol) was refluxed for 1 h with phosphorus oxybromide (9.62 g; 0.0336 mol) in acetonitrile (115 ml). After cooling to room temperature, the reaction mixture was concentrated to half under reduced pressure and poured onto ice-water. The solution was neutralized with saturated sodium hydrogen carbonate solution and extracted with dichloromethane (2×100 ml). The combined organic phases were washed with saturated sodium chloride solution, dried over sodium sulfate, filtered and concentrated in vacuo. The solid was purified by column chromatography (silica gel 230-400, 5% ethyl acetate in hexane). Yield: 62.74% (3.2 g; 0.0167 mol)

Step 4: Caesium carbonate (10 g; 0.032 mol), pd$_2$(dba)$_3$ (1.46 g; 0.0016 mol) and Xantphos (3.6 g; 0.0064 mol) were added at room temperature, with stirring and under an argon atmosphere, to a solution of the product of step 3 (3.2 g; 0.016 mol) in dry toluene (48 ml). The reaction mixture was degassed with argon, and the amine (4.7 g; 0.0192 mol) was added at room temperature. The reaction mixture was again degassed with argon and refluxed for 16 h. After cooling to room temperature, filtration over Celite and concentration under reduced pressure were carried out. The crude product was purified by column chromatography (silica gel 230-400, methanol/dichloromethane). Yield: 22% (1.3 g; 0.0035 mol)

Step 5: 20% palladium hydroxide (0.35 g) and (BOC)$_2$O (1.14 ml; 0.0525 mol) were added to a degassed solution of the product from step 4 (1.3 g; 0.0035 mol) in methanol (25 ml). The reaction mixture was again degassed with argon and stirred for 16 h at room temperature under a hydrogen pressure of 3 kg. Filtration over Celite and concentration under reduced pressure were then carried out. The crude product was purified by column chromatography (silica gel 230-400, 20% ethyl acetate in hexane). Yield: 67.79% (0.8 g; 0.0023 mol)

Synthesis of Lib-02_AMN02: N-Methyl-N-[1-(2-pyrrolidin-1-yl-pyrimidin-4-yl)-piperidin-4-yl]-carbamic acid tert-butyl ester (Lib-02_AMN02)

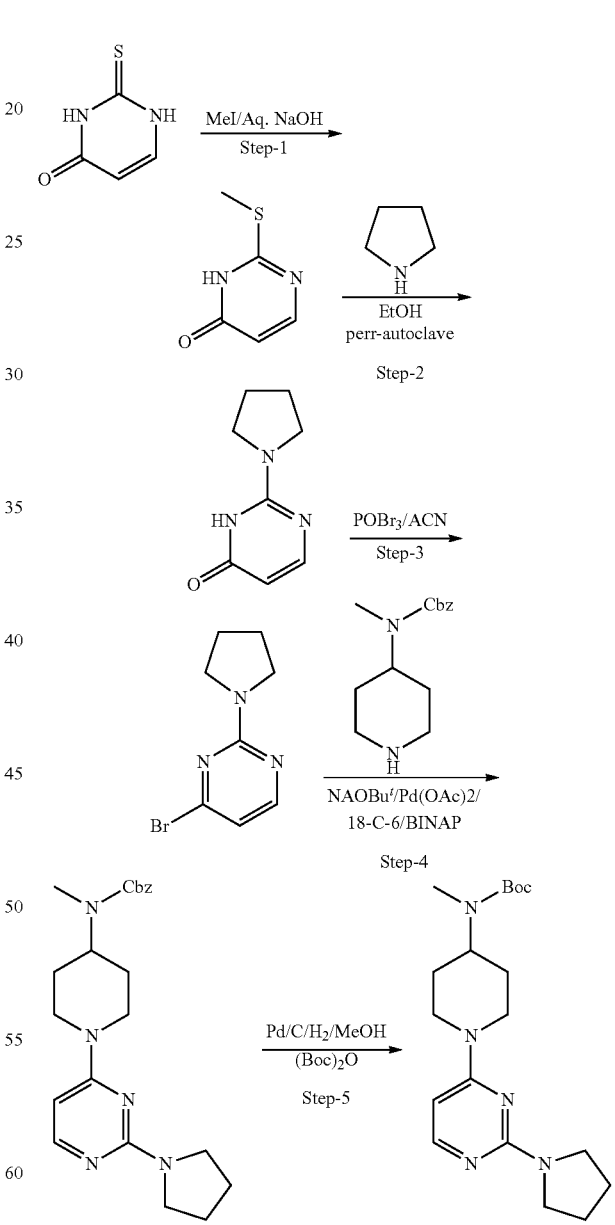

Step 1: 2-Thiouracil (15 g; 0.117 mol) was dissolved in aqueous sodium hydroxide solution (9.3 g of NaOH in 82 ml of water); methyl iodide (8.2 ml; 0.131 mol) was added and stirring was carried out for 16 h at room temperature. The reaction mixture was acidified with glacial acetic acid (20 ml), and the white precipitate was filtered off with suction, washed several time with cold water and dried. Yield: 72.28% (12 g; 0.0084 mol)

Step 2: In a pressure vessel, pyrrolidine (50 ml; 0.6 mol) was placed in ethanol (100 ml). The product from step 1 (20 g; 0.1408 mol) was added and stirring was carried out for 16 h at 100° C. After cooling to room temperature, concentration under reduced pressure was carried out and the crude product was purified by column chromatography (silica gel 100-200, methanol/dichloromethane). Yield: 34% (8 g; 0.0484 mol)

Step 3: The product from step 2 (10 g; 0.0606 mol) was refluxed for 1 h with phosphorus oxybromide (22.5 g; 0.0787 mol) in acetonitrile (100 ml). After cooling to room temperature, the reaction mixture was concentrated to half under reduced pressure and poured onto ice-water. The solution was neutralized with sodium hydrogen carbonate solution and extracted with dichloromethane (2×100 ml). The combined organic phases were washed with saturated sodium chloride solution, dried over sodium sulfate, filtered and concentrated in vacuo. The solid was purified by column chromatography (silica gel 230-400, ethyl acetate in hexane). Yield: 57.97% (8 g; 0.035 mol)

Step 4: Sodium tert-butoxide (3.8 g; 0.04 mol), Pd(OAc)$_2$ (0.27 g; 0.0012 mol), rac-BINAP (0.25 g; 0.0004 mol) and 18-C6 (1 g; 0.00378 mol) were added to a solution of the product from step 3 (4.6 g; 0.02 mol) in dry 1,4-dioxane (100 ml). The reaction mixture was degassed with argon, and the amine (5 g; 0.02 mol) was added. The reaction mixture was again degassed with argon and refluxed for 16 h. After cooling to room temperature, filtration over Celite and concentration under reduced pressure were carried out. The crude product was purified by column chromatography (silica gel 230-400, methanol/dichloromethane). Yield: 35% (2.8 g; 0.007 mol)

Step 5: (20%) Pd/C (1 g) and (BOC$_2$)O (2.52 g; 0.0121 mol) were added to a degassed solution of the product from step 4 (4 g; 0.01 mol) in methanol (100 ml). The reaction mixture was again degassed with argon and stirred for 16 h at room temperature under a hydrogen pressure of 3 kg. Filtration over Celite and concentration under reduced pressure were then carried out. The crude product was purified by column chromatography (silica gel 230-400, ethyl acetate/hexane). Yield: 52.38% (2.2 g; 0.006 mol)

Synthesis of Lib-02_AMN03: N-[1-(2-Dimethylamino-6-methyl-pyrimidin-4-yl)-piperidin-4-yl]-N-methyl-carbamic acid tert-butyl ester (Lib-02_AMN03)

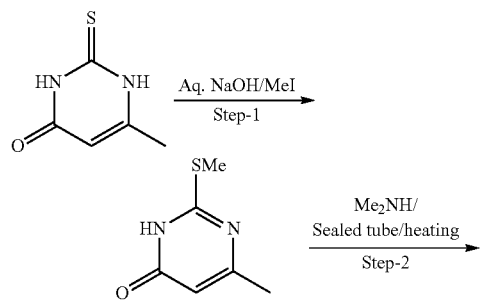

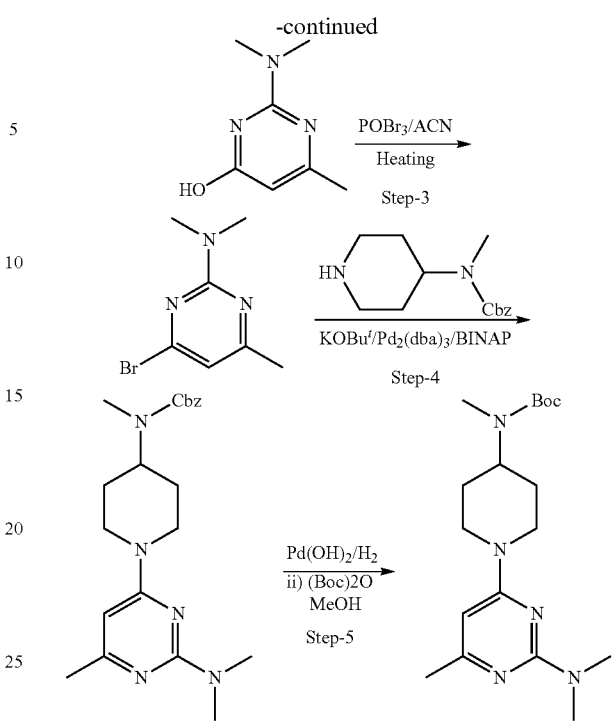

Step 1: 6-Methyl-2-thiouracil (20 g; 0.14 mol) was dissolved in aqueous sodium hydroxide solution (11.8 g of NaOH in 98 ml of water); methyl iodide (9.8 ml; 0.1568 mol) was added and stirring was carried out for 16 h at room temperature. The reaction mixture was acidified with glacial acetic acid (20 ml), and the white precipitate was filtered off with suction, washed several times with cold water and dried. Yield: 81.9% (18 g; 0.1153 mol)

Step 2: In a pressure vessel, N,N-dimethylamine solution was placed in THF (2 mol/l; 71.53 ml; 0.143 mol). The product from step 1 (18 g; 0.11538 mol) was added and stirring was carried out for 16 h at 100° C. After cooling to room temperature, concentration under reduced pressure was carried out and the solid so obtained was washed with ethyl acetate (2×100 ml) and dried in vacuo. The desired product (white solid) was used in the next stage without being purified. Yield: 56.65% (10 g; 0.0653 mol)

Step 3: The product from step 2 (10 g; 0.0653 mol) was refluxed for 1 h with phosphorus oxybromide (24.3 g; 0.0849 mol) in acetonitrile (300 ml). After cooling to room temperature, the reaction mixture was concentrated to half under reduced pressure and poured onto ice-water. The solution was neutralized with saturated sodium hydrogen carbonate solution and extracted with dichloromethane (2×200 ml). The combined organic phases were washed with saturated sodium chloride solution, dried over sodium sulfate, filtered and concentrated in vacuo. The solid was purified by column chromatography (silica gel 230-400, ethyl acetate in hexane). Yield: 57.14% (8 g; 0.0372 mol)

Step 4: Caesium carbonate (18 g; 0.0558 mol), pd$_2$(dba)$_3$ (1.2 g; 0.00139 mol) and Xantphos (8.3 g; 0.0334 mol) were added at room temperature, with stirring and under an argon atmosphere, to a solution of the product from step 3 (6 g; 0.0279 mol) in dry toluene (83 ml). The reaction mixture was degassed with argon, and the amine (8.3 g; 0.0334 mol) was added at room temperature. The reaction mixture was again degassed with argon and refluxed for 16 h. After cooling to room temperature, filtration over Celite and concentration under reduced pressure were carried out. The crude product was purified by column chromatography (silica gel 230-400, methanol/dichloromethane). Yield: 25.28% (2.7 g; 0.007 mol)

Step 5: 20% palladium hydroxide (1.04 g) and (BOC)$_2$O (2.2 ml; 0.0105 mol) were added to a degassed solution of the product from step 4 (2.7 g; 0.007 mol) in methanol (35 ml). The reaction mixture was stirred for 12 h at room temperature under a hydrogen pressure of 3 kg. Filtration over Celite and concentration under reduced pressure were then carried out. The crude product was purified by column chromatography (silica gel 230-400, 20% ethyl acetate in hexane). Yield: 93.49% (2.3 g; 0.0065 mol)

Synthesis of Lib-02_AMN08: N-Methyl-N-[4-(5-methyl-3-oxo-1,2-dihydro-imidazo-[5,1-e]imidazol-2-yl)-cyclohexyl]-carbamic acid tert-butyl ester (Lib-02_AMN08)

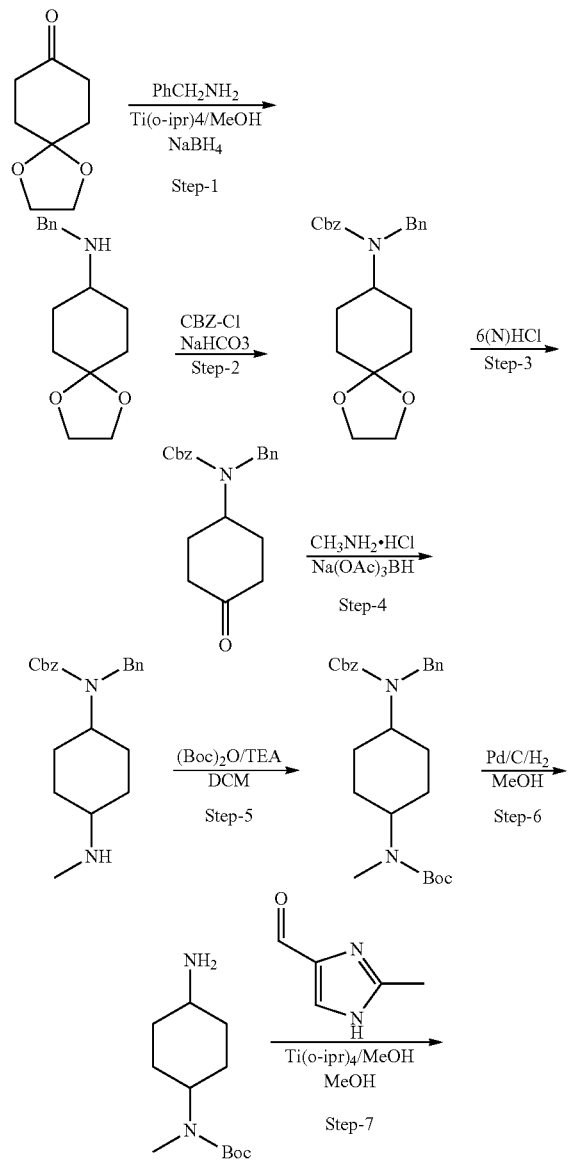

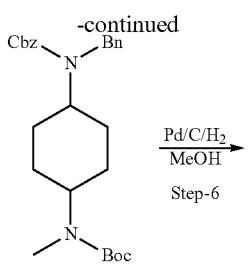

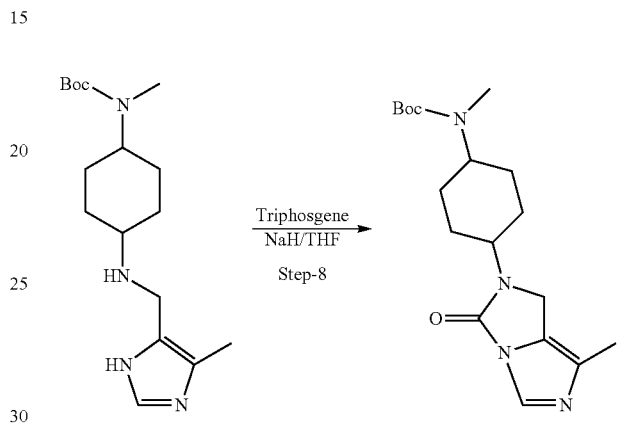

Step 1: A mixture of 1,4-dioxaspiro[4.5]decan-8-one (25 g; 0.16 mol; 1 eq) and benzylamine (17.14 g; 0.16 mol; 1 eq) in Ti(o-ipr)4 (180 ml; 0.128 mol; 5 eq) was stirred for 16 h at room temperature. Methanol (700 ml) was added, the reaction mixture was cooled to 0° C., and NaBH4 (1.8 g; 0.048 mol; 1.5 eq) was added. Stirring was then carried out for 6 h at room temperature. The mixture was hydrolyzed with ammonium chloride solution and concentrated under reduced pressure; extraction with ethyl acetate (2×1000 ml) was carried out. The combined organic phases were washed with water (2×500 ml) and saturated sodium chloride solution (500 ml), dried over sodium sulfate, filtered and concentrated under reduced pressure. The crude product was purified by column chromatography (dichloromethane/methanol). Yield: 75% (30 g; 0.121 mol)

Step 2: CBZ-Cl (55 ml, 0.16 mol, 2 eq) was slowly added at 0° C. to a solution of the product from step 1 (20 g, 0.08 mol, 1 eq) in saturated sodium hydrogen carbonate solution (270 ml). The reaction mixture was stirred for 16 h at room temperature. The mixture was diluted with ethyl acetate (500 ml) and washed with water (2×500 ml) and saturated sodium chloride solution (100 ml). The organic phase was dried over sodium sulfate and concentrated in vacuo, and the crude product was purified by column chromatography (silica gel 100-200, ethyl acetate/hexane). The desired product was in the form of a colourless oil. Yield: 98% (30 g, 0.0787 mol)

Step 3: The product from step 2 (20 g, 0.0787 mol, 1 eq) was added to 6 (N)HCl solution (600 ml) and stirred overnight. The reaction mixture was diluted with ethyl acetate (500 ml) and washed with water (2×100 ml) and saturated sodium chloride solution (100 ml). The organic phase was dried over sodium sulfate and concentrated under reduced pressure, and the crude product was purified by column chromatography (silica gel 100-200, methanol/dichloromethane). The desired product was in the form of a colourless oil. Yield: 75% (20 g, 0.0593 mol)

Step 4: Methylamine hydrochloride (4.0 g, 0.059 mol, 2 eq) was added, with stirring, to a solution of the product from step 3 (10 g, 0.0296 mol) in dichloroethane (150 ml), and stirring was carried out for 1 h at room temperature. Sodium triacetoxyborohydride (18.8 g, 0.088 mol, 3 eq) was then added and stirring was carried out for 16 h at room temperature. The reaction mixture was diluted with dichloromethane (500 ml), washed with saturated sodium hydrogen carbonate solution (500 ml), water (100 ml) and saturated sodium chloride solution (100 ml), dried over sodium sulfate and concentrated under reduced pressure. The crude product was purified by column chromatography (methanol/dichloromethane). Yield: 40% (4.0 g, 0.0118 mol)

Step 5: TEA (17.2 g, 0.17 mol, 3 eq) and BOC anhydride (18.59 g, 0.0852 mol, 1.5 eq) were added at 0° C. to a solution of the product from step 4 (20.0 g, 0.0568 mol) in dichloromethane (200 ml). The reaction mixture was stirred for 16 h at room temperature and then diluted with dichloromethane (500 ml), washed with water (2×200 ml) and saturated sodium chloride solution (100 ml), dried over sodium sulfate and concentrated under reduced pressure. The crude product was purified by column chromatography (silica gel 230-400, methanol/dichloromethane). Yield: 77% (20 g, 0.044 mol)

Step 6: The product from step 5 (25 g, 0.055 mol) was hydrogenated with Pd/C (5 g, 20%) in methanol (1000 ml), hydrogen pressure 30 psi, 3 h. The reaction mixture was filtered over Celite and concentrated under reduced pressure, and the crude product was used in the next step without being purified further. Yield: 95% (12 g, 0.0526 mol)

Step 7: A mixture of the product from step 6 (10 g, 0.04 mol, 1 eq) and 4-methyl-1H-imidazole-2-carbaldehyde (4.8 g, 0.04 mol, 1 eq) in Ti(o-ipr)$_4$ (65 ml, 0.2 mol, 5 eq) was stirred for 16 h at room temperature. Methanol (300 ml) was then added, and the mixture was cooled to 0° C. Sodium triacetoxyborohydride (2.49 g, 0.065 mol, 1.5 eq) was added at that temperature, the cooling bath was removed and stirring was carried out for 16 h at room temperature. The reaction mixture was diluted with ammonium chloride solution (100 ml), concentrated and extracted with ethyl acetate (2×1000 ml). Washing with water (2×200 ml) and saturated sodium chloride solution (200 ml) was carried out, and the combined organic phases were dried over sodium sulfate and concentrated under reduced pressure. The crude product was purified by column chromatography (dichloromethane/methanol). Yield: 77% (10 g, 0.031 mol)

Step 8: A suspension of NaH (2.24 g, 0.055 mol, 3 eq) in THF (50 ml) was cooled to 0° C.; the product from step 7 (6 g, 0.018 mol, 1 eq) was added dropwise in dissolved form, and stirring was carried out for 30 min. Phosgene (20% in toluene, 50 ml, 0.1 mol, 5 eq) was added, and the reaction mixture warmed to room temperature and was stirred for 16 h. It was cooled to 0° C. again, rendered basic by the slow addition of saturated sodium hydrogen carbonate solution and extracted with ethyl acetate (3×500 ml). The combined organic phases were washed with saturated sodium chloride solution, dried over sodium sulfate and concentrated under reduced pressure. The crude product was purified by column chromatography (dichloromethane/methanol). Yield: 47% (3.0 g, 0.0086 mol)

Synthesis of Lib-02 AMN09: N-[1-(2-Dimethylamino-pyrimidin-4-yl)-piperidin-4-yl]-N-methylcarbamic acid tert-butyl ester (Lib-02_AMN09)

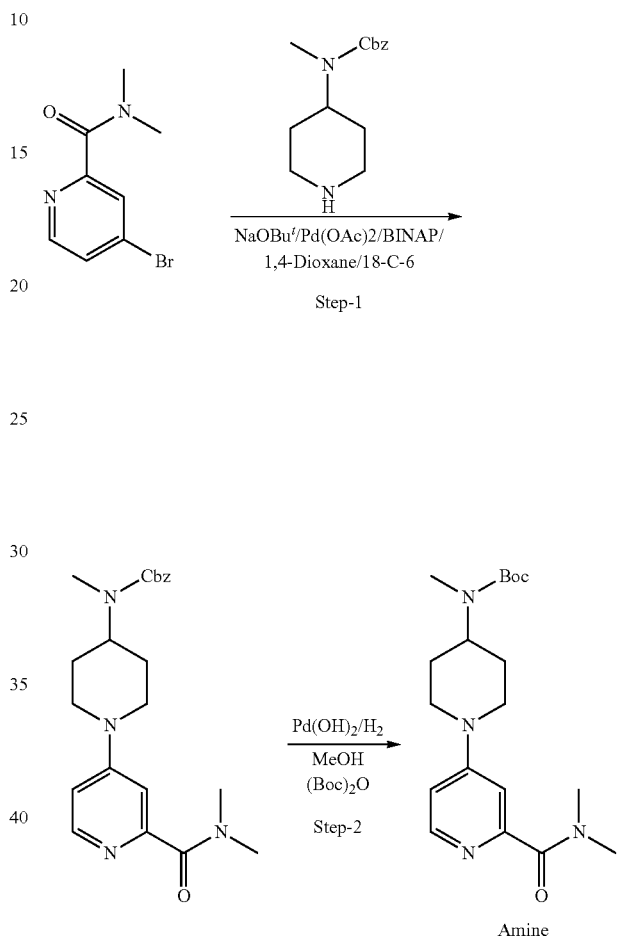

Step 1: NaOBu$^t$ (0.76 g; 0.0008 mol), Pd(OAc)$_2$ (0.053 g; 0.00024 mol), rac-BINAP (0.049 g, 0.00008 mol) and 18-C-6 (0.52 g; 0.0002 mol) were added to a solution of 4-bromopicolinamide (1.1 g; 0.0048 mol) in dry 1,4-dioxane (10 ml). The reaction mixture was rinsed with argon, and the amine (1 g; 0.004 mol) was added. The reaction mixture was again rinsed with argon and then refluxed for 16 h. After cooling to room temperature, filtration over Celite was carried out and the filtrate was concentrated under reduced pressure and purified by column chromatography (silica gel 230-400, methanol/dichloromethane). Yield: 35.22% (0.56 g; 0.0014 mol)

Step 2: 20% PdOH (0.12 g) and (BOC)$_2$O (0.45 ml, 0.0021 mol) were added to a degassed solution of the product from step 1 (0.5 g; 0.0012 mol) in methanol (10 ml). The reaction mixture was rinsed thoroughly with argon and hydrogenated for 16 h at room temperature with a hydrogen pressure of 3 kg. Filtration over Celite and concentration under reduced pressure were then carried out. The crude product was purified by

Synthesis of Lib-02 AMN10: N-Methyl-N-(1-pyridazin-4-yl-piperidin-4-yl)-carbamic acid tert-butyl ester (Lib-02_AMN10)

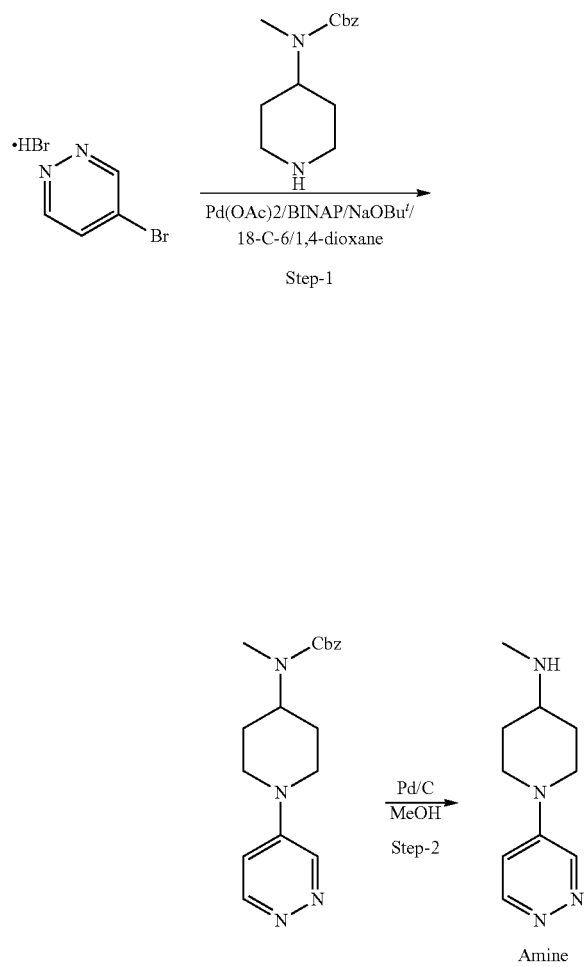

Step 1: NaOBu$^t$ (1.54 g; 0.01612 mol) and 18-C-6 (1.06 g; 0.00403 mol) were added to a solution of 4-bromopyridazine (1.93 g, 0.00806 mol) in 1,4-dioxane (20 ml). Stirring was carried out for 30 min at room temperature, and then the amine (2 g; 0.00806 mol; 1 eq) in 1,4-dioxane (10 ml) was added and the mixture was rinsed thoroughly with argon for 30 min. Pd(OAc)$_2$ (0.108 g; 0.000483 mol; 0.06 eq) and BINAP (0.1 g; 0.000161 mol; 0.02 eq) were added and the mixture was refluxed for 24 h. After cooling to room temperature, filtration was carried out and the filtrate was concentrated under reduced pressure and purified by column chromatography (silica gel 100-200, ethyl acetate/hexane 50/50). Yield: 17.11% (0.45 g; 0.00138 mol)

Step 2: The product from step 1 (0.45 g; 0.00138 mol) was dissolved in methanol (10 ml) and degassed for 15 min with argon. 10% Pd/C (0.15 g) was added and the mixture was degassed again and stirred for 16 h under a hydrogen atmosphere. Filtration over Celite and concentration under reduced pressure were then carried out, and the crude product was used further without being purified. Yield: 89% (0.22 g; 0.00114 mol)

Synthesis of Lib-02_AMN12: N-[1-(5-Fluor-pyrimidin-4-yl)-piperidin-4-yl]-N-methyl-carbamic acid tert-butyl ester (Lib-02_AMN12)

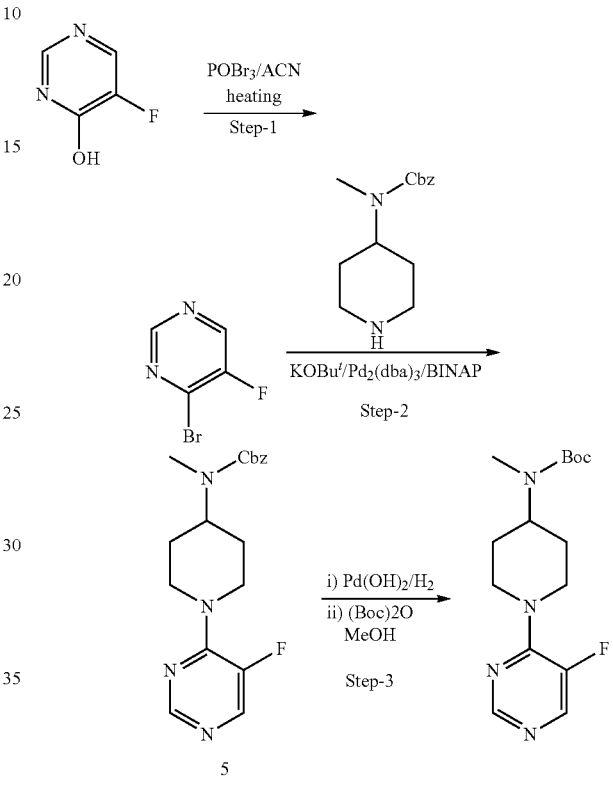

Step 1: 5-Fluoro-4-hydroxypyrimidine (10 g, 0.0877 mol) and phosphorus oxybromide (32.6 g, 0.114 mol) were refluxed for 1 h in acetonitrile (420 ml). The reaction mixture cooled to room temperature, was concentrated to half under reduced pressure and was poured into ice-water. This mixture was neutralized with saturated sodium hydrogen carbonate solution, and extraction with dichloromethane (2×200 ml) was carried out. The combined organic phases were washed with saturated sodium chloride solution, dried over sodium sulfate and concentrated under reduced pressure. The crude product was purified by column chromatography (silica gel 230-400, ethyl acetate/hexane). Yield: 46% (7 g, 0.395 mol)

Step 2: Caesium carbonate (25 g, 0.079 mol), Pd$_2$(dba)$_3$ (1.8 g, 0.0019 mol) and Xantphos (1.09 g, 0.0019 mol) were added to a solution of the product from step 1 (7 g, 0.03954 mol) in dry toluene (150 ml). Argon was passed through the reaction mixture, and then the amine (11.76 g, 0.0474 mol) was added. The mixture was again degassed with argon and then refluxed for 16 h. After cooling to room temperature, the reaction mixture was filtered over Celite and concentrated under reduced pressure. The crude product was purified by column chromatography (silica gel 230-400, dichloromethane/methanol). Yield: 48.94% (7.41 g, 0.0193 mol)

Step 3: 20% Pd(OH)$_2$ (2.84 g) and (BOC)$_2$O (3.03 ml, 0.03 mol) were added to a degassed solution of the product from step 2 (7.4 g, 0.0193 mol) in methanol (100 ml); hydrogenation was carried out for 12 h at room temperature with a hydrogen pressure of 3 kg. The reaction mixture was filtered over Celite and the crude product was purified by column chromatography (silica gel 230-400, ethyl acetate/hexane). Yield: 86.9% (5.2 g, 0.0167 mol)

Synthesis of Lib-02_AMN13: N-[1-(2-tert-Butyl-pyrimidin-4-yl)-piperidin-4-yl]-N-methyl-carbamic acid tert-butyl ester (Lib-02_AMN13)

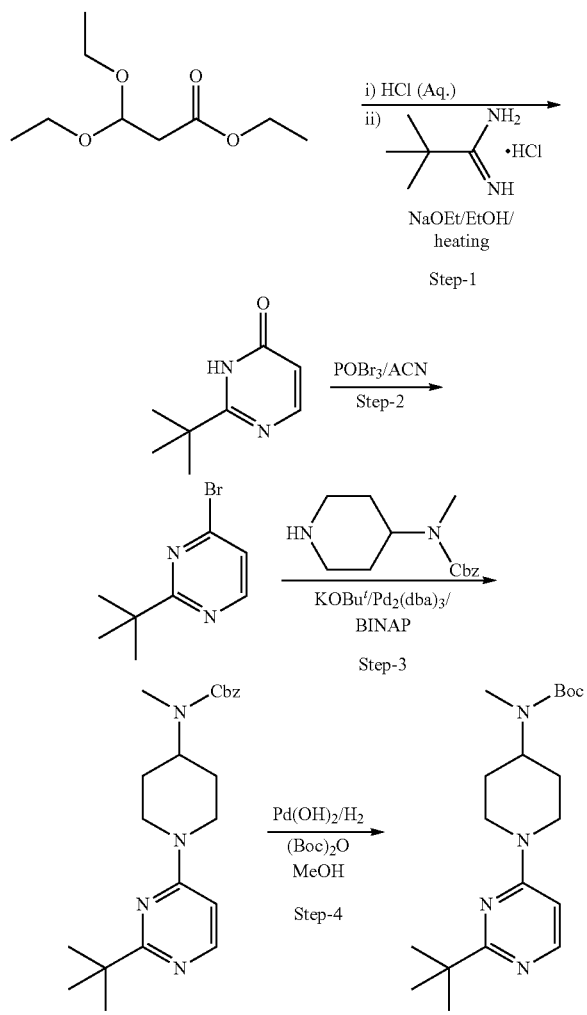

Step 1:
Ethyl 3,3-diethyloxypropionate (50 g, 0.2631 mol) was dissolved at 0° C. in a 6 molar HCl solution (1000 ml) and stirring was carried out for 4 hours at RT. The reaction solution was diluted with ether (1500 ml), the phases were separated, and the org. phase was washed with water (3×200 ml) and sat. NaCl solution (2×200 ml), dried over sodium sulfate and concentrated under reduced pressure. The crude product was immediately reacted further. Sodium (3.5 g, 0.1517 mol) was taken up in ethanol (200 ml), and the crude product was added dropwise at RT. The reaction mixture was stirred overnight at boiling temperature, cooled to RT and concentrated under reduced pressure; the residue was taken up in sodium hydrogen carbonate solution and extracted with ethyl acetate (3×300 ml). The combined org. phases were washed with sat. NaCl solution (2×100 ml), dried over sodium sulfate, concentrated under reduced pressure and purified by column chromatography (silica gel, ethyl acetate/hexane). Yield: 67.3% (7 g, 0.0460 mol)

Step 2:
The product from step 1 (7.2 g, 0.04736 mol) was dissolved in acetonitrile (220 ml); phosphorus oxybromide (16.28 g, 0.05683 mol) was added at RT, and refluxing was carried out for 1 h. The reaction mixture was concentrated under reduced pressure and the residue was taken up in DCM (500 ml), washed with sodium hydrogen carbonate solution (2×100 ml), water (2×100 ml) and sat. NaCl solution (100 ml), dried over sodium sulfate, concentrated under reduced pressure and purified by column chromatography (silica gel, ethyl acetate/hexane). Yield: 70% (7 g, 0.0460 mol)

Step 3:
The product from step 2 (4.0 g, 0.0186 mol) was dissolved in toluene (100 ml) and degassed with argon, and $Cs_2CO_3$ (12.0 g, 0.0372 mol) was added. The amine (5.53 g, 0.02232 mol), $Pd_2dba_3$ (0.85 g, 0.00093 mol) and Xantphos (0.53 g, 0.00093 mol) were then added and refluxing was carried out for 16 hours. The reaction mixture was cooled to RT and filtered off over Celite, and the filtrate was concentrated under reduced pressure and purified by column chromatography (silica gel, ethyl acetate/hexane). Yield: 56.3% (4 g, 0.0104 mol)

Step 4:
The product from step 3 (4.9 g. 0.01282 mol) was dissolved in MeOH (80 ml); $Pd(OH)_2$ (20%, 0.98 g) and $(BOC)_2O$ (4.1 g, 0.01923 mol) were added and hydrogenation was carried out for 12 hours at RT under a hydrogen atmosphere. The reaction mixture was filtered off over Celite, and the filtrate was concentrated under reduced pressure and purified by column chromatography (silica gel, ethyl acetate/hexane). Yield: 59% (2.6 g, 0.00747 mol)

Synthesis of Lib-02_AMN14: N-[1-(2-Cyclopropyl-pyrimidin-4-yl)-piperidin-4-yl]-N-methyl-carbamic acid tert-butyl ester (Lib-02_AMN14)

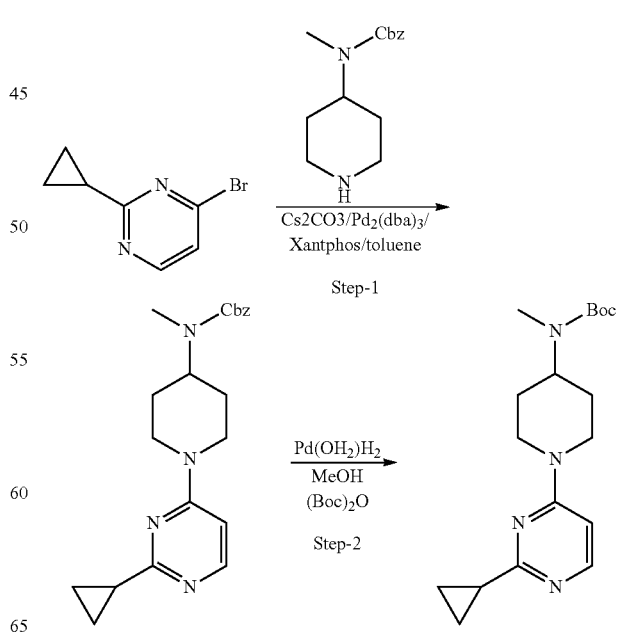

Step 1:

4-Bromo-2-cyclopropyl-pyrimidine (3.0 g, 0.015 mol) was dissolved in toluene, and Cs₂CO₃ (9.81 g, 0.03 mol), Pd₂dba₃ (0.688 g, 0.00075 mol) and Xantphos (0.435 g, 0.00075 mol) were added. Under an argon atmosphere, the amine (3.72 g, 0.015 mol) was added and refluxing was carried out for 16 hours. The reaction mixture was filtered off over Celite, and the filtrate was concentrated under reduced pressure and purified by column chromatography (silica gel, MeOH/DCM). Yield: 38.7% (2.1 g, 0.0058 mol)

Step 2:

The product from step 1 (0.1 g. 0.00027 mol) was dissolved in MeOH (8 ml) and degassed with argon; Pd(OH)₂ (20%, 0.03 g) and (BOC)₂O (0.071 g, 0.00032 mol) were added and hydrogenation was carried out for 16 hours at RT. The reaction mixture was filtered off over Celite, and the filtrate was concentrated under reduced pressure and purified by column chromatography (silica gel). Yield: 77.5% (0.07 g, 0.0002 mol)

Synthesis of Lib-02_AMN15: N-Methyl-N-[1-(2-methylsulfonyl-pyrimidin-4-yl)-piperidin-4-yl]-carbamic acid tert-butyl ester (Lib-02_AMN15)

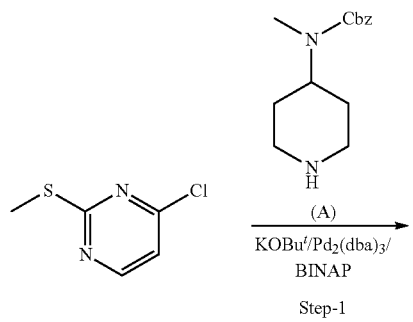

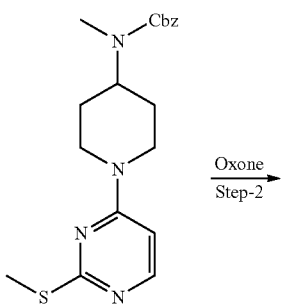

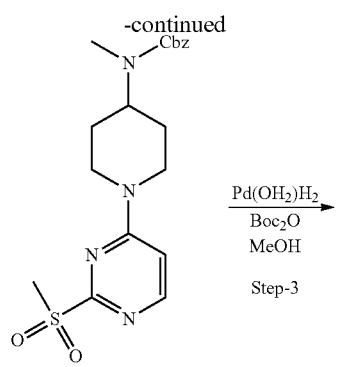

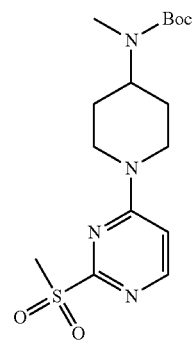

Step 1:

Substance A (10 g, 0.040 mol), 4-chloro-2-methylsulfanylpyrimidine (6.45 g, 0.040 mol) and Cs₂CO₃ (26 g, 0.080 mol) were dissolved in toluene (120 ml) and degassed with argon. X-phos (1.16 g, 0.05 eq) and Pd₂dba₃ (1.8 g, 0.05 eq) were added and refluxing was carried out for 16 hours under argon. The reaction mixture was filtered over Celite, and the filtrate was concentrated under reduced pressure and purified by column chromatography (silica gel, MeOH/DCM). Yield: 53.36% (8 g, 0.0215 mol)

Step 2:

The product from step 1 (4.5 g, 0.012 mol) was dissolved in ethanol:acetic acid:water (3:3:2, 180 ml); ozone (14 g, 0.0241 mol) was added at 0° C. and stirring was carried out for 2 hours at RT. The reaction mixture was diluted with DCM (600 ml), washed with sat. sodium hydrogen carbonate solution (2×150 ml) and sat. NaCl solution (150 ml), dried over sodium sulfate and concentrated under reduced pressure. The crude product was used in the next step without being purified further. Yield: 81.9% (4 g, 0.0099 mol)

Step 3:

The product from step 2 (2.5 g. 0.0061 mol) was dissolved in MeOH/ethyl acetate (1:1, 100 ml) and degassed; Pd(OH)₂ (20%, 0.5 g) and (BOC)₂O (1.6 g, 0.0073 mol) were added and hydrogenation was carried out for 12 hours at RT. The reaction mixture was filtered off over Celite, and the filtrate was concentrated under reduced pressure and purified by column chromatography (silica gel). Yield: 34.94% (0.8 g, 0.00216 mol)

2) Synthesis of the Acid Structural Units (Lib-02_ACI)
Overview:

| Lib-02_ACI | Structure | Name |
|---|---|---|
| Lib-02_ACI-01 | 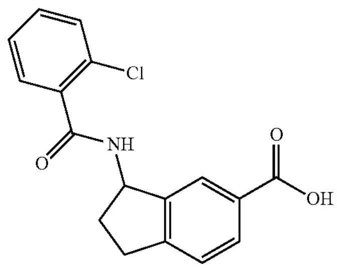 [SMILES: O=C(O)c1ccc2c(c1)C(NC(=O)c1ccccc1Cl)CC2] | 3-[(2-Chloro-benzoyl)amino]-2,3-dihydro-1H-indene-5-carboxylic acid (Lib-02_ACI-01) |
| Lib-02_ACI-02 | 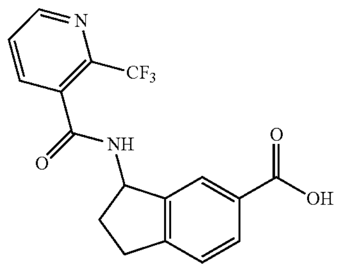 [SMILES: O=C(O)c1ccc2c(c1)C(NC(=O)c1cccnc1C(F)(F)F)CC2] | 3-[[2-(Trifluoromethyl)-pyridine-3-carbonyl]amino]-2,3-dihydro-1H-indene-5-carboxylic acid (Lib-02_ACI-02) |
| Lib-02_ACI-03 | 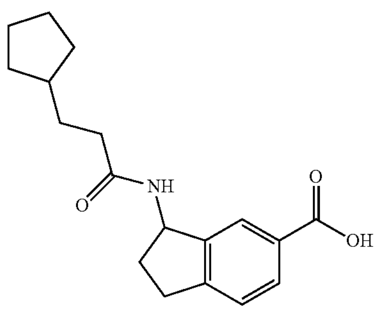 [SMILES: O=C(CCC1CCCC1)NC1CCc2ccc(C(=O)O)cc21] | 3-(3-Cyclopentyl-propanoylamino)-2,3-dihydro-1H-indene-5-carboxylic acid (Lib-02_ACI-03) |

Syntheses of the Structural Units

Synthesis of Lib-02_ACI-01: 3-[(2-Chloro-benzoyl)amino]-2,3-dihydro-1H-indene-5-carboxylic acid (Lib-02_ACI-01)

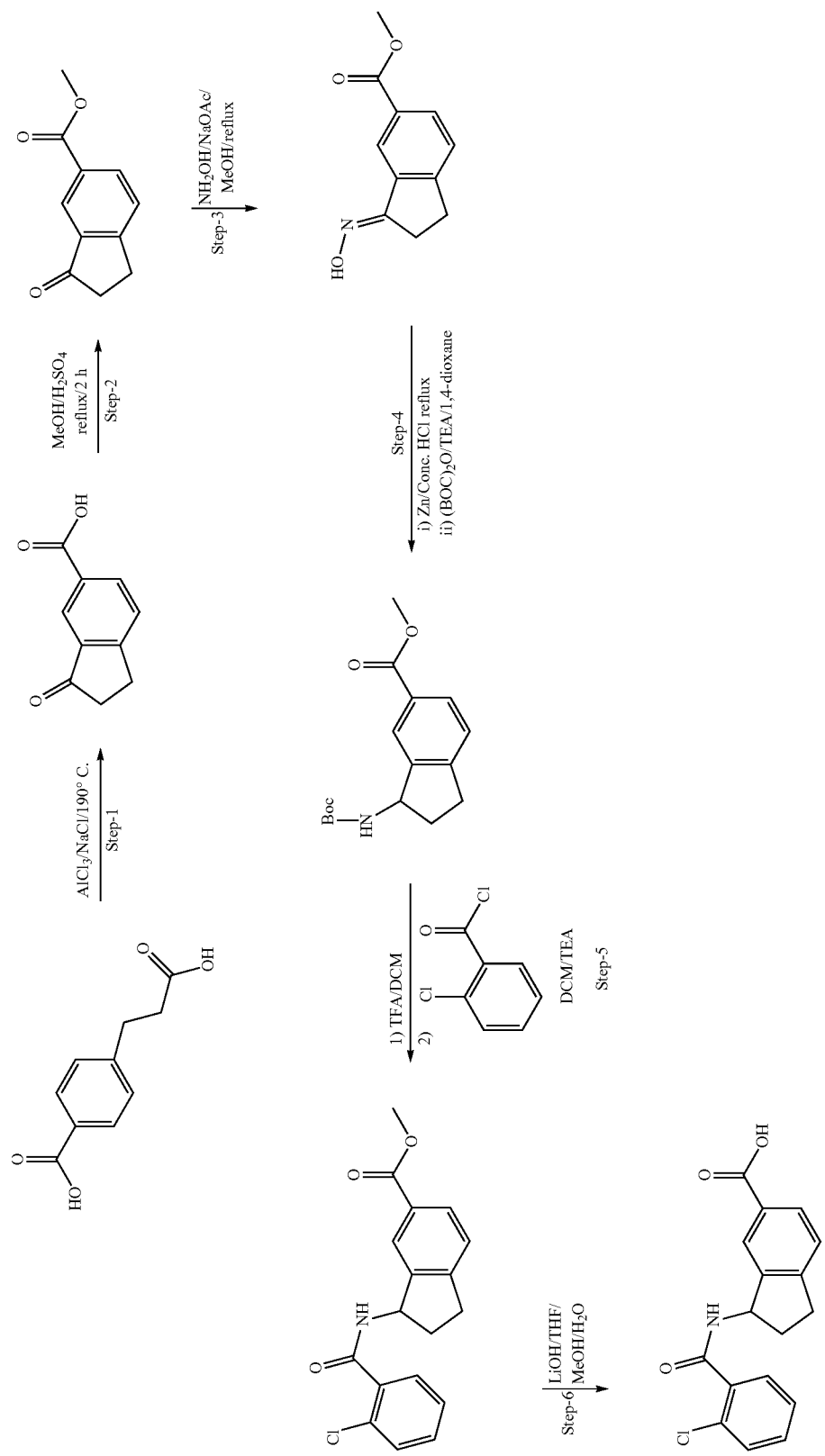

Step 1:
3-(4-Carboxyphenyl)propionic acid (50 g, 0.2577 mol), AlCl$_3$ (240 g, 1.804 mol) and sodium chloride (24 g, 10% of the weighed portion of AlCl$_3$) were mixed in a round-bottomed flask. The reaction mixture was heated for 1 hour at 190° C., cooled to 0° C. and carefully poured onto ice. The reaction mixture was acidified by means of 6 molar HCl (1200 ml) and extracted with ethyl acetate (4×800 ml). The org. phase was washed with water and sat. NaCl solution, dried over sodium sulfate and concentrated under reduced pressure. The crude product was used in the next step without being purified further. Yield: 33% (15 g, 0.035 mol)

Step 2:
The product from step 1 (4 g, 0.022 mol) was dissolved in methanol (100 ml); concentrated sulfuric acid (0.5 ml) was added, and refluxing was carried out for 12 hours. After monitoring by thin-layer chromatography, the reaction mixture was concentrated to dryness and the residue was purified by column chromatography. Yield: 58% (2.5 g, 0.012 mol)

Step 3:
The product from step 2 (2.5 g, 0.012 mol) was dissolved in methanol (50 ml); hydroxylamine HCl (2.72 g, 0.0394 mol) and sodium acetate (6.4 g, 0.0786 mol) were added at RT and the mixture was heated for 2 hours at boiling temperature. After monitoring by thin-layer chromatography, the reaction mixture was concentrated, and the residue was taken up in ethyl acetate, washed with water and sat. NaCl solution, dried over sodium sulfate and concentrated under reduced pressure. The crude product was used in the next step without being purified further. Yield: 90% (2.5 g, 0.0198 mol)

Step 4:
The product from step 3 (21 g, 0.1024 mol) was dissolved in ethanol (300 ml); water (52 ml) and conc. HCl solution (105 ml) were added, and stirring was carried out for 15 minutes. The reaction solution was cooled, Zn powder (40.17 g, 0.1024 mol) was added carefully, and the mixture was heated for 1 hour at boiling temperature. The reaction mixture was cooled to RT, filtered over Celite and washed with ethanol. The filtrate was concentrated under reduced pressure, and the residue was taken up several times in toluene and dried again. The resulting crude amine (100 g) was taken up in 1,4-dioxane (300 ml) and cooled to 0° C., and triethylamine (67 ml; 0.66 mol) was added. Boc anhydride (70 g, 0.3165 mol) was added at the same temperature, and stirring was carried out for 12 hours at RT. The reaction mixture was concentrated and taken up in ethyl acetate (1500 ml) and water (1000 ml). The org. phase was separated off, washed with water and sat. NaCl solution, dried over sodium sulfate and concentrated under reduced pressure. The crude product was purified by column chromatography. A light-yellow solid was obtained. Yield: 53% (16 g, 0.054 mol)

Step 5:
The product from step 4 (4.9 g, 0.0168 mol) was dissolved in dichloromethane (150 ml); TFA (30 ml) was added dropwise at 0° C. and stirring was carried out for 2 hours at RT. The reaction solution was concentrated to yield the free amine. The Boc-deprotected amine (3.2 g, 0.0167 mol) was dissolved in DCM (50 ml), and triethylamine (6.9 ml, 0.06 mol, 3.0 eq.) was added at 0° C. 2-Chlorobenzoic acid chloride (3.0 g, 0.017 mol, 1.0 eq.) dissolved in dichloromethane (10 ml) was added dropwise at the same temperature, and the reaction mixture was stirred for 16 hours at RT. It was then diluted with dichloromethane (200 ml), washed with water and sat. NaCl solution (in each case 2×50 ml), dried over sodium sulfate, concentrated under reduced pressure and purified by column chromatography. Yield: 54% (3.0 g, 0.009 mol)

Step 6:
The product from step 5 (3.0 g, 0.0091 mol) was dissolved in a mixture of THF:MeOH:water (6:4:1, 50 ml) and cooled to 0° C.; LiOH H$_2$O (1.14 g, 0.027 mol, 3.0 eq.) was added in portions and stirring was carried out for 8 hours at RT. The reaction mixture was concentrated under reduced pressure, taken up in a small amount of water and washed with diethyl ether. The aqueous phase was acidified at 0° C. with 2 molar HCl solution. A white solid precipitated, which was filtered off, washed with water and dried for 4 hours at 60° C. in vacuo. Yield: 87% (2.5 g, 0.0079 mol)

Synthesis of Lib-02_ACI-02: 3-[[2-(Trifluoromethyl)-pyridine-3-carbonyl]amino]-2,3-dihydro-1H-indene-5-carboxylic acid (Lib-02_ACI-02)

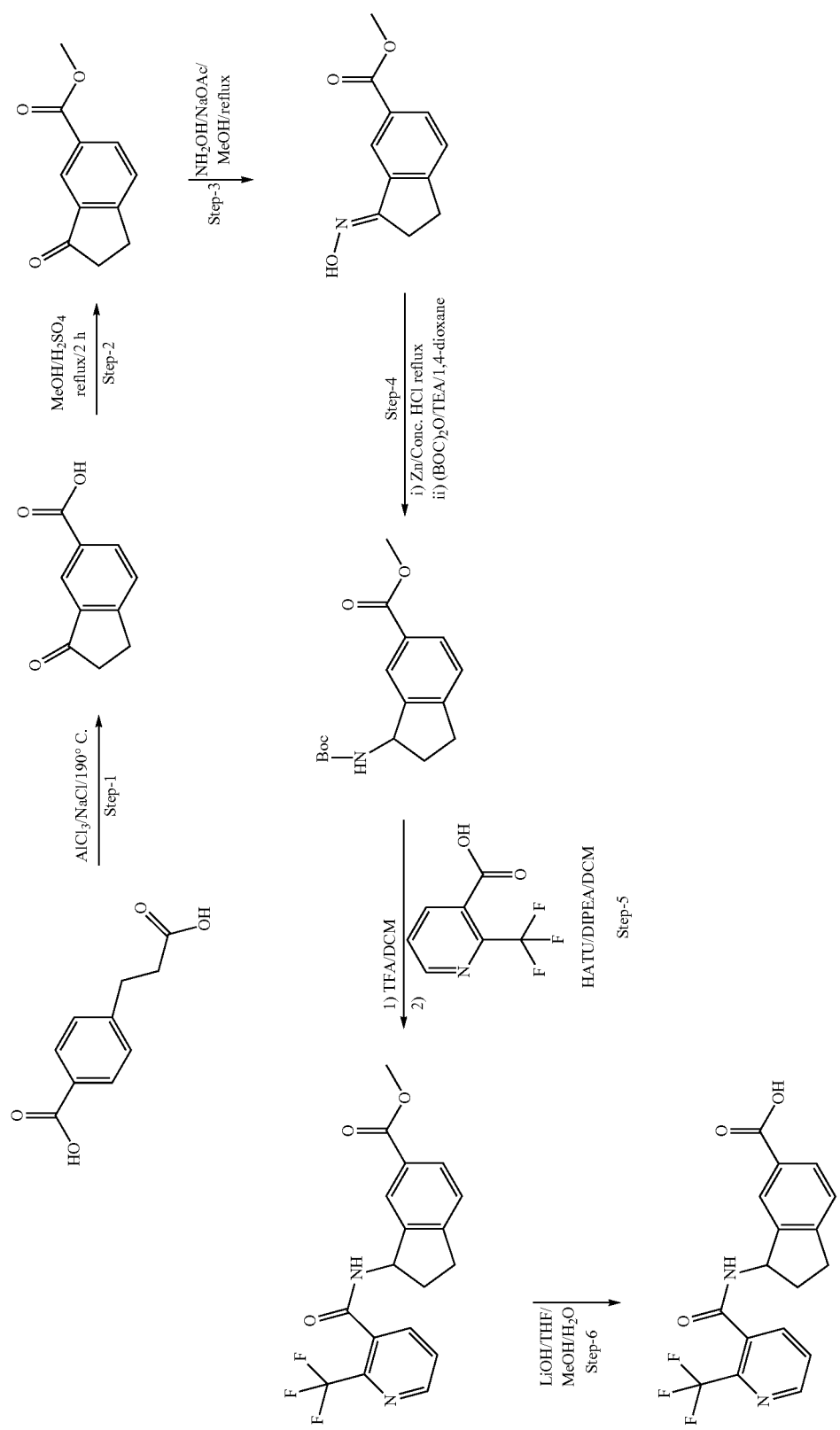

Step 1:
3-(4-Carboxyphenyl)propionic acid (50 g, 0.2577 mol), AlCl$_3$ (240 g, 1.804 mol) and sodium chloride (24 g, 10% of the weighed portion of AlCl$_3$) were mixed in a round-bottomed flask. The reaction mixture was heated for 1 hour at 190° C., cooled to 100° C. and carefully poured onto ice. The reaction mixture was acidified by means of 6 molar HCl (1200 ml) and extracted with ethyl acetate (4×800 ml). The org. phase was washed with water and sat. NaCl solution, dried over sodium sulfate and concentrated under reduced pressure. The crude product was used in the next step without being purified further. Yield: 33% (15 g, 0.035 mol)

Step 2:
The product from step 1 (4 g, 0.022 mol) was dissolved in methanol (100 ml); concentrated sulfuric acid (0.5 ml) was added, and refluxing was carried out for 12 hours. After monitoring by thin-layer chromatography, the reaction mixture was concentrated to dryness and the residue was purified by column chromatography. Yield: 58% (2.5 g, 0.012 mol)

Step 3:
The product from step 2 (2.5 g, 0.012 mol) was dissolved in methanol (50 ml); hydroxylamine HCl (2.72 g, 0.0394 mol) and sodium acetate (6.4 g, 0.0786 mol) were added at RT, and the mixture was heated for 2 hours at boiling temperature. After monitoring by thin-layer chromatography, the reaction mixture was concentrated and the residue was taken up in ethyl acetate, washed with water and sat. NaCl solution, dried over sodium sulfate and concentrated under reduced pressure. The crude product was used in the next step without being purified further. Yield: 90% (2.5 g, 0.0198 mol)

Step 4:
The product from step 3 (21 g, 0.1024 mol) was dissolved in ethanol (300 ml); water (52 ml) and conc. HCl solution (105 ml) were added, and stirring was carried out for 15 minutes. The reaction solution was cooled, Zn powder (40.17 g, 0.1024 mol) was added carefully, and the mixture was heated for 1 hour at boiling temperature. The reaction mixture was cooled to RT, filtered over Celite and washed with ethanol. The filtrate was concentrated under reduced pressure, and the residue was taken up several times in toluene and dried again. The resulting crude amine (100 g) was taken up in 1,4-dioxane (300 ml) and cooled to 0° C., and triethylamine (67 ml, 0.66 mol) was added. Boc anhydride (70 g, 0.3165 mol) was added at the same temperature, and stirring was carried out for 12 hours at RT. The reaction mixture was concentrated and taken up in ethyl acetate (1500 ml) and water (1000 ml). The org. phase was separated off, washed with water and sat. NaCl solution, dried over sodium sulfate and concentrated under reduced pressure. The crude product was purified by column chromatography. A light-yellow solid was obtained. Yield: 53% (16 g, 0.054 mol)

Step 5:
The product from step 4 (2 g, 0.0068 mol) was dissolved in dichloromethane (70 ml); TFA (14 ml) was added dropwise at 0° C., and stirring was carried out for 2 hours at RT. The reaction solution was concentrated to yield the TFA salt of the amine. 2-Trifluoromethyl-pyridine-3-carboxylic acid (1.3 g, 0.0068 mol) was dissolved in dichloromethane (25 ml); HATU (3.87 g, 0.0102 mol) and DIPEA (4.8 ml, 0.0272 mol) were added at 0° C., and stirring was carried out for 15 minutes. The amine-TFA salt was dissolved in dichloromethane (25 ml) and DIPEA (1.5 ml, 0.086 mol), added dropwise at 0° C. to the reaction solution and stirred for 16 hours at RT. The mixture was then diluted with dichloromethane (100 ml), washed in succession with ammonium chloride solution (2×50 ml), sat. sodium hydrogen carbonate solution (2×50 ml), water (50 ml) and sat. NaCl solution (50 ml), dried over sodium sulfate, concentrated under reduced pressure and purified by column chromatography (silica gel, MeOH/DCM). Yield: 66% (1.6 g, 0.0043 mol)

Step 6:
The product from step 5 (1.5 g, 0.0041 mol) was dissolved in a mixture of THF:MeOH:water (6:4:1, 27 ml) and cooled to 0° C.; LiOH H$_2$O (0.519 g, 0.00123 mol, 3.0 eq.) was added in portions, and stirring was carried out for 8 hours at RT. The reaction mixture was concentrated under reduced pressure, taken up in a small amount of water and washed with diethyl ether. The aqueous phase was acidified at 0° C. with 2 molar HCl solution. A white solid precipitated, which was filtered off, washed with water and dried for 4 hours at 60° C. in vacuo. Yield: 90% (1.3 g, 0.0037 mol)

Synthesis of Lib-02 ACI-03: 3-(3-Cyclopentyl-propanoylamino)-2,3-dihydro-1H-indene-5-carboxylic acid (Lib-02_ACI-03)

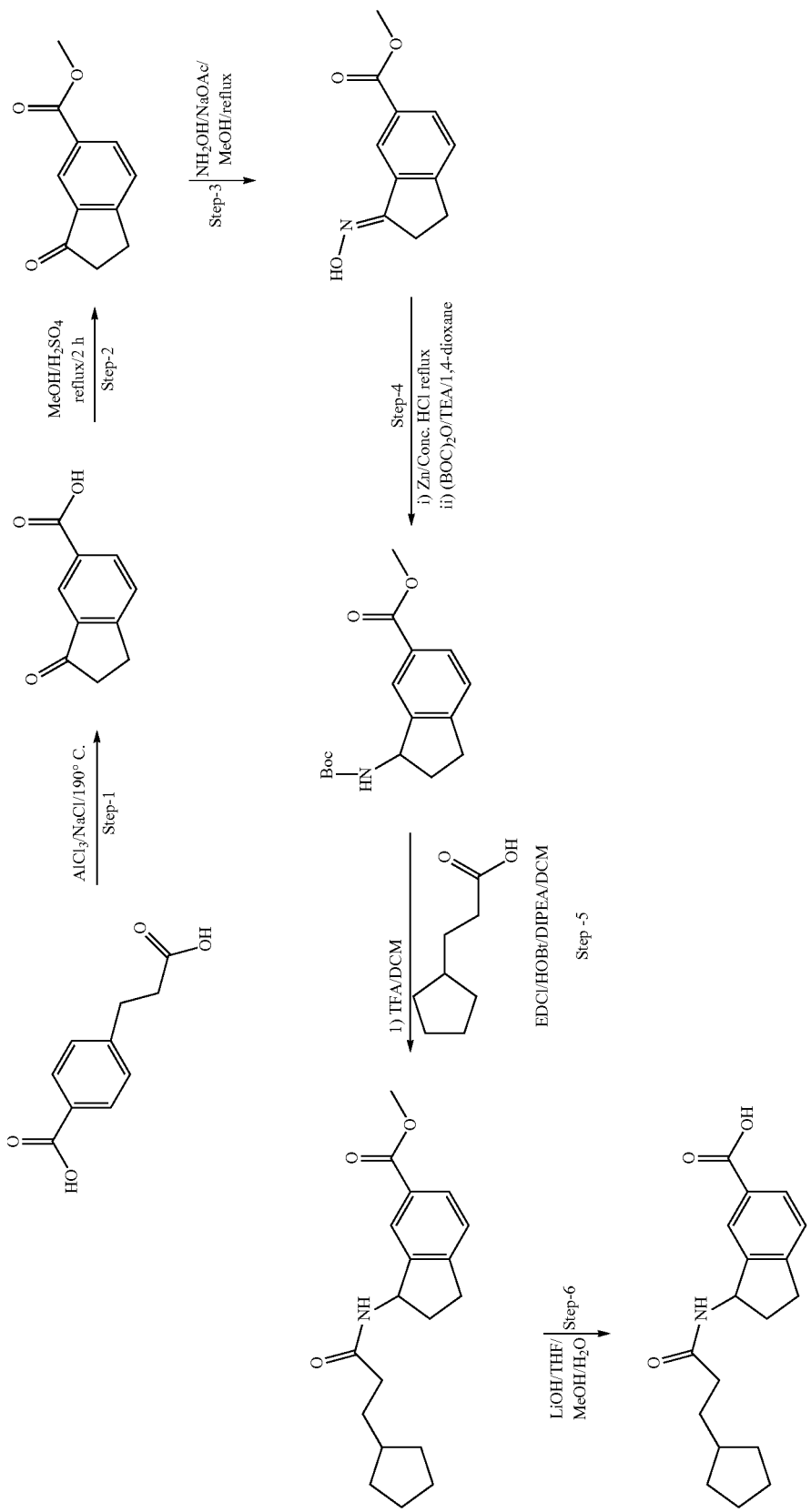

547

Step 1:
3-(4-Carboxyphenyl)propionic acid (50 g, 0.2577 mol), AlCl$_3$ (240 g, 1.804 mol) and sodium chloride (24 g, 10% of the weighed portion of AlCl$_3$) were mixed in a round-bottomed flask. The reaction mixture was heated for 1 hour at 190° C., cooled to 100° C. and carefully poured onto ice. The reaction mixture was acidified by means of 6 molar HCl (1200 ml) and extracted with ethyl acetate (4×800 ml). The org. phase was washed with water and sat. NaCl solution, dried over sodium sulfate and concentrated under reduced pressure. The crude product was used in the next step without being purified further. Yield: 33% (15 g, 0.035 mol)

Step 2:
The product from step 1 (4 g, 0.022 mol) was dissolved in methanol (100 ml); concentrated sulfuric acid (0.5 ml) was added, and refluxing was carried out for 12 hours. After monitoring by thin-layer chromatography, the reaction mixture was concentrated to dryness and the residue was purified by column chromatography. Yield: 58% (2.5 g, 0.012 mol)

Step 3:
The product from step 2 (2.5 g, 0.012 mol) was dissolved in methanol (50 ml); hydroxylamine HCl (2.72 g, 0.0394 mol) and sodium acetate (6.4 g, 0.0786 mol) were added at RT, and the mixture was heated for 2 hours at boiling temperature. After monitoring by thin-layer chromatography, the reaction mixture was concentrated, and the residue was taken up in ethyl acetate, washed with water and sat. NaCl solution, dried over sodium sulfate and concentrated under reduced pressure. The crude product was used in the next step without being purified further. Yield: 90% (2.5 g, 0.0198 mol)

Step 4:
The product from step 3 (21 g, 0.1024 mol) was dissolved in ethanol (300 ml); water (52 ml) and conc. HCl solution (105 ml) were added, and stirring was carried out for 15 minutes. The reaction solution was cooled, Zn powder (40.17 g, 0.1024 mol) was carefully added, and the mixture was heated for 1 hour at boiling temperature. The reaction mixture was cooled to RT, filtered over Celite and washed with ethanol. The filtrate was concentrated under reduced pressure, and the residue was taken up several times in toluene and dried again. The resulting crude amine (100 g) was taken up in 1,4-dioxane (300 ml) and cooled to 0° C., and triethylamine (67 ml, 0.66 mol) was added. Boc anhydride (70 g, 0.3165 mol) was added at the same temperature, and stirring was carried out for 12 hours at RT. The reaction mixture was concentrated and taken up in ethyl acetate (1500 ml) and water (1000 ml). The org. phase was separated off, washed with water and sat. NaCl solution, dried over sodium sulfate and concentrated under reduced pressure. The crude product was purified by column chromatography. A light-yellow solid was obtained. Yield: 53% (16 g, 0.054 mol)

Step 5:
The product from step 4 (2 g, 0.0068 mol) was dissolved in dichloromethane (70 ml); TFA (14 ml) was added dropwise at 0° C. and stirring was carried out for 2 hours at RT. The reaction solution was concentrated to yield the TFA salt of the amine. 3-Cyclopentylpropionic acid (0.966 g, 0.0068 mol) was dissolved in dichloromethane (25 ml); HATU (3.87 g, 0.0102 mol) and DIPEA (4.8 ml, 0.0272 mol) were added at 0° C., and stirring was carried out for 15 minutes. The amine-TFA salt was dissolved in dichloromethane (25 ml) and DIPEA (1.5 ml, 0.0086 mol) and added dropwise at 0° C. to the reaction solution, and stirring was carried out for 16 hours at RT. The mixture was then diluted with dichloromethane (100 ml), washed in succession with ammonium chloride solution (2×50 ml), sat. sodium hydrogen carbonate solution (2×50 ml), water (50 ml) and sat. NaCl solution (50 ml), dried

548 over sodium sulfate, concentrated under reduced pressure and purified by column chromatography (silica gel, MeOH/DCM). Yield: 79% (1.7 g, 0.0053 mol)

Step 6:
The product from step 5 (1.6 g, 0.005 mol) was dissolved in a mixture of THF:MeOH:water (6:4:1, 27 ml) and cooled to 0° C.; LiOH H$_2$O (0.639 g, 0.00152 mol, 3.0 eq.) was added in portions and stirring was carried out for 8 hours at RT. The reaction mixture was concentrated under reduced pressure, taken up in a small amount of water and washed with diethyl ether. The aqueous phase was acidified at 0° C. with 2 molar HCl solution. A white solid precipitated, which was filtered off, washed with water and dried for 4 hours at 60° C. in vacuo. Yield: 90% (1.38 g, 0.0045 mol)

3) Parallel Synthesis of Dihydroindenes
General:

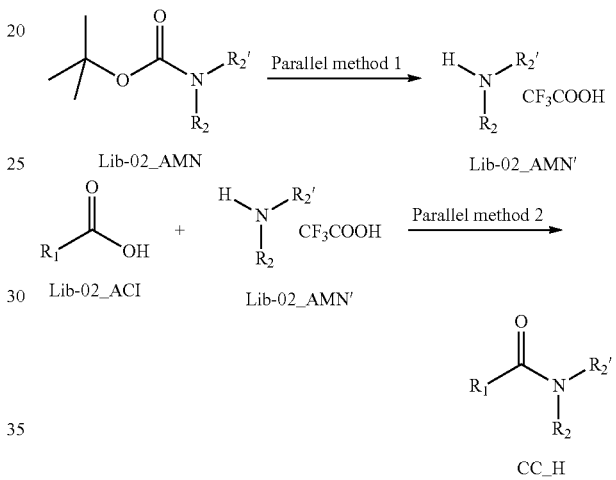

According to the above scheme, the amine structural units Lib-02_AMN' were prepared from the Boc-protected amines Lib-02_AMN by parallel method 1. The resulting amine trifluoroacetic acid salts Lib-02_AMN' were reacted in a parallel synthesis, according to parallel method 2, with the acids Lib-02_ACI to give amidic products CC. The correlation of products (CC) to the structural units used (Lib-02_ACI) is to be found in the synthesis matrix. The crude products of the parallel synthesis were analyzed by HPLC-MS and then purified by means of reverse-phase HPLC-MS. The identity of the products could be demonstrated by analytical HPLC-MS measurements. The crude products of the parallel synthesis were purified by column chromatography. The identity of the products could be demonstrated by analytical HPLC-MS measurements (see HPLC-MS data).

Parallel Method 1: Boc Deprotection
20% trifluoroacetic acid in dichloromethane (10 ml/mol) was added at 0° C. to the corresponding Boc-protected amine (1 eq., Lib-02_AMN). The resulting reaction mixture was stirred for 4 h at 25° C. The progress of the reaction was monitored by means of thin-layer chromatography. The solvent was then removed under reduced pressure and the residue was dried carefully in order to remove traces of trifluoroacetic acid. The crude product so obtained was used for the synthesis of the libraries without being purified further.

Parallel Method 2: Amide Formation
The acid Lib-02 ACI (1 eq.) was dissolved in dichloromethane (3 ml/mol); HATU (2 eq.) was added at 0° C., and stirring was carried out for 15 minutes. In a second reaction flask, the Boc-deprotected amine Lib-02_AMN' (1.5 eq.) was dissolved in dichloromethane (1 ml/mol) and cooled to 0° C.; DIPEA (3 eq.) was added and the mixture was then added to the reaction solution. The reaction mixture was stirred for 16 hours at RT, diluted with dichloromethane, washed in succession with aqueous ammonium chloride solution, sodium hydrogen carbonate solution and sat. NaCl solution, dried over sodium sulfate and reduced under reduced pressure. The crude product was purified by prep. HPLC.

Examples and Synthesis Matrix:

| Example No. | Name | Acid (Lib-02_ACI) | Amine (Lib-02_AMN) | Method No. |
|---|---|---|---|---|
| CC_H-600 | N-[6-[Methyl-[1-(2-methylsulfonyl-pyrimidin-4-yl)-piperidin-4-yl]-carbamoyl]-2,3-dihydro-1H-inden-1-yl]-2-(trifluoromethyl)-pyridine-3-carboxylic acid amide (CC_H-600) | 3-[[2-(Trifluoromethyl)-pyridine-3-carbonyl]amino]-2,3-dihydro-1H-indene-5-carboxylic acid (Lib-02_ACI-02) | N-Methyl-N-[1-(2-methylsulfonyl-pyrimidin-4-yl)-piperidin-4-yl]-carbamic acid tert-butyl ester (Lib-02_AMN15) | No. 1 & No. 2 |
| CC_H-601 | N-[6-[[1-[2-(Dimethyl-carbamoyl)-pyridin-4-yl]-piperidin-4-yl]-methyl-carbamoyl]-2,3-dihydro-1H-inden-1-yl]-2-(trifluoromethyl)-pyridine-3-carboxylic acid amide (CC_H-601) | 3-[[2-(Trifluoromethyl)-pyridine-3-carbonyl]amino]-2,3-dihydro-1H-indene-5-carboxylic acid (Lib-02_ACI-02) | N-[1-[2-(Dimethyl-carbamoyl)-pyridin-4-yl]-piperidin-4-yl]-N-methyl-carbamic acid tert-butyl ester (Lib-02_AMN09) | No. 1 & No. 2 |
| CC_H-603 | N-[6-[Methyl-[1-(2-pyrrolidin-1-yl-pyrimidin-4-yl)-piperidin-4-yl]-carbamoyl]-2,3-dihydro-1H-inden-1-yl]-2-(trifluoromethyl)-pyridine-3-carboxylic acid amide (CC_H-603) | 3-[[2-(Trifluoromethyl)-pyridine-3-carbonyl]amino]-2,3-dihydro-1H-indene-5-carboxylic acid (Lib-02_ACI-02) | N-Methyl-N-[1-(2-pyrrolidin-1-yl-pyrimidin-4-yl)-piperidin-4-yl]-carbamic acid tert-butyl ester (Lib-02_AMN02) | No. 1 & No. 2 |
| CC_H-604 | N-[6-[[1-(2-Dimethylamino-6-methyl-pyrimidin-4-yl)-piperidin-4-yl]-methyl-carbamoyl]-2,3-dihydro-1H-inden-1-yl]-2-(trifluoromethyl)-pyridine-3-carboxylic acid amide (CC_H-604) | 3-[[2-(Trifluoromethyl)-pyridine-3-carbonyl]amino]-2,3-dihydro-1H-indene-5-carboxylic acid (Lib-02_ACI-02) | N-[1-(2-Dimethylamino-6-methyl-pyrimidin-4-yl)-piperidin-4-yl]-N-methyl-carbamic acid tert-butyl ester (Lib-02_AMN03) | No. 1 & No. 2 |
| CC_H-606 | N-[6-[[1-(2-tert-Butyl-pyrimidin-4-yl)-piperidin-4-yl]-methyl-carbamoyl]-2,3-dihydro-1H-inden-1-yl]-2-(trifluoromethyl)-pyridine-3-carboxylic acid amide (CC_H-606) | 3-[[2-(Trifluoromethyl)-pyridine-3-carbonyl]amino]-2,3-dihydro-1H-indene-5-carboxylic acid (Lib-02_ACI-02) | N-[1-(2-tert-Butyl-pyrimidin-4-yl)-piperidin-4-yl]-N-methyl-carbamic acid tert-butyl ester (Lib-02_AMN13) | No. 1 & No. 2 |
| CC_H-607 | N-[6-[Methyl-[4-(5-methyl-3-oxo-1,2-dihydro-imidazo[5,1-e]imidazol-2-yl)-cyclohexyl]-carbamoyl]-2,3-dihydro-1H-inden-1-yl]-2-(trifluoromethyl)-pyridine-3-carboxylic acid amide (CC_H-607) | 3-[[2-(Trifluoromethyl)-pyridine-3-carbonyl]amino]-2,3-dihydro-1H-indene-5-carboxylic acid (Lib-02_ACI-02) | N-Methyl-N-[4-(5-methyl-3-oxo-1,2-dihydro-imidazo[5,1-e]imidazol-2-yl)-cyclohexyl]-carbamic acid tert-butyl ester (Lib-02_AMN08) | No. 1 & No. 2 |
| CC_H-608 | N-[6-[[1-(2-Dimethylamino-pyrimidin-4-yl)-piperidin-4-yl]-methyl-carbamoyl]-2,3-dihydro-1H-inden-1-yl]-2-(trifluoromethyl)-pyridine-3-carboxylic acid amide (CC_H-608) | 3-[[2-(Trifluoromethyl)-pyridine-3-carbonyl]amino]-2,3-dihydro-1H-indene-5-carboxylic acid (Lib-02_ACI-02) | N-[1-(2-Dimethylamino-pyrimidin-4-yl)-piperidin-4-yl]-N-methyl-carbamic acid tert-butyl ester (Lib-02_AMN01) | No. 1 & No. 2 |
| CC_H-609 | 3-[(2-Chloro-benzoyl)amino]-N-methyl-N-[1-(2-methylsulfonyl-pyrimidin-4-yl)-piperidin-4-yl]-2,3-dihydro-1H-indene-5-carboxylic acid amide (CC_H-609) | 3-[(2-Chloro-benzoyl)amino]-2,3-dihydro-1H-indene-5-carboxylic acid (Lib-02_ACI-01) | N-Methyl-N-[1-(2-methylsulfonyl-pyrimidin-4-yl)-piperidin-4-yl]-carbamic acid tert-butyl ester (Lib-02_AMN15) | No. 1 & No. 2 |
| CC_H-610 | N-[6-[[1-(2-Cyclopropyl-pyrimidin-4-yl)-piperidin-4-yl]-methyl-carbamoyl]-2,3-dihydro-1H-inden-1-yl]-2-(trifluoromethyl)-pyridine-3-carboxylic acid amide (CC_H-610) | 3-[[2-(Trifluoromethyl)-pyridine-3-carbonyl]amino]-2,3-dihydro-1H-indene-5-carboxylic acid (Lib-02_ACI-02) | N-[1-(2-Cyclopropyl-pyrimidin-4-yl)-piperidin-4-yl]-N-methyl-carbamic acid tert-butyl ester (Lib-02_AMN14) | No. 1 & No. 2 |
| CC_H-612 | 3-[(2-Chloro-benzoyl)amino]-N-methyl-N-[1-(2-pyrrolidin-1-yl-pyrimidin-4-yl)-piperidin-4-yl]-2,3-dihydro-1H-indene-5-carboxylic acid amide (CC_H-612) | 3-[(2-Chloro-benzoyl)amino]-2,3-dihydro-1H-indene-5-carboxylic acid (Lib-02_ACI-01) | N-Methyl-N-[1-(2-pyrrolidin-1-yl-pyrimidin-4-yl)-piperidin-4-yl]-carbamic acid tert-butyl ester (Lib-02_AMN02) | No. 1 & No. 2 |
| CC_H-613 | 3-(3-Cyclopentyl-propanoylamino)-N-methyl-N-[1-(2-methylsulfonyl-pyrimidin-4-yl)-piperidin-4-yl]-2,3-dihydro-1H-indene-5-carboxylic acid amide (CC_H-613) | 3-(3-Cyclopentyl-propanoylamino)-2,3-dihydro-1H-indene-5-carboxylic acid (Lib-02_ACI-03) | N-Methyl-N-[1-(2-methylsulfonyl-pyrimidin-4-yl)-piperidin-4-yl]-carbamic acid tert-butyl ester (Lib-02_AMN15) | No. 1 & No. 2 |
| CC_H-614 | 3-[(2-Chloro-benzoyl)amino]-N-[1-(2-dimethylamino-6-methyl-pyrimidin-4-yl)-piperidin-4-yl]-N-methyl-2,3-dihydro-1H-indene-5-carboxylic acid amide (CC_H-614) | 3-[(2-Chloro-benzoyl)amino]-2,3-dihydro-1H-indene-5-carboxylic acid (Lib-02_ACI-01) | N-[1-(2-Dimethylamino-6-methyl-pyrimidin-4-yl)-piperidin-4-yl]-N-methyl-carbamic acid tert-butyl ester (Lib-02_AMN03) | No. 1 & No. 2 |
| CC_H-615 | 4-[4-[[3-(3-Cyclopentyl-propanoylamino)-2,3-dihydro-1H-inden-5-carbonyl]-methyl-amino]-piperidin-1-yl]-N,N-dimethyl-pyridine-2-carboxylic acid amide (CC_H-615) | 3-(3-Cyclopentyl-propanoylamino)-2,3-dihydro-1H-indene-5-carboxylic acid (Lib-02_ACI-03) | N-[1-[2-(Dimethyl-carbamoyl)-pyridin-4-yl]-piperidin-4-yl]-N-methyl-carbamic acid tert-butyl ester (Lib-02_AMN09) | No. 1 & No. 2 |

| Example No. | Name | Acid (Lib-02_ACI) | Amine (Lib-02_AMN) | Method No. |
|---|---|---|---|---|
| CC_H-616 | N-[1-(2-tert-Butyl-pyrimidin-4-yl)-piperidin-4-yl]-3-[(2-chloro-benzoyl)amino]-N-methyl-2,3-dihydro-1H-indene-5-carboxylic acid amide (CC_H-616) | 3-[(2-Chloro-benzoyl)amino]-2,3-dihydro-1H-indene-5-carboxylic acid (Lib-02_ACI-01) | N-[1-(2-tert-Butyl-pyrimidin-4-yl)-piperidin-4-yl]-N-methyl-carbamic acid tert-butyl ester (Lib-02_AMN13) | No. 1 & No. 2 |
| CC_H-618 | 3-[(2-Chloro-benzoyl)amino]-N-methyl-N-[4-(5-methyl-3-oxo-1,2-dihydro-imidazo[5,1-e]imidazol-2-yl)-cyclohexyl]-2,3-dihydro-1H-indene-5-carboxylic acid amide (CC_H-618) | 3-[(2-Chloro-benzoyl)amino]-2,3-dihydro-1H-indene-5-carboxylic acid (Lib-02_ACI-01) | N-Methyl-N-[4-(5-methyl-3-oxo-1,2-dihydro-imidazo[5,1-e]imidazol-2-yl)-cyclohexyl]-carbamic acid tert-butyl ester (Lib-02_AMN08) | No. 1 & No. 2 |
| CC_H-620 | 3-(3-Cyclopentyl-propanoylamino)-N-methyl-N-[1-(2-pyrrolidin-1-yl-pyrimidin-4-yl)-piperidin-4-yl]-2,3-dihydro-1H-indene-5-carboxylic acid amide (CC_H-620) | 3-(3-Cyclopentyl-propanoylamino)-2,3-dihydro-1H-indene-5-carboxylic acid (Lib-02_ACI-03) | N-Methyl-N-[1-(2-pyrrolidin-1-yl-pyrimidin-4-yl)-piperidin-4-yl]-carbamic acid tert-butyl ester (Lib-02_AMN02) | No. 1 & No. 2 |
| CC_H-621 | N-[6-[[1-(5-Fluoro-pyrimidin-4-yl)-piperidin-4-yl]-methyl-carbamoyl]-2,3-dihydro-1H-inden-1-yl]-2-(trifluoromethyl)-pyridine-3-carboxylic acid amide (CC_H-621) | 3-[[2-(Trifluoromethyl)-pyridine-3-carbonyl]amino]-2,3-dihydro-1H-indene-5-carboxylic acid (Lib-02_ACI-02) | N-[1-(5-Fluoro-pyrimidin-4-yl)-piperidin-4-yl]-N-methyl-carbamic acid tert-butyl ester (Lib-02_AMN12) | No. 1 & No. 2 |
| CC_H-622 | 3-(3-Cyclopentyl-propanoylamino)-N-[1-(2-dimethylamino-6-methyl-pyrimidin-4-yl)-piperidin-4-yl]-N-methyl-2,3-dihydro-1H-indene-5-carboxylic acid amide (CC_H-622) | 3-(3-Cyclopentyl-propanoylamino)-2,3-dihydro-1H-indene-5-carboxylic acid (Lib-02_ACI-03) | N-[1-(2-Dimethylamino-6-methyl-pyrimidin-4-yl)-piperidin-4-yl]-N-methyl-carbamic acid tert-butyl ester (Lib-02_AMN03) | No. 1 & No. 2 |
| CC_H-623 | 3-[(2-Chloro-benzoyl)amino]-N-[1-(2-dimethylamino-pyrimidin-4-yl)-piperidin-4-yl]-N-methyl-2,3-dihydro-1H-indene-5-carboxylic acid amide (CC_H-623) | 3-[(2-Chloro-benzoyl)amino]-2,3-dihydro-1H-indene-5-carboxylic acid (Lib-02_ACI-01) | N-[1-(2-Dimethylamino-pyrimidin-4-yl)-piperidin-4-yl]-N-methyl-carbamic acid tert-butyl ester (Lib-02_AMN01) | No. 1 & No. 2 |
| CC_H-624 | N-[1-(2-tert-Butyl-pyrimidin-4-yl)-piperidin-4-yl]-3-(3-cyclopentyl-propanoylamino)-N-methyl-2,3-dihydro-1H-indene-5-carboxylic acid amide (CC_H-624) | 3-(3-Cyclopentyl-propanoylamino)-2,3-dihydro-1H-indene-5-carboxylic acid (Lib-02_ACI-03) | N-[1-(2-tert-Butyl-pyrimidin-4-yl)-piperidin-4-yl]-N-methyl-carbamic acid tert-butyl ester (Lib-02_AMN13) | No. 1 & No. 2 |
| CC_H-626 | 3-(3-Cyclopentyl-propanoylamino)-N-methyl-N-[4-(5-methyl-3-oxo-1,2-dihydro-imidazo[5,1-e]imidazol-2-yl)-cyclohexyl]-2,3-dihydro-1H-indene-5-carboxylic acid amide (CC_H-626) | 3-(3-Cyclopentyl-propanoylamino)-2,3-dihydro-1H-indene-5-carboxylic acid (Lib-02_ACI-03) | N-Methyl-N-[4-(5-methyl-3-oxo-1,2-dihydro-imidazo[5,1-e]imidazol-2-yl)-cyclohexyl]-carbamic acid tert-butyl ester (Lib-02_AMN08) | No. 1 & No. 2 |
| CC_H-627 | 3-[(2-Chloro-benzoyl)amino]-N-[1-(2-cyclopropyl-pyrimidin-4-yl)-piperidin-4-yl]-N-methyl-2,3-dihydro-1H-indene-5-carboxylic acid amide (CC_H-627) | 3-[(2-Chloro-benzoyl)amino]-2,3-dihydro-1H-indene-5-carboxylic acid (Lib-02_ACI-01) | N-[1-(2-Cyclopropyl-pyrimidin-4-yl)-piperidin-4-yl]-N-methyl-carbamic acid tert-butyl ester (Lib-02_AMN14) | No. 1 & No. 2 |
| CC_H-628 | N-[6-[Methyl-(1-pyridazin-4-yl-piperidin-4-yl)-carbamoyl]-2,3-dihydro-1H-inden-1-yl]-2-(trifluoromethyl)-pyridine-3-carboxylic acid amide (CC_H-628) | 3-[[2-(Trifluoromethyl)-pyridine-3-carbonyl]amino]-2,3-dihydro-1H-indene-5-carboxylic acid (Lib-02_ACI-02) | N-Methyl-N-(1-pyridazin-4-yl-piperidin-4-yl)-carbamic acid tert-butyl ester (Lib-02_AMN 10) | No. 1 & No. 2 |
| CC_H-629 | 3-(3-Cyclopentyl-propanoylamino)-N-[1-(2-dimethylamino-pyrimidin-4-yl)-piperidin-4-yl]-N-methyl-2,3-dihydro-1H-indene-5-carboxylic acid amide (CC_H-629) | 3-(3-Cyclopentyl-propanoylamino)-2,3-dihydro-1H-indene-5-carboxylic acid (Lib-02_ACI-03) | N-[1-(2-Dimethylamino-pyrimidin-4-yl)-piperidin-4-yl]-N-methyl-carbamic acid tert-butyl ester (Lib-02_AMN01) | No. 1 & No. 2 |
| CC_H-630 | 3-(3-Cyclopentyl-propanoylamino)-N-[1-(2-cyclopropyl-pyrimidin-4-yl)-piperidin-4-yl]-N-methyl-2,3-dihydro-1H-indene-5-carboxylic acid amide (CC_H-630) | 3-(3-Cyclopentyl-propanoylamino)-2,3-dihydro-1H-indene-5-carboxylic acid (Lib-02_ACI-03) | N-[1-(2-Cyclopropyl-pyrimidin-4-yl)-piperidin-4-yl]-N-methyl-carbamic acid tert-butyl ester (Lib-02_AMN14) | No. 1 & No. 2 |
| CC_H-631 | 3-[(2-Chloro-benzoyl)amino]-N-[1-(5-fluoro-pyrimidin-4-yl)-piperidin-4-yl]-N-methyl-2,3-dihydro-1H-indene-5-carboxylic acid amide (CC_H-631) | 3-[(2-Chloro-benzoyl)amino]-2,3-dihydro-1H-indene-5-carboxylic acid (Lib-02_ACI-01) | N-[1-(5-Fluoro-pyrimidin-4-yl)-piperidin-4-yl]-N-methyl-carbamic acid tert-butyl ester (Lib-02_AMN12) | No. 1 & No. 2 |
| CC_H-632 | 3-(3-Cyclopentyl-propanoylamino)-N-[1-(5-fluoro-pyrimidin-4-yl)-piperidin-4-yl]-N-methyl-2,3-dihydro-1H-indene-5-carboxylic acid amide (CC_H-632) | 3-(3-Cyclopentyl-propanoylamino)-2,3-dihydro-1H-indene-5-carboxylic acid (Lib-02_ACI-03) | N-[1-(5-Fluoro-pyrimidin-4-yl)-piperidin-4-yl]-N-methyl-carbamic acid tert-butyl ester (Lib-02_AMN12) | No. 1 & No. 2 |
| CC_H-633 | 3-[(2-Chloro-benzoyl)amino]-N-methyl-N-(1-pyridazin-4-yl-piperidin-4-yl)-2,3-dihydro-1H-indene-5-carboxylic acid amide (CC_H-633) | 3-[(2-Chloro-benzoyl)amino]-2,3-dihydro-1H-indene-5-carboxylic acid (Lib-02_ACI-01) | N-Methyl-N-(1-pyridazin-4-yl-piperidin-4-yl)-carbamic acid tert-butyl ester (Lib-02_AMN10) | No. 1 & No. 2 |
| CC_H-634 | 3-(3-Cyclopentyl-propanoylamino)-N-methyl-N-(1-pyridazin-4-yl-piperidin-4-yl)-2,3-dihydro-1H-indene-5-carboxylic acid | 3-(3-Cyclopentyl-propanoylamino)-2,3-dihydro-1H-indene-5- | N-Methyl-N-(1-pyridazin-4-yl-piperidin-4-yl)-carbamic acid tert-butyl ester (Lib- | |

-continued

| Example No. | Name | Acid (Lib-02_ACI) | Amine (Lib-02_AMN) | Method No. |
|---|---|---|---|---|
| | acid amide (CC_H-634) | carboxylic acid (Lib-02_ACI-03) | 02_AMN10) | |

Analytical and Biological Data:
Representative Examples with % Inhibition ≥50% at 10 μM:

| Entry No. | [M+] found | R.t. [min] | Purity, UV_254 [%] | % Inhibition (r-B1R) at 10 μM | % Inhibition (h-B1R) at 10 μM |
|---|---|---|---|---|---|
| CC_H-600 | Yes | | 98.75 | 91 | |
| CC_H-601 | Yes | | 82.39 | 74 | |
| CC_H-603 | Yes | | 98.07 | 102 | |
| CC_H-604 | Yes | | 94.63 | 102 | |
| CC_H-606 | Yes | | 97.85 | 99 | |
| CC_H-607 | Yes | | 87.29 | 96 | |
| CC_H-608 | Yes | | 95.13 | 102 | |
| CC_H-609 | Yes | | 98.65 | 102 | |
| CC_H-610 | Yes | | 97.27 | 101 | |
| CC_H-612 | Yes | | 96.19 | 101 | |
| CC_H-613 | Yes | | 87.8 | 90 | |
| CC_H-614 | Yes | | 99.15 | 101 | |
| CC_H-615 | Yes | | 87.11 | 65 | |
| CC_H-616 | Yes | | 96.91 | 101 | |
| CC_H-618 | Yes | | 85.92 | 84 | |
| CC_H-620 | Yes | | 95.91 | 102 | |
| CC_H-621 | Yes | | 98.38 | 98 | |
| CC_H-622 | Yes | | 97.69 | 100 | |
| CC_H-623 | Yes | | 94.84 | 101 | |
| CC_H-624 | Yes | | 96.76 | 96 | |
| CC_H-627 | Yes | | 94.53 | 100 | |
| CC_H-628 | Yes | | 55.5 | 99 | |
| CC_H-629 | Yes | | 96.82 | 101 | |
| CC_H-630 | Yes | | 93.83 | 95 | |
| CC_H-631 | Yes | | 97.4 | 94 | |
| CC_H-632 | Yes | | 96.07 | 95 | |
| CC_H-633 | Yes | | 78.37 | 103 | |
| CC_H-634 | Yes | | 76.03 | 93 | |

Pharmacological Data

The pharmacological data were determined as described above. Preferably, the compounds have a B1R-antagonistic activity on the human receptor and/or on the rat receptor. The data in % inhibition are indicated by way of example in the following table.

| Example No. | % inhibition (rat B1R) at 10 μM | % inhibition (human B1R) at 10 μM |
|---|---|---|
| H-01 | 102 | 100 |
| H-03 | 108 | 15 |
| H-04 | 47 | 21 |
| H-06 | 102 | 100 |
| H-07 | 96 | 43 |
| H-09 | 83 | 38 |
| H-10 | 97 | 18 |
| H-11 | 49 | 99 |
| H-12 | 100 | 100 |
| H-14 | 76 | 64 |
| H-15 | 99 | 100 |
| H-16 | 92 | 100 |
| H-17 | 77 | 100 |
| H-18 | 102 | 100 |
| H-19 | 103 | 98 |
| H-20 | 103 | 100 |
| H-21 | 105 | 99 |
| H-22 | 87 | 100 |
| H-23 | 93 | 97 |
| H-24 | 98 | 100 |
| H-25 | 96 | 100 |
| H-26 | 0 | 52 |
| H-27 | 11 | 74 |
| H-28 | 100 | 100 |
| H-29 | 100 | 99 |
| H-30 | 99 | 100 |
| H-31 | 70 | 100 |
| H-32 | 101 | 100 |
| H-33 | 101 | 100 |
| H-34 | 7 | 64 |
| H-35 | 105 | 100 |
| H-36 | 105 | 100 |
| H-37 | 107 | 100 |
| H-38 | 103 | 100 |
| H-39 | 100 | 100 |
| H-40 | 73 | 52 |
| H-41 | 98 | 100 |
| H-42 | 18 | 65 |
| H-43 | 51 | 22 |
| H-44 | 94 | 94 |
| H-45 | 56 | 98 |
| H-46 | 103 | 100 |
| H-47 | 104 | 100 |
| H-48 | 75 | 11 |
| H-49 | 101 | 85 |
| H-50 | 86 | 23 |
| H-51 | 105 | 99 |
| H-52 | 73 | 98 |
| H-53 | 50 | 56 |
| H-54 | 93 | 29 |
| H-55 | 104 | 99 |
| H-56 | 102 | 99 |
| H-57 | 100 | 100 |
| H-58 | 98 | 100 |
| H-59 | 103 | 99 |
| H-60 | 103 | 99 |
| H-61 | 77 | 32 |
| H-62 | 99 | 100 |
| H-63 | 96 | 100 |
| H-64 | 97 | 96 |
| H-65 | 107 | 100 |
| H-66 | 99 | 93 |
| H-67 | 102 | 100 |
| H-68 | 104 | 100 |
| H-69 | 99 | 100 |
| H-70 | 96 | 100 |
| H-71 | 99 | 100 |
| H-72 | 104 | 99 |
| H-73 | 104 | 100 |
| H-74 | 104 | 100 |
| H-75 | 105 | 100 |
| H-76 | 107 | 95 |
| H-77 | 104 | 100 |
| H-78 | 85 | 31 |
| H-79 | 110 | 100 |
| H-80 | 110 | 100 |
| H-81 | 109 | 95 |
| H-82 | 112 | 100 |
| H-83 | 111 | 100 |
| H-84 | 103 | 100 |
| H-85 | 103 | 100 |
| H-86 | 98 | 100 |
| H-87 | 104 | 39 |
| H-88 | 104 | 96 |

| Example No. | % inhibition (rat B1R) at 10 μM | % inhibition (human B1R) at 10 μM |
|---|---|---|
| H-89 | 89 | 74 |
| H-90 | 105 | 62 |
| H-91 | 108 | 100 |
| H-92 | 106 | 100 |
| H-93 | 103 | 100 |
| H-94 | 99 | 100 |
| H-95 | 104 | 100 |
| H-96 | 104 | 100 |
| H-98 | 105 | 100 |
| H-99 | 104 | 81 |
| H-100 | 103 | 100 |
| H-101 | 95 | 13 |
| H-102 | 103 | 68 |
| H-103 | 72 | 27 |
| H-104 | 37 | 75 |
| H-110 | 26 | 23 |
| H-111 | 10 | 65 |
| H-112 | 99 | 99 |
| H-113 | 100 | 98 |
| H-114 | 96 | 38 |
| H-115 | 63 | 13 |
| H-116 | 103 | 99 |
| H-117 | 105 | 99 |
| H-118 | 104 | 100 |
| H-119 | 52 | 91 |
| H-120 | 78 | 98 |
| H-122 | 103 | 100 |
| H-123 | 107 | 97 |
| H-124 | 108 | 100 |
| H-125 | 104 | 70 |
| H-126 | 104 | 100 |
| H-127 | 91 | 96 |
| H-128 | 100 | 99 |
| H-129 | 98 | 100 |
| H-130 | 101 | 99 |
| H-131 | 77 | 55 |
| H-132 | 99 | 99 |
| H-133 | 100 | 99 |
| H-134 | 55 | 8 |
| H-135 | 106 | 99 |
| H-136 | 107 | 41 |
| H-137 | 109 | 99 |
| H-138 | 41 | 91 |
| H-139 | 97 | 100 |
| H-140 | 49 | 47 |
| H-141 | 105 | 99 |
| H-142 | 98 | 99 |
| H-143 | 31 | 98 |
| H-144 | 77 | 91 |
| H-145 | 106 | 100 |
| H-146 | 107 | −1 |
| H-147 | 107 | 99 |
| H-148 | 99 | 89 |
| H-149 | 101 | 100 |
| H-150 | 98 | 89 |
| H-151 | 96 | 100 |
| H-152 | 93 | 82 |
| H-153 | 101 | 100 |
| H-155 | 104 | 62 |
| H-156 | 101 | 90 |
| H-158 | 61 | 23 |
| H-160 | 109 | 100 |
| H-161 | 111 | 99 |
| H-162 | 105 | 100 |
| H-163 | 104 | 99 |
| H-164 | 105 | 100 |
| H-165 | 105 | 100 |
| H-166 | 55 | 100 |
| H-167 | 109 | 100 |
| H-168 | 104 | 100 |
| H-169 | 106 | 100 |
| H-170 | 106 | 100 |
| H-171 | 104 | 100 |
| H-172 | | 65 |
| H-174 | | 100 |
| H-175 | | 97 |
| H-176 | | 97 |
| H-178 | 101 | 100 |
| H-179 | 100 | 94 |
| H-180 | 104 | 89 |
| H-181 | 100 | 77 |
| H-182 | 59 | 15 |
| H-183 | 101 | 93 |
| H-184 | 105 | 72 |
| H-185 | 105 | 100 |
| H-186 | 103 | 99 |
| H-188 | | 100 |
| H-191 | | 100 |
| H-195 | | 100 |
| H-196 | | 98 |
| H-197 | | 100 |
| H-198 | | 76 |
| H-199 | | 94 |
| H-202 | | 100 |
| H-203 | | 100 |
| H-204 | | 100 |
| H-205 | | 100 |
| H-206 | | 94 |
| H-207 | | 44 |
| H-208 | | 45 |
| H-209 | | 10 |
| H-210 | | 99 |
| H-211 | | 99 |
| H-212 | | 82 |
| H-213 | | 100 |
| H-214 | | 100 |
| H-215 | | 95 |
| H-216 | | 98 |
| H217 | | 97 |
| H-219 | | 79 |
| H-220 | | 99 |
| H-221 | | 99 |
| H-222 | | 99 |
| H-223 | | 96 |
| H-224 | | 98 |
| H-225 | | 100 |
| H-226 | | 99 |
| H-227 | | 100 |
| H-228 | | 96 |
| H-229 | | 98 |
| H-230 | | 98 |
| H-231 | | |
| H-232 | | |
| H-233 | | |
| H-234 | | |
| H-235 | | |
| H-236 | | |
| H-237 | | |
| H-238 | | |
| H-239 | | |
| H-240 | | |
| H-241 | | |
| H-242 | | |
| H-243 | | |
| H-244 | | 100 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A compound corresponding to formula (I):

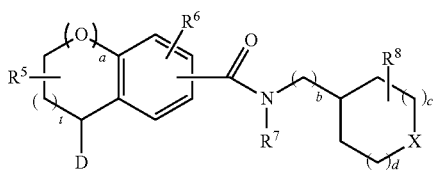

wherein
a represents 0;
t represents 1 or 2;
b represents 0, 1 or 2;
c and d each independently represent 0, 1 or 2, with the proviso that c+d is less than or equal to 3;
X represents $N(R^{9a})$ or $C(R^{9b})(H)$;
D represents

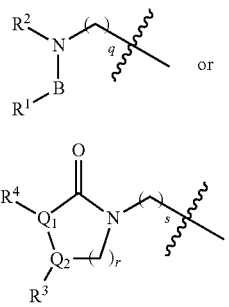

q represents 0 or 1;
s represents 0 or 1;
r represents 1, 2 or 3;
B represents C(=O), S(=O)$_2$ or the group C(=O)—N(R$^{10}$), wherein the nitrogen atom thereof is bonded to the radical R$^1$;
$Q_1$ and $Q_2$ each independently represent C, CH or N;
R$^1$ represents $C_{1-9}$-alkyl, aryl, heteroaryl, CH(aryl)$_2$, $C_{3-8}$-cycloalkyl, heterocyclyl, or aryl, heteroaryl, CH(aryl)$_2$, $C_{3-8}$-cycloalkyl or heterocyclyl bonded via a $C_{1-6}$-alkylene group,
wherein said alkyl, heterocyclyl and cycloalkyl may each be unsubstituted or substituted one or more times by identical or different substituents, independently selected from the group consisting of F, Cl, Br, I, CF$_3$, OCF$_3$, CN, NH$_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, NO$_2$, SH, S—$C_{1-6}$-alkyl, $C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, CO$_2$H, CO$_2$—$C_{1-6}$-alkyl, phenyl, phenoxy, benzyl, naphthyl, furyl, thienyl and pyridinyl,
wherein phenyl, phenoxy, naphthyl, furyl, thienyl and pyridinyl substituents may themselves each be unsubstituted or substituted one or more times by identical or different substituents independently selected from the group consisting of $C_{1-4}$-alkyl, O—$C_{1-3}$-alkyl, F, Cl, CF$_3$, OCF$_3$ and OH, and wherein
said aryl and heteroaryl groups may each be unsubstituted or substituted one or more times by identical or different substituents independently selected from the group consisting of F, Cl, Br, I, CN, NH$_2$, N(CH$_3$)$_2$, C(=O)—NH$_2$, C(=O)—N(CH$_3$)$_2$,

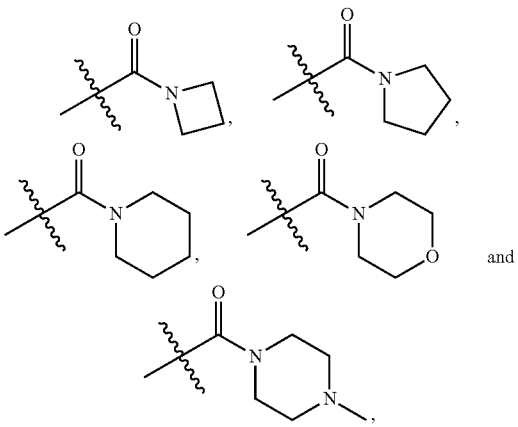

NH—$C_{1-6}$-alkyl, NH—$C_{1-6}$-alkylene-OH, N($C_{1-6}$-alkyl)$_2$, N($C_{1-6}$-alkylene-OH)$_2$, pyrrolinyl, pyrrolidinyl, piperazinyl, N-methyl-piperazinyl, morpholinyl, azetidinyl, piperidinyl, thiazolinyl, azepanyl, diazepanyl, ($C_{1-3}$-alkylene)-azetidinyl, ($C_{1-3}$-alkylene)-pyrrolinyl, ($C_{1-3}$-alkylene)-piperidinyl, ($C_{1-3}$-alkylene)-morpholinyl, ($C_{1-3}$-alkylene)-piperazinyl, ($C_{1-3}$-alkylene)-thiazolinyl, ($C_{1-3}$-alkylene)-azepanyl, ($C_{1-3}$-alkylene)-diazepanyl, NO$_2$, SH, S—$C_{1-6}$-alkyl, OH, O—$C_{1-6}$-alkyl, O—$C_{1-6}$-alkyl-OH, C(=O)$C_{1-6}$-alkyl, NHSO$_2$$C_{1-6}$-alkyl, NHCOC$_{1-6}$-alkyl, CO$_2$H, CH$_2$SO$_2$-phenyl, CO$_2$—$C_{1-6}$-alkyl, OCF$_3$, CF$_3$, —O—CH$_2$—O—, —O—CH$_2$—CH$_2$—O—, —O—C(CH$_3$)$_2$—CH$_2$—, $C_{1-6}$-alkyl, $C_{3-6}$-cycloalkyl, O—$C_{3-6}$-cycloalkyl, pyrrolidinyl, imidazolyl, benzyloxy, phenoxy, phenyl, naphthyl, pyridinyl, pyrimidinyl, benzyl, thienyl, furyl, or OCF$_3$, OH, O—$C_{1-6}$-alkyl, SH, S—$C_{1-6}$-alkyl, $C_{3-6}$-cycloalkyl, O—$C_{3-6}$-cycloalkyl, phenyl, pyridyl or pyrimidyl bonded via a $C_{1-6}$-alkylene group;
R$^2$ represents H, $C_{1-6}$-alkyl or $C_{3-8}$-cycloalkyl, wherein said $C_{1-6}$-alkyl and $C_{3-8}$-cycloalkyl may each be unsubstituted or substituted one or more times by identical or different substituents, independently selected from the group consisting of F, Cl and O—$C_{1-6}$-alkyl;
R$^3$ and R$^4$, together with the group -$Q_1$-$Q_2$- linking them, form a ring which is unsubstituted or substituted on one or more of its carbon ring members by one or more substituents independently selected from the group consisting of F, Cl, Br, I, CF$_3$, $C_{1-6}$-alkyl, O—$C_{1-6}$-alkyl, OH, OCF$_3$, SH, SCF$_3$, aryl and heteroaryl and/or can be fused with at least one aryl or heteroaryl, wherein the ring is saturated, mono- or poly-unsaturated or aromatic, is 4-, 5-, 6- or 7-membered and can optionally contain one or more heteroatoms or heteroatom groups independently selected from the group consisting of N, NR$^{11}$, O, S, S(=O) and S(=O)$_2$; wherein
R$^{11}$ denotes H, $C_{1-6}$-alkyl, C(=O)—R$^{12}$, $C_{3-8}$-cycloalkyl, aryl or heteroaryl, and
R$^{12}$ denotes $C_{1-6}$-alkyl, $C_{3-8}$-cycloalkyl, aryl or heteroaryl;

$R^5$ represents 0, 1, 2, 3 or 4 substituents independently selected from the group consisting of F, Cl, $CF_3$, $OCF_3$, $C_{1-6}$-alkyl and O—$C_{1-6}$-alkyl;

$R^6$ represents 0, 1, 2 or 3 substituents independently selected from the group consisting of F, Cl, Br, $CF_3$, $OCF_3$, OH, $C_{1-6}$-alkyl, $C_{3-8}$-cycloalkyl, O—$C_{1-6}$-alkyl, $NO_2$, $NH_2$, N(H)($C_{1-6}$-alkyl) and N($C_{1-6}$-alkyl)$_2$;

$R^7$ represents H, $C_{1-6}$-alkyl, $C_{3-8}$-cycloalkyl, heterocyclyl, aryl or heteroaryl, or denotes $C_{3-8}$-cycloalkyl, heterocyclyl, aryl or heteroaryl bonded via a $C_{1-6}$-alkylene group;

$R^8$ represents 0, 1, 2, 3 or 4 substituents independently selected from the group consisting of $CF_3$, $C_{1-6}$-alkyl, $C_{3-8}$-cycloalkyl and aryl, and/or two substituents $R^8$ bonded to a carbon atom form a C(=O) group;

$R^{9a}$ represents $CHR^{15}R^{16}$, heterocyclyl, aryl or heteroaryl, or represents $CHR^{15}R^{16}$, heterocyclyl, aryl or heteroaryl bonded via a $C_{1-6}$-alkylene group, wherein said $C_{1-6}$-alkylene and heterocyclyl groups may each be unsubstituted or substituted one or more times by identical or different substituents, independently selected from the group consisting of F, Cl, Br, I, $CF_3$, $OCF_3$, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, $C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl, phenyl, phenoxy, benzyl, naphthyl, furyl, thienyl and pyridinyl, and wherein said aryl and heteroaryl groups may each be unsubstituted or substituted one or more times by identical or different substituents independently selected from the group consisting of azetidinyl, pyrrolidinyl, piperidinyl, morpholinyl, N-methylpiperazinyl, cyclopropyl, pyridinyl, O—$C_{1-3}$-alkyl, $C_{1-4}$-alkyl, F, Cl, $CF_3$, $OCF_3$, OH, CN, $NH_2$, N($C_{1-4}$-alkyl)$_2$, NH($C_{1-4}$-alkyl), C(=O)—$NH_2$, C(=O)—N($C_{1-4}$-alkyl)$_2$, C(=O)—NH($C_{1-4}$-alkyl), S(=O)$_2$—$C_{1-4}$-alkyl,

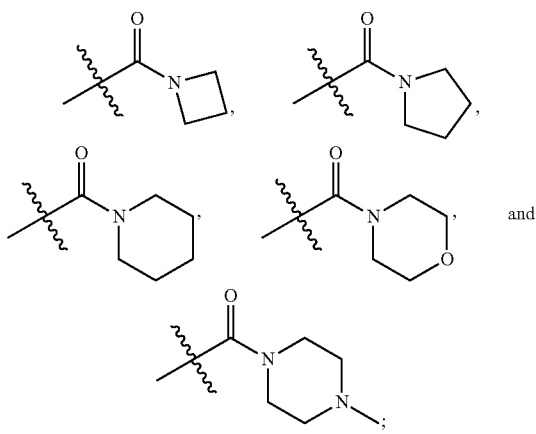

$R^{9b}$ represents $NR^{17}R^{18}$, $C_{1-6}$-alkylene-$NR^{17}R^{18}$, O—$C_{1-6}$-alkylene-$NR^{17}R^{18}$, C(O)—$NR^{17}R^{18}$, $OR^{19}$, $C_{1-6}$-alkylene-$OR^{19}$, $C_{3-8}$-cycloalkyl, heterocyclyl, aryl, heteroaryl, or $C_{3-8}$-cycloalkyl, heterocyclyl, aryl or heteroaryl bonded via a $C_{1-6}$-alkylene group, wherein said $C_{1-6}$-alkylene, $C_{3-8}$-cycloalkyl and heterocyclyl groups may each be unsubstituted or substituted one or more times by identical or different substituents, independently selected from the group consisting of F, Cl, Br, I, $CF_3$, $OCF_3$, CN, $NH_2$, NH—$C_{1-6}$-alkyl, NH—$C_{1-6}$-alkylene-OH, $C_{1-6}$-alkyl, N($C_{1-6}$-alkyl)$_2$, N($C_{1-6}$-alkylene-OH)$_2$, $NO_2$, SH, S—$C_{1-6}$-alkyl, $C_{1-6}$-alkyl, S-benzyl, O—$C_{1-6}$-alkyl, OH, O—$C_{1-6}$-alkylene-OH, =O, O-benzyl, C(=O)$C_{1-6}$-alkyl, $CO_2H$, $CO_2$—$C_{1-6}$-alkyl, phenyl, phenoxy, benzyl, naphthyl, furyl, thienyl and pyridinyl, and wherein said aryl and heteroaryl groups may each be unsubstituted or substituted one or more times by identical or different substituents independently selected from the group consisting of azetidinyl, pyrrolidinyl, piperidinyl, morpholinyl, N-methylpiperazinyl, cyclopropyl, pyridinyl, O—$C_{1-3}$-alkyl, $C_{1-4}$-alkyl, F, Cl, $CF_3$, $OCF_3$, OH, CN, $NH_2$, N($C_{1-4}$-alkyl)$_2$, NH($C_{1-4}$-alkyl), C(=O)—$NH_2$, C(=O)—N($C_{1-4}$-alkyl)$_2$, C(=O)—NH($C_{1-4}$-alkyl), S(=O)$_2$—$C_{1-4}$-alkyl,

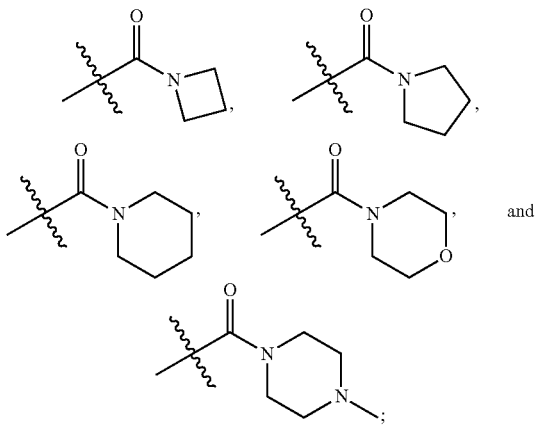

$R^{10}$ represents H, $C_{1-6}$-alkyl or $C_{3-8}$-cycloalkyl, wherein said $C_{1-6}$-alkyl and $C_{3-8}$-cycloalkyl may each be unsubstituted or substituted one or more times by identical or different substituents, independently selected from the group consisting of F, Cl, =O and O—$C_{1-6}$-alkyl;

$R^{15}$ and $R^{16}$ each independently represent H, $C_{1-4}$-alkyl, $C_{3-8}$-cycloalkyl, aryl or heteroaryl, or $R^{15}$ and $R^{16}$, together with the CH grouping linking them, form a 4-, 5-, 6- or 7-membered ring which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, $NR^{20}R^{21}$, aryl and heteroaryl, wherein said ring may be saturated or mono- or poly-unsaturated but not aromatic, and can optionally contain one or more heteroatoms or heteroatom groups independently selected from the group consisting of N, $NR^{24}$, O, S, S(=O) and S(=O)$_2$;

wherein $R^{24}$ denotes H, $C_{1-6}$-alkyl, C(=O)—$R^{25}$, $C_{3-8}$-cycloalkyl, aryl, heteroaryl, or $C_{3-8}$-cycloalkyl, aryl or heteroaryl bonded via a $C_{1-3}$-alkylene group, and $R^{25}$ denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

R[17] and R[18] each independently represent H, $C_{1-6}$-alkyl or $C_{3-8}$-cycloalkyl, or R[17] and R[18], together with the nitrogen atom linking them, form a 4-, 5-, 6- or 7-membered heterocyclic ring which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, NR[20]R[21], aryl and heteroaryl and/or can be fused with at least one aryl or heteroaryl, wherein said aryl and heteroaryl groups may each be unsubstituted or substituted one or more times by identical or different substituents independently selected from the group consisting of azetidinyl, pyrrolidinyl, piperidinyl, morpholinyl, N-methylpiperazinyl, cyclopropyl, pyridinyl, O—$C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), $C(=O)$—$NH_2$, $C(=O)$—$N(C_{1-4}$-alkyl$)_2$, $C(=O)$—$NH(C_{1-4}$-alkyl), $S(=O)_2$—$C_{1-4}$-alkyl,

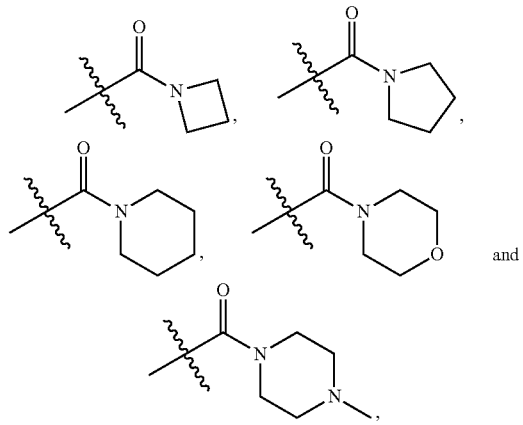

wherein the heterocyclic ring is saturated or mono- or poly-unsaturated, and can optionally contain 1, 2 or 3 heteroatoms or heteroatom groups independently selected from the group consisting of N, NR[22], O, S, $S(=O)$ and $S(=O)_2$; wherein R[22] denotes H, $C_{1-6}$-alkyl, —$C(=O)$—R[23], $C_{3-8}$-cycloalkyl, aryl, heteroaryl, or $C_{3-8}$-cycloalkyl, aryl or heteroaryl bonded via a $C_{1-3}$-alkylene group, and R[23] denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

R[19] represents H, $C_{1-6}$-alkyl, $C_{3-8}$-cycloalkyl, heterocyclyl, aryl, heteroaryl or $C_{2-6}$-alkylene-NR[17]R[18], or heterocyclyl, $C_{3-8}$-cycloalkyl, aryl or heteroaryl bonded via a $C_{1-6}$-alkylene group, wherein said aryl and heteroaryl groups may each be unsubstituted or substituted one or more times by identical or different substituents independently selected from the group consisting of azetidinyl, pyrrolidinyl, piperidinyl, morpholinyl, N-methylpiperazinyl, cyclopropyl, pyridinyl, O—$C_{1-3}$-alkyl, $C_{1-4}$-alkyl, F, Cl, $CF_3$, $OCF_3$, OH, CN, $NH_2$, $N(C_{1-4}$-alkyl$)_2$, $NH(C_{1-4}$-alkyl), $C(=O)$—$NH_2$, $C(=O)$—$N(C_{1-4}$-alkyl$)_2$, $C(=O)$—$NH(C_{1-4}$-alkyl), $S(=O)_2$—$C_{1-4}$-alkyl,

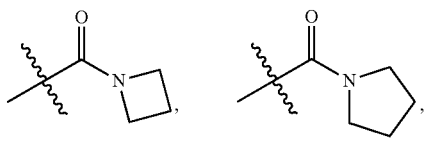

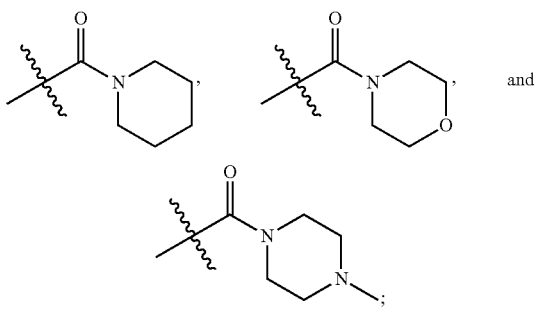

R[20] and R[21] each independently represent H, $C_{1-6}$-alkyl or $C_{3-8}$-cycloalkyl, or R[20] and R[21], together with the nitrogen atom linking them, form a 4-, 5-, 6- or 7-membered heterocyclic ring which is unsubstituted or substituted on one or more of its carbon ring members by one or more substituents independently selected from the group consisting of F, Cl, Br, I, $CF_3$, $C_{1-6}$-alkyl, O—$C_{1-6}$-alkyl, OH, $OCF_3$, SH, $SCF_3$, aryl and heteroaryl, wherein the heterocyclic ring may be saturated or mono- or poly-unsaturated but not aromatic, and can optionally contain one or more heteroatoms or heteroatom groups independently selected from the group consisting of N, NR[26], O, S, $S(=O)$ and $S(=O)_2$; wherein R[26] denotes H, $C_{1-6}$-alkyl, $C(=O)$—R[27], $C_{3-8}$-cycloalkyl, aryl, heteroaryl, or $C_{3-8}$-cycloalkyl, aryl or heteroaryl bonded via a $C_{1-3}$-alkylene group, and R[27] denotes $C_{1-6}$-alkyl, $C_{3-8}$-cycloalkyl, aryl, heteroaryl, or $C_{3-8}$-cycloalkyl, aryl or heteroaryl bonded via a $C_{1-3}$-alkylene group;

or an N-oxide or physiologically acceptable salt thereof.

2. A compound according to claim 1, wherein said compound is in the form of a mixture of stereoisomers.

3. A compound according to claim 2, wherein said mixture is a racemic mixture.

4. A compound according to claim 1, wherein said compound is in the form of a single stereoisomer.

5. A compound according to claim 1, wherein in formula (I) the partial structure (Ac)

(Ac)

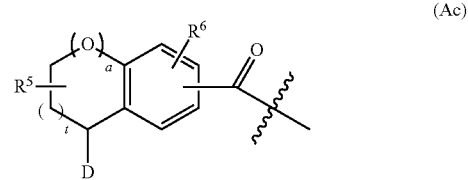

represents a partial structure selected from the group consisting of:
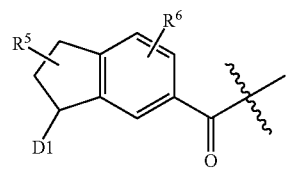 (Ac 1)
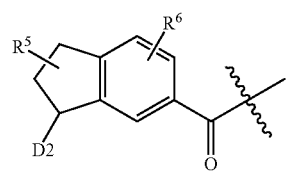 (Ac 2)
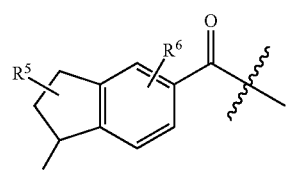 (Ac 3)
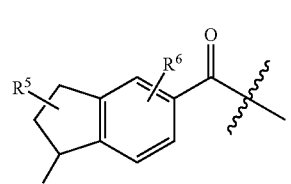 (Ac 4)
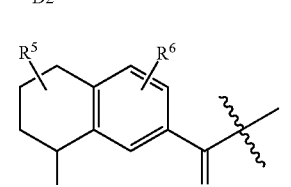 (Ac 5)
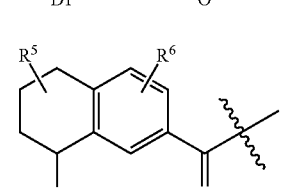 (Ac 6)
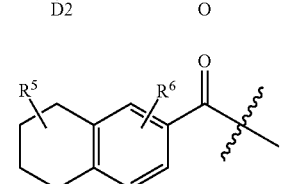 (Ac 7)
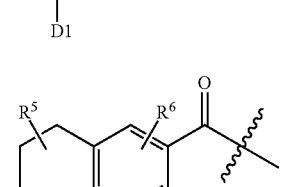 (Ac 8)
-continued
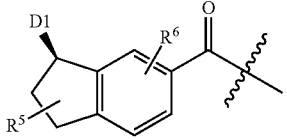 (Ac 17)
(Ac 18)
(Ac 19)
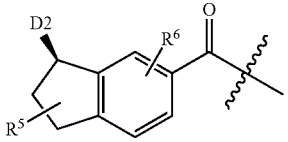 (Ac 20)
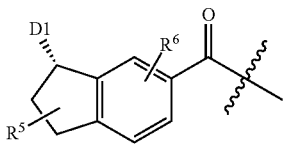 (Ac 21)
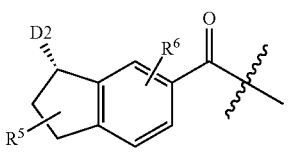 (Ac 22)
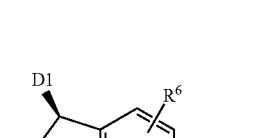 (Ac 23)
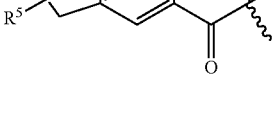 and
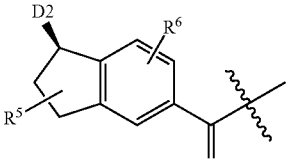 (Ac 24)

6. A compound according to claim 1, wherein D1 is selected from the group consisting of:

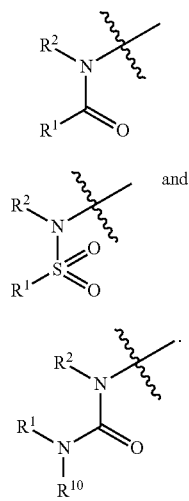

7. A compound according to claim 1, wherein $R^1$ represents $C_{1-9}$-alkyl, $CH(phenyl)_2$, $C_{3-8}$-cycloalkyl, heterocyclyl, phenyl, naphthyl, tetrahydronaphthyl, chromanyl, indolyl, benzofuranyl, benzothiophenyl, benzooxazolyl, benzooxadiazolyl, pyrrolyl, furanyl, thienyl, oxazolyl, isoxazolyl, pyridinyl, pyridazinyl, pyrimidinyl, pyrazolo[1,5-a]pyrimidinyl, pyrazinyl, imidazothiazolyl, carbazolyl, dibenzofuranyl, dibenzothiophenyl, dihydroindenyl, isoquinolinyl, or phenyl, naphthyl, $C_{3-8}$-cycloalkyl or heterocyclyl bonded via a $C_{1-3}$-alkylene group, wherein
  the above-mentioned aryl or heteroaryl groups may each be unsubstituted or substituted one or more times by identical or different substituents independently selected from the group consisting of $O$—$C_{1-3}$-alkyl, $C_{1-6}$-alkyl, F, Cl, CN, $CF_3$, $OCF_3$, and OH;
  the above-mentioned alkyl, alkylene, cycloalkyl and heterocyclyl groups may each be unsubstituted or substituted one or more times by identical or different substituents independently selected from the group consisting of $O$—$C_{1-3}$-alkyl, $C_{1-4}$-alkyl, F, Cl, $CF_3$, $OCF_3$, OH, cyclopropyl, cyclobutyl, cyclopentyl, cyclohexyl, phenyl, phenoxy, naphthyl, thienyl, furyl and pyridinyl; and
  phenyl, phenoxy, naphthyl, furyl, thienyl and pyridinyl substituents may themselves each be unsubstituted or substituted one or more times by identical or different substituents independently selected from the group consisting of $C_{1-4}$-alkyl, $O$—$C_{1-3}$-alkyl, F, Cl, $CF_3$, $OCF_3$ and OH.

8. A compound according to claim 7, wherein $R^1$ represents unsubstituted or mono- or poly-substituted $C_{1-6}$-alkyl, $CH(phenyl)_2$, $C_{3-6}$-cycloalkyl, $C_{4-6}$-heterocyclyl, phenyl, naphthyl, tetrahydronaphthyl, chromanyl, dihydroindenyl, isoquinolinyl, benzothiophenyl, benzooxadiazolyl, thienyl, oxazolyl, isoxazolyl, pyridinyl, pyrimidinyl, pyrazolo[1,5-a]pyrimidinyl, imidazothiazolyl, dibenzofuranyl, or phenyl, $C_{3-6}$-cycloalkyl or $C_{4-6}$-heterocyclyl bonded via a $C_{1-3}$-alkylene group.

9. A compound according to claim 8, wherein $R^1$ represents unsubstituted or mono- or poly-substituted $C_{1-6}$-alkyl, $CH(phenyl)_2$, cyclopropyl, cyclobutyl, cyclopentyl, cyclohexyl, tetrahydropyranyl, oxetanyl, tetrahydrofuranyl, piperidinyl, phenyl, naphthyl, tetrahydronaphthyl, pyridinyl, pyrimidinyl, pyrazolo[1,5-a]pyrimidinyl, oxazolyl, isoxazolyl, dihydroindenyl, chromanyl, isoquinolinyl or phenyl, cyclopropyl, cyclobutyl, cyclopentyl, cyclohexyl, tetrahydropyranyl, oxetanyl, tetrahydrofuranyl or piperidinyl bonded via a $C_{1, 2 \text{ or } 3}$-alkylene group.

10. A compound according to claim 1, wherein $R^2$ represents H, methyl, ethyl, n-propyl, isopropyl, n-butyl, isobutyl, sec-butyl, tert-butyl, $CH_2$—$CF_3$, cyclopropyl, cyclobutyl, cyclopentyl or cyclohexyl.

11. A compound according to claim 10, wherein $R^2$ represents H, methyl, ethyl, isopropyl, isobutyl, tert-butyl or cyclopropyl.

12. A compound according to claim 1, wherein $R^{10}$ represents H, methyl, ethyl, n-propyl, isopropyl, n-butyl, isobutyl, sec-butyl, tert-butyl, $CH_2$—$CF_3$, cyclopropyl, cyclobutyl, cyclopentyl or cyclohexyl.

13. A compound according to claim 12, wherein $R^2$ represents H, methyl, ethyl, isopropyl, isobutyl, tert-butyl or cyclopropyl.

14. A compound according to claim 1, wherein D2 represents a group selected from the group consisting of:

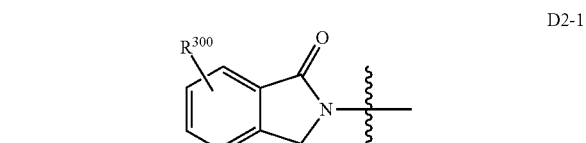

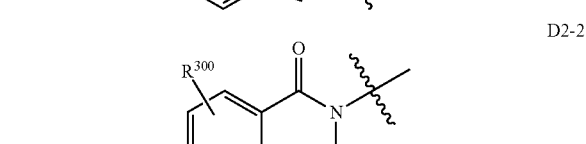

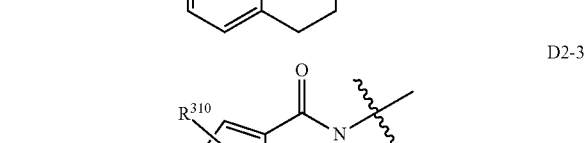

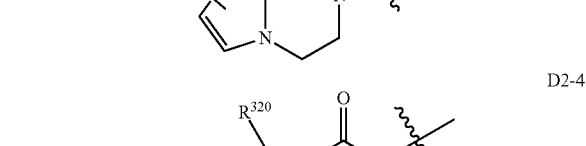

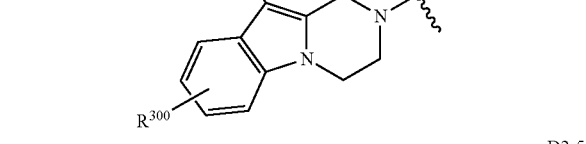

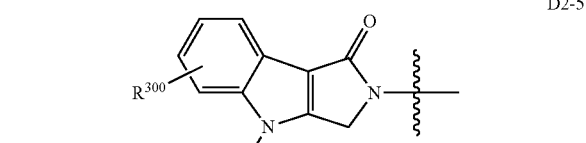

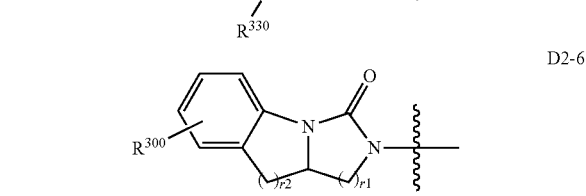

-continued

D2-7
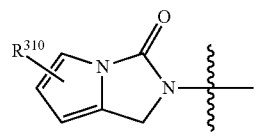

D2-8
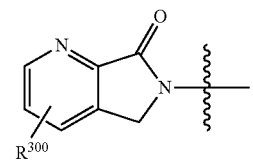

D2-9
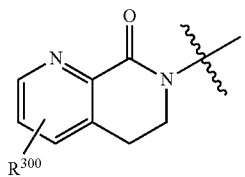 and

D2-10
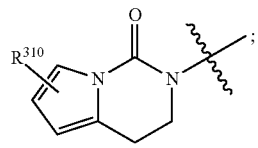;

wherein $R^{300}$ represents 0, 1, 2, 3 or 4 substituents independently selected from the group consisting of F, Cl, Br, I, $CF_3$, O—$CF_3$, $C_{1-4}$-alkyl and O—$C_{1-4}$-alkyl;

$R^{310}$ represents 0, 1, 2 or 3 substituents independently selected from the group consisting of F, Cl, Br, I, $CF_3$, O—$CF_3$, $C_{1-4}$-alkyl and O—$C_{1-4}$-alkyl;

$R^{320}$ represents a substituent selected from the group consisting of H, F, Cl, Br, I, $CF_3$, O—$CF_3$ and $C_{1-4}$-alkyl;

$R^{330}$ represents a substituent selected from the group consisting of H, $C_{1-4}$-alkyl, aryl, $CH_2$-aryl and heteroaryl;

r1 represents 1 or 2, and r2 represents 1 or 2.

15. A compound according to claim 1, wherein $R^7$ represents H, methyl, ethyl, n-propyl, isopropyl, n-butyl, isobutyl, sec-butyl, tert-butyl, cyclopropyl, cyclobutyl, cyclopentyl or cyclohexyl.

16. A compound according to claim 15, wherein $R^7$ represents H, methyl, ethyl, isopropyl, isobutyl, tert-butyl or cyclopropyl.

17. A compound according to claim 1, wherein the partial structure (Cy)

(Cy)
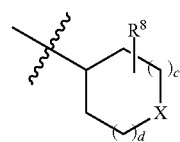

is selected from the group consisting of:

(Cy 1)
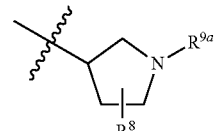

(Cy 2)
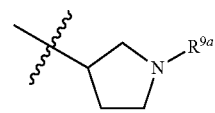

(Cy 3)
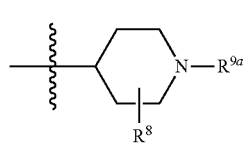

(Cy 4)
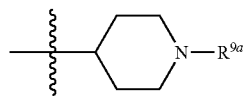

(Cy 5)
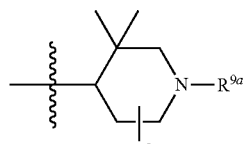

(Cy 6)
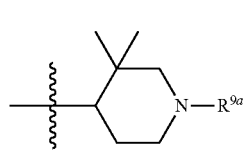

(Cy 7)
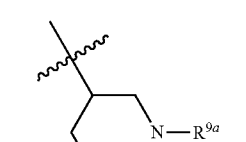

(Cy 8)
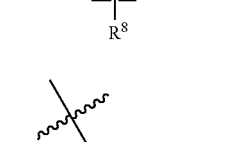

(Cy 9)
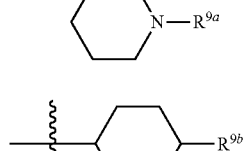

(Cy 10)
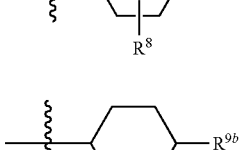

-continued (Cy 11) 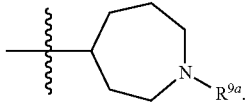

(Cy 12) 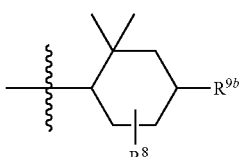

(Cy 13)

(Cy 14) 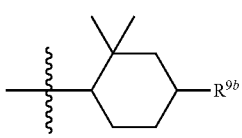

(Cy 15) 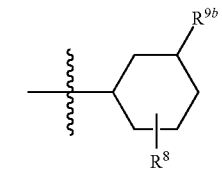

(Cy 16) 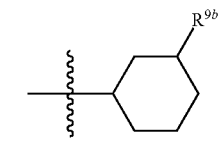

(Cy 17) 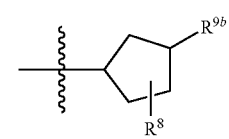

(Cy 18) 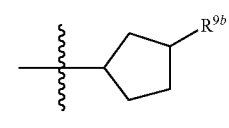

(Cy 19) 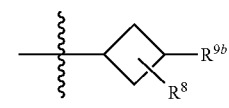

(Cy 20) 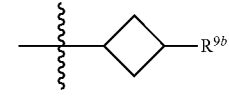

(Cy 21) 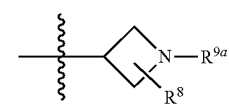

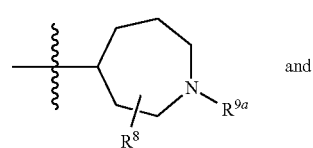 and

-continued (Cy 22)

18. A compound according to claim 1, wherein $R^8$ represents 0, 1 or 2 substituents independently selected from the group consisting of methyl, ethyl, n-propyl, isopropyl, n-butyl, isobutyl, tert-butyl and phenyl, and/or two substituents $R^8$ bonded to a carbon atom form a C(=O) group.

19. A compound according to claim 1, wherein
$R^{9a}$ represents $CHR^{15}R^{16}$, aryl, heteroaryl, or $CHR^{15}R^{16}$, aryl or heteroaryl bonded via a $C_{1-3}$-alkylene group;
$R^{15}$ and $R^{16}$, together with the CH grouping linking them, form a 4-, 5-, 6- or 7-membered ring which may be unsubstituted or substituted by 1, 2, 3 or 4 substituents independently selected from the group consisting of F, Cl, Br, I, $CF_3$, $C_{1-4}$-alkyl, O—$C_{1-4}$-alkyl, OH, =O, $OCF_3$, SH, $SCF_3$, $NR^{20}R^{21}$, aryl and heteroaryl, wherein said ring may be saturated or mono- or poly-unsaturated but not aromatic, and can optionally contain one or more heteroatoms or heteroatom groups independently selected from the group consisting of N, $NR^{24}$, O, S, S(=O) and S(=O)$_2$; wherein
$R^{24}$ denotes H, $C_{1-4}$-alkyl, C(=O)—$R^{25}$, $C_{3-6}$-cycloalkyl, aryl, heteroaryl, or $C_{3-6}$-cycloalkyl, aryl or heteroaryl bonded via a $C_{1-3}$-alkylene group, and
$R^{25}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group;
$R^{20}$ and $R^{21}$, together with the nitrogen atom linking them, form a 4-, 5-, 6- or 7-membered heterocyclic ring which may be unsubstituted or substituted by 1, 2, 3 or 4 substituents independently selected from the group consisting of F, Cl, Br, I, $CF_3$, $C_{1-4}$-alkyl, O—$C_{1-4}$-alkyl, OH, $OCF_3$, SH, $SCF_3$, aryl and heteroaryl, wherein said heterocyclic ring may be saturated or mono- or poly-unsaturated but not aromatic, and may optionally contain one or more heteroatoms or heteroatom groups independently selected from the group consisting of N, $NR^{26}$, O, S, S(=O) and S(=O)$_2$; wherein
$R^{26}$ denotes H, $C_{1-4}$-alkyl, C(=O)—$R^{27}$, $C_{3-6}$-cycloalkyl, aryl, heteroaryl, or $C_{3-6}$-cycloalkyl, aryl or heteroaryl bonded via a $C_{1-3}$-alkylene group, and
$R^{27}$ denotes $C_{1-4}$-alkyl, $C_{3-6}$-cycloalkyl, aryl, heteroaryl, or $C_{3-6}$-cycloalkyl, aryl or heteroaryl bonded via a $C_{1-3}$-alkylene group;
wherein:
aryl represents phenyl or naphthyl; and
heteroaryl represents pyridinyl, triazinyl, pyrimidinyl, pyrazinyl, pyridazinyl, quinolinyl, isoquinolinyl, quinazolinyl, purinyl, thiazolyl, thiadiazolyl, imidazolyl, triazolyl, oxazolyl, isoxazolyl, thienyl, pyrrolyl, tetrazolyl, oxadiazolyl, or oxathiazolyl.

20. A compound according to claim 19, wherein:
aryl represents phenyl or naphthyl;
heteroaryl represents pyridinyl, pyrimidinyl, pyrazinyl, pyridazinyl, isoquinolinyl, thiazolyl or imidazolyl; and
said aryl or heteroaryl groups may each be unsubstituted or substituted one or more times by identical or different substituents independently selected from the group consisting of methyl, isopropyl, tert-butyl, F, Cl, $CF_3$, $OCF_3$, methoxy, OH, S(=O)$_2$—CH$_3$, NH$_2$, N(CH$_3$)$_2$, pyrrolidinyl, piperidinyl, cyclopropyl, CN, C(=O)—NH$_2$, C(=O)—N(CH$_3$)$_2$, and

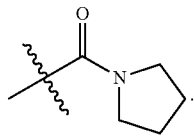 [SMILES: *C(=O)N1CCCC1]

21. A compound according to claim 1, wherein
R$^{9b}$ represents NR$^{17}$R$^{18}$, C$_{1-3}$alkylene-NR$^{17}$R$^{18}$, O—C$_{1-3}$-alkylene-NR$^{17}$R$^{18}$, C(O)—NR$^{17}$R$^{18}$, OR$^{19}$, C$_{1-3}$-alkylene-OR$^{19}$, C$_{3-6}$-cycloalkyl, aryl, heteroaryl, or C$_{3-6}$-cycloalkyl, -aryl or heteroaryl bonded via a C$_{1-3}$-alkylene group, wherein:
  R$^{17}$ and R$^{18}$ each independently represent H, C$_{1-4}$-alkyl or C$_{3-6}$-cycloalkyl, or
  R$^{17}$ and R$^{18}$, together with the nitrogen atom linking them, form a 4-, 5-, 6- or 7-membered heterocyclic ring which may be unsubstituted or substituted by 1, 2, 3 or 4 substituents independently selected from the group consisting of F, Cl, CF$_3$, C$_{1-4}$-alkyl, O—C$_{1-4}$-alkyl, OH, =O, OCF$_3$, NR$^{20}$R$^{21}$, aryl and heteroaryl and/or can be fused with at least one aryl or heteroaryl, wherein said heterocyclic ring may be saturated or mono- or poly-unsaturated, and may optionally contain one or more heteroatoms or heteroatom groups independently selected from the group consisting of N, NR$^{22}$, O, S, S(=O) and S(=O)$_2$; wherein
    R$^{22}$ denotes H, C$_{1-4}$-alkyl, C(=O)—R$^{23}$, C$_{3-6}$-cycloalkyl, aryl, heteroaryl, or C$_{3-6}$-cycloalkyl, aryl or heteroaryl bonded via a C$_{1-3}$-alkylene group, and
    R$^{23}$ denotes C$_{1-4}$-alkyl, C$_{3-6}$-cycloalkyl, aryl, heteroaryl, or C$_{3-6}$-cycloalkyl, aryl or heteroaryl bonded via a C$_{1-3}$-alkylene group;
  R$^{19}$ represents H, C$_{1-4}$-alkyl, C$_{3-6}$-cycloalkyl, aryl, heteroaryl or C$_{2-3}$-alkylene-NR$^{17}$R$^{18}$, or C$_{3-6}$-cycloalkyl, aryl or heteroaryl bonded via a C$_{1-4}$-alkylene group;
  R$^{20}$ and R$^{21}$, together with the nitrogen atom linking them, form a 4-, 5-, 6- or 7-membered heterocyclic ring which may be unsubstituted or substituted by 1, 2, 3 or 4 substituents independently selected from the group consisting of F, Cl, CF$_3$, C$_{1-4}$-alkyl, O—C$_{1-4}$-alkyl, OH, OCF$_3$, SCF$_3$, aryl and heteroaryl, wherein said heterocyclic ring may be saturated or mono- or poly-unsaturated but not aromatic, and may optionally contain one or more heteroatoms or heteroatom groups independently selected from the group consisting of N, NR$^{26}$, O, S, S(=O) and S(=O)$_2$; wherein
    R$^{26}$ denotes H, C$_{1-4}$-alkyl, C(=O)—R$^{27}$, C$_{3-6}$-cycloalkyl, aryl, heteroaryl, or C$_{3-6}$-cycloalkyl, aryl or heteroaryl bonded via a C$_{1-3}$-alkylene group, and
    R$^{27}$ denotes C$_{1-4}$-alkyl, C$_{3-6}$-cycloalkyl, aryl, heteroaryl, or C$_{3-6}$-cycloalkyl, aryl or heteroaryl bonded via a C$_{1-3}$-alkylene group;
wherein
  aryl represents phenyl or naphthyl; and
  heteroaryl represents pyridinyl, triazinyl, pyrimidinyl, pyrazinyl, pyridazinyl, quinolinyl, isoquinolinyl, quinazolinyl, thiazolyl, thiadiazolyl, imidazolyl, triazolyl, oxazolyl, isoxazolyl, thienyl, pyrrolyl, tetrazolyl, oxadiazolyl, or oxathiazolyl.

22. A compound according to claim 21, wherein
aryl represents phenyl or naphthyl;
heteroaryl represents pyridinyl, pyrimidinyl, pyrazinyl, pyridazinyl, pyrrolyl, isoquinolinyl, thiazolyl or imidazolyl; and
said aryl or heteroaryl groups each may be unsubstituted or substituted one or more times by identical or different substituents independently selected from the group consisting of methyl, F, Cl, CF$_3$, OCF$_3$, methoxy, OH, NH$_2$, N(CH$_3$)$_2$, pyrrolidinyl, CN, C(=O)—NH$_2$, C(=O)—N(CH$_3$)$_2$ and

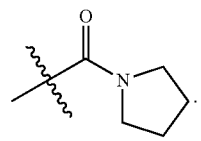

23. A compound according to claim 1, selected from the group consisting of:
3-[(2-Chloro-benzoyl)amino]-N-[2-(1-pyridin-4-yl-piperidin-4-yl)-ethyl]-2,3-dihydro-1H-indene-5-carboxylic acid amide,
(3R)-3-[(2-Chloro-benzoyl)amino]-N-[(1-pyridin-4-yl-piperidin-4-yl)-methyl]-2,3-dihydro-1H-indene-5-carboxylic acid amide,
(3R)-3-[(2-Chloro-benzoyl)amino]-N-[1-[5-(trifluoromethyl)-pyridin-2-yl]-pyrrolidin-3-yl]-2,3-dihydro-1H-indene-5-carboxylic acid amide,
(3R)-3-[(2-Chloro-benzoyl)amino]-N-methyl-N-(1-pyridin-4-yl-piperidin-4-yl)-2,3-dihydro-1H-indene-5-carboxylic acid amide,
(3R)-3-[(2-Chloro-benzoyl)amino]-N-(1-pyridin-4-yl-piperidin-4-yl)-2,3-dihydro-1H-indene-5-carboxylic acid amide,
(3R)-3-[(2-Chloro-benzoyl)amino]-N-[(3S)-1-(1-cyclopropyl-piperidin-4-yl)-pyrrolidin-3-yl]-2,3-dihydro-1H-indene-5-carboxylic acid amide,
(3R)-3-[(2-Chloro-benzoyl)amino]-N-[(1-pyridin-4-yl-piperidin-3-yl)-methyl]-2,3-dihydro-1H-indene-5-carboxylic acid amide,
(1R)-1-(4-Chloro-3-oxo-1,2-dihydro-isoindol-2-yl)-N-methyl-N-(1-pyridin-4-yl-piperidin-4-yl)-2,3-dihydro-1H-indene-5-carboxylic acid amide,
(3R)-3-(4-Chloro-3-oxo-1,2-dihydro-isoindol-2-yl)-N-methyl-N-(1-pyridin-4-yl-piperidin-4-yl)-2,3-dihydro-1H-indene-5-carboxylic acid amide,
(3R)-3-[(2-Chloro-benzoyl)amino]-N-[2,2-dimethyl-4-(4-methyl-piperazin-1-yl)-cyclohexyl]-2,3-dihydro-1H-indene-5-carboxylic acid amide,
(3R)-3-[(2-Chloro-benzoyl)amino]-N-[2-(1-pyridin-4-yl-piperidin-4-yl)-ethyl]-2,3-dihydro-1H-indene-5-carboxylic acid amide,
(1R)-1-[[(2-Chlorophenyl)sulfonyl]amino]-N-methyl-N-(1-pyridin-4-yl-piperidin-4-yl)-2,3-dihydro-1H-indene-5-carboxylic acid amide,
(1R)-1-[(2-Chloro-benzoyl)amino]-N-methyl-N-(1-pyridin-4-yl-piperidin-4-yl)-2,3-dihydro-1H-indene-5-carboxylic acid amide,
(3R)-3-(Cyclobutanecarbonylamino)-N-methyl-N-(1-pyridin-4-yl-piperidin-4-yl)-2,3-dihydro-1H-indene-5-carboxylic acid amide, (3R)-3-(2,2-Dimethyl-propanoylamino)-N-methyl-N-(1-pyridin-4-yl-piperidin-4-yl)-2,3-dihydro-1H-indene-5-carboxylic acid amide, (3S)-3-[(2-Chloro-benzoyl)amino]-N-methyl-N-(1-pyridin-4-yl-piperidin-4-yl)-2,3-dihydro-1H-indene-5-carboxylic acid amide, N-[(1R)-6-[Methyl-(1-pyridin-4-yl-piperidin-4-yl)-carbamoyl]-2,3-dihydro-1H-inden-1-yl]-pyrazolo[1,5-a]pyrimidine-3-carboxylic acid amide, (3R)-3-[(2-Chloro-benzoyl)amino]-N-methyl-N-(1-pyridin-2-yl-piperidin-4-yl)-2,3-dihydro-1H-indene-5-carboxylic acid amide, (3R)-3-[[2-Chloro-3-(trifluoromethyl)-benzoyl]amino]-N-methyl-N-(1-pyridin-4-yl-piperidin-4-yl)-2,3-dihydro-1H-indene-5-carboxylic acid amide, (3R)—N-Methyl-3-[(2-phenyl-acetyl)amino]-N-(1-pyridin-4-yl-piperidin-4-yl)-2,3-dihydro-1H-indene-5-carboxylic acid amide, (1R)-1-(4-Chloro-3-oxo-1,2-dihydro-isoindol-2-yl)-N-methyl-N-(1-pyridin-2-yl-piperidin-4-yl)-2,3-dihydro-1H-indene-5-carboxylic acid amide, (1R)-1-(4-Chloro-3-oxo-1,2-dihydro-isoindol-2-yl)-N-methyl-N-[1-(pyridin-4-yl-methyl)-piperidin-4-yl]-2,3-dihydro-1H-indene-5-carboxylic acid amide, (3R)—N-Methyl-3-(3-methyl-butanoylamino)-N-(1-pyridin-4-yl-piperidin-4-yl)-2,3-dihydro-1H-indene-5-carboxylic acid amide, (3R)-3-[(2-Fluoro-benzoyl)amino]-N-methyl-N-(1-pyridin-4-yl-piperidin-4-yl)-2,3-dihydro-1H-indene-5-carboxylic acid amide, (3R)—N-Methyl-N-(1-pyridin-4-yl-piperidin-4-yl)-3-[[2-(trifluoromethyl)-benzoyl]amino]-2,3-dihydro-1H-indene-5-carboxylic acid amide, N-[(1R)-6-[Methyl-(1-pyridin-4-yl-piperidin-4-yl)-carbamoyl]-2,3-dihydro-1H-inden-1-yl]-pyrimidine-5-carboxylic acid amide, (3R)-3-[(2-Chloro-6-fluoro-benzoyl)amino]-N-methyl-N-(1-pyridin-4-yl-piperidin-4-yl)-2,3-dihydro-1H-indene-5-carboxylic acid amide, (3R)-3-[[(2-Chlorophenyl)sulfonyl]amino]-N-methyl-N-(1-pyridin-4-yl-piperidin-4-yl)-2,3-dihydro-1H-indene-5-carboxylic acid amide, (1R)—N-Methyl-1-(3-methyl-butanoylamino)-N-(1-pyridin-4-yl-piperidin-4-yl)-2,3-dihydro-1H-indene-5-carboxylic acid amide, (3R)-3-[[2-(2-Chlorophenyl)-acetyl]amino]-N-methyl-N-(1-pyridin-4-yl-piperidin-4-yl)-2,3-dihydro-1H-indene-5-carboxylic acid amide, N-[(1R)-6-[Methyl-(1-pyridin-4-yl-piperidin-4-yl)-carbamoyl]-2,3-dihydro-1H-inden-1-yl]-4-(trifluoromethyl)-pyridine-3-carboxylic acid amide, N-[(1R)-6-[Methyl-(1-pyridin-4-yl-piperidin-4-yl)-carbamoyl]-2,3-dihydro-1H-inden-1-yl]-2-(trifluoromethyl)-pyridine-3-carboxylic acid amide, (3R)-3-[(2-Chloro-benzoyl)amino]-N-cyclopropyl-N-(1-pyridin-4-yl-piperidin-4-yl)-2,3-dihydro-1H-indene-5-carboxylic acid amide, (3R)-3-[(2-Chloro-benzoyl)amino]-N-methyl-N-(1-pyridin-4-yl-pyrrolidin-3-yl)-2,3-dihydro-1H-indene-5-carboxylic acid amide, (3R)-3-[(2-Chloro-benzoyl)amino]-N-methyl-N-[1-(1-methyl-piperidin-4-yl)-piperidin-4-yl]-2,3-dihydro-1H-indene-5-carboxylic acid amide, 2-Methoxy-N-[(1R)-6-[methyl-(1-pyridin-4-yl-piperidin-4-yl)-carbamoyl]-2,3-dihydro-1H-inden-1-yl]-pyridine-3-carboxylic acid amide, (1R)-1-(4-Chloro-3-oxo-1,2-dihydro-isoindol-2-yl)-N-[1-(1-methyl-piperidin-4-yl)-piperidin-4-yl]-2,3-dihydro-1H-indene-5-carboxylic acid amide, (1R)-1-(4-Chloro-3-oxo-1,2-dihydro-isoindol-2-yl)-N-methyl-N-[1-(2-pyridin-4-yl-ethyl)-piperidin-4-yl]-2,3-dihydro-1H-indene-5-carboxylic acid amide, (3R)-3-[[1-(2-Fluorophenyl)-cyclopropanecarbonyl]amino]-N-methyl-N-(1-pyridin-4-yl-piperidin-4-yl)-2,3-dihydro-1H-indene-5-carboxylic acid amide, (3R)-3-[[1-(2-Fluorophenyl)-cyclopentanecarbonyl]amino]-N-methyl-N-(1-pyridin-4-yl-piperidin-4-yl)-2,3-dihydro-1H-indene-5-carboxylic acid amide, (3R)-3-[(2-Chloro-benzoyl)amino]-N-methyl-N-[1-[(2-pyrrolidin-1-yl-pyridin-4-yl)-methyl]-piperidin-4-yl]-2,3-dihydro-1H-indene-5-carboxylic acid amide, (3R)-3-[(2-Chloro-benzoyl)amino]-N-methyl-N-[[1-(2-methyl-pyridin-4-yl)-piperidin-4-yl]-methyl]-2,3-dihydro-1H-indene-5-carboxylic acid amide, (3R)-3-[(2-Chloro-benzoyl)amino]-N-[1-(4-methoxyphenyl)-piperidin-4-yl]-N-methyl-2,3-dihydro-1H-indene-5-carboxylic acid amide, (3R)-3-[[1-(2-Chlorophenyl)-cyclopropanecarbonyl]amino]-N-methyl-N-(1-pyridin-4-yl-piperidin-4-yl)-2,3-dihydro-1H-indene-5-carboxylic acid amide, (1R)-1-(4-Chloro-3-oxo-1,2-dihydro-isoindol-2-yl)-N-methyl-N-[[1-(2-methyl-pyridin-4-yl)-piperidin-4-yl]-methyl]-2,3-dihydro-1H-indene-5-carboxylic acid amide, (1R)-1-(4-Chloro-3-oxo-1,2-dihydro-isoindol-2-yl)-N-methyl-N-[1-[(2-pyrrolidin-1-yl-pyridin-4-yl)-methyl]-piperidin-4-yl]-2,3-dihydro-1H-indene-5-carboxylic acid amide, (3R)-3-[(2-Chloro-benzoyl)amino]-N-[1-(4-chlorophenyl)-piperidin-4-yl]-N-methyl-2,3-dihydro-1H-indene-5-carboxylic acid amide, (3R)-3-[(2-Chloro-benzoyl)amino]-N-methyl-N-[1-(2-methyl-pyridin-4-yl)-piperidin-4-yl]-2,3-dihydro-1H-indene-5-carboxylic acid amide, (3R)-3-[(2-Chloro-benzoyl)amino]-N-methyl-N-[2-[1-(2-methyl-pyridin-4-yl)-piperidin-4-yl]-ethyl]-2,3-dihydro-1H-indene-5-carboxylic acid amide, (1R)-1-[(2-Chloro-benzoyl)amino]-6-fluoro-N-methyl-N-(1-pyridin-4-yl-piperidin-4-yl)-2,3-dihydro-1H-indene-5-carboxylic acid amide, (3R)-3-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide, (3R)-3-[(2-Chloro-benzoyl)amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-(3,3-dimethyl-1-pyridin-4-yl-piperidin-4-yl)-N-methyl-2,3-dihydro-1H-indene-5-carboxylic acid amide, (3R)-3-[(2-Chloro-benzoyl)amino]-N-methyl-N-(4-pyridin-4-yl-cyclohexyl)-2,3-dihydro-1H-indene-5-carboxylic acid amide, 5-Methyl-N-[(1R)-6-[methyl-(1-pyridin-4-yl-piperidin-4-yl)-carbamoyl]-2,3-dihydro-1H-inden-1-yl]-isoxazole-3-carboxylic acid amide, (3R)—N-Methyl-N-(1-pyridin-4-yl-piperidin-4-yl)-3-(3,3,3-trifluoro-propanoylamino)-2,3-dihydro-1H-indene-5-carboxylic acid amide, (3R)-3-[(2-Chloro-benzoyl)amino]-N-methyl-N-[(1-pyridin-4-yl-piperidin-4-yl)-methyl]-2,3-dihydro-1H-indene-5-carboxylic acid amide, (3R)-3-[(2-Chloro-benzoyl)-(2-methyl-propyl)-amino]-N-methyl-N-(1-pyridin-4-yl-piperidin-4-yl)-2,3-dihydro-1H-indene-5-carboxylic acid amide, (3R)-3-[(2-Chloro-benzoyl)amino]-N-methyl-N-[2-(1-pyridin-4-yl-piperidin-4-yl)-ethyl]-2,3-dihydro-1H-indene-5-carboxylic acid amide, (3R)-3-[(2-tert-Butyl-benzoyl)amino]-N-methyl-N-(1-pyridin-4-yl-piperidin-4-yl)-2,3-dihydro-1H-indene-5-carboxylic acid amide, (3R)—N-Methyl-3-[(2-methyl-propylsulfonyl)amino]-N-(1-pyridin-4-yl-piperidin-4-yl)-2,3-dihydro-1H-indene-5-carboxylic acid amide, (1S)—N-[(1R)-6-[Methyl-(1-pyridin-4-yl-piperidin-4-yl)-carbamoyl]-2,3-dihydro-1H-inden-1-yl]-1,2,3,4-tetrahydro-naphthalene-1-carboxylic acid amide, N-[(1R)-6-[Methyl-(1-pyridin-4-yl-piperidin-4-yl)-carbamoyl]-2,3-dihydro-1H-inden-1-yl]-1,2,3,4-tetrahydro-naphthalene-1-carboxylic acid amide, (3R)-3-Benzoylamino-N-methyl-N-(1-pyridin-4-yl-piperidin-4-yl)-2,3-dihydro-1H-indene-5-carboxylic acid amide, (3R)-3-[[(4-Fluorophenyl)sulfonyl]amino]-N-methyl-N-(1-pyridin-4-yl-piperidin-4-yl)-2,3-dihydro-1H-indene-5-carboxylic acid amide, N-[(1R)-6-[Methyl-(1-pyridin-4-yl-piperidin-4-yl)-carbamoyl]-2,3-dihydro-1H-inden-1-yl]-naphthalene-1-carboxylic acid amide, (3R)-3-(Benzenesulfonamido)-N-methyl-N-(1-pyridin-4-yl-piperidin-4-yl)-2,3-dihydro-1H-indene-5-carboxylic acid amide, (3R)-3-[(4-Fluoro-benzoyl)amino]-N-methyl-N-(1-pyridin-4-yl-piperidin-4-yl)-2,3-dihydro-1H-indene-5-carboxylic acid amide, N-[(1R)-6-[Methyl-(1-pyridin-4-yl-piperidin-4-yl)-carbamoyl]-2,3-dihydro-1H-inden-1-yl]-tetrahydro-pyran-4-carboxylic acid amide, (3R)-3-[(2-Chloro-benzoyl)amino]-N-ethyl-N-(1-pyridin-4-yl-piperidin-4-yl)-2,3-dihydro-1H-indene-5-carboxylic acid amide, (3R)-3-[(2-Chloro-benzoyl)amino]-N-[1-(4-fluorophenyl)-piperidin-4-yl]-N-methyl-2,3-dihydro-1H-indene-5-carboxylic acid amide, (3R)-3-[(2-Chloro-benzoyl)amino]-N-ethyl-N-[1-(2-methyl-pyridin-4-yl)-piperidin-4-yl]-2,3-dihydro-1H-indene-5-carboxylic acid amide, (3R)-3-(2,3-Dihydro-1H-indene-1-carbonylamino)-N-methyl-N-(1-pyridin-4-yl-piperidin-4-yl)-2,3-dihydro-1H-indene-5-carboxylic acid amide, N-[(1R)-6-[Methyl-(1-pyridin-4-yl-piperidin-4-yl)-carbamoyl]-2,3-dihydro-1H-inden-1-yl]-isoquinoline-4-carboxylic acid amide, N-[(1R)-6-[Methyl-(1-pyridin-4-yl-piperidin-4-yl)-carbamoyl]-2,3-dihydro-1H-inden-1-yl]-3,4-dihydro-2H-chromene-4-carboxylic acid amide, (3R)—N-Methyl-3-(3-methyl-butanoylamino)-N-[1-(2-methyl-pyridin-4-yl)-piperidin-4-yl]-2,3-dihydro-1H-indene-5-carboxylic acid amide, (3R)—N-[1-(2,6-Dimethyl-pyrimidin-4-yl)-piperidin-4-yl]-N-methyl-3-(3-methyl-butanoylamino)-2,3-dihydro-1H-indene-5-carboxylic acid amide, N-[(1R)-6-[Methyl-[1-(2-methyl-pyridin-4-yl)-piperidin-4-yl]-carbamoyl]-2,3-dihydro-1H-inden-1-yl]-tetrahydro-pyran-4-carboxylic acid amide, N-[(1R)-6-[[1-(2,6-Dimethyl-pyrimidin-4-yl)-piperidin-4-yl]-methyl-carbamoyl]-2,3-dihydro-1H-inden-1-yl]-tetrahydro-pyran-4-carboxylic acid amide, (3R)-3-[(2-Chloro-benzoyl)amino]-N-methyl-N-[1-(3-piperidin-1-yl-propanoyl)-piperidin-4-yl]-2,3-dihydro-1H-indene-5-carboxylic acid amide, N-[(1R)-6-[[1-(2,6-Dimethyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, N-[(1R)-6-[Methyl-[1-(2-methyl-pyridin-4-yl)-piperidin-4-yl]-carbamoyl]-2,3-dihydro-1H-inden-1-yl]-2-(trifluoromethyl)-pyridine-3-carboxylic acid amide, (3R)-3-(3-Cyclopentyl-propanoylamino)-N-methyl-N-[1-(2-methyl-pyridin-4-yl)-piperidin-4-yl]-2,3-dihydro-1H-indene-5-carboxylic acid amide, (3R)-3-(3-Cyclopentyl-propanoylamino)-N-[1-(2,6-dimethyl-pyrimidin-4-yl)-piperidin-4-yl]-N-methyl-2,3-dihydro-1H-indene-5-carboxylic acid amide, 5-Methyl-N-[(1R)-6-[methyl-[1-(2-methyl-pyridin-4-yl)-piperidin-4-yl]-carbamoyl]-2,3-dihydro-1H-inden-1-yl]-isoxazole-3-carboxylic acid amide, N-[(1R)-6-[[1-(2,6-Dimethyl-pyrimidin-4-yl)-piperidin-4-yl]-methyl-carbamoyl]-2,3-dihydro-1H-inden-1-yl]-5-methyl-isoxazole-3-carboxylic acid amide, (3R)-3-[(2-Chloro-benzoyl)amino]-N-methyl-N-[1-(1-oxido-pyridin-1-ium-4-yl)-piperidin-4-yl]-2,3-dihydro-1H-indene-5-carboxylic acid amide, (3R)-3-[(2-Chloro-benzoyl)amino]-N-methyl-N-[4-(1,2,3,4-tetrahydro-[2,6]naphthyridin-2-yl)-cyclohexyl]-2,3-dihydro-1H-indene-5-carboxylic acid amide, (3R)-3-[(2-Chloro-benzoyl)amino]-N-[1-(2-dimethylamino-pyridin-4-yl)-piperidin-4-yl]-N-methyl-2,3-dihydro-1H-indene-5-carboxylic acid amide, (3R)-3-[(2-Chloro-benzoyl)amino]-N-[1-(6-methoxy-pyridin-3-yl)-piperidin-4-yl]-N-methyl-2,3-dihydro-1H-indene-5-carboxylic acid amide, (3R)-3-[(2-Chloro-benzoyl)amino]-N-[4-(2-dimethylamino-5,6,7,8-tetrahydro-pyrido[4,3-d]pyrimidin-6-yl)-cyclohexyl]-N-methyl-2,3-dihydro-1H-indene-5-carboxylic acid amide, (3R)-3-[(2-Chloro-benzoyl)amino]-N-methyl-N-[(1S,3R)-3-(4-methyl-piperazin-1-yl)-cyclohexyl]-2,3-dihydro-1H-indene-5-carboxylic acid amide, (3R)-3-[[(2-Chlorophenyl)sulfonyl]amino]-N-methyl-N-[(1S,3R)-3-(4-methyl-piperazin-1-yl)-cyclohexyl]-2,3-dihydro-1H-indene-5-carboxylic acid amide, 3-[tert-Butyl-(2-chloro-benzoyl)-amino]-N-methyl-N-(1-pyridin-4-yl-piperidin-4-yl)-2,3-dihydro-1H-indene-5-carboxylic acid amide, (1R)-1-(4-Chloro-3-oxo-1,2-dihydro-isoindol-2-yl)-N-methyl-N-[(1S,3R)-3-(4-methyl-piperazin-1-yl)-cyclohexyl]-2,3-dihydro-1H-indene-5-carboxylic acid amide, (3R)-3-[(2-Chloro-benzoyl)amino]-N-[1-(2-methoxy-pyridin-4-yl)-piperidin-4-yl]-N-methyl-2,3-dihydro-1H-indene-5-carboxylic acid amide, (3R)-3-[(2-Chloro-benzoyl)amino]-N-[1-(6-dimethylamino-pyridin-3-yl)-piperidin-4-yl]-N-methyl-2,3-dihydro-1H-indene-5-carboxylic acid amide, (3R)-3-[(2-Chloro-benzoyl)amino]-N-methyl-N-(4-pyridin-4-yloxy-cyclohexyl)-2,3-dihydro-1H-indene-5-carboxylic acid amide, (3R)-3-[(2-Chloro-benzoyl)amino]-N-methyl-N-(1-pyridin-4-yl-piperidin-3-yl)-2,3-dihydro-1H-indene-5-carboxylic acid amide, (3R)-3-[(2-Chloro-benzoyl)amino]-N-methyl-N-(1-pyridin-4-yl-azepan-4-yl)-2,3-dihydro-1H-indene-5-carboxylic acid amide, (3R)-3-[(2-Chloro-benzoyl)amino]-N-[1-(3-fluoro-pyridin-4-yl)-piperidin-4-yl]-N-methyl-2,3-dihydro-1H-indene-5-carboxylic acid amide, (3R)-3-[(2-Chloro-benzoyl)amino]-N-[1-(2-dimethylamino-pyrimidin-4-yl)-piperidin-4-yl]-N-methyl-2,3-dihydro-1H-indene-5-carboxylic acid amide, (3R)—N-[1-(2-Dimethylamino-pyridin-4-yl)-piperidin-4-yl]-3-[isopropyl-(3-methyl-butanoyl)-amino]-N-methyl-2,3-dihydro-1H-indene-5-carboxylic acid amide, (3R)—N-[1-(2-Dimethylamino-pyrimidin-4-yl)-piperidin-4-yl]-3-[isopropyl-(3-methyl-butanoyl)-amino]-N-methyl-2,3-dihydro-1H-indene-5-carboxylic acid amide, (3R)-3-[(2-Chloro-benzoyl)amino]-N-methyl-N-[1-(2-methyl-pyrimidin-4-yl)-piperidin-4-yl]-2,3-dihydro-1H-indene-5-carboxylic acid amide, (3R)-3-[(2-Chloro-benzoyl)amino]-N-[1-(2-cyano-pyridin-4-yl)-piperidin-4-yl]-N-methyl-2,3-dihydro-1H-indene-5-carboxylic acid amide, (3R)-3-[(2-Chloro-benzoyl)amino]-N-methyl-N-[1-(2-pyrrolidin-1-yl-pyridin-4-yl)-piperidin-4-yl]-2,3-dihydro-1H-indene-5-carboxylic acid amide, (3R)-3-[(2-Chloro-benzoyl)amino]-N-methyl-N-[1-(3-methyl-[1,2,4]thiadiazol-5-yl)-piperidin-4-yl]-2,3-dihydro-1H-indene-5-carboxylic acid amide, (3R)-3-[(2-Chloro-benzoyl)amino]-N-[1-(2-methoxy-6-methyl-pyrimidin-4-yl)-piperidin-4-yl]-N-methyl-2,3-dihydro-1H-indene-5-carboxylic acid amide, (3R)-3-[(2-Chloro-benzoyl)amino]-N-methyl-N-(1-quinazolin-4-yl-piperidin-4-yl)-2,3-dihydro-1H-indene-5-carboxylic acid amide, (3R)—N-[1-(2,6-Dimethyl-pyrimidin-4-yl)-piperidin-4-yl]-3-[(2-fluoro-benzoyl)amino]-N-methyl-2,3-dihydro-1H-indene-5-carboxylic acid amide, (3R)-3-[(2-Chloro-3-fluoro-benzoyl)amino]-N-[1-(2,6-dimethyl-pyrimidin-4-yl)-piperidin-4-yl]-N-methyl-2,3-dihydro-1H-indene-5-carboxylic acid amide, (3R)-3-(4-Chloro-3-oxo-1,2-dihydro-isoindol-2-yl)-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-[1-[(4-methoxy-3,5-dimethyl-pyridin-2-yl)-methyl]-piperidin-4-yl]-N-methyl-2,3-dihydro-1H-indene-5-carboxylic acid amide, (3R)—N-[1-(2,6-Dimethyl-pyrimidin-4-yl)-piperidin-4-yl]-N-methyl-3-[[2-(trifluoromethyl)-benzoyl]amino]-2,3-dihydro-1H-indene-5-carboxylic acid amide, (3R)-3-[(2-Chloro-5-fluoro-benzoyl)amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-methyl-N-[1-[(3-methyl-isoxazol-5-yl)-methyl]-piperidin-4-yl]-2,3-dihydro-1H-indene-5-carboxylic acid amide, (3R)-3-[[2-Chloro-3-(trifluoromethyl)-benzoyl]amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-methyl-N-[(1-pyrimidin-4-yl-piperidin-4-yl)-methyl]-2,3-dihydro-1H-indene-5-carboxylic acid amide, (3R)-3-[[2-Chloro-5-(trifluoromethyl)-benzoyl]amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-methyl-N-[1-[2-(4-methyl-piperazin-1-yl)-2-oxo-ethyl]-piperidin-4-yl]-2,3-dihydro-1H-indene-5-carboxylic acid amide, (3R)-3-[(2-Chloro-benzoyl)amino]-N-[1-(2-isopropyl-6-methyl-pyrimidin-4-yl)-piperidin-4-yl]-N-methyl-2,3-dihydro-1H-indene-5-carboxylic acid amide, (3R)-3-[(2-Chloro-benzoyl)amino]-N-methyl-N-[1-(2-oxo-2-pyrrolidin-1-yl-ethyl)-piperidin-4-yl]-2,3-dihydro-1H-indene-5-carboxylic acid amide, (3R)-3-[(2-Chloro-benzoyl)amino]-N-methyl-N-[1-(6-methyl-pyrimidin-4-yl)-piperidin-4-yl]-2,3-dihydro-1H-indene-5-carboxylic acid amide, (1R)-1-(4-Chloro-3-oxo-1,2-dihydro-isoindol-2-yl)-N-[1-(2,6-dimethyl-pyrimidin-4-yl)-piperidin-4-yl]-6-fluoro-N-methyl-2,3-dihydro-1H-indene-5-carboxylic acid amide, N-[(1R)-5-[[1-(2,6-Dimethyl-pyrimidin-4-yl)-piperidin-4-yl]-methyl-carbamoyl]-6-fluoro-2,3-dihydro-1H-inden-1-yl]-5-methyl-isoxazole-3-carboxylic acid amide, (3R)-3-[(2-Chloro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-methyl-N-(1-pyridin-4-yl-azetidin-3-yl)-2,3-dihydro-1H-indene-5-carboxylic acid amide, (3R)-3-[(2-Chloro-benzoyl)amino]-N-methyl-N-(1-pyrimidin-4-yl-piperidin-4-yl)-2,3-dihydro-1H-indene-5-carboxylic acid amide, (3R)-3-[(2-Chloro-benzoyl)-methyl-amino]-N-methyl-N-(1-pyrimidin-4-yl-piperidin-4-yl)-2,3-dihydro-1H-indene-5-carboxylic acid amide, (3R)-3-[(2-Chloro-benzoyl)-methyl-amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)-isopropyl-amino]-N-methyl-N-(1-pyridin-4-yl-piperidin-4-yl)-2,3-dihydro-1H-indene-5-carboxylic acid amide, (1R)-1-[(2-Chloro-benzoyl)amino]-N-[1-(2,6-dimethyl-pyrimidin-4-yl)-piperidin-4-yl]-6-fluoro-N-methyl-2,3-dihydro-1H-indene-5-carboxylic acid amide, (1R)-1-[(2-Chloro-benzoyl)amino]-6-fluoro-N-methyl-N-[1-(6-methyl-pyrimidin-4-yl)-piperidin-4-yl]-2,3-dihydro-1H-indene-5-carboxylic acid amide, (3R)-3-[(2-Chloro-benzoyl)-methyl-amino]-N-methyl-N-(1-pyridin-4-yl-piperidin-4-yl)-2,3-dihydro-1H-indene-5-carboxylic acid amide, (3R)-3-[(2-Chloro-benzoyl)-isopropyl-amino]-6-fluoro-N-methyl-N-(1-pyridin-4-yl-piperidin-4-yl)-2,3-dihydro-1H-indene-5-carboxylic acid amide, (3R)-3-[(2-Chloro-benzoyl)amino]-N-ethyl-N-[1-(7H-purin-6-yl)-piperidin-4-yl]-2,3-dihydro-1H-indene-5-carboxylic acid amide, (1R)-1-[(2-Chloro-benzoyl)-isopropyl-amino]-6-fluoro-N-methyl-N-(1-pyridin-4-yl-piperidin-4-yl)-2,3-dihydro-1H-indene-5-carboxylic acid amide, (3R)-3-[(2-Chloro-benzoyl)amino]-N-methyl-N-[1-(2-methyl-pyridin-4-yl)-azetidin-3-yl]-2,3-dihydro-1H-indene-5-carboxylic acid amide, (3R)-3-(4-Chloro-3-oxo-1,2-dihydro-isoindol-2-yl)-N-methyl-N-[1-(2-methyl-pyridin-4-yl)-azetidin-3-yl]-2,3-dihydro-1H-indene-5-carboxylic acid amide, (3R)—N-[1-(2,6-Dimethyl-pyrimidin-4-yl)-piperidin-4-yl]-N-methyl-3-[(2-methyl-benzoyl)amino]-2,3-dihydro-1H-indene-5-carboxylic acid amide, (3R)-3-[(2-Chloro-6-fluoro-benzoyl)amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-3-fluoro-benzoyl)amino]-N-methyl-N-(1-pyrimidin-4-yl-piperidin-4-yl)-2,3-dihydro-1H-indene-5-carboxylic acid amide,
(3R)-3-[(2-Chloro-4-fluoro-benzoyl)amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-benzoyl)-isopropyl-amino]-N-[1-(2-isopropyl-6-methyl-pyrimidin-4-yl)-piperidin-4-yl]-N-methyl-2,3-dihydro-1H-indene-5-carboxylic acid amide,
(3R)-3-[(2-Chloro-4-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-4-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide,
(3R)—N-[1-(2,6-Dimethyl-pyrimidin-4-yl)-piperidin-4-yl]-N-methyl-3-[methyl-(2-methyl-benzoyl)-amino]-2,3-dihydro-1H-indene-5-carboxylic acid amide,
(3R)—N-[1-(2,6-Dimethyl-pyrimidin-4-yl)-piperidin-4-yl]-3-[ethyl-(2-methyl-benzoyl)-amino]-N-methyl-2,3-dihydro-1H-indene-5-carboxylic acid amide,
N-[(1R)-6-[[1-(2,6-Dimethyl-pyrimidin-4-yl)-piperidin-4-yl]-methyl-carbamoyl]-2,3-dihydro-1H-inden-1-yl]-N-methyl-2-(trifluoromethyl)-pyridine-3-carboxylic acid amide,
(3R)—N-[1-(2,6-Dimethyl-pyrimidin-4-yl)-piperidin-4-yl]-3-[isopropyl-(2-methyl-benzoyl)-amino]-N-methyl-2,3-dihydro-1H-indene-5-carboxylic acid amide,
N-[(1R)-6-[[1-(2,6-Dimethyl-pyrimidin-4-yl)-piperidin-4-yl]-methyl-carbamoyl]-2,3-dihydro-1H-inden-1-yl]-N-ethyl-2-(trifluoromethyl)-pyridine-3-carboxylic acid amide,
(3R)-3-[(2-Chloro-6-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-6-fluoro-benzoyl)-ethyl-amino]-N-[4-(2,6-dimethyl-pyrimidin-4-yl)-cyclohexyl]-N-methyl-2,3-dihydro-1H-indene-5-carboxylic acid amide,
(3R)-3-[(2-Chloro-benzoyl)amino]-N-isopropyl-N-(1-pyridin-4-yl-piperidin-4-yl)-2,3-dihydro-1H-indene-5-carboxylic acid amide,
(3R)-3-[(2-Fluoro-2-methyl-propanoyl)amino]-N-methyl-N-[1-(2-methyl-pyridin-4-yl)-piperidin-4-yl]-2,3-dihydro-1H-indene-5-carboxylic acid amide,
(3R)-3-[(2-Chloro-benzoyl)amino]-N-methyl-N-[1-(1-methyl-1H-imidazol-2-yl)-piperidin-4-yl]-2,3-dihydro-1H-indene-5-carboxylic acid amide,
(3R)-3-[(2-Chloro-benzoyl)amino]-N-methyl-N-[1-(6-methyl-pyrazin-2-yl)-piperidin-4-yl]-2,3-dihydro-1H-indene-5-carboxylic acid amide,
(3R)-3-[(2-Chloro-benzoyl)amino]-N-methyl-N-(2-oxo-1-pyridin-4-yl-piperidin-4-yl)-2,3-dihydro-1H-indene-5-carboxylic acid amide,
(3R)-3-[(2-Chloro-benzoyl)amino]-N-methyl-N-[1-[3-(trifluoromethyl)-pyridin-4-yl]-piperidin-4-yl]-2,3-dihydro-1H-indene-5-carboxylic acid amide,
(3R)-3-[(2-Chloro-benzoyl)amino]-N-[4-(2-dimethylamino-pyridin-4-yl)-cyclohexyl]-N-methyl-2,3-dihydro-1H-indene-5-carboxylic acid amide,
(3R)-3-(3-Cyclopentyl-propanoyl-methyl-amino)-N-[1-(2-dimethylamino-pyridin-4-yl)-piperidin-4-yl]-N-methyl-2,3-dihydro-1H-indene-5-carboxylic acid amide,
(3R)-3-(3-Cyclopentyl-propanoyl-methyl-amino)-N-[1-(2-dimethylamino-pyridin-4-yl)-piperidin-4-yl]-N-methyl-2,3-dihydro-1H-indene-5-carboxylic acid amide,
(3R)-3-(3-Cyclopentyl-propanoyl-methyl-amino)-N-[1-(3-fluoro-pyridin-4-yl)-piperidin-4-yl]-N-methyl-2,3-dihydro-1H-indene-5-carboxylic acid amide,
(3R)—N-[1-(2,6-Dimethyl-pyrimidin-4-yl)-piperidin-4-yl]-N-methyl-3-[(2-methyl-propylsulfonyl)amino]-2,3-dihydro-1H-indene-5-carboxylic acid amide,
(3R)-3-[(2-Chloro-3-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-3-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-3-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-4-fluoro-benzoyl)-isopropyl-amino]-N-[1-(2,6-dimethyl-pyrimidin-4-yl)-piperidin-4-yl]-6-fluoro-N-methyl-2,3-dihydro-1H-indene-5-carboxylic acid amide,
(3R)-3-[(2-Chloro-4-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-3-fluoro-benzoyl)-isopropyl-amino]-N-methyl-N-(1-pyridin-4-yl-piperidin-4-yl)-2,3-dihydro-1H-indene-5-carboxylic acid amide,
(3R)-3-[(2-Chloro-3-fluoro-benzoyl)-ethyl-amino]-N-methyl-N-(1-pyridin-4-yl-piperidin-4-yl)-2,3-dihydro-1H-indene-5-carboxylic acid amide,
(3R)-3-[(2-Chloro-4-fluoro-benzoyl)-isopropyl-amino]-N-methyl-N-(1-pyridin-4-yl-piperidin-4-yl)-2,3-dihydro-1H-indene-5-carboxylic acid amide,
(3R)-3-[(2-Chloro-3-fluoro-benzoyl)-methyl-amino]-N-methyl-N-(1-pyridin-4-yl-piperidin-4-yl)-2,3-dihydro-1H-indene-5-carboxylic acid amide,
(3R)-3-[(2-Chloro-4-fluoro-benzoyl)-isopropyl-amino]-6-fluoro-N-methyl-N-(1-pyridin-4-yl-piperidin-4-yl)-2,3-dihydro-1H-indene-5-carboxylic acid amide,
N-[(1R)-6-[[1-(2,6-Dimethyl-pyrimidin-4-yl)-piperidin-4-yl]-methyl-carbamoyl]-2,3-dihydro-1H-inden-1-yl]-N-isopropyl-2-(trifluoromethyl)-pyridine-3-carboxylic acid amide,
N-Isopropyl-N-[(1R)-6-[methyl-(1-pyridin-4-yl-piperidin-4-yl)-carbamoyl]-2,3-dihydro-1H-inden-1-yl]-2-(trifluoromethyl)-pyridine-3-carboxylic acid amide,
N-[(1R)-6-[[1-(2,6-Dimethyl-pyrimidin-4-yl)-piperidin-4-yl]-methyl-carbamoyl]-5-fluoro-2,3-dihydro-1H-inden-1-yl]-N-isopropyl-2-(trifluoromethyl)-pyridine-3-carboxylic acid amide,
(3R)-3-[(2-Chloro-5-fluoro-benzoyl)-methyl-amino]-N-[1-(2,6-dimethyl-pyrimidin-4-yl)-piperidin-4-yl]-N-methyl-2,3-dihydro-1H-indene-5-carboxylic acid amide,
(3R)-3-[(2-Chloro-5-fluoro-benzoyl)-ethyl-amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-5-fluoro-benzoyl)-isopropyl-amino]-N-[1-(2,6-dimethyl-pyrimidin-4-yl)-piperidin-4-yl]-N-methyl-2,3-dihydro-1H-indene-5-carboxylic acid amide, (3R)-3-[(2-Chloro-benzoyl)amino]-N-[1-(2,6-dimethyl-pyrimidin-4-yl)-piperidin-4-yl]-6-fluoro-N-methyl-2,3-dihydro-1H-indene-5-carboxylic acid amide, (3R)-3-[(2-Chloro-benzoyl)amino]-N-methyl-N-[1-(2-methylamino-pyrimidin-4-yl)-piperidin-4-yl]-2,3-dihydro-1H-indene-5-carboxylic acid amide, (3R)-3-[(2-Chloro-benzoyl)amino]-N-[2-[1-(2,6-dimethyl-pyrimidin-4-yl)-piperidin-4-yl]-ethyl]-2,3-dihydro-1H-indene-5-carboxylic acid amide, (3R)-3-[(2-Chloro-benzoyl)amino]-N-[1-(2,6-dimethyl-pyrimidin-4-yl)-piperidin-4-yl]-N-ethyl-2,3-dihydro-1H-indene-5-carboxylic acid amide, (3R)-3-[(2-Chloro-benzoyl)amino]-N-[1-(2,6-dimethyl-pyrimidin-4-yl)-piperidin-4-yl]-7-fluoro-N-methyl-2,3-dihydro-1H-indene-5-carboxylic acid amide, (3R)-3-[(2-Chloro-benzoyl)amino]-N-methyl-N-[1-(2-oxo-1H-pyridin-4-yl)-piperidin-4-yl]-2,3-dihydro-1H-indene-5-carboxylic acid amide, (3R)-3-[(2-Chloro-6-fluoro-benzoyl)-ethyl-amino]-N-methyl-N-(1-pyridin-4-yl-piperidin-4-yl)-2,3-dihydro-1H-indene-5-carboxylic acid amide, (3R)-3-[(2-Chloro-5-fluoro-benzoyl)-ethyl-amino]-N-methyl-N-(1-pyridin-4-yl-piperidin-4-yl)-2,3-dihydro-1H-indene-5-carboxylic acid amide, (3R)-3-(3,4-Dimethyl-pentanoylamino)-N-methyl-N-[1-(2-methyl-pyridin-4-yl)-piperidin-4-yl]-2,3-dihydro-1H-indene-5-carboxylic acid amide, (3R)-3-(3,4-Dimethyl-pentanoylamino)-N-[1-(2,6-dimethyl-pyrimidin-4-yl)-piperidin-4-yl]-N-methyl-2,3-dihydro-1H-indene-5-carboxylic acid amide, N-[(1R)-6-[[1-(2,6-Dimethyl-pyrimidin-4-yl)-piperidin-4-yl]-methyl-carbamoyl]-2,3-dihydro-1H-inden-1-yl]-3-methoxy-isoxazole-5-carboxylic acid amide, 3-Methoxy-N-[(1R)-6-[methyl-[1-(2-methyl-pyridin-4-yl)-piperidin-4-yl]-carbamoyl]-2,3-dihydro-1H-inden-1-yl]-isoxazole-5-carboxylic acid amide, (3R)-3-(Cyclopentanecarbonylamino)-N-[1-(2,6-dimethyl-pyrimidin-4-yl)-piperidin-4-yl]-N-methyl-2,3-dihydro-1H-indene-5-carboxylic acid amide, (3R)-3-(Cyclopentanecarbonylamino)-N-methyl-N-[1-(2-methyl-pyridin-4-yl)-piperidin-4-yl]-2,3-dihydro-1H-indene-5-carboxylic acid amide, (3R)-3-(Cyclopentanecarbonylamino)-N-[1-(2-dimethylamino-pyrimidin-4-yl)-piperidin-4-yl]-N-methyl-2,3-dihydro-1H-indene-5-carboxylic acid amide, (3R)-3-(Cyclopentanecarbonyl-ethyl-amino)-N-[1-(2,6-dimethyl-pyrimidin-4-yl)-piperidin-4-yl]-N-methyl-2,3-dihydro-1H-indene-5-carboxylic acid amide, (3R)-3-(Cyclopentanecarbonyl-methyl-amino)-N-[1-(2,6-dimethyl-pyrimidin-4-yl)-piperidin-4-yl]-N-methyl-2,3-dihydro-1H-indene-5-carboxylic acid amide, (3R)-3-[(2-Cyclopentyl-acetyl)-methyl-amino]-N-[1-(2,6-dimethyl-pyrimidin-4-yl)-piperidin-4-yl]-N-methyl-2,3-dihydro-1H-indene-5-carboxylic acid amide, (3R)-3-(3,4-Dimethyl-pentanoyl-methyl-amino)-N-[1-(2,6-dimethyl-pyrimidin-4-yl)-piperidin-4-yl]-N-methyl-2,3-dihydro-1H-indene-5-carboxylic acid amide, (3R)-3-(3,4-Dimethyl-pentanoyl-ethyl-amino)-N-[1-(2,6-dimethyl-pyrimidin-4-yl)-piperidin-4-yl]-N-methyl-2,3-dihydro-1H-indene-5-carboxylic acid amide, (8R)-8-[(2-Chloro-benzoyl)amino]-N-[1-(2,6-dimethyl-pyrimidin-4-yl)-piperidin-4-yl]-N-methyl-5,6,7,8-tetrahydro-naphthalene-2-carboxylic acid amide, (8R)-8-(4-Chloro-3-oxo-1,2-dihydro-isoindol-2-yl)-N-[1-(2,6-dimethyl-pyrimidin-4-yl)-piperidin-4-yl]-N-methyl-5,6,7,8-tetrahydro-naphthalene-2-carboxylic acid amide, (8R)-8-[(2-Chloro-benzoyl)amino]-N-[1-(2-dimethylamino-pyrimidin-4-yl)-piperidin-4-yl]-N-methyl-5,6,7,8-tetrahydro-naphthalene-2-carboxylic acid amide, (8R)-8-[(2-Chloro-benzoyl)amino]-N-[1-(2-dimethylamino-6-methyl-pyrimidin-4-yl)-piperidin-4-yl]-N-methyl-5,6,7,8-tetrahydro-naphthalene-2-carboxylic acid amide, (3R)-3-[(2-Cyclopentyl-acetyl)amino]-N-[1-(2,6-dimethyl-pyrimidin-4-yl)-piperidin-4-yl]-N-methyl-2,3-dihydro-1H-indene-5-carboxylic acid amide, N-[(1R)-6-[[1-(2-Dimethylamino-pyrimidin-4-yl)-piperidin-4-yl]-methyl-carbamoyl]-2,3-dihydro-1H-inden-1-yl]-3-methoxy-isoxazole-5-carboxylic acid amide, (8R)—N-[1-(2,6-Dimethyl-pyrimidin-4-yl)-piperidin-4-yl]-N-methyl-8-(3-methyl-butanoylamino)-5,6,7,8-tetrahydro-naphthalene-2-carboxylic acid amide, (3R)-3-[(2-Chloro-benzoyl)amino]-N-methyl-N-[1-(2-pyrrolidin-1-yl-pyrimidin-4-yl)-piperidin-4-yl]-2,3-dihydro-1H-indene-5-carboxylic acid amide, (8R)-8-[(2-Chloro-benzoyl)amino]-N-methyl-N-(1-pyridin-4-yl-piperidin-4-yl)-5,6,7,8-tetrahydro-naphthalene-2-carboxylic acid amide, (3R)-3-[(2-Chloro-benzoyl)amino]-N-[1-(2-dimethylamino-6-methyl-pyrimidin-4-yl)-piperidin-4-yl]-N-methyl-2,3-dihydro-1H-indene-5-carboxylic acid amide, (3R)—N-[1-(2-Amino-pyrimidin-4-yl)-piperidin-4-yl]-3-[(2-chloro-benzoyl)amino]-N-methyl-2,3-dihydro-1H-indene-5-carboxylic acid amide, 3-Chloro-N-[6-[2-(1-pyridin-4-yl-piperidin-4-yl)-ethyl-carbamoyl]-2,3-dihydro-1H-inden-1-yl]-thiophene-2-carboxylic acid amide, 3-[[(2-Chlorophenyl)-methyl-carbamoyl]amino]-N-[2-(1-pyridin-4-yl-piperidin-4-yl)-ethyl]-2,3-dihydro-1H-indene-5-carboxylic acid amide, 8-[(2,3-Dichloro-benzoyl)amino]-N-methyl-N-(1-pyridin-4-yl-piperidin-4-yl)-5,6,7,8-tetrahydro-naphthalene-2-carboxylic acid amide, 8-[(2-Chloro-5-fluoro-benzoyl)amino]-N-methyl-N-(1-pyridin-4-yl-piperidin-4-yl)-5,6,7,8-tetrahydro-naphthalene-2-carboxylic acid amide, 8-(Cyclohexanecarbonylamino)-N-methyl-N-(1-pyridin-4-yl-piperidin-4-yl)-5,6,7,8-tetrahydro-naphthalene-2-carboxylic acid amide, 8-(3-Cyclopentyl-propanoylamino)-N-methyl-N-(1-pyridin-4-yl-piperidin-4-yl)-5,6,7,8-tetrahydro-naphthalene-2-carboxylic acid amide, 3-Chloro-N-[7-[methyl-(1-pyridin-4-yl-piperidin-4-yl)-carbamoyl]-1,2,3,4-tetrahydro-naphthalen-1-yl]-thiophene-2-carboxylic acid amide, N-[7-[Methyl-(1-pyridin-4-yl-piperidin-4-yl)-carbamoyl]-1,2,3,4-tetrahydro-naphthalen-1-yl]-pyrimidine-5-carboxylic acid amide, 8-[(2,6-Dimethyl-benzoyl)amino]-N-methyl-N-(1-pyridin-4-yl-piperidin-4-yl)-5,6,7,8-tetrahydro-naphthalene-2-carboxylic acid amide, N-[7-[Methyl-(1-pyridin-4-yl-piperidin-4-yl)-carbamoyl]-1,2,3,4-tetrahydro-naphthalen-1-yl]-4-(trifluoromethyl)-pyridine-3-carboxylic acid amide, 8-[[2-Chloro-6-(trifluoromethyl)-benzoyl]amino]-N-methyl-N-(1-pyridin-4-yl-piperidin-4-yl)-5,6,7,8-tetrahydro-naphthalene-2-carboxylic acid amide, N-[3,3-Dimethyl-6-[methyl-(1-pyridin-4-yl-piperidin-4-yl)-carbamoyl]-1,2-dihydro-inden-1-yl]-4-(trifluoromethyl)-pyridine-3-carboxylic acid amide, 3-Chloro-N-[5-[methyl-(1-pyridin-4-yl-piperidin-4-yl)-carbamoyl]-2,3-dihydro-1H-inden-1-yl]-thiophene-2-carboxylic acid amide, 3-(Cyclohexanecarbonylamino)-N,1,1-trimethyl-N-(1-pyridin-4-yl-piperidin-4-yl)-2,3-dihydro-indene-5-carboxylic acid amide, 3-[[(2-Chlorophenyl)-methyl-carbamoyl]amino]-N,1,1-trimethyl-N-(1-pyridin-4-yl-piperidin-4-yl)-2,3-dihydro-indene-5-carboxylic acid amide, 8-[[[2-Chloro-6-(trifluoromethyl)-phenyl]sulfonyl]amino]-N-methyl-N-(1-pyridin-4-yl-piperidin-4-yl)-5,6,7,8-tetrahydro-naphthalene-2-carboxylic acid amide, 3-[[2-Chloro-6-(trifluoromethyl)-benzoyl]amino]-N,1,1-trimethyl-N-(1-pyridin-4-yl-piperidin-4-yl)-2,3-dihydro-indene-5-carboxylic acid amide, 3-(3-Cyclopentyl-propanoylamino)-N,1,1-trimethyl-N-(1-pyridin-4-yl-piperidin-4-yl)-2,3-dihydro-indene-5-carboxylic acid amide, 3-[(2,3-Dichloro-benzoyl)amino]-N,1,1-trimethyl-N-(1-pyridin-4-yl-piperidin-4-yl)-2,3-dihydro-indene-5-carboxylic acid amide, 3-Chloro-N-[3,3-dimethyl-6-[methyl-(1-pyridin-4-yl-piperidin-4-yl)-carbamoyl]-1,2-dihydro-inden-1-yl]-thiophene-2-carboxylic acid amide, 3-[(2-Chloro-5-fluoro-benzoyl)amino]-N,1,1-trimethyl-N-(1-pyridin-4-yl-piperidin-4-yl)-2,3-dihydro-indene-5-carboxylic acid amide, N-[3,3-Dimethyl-6-[methyl-(1-pyridin-4-yl-piperidin-4-yl)-carbamoyl]-1,2-dihydro-inden-1-yl]-pyrimidine-5-carboxylic acid amide, 3-[(2-Chloro-benzoyl)amino]-N,1,1-trimethyl-N-(1-pyridin-4-yl-piperidin-4-yl)-2,3-dihydro-indene-5-carboxylic acid amide, 3-[(2-Chloro-benzoyl)amino]-N-methyl-N-(1-pyridin-4-yl-piperidin-4-yl)-2,3-dihydro-1H-indene-5-carboxylic acid amide, 3-[(2,3-Dichloro-benzoyl)-methyl-amino]-N-methyl-N-(1-pyridin-4-yl-piperidin-4-yl)-2,3-dihydro-1H-indene-5-carboxylic acid amide, 3-[(2-Chloro-5-fluoro-benzoyl)amino]-N-methyl-N-(1-pyridin-4-yl-piperidin-4-yl)-2,3-dihydro-1H-indene-5-carboxylic acid amide, 3-[(2-Chloro-5-fluoro-benzoyl)-methyl-amino]-N-methyl-N-(1-pyridin-4-yl-piperidin-4-yl)-2,3-dihydro-1H-indene-5-carboxylic acid amide, N-Methyl-3-[methyl-(3-methyl-butanoyl)-amino]-N-(1-pyridin-4-yl-piperidin-4-yl)-2,3-dihydro-1H-indene-5-carboxylic acid amide, 3-Chloro-N-[6-[methyl-(1-pyridin-4-yl-piperidin-4-yl)-carbamoyl]-2,3-dihydro-1H-inden-1-yl]-thiophene-2-carboxylic acid amide, 3-Chloro-N-methyl-N-[6-[methyl-(1-pyridin-4-yl-piperidin-4-yl)-carbamoyl]-2,3-dihydro-1H-inden-1-yl]-thiophene-2-carboxylic acid amide, N-[6-[Methyl-(1-pyridin-4-yl-piperidin-4-yl)-carbamoyl]-2,3-dihydro-1H-inden-1-yl]-4-(trifluoromethyl)-pyridine-3-carboxylic acid amide, N-Methyl-N-[6-[methyl-(1-pyridin-4-yl-piperidin-4-yl)-carbamoyl]-2,3-dihydro-1H-inden-1-yl]-4-(trifluoromethyl)-pyridine-3-carboxylic acid amide, 3-[(2-Chloro-benzoyl)amino]-N-[2-(1-pyridin-4-yl-piperidin-4-yl)-ethyl]-2,3-dihydro-1H-indene-5-carboxylic acid amide, 3-[(2-Chloro-5-fluoro-benzoyl)amino]-N-[2-(1-pyridin-4-yl-piperidin-4-yl)-ethyl]-2,3-dihydro-1H-indene-5-carboxylic acid amide, N-[6-[2-(1-Pyridin-4-yl-piperidin-4-yl)-ethyl-carbamoyl]-2,3-dihydro-1H-inden-1-yl]-4-(trifluoromethyl)-pyridine-3-carboxylic acid amide, N-Methyl-3-(3-methyl-butanoylamino)-N-(1-pyridin-4-yl-piperidin-4-yl)-2,3-dihydro-1H-indene-5-carboxylic acid amide, N,1,1-Trimethyl-3-(3-methyl-butanoylamino)-N-(1-pyridin-4-yl-piperidin-4-yl)-2,3-dihydro-indene-5-carboxylic acid amide, 3-[[(2-Chlorophenyl)-methyl-carbamoyl]amino]-N-methyl-N-(1-pyridin-4-yl-piperidin-4-yl)-2,3-dihydro-1H-indene-5-carboxylic acid amide, N-Methyl-N-[6-[methyl-(1-pyridin-4-yl-piperidin-4-yl)-carbamoyl]-2,3-dihydro-1H-inden-1-yl]-pyrimidine-5-carboxylic acid amide N-Methyl-3-[methyl-[[2-(trifluoromethyl)-phenyl]-methylsulfonyl]-amino]-N-(1-pyridin-4-yl-piperidin-4-yl)-2,3-dihydro-1H-indene-5-carboxylic acid amide, N-[6-[Methyl-(1-pyridin-4-yl-piperidin-4-yl)-carbamoyl]-2,3-dihydro-1H-inden-1-yl]-pyrimidine-5-carboxylic acid amide, 3-[[[2-Chloro-6-(trifluoromethyl)-phenyl]sulfonyl]amino]-N-[2-(1-pyridin-4-yl-piperidin-4-yl)-ethyl]-2,3-dihydro-1H-indene-5-carboxylic acid amide, 3-[[(2-Chlorophenyl)-methyl-carbamoyl]-methyl-amino]-N-methyl-N-(1-pyridin-4-yl-piperidin-4-yl)-2,3-dihydro-1H-indene-5-carboxylic acid amide, 3-[(2,3-Dichloro-benzoyl)amino]-N-(1-isoquinolin-6-yl-piperidin-4-yl)-N-methyl-2,3-dihydro-1H-indene-5-carboxylic acid amide, N-[5-[Methyl-(1-pyridin-4-yl-piperidin-4-yl)-carbamoyl]-2,3-dihydro-1H-inden-1-yl]-pyrimidin-5-carboxylic acid amide, 3-[[[2-Chloro-6-(trifluoromethyl)-phenyl]sulfonyl]amino]-N-methyl-N-(1-pyridin-4-yl-piperidin-4-yl)-2,3-dihydro-1H-indene-5-carboxylic acid amide, N-(1-Isoquinolin-6-yl-piperidin-4-yl)-N-methyl-3-[[[2-(trifluoromethyl)-phenyl]-methylsulfonyl]amino]-2,3-dihydro-1H-indene-5-carboxylic acid amide, 1-(Cyclohexanecarbonylamino)-N-methyl-N-(1-pyridin-4-yl-piperidin-4-yl)-2,3-dihydro-1H-indene-5-carboxylic acid amide, 3-(3-Cyclopentyl-propanoylamino)-N-methyl-N-(1-pyridin-4-yl-piperidin-4-yl)-2,3-dihydro-1H-indene-5-carboxylic acid amide, N-[6-[(1-Isoquinolin-6-yl-piperidin-4-yl)-methyl-carbamoyl]-2,3-dihydro-1H-inden-1-yl]-4-(trifluoromethyl)-pyridine-3-carboxylic acid amide, N-Methyl-N-(1-pyridin-4-yl-piperidin-4-yl)-1-[[[2-(trifluoromethyl)-phenyl]-methylsulfonyl]amino]-2,3-dihydro-1H-indene-5-carboxylic acid amide, 3-[[2-Chloro-6-(trifluoromethyl)-benzoyl]amino]-N-(1-isoquinolin-6-yl-piperidin-4-yl)-N-methyl-2,3-dihydro-1H-indene-5-carboxylic acid amide, 1-[(2-Chloro-5-fluoro-benzoyl)amino]-N-methyl-N-(1-pyridin-4-yl-piperidin-4-yl)-2,3-dihydro-1H-indene-5-carboxylic acid amide, 1-(3-Cyclopentyl-propanoylamino)-N-methyl-N-(1-pyridin-4-yl-piperidin-4-yl)-2,3-dihydro-1H-indene-5-carboxylic acid amide, 1-[(2,6-Dimethyl-benzoyl)amino]-N-methyl-N-(1-pyridin-4-yl-piperidin-4-yl)-2,3-dihydro-1H-indene-5-carboxylic acid amide, 1-[(2,3-Dichloro-benzoyl)amino]-N-methyl-N-(1-pyridin-4-yl-piperidin-4-yl)-2,3-dihydro-1H-indene-5-carboxylic acid amide, 1-[(2-Chloro-benzoyl)amino]-N-methyl-N-(1-pyridin-4-yl-piperidin-4-yl)-2,3-dihydro-1H-indene-5-carboxylic acid amide, 3-(Cyclohexanecarbonyl-methyl-amino)-N-methyl-N-(1-pyridin-4-yl-piperidin-4-yl)-2,3-dihydro-1H-indene-5-carboxylic acid amide, 3-(3-Cyclopentyl-propanoyl-methyl-amino)-N-methyl-N-(1-pyridin-4-yl-piperidin-4-yl)-2,3-dihydro-1H-indene-5-carboxylic acid amide, 8-[(2-Chloro-benzoyl)amino]-N-methyl-N-(1-pyridin-4-yl-piperidin-4-yl)-5,6,7,8-tetrahydro-naphthalene-2-carboxylic acid amide, 3-[(2,3-Dichloro-benzoyl)amino]-N-[2-(1-pyridin-4-yl-piperidin-4-yl)-ethyl]-2,3-dihydro-1H-indene-5-carboxylic acid amide, 3-[(2-Chloro-benzoyl)amino]-N-(1-isoquinolin-6-yl-piperidin-4-yl)-N-methyl-2,3-dihydro-1H-indene-5-carboxylic acid amide, 3-[(2-Chloro-5-fluoro-benzoyl)amino]-N-(1-isoquinolin-6-yl-piperidin-4-yl)-N-methyl-2,3-dihydro-1H-indene-5-carboxylic acid amide, 3-(Cyclohexanecarbonylamino)-N-(1-isoquinolin-6-yl-piperidin-4-yl)-N-methyl-2,3-dihydro-1H-indene-5-carboxylic acid amide, 3-(3-Cyclopentyl-propanoylamino)-N-(1-isoquinolin-6-yl-piperidin-4-yl)-N-methyl-2,3-dihydro-1H-indene-5-carboxylic acid amide, N-(1-Isoquinolin-6-yl-piperidin-4-yl)-N-methyl-3-(3-methyl-butanoylamino)-2,3-dihydro-1H-indene-5-carboxylic acid amide, 3-Chloro-N-[6-[(1-isoquinolin-6-yl-piperidin-4-yl)-methyl-carbamoyl]-2,3-dihydro-1H-inden-1-yl]-thiophene-2-carboxylic acid amide, 3-(Cyclohexanecarbonyl-methyl-amino)-N-[1-(2,6-dimethyl-pyridin-4-yl)-piperidin-4-yl]-N-methyl-2,3-dihydro-1H-indene-5-carboxylic acid amide, 3-[(2-Chloro-5-fluoro-benzoyl)-methyl-amino]-N-[1-(2,6-dimethyl-pyridin-4-yl)-piperidin-4-yl]-N-methyl-2,3-dihydro-1H-indene-5-carboxylic acid amide, 3-[(2,3-Dichloro-benzoyl)-methyl-amino]-N-[1-(2,6-dimethyl-pyridin-4-yl)-piperidin-4-yl]-N-methyl-2,3-dihydro-1H-indene-5-carboxylic acid amide, 3-(3-Cyclopentyl-propanoyl-methyl-amino)-N-[1-(2,6-dimethyl-pyridin-4-yl)-piperidin-4-yl]-N-methyl-2,3-dihydro-1H-indene-5-carboxylic acid amide, 3-[(2,6-Dimethyl-benzoyl)amino]-N,1,1-trimethyl-N-(1-pyridin-4-yl-piperidin-4-yl)-2,3-dihydro-indene-5-carboxylic acid amide, N-[6-[[1-(2,6-Dimethyl-pyridin-4-yl)-piperidin-4-yl]-methyl-carbamoyl]-2,3-dihydro-1H-inden-1-yl]-N-methyl-4-(trifluoromethyl)-pyridine-3-carboxylic acid amide, 3-[(2-Chloro-benzoyl)-methyl-amino]-N-[1-(2,6-dimethyl-pyridin-4-yl)-piperidin-4-yl]-N-methyl-2,3-dihydro-1H-indene-5-carboxylic acid amide, 3-Chloro-N-[6-[[1-(2,6-dimethyl-pyridin-4-yl)-piperidin-4-yl]-methyl-carbamoyl]-2,3-dihydro-1H-inden-1-yl]-N-methyl-thiophene-2-carboxylic acid amide, N,1,1-Trimethyl-N-(1-pyridin-4-yl-piperidin-4-yl)-3-[[[2-(trifluoromethyl)-phenyl]-methylsulfonyl]amino]-2,3-dihydro-indene-5-carboxylic acid amide, N-[1-(2,6-Dimethyl-pyridin-4-yl)-piperidin-4-yl]-N-methyl-3-[methyl-(3-methyl-butanoyl)-amino]-2,3-dihydro-1H-indene-5-carboxylic acid amide, 3-[(2,6-Dimethyl-benzoyl)-methyl-amino]-N-[1-(2,6-dimethyl-pyridin-4-yl)-piperidin-4-yl]-N-methyl-2,3-dihydro-1H-indene-5-carboxylic acid amide, N-[6-[[1-(2,6-Dimethyl-pyridin-4-yl)-piperidin-4-yl]-methyl-carbamoyl]-2,3-dihydro-1H-inden-1-yl]-N-methyl-pyrimidine-5-carboxylic acid amide, 3-[[[2-Chloro-6-(trifluoromethyl)-phenyl]sulfonyl]amino]-N,1,1-trimethyl-N-(1-pyridin-4-yl-piperidin-4-yl)-2,3-dihydro-indene-5-carboxylic acid amide, 8-[[(2-Chlorophenyl)-methyl-carbamoyl]amino]-N-methyl-N-(1-pyridin-4-yl-piperidin-4-yl)-5,6,7,8-tetrahydro-naphthalene-2-carboxylic acid amide, 3-[[2-(2-Chlorophenyl)-2-methyl-propanoyl]amino]-N,1,1-trimethyl-N-(1-pyridin-4-yl-piperidin-4-yl)-2,3-dihydro-indene-5-carboxylic acid amide, 3-[(2,3-Dichloro-benzoyl)amino]-N-[1-(2,6-dimethyl-pyridin-4-yl)-piperidin-4-yl]-N-methyl-2,3-dihydro-1H-indene-5-carboxylic acid amide, 3-[[2-(2-Chlorophenyl)-2-methyl-propanoyl]amino]-N-(1-isoquinolin-6-yl-piperidin-4-yl)-N-methyl-2,3-dihydro-1H-indene-5-carboxylic acid amide, 3-[(2-Chloro-benzoyl)amino]-N-[1-(2,6-dimethyl-pyridin-4-yl)-piperidin-4-yl]-N-methyl-2,3-dihydro-1H-indene-5-carboxylic acid amide, 1-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide, 3-(3-Cyclopentyl-propanoylamino)-N-[2-(1-pyridin-4-yl-piperidin-4-yl)-ethyl]-2,3-dihydro-1H-indene-5-carboxylic acid amide, 8-[[2-(2-Chlorophenyl)-2-methyl-propanoyl]amino]-N-methyl-N-(1-pyridin-4-yl-piperidin-4-yl)-5,6,7,8-tetrahydro-naphthalene-2-carboxylic acid amide, 3-[[2-(2-Chlorophenyl)-2-methyl-propanoyl]amino]-N-[2-(1-pyridin-4-yl-piperidin-4-yl)-ethyl]-2,3-dihydro-1H-indene-5-carboxylic acid amide, 3-[[(2-Chlorophenyl)-methyl-carbamoyl]amino]-N-(1-isoquinolin-6-yl-piperidin-4-yl)-N-methyl-2,3-dihydro-1H-indene-5-carboxylic acid amide, 3-[(2,6-Dimethyl-benzoyl)amino]-N-[2-(1-pyridin-4-yl-piperidin-4-yl)-ethyl]-2,3-dihydro-1H-indene-5-carboxylic acid amide, 3-[(2-Chloro-benzoyl)-methyl-amino]-N-methyl-N-(1-pyridin-4-yl-piperidin-4-yl)-2,3-dihydro-1H-indene-5-carboxylic acid amide, 3-[[2-Chloro-6-(trifluoromethyl)-benzoyl]amino]-N-[1-(2,6-dimethyl-pyridin-4-yl)-piperidin-4-yl]-N-methyl-2,3-dihydro-1H-indene-5-carboxylic acid amide, 3-[[2-Chloro-6-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide, 3-Chloro-N-[6-[[1-(2,6-dimethyl-pyridin-4-yl)-piperidin-4-yl]-methyl-carbamoyl]-2,3-dihydro-1H-inden-1-yl]-thiophene-2-carboxylic acid amide, N-[5-[Methyl-(1-pyridin-4-yl-piperidin-4-yl)-carbamoyl]-2,3-dihydro-1H-inden-1-yl]-4-(trifluoromethyl)-pyridine-3-carboxylic acid amide, 3-[[[2-Chloro-6-(trifluoromethyl)-phenyl]sulfonyl]amino]-N-[1-(2,6-dimethyl-pyridin-4-yl)-piperidin-4-yl]-N-methyl-2,3-dihydro-1H-indene-5-carboxylic acid amide, N-[6-[[1-(2,6-Dimethyl-pyridin-4-yl)-piperidin-4-yl]-methyl-carbamoyl]-2,3-dihydro-1H-inden-1-yl]-4-(trifluoromethyl)-pyridine-3-carboxylic acid amide, N-Methyl-1-(3-methyl-butanoylamino)-N-(1-pyridin-4-yl-piperidin-4-yl)-2,3-dihydro-1H-indene-5-carboxylic acid amide, N-[6-[2-(1-Pyridin-4-yl-piperidin-4-yl)-ethyl-carbamoyl]-2,3-dihydro-1H-inden-1-yl]-pyrimidine-5-carboxylic acid amide, 3-[(2,6-Dimethyl-benzoyl)amino]-N-[1-(2,6-dimethyl-pyridin-4-yl)-piperidin-4-yl]-N-methyl-2,3-dihydro-1H-indene-5-carboxylic acid amide, 3-(Cyclohexanecarbonylamino)-N-[2-(1-pyridin-4-yl-piperidin-4-yl)-ethyl]-2,3-dihydro-1H-indene-5-carboxylic acid amide, 3-[(2,3-Dichloro-benzoyl)amino]-N-methyl-N-(1-pyridin-4-yl-piperidin-4-yl)-2,3-dihydro-1H-indene-5-carboxylic acid amide, N-[6-[[1-(2,6-Dimethyl-pyridin-4-yl)-piperidin-4-yl]-methyl-carbamoyl]-2,3-dihydro-1H-inden-1-yl]-pyrimidine-5-carboxylic acid amide, 3-[(2-Chloro-5-fluoro-benzoyl)amino]-N-[1-(2,6-dimethyl-pyridin-4-yl)-piperidin-4-yl]-N-methyl-2,3-dihydro-1H-indene-5-carboxylic acid amide, 3-(3-Cyclopentyl-propanoylamino)-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-N-methyl-3-[[[2-(trifluoromethyl)-phenyl]-methylsulfonyl]amino]-2,3-dihydro-1H-indene-5-carboxylic acid amide, N-[1-(2,6-Dimethyl-pyridin-4-yl)-piperidin-4-yl]-N-methyl-3-(3-methyl-butanoylamino)-2,3-dihydro-1H-indene-5-carboxylic acid amide, 3-(Cyclohexanecarbonylamino)-N-[1-(2,6-dimethyl-pyridin-4-yl)-piperidin-4-yl]-N-methyl-2,3-dihydro-1H-indene-5-carboxylic acid amide, N-Methyl-N-(1-pyridin-4-yl-piperidin-4-yl)-8-[[[2-(trifluoromethyl)-phenyl]-methylsulfonyl]amino]-5,6,7,8-tetrahydro-naphthalene-2-carboxylic acid amide, 1-[[(2-Chlorophenyl)-methyl-carbamoyl]amino]-N-methyl-N-(1-pyridin-4-yl-piperidin-4-yl)-2,3-dihydro-1H-indene-5-carboxylic acid amide, 1-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide, N-[2-(1-Pyridin-4-yl-piperidin-4-yl)-ethyl]-3-[[[2-(trifluoromethyl)-phenyl]-methylsulfonyl]amino]-2,3-dihydro-1H-indene-5-carboxylic acid amide, N-[1-(2,6-Dimethyl-pyridin-4-yl)-piperidin-4-yl]-N-methyl-3-[methyl-[[2-(trifluoromethyl)-phenyl]-methylsulfonyl]-amino]-2,3-dihydro-1H-indene-5-carboxylic acid amide, N-[6-[(1-Isoquinolin-6-yl-piperidin-4-yl)-methyl-carbamoyl]-2,3-dihydro-1H-inden-1-yl]-pyrimidine-5-carboxylic acid amide, 3-[[2-(2-Chlorophenyl)-2-methyl-propanoyl]amino]-N-[1-(2,6-dimethyl-pyridin-4-yl)-piperidin-4-yl]-N-methyl-2,3-dihydro-1H-indene-5-carboxylic acid amide, 3-(3-Methyl-butanoylamino)-N-[2-(1-pyridin-4-yl-piperidin-4-yl)-ethyl]-2,3-dihydro-1H-indene-5-carboxylic acid amide, 3-[(2,6-Dimethyl-benzoyl)amino]-N-(1-isoquinolin-6-yl-piperidin-4-yl)-N-methyl-2,3-dihydro-1H-indene-5-carboxylic acid amide, 3-[[[2-Chloro-6-(trifluoromethyl)-phenyl]sulfonyl]-methyl-amino]-N-[1-(2,6-dimethyl-pyridin-4-yl)-piperidin-4-yl]-N-methyl-2,3-dihydro-1H-indene-5-carboxylic acid amide, N-Methyl-8-(3-methyl-butanoylamino)-N-(1-pyridin-4-yl-piperidin-4-yl)-5,6,7,8-tetrahydro-naphthalene-2-carboxylic acid amide, 3-[[2-Chloro-6-(trifluoromethyl)-benzoyl]amino]-N-[2-(1-pyridin-4-yl-piperidin-4-yl)-ethyl]-2,3-dihydro-1H-indene-5-carboxylic acid amide, 3-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide, 3-[(2,6-Dimethyl-benzoyl)amino]-N-methyl-N-(1-pyridin-4-yl-piperidin-4-yl)-2,3-dihydro-1H-indene-5-carboxylic acid amide, 3-[[2-(2-Chlorophenyl)-2-methyl-propanoyl]amino]-N-methyl-N-(1-pyridin-4-yl-piperidin-4-yl)-2,3-dihydro-1H-indene-5-carboxylic acid amide, 3-(Cyclohexanecarbonylamino)-N-methyl-N-(1-pyridin-4-yl-piperidin-4-yl)-2,3-dihydro-1H-indene-5-carboxylic acid amide, N-Methyl-N-(1-pyridin-4-yl-piperidin-4-yl)-3-[[[2-(trifluoromethyl)-phenyl]-methylsulfonyl]amino]-2,3-dihydro-1H-indene-5-carboxylic acid amide, 3-[[(2-Chlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide, 1-[[[2-Chloro-6-(trifluoromethyl)-phenyl]sulfonyl]amino]-N-methyl-N-(1-pyridin-4-yl-piperidin-4-yl)-2,3-dihydro-1H-indene-5-carboxylic acid amide, 3-[(2-Chloro-5-fluoro-benzoyl)amino]-N-methyl-N-(1-pyridin-4-yl-piperidin-4-yl)-2,3-dihydro-1H-indene-5-carboxylic acid amide, 3-[[2-Chloro-5-(trifluoromethyl)-benzoyl]amino]-N-methyl-N-(1-pyridin-4-yl-piperidin-4-yl)-2,3-dihydro-1H-indene-5-carboxylic acid amide, 3-[(2-Chloro-6-fluoro-3-methyl-benzoyl)amino]-N-methyl-N-(1-pyridin-4-yl-piperidin-4-yl)-2,3-dihydro-1H-indene-5-carboxylic acid amide, 3-[(2,5-Dichloro-benzoyl)amino]-N-methyl-N-(1-pyridin-4-yl-piperidin-4-yl)-2,3-dihydro-1H-indene-5-carboxylic acid amide, 3-[[2-Chloro-6-(trifluoromethyl)-benzoyl]amino]-N-methyl-N-(1-pyridin-4-yl-piperidin-4-yl)-2,3-dihydro-1H-indene-5-carboxylic acid amide, 3-(Cyclopropanecarbonylamino)-N-methyl-N-(1-pyridin-4-yl-piperidin-4-yl)-2,3-dihydro-1H-indene-5-carboxylic acid amide, 3-(3,3-Dimethyl-butanoylamino)-N-methyl-N-(1-pyridin-4-yl-piperidin-4-yl)-2,3-dihydro-1H-indene-5-carboxylic acid amide, 3-[(2-Methoxy-acetyl)amino]-N-methyl-N-(1-pyridin-4-yl-piperidin-4-yl)-2,3-dihydro-1H-indene-5-carboxylic acid amide, 3-[(2-Chloro-5-fluoro-benzoyl)-methyl-amino]-N-methyl-N-(1-pyridin-4-yl-piperidin-4-yl)-2,3-dihydro-1H-indene-5-carboxylic acid amide, 3-[(2-Chloro-6-fluoro-3-methyl-benzoyl)-methyl-amino]-N-methyl-N-(1-pyridin-4-yl-piperidin-4-yl)-2,3-dihydro-1H-indene-5-carboxylic acid amide, 3-[(2,5-Dichloro-benzoyl)-methyl-amino]-N-methyl-N-(1-pyridin-4-yl-piperidin-4-yl)-2,3-dihydro-1H-indene-5-carboxylic acid amide, 3-(Cyclohexanecarbonyl-methyl-amino)-N-methyl-N-(1-pyridin-4-yl-piperidin-4-yl)-2,3-dihydro-1H-indene-5-carboxylic acid amide, 3-(Cyclopropanecarbonyl-methyl-amino)-N-methyl-N-(1-pyridin-4-yl-piperidin-4-yl)-2,3-dihydro-1H-indene-5-carboxylic acid amide, 3-(3,3-Dimethyl-butanoyl-methyl-amino)-N-methyl-N-(1-pyridin-4-yl-piperidin-4-yl)-2,3-dihydro-1H-indene-5-carboxylic acid amide,
3-[(2-Methoxy-acetyl)-methyl-amino]-N-methyl-N-(1-pyridin-4-yl-piperidin-4-yl)-2,3-dihydro-1H-indene-5-carboxylic acid amide,
3-(Acetyl-methyl-amino)-N-methyl-N-(1-pyridin-4-yl-piperidin-4-yl)-2,3-dihydro-1H-indene-5-carboxylic acid amide,
3-[[2-Chloro-3-(trifluoromethyl)-benzoyl]-methyl-amino]-N-methyl-N-(1-pyridin-4-yl-piperidin-4-yl)-2,3-dihydro-1H-indene-5-carboxylic acid amide,
3-[[(2-Chlorophenyl)-carbamoyl]-methyl-amino]-N-methyl-N-(1-pyridin-4-yl-piperidin-4-yl)-2,3-dihydro-1H-indene-5-carboxylic acid amide,
3-[[(3-Chlorophenyl)-carbamoyl]-methyl-amino]-N-methyl-N-(1-pyridin-4-yl-piperidin-4-yl)-2,3-dihydro-1H-indene-5-carboxylic acid amide,
3-[[(2,6-Dichloro-phenyl)-carbamoyl]-methyl-amino]-N-methyl-N-(1-pyridin-4-yl-piperidin-4-yl)-2,3-dihydro-1H-indene-5-carboxylic acid amide,
3-[[(2,3-Dichloro-phenyl)-carbamoyl]-methyl-amino]-N-methyl-N-(1-pyridin-4-yl-piperidin-4-yl)-2,3-dihydro-1H-indene-5-carboxylic acid amide,
3-[[(2,5-Dichloro-phenyl)-carbamoyl]-methyl-amino]-N-methyl-N-(1-pyridin-4-yl-piperidin-4-yl)-2,3-dihydro-1H-indene-5-carboxylic acid amide,
3-[(2-Chloro-5-fluoro-benzoyl)amino]-N,1,1-trimethyl-N-(1-pyridin-4-yl-piperidin-4-yl)-2,3-dihydro-indene-5-carboxylic acid amide,
3-[[2-Chloro-5-(trifluoromethyl)-benzoyl]amino]-N,1,1-trimethyl-N-(1-pyridin-4-yl-piperidin-4-yl)-2,3-dihydro-indene-5-carboxylic acid amide,
3-[(2-Chloro-6-fluoro-3-methyl-benzoyl)amino]-N,1,1-trimethyl-N-(1-pyridin-4-yl-piperidin-4-yl)-2,3-dihydro-indene-5-carboxylic acid amide,
3-[[2-Chloro-6-(trifluoromethyl)-benzoyl]amino]-N,1,1-trimethyl-N-(1-pyridin-4-yl-piperidin-4-yl)-2,3-dihydro-indene-5-carboxylic acid amide,
3-(Cyclopropanecarbonylamino)-N,1,1-trimethyl-N-(1-pyridin-4-yl-piperidin-4-yl)-2,3-dihydro-indene-5-carboxylic acid amide,
3-(3,3-Dimethyl-butanoylamino)-N,1,1-trimethyl-N-(1-pyridin-4-yl-piperidin-4-yl)-2,3-dihydro-indene-5-carboxylic acid amide,
3-[(2-Methoxy-acetyl)amino]-N,1,1-trimethyl-N-(1-pyridin-4-yl-piperidin-4-yl)-2,3-dihydro-indene-5-carboxylic acid amide,
3-Acetylamino-N,1,1-trimethyl-N-(1-pyridin-4-yl-piperidin-4-yl)-2,3-dihydro-indene-5-carboxylic acid amide,
3-[[(2-Chloro-6-methyl-phenyl)sulfonyl]amino]-N,1,1-trimethyl-N-(1-pyridin-4-yl-piperidin-4-yl)-2,3-dihydro-indene-5-carboxylic acid amide,
3-[[2-Chloro-3-(trifluoromethyl)-benzoyl]amino]-N,1,1-trimethyl-N-(1-pyridin-4-yl-piperidin-4-yl)-2,3-dihydro-indene-5-carboxylic acid amide,
3-[[(2-Chlorophenyl)-carbamoyl]amino]-N,1,1-trimethyl-N-(1-pyridin-4-yl-piperidin-4-yl)-2,3-dihydro-indene-5-carboxylic acid amide,
3-[[(3-Chlorophenyl)-carbamoyl]amino]-N,1,1-trimethyl-N-(1-pyridin-4-yl-piperidin-4-yl)-2,3-dihydro-indene-5-carboxylic acid amide,
3-[[(2,6-Dichloro-phenyl)-carbamoyl]amino]-N,1,1-trimethyl-N-(1-pyridin-4-yl-piperidin-4-yl)-2,3-dihydro-indene-5-carboxylic acid amide,
3-[[(2,3-Dichloro-phenyl)-carbamoyl]amino]-N,1,1-trimethyl-N-(1-pyridin-4-yl-piperidin-4-yl)-2,3-dihydro-indene-5-carboxylic acid amide,
3-[[(2,5-Dichloro-phenyl)-carbamoyl]amino]-N,1,1-trimethyl-N-(1-pyridin-4-yl-piperidin-4-yl)-2,3-dihydro-indene-5-carboxylic acid amide,
3-[[(3,5-Dichloro-phenyl)-carbamoyl]amino]-N,1,1-trimethyl-N-(1-pyridin-4-yl-piperidin-4-yl)-2,3-dihydro-indene-5-carboxylic acid amide,
3-[[(2,4-Dichlorophenyl)-carbamoyl]amino]-N,1,1-trimethyl-N-(1-pyridin-4-yl-piperidin-4-yl)-2,3-dihydro-indene-5-carboxylic acid amide,
3-[[[2-Chloro-5-(trifluoromethyl)-phenyl]-carbamoyl]amino]-N,1,1-trimethyl-N-(1-pyridin-4-yl-piperidin-4-yl)-2,3-dihydro-indene-5-carboxylic acid amide,
3-[[[4-Chloro-2-(trifluoromethyl)-phenyl]-carbamoyl]amino]-N,1,1-trimethyl-N-(1-pyridin-4-yl-piperidin-4-yl)-2,3-dihydro-indene-5-carboxylic acid amide,
3-[[(3-Chloro-4-methyl-phenyl)-carbamoyl]amino]-N,1,1-trimethyl-N-(1-pyridin-4-yl-piperidin-4-yl)-2,3-dihydro-indene-5-carboxylic acid amide,
3-[[(3-Chloro-4-fluoro-phenyl)-carbamoyl]amino]-N,1,1-trimethyl-N-(1-pyridin-4-yl-piperidin-4-yl)-2,3-dihydro-indene-5-carboxylic acid amide,
3-[[(2,4-Dimethyl-phenyl)-carbamoyl]amino]-N,1,1-trimethyl-N-(1-pyridin-4-yl-piperidin-4-yl)-2,3-dihydro-indene-5-carboxylic acid amide,
3-[[(5-Chloro-2-methoxy-phenyl)-carbamoyl]amino]-N,1,1-trimethyl-N-(1-pyridin-4-yl-piperidin-4-yl)-2,3-dihydro-indene-5-carboxylic acid amide,
3-[[(2-Chlorophenyl)-methyl-carbamoyl]amino]-N,1,1-trimethyl-N-(1-pyridin-4-yl-piperidin-4-yl)-2,3-dihydro-indene-5-carboxylic acid amide,
8-[(2-Chloro-5-fluoro-benzoyl)amino]-N-methyl-N-(1-pyridin-4-yl-piperidin-4-yl)-5,6,7,8-tetrahydro-naphthalene-2-carboxylic acid amide,
8-[[2-Chloro-5-(trifluoromethyl)-benzoyl]amino]-N-methyl-N-(1-pyridin-4-yl-piperidin-4-yl)-5,6,7,8-tetrahydro-naphthalene-2-carboxylic acid amide,
8-[(2-Chloro-6-fluoro-3-methyl-benzoyl)amino]-N-methyl-N-(1-pyridin-4-yl-piperidin-4-yl)-5,6,7,8-tetrahydro-naphthalene-2-carboxylic acid amide,
8-[[2-Chloro-6-(trifluoromethyl)-benzoyl]amino]-N-methyl-N-(1-pyridin-4-yl-piperidin-4-yl)-5,6,7,8-tetrahydro-naphthalene-2-carboxylic acid amide,
8-(Cyclopropanecarbonylamino)-N-methyl-N-(1-pyridin-4-yl-piperidin-4-yl)-5,6,7,8-tetrahydro-naphthalene-2-carboxylic acid amide,
8-(3,3-Dimethyl-butanoylamino)-N-methyl-N-(1-pyridin-4-yl-piperidin-4-yl)-5,6,7,8-tetrahydro-naphthalene-2-carboxylic acid amide,
8-[(2-Methoxy-acetyl)amino]-N-methyl-N-(1-pyridin-4-yl-piperidin-4-yl)-5,6,7,8-tetrahydro-naphthalene-2-carboxylic acid amide,
8-Acetylamino-N-methyl-N-(1-pyridin-4-yl-piperidin-4-yl)-5,6,7,8-tetrahydro-naphthalene-2-carboxylic acid amide,
8-[[2-Chloro-3-(trifluoromethyl)-benzoyl]amino]-N-methyl-N-(1-pyridin-4-yl-piperidin-4-yl)-5,6,7,8-tetrahydro-naphthalene-2-carboxylic acid amide,
8-[[(2-Chlorophenyl)-carbamoyl]amino]-N-methyl-N-(1-pyridin-4-yl-piperidin-4-yl)-5,6,7,8-tetrahydro-naphthalene-2-carboxylic acid amide,
8-[[(3-Chlorophenyl)-carbamoyl]amino]-N-methyl-N-(1-pyridin-4-yl-piperidin-4-yl)-5,6,7,8-tetrahydro-naphthalene-2-carboxylic acid amide, 8-[[(2,6-Dichloro-phenyl)-carbamoyl]amino]-N-methyl-N-(1-pyridin-4-yl-piperidin-4-yl)-5,6,7,8-tetrahydro-naphthalene-2-carboxylic acid amide, 8-[[(2,3-Dichloro-phenyl)-carbamoyl]amino]-N-methyl-N-(1-pyridin-4-yl-piperidin-4-yl)-5,6,7,8-tetrahydro-naphthalene-2-carboxylic acid amide, 8-[[(2,5-Dichloro-phenyl)-carbamoyl]amino]-N-methyl-N-(1-pyridin-4-yl-piperidin-4-yl)-5,6,7,8-tetrahydro-naphthalene-2-carboxylic acid amide, 8-[[(3,5-Dichloro-phenyl)-carbamoyl]amino]-N-methyl-N-(1-pyridin-4-yl-piperidin-4-yl)-5,6,7,8-tetrahydro-naphthalene-2-carboxylic acid amide, 8-[[[2-Chloro-5-(trifluoromethyl)-phenyl]-carbamoyl]amino]-N-methyl-N-(1-pyridin-4-yl-piperidin-4-yl)-5,6,7,8-tetrahydro-naphthalene-2-carboxylic acid amide, 8-[[(2,4-Dichlorophenyl)-carbamoyl]amino]-N-methyl-N-(1-pyridin-4-yl-piperidin-4-yl)-5,6,7,8-tetrahydro-naphthalene-2-carboxylic acid amide, 8-[[[4-Chloro-2-(trifluoromethyl)-phenyl]-carbamoyl]amino]-N-methyl-N-(1-pyridin-4-yl-piperidin-4-yl)-5,6,7,8-tetrahydro-naphthalene-2-carboxylic acid amide, 8-[[(3-Chloro-4-methyl-phenyl)-carbamoyl]amino]-N-methyl-N-(1-pyridin-4-yl-piperidin-4-yl)-5,6,7,8-tetrahydro-naphthalene-2-carboxylic acid amide, 8-[[(3-Chloro-4-fluoro-phenyl)-carbamoyl]amino]-N-methyl-N-(1-pyridin-4-yl-piperidin-4-yl)-5,6,7,8-tetrahydro-naphthalene-2-carboxylic acid amide, 8-[[(2,4-Dimethyl-phenyl)-carbamoyl]amino]-N-methyl-N-(1-pyridin-4-yl-piperidin-4-yl)-5,6,7,8-tetrahydro-naphthalene-2-carboxylic acid amide, 8-[[(5-Chloro-2-methoxy-phenyl)-carbamoyl]amino]-N-methyl-N-(1-pyridin-4-yl-piperidin-4-yl)-5,6,7,8-tetrahydro-naphthalene-2-carboxylic acid amide, 8-[[(2-Chlorophenyl)-methyl-carbamoyl]amino]-N-methyl-N-(1-pyridin-4-yl-piperidin-4-yl)-5,6,7,8-tetrahydro-naphthalene-2-carboxylic acid amide, 8-[[(2,4-Dichlorophenyl)-methyl-carbamoyl]amino]-N-methyl-N-(1-pyridin-4-yl-piperidin-4-yl)-5,6,7,8-tetrahydro-naphthalene-2-carboxylic acid amide, 8-[(Cyclohexylsulfonyl)amino]-N-methyl-N-(1-pyridin-4-yl-piperidin-4-yl)-5,6,7,8-tetrahydro-naphthalene-2-carboxylic acid amide, N-Methyl-8-(3-methyl-butanoylamino)-N-(1-pyridin-4-yl-piperidin-4-yl)-5,6,7,8-tetrahydro-naphthalene-2-carboxylic acid amide, 3-[(2-Chloro-5-fluoro-benzoyl)amino]-N-[1-(2,6-dimethyl-pyridin-4-yl)-piperidin-4-yl]-N-methyl-2,3-dihydro-1H-indene-5-carboxylic acid amide, 3-[(2-Chloro-6-fluoro-3-methyl-benzoyl)amino]-N-[1-(2,6-dimethyl-pyridin-4-yl)-piperidin-4-yl]-N-methyl-2,3-dihydro-1H-indene-5-carboxylic acid amide, 3-[(2,5-Dichloro-benzoyl)amino]-N-[1-(2,6-dimethyl-pyridin-4-yl)-piperidin-4-yl]-N-methyl-2,3-dihydro-1H-indene-5-carboxylic acid amide, 3-(Cyclohexanecarbonylamino)-N-[1-(2,6-dimethyl-pyridin-4-yl)-piperidin-4-yl]-N-methyl-2,3-dihydro-1H-indene-5-carboxylic acid amide, 3-(Cyclopropanecarbonylamino)-N-[1-(2,6-dimethyl-pyridin-4-yl)-piperidin-4-yl]-N-methyl-2,3-dihydro-1H-indene-5-carboxylic acid amide, 3-(3,3-Dimethyl-butanoylamino)-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-3-[(2-methoxy-acetyl)amino]-N-methyl-2,3-dihydro-1H-indene-5-carboxylic acid amide, 3-Acetylamino-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-N-methyl-3-[[[2-(trifluoromethyl)-phenyl]-methylsulfonyl]amino]-2,3-dihydro-1H-indene-5-carboxylic acid amide, 3-[[2-Chloro-3-(trifluoromethyl)-benzoyl]amino]-N-[1-(2,6-dimethyl-pyridin-4-yl)-piperidin-4-yl]-N-methyl-2,3-dihydro-1H-indene-5-carboxylic acid amide, 3-[[(2-Chlorophenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(3-Chlorophenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(2,6-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(2,3-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(2,5-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(3,5-Dichloro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(2,4-Dichlorophenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[[2-Chloro-5-(trifluoromethyl)-phenyl]-carbamoyl]amino]-N-[1-(2,6-dimethyl-pyridin-4-yl)-piperidin-4-yl]-N-methyl-2,3-dihydro-1H-indene-5-carboxylic acid amide, 3-[[[4-Chloro-2-(trifluoromethyl)-phenyl]-carbamoyl]amino]-N-[1-(2,6-dimethyl-pyridin-4-yl)-piperidin-4-yl]-N-methyl-2,3-dihydro-1H-indene-5-carboxylic acid amide, 3-[[(3-Chloro-4-methyl-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(3-Chloro-4-fluoro-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(5-Chloro-2-methoxy-phenyl)-carbamoyl]amino]-N-[1-(2,6-dimethyl-pyridin-4-yl)-piperidin-4-yl]-N-methyl-2,3-dihydro-1H-indene-5-carboxylic acid amide, 3-[[(2-Chlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide, 3-[[(2,4-Dichlorophenyl)-methyl-carbamoyl]amino]-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-N-methyl-3-(3-methyl-butanoylamino)-2,3-dihydro-1H-indene-5-carboxylic acid amide, 3-(Butanoylamino)-N-[1-(2,6-dimethyl-pyridin-4-yl)-piperidin-4-yl]-N-methyl-2,3-dihydro-1H-indene-5-carboxylic acid amide, 3-(3-Cyclopentyl-propanoylamino)-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-3-[(ethylsulfonyl)amino]-N-methyl-2,3-dihydro-1H-indene-5-carboxylic acid amide, N-[1-(2,6-Dimethyl-pyridin-4-yl)-piperidin-4-yl]-N-methyl-3-[[[3-(trifluoromethyl)phenyl]-methylsulfonyl]amino]-2,3-dihydro-1H-indene-5-carboxylic acid amide, N-[1-(2,6-Dimethyl-pyridin-4-yl)-piperidin-4-yl]-3-[[(2-fluorophenyl)-methylsulfonyl]amino]-N-methyl-2,3-dihydro-1H-indene-5-carboxylic acid amide, 3-[[2-(2-Chlorophenyl)-ethylsulfonyl]amino]-N-[1-(2,6-dimethyl-pyridin-4-yl)-piperidin-4-yl]-N-methyl-2,3-dihydro-1H-indene-5-carboxylic acid amide, 3-[(2-Chloro-5-fluoro-benzoyl)-methyl-amino]-N-[1-(2,6-dimethyl-pyridin-4-yl)-piperidin-4-yl]-N-methyl-2,3-dihydro-1H-indene-5-carboxylic acid amide, 3-[[2-Chloro-5-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide, 3-[(2-Chloro-6-fluoro-3-methyl-benzoyl)-methyl-amino]-N-[1-(2,6-dimethyl-pyridin-4-yl)-piperidin-4-yl]-N-methyl-2,3-dihydro-1H-indene-5-carboxylic acid amide, 3-[(2,5-Dichloro-benzoyl)-methyl-amino]-N-[1-(2,6-dimethyl-pyridin-4-yl)-piperidin-4-yl]-N-methyl-2,3-dihydro-1H-indene-5-carboxylic acid amide, 3-[[2-Chloro-6-(trifluoromethyl)-benzoyl]-methyl-amino]-N-[1-(2,6-dimethyl-pyridin-4-yl)-piperidin-4-yl]-N-methyl-2,3-dihydro-1H-indene-5-carboxylic acid amide, 3-(Cyclohexanecarbonyl-methyl-amino)-N-[1-(2,6-dimethyl-pyridin-4-yl)-piperidin-4-yl]-N-methyl-2,3-dihydro-1H-indene-5-carboxylic acid amide, 3-(Cyclopropanecarbonyl-methyl-amino)-N-[1-(2,6-dimethyl-pyridin-4-yl)-piperidin-4-yl]-N-methyl-2,3-dihydro-1H-indene-5-carboxylic acid amide, 3-(3,3-Dimethyl-butanoyl-methyl-amino)-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-3-[(2-methoxy-acetyl)-methyl-amino]-N-methyl-2,3-dihydro-1H-indene-5-carboxylic acid amide, 3-(Acetyl-methyl-amino)-N-[1-(2,6-dimethyl-pyridin-4-yl)-piperidin-4-yl]-N-methyl-2,3-dihydro-1H-indene-5-carboxylic acid amide, 3-[[(2-Chloro-6-methyl-phenyl)sulfonyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2-Chlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(3-Chlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2,6-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2,3-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2,5-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(3,5-Dichloro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2,4-Dichlorophenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[[2-Chloro-5-(trifluoromethyl)-phenyl]-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[[4-Chloro-2-(trifluoromethyl)-phenyl]-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(3-Chloro-4-methyl-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(3-Chloro-4-fluoro-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2,4-Dimethyl-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(5-Chloro-2-methoxy-phenyl)-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2-Chlorophenyl)-methyl-carbamoyl]-methyl-amino]-N-[1-(2,6-dimethyl-pyridin-4-yl)-piperidin-4-yl]-N-methyl-2,3-dihydro-1H-indene-5-carboxylic acid amide, 3-[[(2,4-Dichlorophenyl)-methyl-carbamoyl]-methyl-amino]-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-N-methyl-3-(methyl-methylsulfonyl-amino)-2,3-dihydro-1H-indene-5-carboxylic acid amide, N-[1-(2,6-Dimethyl-pyridin-4-yl)-piperidin-4-yl]-N-methyl-3-[methyl-(3-methyl-butanoyl)-amino]-2,3-dihydro-1H-indene-5-carboxylic acid amide, 3-(Butanoyl-methyl-amino)-N-[1-(2,6-dimethyl-pyridin-4-yl)-piperidin-4-yl]-N-methyl-2,3-dihydro-1H-indene-5-carboxylic acid amide, 3-(3-Cyclopentyl-propanoyl-methyl-amino)-N-[1-(2,6-dimethyl-pyridin-4-yl)-piperidin-4-yl]-N-methyl-2,3-dihydro-1H-indene-5-carboxylic acid amide, N-[1-(2,6-Dimethyl-pyridin-4-yl)-piperidin-4-yl]-N-methyl-3-[methyl-[[3-(trifluoromethyl)phenyl]-methylsulfonyl]-amino]-2,3-dihydro-1H-indene-5-carboxylic acid amide, 3-[(2-Chloro-5-fluoro-benzoyl)amino]-N-(1-isoquinolin-6-yl-piperidin-4-yl)-N-methyl-2,3-dihydro-1H-indene-5-carboxylic acid amide, 3-[[2-Chloro-5-(trifluoromethyl)-benzoyl]amino]-N-(1-isoquinolin-6-yl-piperidin-4-yl)-N-methyl-2,3-dihydro-1H-indene-5-carboxylic acid amide, 3-[(2-Chloro-6-fluoro-3-methyl-benzoyl)amino]-N-(1-isoquinolin-6-yl-piperidin-4-yl)-N-methyl-2,3-dihydro-1H-indene-5-carboxylic acid amide, 3-[(2,5-Dichloro-benzoyl)amino]-N-(1-isoquinolin-6-yl-piperidin-4-yl)-N-methyl-2,3-dihydro-1H-indene-5-carboxylic acid amide, 3-(Cyclohexanecarbonylamino)-N-(1-isoquinolin-6-yl-piperidin-4-yl)-N-methyl-2,3-dihydro-1H-indene-5-carboxylic acid amide, 3-(Cyclopropanecarbonylamino)-N-(1-isoquinolin-6-yl-piperidin-4-yl)-N-methyl-2,3-dihydro-1H-indene-5-carboxylic acid amide, 3-(3,3-Dimethyl-butanoylamino)-N-(1-isoquinolin-6-yl-piperidin-4-yl)-N-methyl-2,3-dihydro-1H-indene-5-carboxylic acid amide, N-(1-Isoquinolin-6-yl-piperidin-4-yl)-3-[(2-methoxy-acetyl)amino]-N-methyl-2,3-dihydro-1H-indene-5-carboxylic acid amide, 3-[[2-Chloro-3-(trifluoromethyl)-benzoyl]amino]-N-(1-isoquinolin-6-yl-piperidin-4-yl)-N-methyl-2,3-dihydro-1H-indene-5-carboxylic acid amide, 3-[[(2-Chlorophenyl)-carbamoyl]amino]-N-(1-isoquinolin-6-yl-piperidin-4-yl)-N-methyl-2,3-dihydro-1H-indene-5-carboxylic acid amide, 3-[[(2,6-Dichloro-phenyl)-carbamoyl]amino]-N-(1-isoquinolin-6-yl-piperidin-4-yl)-N-methyl-2,3-dihydro-1H-indene-5-carboxylic acid amide, 3-[[(2,3-Dichloro-phenyl)-carbamoyl]amino]-N-(1-isoquinolin-6-yl-piperidin-4-yl)-N-methyl-2,3-dihydro-1H-indene-5-carboxylic acid amide, 3-[[(2,5-Dichloro-phenyl)-carbamoyl]amino]-N-(1-isoquinolin-6-yl-piperidin-4-yl)-N-methyl-2,3-dihydro-1H-indene-5-carboxylic acid amide, 3-[[(2,4-Dichlorophenyl)-carbamoyl]amino]-N-(1-isoquinolin-6-yl-piperidin-4-yl)-N-methyl-2,3-dihydro-1H-indene-5-carboxylic acid amide, 3-[[[2-Chloro-5-(trifluoromethyl)-phenyl]-carbamoyl]amino]-N-(1-isoquinolin-6-yl-piperidin-4-yl)-N-methyl-2,3-dihydro-1H-indene-5-carboxylic acid amide, 3-[[[4-Chloro-2-(trifluoromethyl)-phenyl]-carbamoyl]amino]-N-(1-isoquinolin-6-yl-piperidin-4-yl)-N-methyl-2,3-dihydro-1H-indene-5-carboxylic acid amide, 3-[[(3-Chloro-4-fluoro-phenyl)-carbamoyl]amino]-N-(1-isoquinolin-6-yl-piperidin-4-yl)-N-methyl-2,3-dihydro-1H-indene-5-carboxylic acid amide, 3-[[(2,4-Dimethyl-phenyl)-carbamoyl]amino]-N-(1-isoquinolin-6-yl-piperidin-4-yl)-N-methyl-2,3-dihydro-1H-indene-5-carboxylic acid amide, 3-[[(5-Chloro-2-methoxy-phenyl)-carbamoyl]amino]-N-(1-isoquinolin-6-yl-piperidin-4-yl)-N-methyl-2,3-dihydro-1H-indene-5-carboxylic acid amide, 3-[[(2-Chlorophenyl)-methyl-carbamoyl]amino]-N-(1-isoquinolin-6-yl-piperidin-4-yl)-N-methyl-2,3-dihydro-1H-indene-5-carboxylic acid amide, 3-[[(2,4-Dichlorophenyl)-methyl-carbamoyl]amino]-N-(1-isoquinolin-6-yl-piperidin-4-yl)-N-methyl-2,3-dihydro-1H-indene-5-carboxylic acid amide, N-(1-Isoquinolin-6-yl-piperidin-4-yl)-3-(methanesulfonamido)-N-methyl-2,3-dihydro-1H-indene-5-carboxylic acid amide, N-(1-Isoquinolin-6-yl-piperidin-4-yl)-N-methyl-3-[(propylsulfonyl)amino]-2,3-dihydro-1H-indene-5-carboxylic acid amide, N-(1-Isoquinolin-6-yl-piperidin-4-yl)-N-methyl-3-(3-methyl-butanoylamino)-2,3-dihydro-1H-indene-5-carboxylic acid amide, 3-(Butanoylamino)-N-(1-isoquinolin-6-yl-piperidin-4-yl)-N-methyl-2,3-dihydro-1H-indene-5-carboxylic acid amide, 3-(3-Cyclopentyl-propanoylamino)-N-(1-isoquinolin-6-yl-piperidin-4-yl)-N-methyl-2,3-dihydro-1H-indene-5-carboxylic acid amide, 3-[(Ethylsulfonyl)amino]-N-(1-isoquinolin-6-yl-piperidin-4-yl)-N-methyl-2,3-dihydro-1H-indene-5-carboxylic acid amide, N-(1-Isoquinolin-6-yl-piperidin-4-yl)-N-methyl-3-[[[3-(trifluoromethyl)phenyl]-methylsulfonyl]amino]-2,3-dihydro-1H-indene-5-carboxylic acid amide, 3-[[(2-Fluorophenyl)-methylsulfonyl]amino]-N-(1-isoquinolin-6-yl-piperidin-4-yl)-N-methyl-2,3-dihydro-1H-indene-5-carboxylic acid amide, N-[6-[Methyl-[1-(2-methylsulfonyl-pyrimidin-4-yl)-piperidin-4-yl]-carbamoyl]-2,3-dihydro-1H-inden-1-yl]-2-(trifluoromethyl)-pyridine-3-carboxylic acid amide, N-[6-[[1-[2-(Dimethyl-carbamoyl)-pyridin-4-yl]-piperidin-4-yl]-methyl-carbamoyl]-2,3-dihydro-1H-inden-1-yl]-2-(trifluoromethyl)-pyridine-3-carboxylic acid amide, N-[6-[Methyl-[1-(2-pyrrolidin-1-yl-pyrimidin-4-yl)-piperidin-4-yl]-carbamoyl]-2,3-dihydro-1H-inden-1-yl]-2-(trifluoromethyl)-pyridine-3-carboxylic acid amide, N-[6-[[1-(2-Dimethylamino-6-methyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, N-[6-[[1-(2-tert-Butyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, N-[6-[Methyl-[4-(5-methyl-3-oxo-1,2-dihydro-imidazo[5,1-e]imidazol-2-yl)-cyclohexyl]-carbamoyl]-2,3-dihydro-1H-inden-1-yl]-2-(trifluoromethyl)-pyridine-3-carboxylic acid amide, N-[6-[[1-(2-Dimethylamino-pyrimidin-4-yl)-piperidin-4-yl]-methyl-carbamoyl]-2,3-dihydro-1H-inden-1-yl]-2-(trifluoromethyl)-pyridine-3-carboxylic acid amide, 3-[(2-Chloro-benzoyl)amino]-N-methyl-N-[1-(2-methylsulfonyl-pyrimidin-4-yl)-piperidin-4-yl]-2,3-dihydro-1H-indene-5-carboxylic acid amide, N-[6-[[1-(2-Cyclopropyl-pyrimidin-4-yl)-piperidin-4-yl]-methyl-carbamoyl]-2,3-dihydro-1H-inden-1-yl]-2-(trifluoromethyl)-pyridine-3-carboxylic acid amide, 3-[(2-Chloro-benzoyl)amino]-N-methyl-N-[1-(2-pyrrolidin-1-yl-pyrimidin-4-yl)-piperidin-4-yl]-2,3-dihydro-1H-indene-5-carboxylic acid amide, 3-(3-Cyclopentyl-propanoylamino)-N-methyl-N-[1-(2-methylsulfonyl-pyrimidin-4-yl)-piperidin-4-yl]-2,3-dihydro-1H-indene-5-carboxylic acid amide, 3-[(2-Chloro-benzoyl)amino]-N-[1-(2-dimethylamino-6-methyl-pyrimidin-4-yl)-piperidin-4-yl]-N-methyl-2,3-dihydro-1H-indene-5-carboxylic acid amide, 4-[4-[[3-(3-Cyclopentyl-propanoylamino)-2,3-dihydro-1H-indene-5-carbonyl]-methyl-amino]-piperidin-1-yl]-N,N-dimethyl-pyridine-2-carboxylic acid amide, N-[1-(2-tert-Butyl-pyrimidin-4-yl)-piperidin-4-yl]-3-[(2-chloro-benzoyl)amino]-N-methyl-2,3-dihydro-1H-indene-5-carboxylic acid amide, 3-[(2-Chloro-benzoyl)amino]-N-methyl-N-[4-(5-methyl-3-oxo-1,2-dihydro-imidazo[5,1-e]imidazol-2-yl)-cyclohexyl]-2,3-dihydro-1H-indene-5-carboxylic acid amide, 3-(3-Cyclopentyl-propanoylamino)-N-methyl-N-[1-(2-pyrrolidin-1-yl-pyrimidin-4-yl)-piperidin-4-yl]-2,3-dihydro-1H-indene-5-carboxylic acid amide, N-[6-[[1-(5-Fluoro-pyrimidin-4-yl)-piperidin-4-yl]-methyl-carbamoyl]-2,3-dihydro-1H-inden-1-yl]-2-(trifluoromethyl)-pyridine-3-carboxylic acid amide, 3-(3-Cyclopentyl-propanoylamino)-N-[1-(2-dimethylamino-6-methyl-pyrimidin-4-yl)-piperidin-4-yl]-N-methyl-2,3-dihydro-1H-indene-5-carboxylic acid amide, 3-[(2-Chloro-benzoyl)amino]-N-[1-(2-dimethylamino-pyrimidin-4-yl)-piperidin-4-yl]-N-methyl-2,3-dihydro-1H-indene-5-carboxylic acid amide, N-[1-(2-tert-Butyl-pyrimidin-4-yl)-piperidin-4-yl]-3-(3-cyclopentyl-propanoylamino)-N-methyl-2,3-dihydro-1H-indene-5-carboxylic acid amide, 3-(3-Cyclopentyl-propanoylamino)-N-methyl-N-[4-(5-methyl-3-oxo-1,2-dihydro-imidazo[5,1-e]imidazol-2-yl)-cyclohexyl]-2,3-dihydro-1H-indene-5-carboxylic acid amide, 3-[(2-Chloro-benzoyl)amino]-N-[1-(2-cyclopropyl-pyrimidin-4-yl)-piperidin-4-yl]-N-methyl-2,3-dihydro-1H-indene-5-carboxylic acid amide, N-[6-[Methyl-(1-pyridazin-4-yl-piperidin-4-yl)-carbamoyl]-2,3-dihydro-1H-inden-1-yl]-2-(trifluoromethyl)-pyridine-3-carboxylic acid amide, 3-(3-Cyclopentyl-propanoylamino)-N-[1-(2-dimethylamino-pyrimidin-4-yl)-piperidin-4-yl]-N-methyl-2,3-dihydro-1H-indene-5-carboxylic acid amide, 3-(3-Cyclopentyl-propanoylamino)-N-[1-(2-cyclopropyl-pyrimidin-4-yl)-piperidin-4-yl]-N-methyl-2,3-dihydro-1H-indene-5-carboxylic acid amide, 3-[(2-Chloro-benzoyl)amino]-N-[1-(5-fluoro-pyrimidin-4-yl)-piperidin-4-yl]-N-methyl-2,3-dihydro-1H-indene-5-carboxylic acid amide, 3-(3-Cyclopentyl-propanoylamino)-N-[1-(5-fluoro-pyrimidin-4-yl)-piperidin-4-yl]-N-methyl-2,3-dihydro-1H-indene-5-carboxylic acid amide, 3-[(2-Chloro-benzoyl)amino]-N-methyl-N-(1-pyridazin-4-yl-piperidin-4-yl)-2,3-dihydro-1H-indene-5-carboxylic acid amide, and 3-(3-Cyclopentyl-propanoylamino)-N-methyl-N-(1-pyridazin-4-yl-piperidin-4-yl)-2,3-dihydro-1H-indene-5-carboxylic acid amide;

or an N-oxide or physiologically acceptable salt thereof.

24. A pharmaceutical composition comprising a compound according to claim 1 and at least one pharmaceutically acceptable carrier or auxiliary.

25. A method of inhibiting angiogenesis in a subject, said method comprising administering to said subject a pharmacologically effective amount of a compound according to claim 1.

* * * * *